United States Patent
Yoshida et al.

(10) Patent No.: US 11,414,429 B2
(45) Date of Patent: Aug. 16, 2022

(54) COMPOUND OR PHARMACEUTICALLY ACCEPTABLE SALT THEREOF

(71) Applicants: RIKEN, Saitama (JP); JAPANESE FOUNDATION FOR CANCER RESEARCH, Tokyo (JP); KABUSHIKI KAISHA YAKULT HONSHA, Tokyo (JP)

(72) Inventors: Minoru Yoshida, Wako (JP); Hiroyuki Seimiya, Tokyo (JP); Masayuki Okue, Yokohama (JP); Yoko Yashiroda, Wako (JP); Fumiyuki Shirai, Wako (JP); Takeshi Tsumura, Yokohama (JP); Yuko Kano, Yokohama (JP); Kenichi Washizuka, Wako (JP); Nobuko Yoshimoto, Wako (JP); Yasuko Kouda, Wako (JP); Takehiro Fukami, Wako (JP); Tsubasa Chikada, Yokohama (JP); Takashi Watanabe, Yokohama (JP)

(73) Assignees: RIKEN, Saitama (JP); JAPANESE FOUNDATION FOR CANCER RESEARCH, Tokyo (JP); KABUSHIKI KAISHA YAKULT HONSHA, Tokyo (JP)

( * ) Notice: Subject to any disclaimer, the term of this patent is extended or adjusted under 35 U.S.C. 154(b) by 49 days.

(21) Appl. No.: 16/314,101

(22) PCT Filed: Jun. 30, 2017

(86) PCT No.: PCT/JP2017/024084
§ 371 (c)(1),
(2) Date: Dec. 28, 2018

(87) PCT Pub. No.: WO2018/003962
PCT Pub. Date: Jan. 4, 2018

(65) Prior Publication Data
US 2020/0172554 A1 Jun. 4, 2020

(30) Foreign Application Priority Data

Jun. 30, 2016 (JP) .............................. JP2016-130044

(51) Int. Cl.
*C07D 471/20* (2006.01)
*C07D 519/00* (2006.01)
*C07D 471/10* (2006.01)
*C07D 491/107* (2006.01)

(52) U.S. Cl.
CPC ......... *C07D 519/00* (2013.01); *C07D 471/10* (2013.01); *C07D 471/20* (2013.01); *C07D 491/107* (2013.01)

(58) Field of Classification Search
CPC .............. A61K 31/5377; A61K 31/517; A61K 31/519; A61K 31/522; A61K 31/541; C07D 471/20; C07D 471/04; C07D 491/20; A61P 31/04; A61P 25/16; A61P 35/00
USPC ....................................... 514/234.5; 544/116
See application file for complete search history.

(56) References Cited

U.S. PATENT DOCUMENTS

| | | | |
|---|---|---|---|
| 2005/0033048 A1 | 2/2005 | Bakthavatchalam et al. |
| 2013/0331375 A1 | 12/2013 | Haynes et al. |
| 2013/0345215 A1 | 12/2013 | Feng et al. |
| 2015/0025071 A1 | 1/2015 | Buchstaller et al. |

FOREIGN PATENT DOCUMENTS

| | | |
|---|---|---|
| WO | 02/48152 A2 | 6/2002 |
| WO | 2013/012723 A1 | 1/2013 |
| WO | 2013/117288 A1 | 8/2013 |
| WO | 2013/182546 A1 | 12/2013 |
| WO | 2013/182580 A1 | 12/2013 |

OTHER PUBLICATIONS

Valérie Schreiber et al., "Poly(ADP-ribose): novel functions for an old molecule", Nature Reviews | Molecular Cell Biology, Jul. 2006, pp. 517-528, vol. 7, No. 7.

Jenna L. Riffell et al., "Tankyrase-targeted therapeutics: expanding opportunities in the PARP family", Nature Reviews | Drug Discovery, Dec. 2012, pp. 923-936, vol. 11, No. 12.

Sebastian Guettler et al., "Structural Basis and Sequence Rules for Substrate Recognition by Tankyrase Explain the Basis for Cherubism Disease", Cell, Dec. 9, 2011, pp. 1340-1354, vol. 147, No. 6.

(Continued)

*Primary Examiner* — Jeffrey H Murray
(74) *Attorney, Agent, or Firm* — Sughrue Mion, PLLC

(57) ABSTRACT

Provided are 2-(piperidin-1-yl)pyrimidin-4(3H)-ones or pharmaceutically acceptable salts thereof, each characterized by having a 1,8-diazaspiro[4.5]deca-3-ene, 1-oxa-8-azaspiro[4.5]deca-3-ene, 2,8-diazaspiro[4.5]deca-3-ene, 2-oxa-8-azaspiro[4.5]deca-3-ene, 2,9-diazaspiro[5.5]undeca-3-ene, 1-oxa-9-azaspiro[5.5]undeca-3-ene, 1,9-diazaspiro[5.5]undeca-4-ene, or 3,9-diazaspiro[5.5]undeca-1-ene structure represented by the following general formula (1):

[Chem. 1]

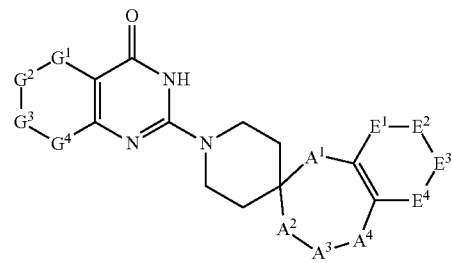

(1)

16 Claims, No Drawings

(56) References Cited

OTHER PUBLICATIONS

Lari Lehtio et al., "Tankyrases as drug targets", FEBS Journal, 2013, pp. 3576-3593, vol. 280, No. 15.
Hans Clevers, "Wnt/β-Catenin Signaling in Development and Disease", Cell, Nov. 3, 2006, pp. 469-480, vol. 127, No. 3.
Li Ma et al., "Tankyrase inhibitors attenuate WNT/p-catenin signaling and inhibit growth of hepatocellular carcinoma cells", Oncotarget, 2015, pp. 25390-25401, vol. 6, No. 28.
Dikshya Bastakoty et al., "Inhibition of Wnt/β-catenin pathway promotes regenerative repair of cutaneous and cartilage injury", The FASEB Journal • Research Communication, 2015, , pp. 4881-4892, vol. 29, No. 12.
Shih-Min A. Huang et al., "Tankyrase inhibition stabilizes axin and antagonizes Wnt signalling", Nature, Oct. 2009, pp. 614-620, vol. 461.
International Search Report of PCT/JP2017/024084 dated Sep. 5, 2017 [PCT/ISA/210].
Communication, dated Jul. 31, 2020, issued by Intellectual Property India in counterpart Indian Patent Application No. 201917001761.

COMPOUND OR PHARMACEUTICALLY ACCEPTABLE SALT THEREOF

CROSS REFERENCE TO RELATED APPLICATIONS

This application is a National Stage of International Application No. PCT/JP2017/024084, filed Jun. 30, 2017, claiming priority based on Japanese Patent Application No. 2016-130044, filed Jun. 30, 2016.

TECHNICAL FIELD

The present invention relates to a novel compound or a pharmaceutically acceptable salt thereof, and more specifically relates to a novel 2-(piperidin-1-yl)pyrimidin-4(3H)-one or a pharmaceutically acceptable salt thereof having tankyrase inhibitory activity and having a spiro structure, and relates to a tankyrase inhibitor and a pharmaceutical composition comprising the same.

BACKGROUND ART

Poly (ADP-ribosylation) is a biochemical reaction of adding a chain of ADP-ribose to a glutamate residue or aspartate residue of a protein by using nicotinamide adenine dinucleotide as a substrate. The poly (ADP-ribose) chain produced is composed of 200 ADP-ribose units at longest. A poly (ADP-ribosylation) polymerase (PARP) family is known as enzymes which catalyze a poly (ADP-ribosylation) reaction (Non Patent Literature 1).

PARP-5a and PARP-5b are called tankyrase-1 and tankyrase-2, respectively, and are usually simply called tankyrase as a general term for both. Tankyrase includes an ankyrin domain which recognizes a protein to be poly-(ADP-ribosylated), a sterile alpha motif (SAM) domain which is involved in self-multimerization, and a PARP catalytic domain which governs poly (ADP-ribosylation) reactions (Non Patent Literatures 2 and 3).

Tankyrase bonds to various proteins via the intramolecular ankyrin domain and converts these proteins into poly (ADP-ribose). Tankyrase-binding proteins include TRF1, NuMA, Plk1, Miki, Axin, TNKS1BP1, IRAP, Mcl-1, 3BP2, and so on (Non Patent Literatures 3 and 4)). Tankyrase adjusts physiological functions of these proteins by poly-ADP-ribosylating the proteins.

Therefore, inhibition of tankyrase is considered to be useful for controlling physiological functions of the proteins, such as cell proliferation, cell differentiation, and tissue formation. Tankyrase inhibitors have potential to produce effects on diseases including: fibrosarcoma, ovarian cancer, glioblastoma, pancreatic adenoma, breast cancer, astrocytoma, lung cancer, gastric cancer, hepatocellular carcinoma, multiple myeloma, colorectal cancer, bladder transitional epithelium cancer, leukemia, infectious diseases such as infections by Herpes simplex virus and Epstein-Barr virus, fibrosis such as pulmonary fibrosis, cherubism, multiple sclerosis, amyotrophic lateral sclerosis, skin and cartilage injuries, metabolic diseases, and so on. Moreover, it has been suggested that tankyrase inhibitors may also be effective for suppressing metastasis of cancer (Non Patent Literatures 2, 4, 5, 6, and 7).

Examples of disclosed compounds having tankyrase inhibitory activity include a compound XAV-939 described in Non Patent Literature 8 and compounds described in Patent Literatures 1 and 2. However, all of these compounds do not have a spiro structure of the compound of the present invention. In addition, any of these compounds has not yet been used as a pharmaceutical drug, and development of new pharmaceutical drugs of these compounds has been demanded.

Meanwhile, as for 2-(piperidin-1-yl)pyrimidin-4(3H)-ones characterized by having a spiro structure, Patent Literature 3 just discloses spiro[isobenzofuran-1,4'-piperidin]-3-ones and 3H-spiroisobenzofuran-1,4'-piperidines, and only teaches that these regulate neuropeptide Y5 receptors and thereby are effective for applications such as treatments of eating disorders, diabetes, and cardiovascular disorders, but does not contain any description about the tankyrase inhibitory activity.

CITATION LIST

Patent Literature

Patent Document 1: WO2013/117288
Patent Document 2: WO2013/182580
Patent Document 3: WO02/48152

Non Patent Literature

Non-Patent Document 1: Schreiber V. et al., Nat. Rev. Mol. Cell Biol., Vol. 7, No. 7, pp. 517-528, 2006
Non-Patent Document 2: Riffell J. L. et al., Nat. Rev. Drug Discov., Vol. 11, No. 12, pp. 923-936, 2012
Non-Patent Document 3: Guettler S. et al., Cell, Vol. 147, No. 6, pp. 1340-1354, 2011
Non-Patent Document 4: Lehtio L. et al., FEBS J., Vol. 280, No. 15, pp. 3576-3593, 2013
Non-Patent Document 5: Clevers H., Cell, Vol. 127, No. 3, pp. 469-480, 2006
Non-Patent Document 6: Ma L. et al., Oncotarget, Vol. 6, No. 28, pp. 25390-25401, 2015
Non-Patent Document 7: Bastakoty D. et al., FASEB J., Vol. 29, No. 12, pp. 4881-4892, 2015
Non-Patent Document 8: Huang S M. et al., Nature, Vol. 461, pp. 614-620, 2009

SUMMARY OF INVENTION

Technical Problem

The present invention aims to provide a compound and a pharmaceutically acceptable salt thereof which have excellent tankyrase inhibitory activity, and which are useful, for example, for treatment and prophylaxis of proliferative diseases such as cancer and are also useful for treatment of other diseases such as Herpes virus, multiple sclerosis, glucose metabolism diseases, skin and cartilage injuries, and pulmonary fibrosis, and also provide a tankyrase inhibitor and a pharmaceutical composition containing the same. Furthermore, the present invention aims to provide a method for producing the compound and the pharmaceutically acceptable salt thereof and to provide an intermediate compound useful for the production.

Solution to Problem

The present inventors have made earnest studies to achieve the above objects and consequently found that a compound and a pharmaceutically acceptable salt thereof having a specific spiro structure have excellent tankyrase inhibitory activity. This finding has led to the completion of the present invention.

3

Specifically, the present invention provides a compound or a pharmaceutically acceptable salt thereof which includes the following inventions.

[1]

A compound or a pharmaceutically acceptable salt thereof, the compound being represented by the following general formula (1):

[Chem. 1]

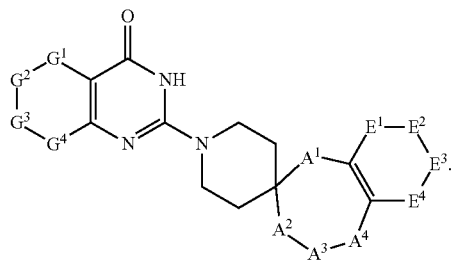

(1)

[in the formula (1), $A^1$, $A^2$, $A^3$, and $A^4$ are defined such that both of $A^1$ and $A^2$ represent a single bond, one of $A^1$ and $A^2$ represents a single bond and the other represents $CH_2$, or $A^1$ represents a single bond and $A^4$ represents $CH_2$, one of $A^3$ and $A^4$ is $CH_2$ or CO and the other is O or $NR^1$ when both of $A^1$ and $A^2$ represent a single bond or when $A^1$ represents $CH_2$ and $A^2$ represents a single bond, one of $A^3$ and $A^4$ is $NR^1$ and the other is $CH_2$ or CO when $A^1$ represents a single bond and $A^2$ represents $CH_2$, or one of $A^2$ and $A^3$ is $NR^1$ and the other is $CH_2$ or CO when $A^1$ represents a single bond and $A^4$ is $CH_2$, where $R^1$ represents a hydrogen atom, an optionally substituted $C_{1-6}$ alkyl group, an optionally substituted heteroaryl group, an optionally substituted $C_{3-8}$ cycloalkyl $C_{1-3}$ alkyl group, an optionally substituted aryl $C_{1-3}$ alkyl group, an optionally substituted heteroaryl $C_{1-3}$ alkyl group, an optionally substituted 3- to 7-membered heterocycloalkyl $C_{1-3}$ alkyl group, a group represented by the following formula: —$(CH_2)_m$—C(=O)—L, or a group represented by the following formula: —S(=O)$_2$—$R^{13}$, m is 0, 1, 2, or 3, and L is $R^{11}$ when m is 0 or L is $R^{12}$ when m is 1, 2, or 3, $R^{11}$ is a hydrogen atom, an optionally substituted $C_{1-6}$ alkyl group, $OR^{51}$, a group represented by the following formula: —C(=O)—$OR^{52}$, or a group represented by the following formula: —N($R^{53a}$)—$R^{53b}$, $R^{51}$ is an optionally substituted aryl $C_{1-3}$ alkyl group, $R^{52}$ is a hydrogen atom or an optionally substituted $C_{1-6}$ alkyl group, $R^{53a}$ and $R^{53b}$ are each independently a hydrogen atom or an optionally substituted $C_{1-6}$ alkyl group, or $R^{53a}$ and $R^{53b}$ together form a 3- to 7-membered heterocycloalkyl group which may contain at least one atom or group selected from the group consisting of an oxygen atom, a sulfur atom, and $NR^{101}$, $R^{101}$ is a hydrogen atom or an optionally substituted $C_{1-6}$ alkyl group, and $R^{12}$ is an optionally substituted aryl group, $OR^{54}$, or a group represented by the following formula: —N($R^{55a}$)—$R^{55b}$,

4

$R^{54}$ is a hydrogen atom, an optionally substituted $C_{1-6}$ alkyl group, an optionally substituted aryl $C_{1-3}$ alkyl group, or an optionally substituted heteroaryl $C_{1-3}$ alkyl group, and $R^{55a}$ and $R^{55b}$ are each independently a hydrogen atom, an optionally substituted $C_{1-6}$ alkyl group, an optionally substituted aryl $C_{1-3}$ alkyl group, an optionally substituted heteroaryl $C_{1-3}$ alkyl group, or a group represented by the following formula: —(C=O)—$R^{102}$, or $R^{55a}$ and $R^{55b}$ together form a 3- to 7-membered heterocycloalkyl group which may contain at least one atom or group selected from the group consisting of an oxygen atom, a sulfur atom, and $NR^{03}$, or together form an optionally substituted 6,8-dihydro-5H-imidazo[1,2-a]pyrazin-7-yl group, $R^{102}$ is a hydrogen atom, an optionally substituted $C_{1-6}$ alkyl group, or an optionally substituted aryl $C_{1-3}$ alkyl group, and $R^{103}$ is a hydrogen atom or an optionally substituted $C_{1-6}$ alkyl group, and $R^{13}$ is an optionally substituted $C_{1-6}$ alkyl group;

a structure composed of $E^1$, $E^2$, $E^3$, and $E^4$ is a group represented by the following formula: -$E^1$-$E^2$-$E^3$-$E^4$- (in this formula, bonds between $E^1$, $E^2$, $E^3$, and $E^4$ each represent a single bond or a double bond) where $E^1$ is N or $CR^2$, $E^2$ is N or $CR^3$, $E^3$ is N or $CR^4$, and $E^4$ is N or $CR^5$, is a group in which $E^1$ represents a single bond and which is represented by the following formula: -$E^2$-$E^3$=$E^4$- where $E^2$ is O or S and $E^3$ and $E^4$ are CH, or is a group in which $E^1$ represents a single bond and which is represented by the following formula: -$E^2$=$E^3$-$E^4$- where $E^2$ and $E^3$ are CH and $E^4$ is O or S, $R^2$, $R^3$, $R^4$, and $R^5$ are each independently a hydrogen atom, a fluorine atom, a chlorine atom, a bromine atom, an iodine atom, a cyano group, an optionally substituted $C_{1-6}$ alkyl group, an optionally substituted aryl group, an optionally substituted heteroaryl group, an optionally substituted 3- to 7-membered heterocycloalkyl group, or a group represented by the following formula: -Q-$(CH_2)_n$—$R^{14}$, n is 0, 1, 2, or 3, and Q is a group represented by the following formula: —CH=CH—, O, CO, a group represented by the following formula: —C(=O)—O—, a group represented by the following formula: —C(=O)—N($R^{56}$)—, $NR^{56}$, a group represented by the following formula: —N($R^{56}$)—C(=O)—, or a group represented by the following formula: —N($R^{56}$)—C(=O)—O—, $R^{56}$ is a hydrogen atom, an optionally substituted $C_{1-3}$ alkyl group or a group represented by the following formula: —C(=O)—$R^{104}$, $R^{104}$ is a hydrogen atom, an optionally substituted $C_{1-6}$ alkyl group, an optionally substituted aryl group, an optionally substituted $C_{1-6}$ alkyloxy group, or an optionally substituted aryloxy group, and $R^{14}$ is a hydrogen atom, an optionally substituted $C_{1-6}$ alkyl group, an optionally substituted aryl group, an optionally substituted heteroaryl group, an optionally substituted $C_{3-8}$ cycloalkyl group, or an optionally substituted 3- to 7-membered heterocycloalkyl group; and a structure composed of $G^1$, $G^2$, $G^3$, and $G^4$ is a group represented by the following formula: -$G^1$-$G^2$-$G^3$-$G^4$- (in this formula, bonds between $G^1$, $G^2$, $G^3$, and $G^4$ each represent a single bond or a double bond), and represented by the following formula: —CH═CH—CH═CR$^6$— (excluding a case where both of A$^1$ and A$^2$ represent a single bond, A$^3$ is O, and A$^4$ is CO), the following formula: —CH═CH—CH═N— (excluding a case where both of A$^1$ and A$^2$ represent a single bond, A$^3$ is O, and A$^4$ is CO), the following formula: —CH$_2$—CH$_2$—CH$_2$—CH$_2$—, the following formula: —CO—CH$_2$—CH$_2$—N(R$^7$)—, the following formula: —CH$_2$—CF$_2$—CH$_2$—CH$_2$—, the following formula: —CH$_2$—O—CH$_2$—CH$_2$—, the following formula: —CH$_2$—S—CH$_2$—CH$_2$—, the following formula: —CH$_2$—CH$_2$—N(R$^7$)—CH$_2$—, the following formula: —CH$_2$—CH$_2$—CH$_2$—O—, the following formula: —CH$_2$—CH$_2$—CH$_2$—N(R$^7$)—, or the following formula: —O—CH$_2$—CH$_2$—N(R$^7$)—, or is a group in which G$^1$ represents a single bond, which is represented by the following formula: -G$^2$-G$^3$-G$^4$- (where bonds between G$^2$, G$^3$, and G$^4$ each represent a single bond or a double bond), and which is represented by the following formula: —CH═CH—N(R$^7$)—, the following formula: —CH$_2$—CH$_2$—N(R$^7$)—, the following formula: —N═CH—N(R$^7$)—, or the following formula: —N(R$^7$)—CH═N—,

- R$^6$ is a hydrogen atom, a fluorine atom, a chlorine atom, a bromine atom, an iodine atom, an optionally substituted C$_{1-6}$ alkyl group, or an optionally substituted C$_{1-6}$ alkyloxy group, and
- R$^7$ is a hydrogen atom, an optionally substituted C$_{1-6}$ alkyl group, an optionally substituted C$_{3-8}$ cycloalkyl group, an optionally substituted C$_{3-8}$ cycloalkyl C$_{1-3}$ alkyl group, an optionally substituted 3- to 7-membered heterocycloalkyl group, an optionally substituted 3- to 7-membered heterocycloalkyl C$_{1-3}$ alkyl group, a group represented by the following formula: —C(═O)—R$^{15}$, or a group represented by the following formula: —(CH$_2$)$_p$—C(═O)—OR$^{16}$,
- p is 0, 1, 2, or 3,
- R$^{15}$ is a hydrogen atom, an optionally substituted C$_{1-6}$ alkyl group, or OR$^{57}$,
  - R$^{57}$ is an optionally substituted C$_{1-6}$ alkyl group or an optionally substituted aryl C$_{1-3}$ alkyl group, and
- R$^{16}$ is a hydrogen atom or an optionally substituted C$_{1-6}$ alkyl group].

[2]

The compound or the pharmaceutically acceptable salt thereof according to [1], wherein in the general formula (1), both of A$^1$ and A$^2$ represent a single bond, while one of A$^3$ and A$^4$ is CH$_2$ or CO and the other is O.

[3]

The compound or the pharmaceutically acceptable salt thereof according to [1], wherein in the general formula (1), both of A$^1$ and A$^2$ represent a single bond, while one of A$^3$ and A$^4$ is CH$_2$ or CO and the other is NR$^1$.

[4]

The compound or the pharmaceutically acceptable salt thereof according to [2] or [3], wherein in the general formula (1), the structure composed of E$^1$, E$^2$, E$^3$, and E$^4$ is a group represented by the formula: -E$^1$-E$^2$-E$^3$-E$^4$- (in this formula, bonds between E$^1$, E$^2$, E$^3$, and E$^4$ each represent a single bond or a double bond) where E$^1$ is N or CR$^2$, E$^2$ is N or CR$^3$, E$^3$ is N or CR$^4$, and E$^4$ is N or CR$^5$.

[5]

The compound or the pharmaceutically acceptable salt thereof according to [2] or [3], wherein in the general formula (1), the structure composed of G$^1$, G$^2$, G$^3$, and G$^4$ is a group which is represented by the formula: -G$^1$-G$^2$-G$^3$-G$^4$- and which is represented by the formula: —CH$_2$—CH$_2$—CH$_2$—CH$_2$—, the formula: —CH$_2$—CF$_2$—CH$_2$—CH$_2$—, the formula: —CH$_2$—O—CH$_2$—CH$_2$—, the formula: —CH$_2$—S—CH$_2$—CH$_2$—, the formula: —CH$_2$—CH$_2$—CH$_2$—O—, the formula: —CH$_2$—CH$_2$—CH$_2$—N(R$^7$)—, or the formula: —O—CH$_2$—CH$_2$—N(R$^7$)—, or is a group in which G$^1$ represents a single bond, which is represented by the formula: -G$^2$-G$^3$-G$^4$- (in this formula, bonds between G$^2$, G$^3$, and G$^4$ each represent a single bond or a double bond), and which is represented by the formula: —CH═CH—N(R$^7$)— or the formula: —CH$_2$—CH$_2$—N(R$^7$)—.

[6]

The compound or the pharmaceutically acceptable salt thereof according to claim 1, wherein the compound represented by the general formula (1) is represented by the following general formula (1-1):

[Chem. 2]

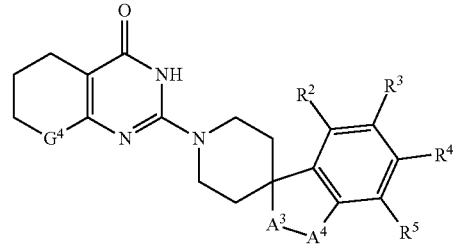

(1-1)

[in the formula (1-1),

A$^3$ is O, CH$_2$, or CO, and A$^4$ is CO or NR (excluding a case where both of A$^3$ and A$^4$ are CO, a case where A$^3$ is CH$_2$ and A$^4$ is CO, and a case where A$^3$ is O and A$^4$ is NR$^1$), and G$^4$ is CH$_2$ or NR$^7$ and R$^7$ is a hydrogen atom or an optionally substituted C$_{1-6}$ alkyl group].

[7]

The compound or the pharmaceutically acceptable salt thereof according to [1], wherein the compound represented by the general formula (1) is selected from the group consisting of 5-[2-(dimethylamino)ethoxy]-7-fluoro-1'-(8-methyl-4-oxo-3,4,5,6,7,8-hexahydropyrido[2,3-d]pyrimidin-2-yl)-3H-spiro[isobenzofuran-1,4'-piperidine]-3-one, 2-[{7-fluoro-1'-(8-methyl-4-oxo-3,4,5,6,7,8-hexahydropyrido[2,3-d]pyrimidin-2-yl)-3-oxo-3H-spiro[isobenzofuran-1,4'-piperidine]-5-yl}oxy]-N,N-dimethylacetamide, 2-[1-[(3-methoxybenzyl)spiro[indoline-3,4'-piperidin]-1'-yl]-5,6,7,8-tetrahydroquinazolin-4(3H)-one, 2-[1-(pyridin-4-ylmethyl)spiro[indoline-3,4'-piperidin]-1'-yl]-5,6,7,8-tetrahydroquinazolin-4(3H)-one, 2-[1-(pyridin-3-ylmethyl)spiro[indoline-3,4'-piperidin]-1'-yl]-5,6,7,8-tetrahydroquinazolin-4(3H)-one, 2-(5-methoxy-1-methylspiro[indoline-3,4'-piperidin]-1'-yl)-5,6,7,8-tetrahydroquinazolin-4(3H)-one, 2-(4-fluoro-2-oxospiro[indoline-3,4'-piperidin]-1'-yl)-8-methyl-5,6,7,8-tetrahydropyrido[2,3-d]pyrimidine-4(3H)-one, Ethyl 4-chloro-1'-(4-oxo-3,4,5,6,7,8-hexahydroquinazolin-2-yl)-1-(pyridin-3-yl)methylspiro[indoline-3,4'-piperidine]-6-carboxylate, 4-chloro-N-(2-morpholinoethyl)-1'-(4-oxo-3,4,5,6,7,8-hexahydroquinazolin-2-yl)-1-(pyridin-3-yl)methylspiro[indoline-3,4'-piperidine]-6-carboxamide, 2-(6-chloro-1-(pyridin-3-yl)methylspiro[indoline-3,4'-piperidin]-1'-yl)-5,6,7,8-tetrahydroquinazolin-4(3H)-one, 2-[4-chloro-1-(pyridin-3-yl)methylspiro[indoline-3,4'-piperidin]-1'-yl]-5,6,7,8-tetrahydroquinazolin-4(3H)-one, 4-chloro-1'-(4-oxo-3,4,5,6,7,8-hexahydroquinazolin-2-yl)-1-(pyridin-3-yl)methylspiro[indoline-3,4'-piperidin]-2-one, 4-chloro-6-hydroxy-1-methyl-1'-(4-oxo-3,4,5,6,7,8-hexahydroquinazolin-2-yl)spiro[indoline-3,4'-piperidin]-2-one, 2-[4,6-difluoro-1-(pyridin-3-yl)methylspiro[indoline-3,4'-piperidin]-1'-yl]-5,6,7,8-tetrahydroquinazolin-4(3H)-one, 2-[4,6-difluoro-1-(pyrimidin-5-yl)methylspiro[indoline-3,4'-piperidin]-1'-yl]-5,6,7,8-tetrahydroquinazolin-4(3H)-one, 2-[4,6-difluoro-1-(pyridin-2-yl)methylspiro[indoline-3,4'-piperidin]-1'-yl]-5,6,7,8-tetrahydroquinazolin-4(3H)-one, 2-[4,6-difluoro-1-(pyridin-4-yl)methylspiro[indoline-3,4'-piperidin]-1'-yl]-5,6,7,8-tetrahydroquinazolin-4(3H)-one, 2-[4,6-difluoro-1-(2-hydroxyethyl)spiro[indoline-3,4'-piperidin]-1'-yl]-8-methylquinazolin-4(3H)-one, 2-[4,6-difluoro-1-(2-hydroxyethyl)spiro[indoline-3,4'-piperidin]-1'-yl]-8-(hydroxymethyl)quinazolin-4(3H)-one, 4,6-difluoro-1'-[8-(hydroxymethyl)-4-oxo-3,4-dihydroquinazolin-2-yl]-1-(pyridin-3-ylmethyl)spiro[indoline-3,4'-piperidin]-2-one, 1-methyl-1'-(8-methyl-4-oxo-3,4,5,6,7,8-hexahydropyrido[2,3-d]pyrimidin-2-yl)spiro[indoline-3,4'-piperidine]-2-one, 2-[4,6-difluoro-1-(pyrimidin-2-ylmethyl)spiro[indoline-3,4'-piperidine]-1'-yl]-5,6,7,8-tetrahydroquinazolin-4 (3H)-one, 4-chloro-1-methyl-6-[4-(morpholine-4-carbonyl)oxazol-2-yl]-1'-(4-oxo-3,4,5,6,7,8-hexahydroquinazolin-2-yl)spiro[indoline-3,4'-piperidine]-2-one, 4-chloro-6-[4-(morpholine-4-carbonyl)oxazol-2-yl]-1-methyl-1'-(8-methyl-4-oxo-3,4,5,6,7,8-hexahydropyrido[2,3-d]pyrimidin-2-yl)spiro[indoline-3,4'-piperidine]-2-one, 4-chloro-1-methyl-1'-(8-methyl-4-oxo-3,4,5,6,7,8-hexahydropyrido[2,3-d]pyrimidin-2-yl)-2-oxospiro[indoline-3,4'-piperidine]-7-carbonitrile, 4-chloro-6-(4-ethoxycarbonyloxazole-2-yl)-1-methyl-1'-(8-methyl-4-oxo-3,4,5,6,7,8-hexahydropyrido[2,3-d]pyrimidin-2-yl) spiro[indoline-3,4'-piperidine]-2-one, 4-chloro-1-methyl-1'-(8-methyl-4-oxo-3,4,5,6,7,8-hexahydropyrido[2,3-d]pyrimidin-2-yl)-6-[4-(pyrrolidin-1-ylmethyl)oxazol-2-yl]spiro[indoline-3,4'-piperidine]-2-one, 4-chloro-1-methyl-1'-(8-methyl-4-oxo-3,4,5,6,7,8-hexahydropyrido[2,3-d]pyrimidin-2-yl)-2-oxospiro[indoline-3,4'-piperidine]-7-carboxamide, 2-[4-chloro-1-methyl-1'-(8-methyl-4-oxo-3,4,5,6,7,8-hexahydropyrido[2,3-d]pyrimidin-2-yl)-2-oxospiro[indoline-3,4'-piperidine]-6-yl]oxazole-4-carboxylic acid, 4,6-difluoro-1'-(4-oxo-3,4,5,6,7,8-hexahydroquinazolin-2-yl)-1-(pyridin-3-ylmethyl)spiro[indoline-3,4'-piperidine]-2-one, 4-chloro-1-methyl-6-(3-morpholinopropoxy)-1'-(4-oxo-3,4,5,6,7,8-hexahydroquinazolin-2-yl)spiro[indoline-3,4'-piperidin]-2-one, 2-(4,6-difluoro-1-methylspiro[indoline-3,4'-piperidine]-1'-yl)-8-methyl-5,6,7,8-tetrahydropyrido[2,3-d]pyrimidin-4(3H)-one, 2-[4,6-difluoro-1-(2-hydroxyethyl)spiro[indoline-3,4'-piperidine]-1'-yl]-8-methyl-5,6,7,8-tetrahydropyrido[2,3-d]pyrimidin-4(3H)-one, 4,6-difluoro-1-methyl-1'-(8-methyl-4-oxo-3,4,5,6,7,8-hexahydropyrido[2,3-d]pyrimidin-2-yl)spiro[indoline-3,4'-piperidine]-2-one, 4,6-difluoro-1-(2-hydroxyethyl)-1'-(8-methyl-4-oxo-3,4,5,6,7,8-hexahydropyrido[2,3-d]pyrimidin-2-yl)spiro[indoline-3,4'-piperidine]-2-one, 2-[4,6-difluoro-1-(2-fluorobenzyl)spiro[indoline-3,4'-piperidin]-1'-yl]-5,6,7,8-tetrahydroquinazolin-4(3H)-one, 2-[4,6-difluoro-1-(3-fluorobenzyl)spiro[indoline-3,4'-piperidine]-1'-yl]-5,6,7,8-tetrahydroquinazolin-4(3H)-one, 2-{1-[(6-chloropyridin-3-yl)methyl]-4,6-difluorospiro[indoline-3,4'-piperidine]-1'-yl}-5,6,7,8-tetrahydroquinazolin-4(3H)-one, 2-[4,6-difluoro-1-(pyridin-3-ylmethyl)spiro[indoline-3,4'-piperidine]-1'-yl]-7-methyl-3,7-dihydro-4H-pyrrolo[2,3-d]pyrimidin-4-one, 2-[4,6-difluoro-1-(pyridin-3-ylmethyl)spiro[indoline-3,4'-piperidine]-1'-yl]-8-methyl-5,6,7,8-tetrahydropyrido[2,3-d]pyrimidin-4(3H)-one, 4-fluoro-6-hydroxy-1-methyl-1'-(8-methyl-4-oxo-3,4,5,6,7,8-hexahydropyrido[2,3-d]pyrimidin-2-yl)spiro[indoline-3,4'-piperidin]-2-one, 4-fluoro-6-(2-hydroxyethoxy)-1-methyl-1'-(8-methyl-4-oxo-3,4,5,6,7,8-hexahydropyrido[2,3-d]pyrimidin-2-yl)spiro[indoline-3,4'-piperidin]-2-one, 6-[2-(dimethylamino)ethoxy]-4-fluoro-1-methyl-1'-(8-methyl-4-oxo-3,4,5,6,7,8-hexahydropyrido[2,3-d]pyrimidin-2-yl)spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-(2-morpholinoethoxy)spiro[indoline-3,4'-piperidin]-2-one, 6-[2-(1,1-dioxidothiomorpholino)ethoxy]-4-fluoro-1-methyl-1'-(8-methyl-4-oxo-3,4,5,6,7,8-hexahydropyrido[2,3-d]pyrimidin-2-yl)spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-[2-(4-methylpiperazin-1-yl)ethoxy]spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-(3-morpholin-4-yl-propoxy)spiro[indoline-3,4'-piperidin]-2-one, 4-fluoro-6-(2-methoxyethoxy)-1-methyl-1'-(8-methyl-4-oxo-3,4,5,6,7,8-hexahydropyrido[2,3-d]pyrimidin-2-yl)spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-[3-(pyrrolidin-1-yl)propoxy]spiro[indoline-3,4'-piperidin]-2-one, 4,6-difluoro-1-(2-hydroxyethyl)-1'-[8-(trideuteriomethyl)-4-oxo-3,4,5,6,7,8-hexapyrido[2,3-d]pyrimidin-2-yl]spiro[indoline-3,4'-piperidin]-2-one, 4-fluoro-6-methoxy-1-methyl-1'-(8-methyl-4-oxo-3,4,5,6,7,8-hexahydropyrido[2,3-d]pyrimidin-2-yl)spiro[indoline-3,4'-piperidin]-2-one, 4-fluoro-1-(2-hydroxyethyl)-6-methoxy-1'-(8-methyl-4-oxo-3,4,5,6,7,8-hexahydropyrido[2,3-d]pyrimidin-2-yl)spiro[indoline-3,4'-piperidin]-2-one, 2-[4,6-difluoro-1'-(8-methyl-4-oxo-3,4,5,6,7,8-hexahydropyrido[2,3-d]pyrimidin-2-yl)-2-oxospiro[indoline-3,4'-piperidin-1-yl]acetonitrile, 4-chloro-6-[2-(dimethylamino)ethoxy]-1-methyl-1'-(8-methyl-4-oxo-3,4,5,6,7,8-hexahydropyrido[2,3-d]pyrimidin-2-yl) spiro[indoline-3,4'-piperidin]-2-one, 4-chloro-1-methyl-1'-(8-methyl-4-oxo-3,4,5,6,7,8-hexahydropyrido[2,3-d]pyrimidin-2-yl)-6-(2-piperidin-1-ylethoxy)spiro[indoline-3,4'-piperidin]-2-one 4-chloro-1-methyl-1'-(8-methyl-4-oxo-3,4,5,6,7,8-hexahydropyrido[2,3-d]pyrimidin-2-yl)-6-(2-morpholin-4-ylethoxy)spiro[indoline-3,4'-piperidin]-2-one, 4-chloro-6-[2-(1,1-dioxidothiomorpholino)ethoxy]-1-methyl-1'-(8-methyl-4-oxo-3,4,5,6,7,8-hexapyrido[2,3-d]pyrimidin-2-yl) spiro[indoline-3,4'-piperidin]-2-one, 2-[4-fluoro-6-methoxy-1'-(8-methyl-4-oxo-3,4,5,6,7,8-hexahydropyrido[2,3-d]pyrimidin-2-yl)-2-oxospiro[indoline-3,4'-piperidine]-1-yl]acetonitrile, 4-fluoro-1-methyl-1'-(8-methyl-4-oxo-3,4,5,6,7,8-hexahydropyrido[2,3-d]pyrimidin-2-yl)-6-(1-methylpiperidin-4-yl)oxyspiro[indoline-3,4'-piperidin]-2-one, 4-fluoro-6-(2-hydroxyethoxy)-1-(2-hydroxyethyl)-1'-(8-methyl-4-oxo-3,4,5,6,7,8-hexahydropyrido[2,3-d]pyrimidin-2-yl)spiro[indoline-3,4'-piperidin]-2-one, 1'-(8-ethyl-4-oxo-3,4,5,6,7,8-hexahydropyrido[2,3-d]pyrimidin-2-yl)-4,6-difluoro-1-(2-hydroxyethyl)spiro[indoline-3,4'-piperidin]-2-one, 4-fluoro-1-(2-hydroxyethyl)-6-(2-methoxyethoxy)-1'-(8-methyl-4-oxo-3,4,5,6,7,8-hexahydropyrido[2,3-d]pyrimidin-2-yl) spiro[indoline-3,4'-piperidin]-2-one, 4-fluoro-6-hydroxy-1-(2-hydroxyethyl)-1'-(8-methyl-4-oxo-3,4,5,6,7,8-hexahydropyrido[2,3-d]pyrimidin-2-yl) spiro[indoline-3,4'-piperidin]-2-one, 4-fluoro-1-(2-hydroxyethyl)-1'-(8-methyl-4-oxo-3,4,5,6,7,8-hexahydropyrido[2,3-d]pyrimidin-2-yl)-6-(2-morpholin-4-ylethoxy)spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-(4-methylpiperazin-1-yl) spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-(oxetan-3-ylmethoxy) spiro[indoline-3,4'-piperidin]-2-one, 4-fluoro-1-methyl,-1'-(8-methyl-4-oxo-3,4,5,6,7,8-hexahydropyrido[2,3-d]pyrimidin-2-yl)-6-[(tetrahydro-2H-pyran-4-yl)oxy]spiro[indoline-3,4'-piperidin]-2-one, 6-(cis-3,5-dimethylpiperazin-1-yl)-4-fluoro-1-methyl-1'-(8-methyl-4-oxo-3,4,5,6,7,8-hexahydropyrido[2,3-d]pyrimidin-2-yl)spiro[indoline-3,4'-piperidin]-2 (1H)-one, 6-(3,8-diazabicyclo[3.2.1]octan-3-yl)-4-fluoro-1-methyl-1'-(8-methyl-4-oxo-3,4,5,6,7,8-hexahydropyrido[2,3-d]pyrimidin-2-yl)spiro[indoline-3,4'-piperidin]-2-one, 2-{[4-fluoro-1-methyl-1'-(8-methyl-4-oxo-3,4,5,6,7,8-hexahydropyrido[2,3-d]pyrimidin-2-yl)-2-oxospiro [indoline-3,4'-piperidin]-6-yl]oxy} acetic acid, 6-[(1H-tetrazol-5-yl)methoxy]-4-fluoro-1-methyl-1'-(8-methyl-4-oxo-3,4,5,6,7,8-hexahydropyrido[2,3-d]pyrimidin-2-yl)spiro[indoline-3,4'-piperidin]-2(1H)-one, 4-fluoro-6-{2-[2-(hydroxymethyl)pyrrolidin-1-yl]ethoxy}-1-methyl-1'-(8-methyl-4-oxo-3,4,5,6,7,8-hexahydropyrido[2,3-d]pyrimidin-2-yl) spiro[indoline-3,4'-piperidin]-2-(1H)-one, 4-fluoro-1'-(4-hydroxy-8-methyl-6,7-dihydro-5H-pyrido[2,3-d]pyrimidin-2-yl)-6-(2-pyrrolidin-1-ylethoxy)spiro[2-benzofuran-3,4'-piperidin]-1-one, 4-chloro-7-[2-(dimethylamino)ethoxy]-1-methyl-1'-(8-methyl-4-oxo-3,4,5,6,7,8-hexahydropyrido[2,3-d]pyrimidin-2-yl) spiro[indoline-3,4'-piperidin]-2-one, 4-fluoro-6-[4-(2-methoxyethyl)piperazin-1-yl]-1-methyl-1'-(8-methyl-4-oxo-3,4,5,6,7,8-hexahydropyrido[2,3-d]pyrimidin-2-yl)spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-[4-(oxetan-3-yl) piperazin-1-yl]spiro[indoline-3,4'-piperidin]-2-one, 4-fluoro-6-(2-hydroxyethoxy)-1'-(8-methyl-4-oxo-3,4,5,6,7,8-hexahydropyrido[2,3-d]pyrimidin-2-yl)-1-(2,2,2-trifluoroethyl)spiro[indoline-3,4'-piperidin]-2-one, 6-[2-(dimethylamino)ethoxy]-4-fluoro-1'-(8-methyl-4-oxo-3,4,5,6,7,8-hexahydropyrido[2,3-d]pyrimidin-2-yl)-1-(2,2,2-trifluoroethyl)spiro[indoline-3,4'-piperidin]-2-one, 7-[2-(dimethylamino)ethoxy]-4-fluoro-1'-(4-hydroxy-8-methyl-6,7-dihydro-5H-pyrido[2,3-d]pyrimidin-2-yl)-1-methyl spiro[indoline-3,4'-piperidin]-2-one,

[4-fluoro-1'-(8-methyl-4-oxo-3,4,5,6,7,8-hexahydropyrido[2,3-d]pyrimidin-2-yl)-6-(4-methylpiperazin-1-yl)-2-oxospiro[indoline-3,4'-piperidin]-1(2H)-yl]acetonitrile, 6-(4-acetylpiperazin-1-yl)-4-fluoro-1-methyl-1'-(8-methyl-4-oxo-3,4,5,6,7,8-hexahydropyrido[2,3-d]pyrimidin-2-yl) spiro[indoline-3,4'-piperidin]-2(1H)-one, 4-fluoro-1'-(8-methyl-4-oxo-3,4,5,6,7,8-hexahydropyrido[2,3-d]pyrimidin-2-yl)-6-(2-pyrrolidin-1-ylethoxy)-1-(2,2,2-trifluoroethyl)spiro[indoline-3,4'-piperidin]-2(1H)-one, 6-[2-(dimethylamino)ethoxy]-4-fluoro-1-(2-methoxyethyl)-1'-(8-methyl-4-oxo-3,4,5,6,7,8-hexahydropyrido[2,3-d]pyrimidin-2-yl) spiro[indoline-3,4'-piperidin]-2(1H)-one, 4-fluoro-1'-(8-methyl-4-oxo-3,4,5,6,7,8-hexahydropyrido[2,3-d]pyrimidin-2-yl)-6-[2-(4-methylpiperazin-1-yl)ethoxy]-1-(2,2,2-trifluoroethyl)spiro[indoline-3,4'-piperidin]-2 (1H)-one, 4-fluoro-1-(2-methoxyethyl)-1'-(8-methyl-4-oxo-3,4,5, 6,7,8-hexahydropyrido[2,3-d]pyrimidin-2-yl)-6-(4-methylpiperazin-1-yl)spiro[indoline-3,4'-piperidin]-2 (1H)-one, {[4-fluoro-1'-(8-methyl-4-oxo-3,4,5,6,7,8-hexahydropyrido[2,3-d]pyrimidin-2-yl)-2-oxo-1-(2,2,2-trifluoroethyl) spiro[indoline-3,4'-piperidin]-6-yl]oxy} acetic acid, {[4-fluoro-1-(2-methoxyethyl)-1'-(8-methyl-4-oxo-3,4,5,6,7,8-hexahydropyrido[2,3-d]pyrimidin-2-yl)-2-oxospiro[indoline-3,4'-piperidin]-6-yl]oxy} acetic acid, 4-fluoro-6-(2-hydroxyethoxy)-1-(2-methoxyethyl)-1'-(8-methyl-4-oxo-3,4,5,6,7,8-hexahydropyrido[2,3-d]pyrimidin-2-yl) spiro[indoline-3,4'-piperidin]-2(1H)-one, 2-[4-fluoro-1'-(4-hydroxy-8-methyl-6,7-dihydro-5H-pyrido[2,3-d]pyrimidin-2-yl)-1-methyl-2-oxospiro[indole-3,4'-piperidin]-7-yl]oxyacetic acid, 4-fluoro-1'-(4-hydroxy-8-methyl-6,7-dihydro-5H-pyrido[2,3-d]pyrimidin-2-yl)-1-methyl-7-[(1-methylpiperidin-4-yl) methoxy]spiro[indole-3,4'-piperidin]-2-one, 4-fluoro-7-(2-hydroxyethoxy)-1'-(4-hydroxy-5,6,7,8-tetrahydropyrido[2,3-d]pyrimidin-2-yl)-1-methyl-spiro[indole-3,4'-piperidin]-2-one, 4-chloro-1'-(4-hydroxy-8-methyl-6,7-dihydro-5H-pyrido[2,3-d]pyrimidin-2-yl)-1-methyl-7-(2H-tetrazol-5-ylmethoxy) spiro[indole-3,4'-piperidin]-2-one, 4-fluoro-1-(2-methoxyethyl)-1'-(8-methyl-4-oxo-3,4,5, 6,7,8-hexahydropyrido[2,3-d]pyrimidin-2-yl)-6-(piperazin-1-yl)spiro[indoline-3,4'-piperidin]-2(1H)-one 6-[cis-3,5-dimethylpiperazin-1-yl]-4-fluoro-1'-(8-methyl-4-oxo-3,4,5,6,7,8-hexahydropyrido[2,3-d]pyrimidin-2-yl) 1-(2,2,2-trifluoroethyl)spiro[indoline-3,4'-piperidin]-2-one, 4-fluoro-1-(2-methoxyethyl)-1'-(8-methyl-4-oxo-3,4,5, 6,7,8-hexahydropyrido[2,3-d]pyrimidin-2-yl)-6-[(1H-tetrazol-5-yl)methoxy]spiro[indoline-3,4'-piperidin]-2-one, 6-[(1H-tetrazol-5-yl)methoxy]-4-fluoro-1'-(8-methyl-4-oxo-3,4,5,6,7,8-hexahydropyrido[2,3-d]pyrimidin-2-yl)-1-(2,2,2-trifluoroethyl)spiro[indoline-3,4'-piperidin]-2 (1H)-one, 4-fluoro-1'-(4-hydroxy-8-methyl-6,7-dihydro-5H-pyrido[2,3-d]pyrimidin-2-yl)-1-methyl-7-(1-methylpiperidin-4-yl)oxyspiro[indole-3,4'-piperidin]-2-one, 4-fluoro-1'-(4-hydroxy-8-methyl-6,7-dihydro-5H-pyrido[2,3-d]pyrimidin-2-yl)-1-methyl-7-(piperidin-4-ylmethoxy)spiro[indole-3,4'-piperidin]-2-one, 1-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]piperidine-4-carboxylic acid, 1-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]azetidine-3-carboxylic acid, 2-[4,6-difluoro-1'-(8-methyl-4-oxo-3,4,5,6,7,8-hexahydropyrido[2,3-d]pyrimidin-2-yl)-2-oxospiro[indoline-3,4'-piperidin]-1(2H)-yl]acetamide, 4-chloro-1'-(4-hydroxy-8-methyl-6,7-dihydro-5H-pyrido[2,3-d]pyrimidin-2-yl)-1-methyl-7-[(8-methyl-8-azabicyclo[3.2.1]octan-3-yl)oxy]spiro[indole-3,4'-piperidin]-2-one, 4-fluoro-7-(2-hydroxy-2-methylpropoxy)-1'-(4-hydroxy-5,6,7,8-tetrahydropyrido[2,3-d]pyrimidin-2-yl)-1-methylspiro[indole-3,4'-piperidin]-2-one, 2-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy-N-(methylsulfonyl)acetamide, 6-[2-(N,N-dimethylsulfamoyl)aminoethoxy]-4-fluoro-1-methyl-1'-(8-methyl-4-oxo-3,4,5,6,7,8-hexahydropyrido[2,3-d]pyrimidin-2-yl) spiro[indoline-3,4'-piperidin]-2(1H)-one, {[4-fluoro-1-(2-hydroxyethyl)-1'-(8-methyl-4-oxo-3,4,5,6,7,8-hexahydropyrido[2,3-d]pyrimidin-2-yl)-2-oxospiro[indoline-3,4'-piperidin]-6-yl]oxy} acetonitrile,

[4,6-difluoro-1'-(8-methyl-4-oxo-3,4,5,6,7,8-hexahydropyrido[2,3-d]pyrimidin-2-yl)-2-oxospiro[indoline-3,4'-piperidin]-1(2H)-yl]ethanimidamide, 4-fluoro-1-methyl-1'-(8-methyl-4-oxo-3,4,5,6,7,8-hexahydropyrido[2,3-d]pyrimidin-2-yl)-2-oxospiro[indoline-3,4'-piperidine]-6-carboxylic acid, N-(2-{[4-fluoro-1-methyl-1'-(8-methyl-4-oxo-3,4,5,6, 7,8-hexahydropyrido[2,3-d]pyrimidin-2-yl)-2-oxospiro[indoline-3,4'-piperidin]-6-yl]oxy}ethyl)methane sulfonamide, 4-chloro-1'-(4-hydroxy-8-methyl-6,7-dihydro-5H-pyrido[2,3-d]pyrimidin-2-yl)-1-methyl-7-(oxolan-3-yloxy)spiro[indole-3,4'-piperidin]-2-one, 6-(4-tert-butylpiperazin-1-yl)-4-fluoro-1'-(4-hydroxy-8-methyl-6,7-dihydro-5H-pyrido[2,3-d]pyrimidin-2-yl) spiro[2-benzofuran-3,4'-piperidin]-1-one, 2-{[4-fluoro-2-oxo-1'-(4-oxo-3,4,5,6,7,8-hexahydropyrido[2,3-d]pyrimidin-2-yl)-1-(2,2,2-trifluoroethyl)spiro[indoline-3, 4'-piperidin]-6-yl]oxy}acetonitrile, 7-[2-(tert-butylamino)ethoxy]-4-fluoro-1'-(4-hydroxy-8-methyl-6,7-dihydro-5H-pyrido [2,3-d]pyrimidin-2-yl)-1-methylspiro[indole-3,4'-piperidin]-2-one, 4-chloro-1'-(4-hydroxy-5,6,7,8-tetrahydropyrido[2,3-d]pyrimidin-2-yl)-1-methyl-7-(oxolan-3-yloxy)spiro[indole-3, 4'-piperidin]-2-one, 4-fluoro-1'-(4-hydroxy-8-methyl-6,7-dihydro-5H-pyrido[2,3-d]pyrimidin-2-yl)-6-[4-(2-hydroxy-2-methylpropyl)piperazin-1-yl]spiro[2-benzofuran-3,4'-piperidin]-1-one, 4-fluoro-6-[4-(2-hydroxyethyl)piperazin-1-yl]-1'-(4-hydroxy-8-methyl-6,7-dihydro-5H-pyrido[2,3-d]pyrimidin-2-yl) spiro[2-benzofuran-3,4'-piperidin]-1-one, 1-[2-(4-acetylpiperazin-1-yl)ethyl]-4-chloro-1'-(4-hydroxy-8-methyl-6,7-dihydro-5H-pyrido[2,3-d]pyrimidin-2-yl)-7-methoxyspiro[indole-3,4'-piperidin]-2-one, ({[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy}methyl) phosphonic acid, 4-chloro-1'-(4-hydroxy-5,6,7,8-tetrahydropyrido[2,3-d]pyrimidin-2-yl)-7-methoxy-1-(2,2,2-trifluoroethyl)spiro[indole-3,4'-piperidin]-2-one, 4-fluoro-1'-(4-hydroxy-8-methyl-6,7-dihydro-5H-pyrido[2,3-d]pyrimidin-2-yl)-6-[4-(4-methylpiperazin-1-yl)phenyl]spiro[2-benzofuran-3,4'-piperidin]-1-one, 4-chloro-1'-(4-hydroxy-8-methyl-6,7-dihydro-5H-pyrido[2,3-d]pyrimidin-2-yl)-7-methoxy-1-[3-oxo-3-[3-(trifluoromethyl)-6,8-dihydro-5H-imidazo[1,2-a]pyrazin-7-yl]propyl]spiro[indole-3,4'-piperidin]-2-one, 4-chloro-1'-(4-hydroxy-8-methyl-6,7-dihydro-5H-pyrido[2,3-d]pyrimidin-2-yl)-1-(2-hydroxy-2-methylpropyl)-7-methoxyspiro[indole-3,4'-piperidin]-2-one, 4-fluoro-1'-(4-hydroxy-8-methyl-6,7-dihydro-5H-pyrido[2,3-d]pyrimidin-2-yl)-1-(2-hydroxy-2-methylpropyl) spiro[indole-3,4'-piperidin]-2-one, 4-chloro-1-(2-hydroxy-2-methylpropyl)-1'-(4-hydroxy-5,6,7,8-tetrahydropyrido[2,3-d]pyrimidin-2-yl)-7-methoxyspiro[indole-3,4'-piperidin]-2-one, 6-[4-(dimethylamino)phenyl]-4-fluoro-1'-(4-hydroxy-8-methyl-6,7-dihydro-5H-pyrido[2,3-d]pyrimidin-2-yl) spiro[2-benzofuran-3,4'-piperidin]-1-one, 4-fluoro-1'-(4-hydroxy-8-methyl-6,7-dihydro-5H-pyrido[2,3-d]pyrimidin-2-yl)-6-(1-methylpyrazol-4-yl)spiro[2-benzofuran-3,4'-piperidin]-1-one, 4-fluoro-1'-(4-hydroxy-5,6,7,8-tetrahydropyrido[2,3-d]pyrimidin-2-yl)-1-(2,2,2-trifluoroethyl)spiro[indole-3,4'-piperidin]-2-one, 4-fluoro-1-(2-hydroxy-2-methylpropyl)-1'-(4-hydroxy-5,6,7,8-tetrahydropyrido[2,3-d]pyrimidin-2-yl)spiro[indole-3,4'-piperidin]-2-one, 1-{[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy}-N-methylmethanesulfonamide, 1-{[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy}methanesulfonamide, 6-(1,1-dioxothiomorpholino)-4-fluoro-1-methyl-1'-(8-methyl-4-oxo-3,4,5,6,7,8-hexahydropyrido[2,3-d]pyrimidin-2-yl)spiro[indoline-3,4'-piperidin]-2-one, N-({[4-fluoro-1-methyl-1'-(8-methyl-4-oxo-3,4,5,6,7, 8-hexahydropyrido[2,3-d]pyrimidin-2-yl)-2-oxospiro[indoline-3,4'-piperidin]-6-yl]oxy}methylsulfonyl)acetamide, 4-fluoro-1-methyl-1'-(8-methyl-4-oxo-3,4,5,6,7,8-hexahydropyrido[2,3-d]pyrimidin-2-yl)-6-(piperazin-1-yl)spiro[indoline-3,4'-piperidin]-2(1H)-one, 4-[4-fluoro-1-methyl-1'-(8-methyl-4-oxo-3,4,5,6,7,8-hexahydropyrido[2,3-d]pyrimidin-2-yl)-2-oxospiro[indoline-3, 4'-piperidin]-6-yl]-N,N-dimethylpiperazine-1-sulfonamide, 1-benzyl-4-[4-fluoro-1-methyl-1'-(8-methyl-4-oxo-3,4, 5,6,7,8-hexahydropyrido[2,3-d]pyrimidin-2-yl)-2-oxospiro[indoline-3,4'-piperidin]-6-yl]piperazine-2,6-dione, 4-fluoro-6-[4-(2-hydroxyacetyl)piperazin-1-yl]-1-methyl-1'-(8-methyl-4-oxo-3,4,5,6,7,8-hexahydropyrido[2,3-d]pyrimidin-2-yl)spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-(4-methylsulfonylpiperazin-1-yl)spiro[indoline-3,4'-piperidin]-2(1H)-one, methyl=4-[4-fluoro-1-methyl-1'-(8-methyl-4-oxo-3,4,5, 6,7,8-hexahydropyrido[2,3-d]pyrimidin-2-yl)-2-oxospiro[indo line-3,4'-piperidin]-6-yl]piperazine-1-carboxylate, 6-[cis-2,6-dimethylmorpholin-4-yl]-4-fluoro-1-methyl-1'-(8-methyl-4-oxo-3,4,5,6,7,8-hexahydropyrido[2,3-d]pyrimidin-2-yl) spiro[indoline-3,4'-piperidin]-2(1H)-one, 4-fluoro-1-methy-1'-(8-methyl-4-oxo-3,4,5,6,7,8-hexahydropyrido[2,3-d]pyrimidin-2-yl)1-6-(4-methylsulfonylpiperidin-1-yl)spiro[indoline-3,4'-piperidin]-2(1H)-one, 4-fluoro-6-(4-methoxypiperidin-1-yl)-1-methyl-1'-(8-methyl-4-oxo-3,4,5,6,7,8-hexahydropyrido[2,3-d]pyrimidin-2-yl)spiro[indoline-3,4'-piperidin]-2(1H)-one, 4-[4-fluoro-1-methyl-1'-(8-methyl-4-oxo-3,4,5,6,7,8-hexahydropyrido[2,3-d]pyrimidin-2-yl)-2-oxospiro[indoline-3, 4'-piperidin]-6-yl]piperazine-1-carboxamide, 1-[4-fluoro-1-methyl-1'-(8-methyl-4-oxo-3,4,5,6,7,8-hexahydropyrido[2,3-d]pyrimidin-2-yl)-2-oxospiro[indoline-3, 4'-piperidin]-6-yl]piperidine-4-carbonitrile, 4-fluoro-6-(4-hydroxycyclohexyl)-1-methyl-1'-(8-methyl-4-oxo-3,4,5,6,7,8-hexahydropyrido[2,3-d]pyrimidin-2-yl)spiro[indoline-3,4'-piperidin]-2(1H)-one, 4-fluoro-1'-(4-hydroxy-5,6,7,8-tetrahydropyrido[2,3-d]pyrimidin-2-yl)-1-(oxolan-2-ylmethyl)spiro[indole-3,4'-piperidin]-2-one, 4-fluoro-1'-(4-hydroxy-5,6,7,8-tetrahydropyrido[2,3-d]pyrimidin-2-yl)-1-(2-methoxyethyl)spiro[indole-3,4'-piperidin]-2-one, 4-fluoro-1'-(4-hydroxy-6,7-dihydro-5H-pyrido[2,3-d]pyrimidin-2-yl)-6-morpholine-4-ylspiro[2-benzofuran-3,4'-piperidin]-1-one, 6-(2,6-dimethylmorpholin-4-yl)-4-fluoro-1'-(4-hydroxy-5,6,7,8-tetrahydropyrido[2,3-d]pyrimidin-2-yl) spiro[2-benzofuran-3,4'-piperidin]-1-one, 2-(4-fluoro-1-(2-hydroxy-2-methylpropyl)-7-methoxyspiro[indoline-3,4'-piperidin]-1'-yl)-5,6,7,8-tetrahydropyrido[2,3-d]pyrimidin-4(3H)-one and 2-(4-fluoro-7-methoxyspiro[indoline-3,4'-piperidin]-1'-yl)-5,6,7,8-tetrahydropyrido[2,3-d]pyrimidin-4(3H)-one.

[8]
A tankyrase inhibitor comprising the compound or the pharmaceutically acceptable salt thereof according to any one of [1] to [7] as an active ingredient.

[9]
A pharmaceutical composition comprising the compound or the pharmaceutically acceptable salt thereof according to any one of [1] to [7] as an active ingredient

[10]
A tumor cell proliferation inhibitor comprising the compound or the pharmaceutically acceptable salt thereof according to any one of [1] to [7] as an active ingredient.

[11]
A prophylactic or therapeutic agent for a malignant tumor comprising the compound or the pharmaceutically acceptable salt thereof according to any one of [1] to [7] as an active ingredient.

[12]
The prophylactic or therapeutic agent for a malignant tumor according to [11], wherein
the malignant tumor is at least one selected from the group consisting of fibrosarcoma, ovarian cancer, glioblastoma, pancreatic adenoma, breast cancer, astrocytoma, lung cancer, gastric cancer, liver cancer, colorectal cancer, bladder transitional epithelium cancer, and leukemia.

[13]
The prophylactic or therapeutic agent for a malignant tumor according to [12], wherein
the malignant tumor is colorectal cancer.

[14]
A prophylactic or therapeutic agent for Herpes simplex virus infections or Epstein-Barr virus infections, comprising the compound or the pharmaceutically acceptable salt thereof according to any one of [1] to [7] as an active ingredient.

[15]
A prophylactic or therapeutic agent for pulmonary fibrosis, comprising the compound or the pharmaceutically acceptable salt thereof according to any one of [1] to [7] as an active ingredient.

[16]
A prophylactic or therapeutic agent for multiple sclerosis, comprising the compound or the pharmaceutically acceptable salt thereof according to any one of [1] to [7] as an active ingredient.

[17]
A prophylactic or therapeutic agent for amyotrophic lateral sclerosis, comprising the compound or the pharmaceutically acceptable salt thereof according to any one of [1] to [7] as an active ingredient.

[18]
A therapeutic agent for diseases caused by tankyrase, comprising the compound or the pharmaceutically acceptable salt thereof according to any one of [1] to [7] as an active ingredient.

[19]
A method for inhibiting tankyrase, comprising: administering the compound or the pharmaceutically acceptable salt thereof according to any one of [1] to [7], the tankyrase inhibitor according to [8], or the pharmaceutical composition according to [9] to a patient.

[20]
A method for treating diseases caused by tankyrase, comprising:
administering the compound or the pharmaceutically acceptable salt thereof according to any one of [1] to [7], the tankyrase inhibitor according to [8], or the pharmaceutical composition according to [9] to a patient.

[21]
The compound or the pharmaceutically acceptable salt thereof according to any one of [1] to [7], which is for use to inhibit tankyrase.

[22]
The compound or the pharmaceutically acceptable salt thereof according to any one of [1] to [7], which is for use to treat diseases caused by tankyrase.

[23]
Use of the compound or the pharmaceutically acceptable salt thereof according to any one of [1] to [7], for producing a tankyrase inhibitor.

[24]
Use of the compound or the pharmaceutically acceptable salt thereof according to any one of [1] to [7], for producing a therapeutic agent for diseases caused by tankyrase.

Advantageous Effects of Invention

The compound and the pharmaceutically acceptable salt thereof of the present invention represented by the general formula (1) have an excellent tankyrase inhibitory action and are particularly useful for treatment and/or prophylaxis of various types of diseases which are caused by and/or related to tankyrase and/or intracellular molecular reactions in which tankyrase is involved.

The diseases which are caused by and/or related to tankyrase and/or intracellular molecular reactions in which tankyrase is involved include, but are not limited to, various solid tumors and blood tumors, for example, fibrosarcoma, ovarian cancer, glioblastoma, pancreatic adenoma, breast cancer, astrocytoma, lung cancer, gastric cancer, liver cancer, colorectal cancer, bladder transitional epithelium cancer, leukemia, and the like, as well as infectious diseases such as infections by Herpes simplex virus and Epstein-Barr virus, fibrosis such as pulmonary fibrosis, neurodegenerative diseases such as multiple sclerosis and amyotrophic lateral sclerosis, inflammatory diseases of various forms such as skin and cartilage injuries, and the like.

DESCRIPTION OF EMBODIMENTS

The present invention provides a compound or a pharmaceutically acceptable salt thereof, the compound represented by the general formula (1):

[Chem. 3]

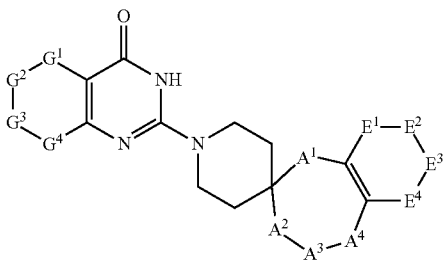

(1)

[in the formula (1), $A^1, A^2, A^3$, and $A^4$ are defined such that both of $A^1$ and $A^2$ represent a single bond, one of $A^1$ and $A^2$ represents a single bond and the other represents $CH_2$, or $A^1$ represents a single bond and $A^4$ represents $CH_2$, one of $A^3$ and $A^4$ is $CH_2$ or CO and the other is O or $NR^1$ when both of $A^1$ and $A^2$ represent a single bond or when $A^1$ represents $CH_2$ and $A^2$ represents a single bond, one of $A^3$ and $A^4$ is NR and the other is $CH_2$ or CO when $A^1$ represents a single bond and $A^2$ represents $CH_2$, or one of $A^2$ and $A^3$ is $NR^1$ and the other is $CH_2$ or CO when $A^1$ represents a single bond and $A^4$ is $CH_2$, where $R^1$ represents a hydrogen atom, an optionally substituted $C_{1-6}$ alkyl group, an optionally substituted heteroaryl group, an optionally substituted $C_{3-8}$ cycloalkyl $C_{1-3}$ alkyl group, an optionally substituted aryl $C_{1-3}$ alkyl group, an optionally substituted heteroaryl $C_{1-3}$ alkyl group, an optionally substituted 3- to 7-membered heterocycloalkyl $C_{1-3}$ alkyl group, a group represented by the following formula: —$(CH_2)_m$—C(=O)-L, or a group represented by the following formula: —$S(=O)_2$—$R^{13}$, m is 0, 1, 2, or 3, and L is $R^{11}$ when m is 0 or L is $R^{12}$ when m is 1, 2, or 3, $R^{11}$ is a hydrogen atom, an optionally substituted $C_{1-6}$ alkyl group, $OR^{51}$, a group represented by the following formula: —C(=O)—$OR^{52}$, or a group represented by the following formula: —N($R^{53a}$)—$R^{53b}$, $R^{51}$ is an optionally substituted aryl $C_{1-3}$ alkyl group, $R^{52}$ is a hydrogen atom or an optionally substituted $C_{1-6}$ alkyl group, $R^{53a}$ and $R^{53b}$ are each independently a hydrogen atom or an optionally substituted $C_{1-6}$ alkyl group, or $R^{53a}$ and $R^{53b}$ together form a 3- to 7-membered heterocycloalkyl group which may contain at least one atom or group selected from the group consisting of an oxygen atom, a sulfur atom, and $NR^{101}$, $R^{101}$ is a hydrogen atom or an optionally substituted $C_{1-6}$ alkyl group, and $R^{12}$ is an optionally substituted aryl group, $OR^{54}$, or a group represented by the following formula: —N($R^{55a}$)—$R^{55b}$, $R^{54}$ is a hydrogen atom, an optionally substituted $C_{1-6}$ alkyl group, an optionally substituted aryl $C_{1-3}$ alkyl group, or an optionally substituted heteroaryl $C_{1-3}$ alkyl group, and $R^{55a}$ and $R^{55b}$ are each independently a hydrogen atom, an optionally substituted $C_{1-6}$ alkyl group, an optionally substituted aryl $C_{1-3}$ alkyl group, an optionally substituted heteroaryl $C_{1-3}$ alkyl group, or a group represented by the following formula: —(C=O)—$R^{102}$, or $R^{55a}$ and $R^{55b}$ together form a 3- to 7-membered heterocycloalkyl group which may contain at least one atom or group selected from the group consisting of an oxygen atom, a sulfur atom, and $NR^{103}$, or together form an optionally substituted 6,8-dihydro-5H-imidazo[1,2-a]pyrazin-7-yl group, $R^{102}$ is a hydrogen atom, an optionally substituted $C_{1-6}$ alkyl group, or an optionally substituted aryl $C_{1-3}$ alkyl group, and $R^{103}$ is a hydrogen atom or an optionally substituted $C_{1-6}$ alkyl group, and $R^{13}$ is an optionally substituted $C_{1-6}$ alkyl group;

a structure composed of $E^1, E^2, E^3$, and $E^4$ is a group represented by the following formula: -$E^1$-$E^2$-$E^3$-$E^4$- (in this formula, bonds between $E^1, E^2, E^3$, and $E^4$ each represent a single bond or a double bond) where $E^1$ is N or $CR^2$, $E^2$ is N or $CR^3$, $E^3$ is N or $CR^4$, and $E^4$ is N or $CR^5$, is a group in which $E^1$ represents a single bond and which is represented by the following formula: -$E^2$-$E^3$=$E^4$- where $E^2$ is O or S and $E^3$ and $E^4$ are CH, or is a group in which $E^1$ represents a single bond and which is represented by the following formula: -$E^2$=$E^3$-$E^4$- where $E^2$ and $E^3$ are CH and $E^4$ is O or S, $R^2, R^3, R^4$, and $R^5$ are each independently a hydrogen atom, a fluorine atom, a chlorine atom, a bromine atom, an iodine atom, a cyano group, an optionally substituted $C_{1-6}$ alkyl group, an optionally substituted aryl group, an optionally substituted heteroaryl group, an optionally substituted 3- to 7-membered heterocycloalkyl group, or a group represented by the following formula: -Q-$(CH_2)_n$—$R^{14}$, n is 0, 1, 2, or 3, and Q is a group represented by the following formula: —CH=CH—, O, CO, a group represented by the following formula: —C(=O)—O—, a group represented by the following formula: —C(=O)—N($R^{56}$)—, $NR^{56}$, a group represented by the following formula: —N($R^{56}$)—C(=O)—, or a group represented by the following formula: —N($R^{56}$)—C(=O)—O—, $R^{56}$ is a hydrogen atom, an optionally substituted $C_{1-3}$ alkyl group or a group represented by the following formula: —C(=O)—$R^{104}$, $R^{104}$ is a hydrogen atom, an optionally substituted $C_{1-6}$ alkyl group, an optionally substituted aryl group, an optionally substituted $C_{1-6}$ alkyloxy group, or an optionally substituted aryloxy group, and $R^{14}$ is a hydrogen atom, an optionally substituted $C_{1-6}$ alkyl group, an optionally substituted aryl group, an optionally substituted heteroaryl group, an optionally substituted $C_{3-8}$ cycloalkyl group, or an optionally substituted 3- to 7-membered heterocycloalkyl group; and a structure composed of $G^1$, $G^2$, $G^3$, and $G^4$ is a group represented by the following formula: -$G^1$-$G^2$-$G^3$-$G^4$- (in this formula, bonds between $G^1$, $G^2$, $G^3$, and $G^4$ each represent a single bond or a double bond), and represented by the following formula: —CH=CH—CH=$CR^6$— (excluding a case where both of $A^1$ and $A^2$ represent a single bond, $A^3$ is O, and $A^4$ is CO), the following formula: —CH=CH—CH=N— (excluding a case where both of $A^1$ and $A^2$ represent a single bond, $A^3$ is O, and $A^4$ is CO), the following formula: —$CH_2$—$CH_2$—$CH_2$—$CH_2$—, the following formula: —CO—$CH_2$—$CH_2$—N($R^7$)—, the following formula: —$CH_2$—$CF_2$—$CH_2$—$CH_2$—, the following formula: —$CH_2$—O—$CH_2$—$CH_2$—, the following formula: —$CH_2$—S—$CH_2$—$CH_2$—, the following formula: —$CH_2$—$CH_2$—N($R^7$)—$CH_2$—, the following formula: —$CH_2$—$CH_2$—$CH_2$—O—, the following formula: —$CH_2$—$CH_2$—$CH_2$—N($R^7$)—, or the following formula: —O—$CH_2$—$CH_2$—N($R^7$)—, or is a group in which $G^1$ represents a single bond, which is represented by the following formula: -$G^2$-$G^3$-$G^4$- (where bonds between $G^2$, $G^3$, and $G^4$ each represent a single bond or a double bond), and which is represented by the following formula: —CH=CH—N($R^7$)—, the following formula: —$CH_2$—$CH_2$—N($R^7$)—, the following formula: —N=CH—N($R^7$)—, or the following formula: —N($R^7$)—CH=N—, $R^6$ is a hydrogen atom, a fluorine atom, a chlorine atom, a bromine atom, an iodine atom, an optionally substituted $C_{1-6}$ alkyl group, or an optionally substituted $C_{1-6}$ alkyloxy group, and $R^7$ is a hydrogen atom, an optionally substituted $C_{1-6}$ alkyl group, an optionally substituted $C_{3-8}$ cycloalkyl group, an optionally substituted $C_{3-8}$ cycloalkyl $C_{1-3}$ alkyl group, an optionally substituted 3- to 7-membered heterocycloalkyl group, an optionally substituted 3- to 7-membered heterocycloalkyl $C_{1-3}$ alkyl group, a group represented by the following formula: —C(=O)—$R^{15}$, or a group represented by the following formula: —$(CH_2)_p$—C(=O)—$OR^{16}$, p is 0, 1, 2, or 3, $R^{15}$ is a hydrogen atom, an optionally substituted $C_{1-6}$ alkyl group, or $OR^{57}$, $R^{57}$ is an optionally substituted $C_{1-6}$ alkyl group or an optionally substituted aryl $C_{1-3}$ alkyl group, and $R^{16}$ is a hydrogen atom or an optionally substituted $C_{1-6}$ alkyl group]. Specifically, the present invention provides a novel compound and a pharmaceutically acceptable salt thereof having a 1,8-diazaspiro[4.5] deca-3-ene, 1-oxa-8-azaspiro[4.5]deca-3-ene, 2,8-diazaspiro[4.5]deca-3-ene, 2-oxa-8-azaspiro[4.5] deca-3-ene, 2,9-diazaspiro[5.5]undeca-3-ene, 1-oxa-9-azaspiro[5.5]undeca-3-ene, 1,9-diazaspiro[5.5] undeca-4-ene, or 3,9-diazaspiro[5.5]undeca-1-ene structure (such compound or salt thereof is hereinafter referred to as a general term, "spiro compound" in some cases).

In the general formula (1), $A^1$, $A^2$, $A^3$, and $A^4$ are defined such that both of $A^1$ and $A^2$ represent a single bond, that one of $A^1$ and $A^2$ represents a single bond and the other represents $CH_2$, or that $A^1$ represents a single bond and $A^4$ represents $CH_2$. When both of $A^1$ and $A^2$ represent a single bond, $A^3$ is $CH_2$ or CO and $A^4$ is O or $NR^1$, or alternatively $A^3$ is O or $NR^1$ and $A^4$ is $CH_2$ or CO. When $A^1$ represents $CH_2$ and $A^2$ represents a single bond, $A^3$ is $CH_2$ or CO and $A^4$ is O or $NR^1$, or alternatively $A^3$ is O or $NR^1$ and $A^4$ is $CH_2$ or CO. When $A^1$ represents a single bond and $A^2$ represents $CH_2$, $A^3$ is $NR^1$ and $A^4$ is $CH_2$ or CO, or alternatively $A^3$ is $CH_2$ or CO and $A^4$ is $NR^1$. Further, when $A^1$ represents a single bond and $A^4$ represents $CH_2$, $A^2$ is $NR^1$ and $A^3$ is $CH_2$ or CO, or alternatively $A^2$ is $CH_2$ or CO and $A^3$ is $NR^1$.

In the general formula (1), as the structure composed of $A^1$, $A^2$, $A^3$ and $A^4$, a structure in which both of $A^1$ and $A^2$ represent a single bond is preferable, a structure in which one of $A^3$ and $A^4$ is $CH_2$ or CO and the other is O or $NR^1$ is more preferable, a structure in which $A^3$ is O, $CH_2$, or CO and $A^4$ is CO or $NR^1$ is further preferable (excluding a case where both of $A^3$ and $A^4$ are CO, a case where $A^3$ is $CH_2$ and $A^4$ is CO, and a case where $A^3$ is O and $A^4$ is $NR^1$), and a structure in which a combination of $A^3$ and $A^4$ is any one of combinations O and CO, $CH_2$ and $NR^1$, and CO and $NR^1$ is most preferable.

Moreover, in the general formula (1), the structure composed of $E^1$, $E^2$, $E^3$, and $E^4$ is a group represented by the following formula: -$E^1$-$E^2$-$E^3$-$E^4$- (in this formula, bonds between $E^1$, $E^2$, $E^3$, and $E^4$ each represent a single bond or a double bond), or a group in which $E^1$ represents a single bond and which is represented by the following formula: -$E^2$-$E^3$=$E^4$- or the following formula: -$E^2$=$E^3$-$E^4$-. In the present description, unless otherwise specified, symbols "-" and "=" each connecting atoms and/or groups in the structural formulas represent a single bond and a double bond, respectively. However, in the above group represented by the formula: -$E^1$-$E^2$-$E^3$-$E^4$-, bonds between $E^1$, $E^2$, $E^3$, and $E^4$ each represent a single bond or a double bond depending on a combination of atoms or groups represented by $E^1$, $E^2$, $E^3$, and $E^4$.

In the general formula (1), the structure composed of $E^1$, $E^2$, $E^3$, and $E^4$ is preferably a group represented by the formula: -$E^1$-$E^2$-$E^3$-$E^4$- (in this formula, bonds between $E^1$, $E^2$, $E^3$, and $E^4$ each represent a single bond or a double bond); where more preferably $E^1$ is N or $CR^2$, $E^2$ is N or $CR^3$, $E^3$ is N or $CR^4$, and $E^4$ is N or $CR^5$; where further preferably $E^1$ is $CR^2$, $E^2$ is $CR^3$, $E^3$ is $CR^4$, and $E^4$ is $CR^5$; and where particularly preferably $E^1$, $E^2$, $E^3$, and $E^4$ (Cs of $CR^2$, $CR^3$, $CR^4$, and $CR^5$) form a 6-membered aromatic hydrocarbon group together with two neighboring carbon atoms.

Further, in the general formula (1), the structure composed of $G^1$, $G^2$, $G^3$, and $G^4$ is a group represented by the following formula: -$G^1$-$G^2$-$G^3$-$G^4$- (in this formula, bonds between $G^1$, $G^2$, $G^3$, and $G^4$ each represent a single bond or a double bond) or a group in which $G^1$ represents a single bond, and which is represented by the following formula: -$G^2$-$G^3$-$G^4$- (where bonds between $G^2$, $G^3$, and $G^4$ each represent a single bond or a double bond). Also in a group represented by the formula: -$G^1$-$G^2$-$G^3$-$G^4$- and in the formula: -$G^2$-$G^3$-$G^4$-, bonds between $G^1$, $G^2$, $G^3$, and $G^4$ each represent a single bond or a double bond depending on a combination of atoms or groups represented by $G^1$, $G^2$, $G^3$, and $G^4$.

In the general formula (1), the structure composed of $G^1$, $G^2$, $G^3$, and $G^4$ is preferably a group represented by the formula: -$G^1$-$G^2$-$G^3$-$G^4$-, and represented by the formula: —$CH_2$—$CH_2$—$CH_2$—$CH_2$—, the formula: —$CH_2$—$CF_2$—$CH_2$—$CH_2$—, the formula: —$CH_2$—O—$CH_2$—$CH_2$—, the formula: —$CH_2$—S—$CH_2$—$CH_2$—, the formula: —$CH_2$—$CH_2$—$CH_2$—O—, the formula: —$CH_2$—$CH_2$—N($R^7$)—, or the formula: —O—$CH_2$—$CH_2$—N($R^7$)—, or a group in which $G^1$ represents a single bond, which is represented by the formula: -$G^2$-$G^3$-$G^4$- (in this formula, bonds between $G^2$, $G^3$, and $G^4$ each represent a single bond or a double bond), and which is represented by the formula: —CH=CH—N(R$^7$)— or the formula: —CH$_2$—CH$_2$—N(R$^7$)—. The structure composed of G$^1$, G$^2$, G$^3$, and G$^4$ is more preferably a group represented by the formula: -G$^1$-G$^2$-G$^3$-G$^4$-, and represented by the formula: —CH$_2$—CH$_2$—CH$_2$—CH$_2$— or the formula: —CH$_2$—CH$_2$—CH$_2$—N(R$^7$)—.

In the general formula (1), the "hydrogen atom" also includes a deuterium atom.

In the general formula (1), the "C$_{1-3}$ alkyl group" and the "C$_{1-6}$ alkyl group" represent linear or branched saturated hydrocarbon groups having 1 to 3 carbon atoms and 1 to 6 carbon atoms, respectively, in each of which any position(s) may be replaced with one or more optional substituents defined in the present description. The linear or branched saturated hydrocarbon groups generally include, but are not particularly limited to, groups such as methyl, ethyl, n-propyl, isopropyl, n-butyl, sec-butyl, isobutyl, tert-butyl, n-pentyl, isopentyl, neopentyl, and n-hexyl.

In the general formula (1), the "aryl group" refers to a 6-membered monocyclic aromatic hydrocarbon group composed only of carbon atoms, or a fused cyclic aromatic hydrocarbon group in which two or more of the aromatic hydrocarbon groups are condensed, and any position(s) thereof may be optionally replaced with one or more of optional substituents defined in the present description. The aryl groups generally include, but are not limited to, groups such as phenyl and naphthyl.

In the general formula (1), the "heteroaryl group" refers to a group derived from a 5- or 6-membered monocyclic aromatic heterocyclic ring having 1 to 4 hetero atoms selected from a nitrogen atom, an oxygen atom, and a sulfur atom; a group derived from a fused cyclic aromatic heterocyclic ring in which a 5- or 6-membered monocyclic aromatic heterocyclic ring having 1 to 4 hetero atoms and a 6-membered monocyclic aromatic ring only composed of carbon atoms are condensed; or a group derived from a fused cyclic aromatic heterocyclic ring in which a 5- or 6-membered monocyclic aromatic heterocyclic ring having 1 to 4 hetero atoms and a 5- or 6-membered monocyclic aromatic heterocyclic ring having 1 to 4 hetero atoms are condensed, in which any position (s) may be replaced with one or more optional substituents defined in the present description. The heteroaryl groups generally include, but are not limited to, groups, each having a bonding moiety at any possible position, such as pyrrolyl, pyrazolyl, furyl, thienyl, oxazolyl, imidazolyl, isoxazolyl, thiazolyl, isothiazolyl, 1,2,3-oxadiazolyl, 1,2,4-oxadiazolyl, 1,2,3-thiadiazolyl, 1,2,4-thiadiazolyl, tetrazolyl, 1,2,4-triazolyl, 1,2,3-triazolyl, pyridyl, pyridazinyl, pyrazyl, pyrimidyl, benzothienyl, benzofuryl, indolyl, isoindolyl, benzimidazolyl, benzopyrazolyl, benzothiazolyl, benzoxazo, benzotriazolyl, quinolyl, isoquinolyl, quinoxalinyl, quinazolinyl, phthalazinyl, and imidazo[5,1-b]thiazolyl.

In the general formula (1), the "C$_{3-8}$ cycloalkyl group" refers to a cyclic saturated hydrocarbon group (cyclic hydrocarbon group) having 3 to 8 carbon atoms. This cyclic hydrocarbon group may form a fused ring, a crosslinking ring, or a spiro ring and any position(s) thereof may be optionally replaced with one or more of the optional substituents defined in the present description. The cyclic saturated hydrocarbon groups generally include, but are not limited to, groups, each having a bonding moiety at any possible position, such as cyclopropyl, cyclobutyl, cyclopentyl, cyclohexyl, cycloheptyl, cyclooctyl, bicyclo[3.1.0]hexyl, bicyclo[3.2.0]heptyl, bicyclo[4.1.0]heptyl, bicyclo[4.2.0]octyl, bicyclo[3.3.0]octyl, bicyclo[1.1.1]pentyl, bicyclo[2.1.1]hexyl, bicyclo[3.1.1]heptyl, bicyclo[2.2.1]heptyl, bicyclo[3.2.1]octyl, bicyclo[2.2.2]octyl, spiro[2.3]hexyl, spiro[2.4]heptyl, spiro[2.5]octyl, spiro[3.3]heptyl, and spiro[3.4]octyl.

In the general formula (1), the "heterocycloalkyl group" refers to any of a 3- to 7-membered saturated heterocyclic ring and a 3- to 7-membered unsaturated heterocyclic ring other than an aromatic ring, the heterocyclic rings each having 1 to 4 hetero atoms selected from a nitrogen atom, an oxygen atom, and a sulfur atom. This heterocyclic ring may form a crosslinking ring or a spiro ring and any position(s) thereof may be optionally replaced with one or more of the optional substituents defined in the present description. The heterocycloalkyl groups include, but are not limited to, groups, each having a bonding moiety at any possible position, such as oxetanyl, tetrahydrofuryl, dihydrofuryl, dihydropyranyl, tetrahydropyranyl, 1,3-dioxanyl, 1,4-dioxanyl, aziridinyl, azetidinyl, pyrrolidinyl, piperidinyl, piperadinyl, 1,1-dioxidothiomorpholinyl (such as Examples 361, 378, and 455), dioxopiperadinyl (such as Example 459), diazepanyl, morpholinyl, 1,3-dioxolanyl, imidazolidinyl, imidazolinyl, pyrrolinyl, oxathiolanyl, dithiolanyl, 1,3-dithianyl, 1,4-dithianyl, oxathianyl, thiomorpholinyl, 3,6-diazabicyclo[3.1.1]heptyl, 8-oxa-3-azabicyclo[3.2.1]octyl, 3,8-diazabicyclo[3.2.1]octyl, 3,9-diazabicyclo[3.3.1]nonyl, and 2-oxa-7-azaspiro[3.5]nonyl.

In the general formula (1), the "aryl C$_{1-3}$ alkyl group", the "heteroaryl C$_{1-3}$ alkyl group", the "C$_{3-8}$ cycloalkyl C$_{1-3}$ alkyl group", and the "heterocycloalkyl C$_{1-3}$ alkyl group" each refer to a group in which a bonding moiety at any possible position in a corresponding one of an aryl group, a heteroaryl group, a C$_{3-8}$ cycloalkyl group and a heterocycloalkyl group (these are represented by the following formula: —Ar$^1$), which are defined in the present description, is bonded to any possible position in the C$_{1-3}$ alkyl group (this is represented by the following formula: -Ak$^1$) defined in the present description (the group is represented by the following formula: -Ak$^1$-Ar$^1$).

In the general formula (1), a "C$_{1-3}$ alkyloxy group" and the "aryloxy group" each refer to a group in which a corresponding one of an C$_{1-3}$ alkyl group (this is represented by the following formula: -Ak$^2$) and an aryl group (this is represented by the following formula: —Ar$^2$), which are defined in the present description, is bonded to an oxygen atom (the group is represented by the following formula: —O-Ak$^2$ or represented by —O—Ar$^2$).

In the general formula (1), a "di C$_{1-3}$ alkylamino group" refers to a group in which two C$_{1-3}$ alkyl groups (these are represented by the following formulas: -Ak$^3$ and -Ak$^4$), which are defined in the present description and may be of the same type or different types, are bonded to a nitrogen atom (the group is represented by the following formula: —N(-Ak$^3$)-Ak$^4$). An "arylamino group" refers to a group in which the aryl group (this is represented by the following formula: —Ar$^3$) defined in the present description is bonded to an amino group (the group is represented by the following formula: —N—Ar$^3$).

In the present description, "broadly-defined acyl groups" include a group in which, in the general formula (1), the hydrogen atom, the amino group, or any of a C$_{1-6}$ alkyl group, an aryl group, a heteroaryl group, a C$_{3-8}$ cycloalkyl group, and a heterocycloalkyl group, which are defined in the present description, (these are represented by the following formula: —Ar$^4$) is bonded to a carbonyl group (the group is represented by the following formula: —C(=O)—Ar$^4$); and a group in which the hydrogen atom, or any of a C$_{1-6}$ alkyl group, an aryl group, a heteroaryl group, a C$_{3-8}$ cycloalkyl group, and a heterocycloalkyl group, which are defined in the present description, (these are represented the following formula: —Ar⁵) is bonded to a carbonyl group via an oxygen atom (a group represented by the following formula: —C(=O)—O—Ar), and any position(s) thereof may be optionally replaced with one or more of the optional substituents defined in the present description. These broadly-defined acyl groups generally include, but are not limited to, groups such as formyl, acetyl, propionyl, butyroyl, valeroyl, pivaloyl, trifluoroacetyl, chloroacetyl, dichloroacetyl, trichloroacetyl, hydroxyacetyl, phenylacetyl, benzoyl, naphthoyl, furoyl, thenoyl, nicotinoyl, isonicotinoyl, methoxycarbonyl, trichloromethoxycarbonyl, ethoxycarbonyl, tert-butyloxycarbonyl, phenyloxycarbonyl, benzyloxycarbonyl, 4-methoxybenzyloxycarbonyl, 2,4-dimethoxybenzyloxycarbonyl, and 4-nitrobenzyloxycarbonyl. For example, the broadly-defined acyl groups include a carboxy group (—COOH) and a group represented by the following formula: —C(=O)—N(R⁵⁸ᵃ)—R⁵⁸ᵇ [in the formula, R⁵⁸ᵃ and R⁵⁸ᵇ each are independently a hydrogen atom, a $C_{1-6}$ alkyl group (such as Example 55), or a group represented by the following formula: —S(=O)₂—CH₃ (such as Example 427)].

In the general formula (1), "optionally substituted" means, unless otherwise specified, that any one hydrogen atom or any two or more hydrogen atoms among hydrogen atoms bonded to a group described as "optionally substituted" are replaced with a substituent(s) (atoms or groups) which are selected from the group consisting of other atoms and groups and which may be of a same type or different types. Examples of such substituents according to the invention of the present application include: substituents such as halogen atoms (a fluorine atom, a chlorine atom, a bromine atom, and an iodine atom), a cyano group, a hydroxy group, a thiol group, a nitro group, the above-described broadly-defined acyl groups, $C_{1-6}$ alkyl groups, aryl groups, heteroaryl groups, $C_{3-8}$ cycloalkyl groups, heterocycloalkyl groups, aryl $C_{1-3}$ alkyl groups, heteroaryl $C_{1-3}$ alkyl groups, $C_{3-8}$ cycloalkyl $C_{1-3}$ alkyl groups, and heterocycloalkyl $C_{1-3}$ alkyl groups; a substituent to which any of the above-described broadly-defined acyl groups, a $C_{1-6}$ alkyl group (alkoxy group or alkylthio group), an aryl group, an aryl $C_{1-3}$ alkyl group, a heteroaryl group, a $C_{3-8}$ cycloalkyl group, a heterocycloalkyl group, and a heterocycloalkyl $C_{1-3}$ alkyl group, or a group represented by the following formula: —SiR³¹ᵃR³¹ᵇR³¹ᶜ [in the formula, R³¹ᵃ, R³¹ᵇ and R³¹ᶜ each independently represent a $C_{1-6}$ alkyl group or an aryl group] is bonded via an oxygen atom or a sulfur atom; a substituent represented by the following formula: —N(R³²ᵃ)—R³²ᵇ [in the formula, R³²ᵃ and R³²ᵇ each independently are a hydrogen atom, any of the above-described broadly-defined acyl groups, a $C_{1-6}$ alkyl group, a group represented by the following formula: —S(=O)₂—N(CH₃)₂ (such as Example 428), or a group represented by the following formula: —S(=O)₂—CH₃ (such as Example 432), or R³²ᵃ and R³²ᵇ together form a 3- to 7-membered heterocycloalkyl group which may contain at least one atom or group selected from the group consisting of an oxygen atom, a sulfur atom, SO, S(=O)₂, and NR³³ [R³³ represents a hydrogen atom or a $C_{1-6}$ alkyl group]]; a substituent represented by the following formula: —C(NH₂)=NH (such as Example 430); a substituent represented by the following formula: —S(=O)₂—N(R⁵⁹ᵃ)—R⁵⁹ᵇ [in the formula, R⁵⁹ᵃ and R⁵⁹ᵇ each independently represent a hydrogen atom (such as Example 454), the above-described broadly-defined acyl group (such as Example 456), or a $C_{1-6}$ alkyl group (such as Examples 453 and 458)]; a substituent represented by the following formula: —S(=O)₂—CH₃ (such as Examples 461 and 464); and a substituent represented by the following formula: —P(=O)—OH (such as Example 442). In addition, among these substituents and the groups involved in the formation of the substituents, the above-described broadly-defined acyl groups, the $C_{1-6}$ alkyl group, the aryl group, the heteroaryl group, the $C_{3-8}$ cycloalkyl group, and the heterocycloalkyl group, and so on may cover an open-end concept that the group may repeat a replacement with any of the optional substituents as defined above.

Among these, the substituent is particularly preferably any of: a methoxy group (—OCH₃), a cyano group, halogen atoms, and a hydroxy group when a substituted group is a $C_{1-6}$ alkyl group, a heteroaryl group, a $C_{3-8}$ cycloalkyl $C_{1-3}$ alkyl group, an aryl $C_{1-3}$ alkyl group, a heteroaryl $C_{1-3}$ alkyl group, or a 3 to 7-membered heterocycloalkyl $C_{1-3}$ alkyl group represented by R¹.

In addition, when a substituted group is a $C_{1-6}$ alkyl group, an aryl group, a heteroaryl group, or a 3- to 7-membered heterocycloalkyl group represented by R², R³, R⁴ or R⁵, the substituent is particularly preferably any of: a cyano group; a hydroxy group; a heterocycloalkyl group; a heterocycloalkyl $C_{1-3}$ alkyl group; an aryl $C_{1-3}$ alkyl group; a carboxy group; a $C_{1-3}$ alkoxy group; a primary amide group; a methoxycarbonyl group; an acetyl group optionally substituted with a hydroxy group; a $C_{1-6}$ alkyl group optionally substituted with a halogen atom, a hydroxy group, or a $C_{1-3}$ alkoxy group; a substituent represented by the following formula: —C(=O)—R⁶⁰ [in the formula, R⁶⁰ is a $C_{1-3}$ alkyl group or a heterocycloalkyl group]; and a substituent represented by the formula: —N(R³²ᵃ)—R³²ᵇ [in the formula, R³²ᵃ and R³²ᵇ each independently and more preferably are a hydrogen atom or a $C_{1-3}$ alkyl group].

In the general formula (1), R¹ is preferably a hydrogen atom, an optionally substituted $C_{1-6}$ alkyl group, an optionally substituted aryl $C_{1-3}$ alkyl group, an optionally substituted heteroaryl $C_{1-3}$ alkyl group, or an optionally substituted 3- to 7-membered heterocycloalkyl $C_{1-3}$ alkyl group; and is preferably a hydrogen atom or a $C_{1-6}$ alkyl group which may be substituted with 1 to 3 substituents selected from the group consisting of a hydroxy group, a $C_{1-6}$ alkoxy group, a fluorine atom, a chlorine atom, a bromine atom, an iodine atom, a cyano group, a nitro group, aryl groups, heteroaryl groups, $C_{3-8}$ cycloalkyl groups, heterocycloalkyl groups, and the above-described broadly-defined acyl groups (when the group contains two or more substituents, the substituents may be of the same type or different types, and the aryl group, the heteroaryl group, the $C_{3-8}$ cycloalkyl group, or the heterocycloalkyl group may be further substituted).

More specific substances as R¹ include a methyl group, an ethyl group, a propyl group, an isopropyl group, a butyl group, an isobutyl group, a sec-butyl group, a tert-butyl group, a pentyl group, an isopentyl group, a hexyl group, an isohexyl group, a 2-hydroxyethyl group, a 2-hydroxypropyl group, a 3-hydroxypropyl group, a 2,3-dihydroxypropyl group, a 2-hydroxy-2-methylpropyl group, a 2-methoxyethyl group, a 3-methoxypropyl group, 2,2,2-trifluoroethyl group, a 2-fluoroethyl group, 2,3-difluoroethyl group, a 2-chloroethyl group, 3-chloropropyl group, 2-bromoethyl group, a 2-iodoethyl group, a cyanomethyl group, a 2-cyanoethyl group, a benzyl group, a 2-fluorophenylmethyl group, a 2-pyridylmethyl group, a 3-pyridylmethyl group, a 4-pyridylmethyl group, a 6-chloro-3-pyridyl group, a 2-pyrimidylmethyl group, a 5-pyrimidylmethyl group, a cyclopropylmethyl group, a 2-tetrahydro furylmethyl group, an amidinomethyl group, and a carbamoylmethyl group.

In the general formula (1), $R^2$, $R^3$, $R^4$, and $R^5$ are preferable such that: all of them are hydrogen atoms; one or two of them are of at least one type selected from the group consisting of halogen atoms (a fluorine atom, a chlorine atom, a bromine atom, and an iodine atom) and a cyano group; or any one of them is an optionally substituted aryl group, an optionally substituted heteroaryl group, an optionally substituted 3- to 7-membered heterocycloalkyl group, or a group represented by the formula: -Q-$(CH_2)_n$—$R^{14}$.

Further, the group represented by the formula: -Q-$(CH_2)_n$—$R^{14}$ is preferably a group represented by the following formula: —O—$R^{14}$ or a group represented by the following formula: —C(=O)—O—$R^{14}$, and is more preferably a group represented by the formula: —O—$R^{14}$. Moreover, when any one of $R^2$, $R^3$, $R^4$, and $R^5$ is a group represented by the formula: -Q-$(CH_2)_n$—$R^{14}$, $R^{14}$ is preferably a hydrogen atom (this means that, any one of $R^2$, $R^3$, $R^4$, and $R^5$, when represented by, for example, the formula: —O—$R^{14}$, represents a hydroxy group), a $C_{1-2}$ alkyl group optionally substituted with one substituent, or an optionally substituted 3- to 7-membered heterocycloalkyl group. The substituent of the optionally substituted $C_{1-2}$ alkyl group is preferably a substituent represented by the following formula: —C(=O)—$R^{61}$, a substituent represented by the formula: —S(=O)$_2$—N($R^{59a}$) $R^{59b}$, a substituent represented by the formula: —S(=O)$_2$—$CH_3$, or a substituent represented by the formula: —P(=O)—OH.

More specifically, $R^2$, $R^3$, $R^4$, and $R^5$ each independently are a hydrogen atom, a fluorine atom, a chlorine atom, a bromine atom, an iodine atom, a cyano group, a hydroxy group, a methoxy group, an ethoxy group, a 2-hydroxyethoxy group, a 2-methoxyethoxy group, a carboxymethoxy group, a 5-tetrazolylmethoxy group, a cyanomethoxy group, a 4-piperidylmethoxy group, a 2-(N,N-dimethylamino) ethoxy group, a 3-oxetanylmethoxy group, a 2-morpholinoethoxy group, a 2-(N-methylpiperazino)ethoxy group, a 2-pyrrolidinoethoxy group, a 2-piperidinoethoxy group, 3-pyrrolidinopropoxy group, a 3-tetrahydro furyloxy group, a 4-tetrahydro pyranyloxy group, a 4-(N-methylpiperidyl) methoxy group, a 2-hydroxy-2-methylpropoxy group, a carbamoylmethoxy group, a piperidino group, a morpholino group, a piperazino group, a 4-cyanopiperidino group, a 4-methoxycarbonylpiperazino group, a 3,5-dimethylmorpholino group, a 3,5-dimethylpiperazino group, a 4-methoxypiperidino group, a 4-carboxypiperidino group, an N-methylsulfonylpiperazino group, a 4-methylsulfonylpiperidino group, an N-2-hydroxy-2-methylpropylpiperazino group, an N-hydroxyacetylpiperazino group, an N-acetylpiperazino group, an N-methylpiperazino group, an N-(3-oxetanyl)piperazino group, a 4-hydroxycyclohexyl group, a 1-methylpyrazole-4-yl group, a 4-(N,N-dimethylamino)phenyl group, a 4-ethoxycarbonyl oxazol-2-yl group, a 4-(N-methylpiperazino)phenyl group, an ethoxycarbonyl group, an N-(2-morpholinoethyl) carbamoyl group, a 2-oxazolyl group, a 4-morpholinocarbonyl oxazol-2-yl group, a 4-pyrrolidinomethyl oxazol-2-yl group, and a 4-carboxy oxazol-2-yl group.

In the general formula (1), $R^7$ is preferably a hydrogen atom or a $C_{1-6}$ alkyl group optionally substituted with 1 to 3 substituents selected from the group consisting of a hydroxy group, a $C_{1-6}$ alkoxy group, a fluorine atom, a chlorine atom, a bromine atom, an iodine atom, and a cyano group (when the group contains two or more substituents, the substituents may be of the same type or different types). More specifically, $R^7$ is a hydrogen atom, a methyl group, an ethyl group, a propyl group, an isopropyl group, a 2-hydroxyethyl group, a 3-hydroxypropyl group, a 2,2,2-trifluoroethyl group, a 2-cyanoethyl group, or a 2-methoxyethyl group.

A preferable mode of the compound represented by the general formula (1) of the present invention is a mode in which a structure represented by the following formula (100):

[Chem. 4]

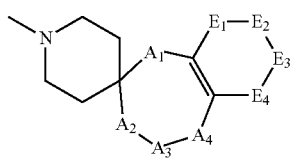
(100)

is represented by any one of the following formulas (101) to (112):

[Chem. 5]

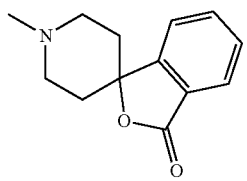
(101)

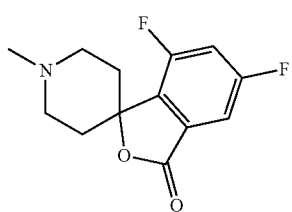
(102)

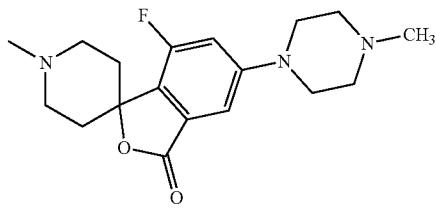
(103)

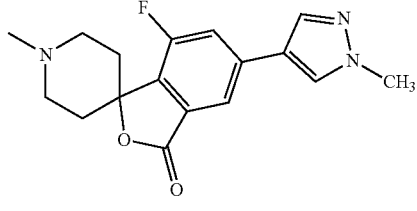
(104)

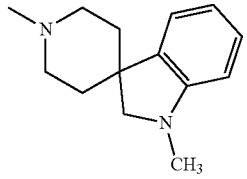
(105)

-continued

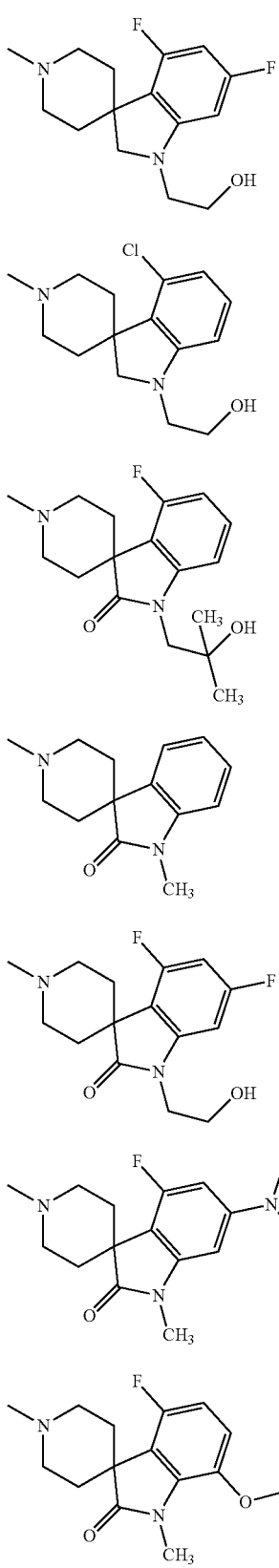

(106)
(107)
(108)
(109)
(110)
(111)
(112)

Moreover, a further preferable mode of the compound represented by the general formula (1) of the present invention is a mode in which the compound represented by the general formula (1) is represented by the following general formula (1-1):

[Chem. 6]

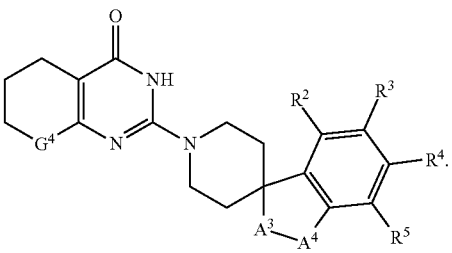

(1-1)

In the general formula (1-1), $A^3$ is O, $CH_2$, or CO, and $A^4$ is CO or $NR^1$, excluding a case where both of $A^3$ and $A^4$ are CO, a case where $A^3$ is $CH_2$ and $A^4$ is CO, and a case where $A^3$ is O and $A^4$ is $NR^1$. $R^1$ represents the same as described for the formula (1).

In addition, in the general formula (1-1), $G^4$ is $CH_2$ or $NR^7$, and $R^7$ is a hydrogen atom or an optionally substituted $C_{1-6}$ alkyl group.

A "protective group" in the present description includes protective groups such as those described in Greene Wuts Protective Groups in Organic Synthesis, Third Edition; John Wiley & Sons, Inc.

A "leaving group" in the present description refers to a functional group known as having a leaving ability to those skilled in the art. Examples of the leaving group include, but are not particularly limited to: halogen atoms such as fluorine, chlorine, bromine, and iodine; alkoxy groups such as a methoxy group, an ethoxy group, an n-propyloxy group, an isopropyloxy group, a tert-butyloxy group, a phenoxy group, a benzyloxy group, a 4-methoxybenzyloxy group, a 2,4-dimethoxybenzyloxy group, a 4-nitrobenzyloxy group, and a 2,4-dinitrobenzyloxy group; alkylthio groups such as a methylthio group, an ethylthio group, an n-propylthio group, an isopropylthio group, a tert-butylthio group, a phenylthio group, a benzylthio group, a 4-methoxybenzylthio group, a 2,4-dimethoxybenzylthio group, a 4-nitrobenzylthio group, and a 2,4-dinitrobenzylthio group; esters such as an acetoxy group, a propionyloxy group, and a benzoyloxy group; sulfonic esters such as a methanesulfonyloxy group, a trifluoromethanesulfonyl group, an ethanesulfonyloxy group, a benzenesulfonyloxy group, a p-toluenesulfonyloxy group, a 2-nitrobenzenesulfonyloxy group, a 4-nitrobenzenesulfonyloxy group, and a 2,4-benzenesulfonyloxy group; sulfinyl groups such as a methanesulfinyl group, an ethanesulfinyl group, an n-propylsulfinyl group, an isopropylsulfinyl group, a tert-butylsulfinyl group, a benzenesulfinyl group, a p-toluenesulfinyl group, a 4-methoxyphenylsulfinyl group, a 4-nitrophenylsulfinyl group, a benzylsulfinyl group, 4-methoxybenzylsulfinyl group, and a 4-nitrobenzylsulfinyl group; sulfonyl groups such as a methanesulfonyl group, an ethanesulfonyl group, an n-propylsulfonyl group, an isopropylsulfonyl group, a tert-butylsulfonyl group, a benzenesulfonyl group, a p-toluenesulfonyl group, a 4-methoxyphenylsulfonyl group, a 4-nitrophenylsulfonyl group, a benzylsulfonyl group, a 4-methoxybenzylsulfonyl group, and a 4-nitrobenzylsulfonyl group; and heterocycles such as a 1-pyrazolyl group, a 1-imidazolyl group, a 1,2,3-triazol-1-yl group, a 1,2,4-triazol-1-yl group, a 1,2,4-triazol-4-yl group, and a 1-tetrazolyl group.

In the present description, "pharmaceutically acceptable" means "adequate to pharmacological use". The pharmaceutically acceptable salts according to the present invention include, but are not limited to, salts of alkali metals or alkaline earth metals such as sodium, potassium, and calcium; hydrohalides such as hydrofluoric acid, hydrochloric acid, hydrobromic acid, and hydroiodic acid; inorganic acid salts such as sulfuric acid, nitric acid, phosphoric acid, perchloric acid, and carbonic acid; organic carboxylic acids such as formic acid, acetic acid, trifluoroacetic acid, trichloroacetic acid, hydroxyacetic acid, propionic acid, lactic acid, citric acid, tartaric acid, oxalic acid, benzoic acid, mandelic acid, butyric acid, fumaric acid, succinic acid, maleic acid, and malic acid; acidic amino acid salts such as aspartic acid and glutamic acid; sulfonic acid salts such as methanesulfonic acid, ethanesulfonic acid, benzenesulfonic acid, and toluenesulfonic acid; and solvates such as hydrates and alcoholates.

In the general formula (1), any of asymmetric atoms, for example, a carbon atom or the like also means its racemic or enantiomeric form. Further, an unsaturated double bond-containing group may exist as a cis-isomer or trans-isomer. Furthermore, the compound represented by the general formula (1) represents one form of possible isomers (rotamers, atropisomers, tautomers, and so on) in addition to the above-mentioned isomers, and these isomers may exist as a single type of isomer or as a mixture of them.

The compound or the pharmaceutically acceptable salt thereof (spiro compound) represented by the general formula (1) of the present invention may be produced by using methods described below as examples. However, the method for producing a spiro compound of the present invention is not limited to these following methods. Then, the scope of the compounds of the present invention is not limited to the compounds produced by the following production methods.

A method for producing a spiro compound of the present invention may use a starting material, a precursor, reagents, and solvents which are commercially available or are synthesizable by methods known to those skilled in the art, and can produce the compound in accordance with a combination of synthesis methods from among various synthesis methods in a wide variety known to those skilled in the art, and methods devised as needed from these synthesis methods by modification such as improvement.

In a method for introduction of, modification with, or conversion to a certain substituent or the like, the introduction of, modification with, or conversion to a target optional substituent itself or a group convertible to the substituent may be performed at the stage of the raw material, the stage of the intermediate substance, or the stage of the final substance, in accordance with a combination of synthesis methods from among the various synthesis methods in the wide variety known to those skilled in the art, and the methods devised as needed from these synthesis methods by modification such as improvement, or may be also achieved with the order of reaction steps and the like changed as appropriate. Further, from among general techniques such as protection and deprotection of a functional group, which are usually used in organic synthetic chemistry (for example, the methods described in, for example, Greene Wuts Protective Groups in Organic Synthesis, Third Edition; John Wiley & Sons, Inc. and the like) and others, any one(s) may be employed and carried out as needed for the convenience of reaction.

As a reaction apparatus for used in production, it is possible to use not only usual reaction vessels made of glass or metallic reaction baths including those provided with glass-lining, but also flow reactors and the like.

For cooling or heating in the process of carrying out a reaction, it is possible to perform cooling of a reaction vessel or a reaction solution not only by air-cooling, water-cooling, ice-cooling, a combination of a cryogen and a refrigerant, and so on, but also by means of a refrigerant cooled by a refrigerator, and perform heating by warm water or steam, heating of a reaction vessel directly with an electric heater or via a heating medium, heating by irradiation of an electromagnetic microwave (what is termed microwave heating). In addition, cooling or heating with a Peltier element applied and the like may also be used.

The spiro compound of the present invention may be obtained, for example, in accordance with a production method 1 or a production method 2 described below.

[Chem. 7]

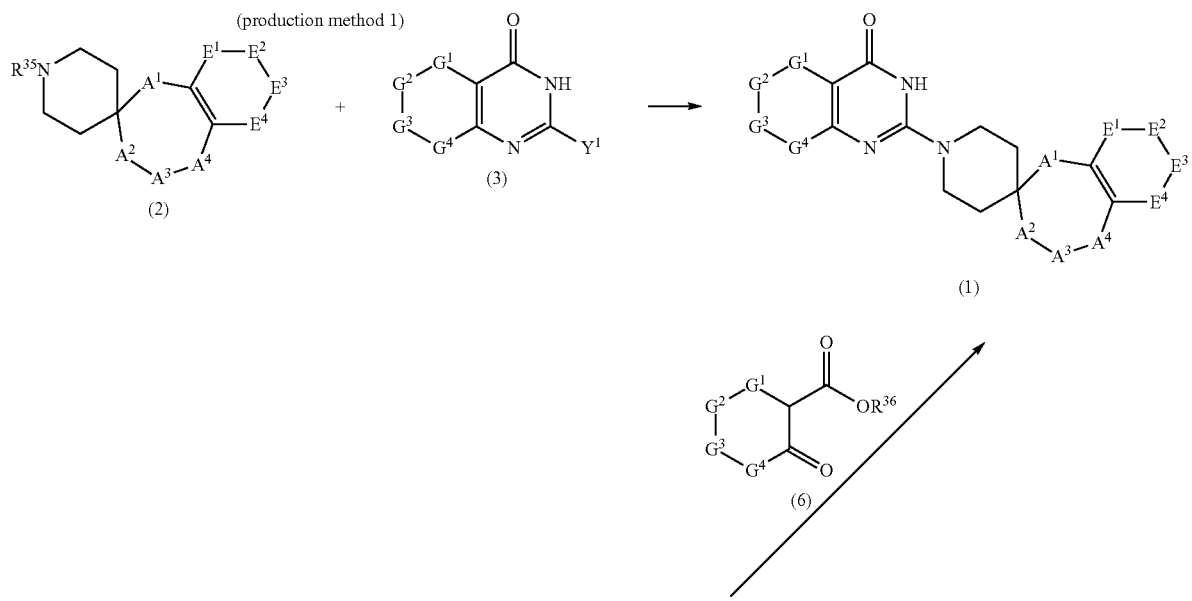

(production method 2)

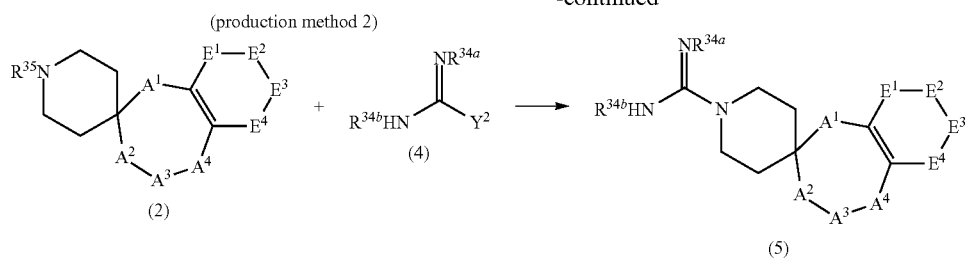

In the above formulas (2) to (6), $A^1$, $A^2$, $A^3$, $A^4$, $E^1$, $E^2$, $E^3$, $E^4$, $G^1$, $G^2$, $G^3$, and $G^4$ have the same meanings as $A^1$, $A^2$, $A^3$, $A^4$, $E^1$, $E^2$, $E^3$, $E^4$, $G^1$, $G^2$, $G^3$, and $G^4$ in the above general formula (1), respectively. Then, in the above formulas (3) and (4), $Y^1$ and $Y^2$ each independently represent a leaving group described above. Moreover, in the above formulas (4) and (5), $R^{34a}$ and $R^{34b}$ each independently represent a hydrogen atom or a protective group described above. Further, in the above formula (2), $R^3$ represents a hydrogen atom or a protective group described above. In the above formula (6), $R^{36}$ represents an optionally substituted $C_{1-6}$ alkyl group.

A compound represented by the formula (2) (hereinafter referred to as "intermediate (2)") and a compound represented by the formula (3) (hereinafter referred to as "raw material (3)") in the production method 1, and the intermediate (2) and compounds represented by the formulas (4) and (6) (hereinafter referred to as "raw material (4)" and "raw material (6)", respectively) in the production method 2 may be commercially available reagents or can be synthesized by publicly known methods or their analogous methods. In addition, in the intermediate (2), a protective group may be present as needed, and the protective group can be deprotected at any stage when necessary.

In the production method 1, the intermediate (2) and the raw material (3) are dissolved or suspended in an appropriate solvent, and are caused to react with each other in the presence or absence of a metal catalyst and its ligand and in the presence or absence of a base, so that the spiro compound of the present invention (the compound represented by the formula (1), hereinafter referred to as "compound (1)" in some cases) can be produced.

In the production method 1, the intermediate (2) and the raw material (3) are generally used in a molar ratio range of 1:1 to 3, and are preferably used in a molar ratio range of 1:1 to 1.5.

In the production method 1, examples of the solvent include: protic solvents such as water, methanol, ethanol, n-propanol, 2-propanol, n-butanol, 2-butanol, and tert-butyl alcohol; hydrocarbon solvents such as petroleum ether, n-pentane, n-hexane, n-heptane, cyclohexane, benzene, toluene, and xylene; halogen solvents such as carbon tetrachloride, dichloromethane, chloroform, 1,2-dichloroethane, chlorobenzene, and trifluoromethyl benzene; ether solvents such as diethyl ether, diisopropyl ether, methyl tert-butyl ether, methyl cyclopentyl ether, tetrahydrofuran, 2-methyl tetrahydrofuran, 1,4-dioxane, 1,2-dimethoxyethane, and diphenyl ether; ester solvents such as methyl acetate, ethyl acetate, n-propyl acetate, isopropyl acetate, n-butyl acetate, isobutyl acetate, tert-butyl acetate, benzyl acetate, methyl propionate, ethyl propionate, n-propyl propionate, isopropyl propionate, n-butyl propionate, isobutyl propionate, and tert-butyl propionate; aprotic polar solvents such as acetone, 2-butanone, methyl isobutyl ketone, cyclohexanone, acetonitrile, propionitrile, N,N-dimethylformamide, N,N-dimethylacetamide, dimethylsulfoxide, and N-methyl-2-pyrrolidone; and the like. These solvents may be each used alone or be used in a mixture of two or more types at an appropriate ratio. Among these, as the solvent, it is preferable to use at least one of toluene, ethanol, 1,4-dioxane, and N,N-dimethylformamide.

Examples of the metal catalyst in the case where the production method 1 is carried out in the presence of the metal catalyst include: zero valent palladium catalysts such as tris(dibenzylideneacetone) dipalladium(0) and tris(dibenzylideneacetone) (chloroform) dipalladium(0); divalent palladium catalysts such as palladium(II) acetate, bis(acetonitrile) dipalladium(II), bis(benzonitrile) dipalladium(II), allylpalladium(II) chloride dimer, and palladium(II) (n-cinnamyl) chloride dimer; palladium-phosphine complexes such as tetrakis(triphenylphosphine) palladium(0), bis(tri-tert-butylphosphine) palladium(0), bistriphenylphosphine palladium(II)dichloride, bis(tri-o-tolylphosphine) palladium (II)dichloride, [1,2-bis(diphenylphosphino)ethane] palladium(II)dichloride, [1,1'-bis(diphenylphosphino)ferrocene]palladium(II)dichloride (dichloromethane adduct), and [1,3-bis (diphenylphosphino)propane] palladium(II)dichloride; and the like. Then, examples of the ligand used in the case where the production method 1 is carried out in the presence of the ligand include di-tert-butylphosphine, tri-tert-butylphosphine, tri-tert-butylphosphonium tetrafluoroborate, di-tert-butylmethylphosphonium tetraphenylborate, tri-tert-butylphosphonium tetraphenylborate, 2-di-tert-butylphosphino-2',4',6'-triisopropylbiphenyl, 2-(di-tert-butylphosphino)biphenyl, 2-(di-tert-butylphosphino)-2'-methylbiphenyl, 2-di-tert-butylphosphino-2'-(N,N-dimethylamino)biphenyl, 2-di-tert-butylphosphino-3,4,5,6-tetramethyl-2',4',6'-triisopropylbiphenyl, [4-(N,N-dimethylamino)phenyl]di-tert-butylphosphine, tricyclohexylphosphine, tricyclophosphonium tetrafluoroborate, 2-dicyclohexylphosphinobiphenyl, 2-dicyclohexylphosphino-2'-methylbiphenyl, 2-dicyclohexylphosphino-2'-(N,N-dimethylamino)biphenyl, 2-dicyclohexylphosphino-2',4',6'-triisopropylbiphenyl, 2-dicyclohexylphosphino-3,6-dimethoxy-2',4',6'-triisopropyl biphenyl, 2-dicyclohexylphosphino-2',6'-dimethoxybiphenyl, 2-dicyclohexylphosphino-2',6'-diisopropyloxybiphenyl, 2'-dicyclohexylphosphino-2,6-dimethoxybiphenyl-3-sodium sulfonate hydrate, tri(2-furyl)phosphine, 2-diphenyl phosphino-2'-(N,N-dimethylamino)biphenyl, 2,2'-bis(diphenyl phosphino)-1,1'-binaphthyl, bis[2-(diphenyl phosphino)phenyl]ether, 4,5-bis(diphenyl phosphino)-9,9-dimethylxanthene, 5-(di-tert-butylphosphino)-1',3',5'-triphenyl-1,4'-bi-1H-pyrazole, 1,1'-bis(diphenylphosphino)ferrocene, 1,1'-bis(di-tert-butylphosphino)ferrocene, and 1,2,3,4,5-pentaphenyl-1'-(di-tert-butylphosphino)ferrocene, and so on. The metal catalyst and its ligand are usually used at a molar ratio of 1:0.5 to 2, and preferably used at a molar ratio of 1:1. An amount of the metal catalyst and its ligand used is in a range of 0.01 to 1% by mole and preferably in a range of 0.1 to 0.5% by mole with respect to the intermediate (2).

Examples of the base in the case where the production method 1 is carried out in the presence of the base include: salts such as sodium hydrogen carbonate, sodium carbonate, potassium hydrogen carbonate, potassium carbonate, cesium carbonate, sodium acetate, potassium acetate, sodium phosphate, potassium phosphate, lithium hydroxide, sodium hydroxide, potassium hydroxide, and barium hydroxide; amines such as ammonia, methylamine, ethylamine, cyclohexylamine, ethanolamine, aniline, dimethylamine, diethylamine, dibutylamine, dicyclohexylamine, bistrimethylsilylamine, pyrrolidine, piperidine, piperazine, morpholine, trimethylamine, triethylamine, tributylamine, diisopropylethylamine, 2-(dimethylamino)ethanol, N-methylpyrrolidine, N-methylpiperidine, N-methylmorpholine, N,N'-dimethylpiperazine, N,N,N',N',-tetramethylethylenediamine, N,N-dimethylaniline, 1,4-diazabicyclo[2.2.2]octane, 1,5-diazabicyclo[4.3.0]non-5-ene, 1,8-diazabicyclo[5.4.0]undec-7-ene, pyridine, picoline, 4-(dimethylamino)pyridine, 2,6-lutidine, and 2,4,6-collidine; metal hydrides such as lithium hydride, sodium hydride, potassium hydride, barium hydride, and calcium hydride; metal alkoxides such as lithium methoxide, sodium methoxide, sodium ethoxide, sodium tert-butoxide, and potassium tert-butoxide; metal amides such as lithium amide, sodium amide, potassium amide, lithium diisopropyl amide, lithium-2,2,6,6-tetramethyl piperidide, lithium bistrimethylsilylamide, sodium bistrimethylsilylamide, and potassium bistrimethylsilylamide; and the like. These bases may be each used alone or be used in a mixture of two or more types at an appropriate ratio. Among these, as the base, it is preferable to use at least one of potassium phosphate, triethylamine, diisopropyl ethylamine, and sodium tert-butoxide. An amount of the base used is in a range of 0.01 to 20 equivalents, preferably in a range of 0.1 to 10 equivalents, more preferably in a range of 1 to 5 equivalents with respect to the amount of the intermediate (2).

In the production method 1, the reaction temperature is in a range of 0 to 250° C., preferably 30 to 200° C., and more preferably 60 to 160° C.

In the production method 1, the reaction time is in a range of 1 minute to 2 days, preferably 5 minutes to 12 hours, and more preferably 10 minutes to 6 hours.

In the production method 1, as for an optional substituent to be substituted at $A^1$, $A^2$, $A^3$, $A^4$, $G^1$, $G^2$, $G^3$, $G^4$, $E^1$, $E^2$, $E^3$, and $E^4$, the target substituent may be contained at the stage of the intermediate (2) or the raw material (3). In this case, the compound (1) obtained contains the target substituent. By use of a combination of synthesis methods in the wide variety of various synthesis methods known to those skilled in the art, the compound (1) containing a target substitute can be produced by subjecting the intermediate (2) and/or the raw material (3) to introduction of, modification with, or conversion to a group that acts as a precursor for the target substituent. Note that the combination of synthesis methods may be any combination formed as appropriate, and protection and deprotection may be conducted as appropriate according to the necessity.

In the production method 2, the intermediate (2) and the raw material (4) are dissolved or suspended in an appropriate solvent, and are caused to react with each other in the presence of a base to synthesize a compound represented by the formula (5) (hereinafter referred to as "intermediate (5)"). Subsequently, the intermediate (5) and the raw material (6) are dissolved or suspended in an appropriate solvent, and are caused to react with each other in the presence of a base, so that the spiro compound of the present invention (compound (1)) can be produced.

The reactions may be conducted in such a way that the intermediate (5) is isolated by purification and is used in the subsequent step, or may be conducted continuously as a one-pot reaction. In addition, steps such as protection and deprotection may be added as appropriate according to the necessity.

In the production method 2, the intermediate (2) and the raw material (4) as well as the intermediate (5) and the raw material (6) are generally used in a molar ratio range of 1:1 to 3, and preferably in a molar ratio range of 1:1 to 2.

Examples of the solvent in the production method 2 are the same solvents as the solvents listed for the production method 1. Among them, it is preferable to use, as the solvent, at least one of water, ethanol, acetonitrile, and N,N-dimethylformamide.

Examples of the base in the production method 2 are the same bases as the bases listed for the production method 1. Among them, it is preferable to use, as the base, at least one of sodium ethoxide, triethylamine, and diisopropyl ethylamine. An amount of the base used is in a range of 0.01 to 20 equivalents, preferably in a range of 0.1 to 10 equivalents, and more preferably in a range of 1 to 5 equivalents with respect to the amount of the intermediate (2) or the intermediate (5).

In the production method 2, the reaction temperature is in a range of −30 to 200° C., preferably 0 to 150° C., and more preferably 20 to 120° C.

In the production method 2, the reaction time is in a range of 1 minute to 2 days, preferably 5 minutes to 12 hours, and more preferably 30 minutes to 6 hours.

In the production method 2, as for an optional substituent to be substituted at $A^1$, $A^2$, $A^3$, $A^4$, $G^1$, $G^2$, $G^3$, $G^4$, $E^1$, $E^2$, $E^3$, and $E^4$, the target substituent may be contained at the stage of the intermediate (2) or the raw material (6). In this case, the compound (1) obtained contains the target substituent. By use of a combination of synthesis methods in the wide variety of various synthesis methods known to those skilled in the art, the compound (1) containing a target substitute can be produced by subjecting the intermediate (2) and/or the raw material (6) to introduction of, modification with, or conversion to a group that acts as a precursor for the target substituent. Note that the combination of synthesis methods may be any combination formed as appropriate, and protection and deprotection may be conducted as appropriate according to the necessity.

The intermediate (2) of the present invention can be produced by methods described below in schemes 1 to 7 or the like.

(scheme 1)

[Chem. 8]

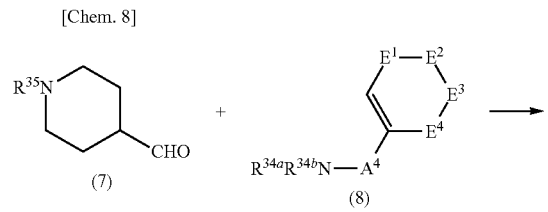

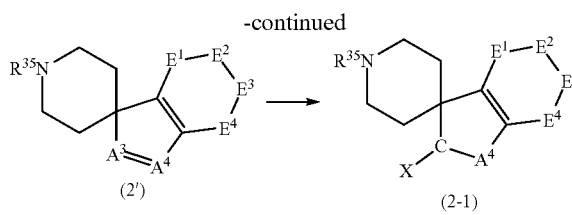

In the above formulas (8), (2'), and (2-1), $A^3$, $A^4$, $E^1$, $E^2$, $E^3$, and $E^4$ have the same meanings as $A^3$, $A^4$, $E^1$, $E^2$, $E^3$, and $E^4$ in the above general formula (1), respectively. Then, in the above formula (8), $R^{34a}$ and $R^{34b}$ each independently represent a hydrogen atom or a protective group described above. In the above formulas (7), (2'), and (2-1), $R^{35}$ has the same meaning as $R^{35}$ in the above formula (2). Moreover, in the above formula (2-1), a group represented by C—X has the same meaning as $CH_2$ or CO represented by $A^3$ in the above formula (1).

Compounds represented by the formulas (7) and (8) (hereinafter referred to as "raw material (7)" and "raw material (8)", respectively) in the scheme 1 may be commercially available reagents or can be synthesized by publicly known methods or their analogous methods.

In the scheme 1, a compound represented by the formula (2-1) (hereinafter referred to as "intermediate (2-1)") is one type of the intermediate (2). In the production of the intermediate (2-1), the raw material (7) and the raw material (8) are dissolved or suspended in an appropriate solvent, and are caused to react with each other in the presence of an acid to synthesize a precursor (a compound represented by the formula (2') (hereinafter referred to as "precursor (2')") of the intermediate (2-1). Then, the precursor (2') is subjected to reduction process to synthesize a compound of the intermediate (2-1) where X is $H_2$, or to oxidation process to synthesize a compound of the intermediate (2-1) where X is (=O).

The reactions may be conducted in such a way that the precursor (2') is isolated by purification and is used in the subsequent step, or may be conducted continuously as a one-pot reaction. In addition, protection, deprotection, and so on may be conducted as appropriate according to the necessity.

In the scheme 1, the raw material (7) and the raw material (8) are used in a molar ratio range of 1:1 to 5, and preferably in a molar ratio range of 1:1.5 to 2.5.

Examples of the solvent used in the scheme 1 include: protic solvents such as water, methanol, ethanol, n-propanol, 2-propanol, n-butanol, 2-butanol, and tert-butyl alcohol; hydrocarbon solvents such as petroleum ether, n-pentane, n-hexane, n-heptane, cyclohexane, benzene, toluene, and xylene; halogen solvents such as carbon tetrachloride, dichloromethane, chloroform, 1,2-dichloroethane, and chlorobenzene; ether solvents such as diethyl ether, diisopropyl ether, methyl tert-butyl ether, methyl cyclopentyl ether, tetrahydrofuran, 2-methyl tetrahydrofuran, 1,4-dioxane, and diphenyl ether; ester solvents such as methyl acetate, ethyl acetate, n-propyl acetate, isopropyl acetate, n-butyl acetate, isobutyl acetate, tert-butyl acetate, benzyl acetate, methyl propionate, ethyl propionate, n-propyl propionate, isopropyl propionate, n-butyl propionate, isobutyl propionate, and tert-butyl propionate; organic acid solvents such as formic acid, acetic acid, and propionic acid; aprotic polar solvents such as acetone, 2-butanone, methyl isobutyl ketone, acetonitrile, propionitrile, N,N-dimethylformamide, N,N-dimethylacetamide, dimethylsulfoxide, and N-methyl-2-pyrrolidone; and the like. These solvents may be each used alone or be used in a mixture of two or more types at an appropriate ratio. Among these, as the solvent, it is preferable to use at least one of acetic acid, methanol, ethanol, tetrahydrofuran, toluene, chloroform, and 1,2-dichloroethane, and it is more preferably to use at least one of methanol, chloroform, and tetrahydrofuran.

As the acid used in the synthesis step of the precursor (2') in the scheme 1, usable acids include: mineral acids such as hydrochloric acid, hydrobromic acid, hydroiodic acid, sulfuric acid, phosphoric acid, and nitric acid; carboxylic acids such as formic acid, acetic acid, propionic acid, and trifluoroacetic acid; Lewis acids such as boron trifluoride diethyl ether complex, boron trichloride, boron tribromide, zinc chloride, stannic chloride, ferric chloride, aluminum chloride, titanium tetrachloride, and zirconium tetrachloride; and the like. Among these, as the acid, at least one of hydrochloric acid, sulfuric acid, and trifluoroacetic acid is preferable, and trifluoroacetic acid is more preferable. An amount of the acid used is in a range of 0.01 to 20 equivalents, preferably in a range of 0.1 to 10 equivalents, and more preferably in a range of 1 to 5 equivalents with respect to the amount of the raw material (7).

In the scheme 1, the reaction temperature in the synthesis step of the precursor (2') is in a range of 0 to 200° C., preferably 20 to 120° C., and more preferably 50 to 80° C.

In the scheme 1, the reaction time in the synthesis step of the precursor (2') is 30 minutes to 24 hours, preferably 1 hour to 12 hours, and more preferably 2 hours to 6 hours.

In the scheme 1, as a reducing agent used in the reduction process, it is possible to use a metal catalyst such as activated carbon with palladium and a hydrogen source (for example, such as hydrogen gas, ammonium formate, or cyclohexadiene); or a boron reducing agent such as diborane, lithium borohydride, sodium borohydride, potassium borohydride, sodium cyanoborohydride, and sodium triacetoxyborohydride; or the like. Preferably, sodium triacetoxyborohydride is used. An amount of the reducing agent used is in a range of 0.001 to 20 equivalents, preferably in a range of 0.005 to 10 equivalents, and more preferably in a range of 0.01 to 5 equivalents with respect to the amount of the precursor (2').

In the scheme 1, the reaction temperature in the reduction process is in a range of −40 to 100° C., preferably 0 to 60° C., and more preferably 20 to 40° C.

In the scheme 1, the reaction time in the reduction process is 30 minutes to 24 hours, preferably 1 hour to 12 hours, and more preferably 2 hours to 6 hours.

In the scheme 1, as an oxidizing agent used in the oxidation process, it is possible to use: peracids such as hydrogen peroxide, performic acid, peracetic acid, perbenzoic acid, and m-chloroperbenzoic acid; halogens such as sodium hypochlorite, sodium chlorite, sodium perchlorate, sodium hypobromite, sodium bromite, sodium perbromate, sodium periodate, potassium hypochlorite, potassium chlorite, potassium perchlorate, potassium hypobromite, potassium bromite, potassium perbromate, and potassium periodate; and the like. Among these, as the oxidizing agent, at least one of hydrogen peroxide, m-chloroperbenzoic acid, and sodium chlorite is preferable, and sodium chlorite is more preferable. An amount of the oxidizing agent used is in a range of 0.01 to 20 equivalents, preferably in a range of 0.1 to 10 equivalents, and more preferably in a range of 1 to 5 equivalents with respect to the amount of the precursor (2').

In the scheme 1, the reaction temperature in the oxidation process is in a range of −40 to 80° C., preferably 0 to 60° C., and more preferably 20 to 40° C.

In the scheme 1, the reaction time in the oxidation process is 30 minutes to 24 hours, preferably 45 minutes to 12 hours, and more preferably 1 hour to 6 hours.

In the scheme 1, as for a substituent to be substituted at $A^4$, $E^1$, $E^2$, $E^3$, and $E^4$, the target substituent may be contained in the stage of the raw material (8). In this case, the intermediate (2-1) obtained contains the target substituent. Alternatively, in some cases, the intermediate (2-1) may be subjected to processes such as protection and deprotection as appropriate according to the necessity, and a substituent in the intermediate (2-1) may be converted to another target substituent, by using a combination of synthesis methods in the wide variety of various synthesis methods known to those skilled in the art, so that the intermediate (2-1) can be converted to the intermediate (2-1) containing the other target substituent.

(scheme 2)

[Chem. 9]

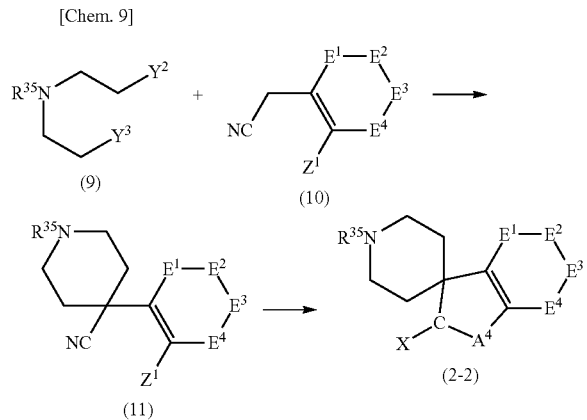

In the above formulas (10), (11), and (2-2), $A^4$, $E^1$, $E^2$, $E^3$, and $E^4$ have the same meanings as $A^4$, $E^1$, $E^2$, $E^3$, and $E^4$ in the above general formula (1), respectively. In the above formulas (9), (11) and (2-2), $R^{35}$ has the same meaning as $R^{35}$ in the above formula (2). In the above formula (2-2), a group represented by C—X has the same meaning as $CH_2$ or CO represented by $A^3$ in the above formula (1). In addition, in the above formula (9), each $Y^3$ independently represents a leaving group described above. In the above formulas (10) and (11), $Z^1$ represents a $C_{1-3}$ alkyloxy group or a leaving group.

Compounds represented by the formulas (9) and (10) (hereinafter referred to as "raw material (9)" and "raw material (10)", respectively) in the scheme 2 may be commercially available reagents or can be synthesized by publicly known methods or their analogous methods.

In the scheme 2, a compound represented by the formula (2-2) (hereinafter referred to as "intermediate (2-2)") is one type of the intermediate (2). In the production of the intermediate (2-2), the raw material (9) and the raw material (10) are dissolved or suspended in an appropriate solvent, and an alkali metallic base is added thereto to allow a reaction to proceed to synthesize a precursor (a compound represented by the formula (11) (hereinafter referred to as "precursor (11)")) of the intermediate (2-2). Here, the intermediate (2-2) in which X is (═O) and $A^4$ is O can be produced in such a way that the precursor (11) containing an alkyloxy group at $Z^1$ is subjected to acid treatment. Instead, the intermediate (2-2) in which X is (═O) and $A^4$ is $NR^1$ can be produced in such a way that the precursor (11) containing a leaving group at $Z^1$ is subjected to a hydrolysis reaction followed by a ring closure reaction (cyclization reaction).

In the scheme 2, the raw material (9) and the raw material (10) are used in a molar ratio range of 0.8 to 2:1, and preferably in a molar ratio range of 0.9 to 1.1:1.

Examples of the solvent used in the scheme 2 include: hydrocarbon solvents such as petroleum ether, n-pentane, n-hexane, n-heptane, cyclohexane, benzene, toluene, and xylene; ether solvents such as diethyl ether, diisopropyl ether, methyl tert-butyl ether, methyl cyclopentyl ether, tetrahydrofuran, 2-methyl tetrahydrofuran, 1,4-dioxane, and diphenyl ether; aprotic polar solvents such as acetonitrile, propionitrile, N,N-dimethylformamide, N,N-dimethylacetamide, dimethylsulfoxide, N-methyl-2-pyrrolidone, N,N,N', N'-tetramethylethylenediamine, and hexamethylphosphoramide; and the like. These solvents may be each used alone or be used in a mixture of two or more types at an appropriate ratio. Preferably, tetrahydrofuran is used.

As the alkali metallic base used in the scheme 2, usable bases include: organic lithium such as methyl lithium, n-butyl lithium, sec-butyl lithium, tert-butyl lithium, and phenyl lithium; metal hydrides such as sodium hydride, potassium hydride, barium hydride, and potassium hydride; metal amides such as lithium amide, sodium amide, potassium amide, lithium diisopropyl amide, lithium bistrimethylsilyl amide, and sodium bistrimethylsilyl amide; and the like. These alkali metallic bases may be each used alone or be used in a mixture of two or more types at an appropriate ratio. Among these, as the alkali metallic base, it is preferable to use at least one of sodium hydride and sodium bistrimethylsilyl amide. An amount of the alkali metallic base used is in a range of 1 to 10 equivalents, preferably in a range of 1.2 to 6 equivalents, and more preferably in a range of 1.5 to 5 equivalents with respect to the amount of the raw material (10).

In the scheme 2, the reaction temperature is in a range of −100 to 200° C., preferably −80 to 150° C., and more preferably −50 to 100° C.

In the scheme 2, the reaction time is in a range of 30 minutes to 48 hours, preferably 45 minutes to 24 hours, and more preferably 60 minutes to 12 hours.

As the acid used in the acid treatment in the scheme 2, usable acids include: mineral acids such as hydrochloric acid, hydrobromic acid, hydroiodic acid, sulfuric acid, phosphoric acid, and nitric acid; carboxylic acids such as formic acid, acetic acid, propionic acid, and trifluoroacetic acid; Lewis acids such as boron trichloride, boron tribromide, and boron triiodide; and the like. These acids may be each used alone or be used in a mixture of two or more types at an appropriate ratio. Preferably, a mixture of acetic acid and hydrobromic acid is used.

In the scheme 2, the reaction temperature in the acid treatment is in a range of 0 to 200° C., and is preferably a temperature at which reflux takes place.

In the scheme 2, the reaction time in the acid treatment is in a range of 30 minutes to 48 hours, preferably 2 hours to 36 hours, and more preferably 6 hours to 24 hours.

Examples of the solvent used in the hydrolysis reaction in the scheme 2 include: protic solvents such as water, methanol, ethanol, n-propanol, 2-propanol, n-butanol, 2-butanol, and tert-butylalcohol; aprotic polar solvents such as acetonitrile, propionitrile, N,N-dimethylformamide, N,N-dimethylacetamide, dimethylsulfoxide, and N-methyl-2-pyrrolidone; and the like. These solvents may be each used alone or be used in a mixture of two or more types at an appropriate ratio. Preferably, dimethylsulfoxide is used.

Bases usable in the hydrolysis reaction in the scheme 2 include lithium hydroxide, sodium hydroxide, potassium hydroxide, and the like. A mixture of the base and a hydrogen peroxide may be used as appropriate according to the necessity.

In the scheme 2, the reaction temperature in the hydrolysis reaction is in a range of 0 to 100° C., and preferably 20 to 60° C.

In the scheme 2, the reaction time in the hydrolysis reaction is in a range of 30 minutes to 48 hours, preferably 60 minutes to 36 hours, and more preferably 2 hours to 24 hours.

Examples of the solvent used in the cyclization reaction in the scheme 2 include: hydrocarbon solvents such as petroleum ether, n-pentane, n-hexane, n-heptane, cyclohexane, benzene, toluene, and xylene; ether solvents such as diethyl ether, diisopropyl ether, methyl tert-butyl ether, methyl cyclopentyl ether, tetrahydrofuran, 2-methyl tetrahydrofuran, 1,4-dioxane, and diphenyl ether; aprotic polar solvents such as acetonitrile, propionitrile, N,N-dimethylformamide, N,N-dimethylacetamide, dimethylsulfoxide, and N-methyl-2-pyrrolidone; and the like. These solvents may be each used alone or be used in a mixture of two or more types at an appropriate ratio. Preferably, at least one of N,N-dimethylacetamide and N-methyl-2-pyrrolidone is used.

As the base used in the cyclization reaction in the scheme 2, for example, metal hydrides such as lithium hydride, sodium hydride, barium hydride, and potassium hydride are used. Preferably, lithium hydride is used.

In the scheme 2, the reaction temperature in the cyclization reaction is in a range of 0 to 200° C., preferably 20 to 160° C., and more preferably 50 to 140° C.

In the scheme 2, the reaction time in the cyclization reaction is in a range of 30 minutes to 48 hours, preferably 60 minutes to 24 hours, and more preferably 2 hours to 12 hours.

In the scheme 2, as for a substituent to be substituted at $A^4$, $E^1$, $E^2$, $E^3$, and $E^4$, the target substituent may be contained at the stage of the raw material (10). In this case, the intermediate (2-2) obtained contains the target substituent. Alternatively, in some cases, any of the precursor (11) and the intermediate (2-2) may be subjected to processes such as protection and deprotection as appropriate according to the necessity, and a substituent in any of the precursor (11) and the intermediate (2-2) may be converted to another target substituent, by using a combination of synthesis methods in the wide variety of various synthesis methods known to those skilled in the art, so that the intermediate (2-2) can be converted to the intermediate (2-2) containing the other target substituent. In addition, when X in the intermediate (2-2) is (═O), the intermediate (2-2) can be converted to the intermediate (2-2) where X is $H_2$ through a common reduction reaction or the like known to those skilled in the art.

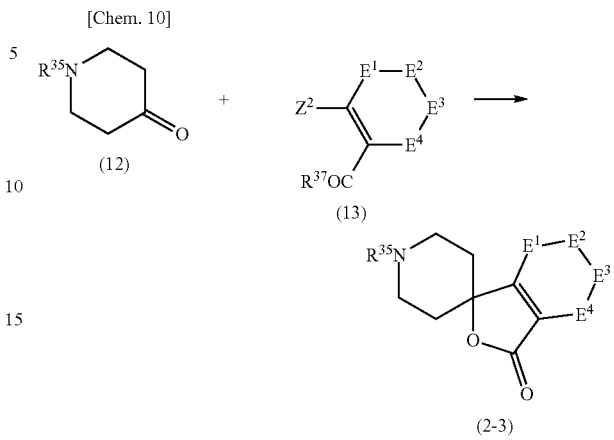

(scheme 3)

[Chem. 10]

In the above formulas (13) and (2-3), $E^1$, $E^2$, $E^3$, and $E^4$ have the same meanings as $E^1$, $E^2$, $E^3$, and $E^4$ in the above general formula (1), respectively. In the above formulas (12) and (2-3), $R^{35}$ has the same meaning as $R^{35}$ in the above formula (2). In the above formula (13), $R^{37}$ represents a hydroxy group, a $C_{1-3}$ alkyloxy group, a di $C_{1-3}$alkylamino group, or an arylamino group, and $Z^2$ represents a hydrogen atom or a leaving group described above.

Compounds represented by the formulas (12) and (13) (hereinafter referred to as "raw material (12)" and "raw material (13)", respectively) in the scheme 3 may be commercially available reagents or can be synthesized by publicly known methods or their analogous methods.

In the scheme 3, the raw material (12) and the raw material (13) are used in a molar ratio range of 0.8 to 2:1, and are preferably used at a molar ratio of 0.9 to 1.1:1.

In the scheme 3, a compound represented by the formula (2-3) (hereinafter referred to as "intermediate (2-3)") is one type of the intermediate (2) of the present invention. The intermediate (2-3) is produced in such away that the raw material (13) is dissolved or suspended in an appropriate solvent, an alkali metallic base is added thereto to allow a reaction to proceed to synthesize an alkali metal compound of the raw material (13), and then the raw material (12) is added to the alkali metal compound.

Examples of the solvent used in the scheme 3 are the same solvents as the solvents listed for the scheme 2. Among them, tetrahydrofuran is preferably used.

Examples of the alkali metallic base in the scheme 3 are the same alkali metallic bases as the bases listed for the scheme 2. Among them, at least one of n-butyl lithium and sec-butyl lithium is preferably used.

In the scheme 3, the reaction temperature for the synthesis of the alkali metal compound is in a range of −100 to 100° C., preferably −90 to 50° C., and more preferably −80 to 30° C.

In the scheme 3, the reaction time for the synthesis of the alkali metal compound is in a range of 30 minutes to 3 hours, and preferably 45 minutes to 2 hours.

In the scheme 3, the reaction temperature after the addition of the raw material (12) is in a range of −100 to 100° C., preferably −90 to 80° C., and more preferably −80 to 60° C.

In the scheme 3, the reaction time after the addition of the raw material (12) is in a range of 30 minutes to 48 hours, preferably 45 minutes to 24 hours, and more preferably 1 hour to 12 hours.

In the scheme 3, as for a substituent to be substituted at $E^1$, $E^2$, $E^3$, and $E^4$, the target substituent may be contained at the stage of the raw material (13). In this case, the intermediate (2-3) obtained contains the target substituent. Alternatively, in some cases, the intermediate (2-3) may be subjected to processes such as protection and deprotection as appropriate according to the necessity, and a substituent in the intermediate (2-3) may be converted to another target substituent, by using a combination of synthesis methods in the wide variety of various synthesis methods known to those skilled in the art, so that the intermediate (2-3) can be converted to the intermediate (2-3) containing the other target substituent.

(scheme 4)

[Chem. 11]

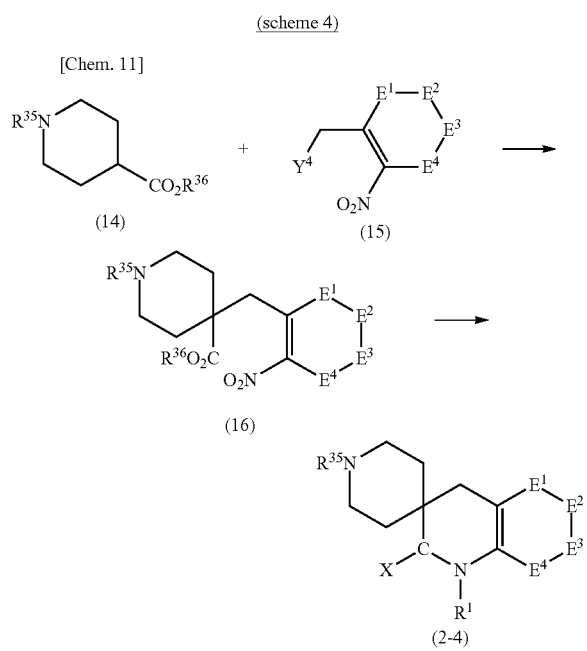

In the above formulas (15), (16), and (2-4), $E^1$, $E^2$, $E^3$, $E^4$, and $R^1$ have the same meanings as $E^1$, $E^2$, $E^3$, $E^4$, and $R^1$ in the above general formula (1), respectively. In the above formulas (14), (16), and (2-4), $R^{35}$ has the same meaning as $R^{35}$ in the above formula (2). In the above formula (2-4), a group represented by C—X has the same meaning as $CH_2$ or CO represented by $A^3$ in the above formula (1). In addition, $R^{36}$ in the above formulas (14) and (16) represents an optionally substituted $C_{1-3}$ alkyl group, and $Y^4$ in the above formula (15) represents a leaving group described above.

Compounds represented by the formulas (14) and (15) (hereinafter referred to as "raw material (14)" and "raw material (15)", respectively) in the scheme 4 may be commercially available reagents or can be synthesized by publicly known methods or their analogous methods.

In the scheme 4, a compound represented by the formula (2-4) (hereinafter referred to as "intermediate (2-4)") is one type of the intermediate (2) of the present invention. The intermediate (2-4) is produced in such away that the raw material (14) is dissolved or suspended in an appropriate solvent, anions of the raw material (14) are formed by an alkali metallic base and are caused to react with the raw material (15) to form the precursor (16), followed by reduction of the nitro group to close the ring.

In the scheme 4, the raw material (14) and the raw material (15) are used in a molar ratio range of 1:1 to 2, and are preferably used in a molar ratio range of 1:1.1 to 1.3.

Examples of the solvent used in the scheme 4 are the same solvents as the solvents listed for the scheme 2. Among them, tetrahydrofuran is preferably used.

Examples of the alkali metallic base in the scheme 4 are the same alkali metallic bases as the bases listed for the scheme 2. Among them, sodium bistrimethylsilyl amide is preferably used. An amount of the alkali metallic base used is in a range of 1 to 2 equivalents, and preferably 1.2 to 1.5 equivalents with respect to the amount of the raw material (14).

In the scheme 4, the reaction temperature for the formation of the anions is in a range of −100 to 100° C., preferably −90 to 50° C., and more preferably −80 to 0° C.

In the scheme 4, the reaction time for the formation of the anions is in a range of 30 minutes to 3 hours, and preferably 45 minutes to 2 hours.

In the scheme 4, the reaction temperature after the addition of the raw material (15) is in a range of −100 to 100° C., preferably −90 to 80° C., and more preferably −80 to 60° C.

In the scheme 4, the reaction time after the addition of the raw material (15) is in a range of 30 minutes to 48 hours, preferably 45 minutes to 24 hours, and more preferably 1 hour to 12 hours.

Examples of a solvent used for the reduction of the nitro group in the intermediate (16) in the scheme 4 include: protic solvents such as water, methanol, ethanol, n-propanol, 2-propanol, n-butanol, 2-butanol, and tert-butylalcohol; hydrocarbon solvents such as petroleum ether, n-pentane, n-hexane, n-heptane, cyclohexane, benzene, toluene, and xylene; halogen solvents such as carbon tetrachloride, dichloromethane, chloroform, 1,2-dichloroethane, and chlorobenzene; ether solvents such as diethyl ether, diisopropyl ether, methyl tert-butyl ether, methyl cyclopentyl ether, tetrahydrofuran, 2-methyl tetrahydrofuran, 1,4-dioxane, and diphenyl ether; ester solvents such as methyl acetate, ethyl acetate, n-propyl acetate, isopropyl acetate, n-butyl acetate, isobutyl acetate, tert-butyl acetate, benzyl acetate, methyl propionate, ethyl propionate, n-propyl propionate, isopropyl propionate, n-butyl propionate, isobutyl propionate, and tert-butyl propionate; aprotic polar solvents such as acetone, 2-butanone, methyl isobutyl ketone, acetonitrile, propionitrile, N,N-dimethylformamide, N,N-dimethylacetamide, dimethylsulfoxide, and N-methyl-2-pyrrolidone; and the like. These solvents may be each used alone or be used in a mixture of two or more types at an appropriate ratio. Among them, as the solvent, at least one of water, methanol, ethanol, and tetrahydrofuran is preferably used, and ethanol is more preferably used. It is also possible to use the solvent to which an acid or a base is added as appropriate, the acid being formic acid, acetic acid, trifluoroacetic acid, hydrochloric acid, sulfuric acid, phosphoric acid, methanesulfonic acid, toluenesulfonic acid, or the like, the base being sodium hydrogen carbonate, potassium hydrogen carbonate, sodium carbonate, potassium carbonate, cesium carbonate, lithium hydroxide, sodium hydroxide, potassium hydroxide, or the like.

As the reducing agent used in the scheme 4, examples of usable agents include: metals such as zinc, aluminum, tin, stannous chloride, and iron; hydrogenation catalysts such as palladium, platinum, rhodium, and nickel, which are used together with a hydrogen source and may be used with a carrier as appropriate; and inorganic salts such as sodium dithionite; and the like.

In the scheme 4, as for a substituent to be substituted at $R^1$, $E^1$, $E^2$, $E^3$, and $E^4$, the target substituent may be contained at the stage of the raw material (15). In this case, the intermediate (2-4) obtained contains the target substituent. Alternatively, in some cases, the intermediate (2-4) may be subjected to processes such as protection and deprotection as appropriate according to the necessity, and a substituent in the intermediate (2-4) may be converted to another target substituent, by using a combination of synthesis methods in the wide variety of various synthesis methods known to those skilled in the art, so that the intermediate (2-4) can be converted to the intermediate (2-4) containing the other target substituent. When X in the intermediate (2-4) is (=O), the intermediate (2-4) can be converted into the intermediate (2-4) in which X is $H_2$ through a common reduction reaction or the like known to those skilled in the art.

(scheme 5)

[Chem. 12]

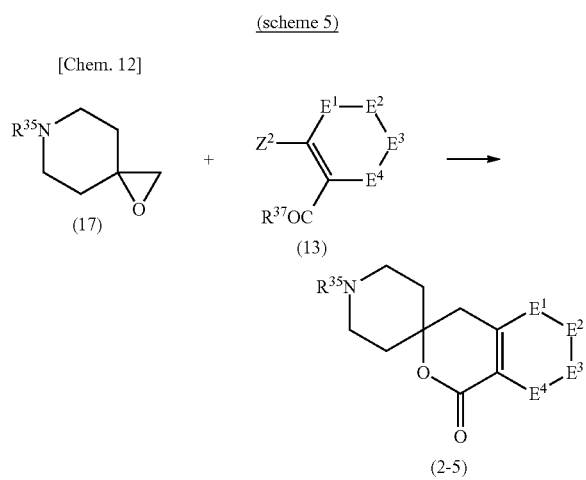

In the above formula (2-5), $E^1$, $E^2$, $E^3$, and $E^4$ have the same meanings as $E^1$, $E^2$, $E^3$, and $E^4$ in the above general formula (1), respectively. In the above formulas (17) and (2-5), $R^{35}$ has the same meaning as $R^{35}$ in the above formula (2).

A compound represented by the formula (17) (hereinafter referred to as "raw material (17)") and the raw material (13) in the scheme 5 may be commercially available reagents or can be synthesized by publicly known methods or their analogous methods.

In the scheme 5, a compound represented by the formula (2-5) (hereinafter referred to as "intermediate (2-5)") is one type of the intermediate (2) of the present invention. The intermediate (2-5) is produced in such away that the raw material (13) is dissolved or suspended in an appropriate solvent, an alkali metallic base is added thereto to allow a reaction to proceed to synthesize an alkali metal compound of the raw material (13), and then the raw material (17) is added to the alkali metal compound in the presence or absence of a Lewis acid.

In the scheme 5, the raw material (17) and the raw material (13) are used in a molar ratio range of 1:1 to 5, and are preferably used in a molar ratio range of 1:2 to 4.

Examples of the solvent used in the scheme 5 are the same solvents as the solvents listed for the scheme 2. Among them, tetrahydrofuran is preferably used.

Examples of the alkali metallic base in the scheme 5 are the same alkali metallic bases as the bases listed for the scheme 2. Among them, at least one of n-butyl lithium and sec-butyl lithium is preferably used. An amount of the alkali metallic base used is in a range of 2 to 10 equivalents and preferably 4 to 8 equivalents with respect to the amount of the raw material (17).

In the scheme 5, the reaction temperature for the synthesis of the alkali metal compound is in a range of −100 to 100° C., preferably −90 to 50° C., and more preferably −80 to 30° C.

In the scheme 5, the reaction time for the synthesis of the alkali metal compound is in a range of 30 minutes to 3 hours, and preferably 45 minutes to 2 hours.

In the scheme 5, the reaction temperature after the addition of the raw material (17) is in a range of −100 to 100° C., preferably −90 to 80° C., and more preferably −80 to 60° C.

In the scheme 5, the reaction time after the addition of the raw material (17) is in a range of 30 minutes to 48 hours, preferably 45 minutes to 24 hours, and more preferably 1 hour to 12 hours.

Examples of the Lewis acid in the case where in the scheme 5 is carried out in the presence of the Lewis acid include zinc chloride, zinc bromide, zinc iodide, stannic chloride, titanium tetrachloride, zirconium tetrachloride, boron trifluoride diethyl ether complex, boron trichloride, boron tribromide, boron triiodide, trimethylsilyl trifluoromethanesulfonate, triethylsilyl trifluoromethanesulfonate, tert-butyldimethylsilyl trifluoromethanesulfonate, and the like. Preferably, a boron trifluoride diethyl ether complex is used. An amount of the Lewis acid used is in a range of 1 to 4 equivalents, and preferably 1.5 to 3 equivalents with respect to the amount of the raw material (17) added.

In the scheme 5, as for a substituent to be substituted at $E^1$, $E^2$, $E^3$, and $E^4$, the target substituent may be contained at the stage of the raw material (13). In this case, the intermediate (2-5) obtained contains the target substituent. Alternatively, in some cases, the intermediate (2-5) may be subjected to processes such as protection and deprotection as appropriate according to the necessity, and a substituent in the intermediate (2-5) may be converted to another target substituent, by using a combination of synthesis methods in the wide variety of various synthesis methods known to those skilled in the art, so that the intermediate (2-5) can be converted to the intermediate (2-5) containing the other target substituent.

(scheme 6)

[Chem. 13]

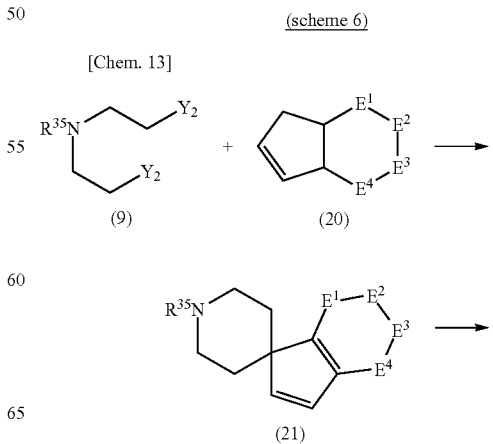

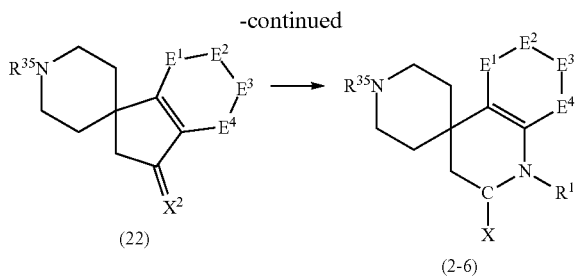

In the above formulas (20) to (22), and (2-6), $E^1$, $E^2$, $E^3$, $E^4$, and $R^1$ have the same meanings as $E^1$, $E^2$, $E^3$, $E^4$, and $R^1$ in the (21), (22), and (2-6), $R^{35}$ has the same meaning as $R^{35}$ in the above above general formula (1), respectively. In the above formulas (21), (22), and (2-6), $R^{35}$ has the same meaning as $R^{35}$ in the above formula (2). In the above formula (2-6), a group represented by C—X has the same meaning as $CH_2$ or CO represented by $A^3$ in the above formula (1). In addition, in the above formula (22), $X^2$ represents O, NOH, or $NR^{39}$, and $R^{39}$ represents a leaving group.

The raw material (9) and a compound represented by the formula (20) (hereinafter referred to as "raw material (20)") in the scheme 6 may be commercially available reagents or can be synthesized by publicly known methods or their analogous methods.

In the scheme 6, a compound represented by the formula (2-6) (hereinafter referred to as "intermediate (2-6)") is one type of the intermediate (2) of the present invention. The intermediate (2-6) is produced in such a way that: the raw material (9) and the raw material (20) are dissolved or suspended in an appropriate solvent; an alkali metallic base is added thereto to allow a reaction to proceed to synthesize a compound represented by the formula (21) (hereinafter referred to as "compound (21)"); the obtained compound (21) is subjected to a hydroboration reaction known to those skilled in the art to introduce a hydroxy group therein; the hydroxy group generated is converted into a ketone by an oxidation reaction known to those skilled in the art, followed by an oximation or the like to lead to a compound represented by the formula (22) (hereinafter referred to as "precursor (22)"); and then the precursor (22) is subjected to a Beckmann rearrangement reaction known to those skilled in the art.

In the scheme 6, the raw material (9) and the raw material (20) are used in a molar ratio range of 0.8 to 2:1, and are preferably used in a molar ratio range of 1 to 1.3:1.

Examples of the solvent used for the synthesis of the compound (21) in the scheme 6 are the same solvents as the solvents listed for the scheme 2. Among them, tetrahydrofuran is preferably used.

Examples of the alkali metallic base used for the synthesis of the compound (21) in the scheme 6 are the same alkali metallic bases as the bases listed for the scheme 2. Among them, sodium bistrimethylsilyl amide is preferably used. An amount of the alkali metallic base used is in a range of 1 to 10 equivalents, preferably in a range of 1.2 to 6 equivalents, and more preferably in a range of 1.5 to 5 equivalents with respect to the amount of the raw material (20).

In the scheme 6, the reaction temperature for the synthesis of the compound (21) is in a range of −100 to 200° C., preferably −80 to 150° C., and more preferably −50 to 100° C.

In the scheme 6, the reaction time for the synthesis of the compound (21) is in a range of 30 minutes to 48 hours, preferably 45 minutes to 24 hours, and more preferably 60 minutes to 12 hours.

It is common practice that the hydroboration reaction in the scheme 6 is carried out in an adequate solvent, usually an ether solvent such as diethyl ether, tetrahydrofuran, or 1,4-dioxane, with a borylation reagent such as diborane or 9-BBN in a temperature range of 0° C. to temperature at which reflux takes place.

In the scheme 6, as the oxidation reaction, it is possible to apply any of various reactions, widely known to those skilled in the art, for oxidizing a variety of secondary hydroxy groups to ketones. For example, it is possible to employ an oxidation reaction using a halogen-based oxidizing agent made of an oxide of a metal such as chromium, manganese, ruthenium, or a salt thereof (a catalyst such as TEMPO may be added), an oxidation reaction such as a Swern oxidation using dimethyl sulfoxide together with a condensing agent, such as acid chloride, acid anhydride, or carbodiimide, and the like, and any other oxidation reaction.

In the scheme 6, the oximation can be carried out in a common method widely known to those skilled in the art, such as mixing with an acid-added salt of hydroxylamine or the like.

In the scheme 6, the Beckmann rearrangement reaction can use various reaction conditions widely known to those skilled in the art, and heating together with an acid is usually employed in particular. In some cases, the Beckmann rearrangement reaction may be carried out after the compound in which $X^2$ is NOH is converted to the compound in which $X^2$ is $NR^{39}$.

In the scheme 6, as for a substituent to be substituted at $E^1$, $E^2$, $E^3$, and $E^4$, the target substituent may be contained at the stage of the raw material (20). In this case, the intermediate (2-6) obtained contains the target substituent. Alternatively, in some cases, the intermediate (2-6) may be subjected to processes such as protection and deprotection as appropriate according to the necessity, and a substituent in the intermediate (2-6) may be converted to another target substituent, by using a combination of synthesis methods in the wide variety of various synthesis methods known to those skilled in the art, so that the intermediate (2-6) can be converted to the intermediate (2-6) having the other target substituent.

Meanwhile, in the scheme 6, as for a substituent to be substituted at $R^1$, the intermediate (2-6) may be subjected to processes such as protection and deprotection as appropriate according to the necessity, and a target substituent is introduced into the compound of the intermediate (2-6) in which $R^1$ is H by using a combination of synthesis methods in the wide variety of various synthesis methods known to those skilled in the art, so that the intermediate (2-6) can be converted to the intermediate (2-6) into which the target substituent is introduced. Meanwhile, when X is (=O) in the intermediate (2-6), the intermediate (2-6) can be converted to the intermediate (2-6) in which X is $H_2$ through a common reduction reaction or the like known to those skilled in the art.

(scheme 7)

[Chem. 14]

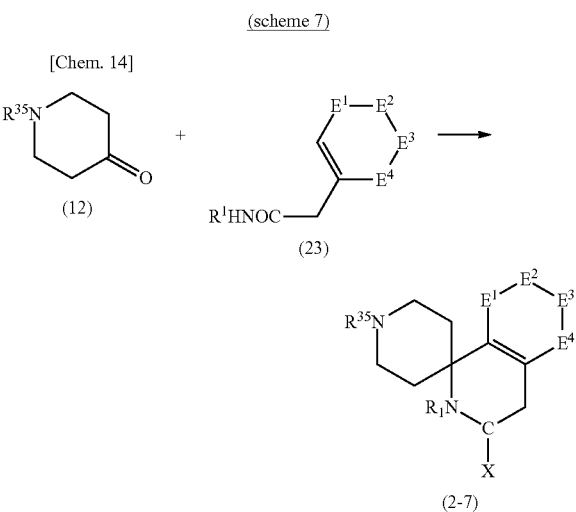

In the above formulas (23) and (2-7), $E^1$, $E^2$, $E^3$, $E^4$, and $R^1$ have the same meanings as $E^1$, $E^2$, $E^3$, $E^4$, and $R^1$ in the above general formula (1), respectively. In the above formula (2-7), $R^{35}$ has the same meaning as $R^{35}$ in the above formula (2). In the above formula (2-7), a group represented by C—X has the same meaning as $CH_2$ or CO represented by $A^3$ in the above formula (1).

The raw material (12) and a compound represented by the formula (23) (hereinafter referred to as "raw material (23)") in the scheme 7 may be commercially available reagents or can be synthesized by publicly known methods or their analogous methods.

In the scheme 7, a compound represented by the formula (2-7) (hereinafter referred to as "intermediate (2-7)") is one type of the intermediate (2) of the present invention. The intermediate (2-7) can be produced from the raw material (12) and the raw material (23) in accordance with a known method such as a method described in Chemical and Pharmaceutical Bulletin, 1998, 46, 242.

In the scheme 7, as for a substituent to be substituted at $R^1$, $E^1$, $E^2$, $E^3$, and $E^4$, the target substituent may be contained at the stage of the raw material (23). In this case, the intermediate (2-7) obtained contains the target substituent. Alternatively, in some cases, the intermediate (2-7) may be subjected to processes such as protection and deprotection as appropriate according to the necessity, and a substituent in the intermediate (2-7) may be converted to another target substituent, by using a combination of synthesis methods in the wide variety of various synthesis methods known to those skilled in the art, so that the intermediate (2-7) can be converted to the intermediate (2-7) containing the other target substituent. Meanwhile, when X is (=O) in the intermediate (2-7), the intermediate (2-7) can be converted to the intermediate (2-7) in which X is $H_2$ through a common reduction reaction or the like known to those skilled in the art.

(scheme 8)

[Chem. 15]

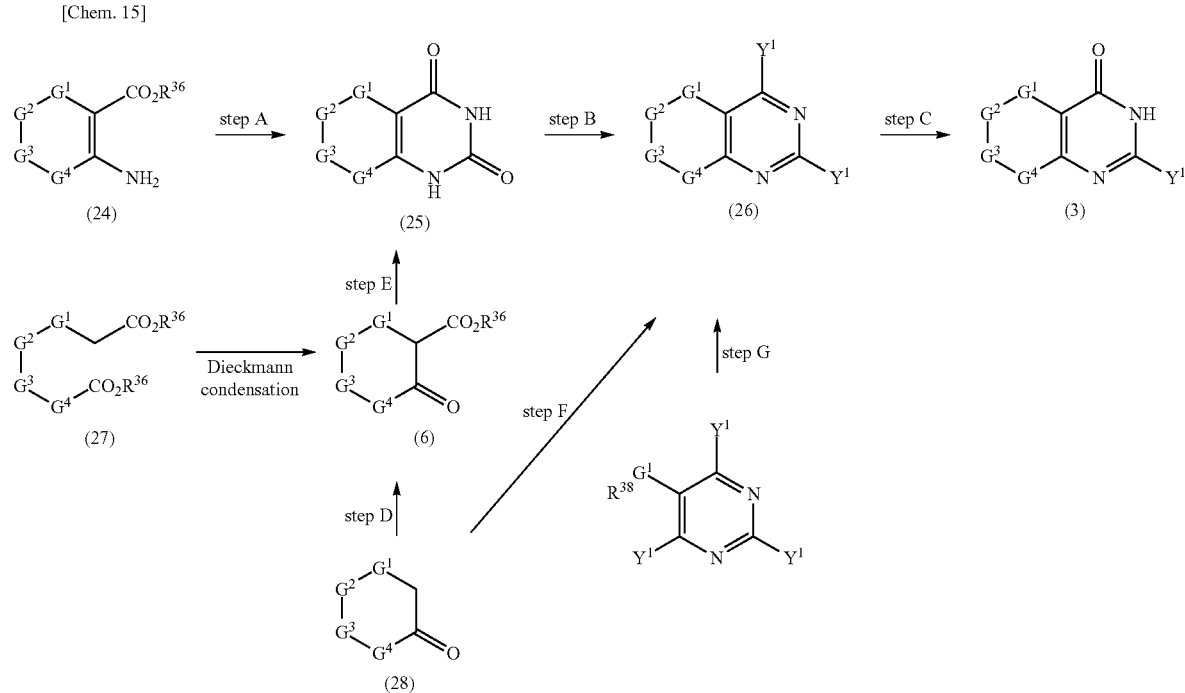

In the above formulas (24) to (29), $G^1$, $G^2$, $G^3$, and $G^4$ have the same meanings as $G^1$, $G^2$, $G^3$, and $G^4$ in the above general formula (1), respectively. In the above formulas (26) and (29), $Y^1$ has the same meaning as $Y^1$ in the above formula (3). Moreover, in the above formulas (24) and (27), $R^{36}$ represents an optionally substituted lower alkyl group. In the above formula (29), $R^3$ represents a precursor group that can form a structure represented by -$G^2$-$G^3$-$G^4$- in the above formula (26).

The raw material (3) or the raw material (6) in the production method 1 or 2 can be produced in accordance with the method described in the scheme 8 or the like. The raw material (6) can be synthesized by subjecting a compound represented by the formula (27) (a dicarboxylic acid deliberative (27)) to a Dieckmann condensation reaction or the like, or by subjecting the a position of a compound represented by the formula (28) (a ketone (28)) to a one-carbon homologation reaction (such as a method described in step D: Journal of the Chemical Society, 1910, 97, 1765). Meanwhile, the raw material (3) can be synthesized by hydrolyzing an unnecessary one of the leaving groups in a compound like a compound represented by the formula (26) (compound (26)) (such as a method described in step C: Journal of Medicinal Chemistry, 1986, 29, 62). Then, the compound (26) can be synthesized by subjecting the ketone (28) or a compound represented by the formula (29) (compound (29)) to a ring closure reaction or the like (such as a method described in step F: Medicinal Chemistry Research, 2014, 23, 3784 and such as a method described in step G: The Journal of Organic Chemistry, 2013, 78, 2144), or can be synthesized in such a way that an amidic carbonyl in a compound represented by the formula (25) (compound (25)) that can be synthesized by a condensation ring closure reaction of a compound represented by the formula (24) (compound (24)) or the raw material (6) with urea is converted to imidoyl as a leaving group (such as a method described in step A: Bioorganic & Medicinal Chemistry, 2008, 16, 7021; such as a method described in step E: Journal of Medicinal Chemistry, 2015, 58, 9480; and such as a method described in step B: Journal of Medicinal Chemistry, 2011, 54, 580). These series of synthesis methods all are methods widely described in general formulation manuals and others in organic chemistry, and can be carried out in accordance with the described methods without any change or with their improved methods.

The spiro compound represented by the general formula (1), the intermediates, the raw materials, and so on synthesized in accordance with the above methods each may be used in the subsequent step in the state of the reaction solution or in the state of the crude product, or be used in the subsequent step after being isolated by a usual purification method known to those skilled in the art. For the purification method for isolation, for example, a method or a combination of methods may be selected as appropriate from among various types of chromatography (column or thin layer, normal phase type or reverse phase type, and so on), distillation, sublimation, precipitation, crystallization, centrifugal separation, and the like.

The spiro compounds of the present invention, tautomers and stereoisomers thereof, and a mixture of these at any ratio have an excellent tankyrase inhibitory action. For this reason, in treatment for diseases caused by tankyrase and/or intracellular molecular reactions in which tankyrase is involved, an appropriate one of the above-specified compounds and others may be administered alone or in combination with at least one type of publicly-known conventional therapeutic methods including conventional surgery, radiotherapy, and anticancer drug therapy, the diseases including: various solid tumors and blood tumors (for example, fibrosarcoma, ovarian cancer, glioblastoma, pancreatic adenoma, breast cancer, astrocytoma, lung cancer, gastric cancer, liver cancer, colorectal cancer, bladder transitional epithelium cancer, leukemia, and so on); infections such as infections by Herpes simplex virus and Epstein-Barr virus; fibrosis such as pulmonary fibrosis; neurodegenerative diseases such as cherubism, multiple sclerosis, and amyotrophic lateral sclerosis; inflammatory diseases in various forms such as skin and cartilage injuries; metabolic diseases such as obesity; and so on.

The tankyrase inhibitor and the pharmaceutical composition of the present invention contain the spiro compound of the present invention as the active ingredient. Thus, the tankyrase inhibitor and the pharmaceutical composition of the present invention can be used as tumor cell proliferation inhibitors, prophylactic or therapeutic agents for malignant tumors (fibrosarcoma, ovarian cancer, glioblastoma, pancreatic adenoma, breast cancer, astrocytoma, lung cancer, gastric cancer, liver cancer, colorectal cancer, and bladder transitional epithelium cancer, and leukemia), prophylactic or therapeutic agents for Herpes simplex virus infections or Epstein-Barr virus infections, prophylactic or therapeutic agents for pulmonary fibrosis, prophylactic or therapeutic agents for multiple sclerosis, and prophylactic or therapeutic agents for amyotrophic lateral sclerosis.

The tankyrase inhibitor and the pharmaceutical composition of the present invention may further contain a therapeutic agent other than the spiro compound of the present invention. Examples of the therapeutic agent include: anticancer agents (cell proliferation inhibitors, antineoplastic agents, DNA damaging agents and combinations thereof), more specifically, alkylating agents, antimetabolites, antitumor antibiotics, antimitotic agents, and topoisomerase inhibitors; growth factor function inhibitors such as mitotic inhibitors and EGFR antibodies; vasodilator inhibitors such as VEGFR antibodies; cancer cell metastasis inhibitors such as metalloprotease inhibitors; antisense therapeutics such as Ras antisense; immunotherapeutic agents with anti-PD-1 antibodies, T cells, and the like; and so on. These agents may be used alone or be used in a combination of two or more.

The tankyrase inhibitor and the pharmaceutical composition of the present invention may be given through any route among oral and parenteral administration routes such as inhalation administration, nasal administration, ophthalmic administration, subcutaneous administration, intravenous administration, intramuscular administration, rectal administration, transdermal administration, and can be administered to human and animals other than the human. Accordingly, the tankyrase inhibitor and the pharmaceutical composition of the present invention can be produced in any dosage form suitable for the administration route.

Specific examples of the dosage forms of the tankyrase inhibitor and the pharmaceutical composition of the present invention include: oral preparations such as tablets, pills, capsules, granules, powders, fine granules, troches, elixirs, suspensions, emulsions, and syrups; external liquid agents such as inhalants, nasal solutions, and ophthalmic solutions; injections such as intravenous injections and intramuscular injections; and parenteral preparations such as rectal administration agents, suppositories, lotions, sprays, ointments, creams, and patches.

The tankyrase inhibitor and the pharmaceutical composition of the present invention may further contain additives usually used in the field of pharmacy depending on the dosage form, the additives including excipients, bulking agents, moisturizers, surfactants, disintegrants, binders, lubricants, dispersants, buffering agents, preservatives, solubilizing agents, antiseptic agents, flavoring agents, analgesic agents, stabilizers, lubricating agents, coloring agents, and the like, and may be produced in accordance with a usual method using the above additives. Examples of the additives include lactose, fructose, glucose, starch, gelatin, magnesium carbonate, synthetic magnesium silicate, talc, magnesium stearate, methyl cellulose, carboxymethyl cellulose or a salt thereof, gum arabic, olive oil, propylene glycol, polyethylene glycol, syrup, petroleum jelly, glycerin, ethanol, citric acid, sodium chloride, sodium sulfite, sodium phosphate, and so on.

In the tankyrase inhibitor and the pharmaceutical composition of the present invention, a content of the spiro compound of the present invention (the total content of a mixture in the case where the spiro compound is the mixture of substances such as the compound represented by the general formula (1), a pharmaceutically acceptable salt thereof, their tautomers and stereoisomers, and so on) cannot be determined unconditionally, because the content is to be adjusted as appropriate depending on the dosage form, but is usually 0.01 to 70% by mass and preferably 0.05 to 50% by mass in terms of a free form with respect to the total mass of the pharmaceutical composition. A dosage of the spiro compound of the present invention cannot be determined unconditionally because the dosage is to be adjusted as appropriate depending on an individual case by taking into account a usage, the age, body weight, and sex of a patient, a disease difference, a degree of symptom, and the like, but a usual dosage for adjust is 0.1 to 2000 mg and preferably 1 to 1000 mg per day, and this dosage is administered once or in several portions a day.

EXAMPLES

Hereinafter, the present invention is described in more details by using Examples. However, the scope of the present invention is not to be limited to Examples below, and it is as a matter of course that the present invention can be applied, modified, and altered in various manners without departing from the scope of the present invention. In addition, although the production methods of the intermediates, the raw materials, and the like used in Examples are described as Reference Examples, they are also just illustrative examples for explaining specific ways to carry out the present invention, and the illustrative examples do not limit the scope of the present invention. It is as a matter of course that the production methods can be applied, modified, and altered in various manners without departing from the scope of the present invention.

Abbreviations used below in Examples and Reference Examples are used to indicate the following meanings.

M: mol/L $^1$H-NMR: Proton nuclear magnetic resonance spectrum (270 MHz or 400 MHz)

MS(ESI): Mass spectrum (electrospray ionization method)

DMSO: Dimethylsulfoxide

Bzl: Benzyl

MPM: 4-methoxyphenylmethyl, 4-methoxybenzyl

TBS: Tert-butyldimethylsilyl

Cbz: Benzyloxycarbonyl

Boc: Tert-butyloxycarbonyl

Ts: Paratoluenesulfonyl

Reference Example 1

2-chloro-8-(trifluoromethyl)quinazolin-4(3H)-one

[Chem. 16]

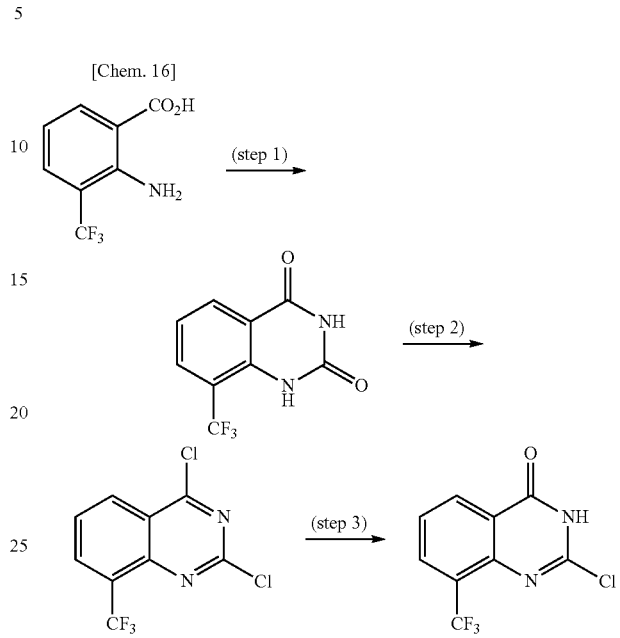

<Step 1>

First, a reaction of 2-amino-3-(trifluoromethyl)benzoic acid (5.0 g) and urea (15 g) proceeded at 200° C. for 8 hours. The obtained reaction mixture wads cooled to 100° C., then water (20 mL) was added thereto, and the precipitate was collected by filtration. The precipitate was dissolved in a 0.5 M sodium hydroxide aqueous solution (150 mL), and unsolved matters were removed by filtration. The resultant solution was acidified with 5 M hydrochloric acid under ice cooling, the precipitate generated was collected by filtration, and the filter cake was washed with water and methanol in sequence, and then was dried under reduced pressure to obtain 8-(trifluoromethyl)quinazoline-2,4(1H,3H)-dione (2.9 g).

<Step 2>

The 8-(trifluoromethyl)quinazoline-2,4(1H,3H)-dione (690 mg) was suspended in phosphorus oxychloride (3.4 mL), followed by addition of N,N-dimethylaniline (1.0 mL) to allow a reaction to proceed at 100° C. for 4 hours. The reaction mixture was condensed under reduced pressure, and the residue was diluted with methylene chloride under ice cooling and was washed with water. Thereafter, the organic layer was dried with anhydrous sodium sulfate, and purified by silica gel column chromatography (ethyl acetate/hexane=15/1 to 5/1) to obtain 2,4-dichloro-8-(trifluoromethyl)quinazoline (407 mg).

<Step 3>

The 2,4-dichloro-8-(trifluoromethyl)quinazoline (407 mg) was dissolved in 1,4-dioxane (11.4 mL), a 1 M sodium hydroxide aqueous solution (3.1 mL) was added thereto, and the mixture was stirred at room temperature for 1 hour. The reaction mixture was cooled by ice, 1 M hydrochloric acid (3.1 mL) was added thereto, and the resultant mixture was subjected to extraction with ethyl acetate. The organic layer was washed with water and saturated brine in sequence and was dried with anhydrous magnesium sulfate, and the solvent was removed by evaporation under reduced pressure.

The residue was precipitated from methylene chloride and n-hexane to obtain the title compound (237 mg).

$^{1}$H-NMR (400 MHz, DMSO-$d_{6}$) δ: 7.68 (t, J=7.8 Hz, 1H), 8.20 (dd, J=7.6, 0.9 Hz, 1H), 8.36 (dd, J=7.9, 1.1 Hz, 1H), 13.62 (br.s, 1H).

Reference Example 2

Methyl 4-oxotetrahydro-2H-thiopyran-3-carboxylate

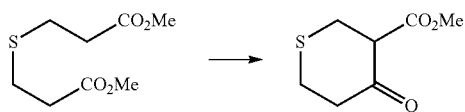

[Chem. 17]

Dimethyl 3,3'-thiodipropionate (2.15 g) was dissolved in tetrahydrofuran, sodium hydride (0.509 g) was added thereto, and the mixture was stirred under reflux by heating for 1 hour. A saturated ammonium chloride aqueous solution was added to the reaction solution, followed by extraction with chloroform. The organic layer was dried with anhydrous magnesium sulfate and was concentrated under reduced pressure, and the obtained residue was purified by silica gel column chromatography (hexane/ethyl acetate=50/50) to obtain the title compound.

MS(ESI) m/z: 175[M+H]$^{+}$.

Reference Example 3

2-chloro-5,6,7,8-tetrahydroquinazolin-4(3H)-one

[Chem. 18]

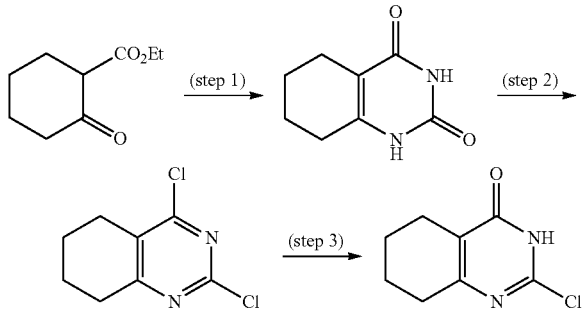

<Step 1>

First, urea (1.2 g) and sodium ethoxide (about 2.88 M ethanol solution) (10.4 mL) were added to a solution of ethyl 2-oxocyclohexane-1-carboxylate (1.7 g) in ethanol (20 mL), and the mixture was refluxed by heating for 3.5 hours. The reaction mixture was diluted with water and was acidified with 5 M hydrochloric acid, and the precipitate generated was collected by filtration, and was dried to obtain 5,6,7,8-tetrahydroquinazoline-2,4(1H,3H)-dione (0.67 g).

<Step 2>

Phosphorus oxychloride (4 mL) was added to the 5,6,7,8-tetrahydroquinazoline-2,4(1H,3H)-dione (0.60 g), and the mixture was stirred at 100° C. for 2.5 hours. The reaction mixture was poured into ice water, and the precipitate generated was collected by filtration and was dried to obtain 2,4-dichloro-5,6,7,8-tetrahydroquinazoline (0.56 g).

<Step 3>

The 2,4-dichloro-5,6,7,8-tetrahydroquinazoline (0.31 g) was suspended in water (5.4 mL), a 5 M sodium hydroxide aqueous solution (3.6 mL) was added thereto, and the mixture was refluxed by heating for 1 hour. After extraction with ethyl acetate, the organic layer was washed with water and saturated brine in sequence, and was dried with anhydrous magnesium sulfate, and the solvent was removed by evaporation under reduced pressure. The obtained residue was precipitated from n-hexane to obtain the title compound (0.19 g).

$^{1}$H-NMR (400 MHz, DMSO-$d_{6}$) δ: 1.62-1.76 (m, 4H), 2.30-2.40 (m. 2H), 2.50-2.59 (m, 2H), 13.07 (br.s, 1H).

Reference Example 4

2-(methylsulfonyl)-3,5,6,7-tetrahydro-4H-pyrano[2,3-d]pyrimidin-4-one

[Chem. 19]

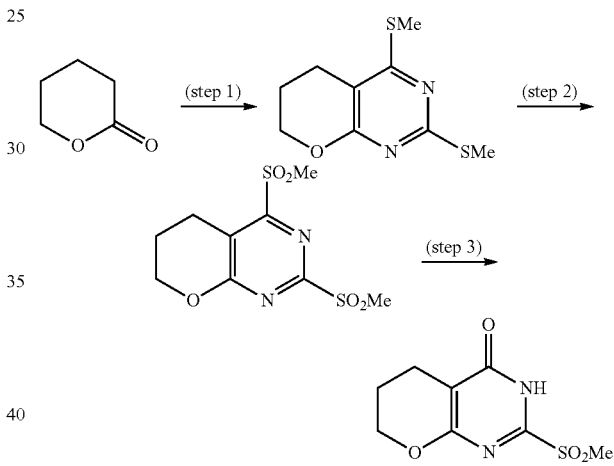

<Step 1>

First, δ-valerolactone (503.0 mg) was dissolved in chloroform, then methyl thiocyanate (1.36 mL) and trifluoromethanesulfonic anhydride (1.65 mL) were added thereto, and the mixture was stirred at room temperature for 60 hours. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (ethyl acetate/hexane=20/80) to obtain 2,4-bis(methylthio)-6,7-dihydro-5H-pyrano[2,3-d]pyrimidine (242.7 mg).

$^{1}$H-NMR (400 MHz, CDCl$_{3}$) δ: 2.00-2.07 (m, 2H), 2.51-2.55 (m, 5H), 2.57 (s, 3H), 4.30-4.34 (m, 2H).

<Step 2>

The 2,4-bis(methylthio)-6,7-dihydro-5H-pyrano[2,3-d]pyrimidine (242.7 mg) was dissolved in chloroform, 3-chloroperbenzoic acid (1.5721 g) was added thereto, and the mixture was stirred at room temperature for 14 hours. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (ethyl acetate/hexane=65/35) to obtain 2,4-bis(methylsulfonyl)-6,7-dihydro-5H-pyrano[2,3-d]pyrimidine (158.3 mg).

$^1$H-NMR (400 MHz, CDCl$_3$) δ: 2.13-2.20 (m, 2H), 3.32-3.37 (m, 5H), 3.44 (s, 3H), 4.57-4.61 (m, 2H).

<Step 3>

The 2,4-bis(methylsulfonyl)-6,7-dihydro-5H-pyrano[2,3-d]pyrimidine (158.3 mg) was dissolved in acetonitrile, a 1 M sodium hydroxide aqueous solution (0.5 mL) was added thereto, and the mixture was stirred at room temperature for 1 hour. A 1 M hydrochloric acid aqueous solution was added to the reaction solution, followed by extraction with chloroform. The organic layer was dried with anhydrous magnesium sulfate and was concentrated under reduced pressure, and the obtained residue was purified by silica gel column chromatography (methanol/chloroform=10/90) to obtain the title compound (124.7 mg).

MS(ESI) m/z: 231[M+H]$^+$.

Reference Example 5

2-chloro-8-methyl-7,8-dihydropyrido[2,3-d]pyrimidin-4,5(3H, 6H)-dione

[Chem. 20]

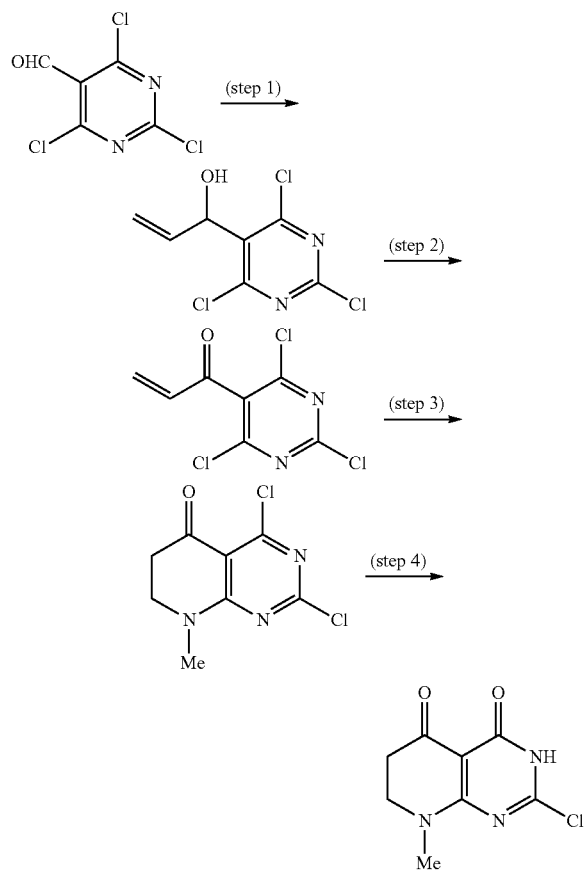

<Step 1>

First, 2,4,6-trichloro-5-pyrimidinecarboxyaldehyde (867.5 mg) was dissolved in tetrahydrofuran, followed by ice-cooling, then vinyl magnesium bromide (about 1 mol/L tetrahydrofuran solution) (4.3 mL) was added thereto, and the mixture was stirred at 0° C. for 1 hour. A saturated ammonium chloride aqueous solution was added to the reaction solution, followed by extraction with chloroform. The organic layer was dried with anhydrous magnesium sulfate and was concentrated under reduced pressure, and the obtained residue was purified by silica gel column chromatography (ethyl acetate/hexane=20/80) to obtain 1-(2,4,6-trichloropyrimidin-5-yl)prop-2-ene-1-ol (753.3 mg).

MS(ESI) m/z: 239[M+H]$^+$.

<Step 2>

The 1-(2,4,6-trichloropyrimidin-5-yl)prop-2-ene-1-ol (753.3 mg) was dissolved in chloroform, a Dess-Martin reagent (1.7344 g) was added thereto, and the mixture was stirred at room temperature for 1 hour. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (ethyl acetate/hexane=20/80) to obtain 1-(2,4,6-trichloropyrimidin-5-yl)prop-2-ene-1-one (422.0 mg).

MS(ESI) m/z: 237 [M+H]$^+$.

<Step 3>

The 1-(2,4,6-trichloropyrimidin-5-yl)prop-2-ene-1-one (398.3 mg) was dissolved in chloroform, methylamine hydrochloride (124.6 mg) and triethylamine (0.514 mL) were added thereto, and the mixture was stirred at room temperature for 1 hour. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (ethyl acetate/hexane=20/80) to obtain 2,4-dichloro-8-methyl-7,8-dihydropyrido[2,3-d]pyrimidin-5(6H)-one (192.4 mg).

MS(ESI) m/z: 232[M+H]$^+$.

<Step 4>

The 2,4-dichloro-8-methyl-7,8-dihydropyrido[2,3-d]pyrimidin-5(6H)-one (23.1 mg) was dissolved in acetonitrile, a 1 M sodium hydroxide aqueous solution (0.2 mL) was added thereto, and the mixture was stirred at room temperature for 1 hour. A saturated ammonium chloride aqueous solution was added to the reaction solution, followed by extraction with chloroform. The organic layer was dried with anhydrous magnesium sulfate and was concentrated under reduced pressure, and the obtained residue was purified by silica gel column chromatography (methanol/chloroform=10/90) to obtain the title compound (19.8 mg).

MS(ESI) m/z: 214 [M+H]$^+$.

Compounds of Reference Example 6 to Reference Example 21 presented below in Tables 1 and 2 were obtained by using the methods used in Reference Examples 1 to 5 described above and their applied methods as well as methods known by literatures and their applied methods.

TABLE 1

| Reference Example | Compound Name | Structural formula | 1H NMR δ ppm | Solvent | ESI MS m/z |
|---|---|---|---|---|---|
| 6 | 2-chloro-7-methyl-3,7-dihydro-4H-pyrrolo[2,3-d]pyrimidin-4-one | | 3.77 (s, 3 H), 6.71 (d, J = 3.4 Hz, 1 H), 6.83 (d, J = 3.4 Hz, 1 H), 12.83 (br. s, 1 H). | CDCl3 | |
| 7 | 2-chloro-7-ethyl-3,7-dihydro-4H-pyrrolo[2,3-d]pyrimidin-4-one | | | | 198 [M + H]+ |
| 8 | 2-chloro-7-(2-hydroxyethyl)-3,7-dihydro-4H-pyrrolo[2,3-d]pyrimidin-4-one | | | | 214 [M + H]+ |
| 9 | 2-chloro-6-((4-methoxybenzyl)oxy)-9-methyl-9H-purine | | | | 305 [M + H]+ |
| 10 | 2-chloro-6-((4-methoxybenzyl)oxy)-7-methyl-7H-purine | | | | 305 [M + H]+ |
| 11 | 2-chloro-8-fluoroquinazolin-4(3H)-one | | 7.45-7.60 (m, 2 H), 8.05-8.10 (m, 1 H), 10.20 (br. s, 1 H). | CDCl3 | 197 [M + H]+ |
| 12 | 2-chloro-8-methylquinazolin-4(3H)-one | | 2.48 (s, 3 H), 7.41-7.45 (m, 1 H), 7.69-7.72 (m, 1 H), 7.92-7.95 (m, 1 H), 13.23 (br. s, 1 H). | DMSO-d6 | |
| 13 | 2-chloro-8-(hydroxymethyl)quinazolin-4(3H)-one | | 4.84 (s, 2 H), 5.28 (br. s, 1 H), 7.52-7.57 (m, 1 H), 7.89-7.93 (m, 1 H), 7.97-8.00 (m, 1 H), 13.27 (br. s, 1 H). | DMSO-d6 | |

TABLE 1-continued

| Reference Example | Compound Name | Structural formula | 1H NMR δ ppm | Solvent | ESI MS m/z |
|---|---|---|---|---|---|
| 14 | (2-chloro-4-oxo-3,4-dihydroquinazolin-8-yl)methyl acetate | | 2.16 (s. 3 H), 5.56 (s, 2 H), 7.51-7.55 (m, 1 H), 7.84-7.87 (m, 1 H), 8.25-8.28 (m, 1 H), 11.07 (br. s, 1 H). | CDCl3 | |

TABLE 2

| Reference Example | Compound Name | Structural formula | 1H NMR δ ppm | Solvent | ESI MS m/z |
|---|---|---|---|---|---|
| 15 | 2-chloropyrido[2,3-d]pyrimidin-4(3H)-one | | 7.55-7.60 (m, 1 H), 8.45-8.52 (m, 1 H), 8.93-8.97 (m, 1 H), 13.55 (br. s, 1 H). | DMSO-d6 | 197 [M + H]+ |
| 16 | 2-chloro-5,6,7,8-tetrahydropyrido[2,3-d]pyrimidin-4(3H)-one | | 1.65-1.80 (m, 2 H), 2.32-2.40 (m, 2 H), 3.17-3.25 (m, 2 H), 7.37 (s, 1 H), 11.80 (br. s, 1 H). | DMSO-d6 | |
| 17 | 2-chloro-8-methyl-5,6,7,8-tetrahydropyrido[2,3-d]pyrimidin-4(3H)-one | | 1.85-1.93 (m, 2 H), 2.55-2.60 (m, 2 H), 3.13 (s, 3 H), 3.30-3.38 (m, 2 H). | CDCl3 | |
| 18 | 2-chloro-8-(methyl-d3)-5,6,7,8-tetrahydropyrido[2,3-d]pyrimidin-4(3H)-one | | 1.85-1.92 (m, 2 H), 2.55-2.61 (m, 2 H), 3.30-3.35 (m, 2 H), 13.23 (br. s, 1 H). | CDCl3 | |
| 19 | 2-chloro-8-ethyl-5,6,7,8-tetrahydropyrido[2,3-d]pyrimidin-4(3H)-one | | 1.14 (t, J = 7.1 Hz, 3H), 1.83-1.90 (m, 2 H), 2.54-2.60 (m, 2 H), 3.31-3.36 (m, 2 H), 3.60 (q, J = 7.1 Hz, 2 H). | CDCl3 | |

TABLE 2-continued

| Reference Example | Compound Name | Structural formula | 1H NMR δ ppm | Solvent | ESI MS m/z |
|---|---|---|---|---|---|
| 20 | methyl 2-(2-chloro-4-oxo-3,5,6,7-tetrahydropyrido[2,3-d]pyrimidin-8(4H)-yl) acetate | | 1.90-1.97 (m, 2 H), 2.58-2.62 (m, 2 H), 3.37-3.42 (m, 2 H), 3.75 (s, 3 H), 4.33 (s, 2 H), 13.23 (br. s, 1 H). | CDCl3 | |
| 21 | 7-(tert-butyloxycarbonyl)-2-chloro-4-[(4-methoxybenzyl)oxy]-5,6,7,8-tetrahydropyrido[3,4-d]pyrimidine | | 1.47 (s, 9 H), 2.61-2.66 (m, 2 H), 3.61-3.66 (m, 2 H), 3.82 (s, 3 H), 4.52 (s, 2 H), 5.39 (s, 2 H), 6.89-6.93 (m, 2 H), 7.36-9.40 (m, 2 H). | CDCl3 | |

Reference Example 23

1'-benzyl-5-methoxy-3H-spiro[isobenzofuran-1,4'-piperidin]-3-one hydrochloride

[Chem. 21]

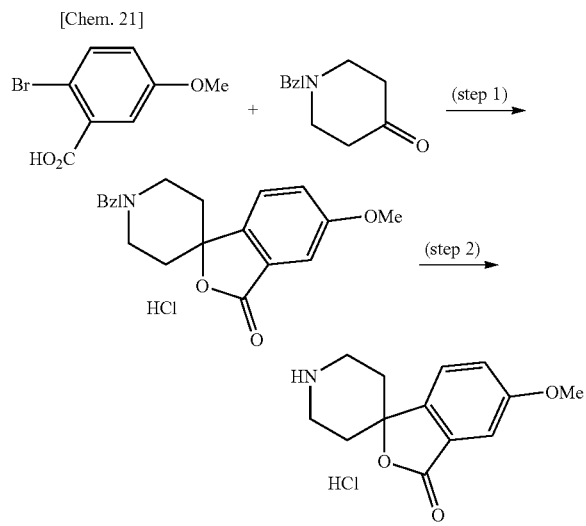

<Step 1>

First, a solution of 2-bromo-5-methoxybenzoic acid (231 mg) in tetrahydrofuran (5 mL) was cooled to −78° C., n-butyl lithium (2.7 M hexane solution) (0.8 mL) was added dropwise thereto, and the mixture was stirred for 1 hour. Then, a solution of 1-benzylpiperidin-4-one (189 mg) in tetrahydrofuran was added dropwise thereto, and the mixture was heated to room temperature and was stirred for 1 hour. A saturated ammonium chloride aqueous solution was added to the reaction mixture, followed by concentration under reduced pressure. Methanol (3 mL) and concentrated hydrochloric acid (1 mL) were added to the residue, and the mixture was stirred at 60° C. for 1.5 hours, then was concentrated under reduced pressure, and was rendered alkaline with a 5 M sodium hydroxide aqueous solution, followed by extraction with ethyl acetate. The organic layer was washed with saturated brine, and wad dried with anhydrous magnesium sulfate, and the solvent was removed by evaporation under reduced pressure. The residue was purified by silica gel column chromatography (ethyl acetate/hexane=33/67), and was precipitated from a 1 M hydrogen chloride/ethyl acetate solution and n-hexane to obtain 1'-benzyl-5-methoxy-3H-spiro[isobenzofuran-1,4'-piperidin]-3-one hydrochloride (250 mg).

$^{1}$H-NMR (400 MHz, D$_2$O) δ: 2.00-2.07 (m, 2H), 2.46 (t, J=12.8 Hz, 2H), 3.41-3.54 (m, 2H), 3.62 (d, J=11.0 Hz, 2H), 3.88 (s, 3H), 4.44 (s, 2H), 7.34-7.45 (m, 2H), 7.50-7.57 (m, 6H).

MS(ESI) m/z: 324[M+H]$^{+}$.

<Step 2>

The 1'-benzyl-5-methoxy-3H-spiro[isobenzofuran-1,4'-piperidin]-3-one hydrochloride (311 mg) was dissolved in methanol (13.6 mL) and a 4 M ethyl chloride hydrogen acetate solution, then 20% palladium hydroxide carbon (64 mg) was added thereto, and the mixture was vigorously stirred under a hydrogen atmosphere at room temperature for 8 hours. The reaction mixture was passed through a membrane filter to remove the catalyst, and then the solvent was removed by evaporation under reduced pressure. The residue was precipitated from methanol, ethyl acetate, and n-hexane to obtain 5-methoxy-3H-spiro[isobenzofuran-1,4'-piperidine]-3-one hydrochloride (209 mg).

$^{1}$H-NMR (400 MHz, D$_2$O) δ: 2.02 (d, J=14.7 Hz, 2H), 2.44 (td, J=14.4, 5.0 Hz, 2H), 3.44 (td, J=13.4, 3.2 Hz, 2H), 3.53-3.62 (m, 2H), 3.89 (s, 3H), 7.41 (d, J=5.2 Hz, 1H), 7.41 (s, 1H), 7.52-7.58 (m, 1H).

Reference Example 24

Spiro[isochroman-3,4'-piperidine]-1-one hydrochloride

[Chem. 22]

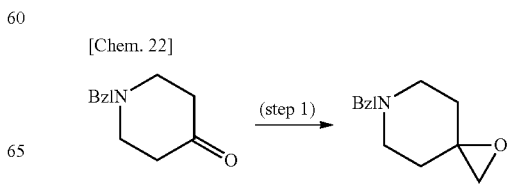

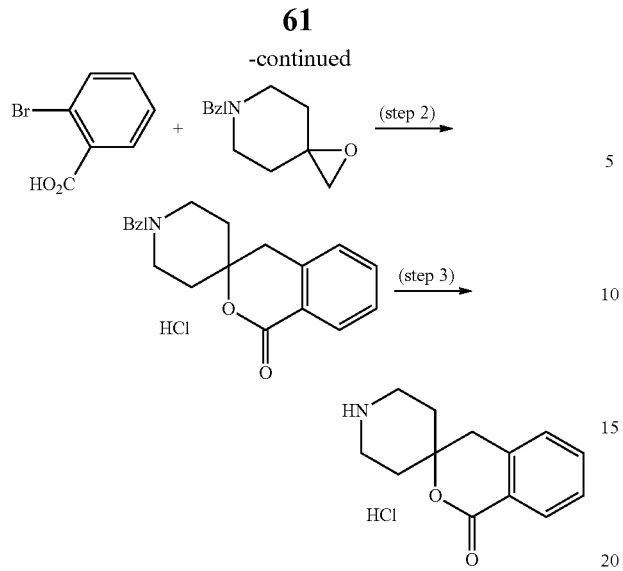

<Step 1>

First, trimethylsulfoxonium iodide (3.3 g) was dissolved in dimethylsulfoxide (12 mL). At room temperature, sodium hydride (0.6 g) was added thereto and the mixture was stirred for 1 hour. A solution of 1-benzylpiperidin-4-one (1.9 g) in dimethylsulfoxide was added dropwise thereto, and the mixture was stirred at the same temperature for 3 hours. The reaction mixture was diluted with water, followed by extraction with diethyl ether. The organic layer was washed with saturated brine, and was dried with anhydrous magnesium sulfate. Then, the solvent was removed by evaporation under reduced pressure. The obtained residue was purified by silica gel column chromatography (ethyl acetate/n-hexane=50/50 to 67/33) to obtain 6-benzyl-1-oxa-6-azaspiro[2.5]octane (1.6 g).

$^1$H-NMR (400 MHz, CDCl$_3$) δ: 1.51-1.62 (m, 2H), 1.84 (ddd, J=13.2, 8.4, 4.6 Hz, 2H), 2.56-2.66 (m, 4H), 2.85 (s, 2H), 3.57 (s, 2H), 7.22-7.30 (m, 1H), 7.28-7.36 (m, 4H).

<Step 2>

A solution of 2-bromobenzoic acid (303 mg) in tetrahydrofuran (9 mL) was cooled to −78° C., n-butyl lithium (2.65 M hexane solution) (1.14 mL) was added dropwise thereto, and the mixture was stirred for 30 minutes. Next, a solution of the 6-benzyl-1-oxa-6-azaspiro[2.5]octane (102 mg) in tetrahydrofuran (1 mL), and a boron trifluoride diethyl ether complex (0.38 mL) were added dropwise thereto in sequence. The mixture was stirred at the same temperature for 1 hour. A saturated ammonium chloride aqueous solution was added to the reaction mixture, and the mixture was heated to room temperature, and then was concentrated under reduced pressure. Methanol (2.6 mL) and concentrated hydrochloric acid (0.9 mL) were added to the residue, the mixture was stirred at 60° C. for 1 hour, then was concentrated under reduced pressure, and was rendered alkaline with a 5 M sodium hydroxide aqueous solution, followed by extraction with ethyl acetate. The organic layer was washed with saturated brine, and was dried with anhydrous sodium sulfate. The solvent was removed by evaporation under reduced pressure. The residue was purified by silica gel column chromatography (ethyl acetate/n-hexane) and was precipitated from methanol, a 1 M hydrogen chloride/ethyl acetate solution, and n-hexane to obtain 1'-benzylspiro[isochroman-3,4'-piperidine]-1-one hydrochloride (125 mg).

<Step 3>

The title compound (88 mg) was obtained from the 1'-benzylspiro[isochroman-3,4'-piperidine]-1-one hydrochloride (125 mg) in the same way as in <step 2> of Reference Example 23.

$^1$H-NMR (400 MHz, CD$_3$OD) δ: 1.94-2.04 (m, 2H), 2.14-2.21 (m, 2H), 3.21 (s, 2H), 3.33-3.39 (m, 4H), 7.40 (d, J=7.6 Hz, 1H), 7.47 (t, J=7.6 Hz, 1H), 7.66 (td, J=7.5, 1.4 Hz, 1H), 8.04 (dd, J=7.8, 0.9 Hz, 1H).

Reference Example 25

7-fluoro-5-[(4-methoxybenzyl)oxy]-3H-spiro[isobenzofuran-1, 4'-piperidin]-3-one hydrochloride

[Chem. 23]

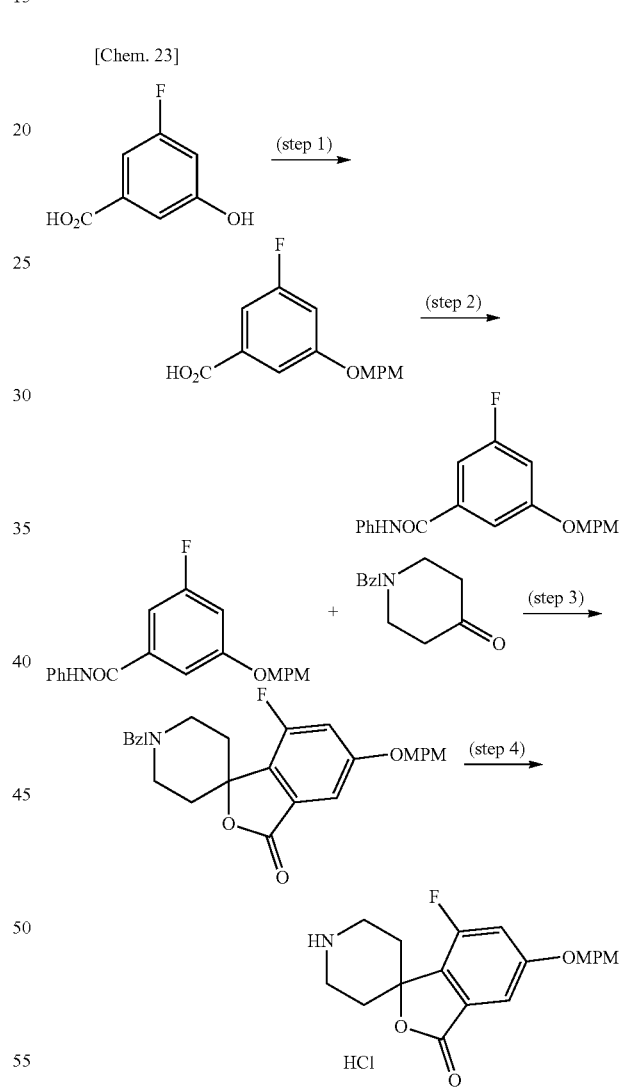

<Step 1>

First, potassium carbonate (2.07 g) and 4-methoxybenzyl chloride (1.43 mL) were added to a solution of 3-fluoro-5-hydroxybenzoic acid (781 mg) in N,N-dimethylformamide (10 mL). The mixture was stirred at room temperature for 15 hours and then was stirred at 50° C. for 3 hours. After cooling, the reaction mixture was diluted with water, followed by extraction with ethyl acetate. The organic layer was washed with saturated brine, and was dried with anhydrous magnesium sulfate. Then, the solvent was removed by evaporation under reduced pressure. The obtained residue was dissolved in methanol (5 mL) and tetrahydrofuran (10 mL), a 5 M sodium hydroxide aqueous solution was added thereto, and the mixture was stirred at room temperature for 1.5 hours. Then, 5 M hydrochloric acid and a 10% potassium dihydrogen phosphate aqueous solution were added to the reaction solution in sequence to adjust the pH to 3 to 4, and most of the tetrahydrofuran was removed by evaporation through concentration under reduced pressure. Then, the resultant mixture was aged at 0° C., and the precipitate was collected by filtration to obtain 3-fluoro-5-[(4-methoxybenzyl)oxy]benzoic acid (1330 mg).

$^1$H-NMR (400 MHz, DMSO-$d_6$) δ: 3.76 (s, 3H), 5.10 (s, 2H), 6.93-6.98 (m, 2H), 7.18 (dt, J=10.7, 2.4 Hz, 1H), 7.21-7.27 (m, 1H), 7.35 (dd, J=2.1, 1.3 Hz, 1H), 7.37-7.41 (m, 2H), 13.30 (br.s, 1H).

<Step 2>

Aniline (0.21 mL), 1-hydroxybenzotriazol (311 mg), 1-(3-dimethylaminopropyl)-3-ethylcarbodiimide hydrochloride (441 mg), and triethylamine (0.36 mL) were added to a solution of 3-fluoro-5-[(4-mgethoxybenzyl)oxy]benzoic acid (553 mg) in N,N-dimethylformamide (4 mL), and the mixture was stirred at room temperature for 14 hours. A 10% citric acid aqueous solution was added to the reaction mixture, followed by extraction with ethyl acetate. The organic layer was washed with a 10% citric acid aqueous solution, a 10% sodium carbonate aqueous solution, and saturated brine in sequence, and was dried with anhydrous magnesium sulfate. Then, the solvent was removed by evaporation under reduced pressure. The obtained residue was precipitated from methanol and water to obtain 3-fluoro-5-[(4-methoxybenzyl)oxy]-N-phenylbenzamide (685 mg).

$^1$H-NMR (400 MHz, CDCl$_3$) δ: 3.84 (s, 3H), 5.05 (s, 2H), 7.70 (br.s, 1H), 6.86 (dt, J=10.2, 2.2 Hz, 1H), 6.91-6.97 (m, 2H), 7.13-7.22 (m, 2H), 7.28 (t, J=1.7 Hz, 1H), 7.34-7.42 (m, 4H), 7.62 (d, J=7.9 Hz, 2H).

<Step 3>

A solution of 3-fluoro-5-[(4-methoxybenzyl)oxy]-N-phenylbenzamide (211 mg) in tetrahydrofuran (4.8 mL) was cooled to −78° C., sec-butyl lithium (1.00 M hexane solution) (1.24 mL) was added dropwise thereto, and the mixture was stirred at −55° C. for 1 hour. Next, a solution of 1-benzylpiperidin-4-one (114 mg) in tetrahydrofuran (1.2 mL) was added dropwise thereto, and the mixture was heated to room temperature and was stirred for 1 hour. The solvent was removed by evaporation under reduced pressure, and the residue was diluted with ethyl acetate. The organic layer was washed with a saturated ammonium chloride aqueous solution, water, and saturated brine in sequence, and was dried with anhydrous sodium sulfate, and the solvent was removed by evaporation under reduced pressure. The obtained residue was purified by silica gel column chromatography (ethyl acetate/n-hexane=20/80 to 50/50), and was precipitated from the ethyl acetate and n-hexane to obtain 1'-benzyl-7-fluoro-5[(4-methoxybenzyl)oxy]-3H-spiro[isobenzofuran-1,4'-piperidin]-3-one (93 mg).

$^1$H-NMR (400 MHz, CDCl$_3$) δ: 1.67 (d, J=12.1 Hz, 2H), 2.42-2.57 (m, 4H), 2.91 (d, J=11.7 Hz, 2H), 3.62 (s, 2H), 3.83 (s, 3H), 5.04 (s, 2H), 6.92-6.97 (m, 3H), 7.22 (d, J=2.1 Hz, 1H), 7.25-7.30 (m, 1H), 7.31-7.41 (m, 6H).

<Step 4>

Then, α-chloroethyl chloroformate (0.014 mL) was added to a solution of 1'-benzyl-7-fluoro-5[(4-methoxybenzyl)oxy]-3H-spiro[isobenzofuran-1,4'-piperidin]-3-one (45 mg) in 1,2-dichloroethane (1 mL), and the mixture was refluxed by heating for 30 minutes.

After the solvent was removed by evaporation under reduced pressure, methanol (1 mL) was added thereto, and the mixture was refluxed by heating for 30 minutes. The reaction mixture was ice-cooled and the precipitate generated was collected by filtration to obtain the title compound (37 mg).

$^1$H-NMR (400 MHz, D$_2$O) δ: 2.06 (d, J=14.5 Hz, 2H), 2.59 (td, J=14.3, 4.3 Hz, 2H), 3.38-3.47 (m, 2H), 3.57 (dd, J=12.8, 4.3 Hz, 2H), 3.82 (s, 3H), 5.15 (s, 2H), 7.02 (d, J=8.6 Hz, 2H), 7.19 (dd, J=10.8, 1.9 Hz, 1H), 7.33 (d, J=1.9 Hz, 1H), 7.44 (d, J=8.6 Hz, 2H).

Reference Example 26

7-fluoro-5-(2-hydroxyethoxy)-3H-spiro[isobenzofuran-1,4'-piperidin]-3-one hydrochloride

[Chem. 24]

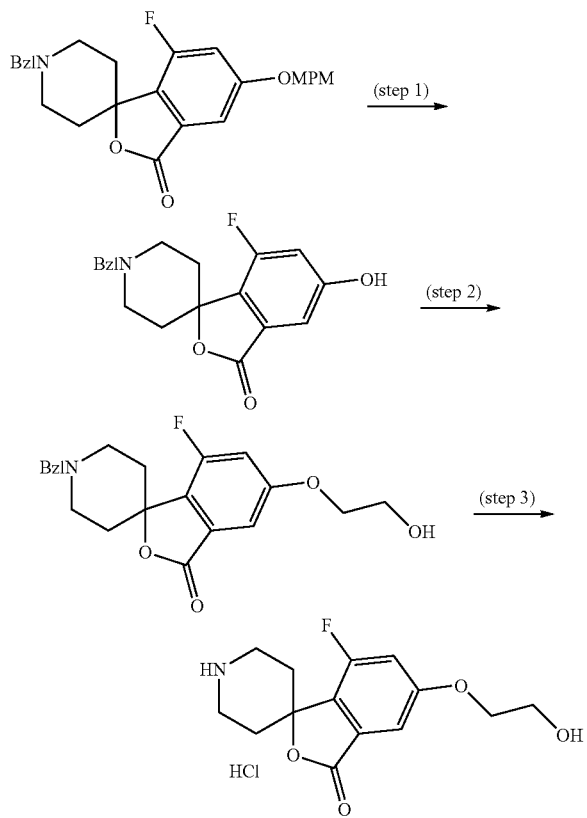

<Step 1>

First, trifluoroacetic acid (1.8 mL) was added to a solution of 1'-benzyl-7-fluoro-5[(4-methoxybenzyl)oxy]-3H-spiro[isobenzofuran-1,4'-piperidin]-3-one (118 mg) in dichloromethane (4.4 mL) under ice cooling, and the mixture was stirred at room temperature for 1 hour. The reaction mixture was diluted with ethyl acetate, and washed with a saturated sodium hydrogen carbonate aqueous solution, water, and saturated brine in sequence, the organic layer was dried with anhydrous sodium sulfate, and the solvent was removed by evaporation under reduced pressure. The obtained residue was precipitated from ethyl acetate and n-hexane to obtain 1'-benzyl-7-fluoro-5-hydroxy-3H-spiro[isobenzofuran-1,4'-piperidin]-3-one (97.4 mg).

$^1$H-NMR (400 MHz, CDCl$_3$) δ: 1.68 (d, J=12.3 Hz, 2H), 2.41-2.60 (m, 4H), 2.93 (d, J=11.7 Hz, 2H), 3.64 (s, 2H), 6.84 (dd, J=10.1, 2.0 Hz, 1H), 7.09 (d, J=2.1 Hz, 1H), 7.28-7.40 (m, 5H).

<Step 2>

The 1'-benzyl-7-fluoro-5-hydroxy-3H-spiro[isobenzofuran-1,4'-piperidin]-3-one (200 mg) was dissolved in N,N-dimethylformamide (2 mL), potassium carbonate (253 mg) and 2-bromoethanol (0.09 mL) were added thereto, and the mixture was stirred at 60° C. for 48 hours. After cooling to room temperature, water (10 mL) was added to the reaction mixture, followed by extraction with ethyl acetate. The organic layer thus collected all together was washed with water and saturated brine in sequence, and was dried with magnesium sulfate. The solvent was concentrated under reduced pressure and the obtained residue was purified by silica gel column chromatography (ethyl acetate/n-hexane=75/25 to 100/0) to obtain 1'-benzyl-7-fluoro-5-(2-hydroxyethoxy)-3H-spiro[isobenzofuran-1,4'-piperidin]-3-one (177 mg).

$^1$H-NMR (270 MHz, CDCl$_3$) δ: 1.65-1.75 (m, 2H), 1.89-2.09 (m, 1H), 2.39-2.58 (m, 4H), 2.90 (br.d, J=8.2 Hz, 2H), 3.62 (s, 2H), 3.96-4.05 (m, 2H), 4.08-4.18 (m, 2H), 6.93 (dd, J=10.2, 2.0 Hz, 1H), 7.16 (d, J=2.0 Hz, 1H), 7.27-7.41 (m, 5H).

MS(ESI) m/z: 372 [M+H]$^+$.

<Step 3>

The title compound (125 mg) was obtained from the 1'-benzyl-7-fluoro-5-(2-hydroxyethoxy)-3H-spiro[isobenzofuran-1,4'-piperidin]-3-one (159 mg) in the same way as in <Step 2> of Reference Example 23.

$^1$H-NMR (400 MHz, DMSO-d$_6$) δ: 1.97 (2H, br.d, J=14.2 Hz), 2.43-2.48 (1H, m), 2.54-2.62 (1H, m), 3.13 (2H, br.t, J=13.2 Hz), 3.38-3.47 (2H, m), 3.68-3.76 (2H, m), 4.13 (2H, t, J=4.8 Hz), 4.96 (1H, br.t, J=5.4 Hz), 7.25 (1H, d, J=2.0 Hz), 7.33 (1H, dd, J=10.9, 2.0 Hz), 9.16 (2H, br.s).

MS(ESI) m/z: 282 [M+H]$^+$.

Reference Example 27

7-fluoro-5-(2-(pyrrolidin-1-yl)ethoxy)-3H-spiro[isobenzofuran-1,4'-piperidin]-3-one dihydrochloride

[Chem. 25]

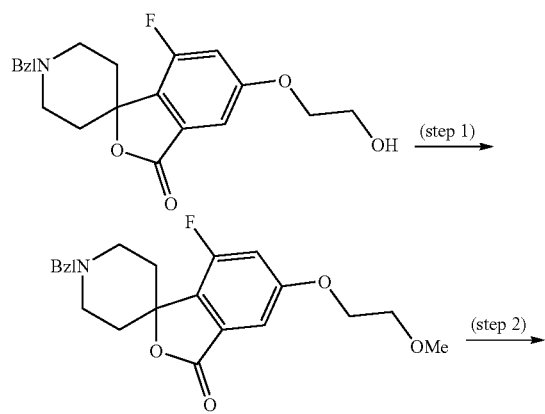

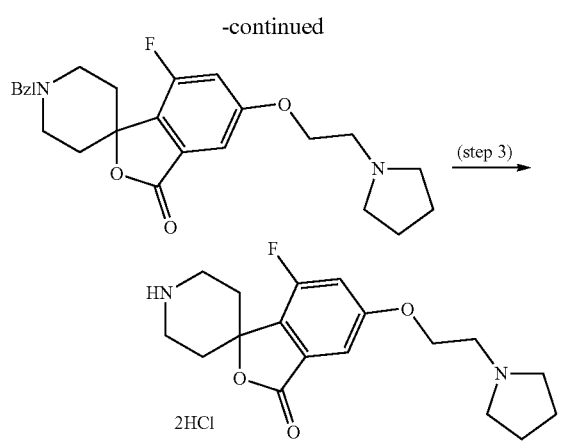

<Step 1>

First, 1'-benzyl-7-fluoro-5-(2-hydroxyethoxy)-3H-spiro[isobenzofuran-1,4'-piperidin]-3-one (300 mg) was dissolved in dichloromethane (6 mL), triethylamine (0.169 mL) was added thereto, and the mixture was stirred under ice cooling. Next, methanesulfonyl chloride (0.075 mL) was added thereto, and the mixture was stirred for 3 hours under ice cooling. The reaction mixture was diluted with dichloromethane, was washed with saturated brine, and was dried with magnesium sulfate. Thereafter, the solvent was concentrated under reduced pressure. The residue was purified by silica gel column chromatography (ethyl acetate/n-hexane=50/50 to 80/20) to obtain 2-[(1'-benzyl-7-fluoro-3-oxo-3H-spiro[isobenzofuran-1,4'-piperidin]-5-yl)oxy]ethyl methanesulfonate (325 mg).

$^1$H-NMR (270 MHz, CDCl$_3$) δ: 1.58-1.71 (m, 2H), 2.39-2.58 (m, 4H), 2.84-2.97 (m, 2H), 3.10 (s, 3H), 3.62 (s, 2H), 4.27-4.33 (m, 2H), 4.56-4.62 (m, 2H), 6.93 (dd, J=10.1, 2.0 Hz, 1H), 7.15 (d, J=2.0 Hz, 1H), 7.28-7.41 (m, 5H).

MS(ESI) m/z: 450[M+H]$^+$.

<Step 2>

Then, the 2-[(1'-benzyl-7-fluoro-3-oxo-3H-spiro[isobenzofuran-1,4'-piperidin]-5-yl)oxy]ethyl methanesulfonate (50 mg) was dissolved in N,N-dimethylformamide (1.0 mL), pyrrolidine (0.0465 mL) was added thereto, and the mixture was stirred at room temperature for 72 hours. The reaction solution was diluted with ethyl acetate and was washed with water. The aqueous layer was subjected to extraction with ethyl acetate. The organic layer thus collected all together was washed with water and saturated brine in sequence, and was dried with magnesium sulfate. Then, the solvent was concentrated under reduced pressure. The residue was purified by silica gel column chromatography (chloroform/methanol=100/0 to 90/10) to obtain 1'-benzyl-7-fluoro-5-[2-(pyrrolidin-1-yl)ethoxy]-3H-spiro[isobenzofuran-1,4'-piperidin]-3-one (39.7 mg).

$^1$H-NMR (270 MHz, CDCl$_3$) δ: 1.62-1.71 (m, 2H), 1.75-1.88 (m, 4H), 2.33-2.55 (m, 4H), 2.55-2.67 (m, 4H), 2.83-2.98 (m, 4H), 3.61 (s, 2H), 4.14 (t, J=5.8 Hz, 2H), 6.93 (dd, J=10.6, 2.0 Hz, 1H), 7.15 (d, J=2.0 Hz, 1H), 7.23-7.41 (m, 5H).

MS(ESI) m/z: 425[M+H]$^+$.

<Step 3>

The title compound (34.2 mg) was obtained from the 1'-benzyl-7-fluoro-5-[2-(pyrrolidin-1-yl)ethoxy]-3H-spiro[isobenzofuran-1,4'-piperidin]-3-one (39.7 mg) in the same way as in <Step 2> of Reference Example 23.

MS(ESI) m/z: 335[M+H]$^+$.

Reference Example 28

5-[methyl(pyridin-3-ylmethyl)amino)-3H-spiro[isobenzofuran-1,4'-piperidin]-3-one

[Chem. 26]

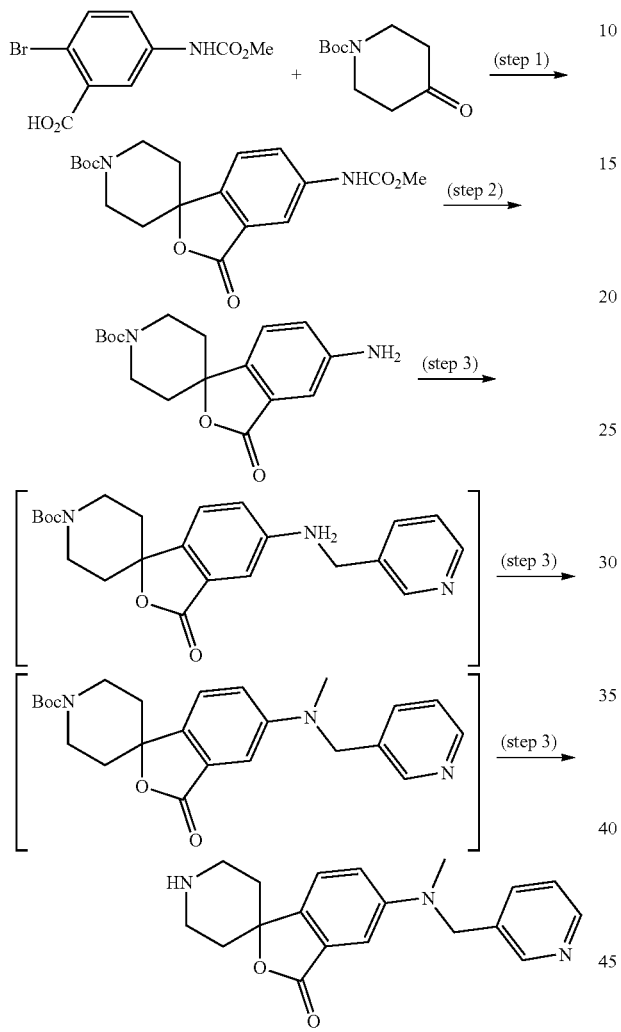

\<Step 1\>

First, 1'-tert-butyloxycarbonyl-5-[(methoxycarbonyl)amino]-3H-spiro[isobenzofuran-1,4'-piperidin]-3-one (350 mg) was obtained from 2-bromo-5-[(methoxycarbonyl)amino]benzoic acid (412 mg) and 1-tert-butyloxycarbonylpiperidin-4-one (313 mg) in the same way as in \<Step 1\> of Reference Example 23.

$^1$H-NMR (400 MHz, CDCl$_3$) δ: 1.51 (s, 9H), 1.68 (d, J=12.6 Hz, 2H), 2.05 (td, J=13.4, 4.6 Hz, 2H), 3.17-3.34 (m, 2H), 3.82 (s, 3H), 4.19 (br.m, 2H), 6.81 (br.s, 1H), 7.33 (d, J=11.0 Hz, 1H), 7.79-7.85 (m, 2H).

\<Step 2\>

A 5 M sodium hydroxide aqueous solution (2.6 mL) was added to a solution of the 1'-tert-butyloxycarbonyl-5-[(methoxycarbonyl)amino]-3H-spiro[isobenzofuran-1,4'-piperidin]-3-one (241 mg) in 1,4-dioxane (7.8 mL), and the mixture was stirred at 100° C. for 5 hours. The reaction mixture was diluted with water, followed by extraction with ethyl acetate. Then, the organic layer was washed with saturated brine, and was dried with anhydrous sodium sulfate. Thereafter, the solvent was removed by evaporation under reduced pressure to obtain 1'-tert-butyloxycarbonyl-5-amino-3H-spiro[isobenzofuran-1,4'-piperidin]-3-one (206 mg).

\<Step 3\>

Acetic acid (0.1 mL), nicotine aldehyde (6.6 mg), and 2-picoline borane (10 mg) were added to a solution of the 1'-tert-butyloxycarbonyl-5-amino-3H-spiro[isobenzofuran-1,4'-piperidin]-3-one (23 mg) in methanol (1 mL), and the mixture was stirred at room temperature for 1 hour. Then, 36% formalin (0.03 mL) and 2-picoline borane (9 mg) were added to this reaction mixture, and the mixture was stirred at room temperature for 1.5 hours. A 10% sodium carbonate aqueous solution was added to the reaction mixture. After stirring, the mixture was subjected to extraction with ethyl acetate, the organic layer was washed with saturated brine and was dried with anhydrous sodium sulfate, and the solvent was removed by evaporation under reduced pressure. The obtained residue was purified by silica gel column chromatography (ethyl acetate/n-hexane=50/50 to ethyl acetate/methanol=95/5) to obtain an intermediate. The intermediate was dissolved in methylene chloride (0.6 mL), trifluoroacetic acid (0.3 mL) was added thereto, and the mixture was stirred at room temperature for 30 minutes. The reaction mixture was concentrated under reduced pressure, 5 M hydrochloric acid (1 mL) was added to the residue, followed by stirring at 90° C. for 1 hour. After cooling, the mixture was concentrated under reduced pressure. A solution of the residue in methanol was passed through a small amount of basic silica gel to obtain the title compound (16 mg).

$^1$H-NMR (400 MHz, CDCl$_3$) δ: 1.69 (d, J=12.2 Hz, 2H), 2.10 (ddd, J=13.9, 11.4, 5.9 Hz, 2H), 3.11 (s, 3H), 3.12-3.22 (m, 4H), 4.61 (s, 2H), 7.02 (dd, J=8.5, 2.5 Hz, 1H), 7.14 (d, J=2.4 Hz, 1H), 7.22-7.26 (m, 2H), 7.52 (dt, J=7.9, 1.9 Hz, 1H), 8.49-8.51 (m, 1H), 8.52-8.54 (m, 1H).

Reference Example 29

7-fluoro-5-methoxy-3H-spiro[isobenzofuran-1,4'-piperidine]

[Chem. 27]

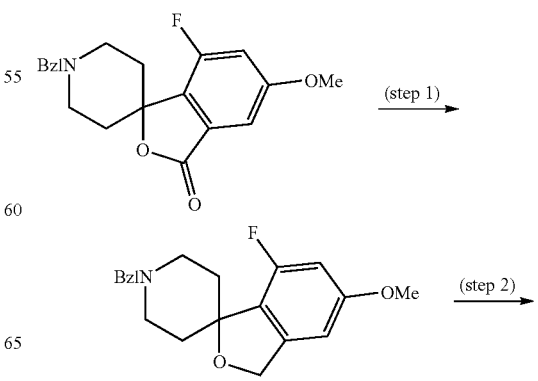

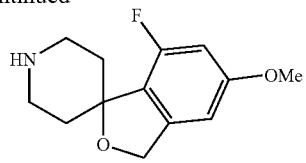

<Step 1>
First, a borane-tetrahydrofuran complex (0.92 M tetrahydrofuran solution) (0.56 mL) was added to a solution of 1'-benzyl-7-fluoro-5-methoxy-3H-spiro[isobenzofuran-1,4'-piperidin]-3-one (38 mg) in tetrahydrofuran (0.44 mL) under ice cooling, and then the mixture was heated and refluxed for 6 hours. The reaction mixture was ice-cooled, 5 M hydrochloric acid (0.5 mL) was added thereto, and the mixture was stirred at 95° C. for 4 hours. After cooling, sodium carbonate was added to the reaction mixture, followed by extraction with ethyl acetate. The organic layer was washed with saturated brine and then was dried with anhydrous sodium sulfate. The solvent was removed by evaporation under reduced pressure. The obtained residue was purified by silica gel column chromatography (ethyl acetate/n-hexane=25/75) to obtain 1'-benzyl-7-fluoro-5-methoxy-3H-spiro[isobenzofuran-1,4'-piperidine] (31 mg).

$^1$H-NMR (400 MHz, CDCl$_3$) δ: 1.68-1.75 (m, 2H), 2.26 (td, J=13.0, 4.2 Hz, 2H), 2.35-2.43 (m, 2H), 2.78-2.85 (m, 2H), 3.57 (s, 2H), 3.78 (s, 3H), 5.02 (s, 2H), 6.46-6.52 (m, 2H), 7.22-7.28 (m, 1H), 7.29-7.38 (m, 4H).

<Step 2>
The title compound (18 mg) was obtained from the 1'-benzyl-7-fluoro-5-methoxy-3H-spiro[isobenzofuran-1,4'-piperidine] (31 mg) in the same way as in <Step 2> of Reference Example 23.

$^1$H-NMR (400 MHz, CDCl$_3$) δ: 1.73 (dd, J=13.8, 2.3 Hz, 2H), 2.10 (td, J=12.4, 6.0 Hz, 2H), 2.98-3.09 (m, 4H), 3.79 (s, 3H), 5.05 (s, 2H), 6.49 (dd, J=11.2, 2.0 Hz, 1H), 6.53 (dt, J=1.9, 0.9 Hz, 1H).

Reference Example 30

1'-benzyl-4-fluoro-2H-spiro[benzofuran-3,4'-piperidine]-2-one hydrobromide

[Chem. 28]

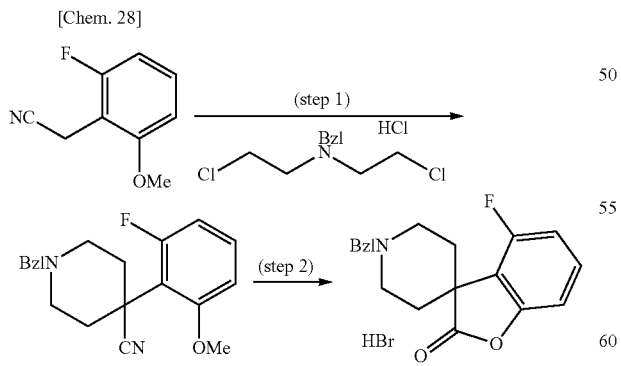

<Step 1>
First, sodium bis(trimethylsilyl) amide (1.0 M tetrahydrofuran solution) (1.6 mL) was added dropwise to a solution of 2-(2-fluoro-6-methoxyphenyl)acetonitrile (86 mg) in tetrahydrofuran (2.4 mL) under ice cooling, and the mixture was stirred at the same temperature for 30 minutes. N-benzyl-bis(2-chloroethyl)amine hydrochloride (140 mg) was added to the resultant solution, followed by reflux for 2 hours. Water was added to the reaction mixture, followed by extraction with ethyl acetate. The organic layer was washed with saturated brine and then was dried with anhydrous magnesium sulfate. the solvent was removed by evaporation under reduced pressure. The obtained residue was purified by silica gel column chromatography (diethylether/n-hexane=50/50) to obtain 1-benzyl-4-(2-fluoro-6-methoxyphenyl)piperidine-4-carbonitrile (132 mg).

$^1$H-NMR (400 MHz, CDCl$_3$) δ: 2.28-2.37 (m, 2H), 2.43-2.50 (m, 2H), 2.50-2.59 (m, 2H), 2.89-2.98 (m, 2H), 3.58 (s, 2H), 3.91 (s, 3H), 6.67 (ddd, J=12.9, 8.4, 1.2 Hz, 1H), 6.74 (d, J=8.3 Hz, 1H), 7.21-7.29 (m, 3H), 7.29-7.36 (m, 4H).

<Step 2>
Then, 47% hydrobromic acid (2.1 mL) was added to a solution of 1-benzyl-4-(2-fluoro-6-methoxyphenyl)piperidine-4-carbonitrile (131 mg) in acetic acid (2.1 mL), and the mixture was refluxed for 22 hours. The reaction mixture was concentrated under reduced pressure, and was precipitated from methanol and diethylether to obtain the title compound 160 mg.

$^1$H-NMR (400 MHz, D$_2$O) δ: 2.31 (d, J=15.0 Hz, 2H), 2.56 (br.m, 2H), 3.54 (d, J=13.2 Hz, 2H), 3.63-3.75 (m, 2H), 4.46 (s, 2H), 6.97-7.09 (m, 2H), 7.42 (td, J=8.4, 5.7 Hz, 1H), 7.50-7.58 (m, 5H).

Reference Example 31

5H-spiro[furo[3,4-b]pyridine-7,4-piperidine]-5-one

[Chem. 29]

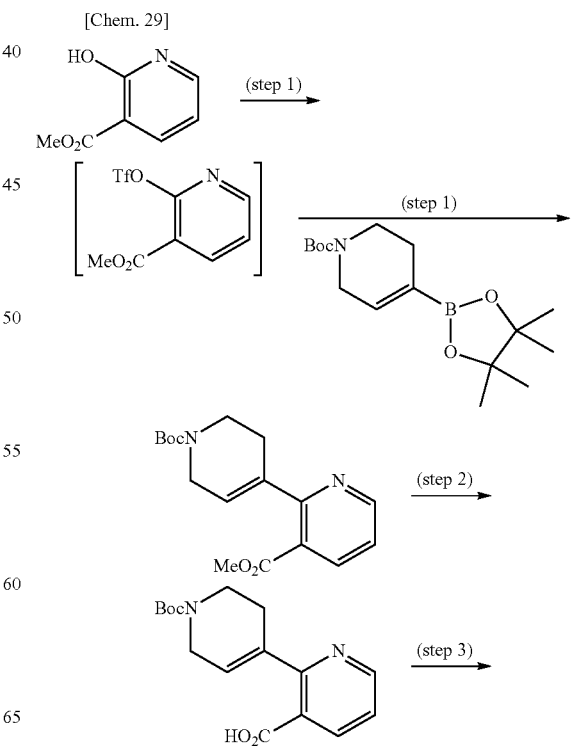

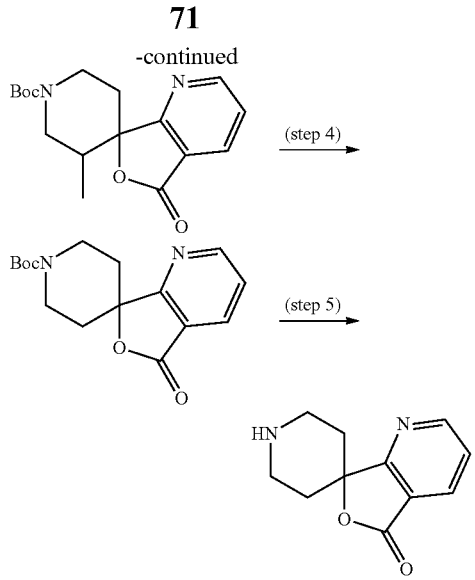

<Step 1>

First, methanesulfonic anhydride (0.321 mL) was added to a methylene chloride solution (2 mL) of methyl 2-hydroxynicotinate (200 mg) and 2,6-lutidine (0.228 mg) and the mixture was stirred for 3 hours. A saturated sodium hydrogen carbonate aqueous solution was added to the reaction solution, and the organic layer was separated. The organic layer was dried with anhydrous sodium sulfate, and concentrated under reduced pressure. Then, [1,1'-bis(diphenylphosphino)ferrocene]dichloropalladium(II) dichloride (a dichloromethane adduct) (53.3 mg), sodium carbonate (415.3 mg), 1-tert-butyloxycarbonyl-4-(4,4,5,5,-tetramethyl-1,3,2-dioxaborolan-2-yl)-1,2,3,6-tetrahydro pyridine (484.6 mg), N,N-dimethylformamide (3.5 mL), and water (1.2 mL) were added to the obtained residue in sequence, and the resultant mixture was stirred under microwave irradiation at 100° C. for 10 minutes. A saturated sodium hydrogen carbonate aqueous solution was added to the reaction solution, the mixture was filtered through celite, and then the organic layer was separated. The organic layer was dried with anhydrous sodium sulfate and was concentrated under reduced pressure. The residue was purified by silica gel column chromatography (ethyl acetate/n-hexane) to obtain methyl 1'-(tert-butyloxycarbonyl)-1',2',3',6'-tetrahydro-[2,4'-bipyridine]-3-carboxylate (313 mg).

$^1$H-NMR (400 MHz, CDCl$_3$) δ: 1.49 (s, 9H), 2.50-2.60 (m, 2H), 3.61-3.72 (m, 2H), 3.87 (s, 3H), 4.07 (q, J=2.8 Hz, 2H), 5.78 (m, 1H), 7.28 (dd, J=7.9, 4.8 Hz, 1H), 8.05 (m, 1H), 8.67 (dd, J=4.8, 1.8, 1.8 Hz, 1H).

MS(ESI) m/z: 319[M+H]$^+$.

<Step 2>

A 1 M sodium hydroxide aqueous solution (0.275 mL) was added to a solution of the methyl 1'-tert-butyloxycarbonyl-1',2',3',6'-tetrahydro-[2,4'-bipyridine]-3-carboxylate (73 mg) in methanol (1 mL), and the mixture was stirred for 24 hours. The reaction solution was concentrated under reduced pressure, water (4 mL) was added to the obtained residue, and then the pH of the obtained mixture was adjusted to 3 with 1 M hydrochloric acid. After extraction with ethyl acetate, the organic layer was washed with water and a 20% brine solution in sequence. After drying over anhydrous sodium sulfate, the residue was concentrated under reduced pressure to obtain 1'-tert-butoxycarbonyl-1',2',3',6'-tetrahydro-[2,4'-bipyridine]-3-carboxylic acid (63.8 mg).

$^1$H-NMR (400 MHz, CDCl$_3$) δ: 1.48 (s, 9H), 2.50-2.65 (m, 2H), 3.67 (t, J=5.1 Hz, 2H), 4.05-4.08 (m, 2H), 5.85 (m, 1H), 7.35 (dd, J=7.8, 4.9 Hz, 1H), 8.21 (m, 1H), 8.74 (dd, J=4.9, 1.7 Hz, 1H).

MS(ESI) m/z: 305[M+H]$^+$.

<Step 3>

A saturated sodium hydrogen carbonate aqueous solution (2.1 mL) and a solution of iodine (50.3 mg) and potassium iodide (126.6 mg) in water (0.73 mL) were added in sequence to a solution of the 1'-tert-butyloxycarbonyl-1',2',3',6'-tetrahydro-[2,4'-bipyridine]-3-carboxylic acid (63.8 mg) in acetonitrile (0.42 mL), and the mixture was stirred at room temperature for 15 hours. Ethyl acetate and a 15% sodium thiosulfate aqueous solution (0.73 mL) were added thereto, and the mixture was stirred at room temperature for 20 minutes. After extraction with ethyl acetate, the organic layer was washed with water and a 20% brine solution in sequence. The organic layer was dried with anhydrous sodium sulfate, and was concentrated under reduced pressure to obtain 1'-tert-butyloxycarbonyl-3'-iodo-5-oxo-5H-spiro[furo[3,4-b]pyridine-7,4'-piperidine] (57.1 mg).

MS(ESI) m/z: 431[M+H]$^+$.

<Step 4>

Then, α,α'-azoisobutyronitrile (2 mg) was added to a solution of the 1'-tert-butyloxycarbonyl-3'-iodo-5-oxo-5H-spiro[furo[3,4-b]pyridine-7,4'-piperidine] (57.1 mg) in toluene (0.51 mL), and the mixture was stirred at 80° C. for 10 minutes. Thereafter, tri-n-butyltin hydride (0.104 mL) was added thereto and the mixture was stirred for 3 hours. The resultant mixture was purified by silica gel thin layer chromatography (ethyl acetate/n-hexane=50/50) to obtain 1'-tert-butyloxycarbonyl-5-oxo-5H-spiro[furo[3,4-b]pyridine-7,4'-piperidine] (38.9 mg).

$^1$H-NMR (400 MHz, CDCl$_3$) δ: 1.50 (s, 9H), 1.64-1.73 (m, 2H), 2.22-2.33 (m, 2H), 3.24-3.43 (m, 2H), 4.05-4.36 (m, 2H), 7.50 (dd, J=7.7, 4.9 Hz, 1H), 8.20 (dd, J=7.7, 1.6 Hz, 1H), 8.85 (dd, J=4.9, 1.6 Hz, 1H).

MS(ESI) m/z: 305[M+H]$^+$.

<Step 5>

After a solution of the 1'-tert-butyloxycarbonyl-5-oxo-5H-spiro[furo[3,4-b]pyridine-7,4'-piperidine] (38.9 mg) in methylene chloride (1 mL) was cooled to 0° C., trifluoroacetic acid (1 mL) was added thereto, and the mixture was stirred at 0° C. for 2 hours. The reaction mixture was concentrated under reduced pressure, and was purified by silica gel thin layer chromatography (chloroform/methanol=20/1) to obtain the title compound (18.8 mg).

$^1$H-NMR (400 MHz, CDCl$_3$) δ: 1.59-1.78 (m, 4H), 2.26 (ddd, J=13.9, 11.1, 5.8 Hz, 2H), 3.10-3.25 (m, 4H), 7.47 (dd, J=7.7, 4.9 Hz, 1H), 8.19 (dd, J=7.7, 1.6 Hz, 1H), 8.85 (dd, J=4.9, 1.6 Hz, 1H).

MS(ESI) m/z: 205 [M+H]$^+$.

Reference Example 32

4H-spiro[furo[3,4-b]furan-6,4'-piperidine]-4-one hydrochloride

[Chem. 30]

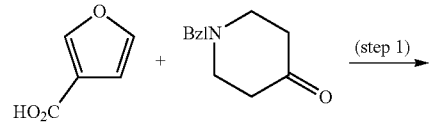

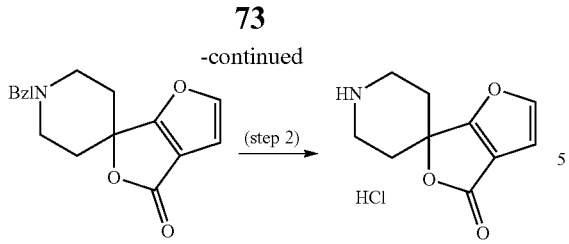 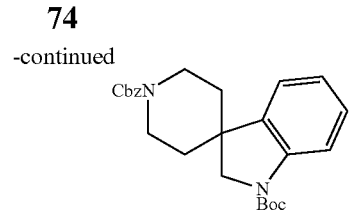

<Step 1>
First, n-butyl lithium (2.65 M hexane solution) (0.79 mL) was added dropwise to a solution of diisopropyl ethylamine (0.31 mL) in tetrahydrofuran (3 mL) under ice cooling, and the mixture was stirred at the same temperature for 15 minutes. The reaction solution was cooled to −78° C., and a solution of furan-3-carboxylic acid (11.2 mg) in tetrahydrofuran (1.5 mL) was added dropwise thereto. After the resultant mixture was stirred at the same temperature for 1 hour, a solution of 1-benzylpiperidin-4-one (190 mg) in tetrahydrofuran (1 mL) was added dropwise thereto, and the mixture was heated to room temperature and stirred overnight. The reaction mixture was concentrated under reduced pressure, pyridine (5 mL) was added to the residue and then methanesulfonyl chloride (0.2 mL) was added thereto. Then, the mixture was stirred at room temperature for 2 hours. The reaction mixture was diluted with water. After extraction with ethyl acetate, the organic layer was washed with saturated brine and was dried with anhydrous magnesium sulfate, and thereafter the solvent was removed by evaporation under reduced pressure. The obtained residue was purified by silica gel column chromatography (ethyl acetate/n-hexane=50/50) to obtain 1'-benzyl-4H-spiro[furo[3,4-b]furan-6,4'-piperidine]-4-one (292 mg).
$^1$H-NMR (400 MHz, CDCl$_3$) δ: 1.92-1.99 (m, 1H), 2.09-2.20 (m, 1H), 2.61-2.71 (m, 1H), 2.71-2.81 (m, 1H), 3.61 (s, 1H), 6.60 (d, J=2.0 Hz, 1H), 7.28-7.37 (m, 5H), 7.52 (d, J=2.0 Hz, 1H).
MS(ESI) m/z: 284 [M+H]$^+$.

<Step 2>
The title compound (45 mg) was obtained from the 1'-benzyl-4H-spiro[furo[3,4-b]furan-6,4'-piperidine]-4-one (128 mg) in the same way as in <Step 4> of Reference Example 25.
$^1$H-NMR (400 MHz, DMSO-d$_6$) δ: 2.06-2.12 (m, 1H), 2.31-3.39 (m, 1H), 3.15-3.25 (m, 1H), 3.31-3.38 (m, 1H), 6.92 (d, J=2.0 Hz, 1H), 8.07 (d, J=2.0 Hz, 1H), 9.07 (brs, 1H).
MS(ESI) m/z: 194 [M+H]$^+$.

Reference Example 33

1'-benzyloxycarbonyl-1-tert-butyloxycarbonylspiro[indoline-3,4'-piperidine]

[Chem. 31]

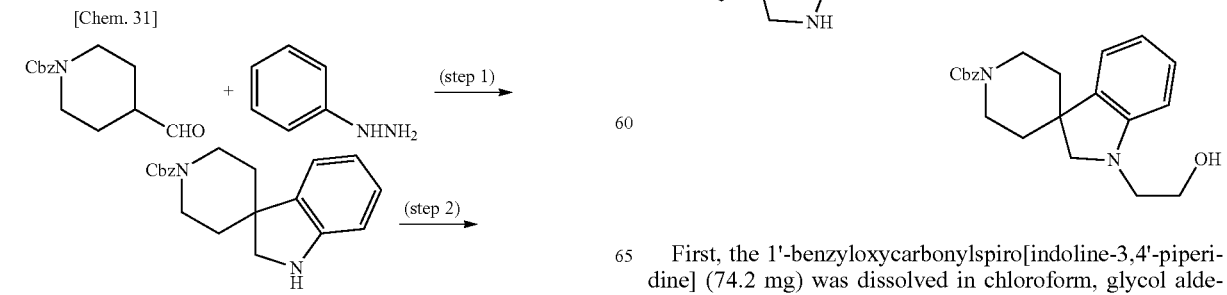

<Step 1>
First, 1-benzyloxycarbonyl-4-formylpiperidine (514.5 mg) was dissolved in chloroform (10 mL), phenylhydrazine (0.245 mL) and trifluoroacetic acid (0.478 mL) were added thereto, and the mixture was stirred at 35° C. for 14 hours. After that, sodium triacetoxyborohydride (881.9 mg) was added thereto, and the mixture was further stirred at room temperature for 1 hour. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (ethyl acetate/n-hexane=50/50) to obtain 1'-benzyloxycarbonyl-spiro[indoline-3,4'-piperidine] (487.0 mg).
MS(ESI) m/z: 323[M+H]$^+$.

<Step 2>
The 1'-benzyloxycarbonylspiro[indoline-3,4'-piperidine] (487.0 mg) was dissolved in chloroform (15 mL), di-tert-butyl dicarbonate (0.416 mL) and dimethylaminopyridine (221.5 mg) were added thereto, and the mixture was stirred at room temperature for 1 hour. Water was added to the reaction solution, followed by extraction with chloroform. The organic layer was dried with anhydrous magnesium sulfate and was concentrated under reduced pressure, and the obtained residue was purified by silica gel column chromatography (ethyl acetate/n-hexane=25/75) to obtain the title compound (587.3 mg).
$^1$H-NMR (400 MHz, CDCl$_3$) δ: 1.58 (br.s, 9H), 1.77-1.88 (m, 2H), 2.90-3.03 (m, 2H), 3.80-3.93 (m, 2H), 4.16-4.29 (m, 2H), 5.17 (s, 2H), 6.95-6.99 (m, 1H), 7.06-7.09 (m, 1H), 7.16-7.22 (m, 1H), 7.30-7.96 (m, 6H).
MS(ESI) m/z: 423[M+H]$^+$.

Reference Example 34

2-(1'-benzyloxycarbonylspiro[indoline-3,4'-piperidine]-1-yl)ethan-1-ol

[Chem. 32]

First, the 1'-benzyloxycarbonylspiro[indoline-3,4'-piperidine] (74.2 mg) was dissolved in chloroform, glycol aldehyde dimer (41.5 mg) and sodium triacetoxyborohydride (146.3 mg) were added thereto, and the mixture was stirred at room temperature for 14 hours. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (ethyl acetate/n-hexane=50/50) to obtain the title compound (80.3 mg).

MS(ESI) m/z: 367[M+H]$^+$.

Reference Example 35

(R)-1'-benzyloxycarbonyl-1-{3-[(tert-butyldimethyl-silyl)oxy]-2-hydroxypropyl}spiro[indoline-3,4'-piperidine]

[Chem. 33]

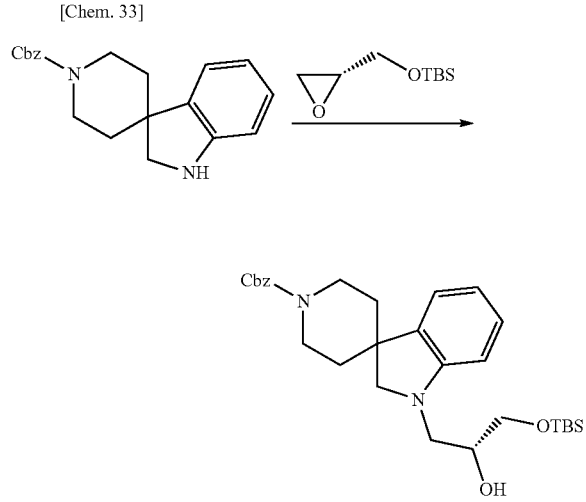

First, the 1'-benzyloxycarbonyl-1-spiro[indoline-3,4'-piperidine] (90.9 mg) was dissolved in ethanol (1 mL), (R)-tert-butyldimethyl(oxiran-2-ylmethoxy)silane (261.4 mg) and potassium carbonate (126.7 mg) were added thereto, and the mixture was stirred at 90° C. for 18 hours 40 minutes. Water was added to the reaction solution, followed by four times of extraction with ethyl acetate. The organic layer was washed with saturated brine, then was dried with anhydrous sodium sulfate, and was concentrated under reduced pressure. The obtained residue was purified by silica gel column chromatography (ethyl acetate/n-hexane=0/100 to 40/60) to obtain 115.4 mg of the title compound (a mixture of isomers at about 3:2).

$^1$H-NMR (270 MHz, CDCl$_3$) δ: 0.09 (s, 3H), 0.10 及び 0.12 (3:2) (s, 3H), 0.919 及び 0.924 (2:3) (s, 9H), 1.63-1.93 (m, 4H), 2.48 (br.d, J=4.6 Hz, 1H), 2.90-3.09 (m, 2H), 3.18 T 及び 3.20 (2:3) (s, 2H), 3.30-3.47 (m, 2H), 3.59-3.75 (m, 2H), 3.88-4.01 (m, 1H), 4.07-4.22 (m, 2H), 5.17 (s, 2H), 6.49-6.56 (m, 1H), 6.66-6.76 (m, 1H), 6.97-7.04 (m, 1H), 7.10 (td, J=7.6, 7.6, 1.3 Hz, 1H), 7.28-7.43 m, 5H).

MS(ESI) m/z: 511[M+H]$^+$.

Reference Example 36

1'-tert-butyloxycarbonyl-1-(2-ethoxy-2-oxoethyl)spiro[indoline-3,4'-piperidine]

[Chem. 34]

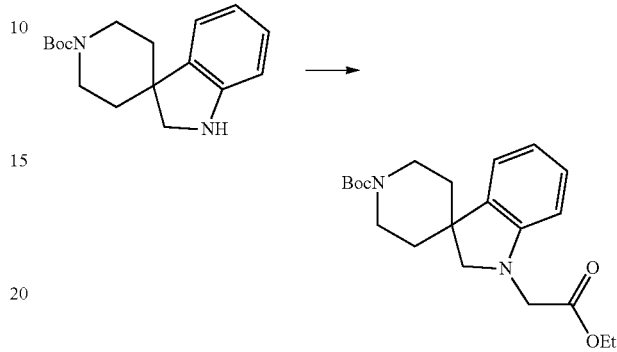

First, 1'-tert-butyl-spiro[indoline-3,4'-piperidine] (57.6 mg) was dissolved in tetrahydrofuran (1 mL), then bromoethyl acetate (0.023 mL) and triethylamine (0.056 mL) were added thereto, and the mixture was stirred at room temperature for 88 hours. Water was added to the reaction solution, followed by four times of extraction with ethyl acetate. The organic layer was washed with saturated brine, then was dried with anhydrous sodium sulfate, and was concentrated under reduced pressure. The obtained residue was purified by silica gel column chromatography (ethyl acetate/n-hexane=0/100 to 30/70) to obtain the title compound (33.5 mg).

$^1$H-NMR (270 MHz, CDCl$_3$) δ: 1.26 (t, J=7.1 Hz, 3H), 1.49 (s, 9H), 1.68-1.88 (m, 4H), 2.90 (br.t, J=1.6 Hz, 2H), 3.49 (s, 2H), 3.92 (s, 2H), 4.07 (br.d, J=11.5 Hz, 2H), 4.19 (q, J=7.1 Hz, 2H), 6.37-6.44 (m, 1H), 6.67-6.76 (m, 1H), 7.00-7.12 (n, 2H).

MS(ESI) m/z: 375[M+H]$^+$.

Reference Example 37

1'-tert-butyloxycarbonyl-1-(pyrimidin-2-yl)spiro[indoline-3,4'-piperidine]

[Chem. 35]

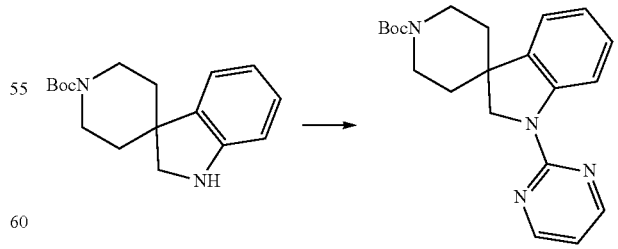

First, 1'-tert-butyloxycarbonylspiro[indoline-3,4'-piperidine] (252.2 mg) was dissolved in 1,4-dioxane (2 mL), then 2-chloropyrimidine (110.6 mg) and N,N-diisopropyl ethylamine (0.20 mL) were added thereto, and the mixture was stirred under microwave irradiation at 140 to 150° C. for 56 hours. Water and saturated brine were added to the reaction solution, followed by four times of extraction with ethyl acetate. The organic layer was washed with 5% citric acid, then was dried with anhydrous sodium sulfate, and was concentrated under reduced pressure. The obtained residue was purified by silica gel column chromatography (ethyl acetate/n-hexane=0/100 to 30/70) to obtain the title compound (148.9 mg).

$^1$H-NMR (270 MHz, CDCl$_3$) δ: 1.50 (s, 9H), 1.59-1.70 (m, 2H), 1.88 (td, J=13.1, 4.5 Hz, 2H), 2.99 (br.t, J=12.7 Hz, 2H), 4.10-4.23 (m, 2H), 4.15 (s, 2H), 6.73 (t, J=4.8 Hz, 1H), 6.95-7.03 (m, 1H), 7.16 (dd, J=7.4, 1.2 Hz, 1H), 7.20-7.32 (m, 1H), 8.42 (d, J=8.2 Hz, 1H), 8.52 (d, J=4.9 Hz, 2H).

MS(ESI) m/z: 311[M-(tert-Bu)+H]$^+$.

Reference Example 38

4-fluorospiro[indoline-3,4'-piperidine]-2-one

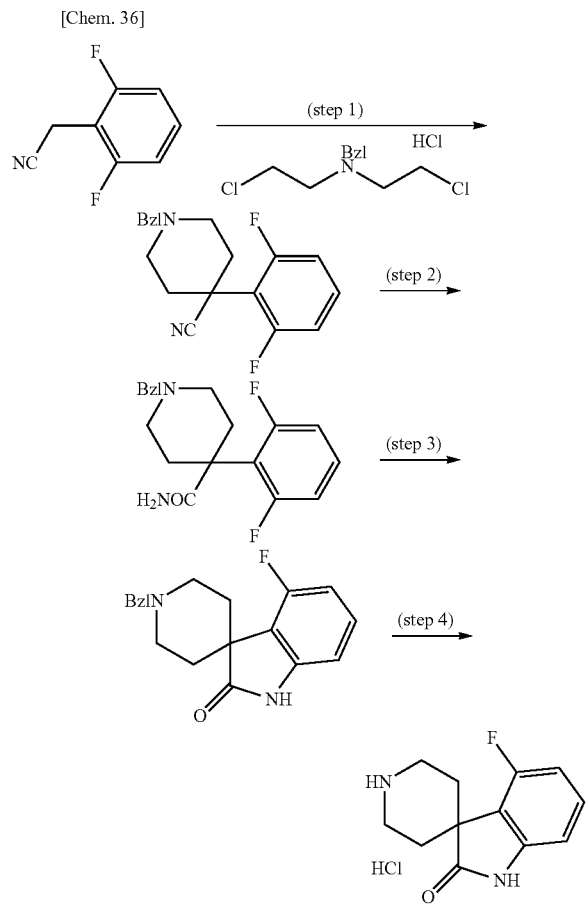

<Step 1>

After 2-(2,6-difluorophenyl)acetonitrile (3.79 g) was dissolved in tetrahydrofuran (90 mL), the mixture was cooled to 0° C., sodium bis(trimethylsilyl) amide (1.0 M tetrahydrofuran solution) (87 mL) was added dropwise thereto. After stirring for 20 minutes, N-benzyl bis(2-chloroethyl) amine hydrochloride (5.96 g) was added thereto, and the mixture was refluxed by heating for 2 hours. Water was added to the reaction solution, followed by four times of extraction with ethyl acetate. The organic layer was washed with saturated brine, then was dried with anhydrous sodium sulfate, and was concentrated under reduced pressure. The obtained residue was purified by silica gel column chromatography (ethyl acetate/n-hexane=0/100 to 30/70) to obtain 1-benzyl-4-(2,6-difluorophenyl)piperidine-4-carbonitrile (2.90 g).

$^1$H-NMR (270 MHz, CDCl$_3$) δ: 2.26-2.44 (m, 4H), 2.56 (td, J=11.5, 3.5 Hz, 2H), 2.90-3.01 (m, 2H), 3.58 (s, 2H), 6.88-6.98 (m, 2H), 7.21-7.38 (m, 6H).

MS(ESI) m/z: 313[M+H]$^+$.

<Step 2>

First, the 1-benzyl-4-(2,6-difluorophenyl)piperidine-4-carbonitrile (2.90 g) was dissolved in ethanol (50 mL), a 10 M sodium hydroxide aqueous solution (8 mL) was added thereto, and the mixture was refluxed by heating for 10 hours. The reaction solution was brought back to room temperature, then water was added thereto, and the mixture was subjected to four times of extraction with ethyl acetate. The organic layer was washed with saturated brine, then was dried with anhydrous sodium sulfate, and was concentrated under reduced pressure. The obtained residue was purified by silica gel column chromatography (ethyl acetate/n-hexane=0/100 to 30/70) to obtain 1-benzyl-4-(2,6-difluorophenyl)piperidine-4-carbamide (1.54 g).

$^1$H-NMR (270 MHz, CDCl$_3$) δ: 2.29-2.56 (m, 6H), 2.64-2.80 (m, 2H), 3.47 (s, 2H), 5.33 (br.s, 2H), 6.85-6.95 (m, 2H), 7.19-7.37 (m, 8H).

MS(ESI) m/z: 331[M+H]$^+$.

<Step 3>

The 1-benzyl-4-(2,6-difluorophenyl)piperidine-4-carbamide (337.0 mg) was dissolved in N-methylpyrrolidone (6 mL), lithium hydride (18.2 mg) was added thereto, and the mixture was stirred at 120° C. for 6 hours. The reaction solution was brought back to room temperature, then saturated brine and a saturated sodium hydrogen carbonate aqueous solution were added thereto, and the mixture was subjected to four times of extraction with ethyl acetate. The organic layer was washed with saturated brine, then was dried with anhydrous sodium sulfate, and was concentrated under reduced pressure. The obtained residue was purified by silica gel column chromatography (ethyl acetate/n-hexane=0/100 to 60/40) to obtain 1'-benzyl-4-fluorospiro[indoline-3,4'-piperidine]-2-one (246.7 mg).

$^1$H-NMR (270 MHz, CDCl$_3$) δ: 1.79-1.90 (m, 2H), 2.29-2.41 (m, 2H), 2.71-2.81 (m, 2H), 2.86-2.99 (m, 2H), 3.66 (s, 2H), 6.59-6.76 (m, 2H), 7.12-7.23 (m, 1H), 7.27-7.45 (m, 5H).

MS(ESI) m/z: 311[M+H]$^+$

<Step 4>

The title compound (196.4 mg) was obtained from the 1'-benzyl-4-fluorospiro[indoline-3,4'-piperidin]-2-one (241.0 mg) in the same way as in <Step 2> of Reference Example 23.

MS(ESI) m/z: 221[M+H]$^+$.

Reference Example 39

2H-spiro[isoquinoline-1,4'-piperidine]-3(4H)-one

[Chem. 37]

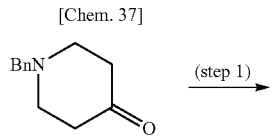

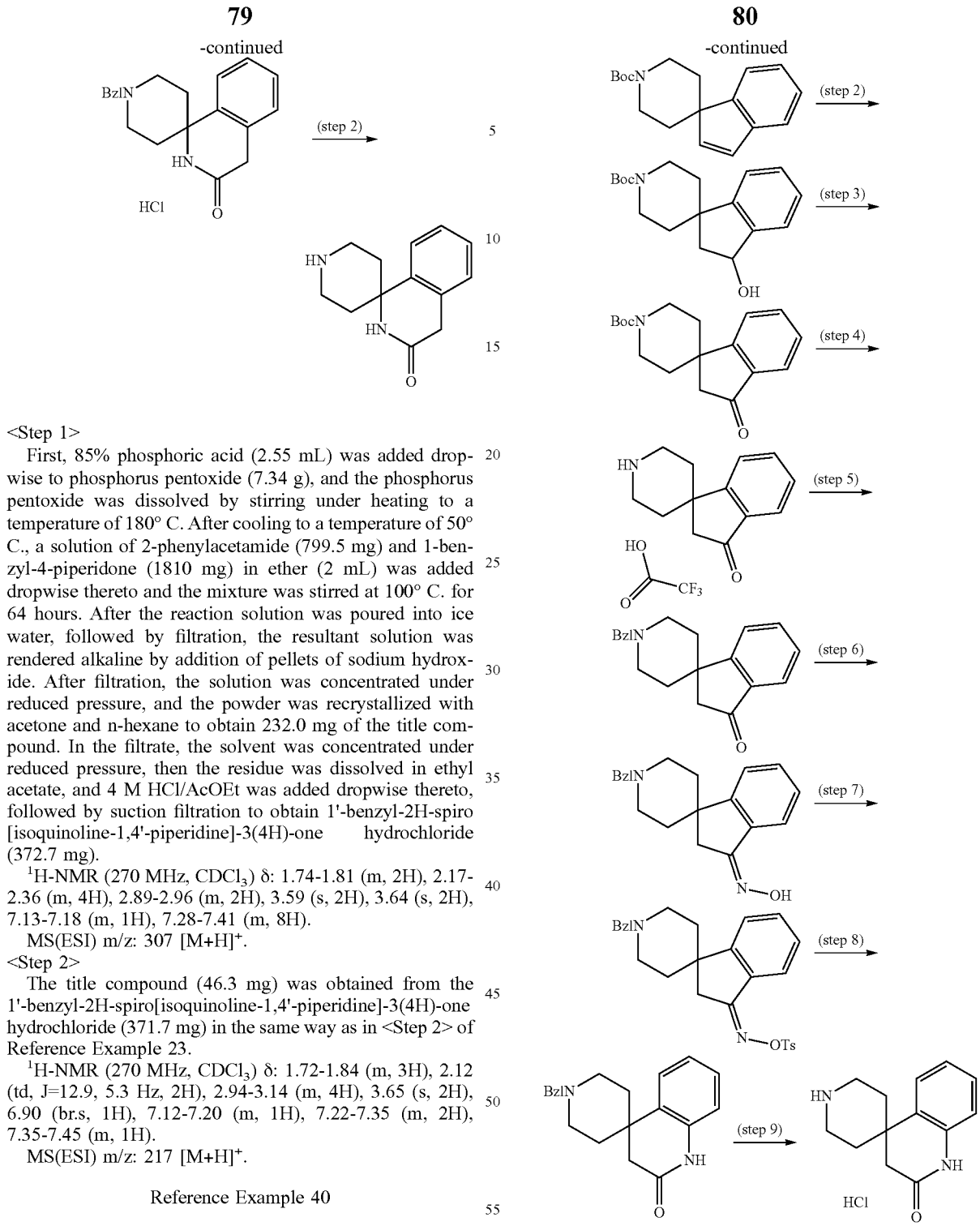

<Step 1>

First, 85% phosphoric acid (2.55 mL) was added dropwise to phosphorus pentoxide (7.34 g), and the phosphorus pentoxide was dissolved by stirring under heating to a temperature of 180° C. After cooling to a temperature of 50° C., a solution of 2-phenylacetamide (799.5 mg) and 1-benzyl-4-piperidone (1810 mg) in ether (2 mL) was added dropwise thereto and the mixture was stirred at 100° C. for 64 hours. After the reaction solution was poured into ice water, followed by filtration, the resultant solution was rendered alkaline by addition of pellets of sodium hydroxide. After filtration, the solution was concentrated under reduced pressure, and the powder was recrystallized with acetone and n-hexane to obtain 232.0 mg of the title compound. In the filtrate, the solvent was concentrated under reduced pressure, then the residue was dissolved in ethyl acetate, and 4 M HCl/AcOEt was added dropwise thereto, followed by suction filtration to obtain 1'-benzyl-2H-spiro[isoquinoline-1,4'-piperidine]-3(4H)-one hydrochloride (372.7 mg).

$^1$H-NMR (270 MHz, CDCl$_3$) δ: 1.74-1.81 (m, 2H), 2.17-2.36 (m, 4H), 2.89-2.96 (m, 2H), 3.59 (s, 2H), 3.64 (s, 2H), 7.13-7.18 (m, 1H), 7.28-7.41 (m, 8H).

MS(ESI) m/z: 307 [M+H]$^+$.

<Step 2>

The title compound (46.3 mg) was obtained from the 1'-benzyl-2H-spiro[isoquinoline-1,4'-piperidine]-3(4H)-one hydrochloride (371.7 mg) in the same way as in <Step 2> of Reference Example 23.

$^1$H-NMR (270 MHz, CDCl$_3$) δ: 1.72-1.84 (m, 3H), 2.12 (td, J=12.9, 5.3 Hz, 2H), 2.94-3.14 (m, 4H), 3.65 (s, 2H), 6.90 (br.s, 1H), 7.12-7.20 (m, 1H), 7.22-7.35 (m, 2H), 7.35-7.45 (m, 1H).

MS(ESI) m/z: 217 [M+H]$^+$.

Reference Example 40

1'H-spiro[piperidine-4,4'-quinolin e]-2' (3'H)-one hydrochloride

[Chem. 38]

<Step 1>

First, indene (3.42 g) was dissolved in tetrahydrofuran (8 mL), the mixture was cooled to 0° C., and lithium bis(trimethylsilyl) amide (1.0 M tetrahydrofuran solution) (60 mL) was added dropwise thereto. After 1 hour, a tetrahydrofuran solution (13 mL) of N-tert-butyloxycarbonylbis(2-chloroethyl)amine (6.44 g) was added dropwise to the reaction solution, and the mixture was stirred at 0° C. for 30 minutes, and then was stirred at room temperature for 2 hours 30 minutes. Water was added to the reaction solution, followed by four times of extraction with chloroform. The organic layer was washed with saturated brine, then was dried with anhydrous sodium sulfate, and was concentrated under reduced pressure. The obtained residue was purified by silica gel column chromatography (ethyl acetate/n-hexane=0/100 to 15/85) to obtain 1'-tert-butyloxycarbonyl-spiro[indene-1,4'-piperidine] (3.74 g).

$^1$H-NMR (270 MHz, CDCl$_3$) δ: 1.33 (br.d, J=12.9 Hz, 2H), 1.51 (s, 9H), 1.90-2.11 (m, 2H), 3.12 (br.t, J=12.2 Hz, 2H), 4.05-4.31 (m, 2H), 6.76-6.89 (m, 2H), 7.14-7.39 (m, 4H).

MS(ESI) m/z: 230[M-(tert-Bu)+H]$^+$.

<Step 2>

The 1'-tert-butyloxycarbonylspiro[indene-1,4'-piperidine] (380 mg) was dissolved in tetrahydrofuran (8 mL), 9-borabicyclo[3,3,1]-nonane (0.5 M tetrahydrofuran solution) (5.3 mL) was added thereto, and the mixture was stirred at 70° C. for 17 hours in a sealed tube. A 1 M sodium hydroxide aqueous solution (2.7 mL) and 30% aqueous hydrogen peroxide (0.272 mL) were added to the reaction solution, the mixture was then brought back to room temperature. After that, water was added to the reaction solution, followed by four times of extraction with ethyl acetate. The organic layer was washed with saturated brine, then was dried with anhydrous sodium sulfate, and was concentrated under reduced pressure. The obtained residue was purified by silica gel column chromatography (ethyl acetate/n-hexane=0/100 to 50/50) to obtain 1'-tert-butyloxycarbonyl-3-hydroxy-2,3-spiro[indene-1,4'-piperidine] (352.4 mg).

$^1$H-NMR (270 MHz, CDCl$_3$) δ: 1.34-1.85 (m, 3H), 1.49 (s, 9H), 1.87-2.02 (m, 2H), 2.53 (dd, J=13.5, 7.3 Hz, 1H), 2.95 (br.t, J=12.7 Hz, 2H), 4.04-4.24 (m, 2H), 5.23-5.35 (m, 1H), 7.17-7.24 (m, 1H), 7.28-7.38 (m, 2H), 7.38-7.44 (m, 1H).

MS(ESI) m/z: 248[M-(tert-Bu)+H]$^+$.

<Step 3>

The 1'-tert-butyloxycarbonyl-3-hydroxy-2,3-spiro[indene-1,4'-piperidine] (343.7 mg) was dissolved in dichloromethane (3 mL), then molecular sieve 4A powder (494 mg), tetrapropylammonium perruthenate (37.3 mg), and 4-methylmorpholine N-oxide (305.8 mg) were added thereto, and the mixture was stirred at room temperature for 2 hours 30 minutes. The reaction solution was filtered through celite, and the filtrate was concentrated under reduced pressure. The obtained residue was purified by silica gel column chromatography (ethyl acetate/n-hexane=0/100 to 50/50) to obtain 1'-tert-butyloxycarbonyl-3-oxo-2,3-dihydrospiro[indene-1,4'-piperidine] (391.0 mg).

$^1$H-NMR (270 MHz, CDCl$_3$) δ: 1.44-1.55 (m, 2H), 1.50 (s, 9H), 1.92-2.06 (m, 2H), 2.64 (s, 2H), 2.87 (br.t, J=12.9 Hz, 2H), 4.23 (br.d, J=12.9 Hz, 2H), 7.39-7.45 (m, 1H), 7.48-7.52 (m, 1H), 7.62-7.68 (m, 1H), 7.72-7.77 (m, 1H)

MS(ESI) m/z: 246[M-(tert-Bu)+H]$^+$.

<Step 4>

The 1'-tert-butyloxycarbonyl-3-oxo-2,3-dihydrospiro[indene-1,4'-piperidine] (272.1 mg) was dissolved in dichloromethane (1.5 mL), then trifluoroacetic acid (1.5 mL) was added thereto, and the mixture was stirred at room temperature for 1 hour. The reaction solution was concentrated under reduced pressure to obtain spiro[indene-1,4'-piperidine]-3(2H)-one trifluoroacetate (124.7 mg).

MS(ESI) m/z: 202[M+H]$^+$.

<Step 5>

The spiro[indene-1,4'-piperidine]-3(2H)-one trifluoroacetate (2.70 g) was dissolved in N,N-dimethylformamide (10 mL), potassium carbonate (2.02 g) and benzyl bromide (0.386 mL) were added thereto, and the mixture was stirred at room temperature for 15 hours. Water was added to the reaction solution, followed by four times of extraction with ethyl acetate. The organic layer was washed with saturated brine, then was dried with anhydrous sodium sulfate, and was concentrated under reduced pressure. The obtained residue was purified by silica gel column chromatography (ethyl acetate/n-hexane=0/100 to 60/40) to obtain 1'-benzyl-spiro[indene-1,4'-piperidine]-3(2H)-one (752.9 mg).

$^1$H-NMR (270 MHz, CDCl$_3$) δ: 1.44-1.57 (m, 2H), 2.07-2.21 (m, 4H), 2.58 (s, 2H), 2.91-3.01 (m, 2H), 3.58 (s, 2H), 7.27-7.43 (m, 6H), 7.53-7.68 (m, 2H), 7.68-7.74 (m, 1H).

MS(ESI) m/z: 292 [M+H]$^+$.

<Step 6>

The 1'-benzylspiro[indene-1,4'-piperidine]-3(2H)-one (118.1 mg) was dissolved in ethanol (2 mL), then hydroxyl amine hydrochloride (61.6 mg) and sodium acetate (66.8 mg) were added thereto, and the mixture was stirred for 1 hour 15 minutes under reflux by heating. After the reaction solution was brought back to room temperature, water was added thereto, and then the solution was subjected to four times of extraction with chloroform. The organic layer was washed with saturated brine, then was dried with anhydrous sodium sulfate, and was concentrated under reduced pressure. The obtained residue was purified by silica gel column chromatography (ethyl acetate/n-hexane=0/100 to 70/30) to obtain (Z)-1'-benzylspiro[indene-1,4'-piperidine]-3(2H)-one oxime (107.4 mg).

$^1$H-NMR (270 MHz, CDCl$_3$) δ: 1.42-1.56 (m, 2H), 2.07-2.29 (m, 4H), 2.88 (s, 2H), 2.98 (br.d, J=8.9 Hz, 2H), 3.63 (s, 2H), 7.20-7.48 (m, 8H), 7.68 (d, J=7.3 Hz, 1H).

MS(ESI) m/z: 307 [M+H]$^+$.

<Step 7>

The (Z)-1'-benzylspiro[indene-1,4'-piperidine]-3(2H)-one oxime (46.9 mg) was dissolved in dichloromethane (1 mL), the mixture was cooled to 0° C., pyridine (0.031 mL) and p-toluenesulfonyl chloride (58.5 mg) were added thereto, and the mixture was stirred at room temperature for 17 hours 20 minutes. Water was added to the reaction solution, followed by four times of extraction with dichloromethane. The organic layer was washed with saturated brine, then was dried with anhydrous sodium sulfate, and was concentrated under reduced pressure. The obtained residue was purified by silica gel column chromatography (methanol/chloroform=0/100 to 4/96) to obtain (Z)-1'-benzylspiro[indene-1,4'-piperidine]-3(2H)-one O-tosyloxime (62.0 mg).

$^1$H-NMR (270 MHz, CDCl$_3$) δ: 1.40 (br.d, J=12.2 Hz, 2H), 1.92-2.20 (m, 4H), 2.44 (s, 3H), 2.83-2.96 (m, 2H), 2.88 (s, 2H), 3.58 (s, 2H), 7.27-7.40 (m, 9H), 7.44 (d, J=7.3 Hz, 1H), 7.64 (d, J=7.3 Hz, 1H), 7.95 (d, J=8.2 Hz, 2H).

MS(ESI) m/z: 461[M+H]$^+$.

<Step 8>

The (Z)-1'-benzylspiro[indene-1,4'-piperidine]-3(2H)-one O-tosyloxime (414.5 mg) was dissolved in chloroform (8 mL), the mixture was cooled to 0° C., aluminum chloride (493.5 mg) was added thereto, and the mixture was stirred at room temperature for 2 hours 30 minutes. A 15% sodium hydroxide aqueous solution was added to the reaction solution, followed by four times of extraction with chloroform. The organic layer was washed with water and subsequently with saturated brine, then was dried with anhydrous sodium sulfate, and was concentrated under reduced pressure. The obtained residue was purified by silica gel column chromatography (ethyl acetate/n-hexane=0/100 to 70/30) to obtain 1-benzyl-1'H-spiro[piperidine-4,4'-quinoline]-2' (3'H)-one (94.0 mg).

¹H-NMR (270 MHz, CDCl₃) δ: 1.63-1.73 (m, 2H), 1.99-2.15 (m, 2H), 2.32-2.44 (m, 2H), 2.68 (s, 2H), 2.73-2.83 (m, 2H), 3.58 (s, 2H), 6.75 (dd, J=7.6, 1.3 Hz, 1H), 7.07 (ddd, J=7.7, 7.7, 1.3 Hz, 1H), 7.18 (dd, J=7.7, 1.3 Hz, 1H), 7.27-7.41 (m, 6H), 7.68 (br.s, 1H).

MS(ESI) m/z: 307[M+H]⁺.

<Step 9>

The title compound (58.8 mg) was obtained from the 1-benzyl-1'H-spiro[piperidine-4,4'-quinoline]-2' (3'H)-one (53.2 mg) in the same way as in <Step 2> of Reference Example 23.

MS(ESI) m/z: 217 [M+H]⁺.

Reference Example 41

1'H-spiro[piperidine-4,3'-quinoline]-2' (4'H)-one

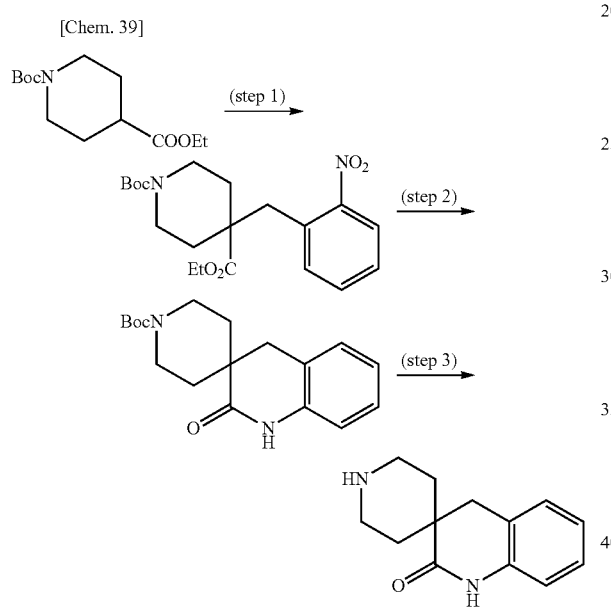

<Step 1>

First, N-tert-butyloxycarbonylpiperidin-4-ethyl carboxylate (6.44 g) was dissolved in tetrahydrofuran (40 mL), the mixture was cooled to −78° C., and sodium bis(trimethylsilyl) amide (1.0 M tetrahydrofuran solution) (35 mL) was added dropwise thereto. In another vessel, 2-nitrobenzyl bromide (6.53 g) was dissolved in tetrahydrofuran (15 mL), and the mixture was cooled to −78° C. After that, the reaction solution previously prepared was added dropwise by cannulation to the mixture. The reaction solution was gradually heated from −78° C. to room temperature, and then was stirred at room temperature for 18 hours. Water was added to the reaction solution, followed by four times of extraction with ethyl acetate. The organic layer was washed with saturated brine, then was dried with anhydrous sodium sulfate, and was concentrated under reduced pressure. The obtained residue was purified by silica gel column chromatography (ethyl acetate/n-hexane=0/100 to 50/50) to obtain ethyl 1-tert-butyloxycarbonyl-4-(2-nitrobenzyl)piperidine-4-carboxylate (1.62 g).

¹H-NMR (270 MHz, CDCl₃) δ: 1.18 (t, J=7.1 Hz, 3H), 1.44 (s, 9H), 2.00-2.10 (m, 2H), 2.58-2.80 (m, 2H), 3.30 (s, 2H), 3.85-4.03 (m, 2H), 4.01 (q, J=7.1 Hz, 3H), 4.13-4.17 (m, 1H), 7.20 (dd, J=7.6, 1.6 Hz, 1H), 7.35-7.43 (m, 1H), 7.45-7.53 (m, 1H), 7.87 (dd, J=7.9, 1.3 Hz, 1H).

MS(ESI) m/z: 293[M-(tert-Bu)+H]⁺.

<Step 2>

The ethyl 1-tert-butyloxycarbonyl-4-(2-nitrobenzyl)piperidine-4-carboxylate (1.27 g) was dissolved in ethanol (1 mL), 10% Pd carbon powder (47 mg) was added thereto, and the mixture was vigorously stirred under a hydrogen atmosphere at room temperature at normal pressure for 15 hours. The reaction solution was filtered through celite, and then the filtrate was concentrated under reduced pressure. The obtained residue was purified by silica gel column chromatography (ethyl acetate/n-hexane=0/100 to 100/0) to obtain 1-tert-butyloxycarbonyl-2'-oxo-2',4'-dihydro-1'H-spiro[piperidine-4,3'-quinoline] (261.1 mg)

¹H-NMR (270 MHz, CDCl₃) δ: 1.34-1.49 (m, 2H), 1.45 (s, 9H), 1.87-2.02 (m, 2H), 2.88 (s, 2H), 3.39-3.50 (m, 2H), 3.58-3.70 (m, 2H), 6.73 (d, J=7.9 Hz, 1H), 6.97-7.04 (m, 1H), 7.12-7.24 (m, 2H), 7.64 (br.s, 1H).

MS(ESI) m/z: 261[M-(tert-Bu)+H]⁺.

<Step 3>

The title compound (87.5 mg) was obtained from the 1-tert-butyloxycarbonyl-2'-oxo-2',4'-dihydro-1'H-spiro[piperidine-4,3'-quinoline] (141.1 mg) in the same way as in <Step 5> of Reference Example 31.

¹H-NMR (270 MHz, CD₃OD) δ: 1.33-1.45 (m, 2H), 1.83-1.94 (m, 2H), 2.76-2.89 (m, 2H), 2.89-3.00 (m, 2H), 2.92 (s, 2H), 6.83 (dd, J=7.7, 0.8 Hz, 1H), 6.93-7.01 (m, 1H), 7.12-7.22 (m, 2H).

Reference Example 42

1'-tert-butyloxycarbonylspiro[isoindoline-1,4'-piperidine]

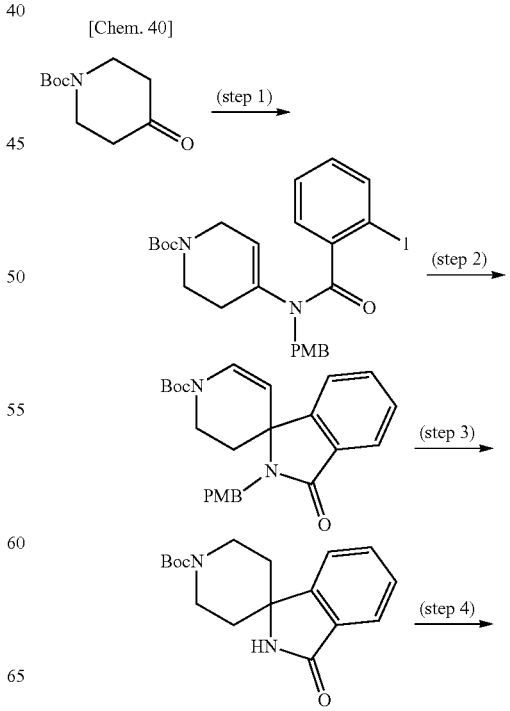

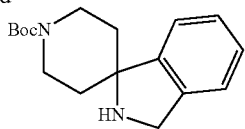

<Step 1>

First, 1-tert-butyloxycarbonyl-4-piperidone (96.3 mg) was dissolved in chloroform, then 4-methoxybenzylamine (0.075 mL) and tetraisopropyl orthotitanate (0.715 mL) were added thereto, and the mixture was stirred for 14 hours under reflux by heating. The reaction solution was ice-cooled, then 2-iodo benzoyl chloride (154.5 mg) and triethylamine (0.081 mL) were added thereto, and the mixture was further stirred at room temperature for 1 hour. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (ethyl acetate/n-hexane=20/80) to obtain N-(1-tert-butyloxycarbonyl-1,2,3,6-tetrahydropyridin-4-yl)2-iodo-N-(4-methoxybenzyl)benzamide (275.0 mg).

MS(ESI) M/Z: 549[m+h]$^+$.

<Step 2>

The N-(1-tert-butyloxycarbonyl-1,2,3,6-tetrahydro pyridin-4-yl)2-iodo-N-(4-methoxybenzyl)benzamide (575.6 mg) was dissolved in acetonitrile, then bis(triphenylphosphine)palladium(II) dichloride (73.7 mg) and potassium carbonate (290.1 mg) were added thereto, and the mixture was stirred under microwave irradiation at 170° C. for 10 minutes. Water was added to the reaction solution, followed by extraction with chloroform. The organic layer was dried with anhydrous magnesium sulfate and was concentrated under reduced pressure, and the obtained residue was purified by silica gel column chromatography (ethyl acetate/n-hexane=20/80) to obtain 1'-tert-butyloxycarbonyl-2-(4-methoxybenzyl)-2',3'-dihydro-1'H-spiro[isoindoline-1,4'-pyridine]-3-one (383.3 mg).

MS(ESI) m/z: 421[M+H]$^+$.

<Step 3>

The 1'-tert-butyloxycarbonyl-2-(4-methoxybenzyl)-2',3'-dihydro-1'H-spiro[isoindoline-1,4'-pyridine]-3-one (383.3 mg) was dissolved in trifluoroacetic acid, then trifluoromethanesulfonic acid (0.5 mL) was added thereto, and the mixture was stirred at 70° C. for 14 hours. A sodium hydrogen carbonate aqueous solution was added to the reaction solution, followed by extraction with chloroform. The organic layer was dried with anhydrous magnesium sulfate and was concentrated under reduced pressure. The obtained residue was dissolved in chloroform, then sodium triacetoxyborohydride (290.0 mg) and acetic acid (0.156 mL) were added thereto, and the mixture was stirred at room temperature for 3 hours. A sodium hydrogen carbonate aqueous solution was added to the reaction solution, followed by extraction with chloroform. The organic layer was dried with anhydrous magnesium sulfate and was concentrated under reduced pressure, the obtained residue was dissolved in chloroform, then di-carbonate-di-tert-butyl (0.251 mL) was added thereto, and the mixture was stirred at room temperature for 1 hour. The reaction solution was concentrated under reduced pressure. The obtained residue was purified by silica gel column chromatography (ethyl acetate/n-hexane=50/50) to obtain 1'-tert-butyloxycarbonyl-spiro[isoindoline-1,4'-piperidine]-3-one (mg)

MS(ESI) m/z: 303[M+H]$^+$.

<Step 4>

The 1'-tert-butyloxycarbonylspiro[isoindoline-1,4'-piperidine]-3-one (166.1 mg) was dissolved in toluene, then a borane dimethyl sulfide complex (0.063 mL) was added thereto, and the mixture was stirred under reflux by heating for 5 hours. A sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (ethyl acetate/n-hexane=50/50) to obtain the title compound (58.1 mg).

MS(ESI) m/z: 289[M+H]$^+$.

Reference Example 43

1'-benzyloxycarbonylspiro[indoline-3,4'-piperidine]-2-one

[Chem. 41]

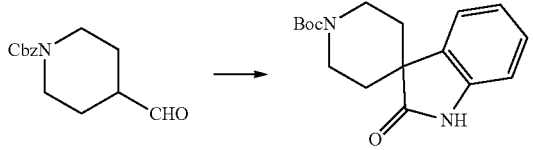

First, 1-benzyloxycarbonyl-4-formylpiperidine (994.7 mg) was dissolved in chloroform, then phenylhydrazine (0.475 ml) and trifluoroacetic acid (0.923 mL) were added thereto, and the mixture was stirred under reflux by heating for 1 hour. After that, 3-chloroperbenzoic acid (1.6659 g) was added thereto, and the mixture was further stirred at room temperature for 1 hour. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (ethyl acetate/n-hexane=50/50) to obtain the title compound (1.026 g).

MS(ESI) m/z: 337[M+H]$^+$.

Reference Example 44

1'-benzyloxycarbonyl-1-methylspiro[indoline-3,4'-piperidine]-2-one

[Chem. 42]

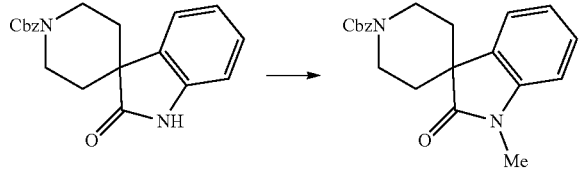

First, 1'-benzyloxycarbonylspiro[indoline-3,4'-piperidine]-2-one (1060 mg) was dissolved in tetrahydrofuran, then iodomethane (0.294 mL) and sodium hydride (189.1 mg) were added thereto, and the mixture was stirred at room temperature for 1 hour. A saturated ammonium chloride aqueous solution was added to the reaction solution, followed by extraction with ethyl acetate. The organic layer was dried with anhydrous magnesium sulfate and was concentrated under reduced pressure, and the obtained residue was purified by silica gel column chromatography (ethyl acetate/n-hexane=50/50) to obtain the title compound (706.8 mg).

MS(ESI) m/z: 351[M+H]$^+$

Reference Example 45

1'-benzyloxycarbonyl-1-(tert-butyloxycarbonyl)spiro[indoline-3,4'-piperidine]-4-carbonitrile

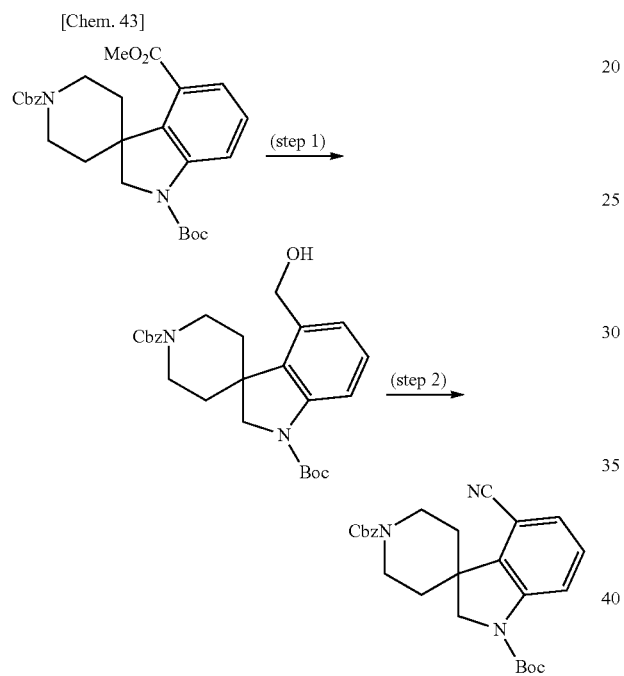

[Chem. 43]

<Step 1>

First, 1'-benzyloxycarbonyl-1-(tert-butyloxycarbonyl)spiro[indoline-3,4'-piperidine]-4-methyl carboxylate (2064 mg) was dissolved in tetrahydrofuran, lithium tetrahydroborate (280.6 mg) was added thereto, and the mixture was stirred under reflux by heating for 14 hours. A saturated ammonium chloride aqueous solution was added to the reaction solution, followed by extraction with chloroform. The organic layer was dried with anhydrous magnesium sulfate and was concentrated under reduced pressure, and the obtained residue was purified by silica gel column chromatography (methanol/chloroform=50/50) to obtain (1'-benzyloxycarbonyl-1-(tert-butyloxycarbonyl)spiro[indoline-3,4'-piperidine]-4-yl)methanol (1.78 g).

MS(ESI) m/z: 453[M+H]$^+$.

<Step 2>

The (1'-benzyloxycarbonyl-1-(tert-butyloxycarbonyl)spiro[indoline-3,4'-piperidine]-4-yl)methanol (307.3 mg) was dissolved in chloroform, a Dess-Martin reagent (345.6 mg) was added thereto, and the mixture was stirred at room temperature for 1 hour. A saturated sodium hydrogen carbonate aqueous solution was added to the reaction solution, followed by extraction with chloroform. The organic layer was dried with anhydrous magnesium sulfate and was concentrated under reduced pressure, and the obtained residue was dissolved in ammonia water. Then, iodine (689.4 mg) was added thereto, and the mixture was stirred for 14 hours. A saturated sodium thiosulfate aqueous solution was added to the reaction solution, followed by extraction with chloroform. The organic layer was dried with anhydrous magnesium sulfate and was concentrated under reduced pressure, and the obtained residue was purified by silica gel column chromatography (ethyl acetate/n-hexane=20/80) to obtain the title compound (256.4 mg).

MS(ESI) m/z: 448 [M+H]$^+$.

Reference Example 46

1'-(tert-butyloxycarbonyl)-4-chloro-6-hydroxy-1-methylspiro [indoline-3,4'-piperidine]-2-one

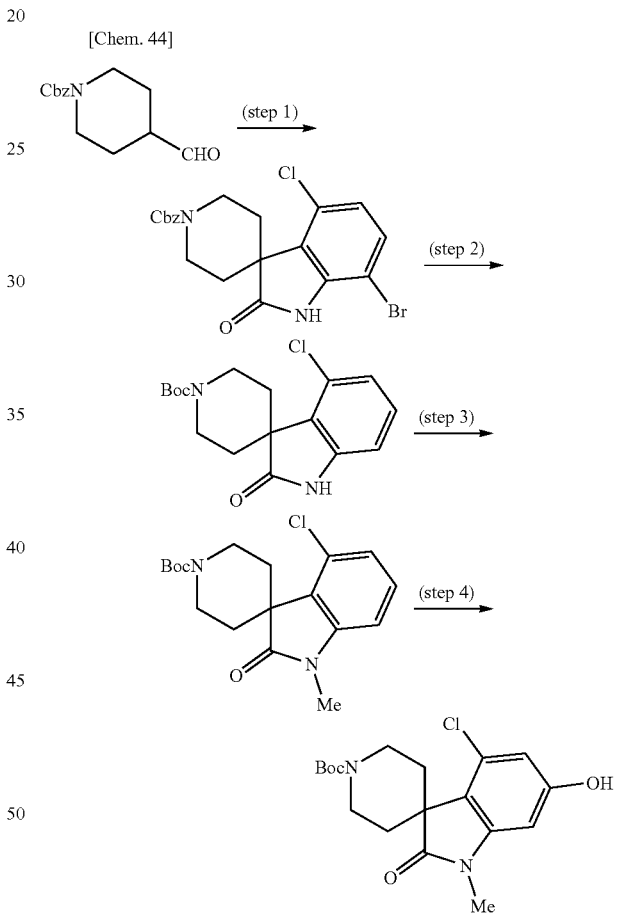

[Chem. 44]

<Step 1>

First, 1-benzyloxycarbonyl-4-formylpiperidine (217.4 mg) was dissolved in chloroform, then 2-bromo-5-chlorophenylhydrazine (233.7 mg) and trifluoroacetic acid (0.336 mL) were added thereto, and the mixture was stirred under reflux by heating for 20 hours. After that, 3-chloroperbenzoic acid (364.1 mg) was added thereto, and the mixture was further stirred at room temperature for 1 hour. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (ethyl acetate/n-hexane=50/50) to obtain 1'-benzyloxycarbonyl-7-bromo-4-chlorospiro[indoline-3,4'-piperidine]-2-one (182.2 mg).

MS(ESI) m/z: 449[M+H]$^+$.

<Step 2>

The 1'-benzyloxycarbonyl-7-bromo-4-chlorospiro[indoline-3,4'-piperidine]-2-one (2514 mg) was dissolved in methanol, 10% palladium carbon (595.0 mg) was added thereto, and the mixture was stirred under a hydrogen atmosphere at room temperature for 14 hours. The reaction solution was filtered through celite, the filtrate was concentrated under reduced pressure, and the obtained residue was dissolved in methanol. Then, di-carbonate-di-tert-butyl (1.54 mL) and triethylamine (0.935 mL) were added thereto, and the mixture was stirred at room temperature for 1 hour. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (ethyl acetate/n-hexane=50/50) to obtain 1'-(tert-butyloxycarbonyl)-4-chlorospiro[indoline-3,4'-piperidine]-2-one (1202 mg).

MS(ESI) m/z: 337[M+H]$^+$.

<Step 3>

The 1'-(tert-butyloxycarbonyl)-4-chlorospiro[indoline-3,4'-piperidine]-2-one (1202 mg) was dissolved in N,N-dimethylformamide, then iodomethane (0.667 mL) and sodium hydride (428.4 mg) were added thereto, and the mixture was stirred at room temperature for 1 hour. A saturated ammonium chloride aqueous solution was added to the reaction solution, followed by extraction with ethyl acetate. The organic layer was dried with anhydrous magnesium sulfate and was concentrated under reduced pressure, and the obtained residue was purified by silica gel column chromatography (ethyl acetate/n-hexane=50/50) to obtain 1'-(tert-butyloxycarbonyl)-4-chloro-1-methylspiro[indoline-3,4'-piperidine]-2-one (1142 mg).

MS(ESI) m/z: 351[M+H]$^+$.

<Step 4>

The 1'-(tert-butyloxycarbonyl)-4-chloro-1-methylspiro[indoline-3,4'-piperidine]-2-one (552.4 mg), bis(pinacolato)diboron (479.8 mg), bis(1,5-cyclooctadiene)di-µ-methoxydiiridium(I) (52.2 mg), and 4,4'-di-tert-butyl-2,2'-dipyridyl (42.3 mg) were dissolved in tetrahydrofuran, and the mixture was stirred under microwave irradiation at 180° C. for 1 hour. Water was added to the reaction solution, followed by extraction with chloroform. The organic layer was dried with anhydrous magnesium sulfate and was concentrated under reduced pressure, and the obtained residue was dissolved in ethanol and water (4:1), then 3-chloroperbenzoic acid (582.4 mg) was added thereto, and the mixture was stirred at room temperature for 6 hours. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (ethyl acetate/n-hexane=50/50) to obtain the title compound (244.0 mg).

MS(ESI) m/z: 367[M+H]$^+$.

Reference Example 47

1-(tert-butyloxycarbonyl)-6'-chloro-1',2'-dihydrospiro[piperidine-4,3'-pyrrolo[3,2-b]pyridine] and 1-(tert-butyloxycarbonyl)-4'-chloro-1',2'-dihydrospiro[piperidine-4,3'-pyrrolo[2,3-c]pyridine]

[Chem. 45]

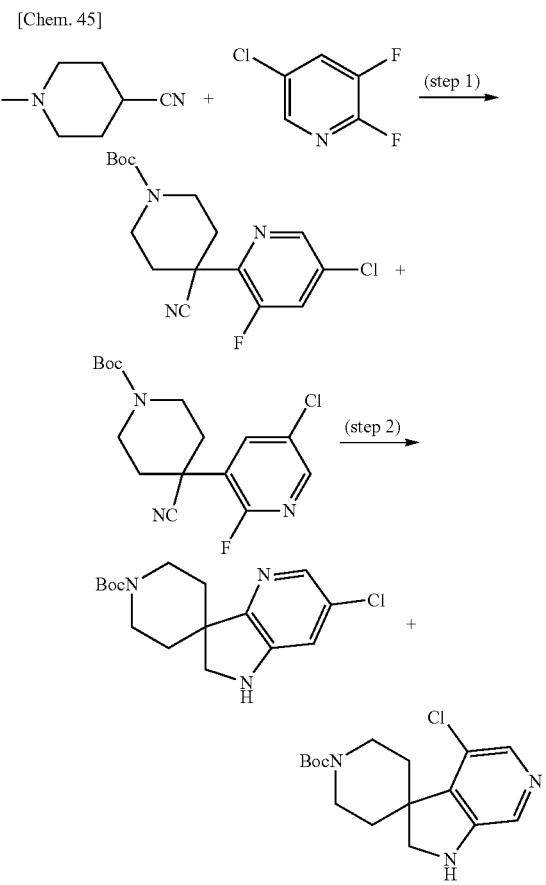

<Step 1>

First, 1-(tert-butyloxycarbonyl)-4-cyanopiperidine (301.9 mg) and 5-chloro-2,3-difluoropyridine (0.298 mL) were dissolved in toluene (2.87 mL), and the mixture was cooled to 0° C. A 0.5 M toluene solution (2.87 mL) of potassium bis(trimethylsilyl) amide was added dropwise to the above mixture, and then the resultant mixture was heated to room temperature and was stirred for 2.5 hours. The reaction solution was placed in a test tube containing 1 M hydrochloric acid (3 mL), and the organic layer was separated, followed by extraction with ethyl acetate. The organic layer thus collected all together was washed with water and saturated brine in sequence, was dried with sodium sulfate, and then was filtered. The filtrate was concentrated and the obtained residue was purified by silica gel column chromatography (ethyl acetate/hexane=5/95 to 40/60) to obtain a mixture (280.7 mg) of 1-(tert-butyloxycarbonyl)-4-(5-chloro-3-fluoropyridin-2-yl)-4-cyanopiperidine and 1-(tert-butyloxycarbonyl)-4-(5-chloro-2-fluoropyridin-3-yl)-4-cyanopiperidine.

MS(ESI) m/z: 340[M+H]$^+$.

<Step 2>

Then, lithium tri-tert-butoxyaluminum hydride and a 1.0 M tetrahydrofuran solution (3.742 mL) were added to a 1,4-dioxane solution (3.852 mL) of the mixture (280 mg) of 1-(tert-butyloxycarbonyl)-4-(5-chloro-3-fluoropyridin-2-yl)-4-cyanopiperidine and 1-(tert-butyloxycarbonyl)-4-(5-chloro-2-fluoropyridin-3-yl)-4-cyanopiperidine, and the mixture was dividedly placed in three reaction vessels, and heated by using microwaves at 130° C. for 20 minutes. After the reaction solution was cooled to 0° C., a 0.5 M sodium hydroxide aqueous solution (12 mL) was slowly added dropwise thereto, followed by celite filtration while washing with deionized water and ethyl acetate. After the organic solvent in the filtrate was removed by evaporation under reduced pressure, the residue was subjected to extraction with ethyl acetate, washing with deionized water, drying with sodium sulfate, and then filtration. The residue obtained by concentrating the filtrate was purified by silica gel thin layer chromatography (ethyl acetate/hexane=50/50) to obtain the title compounds (79.5 mg and 24.1 mg), respectively. 1-(tert-butyloxycarbonyl)-6'-chloro-1',2'-dihydrospiro[piperidine-4,3'-pyrrolo[3,2-b]pyridine]

$^1$H-NMR (400 MHz, CDCl$_3$) δ: 1.47 (s, 9H), 1.57-1.68 (m, 2H), 1.90-2.02 (m, 2H), 2.96-3.13 (m, 2H), 3.55 (s, 2H), 3.82 (br.s, 1H), 3.98-4.15 (m, 2H), 6.78 (d, J=2.0 Hz, 1H), 7.80 (d, J=2.1 Hz, 1H).

MS(ESI) m/z: 324 [M+H]$^+$.

1-(tert-butyloxycarbonyl)-4'-chloro-1',2'-dihydrospiro[piperidine-4,3'-pyrrolo[2,3-c]pyridine]

MS(ESI) m/z: 324[M+H]$^+$.

Reference Example 48

1',2'-dihydrospiro[piperidine-4,3'-pyrrolo[3,2-b]pyridine]trihydrochloride

[Chem. 46]

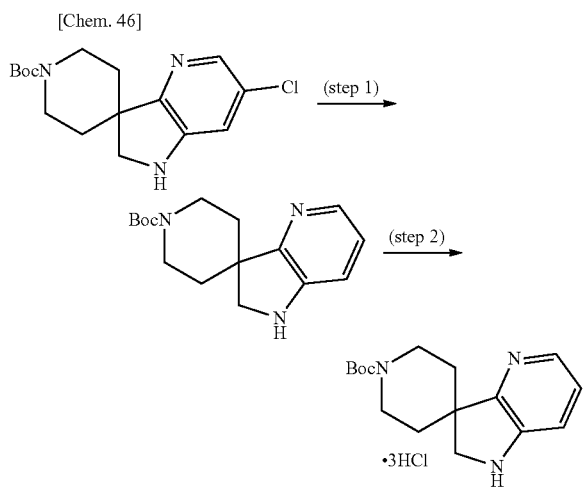

<Step 1>

First, the 1-(tert-butyloxycarbonyl)-6'-chloro-1',2'-dihydrospiro[piperidine-4,3'-pyrrolo[3,2-b]pyridine] (37.8 mg) and triethylamine (0.020 mL) were dissolved in methanol (1.2 mL), followed by purging with argon. After Pd/C (7.9 mg) was added thereto, purging with hydrogen gas was conducted, and then the mixture was stirred at room temperature overnight. The catalyst was removed by millipore filtration, the filtrate was concentrated, and the obtained residue was purified by silica gel thin layer chromatography (ethyl acetate/hexane=50/50) to obtain 1-(tert-butyloxycarbonyl)-1',2'-dihydrospiro[piperidine-4,3'-pyrrolo[3,2-b]pyridine] (12.4 mg).

$^1$H-NMR (400 MHz, CDCl$_3$) δ: 1.47 (s, 9H), 1.61-1.71 (m, 2H), 1.94-2.07 (m, 2H), 2.97-3.11 (m, 2H), 3.53 (s, 2H), 3.74 (br.s, 1H), 4.07 (br.s, 2H), 6.81-6.86 (m, 1H), 6.88-6.94 (m, 1H), 7.85-7.96 (m, 1H).

MS(ESI) m/z: 290[M+H]$^+$.

<Step 2>

The 1-tert-butyloxycarbonyl-1',2'-dihydrospiro[piperidine-4,3'-pyrrolo[3,2-b]pyridine] (12.4 mg) was dissolved in ethanol (0.314 mL), a 4 M 1,4-dioxane hydrochloride solution (0.054 mL) was added thereto, and the mixture was heated at 95° C. for 8 hours.

The solvent was removed by evaporation to obtain the title compound (11.8 mg).

MS(ESI) m/z: 190[M+H]$^+$.

Reference Example 49

1-tert-butyloxycarbonyl-6-(4-morpholinomethyloxazol-2-yl)spiro[indoline-3,4'-piperidine]

[Chem. 47]

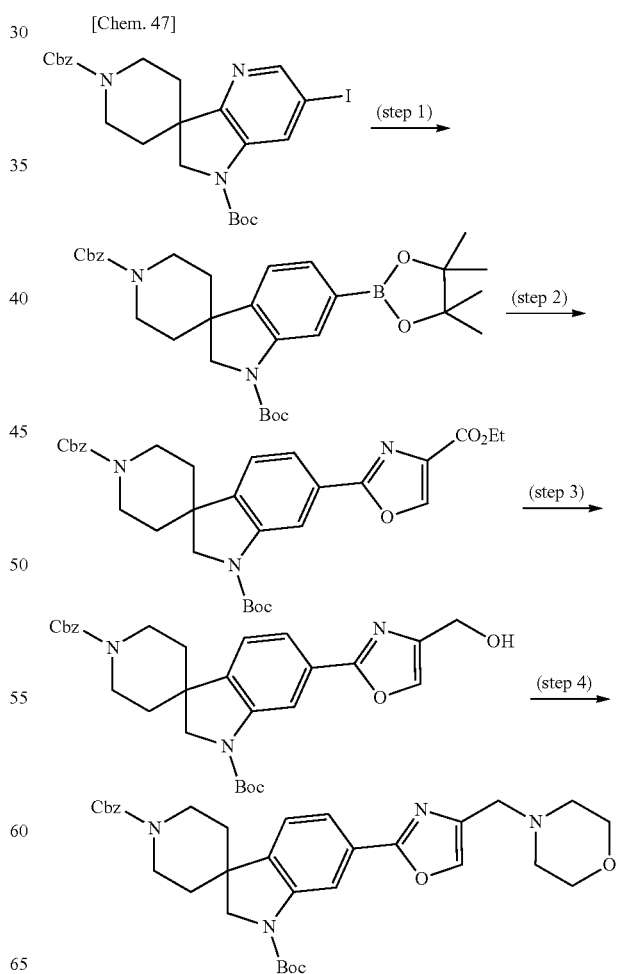

<Step 1>

First, 1'-benzyloxycarbonyl-1-tert-butyloxycarbonyl-6-iodospiro[indoline-3,4'-piperidine] (208 mg) was dissolved in N,N-dimethylformamide (5 mL), then bis(pinacolato)diboron (150 mg), potassium acetate (115 mg), and palladium acetate (9 mg) were added thereto, and the mixture was stirred at 90° C. for 3 hours. Brine was added to the reaction solution, followed by two times of extraction with ethyl acetate. The organic layer was washed with brine, was dried with anhydrous magnesium sulfate, and was concentrated under reduced pressure. The obtained residue was purified by silica gel column chromatography (ethyl acetate/hexane=30/70) to obtain 1'-benzyloxycarbonyl-1-tert-butyloxycarbonyl-6-(4,4,5,5-tetramethyl-1,3,2-dioxaborolan-2-yl)spiro[indoline-3,4'-piperidine] (138 mg).

$^1$H-NMR (400 MHz, CDCl$_3$) δ: 1.31 (s, 12H), 1.50-1.90 (m, 13H), 2.85-3.05 (m, 2H), 3.75-3.95 (m, 2H, 4.15-4.35 (m, 2H), 5.16 (s, 2H), 7.09 (d, J=7.2 Hz, 1H), 7.30-7.50 (m, 6H), 7.90-8.35 (m, 1H).

<Step 2>

The 1'-benzyloxycarbonyl-1-tert-butyloxycarbonyl-6-(4,4,5,5-tetramethyl-1,3,2-dioxaborolan-2-yl)spiro[indoline-3,4'-piperidine] (109 mg) was dissolved in dioxane (2 mL) and water (0.5 mL), then 2-chlorooxazol-4-ethyl carboxylate (52 mg), sodium carbonate (41 mg), and tetrakis(triphenylphosphine)palladium (11 mg) were added thereto, and the mixture was stirred at 90° C. for 1 hour. Brine was added to the reaction solution, followed by two times of extraction with ethyl acetate. The organic layer was washed with brine, was dried with anhydrous magnesium sulfate, and was concentrated under reduced pressure. The obtained residue was purified by silica gel column chromatography (ethyl acetate/chloroform=5/95) to obtain 1'-benzyloxycarbonyl-1-tert-butyloxycarbonyl-6-(4-ethoxycarbonyloxazol-2-yl)spiro[indoline-3,4'-piperidine] (110 mg).

$^1$H-NMR (400 MHz, CDCl$_3$) δ: 1.40 (t, J=7.2 Hz, 3H), 1.50-1.95 (m, 13H), 2.90-3.05 (m, 2H), 3.85-4.00 (m, 2H), 4.10-4.35 (m, 2H), 4.42 (q, J=7.2 Hz, 2H), 5.17 (s, 2H), 7.16 (d, J=8.0 Hz, 1H), 7.30-7.45 (m, 5H), 7.80-7.90 (m, 1H), 8.24 (s, 1H), 8.25-8.60 (m, 1H).

<Step 3>

The 1'-benzyloxycarbonyl-1-tert-butyloxycarbonyl-6-(4-ethoxycarbonyloxazol-2-yl)spiro[indoline-3,4'-piperidine] (18 mg) was dissolved in tetrahydrofuran (1 mL), lithium borohydride (4 mg) was added thereto, and the mixture was stirred at 60° C. for 2 hours. Water was added to the reaction solution, followed by two times of extraction with chloroform. The organic layer was dried with anhydrous magnesium sulfate and was concentrated under reduced pressure to obtain 1'-benzyloxycarbonyl-1-tert-butyloxycarbonyl-6-(4-hydroxymethyloxazol-2-yl)spiro[indoline-3,4'-piperidine] (14 mg).

$^1$H-NMR (400 MHz, CDCl$_3$) δ: 1.50-1.95 (m, 13H), 2.90-3.05 (m, 2H), 3.85-4.00 (m, 2H), 4.15-4.35 (m, 2H), 4.66 (s, 2H), 5.17 (s, 2H), 7.14 (d, J=7.6 Hz, 1H), 7.30-7.45 (m, 5H), 7.61 (s, 1H), 7.65-7.75 (m, 1H), 8.10-8.60 (m, 1H).

<Step 4>

The 1'-benzyloxycarbonyl-1-tert-butyloxycarbonyl-6-(4-hydroxymethyloxazol-2-yl)spiro[indoline-3,4'-piperidine] (22 mg) was dissolved in chloroform (0.5 mL), then triethylamine (0.009 mL) and methanesulfonyl chloride (0.004 mL) were added thereto, and the mixture was stirred at room temperature for 20 minutes. Morpholine (16 mg) was added to the reaction solution, and the mixture was stirred at 50° C. for 3 hours. After that, water was added to the reaction solution, followed by two times of extraction with chloroform. The organic layer was dried with anhydrous magnesium sulfate and was concentrated under reduced pressure, and the obtained residue was purified by silica gel column chromatography (methanol/chloroform=5/95) to obtain the title compound (21 mg).

$^1$H-NMR (400 MHz, CDCl$_3$) δ: 1.50-1.95 (m, 13H), 2.50-2.65 (m, 4H), 2.90-3.05 (m, 2H), 3.52 (s, 2H), 3.70-3.80 (m, 4H), 3.85-4.00 (m, 2H), 4.15-4.40 (m, 2H), 5.17 (s, 2H), 7.13 (d, J=8.0 Hz, 1H), 7.30-7.45 (m, 5H), 7.56 (s, 1H), 7.70-7.80 (m, 1H), 8.10-8.60 (m, 1H).

Compounds of Reference Example 50 to Reference Example 196 presented below in Tables 3 to 22 were obtained by using the methods used in Reference Examples 23 to 49 described above and their applied methods as well as the methods known by literatures and their applied methods.

TABLE 3

| Reference Example | Compound Name | Structural formula | 1H NMR δ ppm | Solvent | ESI MS m/z |
|---|---|---|---|---|---|
| 50 | 3H-spiro[isobenzofuran-1,4'-piperidin]-3-one hydrochloride | | 1.99 (d, J = 14.2 Hz, 2H), 2.47 (dt, J = 4.9, 14.2 Hz, 2H), 3.43 (dt, J = 3.0, 13.3 Hz, 2H), 3.51-3.60 (m, H), 7.63-7.69 (m, 2H), 7.83 (dt, J = 1.1, 7.6 Hz, 1H), 7.92 (td, J = 0.9, 7.7 Hz, 1H). | CD3OD | |
| 51 | 1'-benzyl-4-methoxy-3H-spiro[isobenzofuran-1,4'-piperidin]-3-one hydrochloride | | 1.52-1.57 (m, 2H), 1.70 (dd, J = 14.1, 2.5 Hz, 1H), 2.19 (td, J = 13.2, 4.7 Hz, 1H), 2.56 (td, J = 12.1, 2.5 Hz, 1H), 2.87-2.93 (m, 1H), 3.62 (s, 2H), 4.00 (s, 3H), 6.92 (d, J = 8.3 Hz, 1H), 6.95 (d, J = 7.4 Hz, 1H), 7.26 (br. s., 1H), 7.28-7.38 (m, 4H), 7.60 (t, J = 7.7 Hz, 1H). | CDCl3 | |

TABLE 3-continued

| Reference Example | Compound Name | Structural formula | 1H NMR δ ppm | Solvent | ESI MS m/z |
|---|---|---|---|---|---|
| 52 | 6-methoxy-3H-spiro[isobenzofuran-1,4'-piperidin]-3-one hydrochloride | | 1.97 (d, J = 14.2 Hz, 1H), 2.45 (td, J = 14.2, 5.0 Hz, 1H), 3.35 (s, 1H), 3.42 (td, J = 13.3, 3.1 Hz, 1H), 3.52-3.59 (m, 1H), 3.96 (s, 1H), 4.85 (s, 4H), 7.10-7.15 (m, 1H), 7.13 (s, 1H), 7.16-7.22 (m, 1H), 7.19 (d, J = 8.6 Hz, 1H), 7.81 (d, J = 8.5 Hz, 1H). | CD3OD | |
| 53 | 5H-spiro[furo[3,4-b]pyridine-7,4'-piperidin]-5-one | | | | 205 [M + H]+ |
| 54 | 1H-spiro[furo[3,4-c]pyridine-3,4'-piperidin]-1-one | | 1.71-1.81 (m, 2 H), 2.22 (ddd, J = 14.0, 12.0,5.5 Hz, 2 H), 2.99-3.17 (m, 4 H), 7.84 (dd, J = 5.1, 1.1 Hz, 1 H), 8.84 (d, J = 5.1 Hz, 1 H), 9.00 (d, J = 1.1 Hz, 1 H). | CD3OD | 205 [M + H]+ |
| 55 | 7H-spiro[furo[3,4-b]pyridine-5,4'-piperidin]-7-one | | 1.69-1.79 (m, 2 H), 2.06-2.18 (m, 2 H), 3.08-3.25 (m, 4 H), 7.58 (dd, J = 7.8, 4.7 Hz, 1 H), 7.85 (dd, J = 7.8, 1.4 Hz, 1 H), 8.90 (dd, J = 4.7, 1.4 Hz, 1 H). | CDCl3 | 205 [M + H]+ |
| 56 | 4H-spiro[furo[3,4-b]furan-6,4-piperidin]-4-one hydrochloride | | 2.06-2.12 (m, 1H), 2.31-3.39 (m, 1H), 3.15-3.25 (m, 1H), 3.31-3.38 (m, 1H),6.92 (d, J = 2.0 Hz, 1H), 8.07 (d, J = 2.0 Hz, 1H), 9.07 (br. s, 1H). | DMSO-d6 | 194 [M + H]+ |

TABLE 4

| Reference Example | Compound Name | Structural formula | 1H NMR δ ppm | Solvent | ESI MS m/z |
|---|---|---|---|---|---|
| 57 | 4'H-spiro[piperidine-4,6'-thieno[2,3-c]furan]-4'-one hydrochloride | | 2.10 (d, J = 13.8 Hz, 1H), 2.28-2.43 (m, 1H), 3.15-3.27 (m, 1H), 3.34-3.41 (m, 1H), 7.33 (d, J = 4.9 Hz, 1H), 7.86 (d, J = 4.9 Hz, 1H), 9.02 (br. s., 1H). | DMSO-d6 | |
| 58 | 6'H-spiro[piperidine-4,4'-thieno[2,3-c]furan]-6'-one hydrochloride | | 1.95-2.07 (m, 2H), 2.31-2.44 (m, 2H), 3.12-3.22 (m, 2H), 3.35-3.43 (m, 1H), 7.35 (d, J = 4.8 Hz, 1H), 8.31 (d, J = 4.8 Hz, 1H), 9.08 (br. s, 1H). | DMSO-d6 | |

TABLE 4-continued

| Reference Example | Compound Name | Structural formula | 1H NMR δ ppm | Solvent | ESI MS m/z |
|---|---|---|---|---|---|
| 59 | 7-fluoro-3H-spiro[isobenzofuran-1,4'-piperidin]-3-one hydrochloride | | 2.12 (dd, J = 16.4,1.7 Hz, 2H), 2.66 (td, J = 14.4, 4.8 Hz, 2H), 3.41-3.51 (m, 2H), 3.56-3.64 (m, 2H), 7.55 (t, J = 8.8 Hz, 1H), 7.68 (td, J = 7.9, 4.5 Hz, 1H), 7.72-7.79 (m, 1H). | D2O | |
| 60 | 1'-benzyl-5,7-difluoro-H-spiro[isobenzofuran-1,4'-piperidin]-3-one | | 1.69 (d,J = 11.2 Hz, 2H), 2.44-2.57 (m, 4H), 2.87-2.96 (m, 2H), 3.63 (s, 2H), 7.11 (td, J = 8.8, 2.1 Hz, 1H), 7.28-7.41 (m, 6H). | CDCl3 | |
| 61 | 6-fluoro-3H-spiro[isobenzofuran-1,4'-piperidin]-3-one hydrochloride | | 2.08 (d, J = 14.6 Hz, 2H), 2.44 (td, J = 14.3, 5.0 Hz, 2H) 3.44 (td, J = 13.4, 3.1 Hz, 2H), 3.55-3.62 (m, 2H), 7.37-7.44 (m, 2H), 7.95 (dd, J = 8.1, 4.5 Hz, 1H). | D2O | |
| 62 | 5-fluoro-3H-spiro[isobenzofuran-1,4'-piperidin]-3-one hydrochloride | | 2.06 (d, J = 14.6 Hz, 2H), 2.46 (td, J = 14.3, 4.8 Hz, 2H), 3.44 (td, J = 13.3, 2.9 Hz, 2H), 3.52-3.64 (m, 2H), 7.55-7.69 (m, 3H). | D2O | |
| 63 | 4-fluoro-3H-spiro[isobenzofuran-1,4'-piperidin]-3-one hydrochloride | | 2.09 (d, J = 14.6 Hz, 2H), 2.41-2.53 (m, 2H), 3.44 (td, J = 13.4, 3.0 Hz, 2H), 3.59 (dd, J = 13.2, 4.6 Hz, 2H), 7.33 (t, J = 8.3 Hz, 1H), 7.44 (d, J = 6.8 Hz, 1H), 7.85 (td, J = 8.0, 4.8 Hz, 1H). | D2O | |
| 64 | 7-methoxy-3H-spiro[isobenzofuran-1,4'-piperidin]-3-one hydrochloride | | 1.89-1.97 (m, 2H), 2.82 (td, J = 14.5, 5.1 Hz, 2H), 3.42 (td, J = 13.5, 3.1 Hz, 2H), 3.52-3.59 (m, 2H), 3.94 (s, 3H), 7.39 (d, J = 8.0 Hz, 1H), 7.47 (d, J = 7.5 Hz, 1H), 7.59-7.64 (dd, J = 8.0, 7.5 Hz, 1H). | D2O | |

TABLE 5

| Reference Example | Compound Name | Structural formula | 1H NMR δ ppm | Solvent | ESI MS m/z |
|---|---|---|---|---|---|
| 65 | 6,7-difluoro-3H-spiro[isobenzofuran-1,4'-piperidin]-3-one hydrochloride | | 2.15 (m, 2H), 2.63 (t, J = 14.3 Hz, 2H), 3.45 (td, J = 13.5, 2.9 Hz, 2H), 3.60 (dd, J = 4.9, 4.8 Hz, 2H), 7.55 (dd, J = 10.4, 8.4 Hz, 1H), 7.76 (dd, J = 8.1, 3.4 Hz, 1H). | D2O | |
| 66 | 7-fluoro-5-methoxy-3H-spiro[isobenzofuran-1,4'-piperidin]-3-one hydrochloride | | 2.08 (d, J = 14.5 Hz, 2H), 2.60 (td, J = 14.4, 4.9 Hz, 2H), 3.38-3.48 (m, 2H), 3.58 (dd, J = 13.3, 4.6 Hz, 2H), 3.90 (s, 3H), 7.17 (dd, J = 10.9, 2.1 Hz, 1H), 7.30 (d, J = 2.1 Hz, 1H). | D2O | |
| 67 | 7-fluoro-4-methoxy-3H-spiro[isobenzofuran-1,4'-piperidin]-3-one hydrochloride | | 2.09 (d, J = 14.4 Hz, 2H), 2.61 (td, J = 14.3, 5.0 Hz, 2H), 3.42 (td, J = 13.4, 3.0 Hz, 2H), 3.58 (dd, J = 13.2, 4.8 Hz, 2H), 3.95 (s, 3H), 7.17 (dd, J = 9.1, 3.1 Hz, 1H), 7.52 (t, J = 9.1 Hz, 1H). | D2O | |
| 68 | 7-fluoro-5-((4-methoxybenzyl)oxy)-3H-spiro[isobenzofuran-1,4'-piperidin]-3-one hydrochloride | | 2.06 (d, J = 14.5 Hz, 2H), 2.59 (td, J = 14.3, 4.3 Hz, 2H), 3.38-3.47 (m, 2H), 3.57 (dd, J = 12.8, 4.3 Hz, 2H), 3.82 (s, 3H), 5.15 (s, 2H), 7.02 (d, J = 8.6 Hz, 2H), 7.19 (dd, J = 10.8, 1.9 Hz, 1H), 7.33 (d, J = 1.9 Hz, 1H), 7.44 (d, J = 8.6 Hz, 2H). | D2O | |
| 69 | 5-(2-(dimethylamino)ethoxy)-7-fluoro-5hidoroxy-3H-spiro[isobenzofuran-1,4'-piperidin]-3-one dihydrochloride | | 2.05 (d, J = 14.7 Hz, 2H), 2.63 (t, J = 13.7 Hz, 2H), 3.00 (s, 6H), 3.35-3.42 (m, 2H), 3.52-3.61 (m, 2H), 3.62-3.70 (m, 2H), 4.50 (t, J = 4.4 Hz, 2H), 7.31 (d, J = 10.7 Hz, 1H), 7.39 (d, J = 1.9 Hz, 1H). | CD3OD | |
| 70 | 7-fluoro-5-(2-(4-methylpiperazin-1-yl)ethoxy)-3H-spiro[isobenzofuran-1,4'-piperidin]-3-one trihydrochloride | | | | 364 [M + H]+ |

TABLE 5-continued

| Reference Example | Compound Name | Structural formula | 1H NMR δ ppm | Solvent | ESI MS m/z |
|---|---|---|---|---|---|
| 71 | 5-(2-(1,1-dioxidothiomorpholino)ethoxy)-7-fluoro-3Hspiro[isobenzofuran-1,4'-piperidin]-3-one dihydrochloride | | | | 399 [M + H]+ |

TABLE 6

| Reference Example | Compound Name | Structural formula | 1 H NMR δ ppm | Solvent | ESI MS m/z |
|---|---|---|---|---|---|
| 72 | ethyl 2-[(7-fluoro-3-oxo-377-spiro[isobenzofuran-1,4'-piperidin]-5-yl)oxy]acetate hydrochloride | | 1.22 (t, J = 7.1 Hz, 3 H), 1.93-2.05 (m, 2 H), 3.03-3.23 (m, 2 H), 3.38-3.53 (m, 4 H), 4.18 (q, J = 7.3 Hz, 2 H), 4.99 (s, 2 H), 7.27 (d, J = 2.0 Hz, 1 H), 7.40 (dd, J = 10.9, 2.0 Hz, 1 H), 9.23 (br s, 2 H). | DMSO-d6 | |
| 73 | 5-[methyl(pyridin-3-ylmethyl)amino]-3H-spiro[isobenzofuran-1,4'-piperidin]-3-one | | 1.69 (d, J = 12.2 Hz, 2H), 2.10 (ddd, J = 13.9,11.4, 5.9 Hz, 2H), 3.11 (s, 3H), 3.12-3.22 (m, 4H), 4.61 (s, 2H), 7.02 (dd, J = 8.5,2.5 Hz, 1H), 7.14 (d, J = 2.4 Hz, 1H), 7.22-7.26 (m, 2H), 7.52 (dt, J = 7.9,1.9 Hz, 1H), 8.49-8.51 (m, 1H), 8.52-8.54 (m, 1H). | CDCl3 | |
| 74 | 5-{methyl[(1-methylpiperidin-4-yl)methyl]amino}-3H-spiro[isobenzofuran-1,4'-piperidin]-3-one | | 1.24-1.41 (m, 2H), 1.63-1.78 (m, 5H), 1.82-1.94 (m, 3H), 2.04 (td, J = 12.9, 5.1 Hz, 2H), 2.26 (s, 3H), 2.87 (d, J = 11.5 Hz, 2H), 3.02 (s, 3H), 3.04-3.16 (m, 4H), 3.25 (d, J = 7.0 Hz, 2H), 6.95 (dd, J = 8.5,2.5 Hz, 1H), 7.02 (d, J = 2.4 Hz, 1H), 7.22 (d, J = 8.6 Hz, 1H). | CDCl3 | |
| 75 | 7-fluoro-5-methoxy-3H-spiro[isobenzofuran-1,4'-piperidine] | | 1.73 (dd, J = 13.8, 2.3 Hz, 2H), 2.10 (td, J = 12.4, 6.0 Hz, 2H), 2.98-3.09 (m, 4H), 3.79 (s, 3H), 5.05 (s, 2H), 6.49 (dd, J = 11.2,2.0 Hz, 1H), 6.53 (dt, J = 1.9, 0.9 Hz, 1H). | CDCl3 | |
| 76 | 7-methoxy-3H-spiro[isobenzofuran-1,4'-piperidine] | | 1.60-1.71 (m, 2H), 2.32 (td, J = 13.0, 5.4 Hz, 2H), 2.96-3.09 (m, 4H), 3.83 (s, 3H), 5.06 (s, 2H), 6.75 (d, J = 8.1 Hz, 1H), 6.79 (dd, J = 7.5, 0.7 Hz, 1H), 7.23 (dd, J = 8.1, 7.5 Hz, 1H). | CDCl3 | |

TABLE 6-continued

| Reference Example | Compound Name | Structural formula | 1 H NMR δ ppm | Solvent | ESI MS m/z |
|---|---|---|---|---|---|
| 77 | 7-fluoro-4-methoxy-3H-spiro[isobenzofuran-1,4'-piperidine] | | 1.75 (dd, J = 13.7, 2.3 Hz, 2H), 2.12 (td, J = 12.6, 5.6 Hz, 2H), 2.99-3.10 (m, 4H), 3.81 (s, 3H), 5.06 (s, 2H), 6.67 (dd, J = 8.7, 3.2 Hz, 1H), 6.89 (t, J = 8.7Hz, 1H). | CDCl3 | |

TABLE 7

| Reference Example | Compound Name | Structural formula | 1H NMR δ ppm | Solvent | ESI MS m/z |
|---|---|---|---|---|---|
| 78 | 5,7-difluoro-3H-spiro[isobenzofuran-1,4'-piperidine] | | 1.74 (dd, J = 13.7, 2.3 Hz, 2H), 2.05-2.16 (m, 2H), 2.99-3.09 (m, 4H), 5.06 (s, 2H), 6.66-6.73 (m, 2H). | CDCl3 | |
| 79 | 7-fluoro-5-[methyl(pyridin-3-ylmethyl)amino]-3H-spiro[isobenzofuran-1,4'-piperidin]-3-one | | 1.62-1.69 (m, 2H), 2.20-2.32 (m, 2H), 3.07-3.17 (m, 7H), 4.38-4.46 (m, 1H), 4.60 (s, 2H), 6.59-6.67 (m, 1H), 6.93-6.97 (m, 1H), 7.24-7.33 (m, 1H), 7.48-7.54 (m, 1H), 8.46-8.50 (m, 1H), 8.52-8.58 (m, 1H). | CDCl3 | |
| 80 | 5-{[3-(dimethylamino)propyl](methyl)amino}-7-fluoro-3H-spiro[isobenzofuran-1,4'-piperidin]-3-one | | 1.63-1.79 (m, 4H), 2.18-2.31 (m, 10H), 2.98 (s, 3H), 3.06-3.18 (m, 4H), 3.41 (t, J = 7.2 Hz, 2H), 6.66 (dd, J = 12.8, 2.1 Hz, 1H), 6.90 (d, J = 2.1 Hz, 1H). | CDCl3 | |
| 81 | 2-(dimethylamino)-N-(3-oxo-3H-spiro[isobenzofuran-1,4'-piperidin]-5-yl)acetamide | | 1.64-1.72 (m, 2H), 2.10-2.21 (m, 2H), 2.38 (s, 6H), 3.03-3.16 (m, 4H), 3.18 (s, 2H), 7.55 (d, J = 8.4 Hz, 1H), 7.91 (d, J = 8.2 Hz, 1H), 8.20 (s, 1H). | CD3OD | |
| 82 | 1'-benzyl-4-fluoro-2H-spiro[benzofuran-3,4'-piperidin]-2-one hydrobromide | | 2.31 (d, J = 15.0 Hz, 2H), 2.56 (br. m, 2H), 3.54 (d, J = 13.2 Hz, 2H), 3.63-3.75 (m, 2H), 4.46 (s, 2H), 6.97-7.09 (m, 2H), 7.42 (td, J = 8.4, 5.7 Hz, 1H), 7.50-7.58 (m, 5H). | D2O | |
| 83 | 1'-benzyloxycarbonyl-1-tert-butyloxycarbonyl spiro[indoline-3,4'-piperidine] | | 1.58 (br. s, 9 H), 1.77-1.88 (m, 2 H), 2.90-3.03 (m, 2 H), 3.80-3.93 (m, 2 H), 4.16-4.29 (m, 2 H), 5.17 (s, 2 H), 6.95-6.99 (m, 1 H), 7.06-7.09 (m, 1 H), 7.16-7.22 (m, 1 H), 7.30-7.96 (m, 6 H). | CDCl3 | 423 [M + H]+ |

TABLE 7-continued

| Reference Example | Compound Name | Structural formula | 1H NMR δ ppm | Solvent | ESI MS m/z |
|---|---|---|---|---|---|
| 84 | 1'-benzyloxycarbonyl-1-methylspiro[indoline-3,4'-piperidine] | | | | [M + H]+ |
| 85 | 2-methyl-1-(spiro[indoline-3,4'-piperidin]-1-yl)propan-2-ol | | | | 261 [M + H]+ |

TABLE 8

| Reference Example | Compound Name | Structural formula | 1H NMR δ ppm | Solvent | ESI MS m/z |
|---|---|---|---|---|---|
| 86 | 1-(spiro[indoline-3,4'-piperidin]-1-yl)propan-2-ol | | | | 247 [M + H]+ |
| 87 | 1-(2-methoxyethyl)spiro[indoline-3,4'-piperidine] | | | | 247 [M + H]+ |
| 88 | 1-(3-methoxypropyl)spiro[indoline-3,4'-piperidine] | | | | 261 [M + H]+ |
| 89 | (S)-1-{3-[(tert-butyldimethylsilyl)oxy]-3-{spiro[indoline-3,4'-piperidin]-1-yl}propan-2-ol | | | | 377 [M + H]+ |

TABLE 8-continued

| Reference Example | Compound Name | Structural formula | 1H NMR δ ppm | Solvent | ESI MS m/z |
|---|---|---|---|---|---|
| 90 | 1-methoxy-3-spiro[indoline-3,4'-piperidin]-1-ylpropan-2-ol | | | | 277 [M + H]+ |
| 91 | benzyl spiro[indoline-3,4'-piperidine]-1-carboxylate | | 1.78 (br d, J = 14.8 Hz, 2 H), 2.12 (td, J = 13.5, 4.3 Hz, 2 H) 2.85-3.00 (m, 2 H), 3.32 (br d, J = 12.9 Hz, 2 H), 3.94 (s, 2 H), 5.29 (s, 2 H), 6.99-7.09 (m, 1 H), 7.16-7.26 (m, 2 H), 7.27-7.50 (m, 6 H). | CDCl3 | 323 [M + H]+ |
| 92 | 2-(1'-benzyloxycarbonylspiro[indoline-3,4'-piperidine]-1-yl)ethan-1-ol | | | | 367 [M + H]+ |
| 93 | 1'-benzyloxycarbonyl-1-2-(tert-butyloxycarbonylaminoethyl)spiro[indoline-3,4-piperidine] | | | CDCl3 | 466 [M + H]+ |

TABLE 9

| Reference Example | Compound Name | Structural formula | 1H NMR δ ppm | Solvent | ESI MS m/z |
|---|---|---|---|---|---|
| 94 | 1'-benzyloxycarbonyl-1-tert-butyloxycarbonyl-5-methoxyspiro[indoline-3,4'-piperidine] | | | | 453 [M + H]+ |
| 95 | 7-methoxyspiro[indoline-3,4'-piperidine] | | | | 219 [M + H]+ |

TABLE 9-continued

| Reference Example | Compound Name | Structural formula | 1H NMR δ ppm | Solvent | ESI MS m/z |
|---|---|---|---|---|---|
| 96 | 1-(4-oxo-3,4,5,6,7,8-hexahydroquinazolin-2-yl)piperidine-4-carbaldehyde | | | | 262 [M + H]+ |
| 97 | 1-benzyloxycarbonyl-6-bromospiro[indoline-3,4'-piperidine] | | 1.66-1.81 (m, 4 H), 2.91-3.03 (m, 2 H), 3.48 (s, 2 H), 4.08-4.19 (m, 2 H), 5.16 (s, 2 H), 6.73-6.75 (m, 1 H), 6.82-6.84 (m, 2 H), 7.30-7.39 (m, 5 H). | CDCl3 | 401 [M + H]+ |
| 98 | 1'-benzyloxycarbonyl-6-bromospiro[indoline-3,4'-piperidine] | | 1.55-1.64 (m, 2 H), 2.58-2.69 (m, 2 H), 2.82-2.95 (m, 2 H), 3.55 (s, 2 H), 3.84 (br s, 1 H), 4.17-4.32 (m, 2 H), 5.17 (s, 2 H), 6.52-6.55 (m, 1 H), 6.80-6.83 (m, 1 H), 6.85-6.89 (m, 1 H), 7.29-7.40 (m, 5 H). | CDCl3 | 401 [M + H]+ |
| 99 | methyl 1'-benzyloxycarbonyl-1-tert-butyloxycarbonyl spiro[indoline-3,4'-piperidine]-5-carboxylate | | 1.55-1.71 (m, 11 H), 1.83-1.93 (m, 2 H), 2.91-3.02 (m, 2 H), 3.86-3.95 (m, 5 H), 4.18-4.31 (m, 2 H), 5.18 (s, 2 H), 7.30-7.40 (m, 5 H), 7.48-7.96 (m, 3 H). | CDCl3 | 481 [M + H]+ |
| 100 | methyl 1'-benzyloxycarbonyl-1-tert-butyloxycarbonyl spiro[indoline-3,4'-piperidine]-6-carboxylate | | 1.53-1.72 (m, 11 H), 1.77-1.89 (m, 2 H), 2.90-3.03 (m, 2 H), 3.85-3.96 (m, 5 H), 4.17-4.31 (m, 2 H), 5.17 (s, 2 H), 7.10-7.14 (m, 1 H), 7.30-7.40 (m, 5 H), 7.67-7.72 (m, 1 H), 8.09-8.57 (m, 1 H). | CDCl3 | 481 [M + H]+ |
| 101 | methyl 1'-benzyloxycarbonyl-1-tert-butyloxycarbonyl spiro[indoline-3,4'-piperidine]-4-carboxylate | | 1.45-1.62 (m, 11 H), 2.53-2.65 (m, 2 H), 2.81-3.01 (m, 2 H), 3.81 (s, 3 H), 3.89 (s, 2 H), 4.15-4.31 (m, 2 H), 5.18 (s, 2 H), 7.21-7.43 (m, 7 H), 7.69-8.28 (m, 1 H). | CDCl3 | 481 [M + H]+ |

TABLE 10

| Reference Example | Compound Name | Structural formula | 1H NMR δ ppm | Solvent | ESI MS m/z |
|---|---|---|---|---|---|
| 102 | 1'-benzyloxycarbonyl-1-(tert-butyloxycarbonyl)spiro[indoline-3,4'-piperidine]-4-carbonitrile | | | | 448 [M+H]+ |
| 103 | 1'-benzyloxycarbonyl-1-(tert-butyloxycarbonyl)-N-(2-morpholinoethyl)spiro[indoline-3,4'-piperidine]-6-carboxamide | | | | 579 [M+H]+ |
| 104 | 1'-benzyloxycarbonyl-1-(tert-butyloxycarbonyl)-N-methyl-N-(2-morpholinoethyl)spiro[indoline-3,4'-piperidine]-6-carboxamide | | | | 593 [M+H]+ |
| 105 | 1'-benzyloxycarbonyl-1-methyl-N-(2-morpholinoethyl)spiro[indoline-3,4'-piperidine]-6-carboxamide | | | | 493 [M+H]+ |
| 106 | N-(2-(dimethylamino)ethyl)-1-methyl spiro[indoline-3,4'-piperidine]-6-carboxamide | | 1.65-1.95 (m, 4 H), 2.26 (s, 6 H), 2.50-2.60 (m, 2 H), 2.75-2.90 (m, 5 H), 3.10-3.20 (m, 2 H), 3.30 (s, 2 H), 3.45-3.55 (m, 2 H), 6.78 (br. s, 1 H), 6.93 (s, 1 H), 7.00-7.10 (m, 2 H). | CDCl3 | |
| 107 | 1-methyl-N-(2-(piperidin-1-yl)ethyl)spiro[indoline-3,4'-piperidine]-6-carboxamide hydrobromide | | 1.65-1.75 (m, 2 H), 1.85-2.00 (m, 6 H), 2.05-2.25 (m, 2 H), 2.86 (s, 3 H), 3.15-3.50 (m, 12 H), 3.70-3.80 (m, 2 H), 7.00-7.05 (m, 1 H), 7.15-7.20 (m, 1 H), 7.25-7.30 (m, 1 H). | CD3OD | |
| 108 | 4-hydroxymethyl spiro[indoline-3,4'-piperidine] | | 1.70-1.80 (m, 2 H), 2.25-2.35 (m, 2 H), 2.80-2.95 (m, 2 H), 3.10-3.20 (m, 2 H), 3.44 (s, 2 H), 4.73 (s, 2 H), 6.60-6.65 (m, 1 H), 6.75-6.80 (m, 1 H), 6.95-7.05 (m, 1 H). | CD3OD | |

TABLE 11

| Reference Example | Compound Name | Structural formula | 1H NMR δ ppm | Solvent | ESI MS m/z |
|---|---|---|---|---|---|
| 109 | 1,1'-bis-tert-butyloxycarbonyl-6-hydroxymethyl spiro[indoline-3,4'-piperidine] | | 1.49 (s, 9 H), 1.55-1.70 (m, 11 H), 1.75-1.90 (m, 2 H), 2.80-3.00 (m, 2 H), 3.80-3.95 (m, 2 H), 4.05-4.25 (m, 2 H), 4.66 (d, J = 6.0 Hz, 2 H), 6.95-7.10 (m, 2 H), 7.40-8.00 (m, 1 H). | CDCl3 | |
| 110 | 1,1'-bis-tert-butyloxycarbonyl spiro[indoline-3,4'-piperidine]-6-aldehyde | | 1.49 (s, 9 H), 1.50-1.90 (m, 13 H), 2.80-2.95 (m, 2 H), 3.85-4.00 (m, 2 H), 4.10-4.25 (m, 2 H), 7.25 (d, J = 7.6 Hz, 1 H), 7.50-7.60 (m, 1 H), 7.90-8.40 (m, 1 H), 9.96 (s, 1 H). | CDCl3 | |
| 111 | spiro[indoline-3,4'-piperidine]-6-carboxamide hydrobromide | | 1.70-1.80 (m, 2 H), 1.85-1.95 (m, 2 H), 2.90-3.00 (m, 2 H), 3.20-3.30 (m, 2 H), 3.42 (s, 2 H), 5.79 (s, 1 H), 6.95-7.05 (m, 2 H), 7.10-7.15 (m, 2 H), 7.72 (br. s, 1 H), 8.00-8.20 (m, 2 H). | DMSO-d6 | |
| 112 | 7-bromo-N-(2-morpholinoethyl) spiro[indoline-3,4'-piperidine]-6-carboxamide | | 1.70-1.90 (m, 4 H), 2.45-2.60 (m, 6 H), 2.90-3.05 (m, 2 H), 3.50-3.60 (m, 4 H), 3.65-3.75 (m, 4 H), 4.10-4.25 (m, 3 H), 5.16 (s, 2 H), 6.50-6.55 (m, 1 H), 6.87 (d, J = 7.6 Hz, 1 H), 6.95 (d, J = 7.6 Hz, 1 H), 7.30-7.45 (m, 5 H). | CDCl3 | |
| 113 | N-(2-morpholino ethyl)-2-oxo spiro[indoline-3,4'-piperidine]-6-carboxamide | | 1.60-1.80 (m, 2 H), 1.85-1.95 (m, 2 H), 2.45-2.55 (m, 4 H), 2.55-2.65 (m, 2 H), 3.00-3.15 (m, 2 H), 3.35-3.45 (m, 2 H), 3.55-3.60 (m, 2 H), 3.70-3.75 (m, 4 H), 6.80 (br. s, 1 H), 7.35-7.50 (m, 3 H), 8.15 (br. s, 1 H). | CDCl3 | |
| 114 | N-(2-morpholino ethyl)-2-oxo-1-(pyridin-3-yl methyl)spiro[indoline-3,4'-piperidine]-6-carboxamide | | 1.85-2.00 (m, 4 H), 2.45-2.55 (m, 4 H), 2.55-2.65 (m, 2 H), 3.10-3.20 (m, 2 H), 3.45-3.55 (m, 4 H), 3.65-3.75 (m, 4 H), 4.96 (s, 2 H), 6.70-6.80 (m, 1 H), 7.20-7.30 (m, 2 H), 7.35-7.45 (m, 1 H), 7.45-7.50 (m, 1 H), 7.60-7.65 (m, 1 H), 8.50-8.60 (m, 2 H). | CDCl3 | |

TABLE 12

| Reference Example | Compound Name | Structural formula | 1H NMR δ ppm | Solvent | ESI MS m/z |
|---|---|---|---|---|---|
| 115 | N-(2-morpholino ethyl)-2-oxo spiro[indoline-3,4'-piperidine]-4-carboxamide | | 1.65-1.75 (m, 2 H), 2.45-2.80 (m, 8 H), 3.00-3.10 (m, 2 H), 3.50-3.60 (m, 2 H), 3.60-3.75 (m, 6 H), 6.95-7.05 (m, 1 H), 7.05-7.10 (m, 1 H), 7.25-7.35 (m, 1 H). | CD3OD | |
| 116 | N-(2-morpholino ethyl)-2-oxo-1-(pyridin-3-yl)methyl spiro[indoline-3,4'-piperidine]-4-carboxamide | | 1.55-1.70 (m, 2 H), 2.45-2.55 (m, 4 H), 2.60-2.65 (m, 2 H), 2.70-2.80 (m, 2 H), 3.00-3.10 (m, 2 H), 3.55-3.75 (m, 8 H), 4.92 (s, 2 H), 6.45-6.55 (m, 1 H), 6.75-6.85 (m, 1 H), 7.00-7.05 (m, 1 H), 7.20-7.30 (m, 2 H), 7.55-7.60 (m, 1 H), 8.50-8.60 (m, 2 H). | CDCl3 | |
| 117 | 4-chloro-N-(2-morpholino ethyl)-2-oxo spiro[indoline-3,4'-piperidine]-6-carboxamide | | 1.70-1.85 (m, 2 H), 2.50-2.55 (m, 4 H), 2.55-2.75 (m, 4 H), 3.50-3.60 (m, 2 H), 3.65-3.85 (m, 6 H), 4.05-4.30 (m, 2 H), 5.20 (d, J = 6.4 Hz, 2 H), 6.75-6.80 (m, 1 H), 7.25-7.45 (m, 7 H), 8.25-8.45 (m, 1 H). | CDCl3 | |
| 118 | 4-chloro-2-oxo spiro[indoline-3,4'-piperidine]-6-carboxamide trifluoroacetate | | 1.90-2.00 (m, 2 H), 2.90-3.00 (m, 2 H), 3.35-3.45 (m, 2 H), 3.90-4.00 (m, 2 H), 7.35 (d, J = 1.2 Hz, 1 H), 7.54 (d, J = 1.2 Hz, 1 H). | CD3OD | |
| 119 | ethyl 4-chlorospiro[indoline-3,4'-piperidine]-6-carboxylate | | 1.36 (t, J = 7.2 Hz, 3H), 1.55-1.65 (m, 2 H), 2.45-2.55 (m, 2 H), 2.65-2.80 (m, 2 H), 3.05-3.15 (m, 2 H), 3.61 (s, 2 H), 3.90-4.00 (m, 1 H), 4.33 (q, J = 7.2 Hz, 2 H), 7.10 (d, J = 1.2 Hz, 1 H), 7.32 (d, J = 1.2 Hz, 1 H). | CDCl3 | |
| 120 | 4-chloro-N-(2-morpholino ethyl)spiro[indoline-3,4'-piperidine]-6-carboxamide | | 1.55-1.65 (m, 2 H), 2.45-2.65 (m, 6 H), 2.70-2.80 (m, 2 H), 3.05-3.10 (m, 2 H), 3.45-3.55 (m, 2 H), 3.55-3.60 (m, 2 H), 3.70-3.75 (m, 4 H), 4.69 (s, 2 H), 6.65-6.75 (m, 1 H), 6.86 (d, J = 1.2 Hz, 1 H), 6.94 (d, J = 1.2 Hz, 1 H), 7.25-7.40 (m, 5 H). | CDCl3 | |

TABLE 13

| Reference Example | Compound Name | Structural formula | 1H NMR δ ppm | Solvent | ESI MS m/z |
|---|---|---|---|---|---|
| 121 | 4-chlorospiro [indoline-3,4'-piperidine]-6-carbonitrile | | 1.45-1.65 (m, 11 H), 2.55-2.70 (m, 2 H), 2.80-3.00 (m, 2 H), 3.92 (s, 2 H), 4.20-4.40 (m, 2 H), 5.17 (s, 2 H), 7.19 (s, 1 H), 7.30-7.40 (m, 5 H), 7.90-8.35 (m, 1 H). | CDCl3 | |
| 122 | 4-chlorospiro [indoline-3,4'-piperidine]-6-carboxamide | | 1.50-1.65 (m, 11 H), 2.30-2.45 (m, 2 H), 2.85-3.10 (m, 2 H), 3.96 (s. 2 H), 4.00-4.10 (m, 2 H), 5.13 (s, 2 H), 7.30-7.40 (m, 6 H), 7.46 (s, 1 H), 7.99 (s, 1 H), 8.10-8.25 (m, 1 H). | DMSO-d6 | |
| 123 | methyl 1-benzyloxy carbonyl spiro[indoline-3,4'-piperidine]-7-carboxylate | | | | 381 [M+H]+ |
| 124 | 1'-benzyloxy carbonyl-6-iodo spiro[indoline-3,4'-piperidine] | | | | 449 [M+H]+ |
| 125 | 6-iodospiro [indoline-3,4'-piperidin]-2-one | | | | 329 [M+H]+ |
| 126 | 4-iodospiro [indoline-3,4'-piperidin]-2-one | | | | 329 [M+H]+ |
| 127 | 4-iodospiro [indole-3,4'-piperidine] | | | | 313 [M+H]+ |
| 128 | 6-bromospiro [indoline-3,4'-piperidin]-2-one | | | | 281 [M+H]+ |

TABLE 13-continued

| Reference Example | Compound Name | Structural formula | 1H NMR δ ppm | Solvent | ESI MS m/z |
|---|---|---|---|---|---|
| 129 | 4-bromospiro[indole-3,4'-piperidine] | | | | 265 [M+H]+ |

TABLE 14

| Reference Example | Compound Name | Structural formula | 1H NMR δ ppm | Solvent | ESI MS m/z |
|---|---|---|---|---|---|
| 130 | 7-chlorospiro[indoline-3,4'-piperidine] | | | | 223 [M+H]+ |
| 131 | 1-(tert-butyloxycarbonyl)-5-chlorospiro[indoline-3,4'-piperidine] | | | | 323 [M+H]+ |
| 132 | 1'-benzyloxycarbonyl-1-tert-butyloxycarbonyl-6-chlorospiro[indoline-3,4'-piperidine] | | | | 457 [M+H]+ |
| 133 | 1'-benzyloxycarbonyl-1-tert-butyloxycarbonyl-4-chlorospiro[indoline-3,4'-piperidine] | | | | 457 [M+H]+ |
| 134 | 6-chlorospiro[indoline-3,4'-piperidine]-2-one | | | | 371 [M+H]+ |
| 135 | 1'-benzyloxycarbonyl-6-chloro-1-(2-hydroxyethyl)spiro[indoline-3,4'-piperidine]-2-one | | | | 415 [M+H]+ |

TABLE 14-continued

| Reference Example | Compound Name | Structural formula | 1H NMR δ ppm | Solvent | ESI MS m/z |
|---|---|---|---|---|---|
| 136 | 4-chlorospiro[indoline-3,4'-piperidine]-2-one | | | | 371 [M+H]+ |
| 137 | 1'-benzyloxycarbonyl-4-chloro-1-(2-hydroxyethyl)spiro[indoline-3,4'-piperidine]-2-one | | | | 415 [M+H]+ |
| 138 | 4-chloro-1-(pyridin-3-yl)methylspiro[indoline-3,4'-piperidin]-2-one | | 1.55-1.70 (m, 2 H), 2.65-2.80 (m, 2 H), 3.70-3.90 (m, 2 H), 4.10-4.35 (m, 2 H), 4.89 (s, 2 H), 5 15-5 30 (m, 2 H), 6.60-6.65 (m, 1 H), 6.95-7.00 (m, 1 H), 7.05-7.15 (m, 1 H), 7.25-7.45 (m, 6 H), 7.50-7.60 (m, 1 H), 8.50-8.60 (m, 2 H). | CDCl3 | |

TABLE 15

| Reference Example | Compound Name | Structural formula | 1H NMR δ ppm | Solvent | ESI MS m/z |
|---|---|---|---|---|---|
| 139 | 4,6-dichlorospiro[indoline-3,4'-piperidine] | | 1.55-1.65 (m, 2 H), 2.40-2.55 (m, 2 H), 2.65-2.75 (m, 2 H), 3.00-3.15 (m, 2 H), 3.58 (s, 2 H), 3.94 (br. s, 1 H), 6.44 (d, J = 1.6 Hz, 1 H), 6.61 (d, J = 1.6 Hz, 1 H). | CDCl3 | |
| 140 | 4,6-dichlorospiro[indoline-3,4'-piperidin]-2-one | | 1.55-1.60 (m, 2 H), 2.55-2.70 (m, 2 H), 2.90-2.95 (m, 2 H), 3.45-3.60 (m, 2 H), 6.84 (d, J = 2.0 Hz, 1 H), 7.00 (d, J = 2.0 Hz, 1 H). | CD3OD | |
| 141 | 1'-benzyloxycarbonyl-4,6-dichloro-1-methylspiro[indoline-3,4'-piperidine]-2-one | | | | 419 [M+H]+. |

TABLE 15-continued

| Reference Example | Compound Name | Structural formula | 1H NMR δ ppm | Solvent | ESI MS m/z |
|---|---|---|---|---|---|
| 142 | 1'-benzyloxy carbonyl-4,6-dichloro-1-(2-hydroxyethyl) spiro[indoline-3,4'-piperidine]-2-one | | | | 449 [M+H]+. |
| 143 | 4,7-dichlorospiro [indoline-3,4'-piperidine] | | | | 257 [M+H]+ |
| 144 | 4,7-dichlorospiro [indoline-3,4'-piperidin]-2-one | | | | 271 [M+H]+ |
| 145 | 1'-(tertbutyloxy carbonyl)-4-chloro-6-hydroxy-1-methyl spiro[indoline-3,4'-piperidine]-2-one | | | | 367 [M+H]+. |
| 146 | 1'-benzyloxycarbonyl-1-tert-butyl oxycarbonyl-5-fluorospiro[indoline-3,4'-piperidine] | | | | 441 [M+H]+. |
| 147 | 7-fluorospiro [indoline-3,4'-piperidine] | | | | 207 [M+H]+ |

TABLE 16

| Reference Example | Compound Name | Structural formula | 1H NMR δ ppm | Solvent | ESI MS m/z |
|---|---|---|---|---|---|
| 148 | 1-(tert-butyloxy carbonyl)-6-fluoro spiro[indoline-3,4'-piperidine] | | | | 307 [M+H]+ |

TABLE 16-continued

| Reference Example | Compound Name | Structural formula | 1H NMR δ ppm | Solvent | ESI MS m/z |
|---|---|---|---|---|---|
| 149 | 1-(tert-butyloxy carbonyl)-4-fluoro spiro[indoline-3,4'-piperidine] | | | | 307 [M+H]+ |
| 150 | 1'-benzyloxy carbonyl-1-tert-butyloxycarbonyl-5,7-difluorospiro [indoline-3,4'-piperidine] | | 1.51 (s, 9 H), 1.57-1.82 (m, 4 H), 2.88-3.02 (m, 2 H), 3.97 (s, 2 H), 4.15-4.28 (m, 2 H), 5.16 (s, 2 H), 6.59-6.63 (m, 1 H), 6.66-6.73 (m, 1 H), 7.30-7.39 (m, 5 H). | CDCl3 | 459 [M+H]+. |
| 151 | 1'-benzyloxy carbonyl-4,7-difluoro spiro[indoline-3,4'-piperidine] | | 1.72-1.80 (m, 2 H), 2.12-2.23 (m, 2 H), 2.84-2.96 (m, 2 H), 3.59 (s, 2 H), 3.92 (br. s, 1 H), 4.14-4.27 (m, 2 H), 5.16 (s, 2 H), 6.26-6.32 (m, 1 H), 6.73-6.79 (m, 1H), 7.29-7.39 (m, 5 H) | CDCl3 | 359 [M+H]+. |
| 152 | 1'-benzyloxy carbonyl-1-tert-butyl oxycarbonyl-4,6-difluorospiro[indoline-3,4'-piperidine] | | | | 359 [M+H]+. |
| 153 | 1'-benzyloxy carbonyl-4,6-difluoro-1-methylspiro [indoline-3,4'-piperidine] | | | | 373 [M+H]+. |
| 154 | 2-(1'-benzyloxy carbonyl-4,6-difluoro spiro[indoline-3,4'-piperidine]-1-yl)ethan-1-ol | | | | 403 [M+H]+. |
| 155 | 1'-benzyloxy carbonyl-4,6-difluoro-1-(pyridine-3-yl methyl)spiro[indoline-3,4'-piperidine] | | | | 449 [M+H]+ |

TABLE 17

| Reference Example | Compound Name | Structural formula | 1H NMR δ ppm | Solvent | ESI MS m/z |
|---|---|---|---|---|---|
| 156 | 6-fluorospiro[indoline-3,4'-piperidin]-2-one | | | | 221 [M+H]+. |
| 157 | 4-fluorospiro[indoline-3,4'-piperidin]-2-one | | | | 221 [M+H]+. |
| 158 | 1'-benzyloxycarbonyl-4,7-difluorospiro[indoline-3,4'-piperidine]-2-one | | 1.79-1.89 (m, 2 H), 2.14-2.26 (m, 2 H), 3.72-3.86 (m, 2 H), 3.96-4.10 (m, 2 H), 5.19 (s, 2 H), 6.63-6.69 (m, 1 H), 6.94-7.00 (m, 1 H), 7.30-7.42 (m, 5 H), 8.25 (br. s, 1 H) | CDCl3 | 373 [M+H]+. |
| 159 | 1'-benzyloxycarbonyl-4,7-difluoro-1-(2-hydroxyethyl)spiro[indoline-3,4'-piperidine]-2-one | | | | 417 [M+H]+. |
| 160 | 1'-benzyloxycarbonyl-4,6-difluorospiro[indoline-3,4'-piperidine]-2-one | | | | 373 [M+H]+. |
| 161 | 1'-benzyloxycarbonyl-4,6-difluoro-1-(2-hydroxyethyl)spiro[indoline-3,4'-piperidine]-2-one | | | | 417 [M+H]+. |
| 162 | 1'-benzyloxycarbonyl-4,6-difluoro-1-methylspiro[indoline-3,4'-piperidine]-2-one | | | | 387 [M+H]+. |

TABLE 17-continued

| Reference Example | Compound Name | Structural formula | 1H NMR δ ppm | Solvent | ESI MS m/z |
|---|---|---|---|---|---|
| 163 | 1'-benzyloxy carbonyl-4,6-difluoro-1-(pyridin-3-yl methyl)spiro[indoline-3,4'-piperidine]-2-one | | | | 464 [M+H]+. |

TABLE 18

| Reference Example | Compound Name | Structural formula | 1H NMR δ ppm | Solvent | ESI MS m/z |
|---|---|---|---|---|---|
| 164 | 4,6-difluoro-1-(2-oxo-2-phenylethyl)spiro[indoline-3,4'-piperidin]-2-one | | 1.85 (d, J = 14.2 Hz, 2H), 2.03 (br. m, 1H), 2.22 (ddd, J = 13 8, 11.4, 4.4 Hz, 2H), 3.04 (dt, J = 12.8, 3.8 Hz, 2H), 3.48 (tt, J = 11.4, 1.5 Hz, 2H), 5.08 (s, 2H), 6.21 (dd, J = 8.3, 1.7 Hz, 1H), 6.48 (td, J = 9.8, 2.1 Hz, 1H), 7.53 (t, J = 7.6 Hz, 2H), 7.66 (tt, J = 7.5 Hz, 1H), 8.01 (d, J = 7.2 Hz, 2H). | CDCl3 | |
| 165 | 1-(tert-butyloxy carbonyl)-4,7-dimethylspiro[indoline-3,4'-piperidine] | | | | 317 [M+H]+ |
| 166 | 1',2'-dihydrospiro[piperidine-4,3'-pyrrolo[2,3-c]pyridine] trihydrochloride | | 1.96-2.12 (m, 4 H) 3.06-3.22 (m, 2 H) 3.41-3.51 (m, 2 H) 3.71 (s, 2 H) 7.60 (d, J = 5.7 Hz, 1 H) 7.83 (s, 1 H) 7.96 (d, J = 5.7 Hz, 1 H) | D2O | 190 [M+H]+ |
| 167 | 1',2'-dihydrospiro[piperidine-4,3'-pyrrolo[3,2-b]pyridine] trihydrochloride | | | | 190 [M+H]+ |
| 168 | 6'-chloro-1',2'-dihydrospiro[piperidine-4,3'-pyrrolo[3,2-b]pyridine] trihydrochloride | | 1.90-2.00 (m, 2 H) 2.02-2.19 (m, 2 H) 3.10-3.24 (m, 2 H) 3.33 (s, 1 H) 3.47-3.57 (m, 2 H) 3.61 (s, 2H) 7.16 (d, J = 2.0 Hz, 1 H) 7.84 (d, J = 2.0 Hz, 1 H) | D2O | 224 [M+H]+ |

TABLE 18-continued

| Reference Example | Compound Name | Structural formula | 1H NMR δ ppm | Solvent | ESI MS m/z |
|---|---|---|---|---|---|
| 169 | 4'-chloro-1',2'-dihydrospiro[piperidine-4,3'-pyrrolo[2,3-c]pyridine] trihydrochloride | | | | 224 [M+H]+ |
| 170 | spiro[piperidine-4,3'-pyrrolo[2,3-b]pyridin]-2'(1'H)-one dihydrochloride | | | | 204 [M+H]+ |
| 171 | 7-methyl-N-(2-morpholinoethyl)-2-oxospiro[indoline-3,4'-piperidine]-6-carboxamide | | .95-2.05 (m, 2 H), 2.15-2.25 (m, 2 H), 2.31 (s, 3 H), 2.55-2.70 (m, 6 H), 3.35-3.45 (m, 2 H), 3.50-3.55 (m, 2 H), 3.65-3.75 (m, 4 H), 3.80-3.90 (m, 2 H), 7.11 (d. J = 8.0 Hz, 1 H), 7.21 (d, J = 8.0 Hz, 1 H). | CD3OD | |

TABLE 19

| Reference Example | Compound Name | Structural formula | 1H NMR δ ppm | Solvent | ESI MS m/z |
|---|---|---|---|---|---|
| 172 | 1'-tert-butyloxycarbonylspiro[isoindoline-1,4'-piperidine] | | | | 289 [M+H]+. |
| 173 | methyl 1'-benzyloxycarbonyl spiro[indoline-3,4'-piperidine]-7-carboxylate | | | | 381 [M+H]+. |
| 174 | 1'-benzyloxycarbonyl-1-tert-butyloxycarbonyl-6-(4-morpholinomethyl oxazol-2-yl)spiro[indoline-3,4'-piperidine] | | 1.50-1.95 (m, 13 H), 2.50-2.65 (m, 4 H), 2.90-3.05 (m, 2 H), 3.52 (s, 2 H), 3.70-3.80 (m, 4 H), 3.85-4.00 (m, 2 H), 4.15-4.40 (m, 2 H), 5.17 (s, 2 H), 7.13 (d, J = 8.0 Hz, 1 H), 7.30-7.45 (m, 5 H), 7.56 (s, 1 H), 7.70-7.80 (m, 1 H), 8.10-8.60 (m, 1 H). | CDCl3 | |
| 175 | 1'-benzyloxycarbonyl-1-tert-butyloxycarbonyl-6-(4-(morpholine-4-carbonyl)oxazol-2-yl)spiro(indoline-3,4'-piperidine] | | 1.50-1.95 (m, 13 H), 2.90-3.05 (m, 2 H), 3.70-3.85 (m, 6 H), 3.85-4.00 (m, 2 H), 4.15-4.40 (m, 4 H), 5.17 (s, 2 H), 7.16 (d, J = 7.6 Hz, 1 H), 7.30-7.40 (m, 5 H), 7.65-7.75 (m, 1 H), 8.10-8.60 (m, 2 H). | CDCl3 | |

TABLE 19-continued

| Reference Example | Compound Name | Structural formula | 1H NMR δ ppm | Solvent | ESI MS m/z |
|---|---|---|---|---|---|
| 176 | 1'-benzyloxy carbonyl-1-methyl spiro[indoline-3,4'-piperidine]-2-one | | | | 351 [M+H]+. |
| 177 | 1'-benzyloxy carbonyl-2-oxospiro [indoline-3,4'-piperidine]-4-carbonitrile | | | | 362 [M+H]+. |
| 178 | 1'-benzyloxy carbonyl-1-methyl-2-oxospiro[indoline-3,4'-piperidine]-4-carbonitrile | | | | 376 [M+H]+. |
| 179 | 1'-benzyloxy carbonyl-1-(2-hydroxyethyl)-2-oxospiro [indoline-3,4'-piperidine]-4-carbonitrile | | | | 406 [M+H]+. |

TABLE 20

| Reference Example | Compound Name | Structural formula | 1H NMR δ ppm | Solvent | ESI MS m/z |
|---|---|---|---|---|---|
| 180 | 1'-benzyloxy carbonyl-6-(trifluoro methyl)spiro[indoline-3,4'-piperidine] | | | | 391 [M+H]+. |
| 181 | 1'-benzyloxy carbonyl-4-(trifluoro methyl)spiro[indoline-3,4'-piperidine] | | | | 391 [M+H]+. |
| 182 | 1'-(tert-butyloxy carbonyl)-5-hydroxy-1-methylspiro [indoline-3,4'-piperidine]-2-one | | | | 333 [M+H]+. |

TABLE 20-continued

| Reference Example | Compound Name | Structural formula | 1H NMR δ ppm | Solvent | ESI MS m/z |
|---|---|---|---|---|---|
| 183 | 1'-benzyloxy carbonyl-4-hydroxy spiro[indoline-3,4'-piperidine]-2-one | | 1.55-1.70 (m, 2 H), 2.45-2.61 (m, 2 H), 3.64-3.90 (m, 2 H), 4.05-4.12 (m, 2 H), 5.18 (s, 2 H), 6.41 (d, J = 7.6 Hz. 1 H), 6.57 (d. J = 8.2 Hz, 1 H), 6.99-7.05 (m, 1 H), 7.27-7.39 (m, 5 H), 8.29 (br. s, 1 H). | CDCl3 | 353 [M+H]+. |
| 184 | 1'-benzyloxy carbonyl-4-methoxy-1-methylspiro [indoline-3,4'-piperidine]-2-one | | 1.51-1.64 (m, 2 H), 2.39-2.56 (m, 2 H), 3.16 (s, 3 H), 3.69-3.84 (m, 5 H), 4.01-4.17 (m, 2 H), 5.20 (s, 2 H), 6.49 (d, J = 7.7 Hz, 1 H), 6.61 (d, J = 8.4 Hz, 1 H), 7.21-7.26 (m, 1 H), 7.30-7.42 (m, 5 H). | CDCl3 | 381 [M+H]+. |
| 185 | 1'-benzyloxy carbonyl-6-(3-morpholino propoxy)spiro [indoline-3,4'-piperidine]-2-one | | 1.68-2.00 (m, 6 H), 2.38-2.55 (m, 6 H), 3.68-4.02 (m, 10 H), 5.18 (s, 3 H), 6.48-6.50 (m, 1 H), 6.54 (dd, J = 8.3, 2.3 Hz, 1 H), 7.12 (d, J = 8.3 Hz, 1 H), 7.30-7.42 (m, 5 H), 8.18 (br. s, 1 H). | CDCl3 | 480 [M+H]+. |
| 186 | 1'-benzyloxy carbonyl-1-methyl-6-(3-morpholino propoxy)spiro [indoline-3,4'-piperidine]-2-one | | | | 494 [M+H]+. |

TABLE 21

| Reference Example | Compound Name | Structural formula | 1H NMR δ ppm | Solvent | ESI MS m/z |
|---|---|---|---|---|---|
| 187 | 1-tert-butyloxy carbonyl-6-(1-tert-butyloxycarbonyl piperidin-4-yl)spiro [indoline-3,4'-piperidine] | | 1.50-1.70 (m, 11 H), 1.70-1.90 (m, 4 H), 2.05-2.40 (m, 2 H), 2.60-2.70 (m, 1 H), 2.70-2.85 (m, 2 H), 2.85-3.00 (m, 2 H), 3.30-3.40 (m, 2 H), 3.70-3.95 (m, 3 H), 4.15-4.35 (m, 2 H), 6.80-6.85 (m, 1 H), 7.13 (d, J = 8.0 Hz, 1 H), 7.70-7.85 (m, 1 H). | CDCl3 | |
| 188 | 1'-benzyloxy carbonyl-4-chloro-7-iodospiro[indoline-3,4'-piperidine] | | 1.60-1.75 (m, 2 H), 2.45-2.60 (m, 2 H), 2.75-2.95 (m, 2 H), 3.60 (s, 2 H), 4.02 (br. s, 1 H), 4.15-4.35 (m, 2 H), 5.17 (s, 2 H), 6.39 (d, J = 8.4 Hz, 1 H), 7.25-7.45 (m, 6 H). | CDCl3 | |

TABLE 21-continued

| Reference Example | Compound Name | Structural formula | 1H NMR δ ppm | Solvent | ESI MS m/z |
|---|---|---|---|---|---|
| 189 | 1'-benzyloxy carbonyl-4-chloro-1-methyl-2-oxospiro[indoline-3,4'-piperidine]-6-carboxamide | | 1.45-1.65 (m, 2 H), 2.60-2.75 (m, 2 H), 3.22 (s, 3 H), 3.65-3.90 (m, 2 H), 4.10-4.25 (m, 2 H), 5.15-5.25 (m, 2 H), 5.60-6.50 (m, 1 H), 7.26 (d, J = 1.2 Hz, 1 H), 7.30-7.45 (m, 6 H). | CDCl3 | |
| 190 | 4-chloro-1-methyl-6-(4-(morpholine-4-carbonyl)oxazol-2-yl)spiro[indoline-3,4'-piperidin]-2-one | | 1.55-1.60 (m, 2 H), 2.60-2.70 (m, 2 H), 2.95-3.05 (m, 2 H), 3.26 (s, 3 H), 3.55-3.65 (m, 2 H), 3.75-3.90 (m, 6 H), 4.10-4.30 (m, 2 H), 7.33 (d, J = 1.2 Hz, 1 H), 7.69 (d, J = 1.2 Hz, 1 H), 8.25 (s, 1 H). | CDCl3 | |
| 191 | 1'-benzyloxy carbonyl-4-chloro-7-iodo-1-methylspiro[indoline-3,4'-piperidine]-2-one | | 1.40-1.50 (m, 2 H), 2.60-2.75 (m, 2 H), 3.59 (s, 3 H), 3.65-3.85 (m, 2 H), 4.05-4.25 (m, 2 H), 5.15-5.25 (m, 2H), 6.70 (d, J = 8.8 Hz, 1 H), 7.30-7.45 (m, 5 H), 7.60 (d, J = 8.8 Hz, 1 H). | CDCl3 | |
| 192 | 1'-benzyloxy carbonyl-4-chloro-1-methyl-2-oxospiro[indoline-3,4'-piperidine]-7-carbonitrile | | 1.45-1.60 (m, 2 H), 2.60-2.75 (m, 2 H), 3.56 (s, 3 H), 3.60-3.85 (m, 2 H), 4.05-4.25 (m, 2 H), 5.15-5.25 (m, 2 H), 7.02 (d, J = 8.4 Hz, 1 H), 7.30-7.45 (m, 6 H). | CDCl3 | |

TABLE 22

| Reference Example | Compound Name | Structural formula | 1H NMR δ ppm | Solvent | ESI MS m/z |
|---|---|---|---|---|---|
| 193 | 1'-tert-butyloxy carbonyl-4-chloro-1-methyl-6-(4-ethoxy carbonyloxazol-2-yl)spiro[indoline-3,4'-piperidine]-2-one | | 1.42 (t, J = 7.2 Hz, 3 H), 1.45-1.60 (m, 11 H), 2.60-2.75 (m, 2 H), 3.25 (s, 3 H), 3.55-3.80 (m, 2 H), 3.90-4.20 (m, 2 H), 4.45 (q, J = 7.2 Hz, 2 H), 7.52 (d, J = 1.2 Hz, 1 H), 7.74 (d, J = 1.2 Hz, 1 H), 8.29 (s, 1 H). | CDCl3 | |
| 194 | 1'-tert-butyloxy carbonyl-4-chloro-1-methyl-6-(4-(pyrrolidin-1-yl)methyloxazol-2-yl)spiro[indoline-3,4'-piperidine]-2-one | | 1.45-1.55 (m, 11 H), 1.80-1.85 (m, 4 H), 2.55-2.70 (m, 6 H), 3.24 (s, 3 H), 3.55-3.80 (m, 4 H), 3.95-4.20 (m, 2 H), 7.44 (d, J = 1.2 Hz, 1 H), 7.62 (s, 1 H), 7.69 (d, J = 1.2 Hz, 1 H). | CDCl3 | |

TABLE 22-continued

| Reference Example | Compound Name | Structural formula | 1H NMR δ ppm | Solvent | ESI MS m/z |
|---|---|---|---|---|---|
| 195 | 1'-benzyloxy carbonyl-4-chloro-1-methyl-2-oxospiro[indoline-3,4'-piperidine]-7-carboxamide | | 1.45-1.55 (m, 2 H), 2.60-2.75 (m, 2 H), 3.29 (s, 3 H), 3.65-3.85 (m, 2 H), 4.05-4.25 (m, 2 H), 5.15-5.25 (m, 2 H), 5.90-6.00 (m, 2 H), 6.99 (d, J = 8.4 Hz, 1 H), 7.25 (d, J = 8.4 Hz, 1 H), 7.30-7.45 (m, 5 H). | CDCl3 | |
| 196 | 2-(4-chloro-1-methyl-2-oxospiro[indoline-3,4'-piperidine]-6-yl)oxazole-4-carboxylic acid trifluoroacetate | | 1.90-2.00 (m, 2 H), 2.90-3.05 (m, 2 H), 3.27 (s, 3 H), 3.40-3.50 (m, 2 H), 3.90-4.00 (m, 2 H), 7.58 (d, J = 1.2 Hz, 1 H), 7.71 (d, J = 1.2 Hz, 1 H), 8.59 (s, 1 H). | CD3OD | |

Reference Example 197

7-(2-(dimethylamino)ethoxy)-4-fluoro-1-methyl-2-oxospiro[indoline-3,4'-piperidine]-1'-carboxylic acid tert-butyl ester

[Chem. 48]

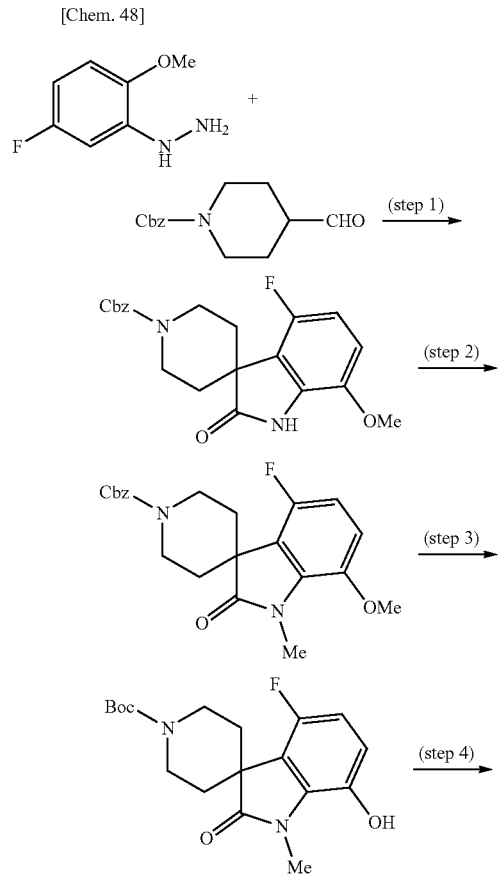

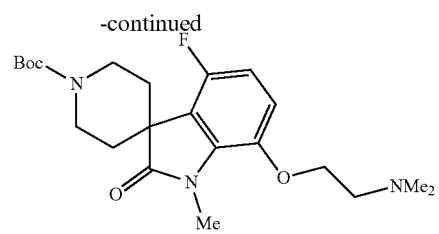

\<Step 1\>

First, a solution of 8.35 g of 4-formyl-1-piperidinecarboxylic acid phenylmethyl ester in chloroform (20 mL) was added dropwise to a solution of (5-fluoro-2-methoxyphenyl)hydrazine (5.27 g) in chloroform (100 mL) at room temperature, and the mixture was stirred for 10 minutes. Next, trifluoroacetic acid (7.75 mL) was added dropwise thereto, and the reaction solution was heated to 50° C. and was stirred to allow a reaction to proceed for 2 hours. The reaction solution was left to cool to room temperature, and was rendered basic by dropwise addition of saturated sodium bicarbonate water (120 mL). After the organic layer was separated, the aqueous layer was subjected to extraction with chloroform (60 mL). The organic layer thus collected all together was dried with anhydrous magnesium sulfate, and then was concentrated. Tetrahydrofuran (100 mL), water (40 mL), 2-methyl-2-butene (17.9 mL), and sodium dihydrogen phosphate (12.1 g) were added to the obtained residue, followed by stirring. Sodium chlorite (4.58 g) was added little by little to this solution, and the mixture was stirred at room temperature for 90 minutes. The reaction solution was separated into layers by addition of ethyl acetate (100 mL) and water (100 mL), and the aqueous layer was further subjected to extraction with ethyl acetate (50 mL). The organic layer thus collected all together was washed with water (150 mL), was further washed with saturated brine (150 mL), and then was dried with anhydrous magnesium sulfate. The solvent was concentrated, and the obtained residue was purified by silica gel column chromatography (hexane/ethyl acetate=80/20 to 32/68) to obtain 4-fluoro-7-methoxy-2-oxospiro[indoline-3,4'-piperidine]-1'-carboxylic acid benzyl ester (3.00 g) as a dark orange solid.

¹H-NMR (270 MHz, CDCl₃) δ: 1.73-1.91 (m, 2H), 2.08-2.29 (m, 2H), 3.66-3.90 (m, 5H), 3.90-4.17 (m, 2H), 5.19 (s, 2H), 6.67 (t, J=9.2 Hz, 1H), 6.73 (dd, J=9.2, 4.0 Hz, 1H), 7.28-7.41 (m, 5H), 7.57 (br.s, 1H).

MS(ESI) m/z: 385[M+H]⁺.

<Step 2>

The 4-fluoro-7-methoxy-2-oxospiro[indoline-3,4'-piperidine]-1'-carboxylic acid benzyl ester (2.68 g) was dissolved in N,N-dimethylformamide (27 mL). Sodium hydride (60%, dispersed in liquid paraffin, 418 mg) was added little by little under ice cooling and the mixture was stirred for 5 minutes. Then, methyl iodide (868 μL) was added thereto, followed by stirring for 1 hour under ice cooling. The reaction was terminated by adding a 5% ammonium chloride aqueous solution (60 mL) little by little, followed by extraction with ethyl acetate (60 mL and 30 mL). The organic layer thus collected all together was washed with water (90 mL×2 times), was further washed with saturated brine (90 mL), and then was dried with anhydrous magnesium sulfate. The solvent was concentrated and the obtained residue was purified by silica gel chromatography (hexane/ethyl acetate 90/10 to 55/45) to obtain 4-fluoro-7-methoxy-1-methyl-2-oxospiro[indoline-3,4'-piperidine]-1'-carboxylic acid benzyl ester (2.30 g) as a light-orange solid.

¹H-NMR (270 MHz, CDCl₃) δ: 1.64-1.78 (m, 2H), 2.13-2.30 (m, 2H), 3.44 (s, 3H), 3.74-3.90 (m, 5H), 3.95-4.14 (m, 2H), 5.18 (s, 2H), 6.66 (t, J=8.9 Hz, 1H), 6.79 (dd, J=9.2, 4.3 Hz, 1H), 7.28-7.41 (m, 5H).

MS(ESI) m/z: 399[M+H]⁺.

<Step 3>

The 4-fluoro-7-methoxy-1-methyl-2-oxospiro[indoline-3,4'-piperidine]-1'-carboxylic acid benzyl ester (552 mg) was dissolved in dichloromethane (5.5 mL), and the mixture was cooled to −78° C. After a boron tribromide dichloromethane solution (1 mol/L, 4.17 mL) was added dropwise over 5 minutes, the mixture was heated to room temperature and then was stirred for 17 hours. The reaction solution was ice-cooled, and the reaction was terminated by adding methanol (5.5 mL) little by little. After stirring at room temperature for 20 minutes, the reaction solution was filtered through celite to remove unsolved matters, followed by washing with methanol and chloroform. After the filtrate was concentrated, the residue was dissolved in water (20 mL), followed by washing with diisopropyl ether (10 mL×2 times). The resultant solution was diluted with water such that the total amount of the aqueous layer was 40 mL, and then tetrahydrofuran (40 mL) was further added thereto. After that, a 1 N sodium hydroxide aqueous solution was added dropwise thereto so that the pH of the resultant mixture was adjusted to 8.0. Di-tert-butyl dicarbonate (477 μL) was added to the mixture at room temperature, and the pH of the mixture was adjusted to 8.0 by addition of a 1 N sodium hydroxide aqueous solution. After stirring for 30 minutes, the mixture was subjected to extraction with ethyl acetate (40 mL and 20 mL). The organic layer thus collected all together was washed with water (60 mL×2 times), was further washed with saturated brine (60 mL), and then was dried with anhydrous magnesium sulfate. The solvent was concentrated and the obtained residue was purified by silica gel chromatography (hexane/ethyl acetate=80/20 to 50/50) to obtain 4-fluoro-7-hydroxy-1-methyl-2-oxospiro[indoline-3,4'-piperidine]-1'-carboxylic acid tert-butyl ester (297 mg) as a light-yellow solid.

MS(ESI) m/z: 351[M+H]⁺.

<Step 4>

The 4-fluoro-7-hydroxy-1-methyl-2-oxospiro[indoline-3,4'-piperidine]-1'-carboxylic acid tert-butyl ester (50 mg) was placed in a microwave reaction vessel and was dissolved in tetrahydrofuran (1 mL). Then, 2-(dimethylamino)ethanol (28.7 μL) and di-tert-butyl azodicarboxylate (65.7 mg) were added thereto. The mixture was ice-cooled and triphenylphosphine (74.9 mg) was added thereto. The mixture was heated to room temperature and then was stirred for 5 minutes. After that, the vessel was set in a microwave reaction apparatus to allow a reaction to proceed at 100° C. for 1 hour. After the termination of the reaction, the solvent was concentrated and the residue was purified by silica gel column chromatography (chloroform/methanol=100/0 to 92/8) to obtain the title compound (55.5 mg) as a white solid.

¹H-NMR (270 MHz, CDCl₃) δ: 1.49 (s, 9H), 1.65-1.75 (m, 2H), 2.10-2.26 (m, 2H), 2.33 (s, 6H), 2.73 (t, J=5.9 Hz, 2H), 3.46 (s, 3H), 3.60-3.81 (m, 2H), 3.83-4.04 (m, 2H), 4.07 (t, J=5.9 Hz, 2H), 6.64 (t, J=9.2 Hz, 1H), 6.79 (dd, J=9.2, 4.3 Hz, 1H)

MS(ESI) m/z: 422 [M+H]⁺.

Reference Example 198

5-(4-(tert-butyl)piperazin-1-yl)-7-fluoro-3H-spiro[isobenzofuran-1,4'-piperidin]-3-one dihydrochloride

[Chem. 49]

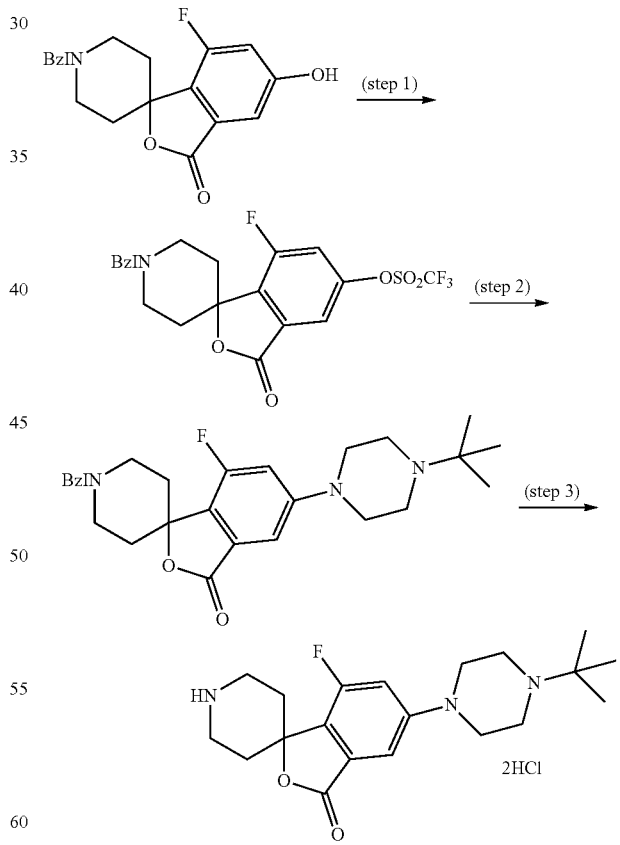

<Step 1>

First, 1'-benzyl-7-fluoro-5-hydroxy-3H-spiro[isobenzofuran-1,4'-piperidin]-3-one (500 mg) was suspended in dichloromethane (5 mL), and pyridine (247 μL) was added thereto. The obtained solution was ice-cooled and trifluoromethanesulfonic anhydride (308 μL) was added thereto. The mixture was heated to room temperature and then was stirred for 40 minutes, and the solvent was concentrated. The residue was dissolved in ethyl acetate (10 mL), and the resultant mixture was washed with 0.5 N hydrochloric acid (10 mL). The mixture was further washed with saturated sodium bicarbonate water (10 mL) and saturated brine (10 mL), and then was dried with anhydrous magnesium sulfate. The solvent was concentrated and the obtained residue was purified by silica gel column chromatography (hexane/ethyl acetate=90/10 to 70/30) to obtain 1'-benzyl-7-fluoro-3-oxo-3H-spiro[isobenzofuran-1,4'-piperidine]-5-yl trifluoromethanesulfonate (645 mg) as a white crystalline solid.

$^1$H-NMR (270 MHz, CDCl$_3$) δ: 1.65-1.79 (m, 2H), 2.42-2.60 (m, 4H), 2.84-3.03 (m, 2H), 3.62 (s, 2H), 7.27-7.42 (m, 6H), 7.62 (d, J=1.6 Hz, 1H).

MS(ESI) m/z: 460[M+H]$^+$.

<Step 2>

The 1'-benzyl-7-fluoro-3-oxo-3H-spiro[isobenzofuran-1,4'-piperidine]-5-yl trifluoromethanesulfonate (50.0 mg), 4-(tert-butyl)piperazine (31.0 mg), palladium acetate (4.89 mg), (±)-2,2'-bis(diphenylphosphino)-1,1'-binaphthyl (27.1 mg), and cesium carbonate (53.3 mg) were placed in a reaction vessel, and toluene (1 mL) was added thereto under an argon atmosphere. The mixture was heated to 100° C., and then was stirred for 7 hours. The reaction solution was left to cool to room temperature, and then was purified by silica gel column chromatography (hexane/ethyl acetate=70/30 to 20/80) to obtain 1'-benzyl-5-(4-(tert-butyl)piperazin-1-yl)-7-fluoro-3H-spiro[isobenzofuran-1,4'-piperidin]-3-one (37.9 mg) as a color-less oily compound.

$^1$H-NMR (270 MHz, CDCl$_3$) δ: 1.11 (s, 9H), 1.65-1.74 (m, 2H), 2.36-2.58 (m, 4H), 2.65-2.76 (m, 4H), 2.81-2.95 (m, 2H), 3.18-3.28 (m, 4H), 3.61 (s, 2H), 6.82 (dd, J=12.5, 2.0 Hz, 1H), 7.10 (d, J=2.0 Hz, 1H), 7.28-7.41 (m, 5H).

MS(ESI) m/z: 452[M+H]$^+$.

<Step 3>

The 1'-benzyl-5-(4-(tert-butyl)piperazin-1-yl)-7-fluoro-3H-spiro[isobenzofuran-1,4'-piperidin]-3-one (36.0 mg) was dissolved in tetrahydrofuran (1 mL) and methanol (1 mL), then 1 N hydrochloric acid (200 mL) and 20% palladium hydroxide carbon (containing water at about 50%, 7.0 mg) were added thereto, and the mixture was vigorously stirred under a hydrogen atmosphere at room temperature for 16 hours. The catalyst was removed through filtration with a membrane filter, and the filtrate was washed with methanol. The filtrate was concentrated to obtain the title compound (33.1 mg) as a light-pink solid.

MS(ESI) m/z: 362[M+H]$^+$.

Reference Example 199

1'-benzyloxycarbonyl-4-fluoro-1-methyl-6-[2-(methylsulfonamide)-2-oxoethoxy]spiro[indoline-3,4'-piperidine]-2(1H)-one

[Chem. 50]

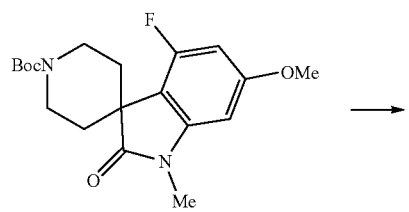

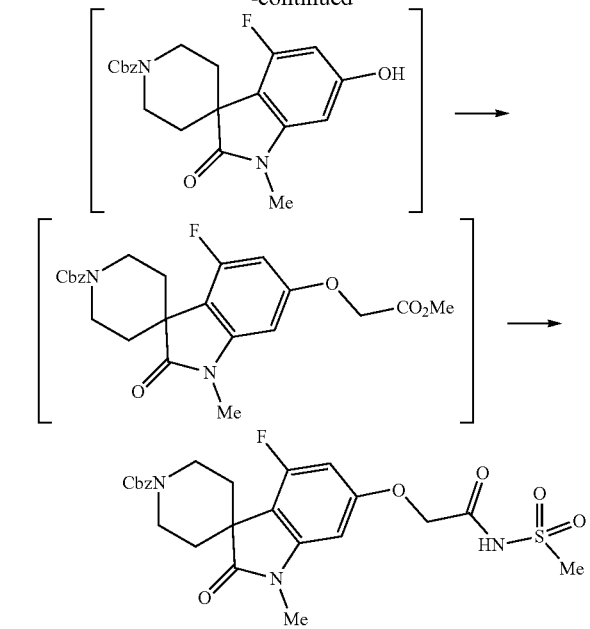

First, 1'-tert-butyloxycarbonyl-4-fluoro-6-methoxy-1-methylspiro[indoline-3,4'-piperidine]-2(1H)-one (157 mg) was dissolved in methylene chloride (4.3 mL), and the mixture was cooled in an ice bath. A methylene chloride solution (4.3 mL) of 1 M boron tribromide was added dropwise to the mixture, and the ice bath was removed. The mixture was stirred at room temperature for 3 hours. The reaction mixture was cooled in the ice bath. After excess boron tribromide was decomposed by addition of methanol as appropriate, a 5 M sodium hydroxide aqueous solution (3.2 mL) was added thereto. The obtained mixture was heated to room temperature. Then, the mixture was stirred for a total of 4 hours while benzyl chloroformate (2.79 mL) was added thereto in three portions every approximately 1 hour. The reaction mixture was diluted with diethylether, was washed with water and saturated brine in sequence, and was dried with anhydrous magnesium sulfate. The solvent was concentrated under reduced pressure. The obtained residue was dissolved in methanol (4 mL), a 5 M sodium hydroxide aqueous solution (2 mL) was added thereto, and the mixture was stirred at room temperature for 1 hour. The reaction mixture was concentrated under reduced pressure to remove most of the methanol. Thereafter, water (4 mL) was added thereto, and the aqueous layer was washed with diethylether. The aqueous layer was rendered acidic by concentrated hydrochloric under ice cooling, followed by extraction with ethyl acetate. The organic layer was washed with saturated brine and then was dried with anhydrous magnesium sulfate, and the solvent was concentrated under reduced pressure to obtain 1'-benzyloxycarbonyl-4-fluoro-6-hydroxy-1-methylspiro[indoline-3,4'-piperidine]-2(1H)-one (146 mg) as a crude product.

Next, the obtained crude product (44 mg) was dissolved in N,N-dimethylformamide (1.1 mL), then potassium carbonate (30 mg) and bromomethyl acetate (0.014 mL) were added in sequence, and the mixture was stirred at room temperature for 30 minutes. The reaction mixture was diluted with water, and was subjected to extraction with diethylether. The organic layer was dried with anhydrous magnesium sulfate, and then the solvent was concentrated under reduced pressure to obtain 1'-benzyloxycarbonyl-4- fluoro-6-(2-methoxy-2-oxoethoxy)-1-m ethylspiro[indoline-3,4'-piperidine]-2(1H)-one (44 mg) as a crude product.

Subsequently, the obtained crude product was dissolved in a mixture solvent of tetrahydrofuran (0.5 mL) and methanol (0.25 mL), and a 5 M sodium hydroxide aqueous solution (0.25 mL) was added thereto, followed by stirring at room temperature for 1 hour. Then, 5 M hydrochloric acid (0.3 mL) was added to the reaction mixture, followed by extraction with ethyl acetate. The organic layer was dried with anhydrous magnesium sulfate, and the solvent was concentrated under reduced pressure. The obtained residue was dissolved in methylene chloride (1.5 mL), then methanesulfon amide (11 mg), 4-dimethylaminopyridine (16.3 mg), and 1-(3-dimethylaminopropyl)-3-ethylcarbodiimide hydrochloride (28 mg) were added in sequence, and the obtained mixture was stirred at room temperature for 20 hours. The reaction mixture was diluted with methylene chloride (20 mL), was washed with 1 M hydrochloric acid, and then was dried with anhydrous magnesium sulfate. Then, the solvent was concentrated under reduced pressure. The obtained residue was purified by silica gel column chromatography (ethyl acetate/methanol=90/10) to obtain the title compound (48 mg).

$^1$H-NMR (400 MHz, CDCl$_3$) δ: 1.73 (br.d, J=13.0 Hz, 2H), 2.05-2.20 (br.m, 2H), 3.16 (s, 3H), 3.35 (br.s, 3H), 3.69-3.88 (br.m, 2H), 3.89-4.09 (br.m, 2H), 4.57 (br.s, 2H), 5.18 (s, 2H), 6.19-6.39 (m, 2H), 7.28-7.43 (m, 5H), 8.93 (br.s, 1H)

MS(ESI) m/z: 520[M+H]$^+$.

Compounds of Reference Example 200 to Reference Example 289 presented below in Tables 23 to 36 were obtained by using the methods used in Reference Examples 23 to 49 or Reference Examples 197 to 199 described above and their applied methods as well as the methods known by literatures and their applied methods.

TABLE 23

| Reference Example | Compound Name | Structural formula | 1H NMR δ ppm | Solvent | ESI MS m/z |
|---|---|---|---|---|---|
| 200 | 6-(cis-3,5-dimethyl piperazin-1-yl)-4-fluoro-1-methylspiro [indoline-3,4'-piperidin]-2(1H)-one | | 1.15 (d, J = 6.0 Hz, 6 H), 1.70-1.85 (m, 2 H), 2.00-2.10 (m, 2 H), 2.30-2.40 (m, 2 H), 2.95-3.10 (m, 4 H), 3.17 (s, 3 H), 3.40-3.50 (m, 4 H), 6.15-6.25 (m, 2 H). | CDCl3 | 347 [M + H]+ |
| 201 | 6-(3,8-diazabicyclo [3.2.1]octan-3-yl)-4-fluoro-1-methyl-spiro[indoline-3,4'-piperidin]-2-one | | 1.70-1.80 (m, 2 H), 1.80-1.95 (m, 4 H), 2.00-2.10 (m, 2 H), 2.90-3.00 (m, 2 H), 3.00-3.10 (m, 2 H), 3.15 (s, 3 H), 3.35-3.50 (m, 4 H), 3.65-3.75 (m, 2 H), 6.05-6.15 (m, 2 H). | CDCl3 | 345 [M + H]+ |
| 202 | methyl {[1'-(tert-butyloxy-carbonyl)-4-fluoro-1-methyl-2-oxospiro [indoline-3,4'-piperidine]-6-yloxy}acetate | | | | 423 [M + H]+ |
| 203 | {[1'-(tert-butyloxy-carbonyl)-4-fluoro-1-methyl-2-oxospiro [indoline-3,4'-piperidine]-6-yl]oxy}acetonitrile | | | | 390 [M + H]+ |
| 204 | 1'-(tert-butyloxy-carbonyl)-4-fluoro-1-methyl-6-[(1H-tetrazol-5-yl) methoxy] spiro[indoline-3,4'-piperidine]-2-one | | | | 433 [M + H]+ |

TABLE 23-continued

| Reference Example | Compound Name | Structural formula | 1H NMR δ ppm | Solvent | ESI MS m/z |
|---|---|---|---|---|---|
| 205 | 1'-(tert-butyloxy-carbonyl)-4-fluoro-6-{2-[2-(hydroxy-methyl)pyrrolidin-1-yl]ethoxy}-1-methylspiro[indoline-3,4'-piperidine]-2(1H)-one | | | | 478 [M + H]+ |

TABLE 24

| Reference Example | Compound Name | Structural formula | 1H NMR δ ppm | Solvent | ESI MS m/z |
|---|---|---|---|---|---|
| 206 | 4-chloro-7-[2-(dimethylamino)ethoxy]-1-methylspiro[indoline-3,4'-piperidin]-2(1H)-one | | 1.45-1.55 (m, 2 H), 2.33 (s, 6 H), 2.60-2.75 (m, 4 H), 2.95-3.05 (m, 2 H), 3.46 (s, 3 H), 3.55-3.65 (m, 2 H), 4.05-4.10 (m, 2 H), 6.78 (d, J = 8.8 Hz, 1 H), 6.89 (d, J = 8.8 Hz, 1 H). | CDCl3 | |
| 207 | 1'-(tert-butyloxy-carbonyl)-4-fluoro-6-[4-(2-methoxyethyl)piperazin-1-yl]-1-methyl-spiro[indoline-3,4'-piperidine]-2(1H)-one | | | | 477 [M + H]+ |
| 208 | 1'-(tert-butyloxy-carbonyl)-4-fluoro-1-methyl-6-[4-(oxetan-3-yl)piperazin-1-yl]spiro[indoline-3,4'-piperidine]-2(1H)-one | | | | 475 [M + H]+ |
| 209 | 1'-(tert-butyloxy-carbonyl)-4-fluoro-6-hydroxy-1-(2,2,2-trifluoroethyl)spiro[indoline-3,4'-piperidine]-2(1H)-one | | | | 419 [M + H]+ |
| 210 | 1'-(tert-butyloxy-carbonyl)-4-fluoro-6-(2-hydroxyethoxy)-1-(2,2,2-trifluoroethyl)spiro[indoline-3,4'-piperidine]-2(1H)-one | | | | 462 [M + H]+ |

TABLE 24-continued

| Reference Example | Compound Name | Structural formula | 1H NMR δ ppm | Solvent | ESI MS m/z |
|---|---|---|---|---|---|
| 211 | 1'-(tert-butyloxy-carbonyl)-6-[2-(dimethylamino)ethoxy]-4-fluoro-1-(2,2,2-trifluoroethyl)spiro[indoline-3,4'-piperidine]-2(1H)-one | | | | 490 [M + H]+ |

TABLE 25

| Reference Example | Compound Name | Structural formula | 1H NMR δ ppm | Solvent | ESI MS m/z |
|---|---|---|---|---|---|
| 212 | 1'-(tert-butyloxy-carbonyl)-4-fluoro-2-oxo-1-(2,2,2-trifluoroethyl)spiro[indoline-3,4'-piperidin]-6-yl trifluoromethane-sulfonate | | | | 551 [M + H]+ |
| 213 | 1'-(tert-butyloxy-carbonyl)-4-fluoro-6-hydroxyspiro[indoline-3,4'-piperidine]-2(1H)-one | | | | 337 [M + H]+ |
| 214 | 1'-(tert-butyloxy-carbonyl)-4-fluoro-2-oxospiro[indoline-3,4'-piperidine]-6-yl trifluoromethane-sulfonate | | | | 469 [M + H]+ |
| 215 | 1'-(tert-butyloxy-carbonyl)-1-(cyano-methyl)-4-fluoro-2-oxospiro[indoline-3,4'-piperidine]-6-yl trifluoromethane-sulfonate | | | | 508 [M + H]+ |
| 216 | 1'-(tert-butyloxy-carbonyl)-1-(cyano-methyl)-4-fluoro-6-hydroxyspiro[indoline-3,4'-piperidine]-2(1H)-one | | 1.50 (s, 9 H), 1.70-1.76 (m, 2 H), 2.10-2.20 (m, 2 H), 3.56-3.71 (m, 2 H), 3.87-4.02 (m, 2 H), 4.53-4.62 (m, 1 H), 6.30-6.36 (m, 2 H). | CDCl3 | 332 [M + H]+ |

TABLE 25-continued

| Reference Example | Compound Name | Structural formula | 1H NMR δ ppm | Solvent | ESI MS m/z |
|---|---|---|---|---|---|
| 217 | 1'-(tert-butyloxy-carbonyl)-1-(cyano-methyl)-4-fluoro-6-(4-methyl-piperazin-1-yl)spiro[indoline-3,4'-piperidine]-2(1H)-one | | | | 458 [M + H]+ |
| 218 | 1'-(tert-butyloxy-carbonyl)-6-(4-acetylpiperazin-1-yl)-4-fluoro-1-methylspiro[indoline-3,4'-piperidine]-2(1H)-one | | 1.50 (s, 9 H), 1.74 (d, J = 14.2 Hz, 2 H), 2.03-2.13 (m, 2 H), 2.16 (s, 3 H), 3.12-3.28 (m, 7 H), 3.57-4.01 (m, 8 H), 6.17-6.26 (m, 2 H). | CDCl3 | 461 [M + H]+ |

TABLE 26

| Reference Example | Compound Name | Structural formula | 1H NMR δ ppm | Solvent | ESI MS m/z |
|---|---|---|---|---|---|
| 219 | 1'-(tert-butylcarbonyl)-4-fluoro-6-(2-(pyrrolidin-1-yl)ethoxy)-1-(2,2,2-trifluoroethyl)spiro[indoline-3,4'-piperidin]-2(1H)-one | | | | 516 [M + H]+ |
| 220 | (tert-butylcarbonyl)-6-(2-(dimethylamino)ethoxy)-4-fluoro-1-(2-methoxyethyl)spiro[indoline-3,4'-piperidin]-2(1H)-one | | 1.49 (s, 9 H), 1.70-1.80 (m, 2 H), 2.05-2.20 (m, 2 H), 2.35 (s, 6 H), 2.70-2.80 (m, 2 H), 3.32 (s, 3 H), 3.55-4.30 (m, 10 H), 6.26 (dd, J = 11.6, 2.0 Hz, 1 H), 6.41 (d, J = 2.0 Hz, 1 H). | CDCl3 | |
| 221 | 1'-(tert-butylcarbonyl)-4-fluoro-6-(2-(4-methylpiperazin-1-yl)ethoxy)-1-(2,2,2-trifluoroethyl)spiro[indoline-3,4'-piperidin]-2(1H)-one | | | | 545 [M + H]+ |

TABLE 26-continued

| Reference Example | Compound Name | Structural formula | 1H NMR δ ppm | Solvent | ESI MS m/z |
|---|---|---|---|---|---|
| 222 | '-(tert-butylcarbonyl)-4-fluoro-1-(2-methoxyethyl)-6-(2-(4-methylpiperazin-1-yl)ethoxy)spiro[indoline-3,4'-piperidin]-2(1H)-one | | 1.49 (s, 9 H), 1.65-1.80 (m, 2 H), 2.00-2.15 (m, 2 H), 2.38 (s, 3 H), 2.55-2.65 (m, 4 H), 3.20-3.25 (m, 4 H), 3.33 (s, 3 H), 3.55-3.95 (m, 8 H), 6.22 (dd, J = 12.8, 2.0 Hz, 1 H), 6.35 (d, J = 2.0 Hz, 1 H). | CDCl3 | |
| 223 | 1'-(tert-butylcarbonyl)-methyl 2-((4-fluoro-2-oxo-1-(2,2,2-trifluoroethyl)spiro[indoline-3,4'-piperidin]-6-yl)oxy)acetate | | | | 491 [M + H]+ |
| 224 | 1'-(tert-butylcarbonyl)-4-fluoro-6-(2-hydroxyethoxy)-1-(2-methoxyethyl)spiro[indoline-3,4'-piperidin]-2(1H)-one | | 1.50 (s, 9 H), 1.65-1.80 (m, 2 H), 2.05-2.15 (m, 2 H), 3.33 (s, 3 H), 3.55-3.60 (m, 2 H), 3.60-3.75 (m, 2 H), 3.75-4.00 (m, 6 H), 4.05-4.10 (m, 2 H), 6.27 (dd, J = 11.6, 2.0 Hz, 1 H), 6.41 (d, J = 2.0 Hz, 1 H). | CDCl3 | |

TABLE 27

| Reference Example | Compound Name | Structural formula | 1H NMR δ ppm | Solvent | ESI MS m/z |
|---|---|---|---|---|---|
| 225 | 1'-(tert-butylcarbonyl)-1-(cyanomethyl)-4-fluoro-2-oxo-6-(2-(pyrrolidin-1-yl)ethoxy)spiro[indoline-3,4'-piperidine]-2(1H)-one | | | | 473 [M + H]+ |
| 226 | 6-(4-benzyloxycarbonyl-piperazin-1-yl)-4-fluoro-1-(2-methoxyethyl)spiro[indoline-3,4'-piperidine]-2(1H)-one | | 1.70-1.80 (m, 2 H), 2.00-2.15 (m, 2 H), 3.00-3.05 (m, 2 H), 3.10-3.20 (m, 4 H), 3.33 (s, 3 H), 3.35-3.50 (m, 2 H), 3.55-3.60 (m, 2 H), 3.60-3.70 (m, 4 H), 3.80-3.85 (m, 2 H), 5.17 (s, 2 H), 6.21 (dd, J = 12.8, 2.0 Hz, 1 H), 6.35 (d, J = 2.0 Hz, 1 H), 7.30-7.40 (m, 5 H). | CDCl3 | |

TABLE 27-continued

| Reference Example | Compound Name | Structural formula | 1H NMR δ ppm | Solvent | ESI MS m/z |
|---|---|---|---|---|---|
| 227 | 1'-(tert-butyloxycarbonyl)-6-(cis-3,5-dimethyl-piperazine-1-yl)-4-fluoro-1-(2,2,2-trifluoroethyl)spiro[indoline-3,4'-piperidine-2(1H)-one |  | 1.16 (d, J = 6.4 Hz, 6 H), 1.49 (s, 9 H), 1.69-1.78 (m, 2 H), 2.08-2.18 (m, 2 H), 2.31-2.39 (m, 2 H), 2.97-3.07 (m, 2 H), 3.43-3.49 (m, 2 H), 3.60-3.72 (m, 2 H), 3.84-4.01 (m, 2 H), 4.28 (q, J = 8.6 Hz, 2 H), 6.23-6.29 (m, 2 H). | CDCl3 | 515 [M + H]+ |
| 228 | {[1'-(tert-butylcarbonyl)-4-fluoro-1-(2-methoxyethyl)-2-oxospiro 2[indoline-3,4'-piperidin]-6-yl]oxy}acetonitrile |  | 1.50 (s, 9 H), 1.70-1.80 (m, 2 H), 2.10-2.20 (m, 2 H), 3.33 (s, 3 H), 3.55-3.80 (m, 4 H), 3.80-4.00 (m, 4 H), 4.77 (s, 2 H), 6.34 (dd, J = 10.8, 2.0 Hz, 1 H), 6.51 (d, J = 2.0 Hz, 1 H). | CDCl3 | |
| 229 | {[1'-(tert-butylcarbonyl)-4-fluoro-2-oxo-1-(2,2,2-trifluoroethyl)spiro[indoline-3,4'-piperidine]-6-yl]oxy}acetonitrile |  | | | 458 [M + H]+ |
| 230 | Ethyl 1-[1'-(tert-butyloxy-carbonyl)-4-fluoro-1-methyl-2-oxospiro[indoline-3,4'-piperidine]-6-yl]piperidine-4-carboxylate |  | | | 490 [M + H]+ |

TABLE 28

| Reference Example | Compound Name | Structural formula | 1H NMR δ ppm | Solvent | ESI MS m/z |
|---|---|---|---|---|---|
| 231 | Methyl 1-[1'-(tert-butyloxycarbonyl)-4-fluoro-1-methyl-2-oxo-spiro[indoline-3,4'-piperidine]-6-yl]azetidin-3-carboxylate |  | | | 448 [M + H]+ |
| 232 | Methyl 2-[1'-(tert-butuloxycarbonyl)-4,6-difluoro-2-oxospiro[indoline-3,4'-piperidine]-1-yl]acetate |  | | | 411 [M + H]+ |

TABLE 28-continued

| Reference Example | Compound Name | Structural formula | 1H NMR δ ppm | Solvent | ESI MS m/z |
|---|---|---|---|---|---|
| 233 | [1'-(tert-butoxycarbonyl)-4,6-difluoro-2-oxospiro[indoline-3,4'-piperidin]-1-yl)acetic acid | | | | 397 [M + H]+ |
| 234 | [1'-(tert-butyloxycarbonyl)-4,6-difluoro-2-oxospiro[indoline-3,4'-piperidine]-1(2H)-yl]acetamide | | | | 396 [M + H]+ |
| 235 | 1'benzyloxycarbonyl-6-(2-amino-2-oxoethoxy)-4-fluoro-1-methylspiro[indoline-3,4'-piperidine]-2(1H)-one | | | | 442 [M + H]+ |
| 236 | 1'-benzyloxycarbonyl-6-{2-[(tert-butyl oxycarbonyl)amino)ethoxy)-4-fluoro-1-methylspiro[indoline-3,4'-piperidine]-2(1H)-one | | 1.45 (s, 9 H), 1.75-1.85 (m, 2 H), 2.05-2.20 (m, 2 H), 3.15 (s, 3 H), 3.50-3.60 (m, 2 H), 3.75-4.10 (m, 6 H), 4.90-5.00 (m, 1 H), 5.18 (s, 2 H), 6.20-6.30 (m, 2 H), 7.30-7.45 (m, 5 H). | CDCl3 | |
| 237 | 1'-benzyloxycarbonyl-6-(2-aminoethoxy)-4-fluoro-1-methyl-spiro[indoline-3,4'-piperidine]-2(1H)-one | | 1.70-1.85 (m, 2 H), 2.05-2.20 (m, 2 H), 3.05-3.10 (m, 2 H), 3.15 (s, 3 H), 3.75-3.90 (m, 2 H), 3.90-4.10 (m, 4 H), 5.18 (s, 2 H), 6.25-6.30 (m, 2 H), 7.30-7.45 (m, 5 H). | CDCl3 | |

TABLE 29

| Reference Example | Compound Name | Structural formula | 1H NMR δ ppm | Solvent | ESI MS m/z |
|---|---|---|---|---|---|
| 238 | 1'-benzylcarbonyl-6-[2-((N,N-dimethylsulfamoyl)aminoethoxy)-4-fluoro-1-methyl-spiro[indoline-3,4'-piperidine]-2(1H)-one | | 1.70-1.85 (m, 2 H), 2.05-2.20 (m, 2 H), 2.83 (s, 6 H), 3.16 (s, 3 H), 3.45-3.50 (m, 2 H), 3.75-4.15 (m, 6 H), 4.55-4.60 (m, 1 H), 5.18 (s, 2 H), 6.20-6.30 (m, 2 H), 7.30-7.40 (m, 5 H). | CDCl3 | |

TABLE 29-continued

| Reference Example | Compound Name | Structural formula | 1H NMR δ ppm | Solvent | ESI MS m/z |
|---|---|---|---|---|---|
| 239 | {[1'-tert-butylcarboxy-carbonyl)-4-fluoro-1-(2-hydroxyethyl)-2-oxospiro[indoline-3,4'-piperidine]-6-yl]oxy} acetonitrile | | 1.50 (s, 9 H), 1.70-1.80 (m, 2 H), 2.10-2.20 (m, 2 H), 3.60-3.75 (m, 2 H), 3.75-4.05 (m, 6 H), 4.77 (s, 2 H), 6.35 (dd, J = 10.8, 2.0 Hz, 1 H), 6.46 (d, J = 2.0 Hz, 1 H). | CDCl3 | |
| 240 | 2,4,6-(trichlorophenyl) 1'-tert-butoxycarbonyl-4-fluoro-1-methyl-2-oxospiro[indoline-3,4'-piperidine]-6-dicarboxylate | | 1.51 (s, 9 H), 1.72-1.80 (m, 2 H), 2.18-2.29 (m, 2 H), 3.27 (s, 3 H), 3.65-3.80 (m, 2 H), 3.90-4.08 (m, 2 H), 7.44 (s, 2 H), 7.46 (d, J = 1.2 Hz, 1 H), 7.67 (dd, J = 9.7, 1.2 Hz, 1 H). | CDCl3 | 557 [M + H]+ |
| 241 | Ethyl 1'-tert-butyloxycarbonyl)-4-fluoro-1-methyl-2-oxospiro[indoline-3,4'-piperidine]-6-dicarboxylate | | 1.41 (t, J = 7.1, 3 H), 1.50 (s, 9 H), 1.69-1.77 (m, 2 H), 2.14-2.24 (m, 2 H), 3.24 (s, 3 H), 3.66-3.78 (m, 2 H), 3.87-4.04 (m, 2 H), 4.40 (q, J = 7.1 Hz, 2 H), 7.30 (d, J = 1.2 Hz, 1 H), 7.45 (dd, J = 10.0, 1.2 Hz, 1 H). | CDCl3 | 407 [M + H]+ |
| 242 | N-{2-[(1'-benzyloxy carbonyl-4-fluoro-1-methyl-2-oxospiro [indoline-3,4'-piperidine]-6-yl)oxy] ethyl}methanesulfone amide | | 1.65-1.80 (m, 2 H), 2.05-2.20 (m, 2 H), 3.03 (s, 3 H), 3.16 (s, 3 H), 3.50-3.60 (m, 2 H), 3.70-3.90 (m, 2 H), 3.90-4.15 (m, 4 H), 4.70-4.85 (m, 1 H), 5.18 (s, 2 H), 6.20-6.30 (m, 2 H), 7.30-7.40 (m, 5 H). | CDCl3 | |
| 243 | Diethyl ({[1'-(tert-butyloxy-carbonyl)-4-fluoro-1-methyl-2-oxospiro [indoline-3,4'-piperidine]-6-yl]oxy}methyl) sulfonate | | 1.38 (t, J = 6.8 Hz, 6 H), 1.50 (s, 9 H), 1.70-1.80 (m, 2 H), 2.05-2.15 (m, 2 H), 3.16 (s, 3 H), 3.65-4.00 (m, 4 H), 4.20-4.30 (m, 6 H), 6.30-6.35 (m, 2 H). | CDCl3 | 501 [M + H]+ |

TABLE 30

| Reference Example | Compound Name | Structural formula | 1H NMR δ ppm | Solvent | ESI MS m/z |
|---|---|---|---|---|---|
| 244 | 1-{[1'-(tert-butyloxy-carbonyl)-4-fluoro-1-methyl-2-oxospiro [indoline-3,4'-piperidine]-6-yl}-N-methyl methane sulfoamide | | 1.49 (s, 9 H), 1.67-1.76 (m, 2 H), 2.03-2.16 (m, 2 H), 3.16 (s, 3 H), 3.26 (s, 3 H), 3.63-4.02 (m, 4 H), 5.02 (s, 2 H), 6.39-6.46 (m, 2 H). | CDCl3 | 458 [M + H]+ |

TABLE 30-continued

| Reference Example | Compound Name | Structural formula | 1H NMR δ ppm | Solvent | ESI MS m/z |
|---|---|---|---|---|---|
| 245 | {[1'-(tert-butyloxy-carbonyl)-4-fluoro-1-methyl-2-oxospiro[indoline-3,4'-piperidine]oxy}meethanesulfoamide | | 1.49 (s, 9 H), 1.64-1.77 (m, 2 H), 2.02-2.16 (m, 2 H), 3.16 (s, 3 H), 3.60-3.78 (m, 2 H), 3.80-4.01 (m, 2 H), 4.97 (br. s, 2 H), 5.06 (s, 2 H), 6.39-6.48 (m, 2 H). | CDCl3 | 444 [M + H]+ |
| 246 | 1'-{[1'-(tert-butyloxy-carbonyl)-6-[(1,1-dioxidothiomorpho-line)-4-yl-]-4fluoro-1-methylspiro[indoline-3,4'-piperidine]-2(1H)-one | | | | 468 [M + H]+ |
| 247 | N-({[1'-(tert-butyloxy-carbonyl)-4-fluoro-1-methyl-2-oxospiro[indoline-3,4'-piperidine]-6-yl]oxy}methanesulfonyl)acetamide | | 1.49 (s, 9 H), 1.54-1.76 (m, 2 H), 1.77-2.11 (m, 2 H), 2.19 (s, 3 H), 3.14 (s, 3 H), 3.47-3.93 (m, 4 H), 5.36 (s, 2 H), 6.39-6.50 (m, 2 H). | CDCl3 | 486 [M + H]+ |
| 248 | 1-Benzyl-4-[1'-(tert-butyloxycarbonyl)-4-fluoro-1-methyl-2-oxospiro[indoline-3,4'-piperidine]-6-yl]piperazine-2,6-dione | | 1.50 (s, 9 H), 1.65-1.75 (m, 2 H), 2.05-2.15 (m, 2 H), 3.13 (s, 3 H), 3.65-4.00 (m, 4 H), 4.16 (s, 4 H), 4.99 (s, 2 H), 6.15-6.25 (m, 2 H), 7.25-7.40 (m, 5 H). | CDCl3 | 537 [M + H]+ |
| 249 | 1'-(tert-butyloxy-carbonyl)-6-(cis-2,6-dimethylmopholine-4-yl)-4-fluoro-1-methylspiro[indoline-3,4'-piperidine]2-(1H)-one | | 1.27 (d, J = 6.2 Hz, 6 H), 1.49 (s, 9 H), 1.70-1.77 (m, 2 H), 2.01-2.11 (m, 2 H), 2.41-2.49 (m, 2 H), 3.17 (s, 3 H), 3.40-3.45 (m, 2 H), 3.68-3.94 (m, 6 H), 6.15-6.23 (m, 2 H). | CHCl3 | 448 [M + H]+ |

TABLE 31

| Reference Example | Compound Name | Structural formula | 1H NMR δ ppm | Solvent | ESI MS m/z |
|---|---|---|---|---|---|
| 250 | 1'-(tert-butyloxycarbonyl)4-fluoro-6-[4-(methane-sulfonyl)piperidin-1-yl]-1-methylspiro[indoline-3,4'-piperidine]-2(1H)-one | | 1.49 (s, 9 H), 1.70-1.77 (m, 2 H), 1.91-2.12 (m, 4 H), 2.21-2.28 (m, 2 H), 2.80-2.89 (m, 5 H), 2.97-3.07 (m, 1 H), 3.16 (s, 3 H), 3.68-3.94 (m, 6 H), 6.18-6.25 (m, 2 H). | CHCl3 | 496 [M + H]+ |

TABLE 31-continued

| Reference Example | Compound Name | Structural formula | 1H NMR δ ppm | Solvent | ESI MS m/z |
|---|---|---|---|---|---|
| 251 | 1'-(tert-butyloxycarbonyl)-4-fluoro-6-(4-methoxypiperidin-1-yl)-1-methylspiro[indoline-3,4'-piperidine]-2(1H)-one | | 1.49 (s, 9 H), 1.67-1.77 (m, 4 H), 1.96-2.10 (m, 4 H), 2.96-3.04 (m, 2 H), 3.16 (s, 3 H), 3.36-3.43 (m, 4 H), 3.47-3.54 (m, 2 H), 3.69-3.93 (m, 4 H), 6.18-6.25 (m, 2 H). | CHCl3 | 448 [M + H]+ |
| 252 | 1-[1'-(tert-butyloxycarbonyl)-4-fluoro-1-methyl-2-oxospiro[indoline-3,4'-piperidine]-6-yl]piperidine-4-carbonitrile | | 1.49 (s, 9 H), 1.70-1.77 (m, 2 H), 1.95-2.12 (m, 6 H), 2.81-2.88 (m, 1 H), 3.12-3.20 (m, 5 H), 3.40-3.48 (m, 2 H), 3.67-3.95 (m, 4 H), 6.19 (d, J = 2.1 Hz, 1 H), 6.22 (dd, J = 12.7, 2.1 Hz, 1 H). | CHCl3 | [M + H]+ |
| 253 | 6-(3,3-dimethylazetidin-1-yl)-4-fluoro-1-methylspiro[indoline-3,4'-piperidin]-2(1H)-one | | 1.33 (s, 6 H), 1.67-1.77 (m, 2 H), 1.95-2.08 (m, 2 H), 2.95-3.05 (m, 2 H), 3.13 (s, 3 H), 3.36-3.46 (m, 2 H), 3.58 (s, 4 H), 5.67 (d, J = 1.83 Hz, 1 H), 5.72 (dd, J = 11.86, 1.83 Hz, 1 H). | CDCl3 | |
| 254 | 1'-(tert-butyloxycarbonyl)-4-fluoro-6-(4-hydroxycyclohexyl)-1-methyl-2-oxospiro[indoline-3,4'-piperidine]-2(1H)-one | | 1.37-1.78 (m, 13 H), 1.68-1.77 (m, 2 H), 1.88-1.99 (m, 2 H), 2.08-2.18 (m, 4 H), 2.46-2.57 (m, 1 H), 3.18 (s, 3 H), 3.65-4.04 (m, 5 H), 6.47 (d, J = 1.0 Hz, 1 H) 6.58 (dd, J = 11.1, 1.0 Hz, 1 H). | CDCl3 | 433 [M + H]+ |
| 255 | tert-butyl 7-(2-(ethoxy-2-oxoethoxy)-4-fluoro-1-methyl-2-oxospiro[indoline-3,4'-piperidine]-1'-carboxylate | | | | 437 [M + H]+ |

TABLE 32

| Reference Example | Compound Name | Structural formula | 1H NMR δ ppm | Solvent | ESI MS m/z |
|---|---|---|---|---|---|
| 256 | tert-butyl 4-fluoro-1-methyl-7-((1-methylpiperidin-4-yl)methoxy)-2-oxospiro[indoline-3,4'-piperidine]-1'-carboxylate | | | | 462 [M + H]+ |

TABLE 32-continued

| Reference Example | Compound Name | Structural formula | 1H NMR δ ppm | Solvent | ESI MS m/z |
|---|---|---|---|---|---|
| 257 | tert-butyl 4-fluoro-7-(2-hydroxyethoxy)-1-methyl-2-oxospiro[indoline-3,4'-piperidine]-1'-carboxylate | | | | 395 [M + H]+ |
| 258 | tert-butyl 4-fluoro-1-methyl-7-((1-methylpiperidin-4-yl)oxy)-2-oxospiro[indoline-3,4'-piperidine]-1'-carboxylate | | | | 448 [M + H]+ |
| 259 | tert-Butyl 7-((1-benzylpiperidin-4-yl)methoxy)-4-fluoro-1-methyl-2-oxospiro[indoline-3,4'-piperidine]-1'-carboxylate | | | | 538 [M + H]+ |
| 260 | tert-Butyl 4-fluoro-7-(2-hydroxy-2-methylpropoxy)-1-methyl-2-oxospiro[indoline-3,4'-piperidine]-1'-carboxylate | | | | 423 [M + H]+ |
| 261 | tert-Butyl 7-(2-(tert-butylamino)ethoxy)-4-fluoro-1-methyl-2-oxospiro[indoline-3,4'-piperidine]-1'-carboxylate | | | | 450 [M + H]+ |
| 262 | Tert-Bytyl 4-(7-fluoro-3-oxo-3H-spiro[isobenzofuran-1,4'-piperidin]-5-yl)piperazine-1-carboxylate 2hydrochloride | | | | 406 [M + H]+ |
| 263 | 7-fluoro-5-(4-(2-hydroxy-2-methylpropyl)piperazin-1-yl)-3H-spiro[isobenzofuran-1,4'-piperidin]-3-one 2hydrochloride | | | | 468 [M + H]+ |

TABLE 33

| Reference Example | Compound Name | Structural formula | 1H NMR δ ppm | Solvent | ESI MS m/z |
|---|---|---|---|---|---|
| 264 | 7-fluoro-5-(4-(2-hydroxyethyl)piperazin-1-yl)-3H-spiro[isobenzofuran-1,4'-piperidin]-3-one 2hydrochloride | 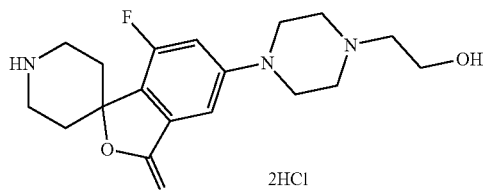 | | | 440 [M + H]+ |
| 265 | 7-fluoro-5-(4-(4-methylpiperazin-1-yl)phenyl)-3H-spiro[isobenzofuran-1,4'-piperidin]-3-one 2hydrochloride | 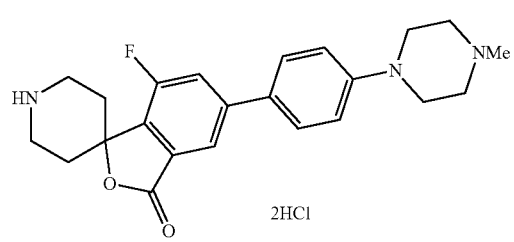 [SMILES: CN1CCN(c2ccc(-c3cc(F)c4c(c3)C(=O)OC43CCNCC3)cc2)CC1 ; "2HCl"] | | | 396 [M + H]+ |
| 266 | 5-(4-(dimethylamino)phenyl)-7-fluoro-3H-spiro[isobenzofuran-1,4'-piperidin]-3-one 2hydrochloride | 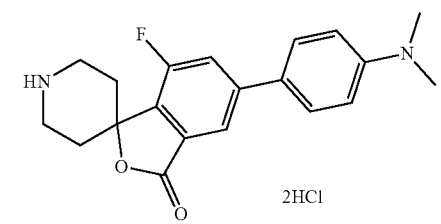 [SMILES: CN(C)c1ccc(-c2cc(F)c3c(c2)C(=O)OC32CCNCC2)cc1 ; "2HCl"] | | | 341 [M + H]+ |
| 267 | 7-fluoro-5-(1-methyl-1H-pyrazol-4-yl)-3H-spiro[isobenzofuran-1,4'-piperidin]-3-one 2hydrochloride | 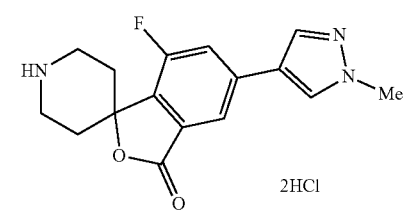 [SMILES: Cn1cc(-c2cc(F)c3c(c2)C(=O)OC32CCNCC2)cn1 ; "2HCl"] | | | 302 [M + H]+ |
| 268 | 7-fluoro-5-morpholino-3H-spiro[isobenzofuran-1,4'-piperidin]-3-one 2hydrochloride | 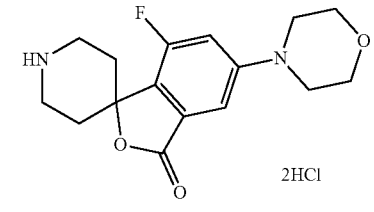 [SMILES: O=C1OC2(CCNCC2)c2c(F)cc(N3CCOCC3)cc21 ; "2HCl"] | | | 307 [M + H]+ |
| 269 | 5-(2,6-dimethylmorpholino)-7-fluoro-3H-spiro[isobenzofuran-1,4'-piperidin]-3-one 2hydrochloride | 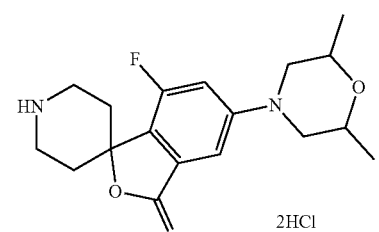 | | | 335 [M + H]+ |

TABLE 33-continued

| Reference Example | Compound Name | Structural formula | 1H NMR δ ppm | Solvent | ESI MS m/z |
|---|---|---|---|---|---|
| 270 | 2-((4-chloro-1-methyl-1'-(8-methyl-4-oxo-3,4,5,6,7,8-hexahydro-pyrido[2,3-d]pyrimidin-2-yl)-2-oxospiro[indoline-3,4'-piperidin]-7-yl)oxy)acetonitrile | | 1.53-1.61 (m, 2 H), 1.80-1.88 (m, 2 H), 2.47 (t, J = 6.3 Hz, 2 H), 2.68-2.84 (m, 2 H), 3.08 (s, 3 H), 3.17-3.32 (m, 2 H), 3.45 (br s, 3 H), 3.79-3.97 (m, 2 H), 4.27-4.41 (m, 2 H), 4.82 (s, 2 H), 6.89 (d, J = 8.9 Hz, 1 H), 6.96 (d, J = 8.9 Hz, 1 H) | CDCl3 | 469 [M + H]+ |
| 271 | tert-butyl 4-chloro-7-(cyano-methoxy)-1-methyl-2-oxospiro[indoline-3,4'-piperidine]-1'-carboxylate | | 1.44-1.47 (m, 2 H), 1.50 (s, 9 H), 2.60-2.73 (m, 2 H), 3.43 (s, 3 H), 3.51-3.85 (m, 2 H), 3.88-4.21 (m, 2 H), 4.81 (s, 2 H), 6.84-6.91 (m, 1 H), 6.94-7.00 (m, 1H) | CDCl3 | 428 [M + Na]+ |

TABLE 34

| Reference Example | Compound Name | Structural formula | 1H NMR δ ppm | Solvent | ESI MS m/z |
|---|---|---|---|---|---|
| 272 | 4-chloro-1-methyl-7-(((1R,5S)-8-methyl-8-azabicyclo[3.2.1]octan-3-yl)oxy)-2-oxo-spiro[indoline-3,4'-piperidine]-1'-carboxylate | | | | 490 [M + H]+ |
| 273 | 4-chloro-1-methyl-2-oxo-7-((tetrahydrofuran-3-yl)oxy)spiro[indoline-3,4'-piperidin]-1'carboxylate | | 1.73 (br d, J = 14.5 Hz, 2 H), 1.99-2.27 (m, 2 H), 2.77-2.95 (m, 2 H), 3.25 (s, 3 H), 3.26-3.31 (m, 2 H), 3.76-3.92 (m, 6 H), 4.96-5.08 (m, 1 H), 6.92 (s, 2 H) | CD3OD | 337 [M + H]+ |
| 274 | benzyl 1-(3-(4-acetylpiperazin-1-yl)-3-oxopropyl)-4-chloro-7-methoxy-2-oxospiro[indoline-3,4'-piperidine]-1'-carboxylate | | 1.41-1.56 (m, 2 H), 2.07 (s, 3 H), 2.33-2.81 (m, 8 H), 3.31-3.43 (m, 2 H), 3.45-3.60 (m, 2 H), 3.63-3.82 (m, 3 H), 3.85 (s, 3 H), 4.01-4.23 (m, 4 H), 5.19 (d, J = 3.6 Hz, 2 H), 6.76-6.83 (m, 1 H), 6.89-6.99 (m, 1 H), 7.30-7.42 (m, 5 H) | CDCl3 | |

TABLE 34-continued

| Reference Example | Compound Name | Structural formula | 1H NMR δ ppm | Solvent | ESI MS m/z |
|---|---|---|---|---|---|
| 275 | 1-(3-(4-acetyl-piperazin-1-yl)-3-oxopropyl)-4-chloro-7-methoxyspiro[indoline-3,4'-piperidin]-2-one | | 1.59-1.69 (m, 2 H), 2.08 (s, 3 H), 2.39-2.47 (m, 2 H), 2.48-2.64 (m, 4 H), 2.83-3.08 (m, 2 H), 3.10-3.28 (m, 2 H), 3.31-3.42 (m, 2 H), 3.44-3.59 (m, 2 H), 3.71-3.84 (m, 2 H), 3.86 (s, 3 H), 4.07 (t, J = 6.3 Hz, 2 H), 5.64-5.98 (m, 1 H), 6.82 (d, J = 8.9 Hz, 1 H), 6.95 (d, J = 8.9 Hz, 1 H), 7.27 (s, 1 H) | CDCl3 | 421 [M + H]+ |
| 276 | benzyl 4-chloro-7-methoxy-2-oxo-1-(2,2,2-trifluoroethyl)spiro[indoline-3,4'-piperidine]-1'-carboxylate | | 1.47-1.55 (m, 2 H), 2.62-2.79 (m, 2 H), 3.61-3.82 (m, 2 H), 3.84-3.91 (m, 3 H), 4.06-4.25 (m, 2 H), 4.63-4.73 (m, 2 H), 5.20 (d, J = 4.6 Hz, 2 H), 6.83 (d, J = 9.2 Hz, 1 H), 6.98 (d, J = 9.2 Hz, 1 H), 7.29-7.42 (m, 5 H) | CDCl3 | 483 [M + H]+ |

TABLE 35

| Reference Example | Compound Name | Structural formula | 1H NMR δ ppm | Solvent | ESI MS m/z |
|---|---|---|---|---|---|
| 277 | 4-chloro-7-methoxy-1-(2,2,2-trifluoroethyl)spiro[indoline-3,4'-piperidin]-2-one | | 1.48-1.59 (m, 2 H), 2.08-2.28 (m, 1 H), 2.69 (td, J = 13.4, 4.9 Hz, 2 H), 2.94-3.07 (m, 2 H), 3.48-3.62 (m, 2 H), 3.87 (s, 3 H), 4.68 (q, J = 8.6 Hz, 2 H), 6.82 (d, J = 8.9 Hz, 1 H), 6.99 (d, J = 8.9 Hz, 1 H) | CDCl3 | 349 [M + H]+ |
| 278 | benzyl 4-chloro-7-methoxy-2-oxo-1-(3-oxo-3-(2-(trifluoromethyl)-5,6,8,8a-tetrahydroimidazo[1,2-a]pyrazin-7(3H)-yl)propyl)spiro[indoline-3,4'-piperidine]-1'-carboxylate | | 1.47-1.57 (m, 2 H), 2.53-2.80 (m, 4 H), 3.64-3.88 (m, 5 H), 3.94-3.95 (m, 1 H), 3.96-4.09 (m, 5 H), 4.15 (s, 2 H), 4.22-4.32 (m, 2 H), 4.79 (s, 1 H), 5.19 (d, J = 3.6 Hz, 2 H), 6.75-6.84 (m, 1 H), 6.89-6.97 (m, 1 H), 7.33-7.42 (m, 5 H) | CDCl3 | 646 [M + H]+ |

TABLE 35-continued

| Reference Example | Compound Name | Structural formula | 1H NMR δ ppm | Solvent | ESI MS m/z |
|---|---|---|---|---|---|
| 279 | 4-chloro-7-methoxy-1-(3-oxo-3-(2-(trifluoromethyl)-5,6,8,8a-tetrahydroimidazo[1,2-a]pyrazin-7(3H)-yl)propyl)spiro[indoline-3,4'-piperidin]-2-one | | 1.70-1.82 (m, 2 H), 3.29-3.42 (m, 2 H), 3.43-3.55 (m, 2 H), 3.79-3.93 (m, 5 H), 4.04 (br d, J = 4.9 Hz, 4 H), 4.10-4.33 (m, 6 H), 4.81 (s, 1 H), 6.80-6.87 (m, 1 H), 6.95-7.02 (m, 1 H), 8.02 (s, 2 H) | CDCl3 | 512 [M + H]+ |
| 280 | 4-chloro-1-(2-hydroxy-2-methylpropyl)-7-methoxyspiro[indoline-3,4'-piperidine]-2-one | | 1.22 (s, 6 H), 1.45-1.56 (m, 2 H), 2.65-2.80 (m, 2 H), 3.61-3.84 (m, 2 H), 3.88 (s, 3 H), 4.01-4.26 (m, 4 H), 5.20 (d, J = 4.6 Hz, 2 H), 6.82 (d, J = 8.9 Hz, 1 H), 6.95 (d, J = 8.9 Hz, 1 H), 7.32-7.43 (m, 5 H) | CDCl3 | 473 [M + H]+ |
| 281 | Benzyl 4-chloro-1-(2-hydroxy-2-methylpropyl)-7-methoxyspiro[indoline-3,4'-piperidin]-1'-carboxylate | | | | 339 [M + H]+ |
| 282 | 1'-benzyl-4-fluoro-1-(2,2,2-trifluoroethyl)spiro[indoline-3,4'-piperidin]-2-one | | 1.72-1.92 (m, 2 H), 2.32-2.49 (m, 2 H), 2.73-2.98 (m, 4 H), 3.58-3.70 (m, 2 H), 4.28 (q, J = 8.9 Hz, 2 H), 6.69-6.87 (m, 2 H), 7.05-7.23 (m, 1 H), 7.29-7.47 (m, 5 H) | CDCl3 | 393 [M + H]+ |

TABLE 36

| Reference Example | Compound Name | Structural formula | 1H NMR δ ppm | Solvent | ESI MS m/z |
|---|---|---|---|---|---|
| 283 | 4-fluoro-1-(2,2,2-trifluoroethyl)spiro[indoline-3,4'-piperidin]-2-one | | 1.69-1.85 (m, 2 H), 2.19-2.42 (m, 2 H), 2.97-3.11 (m, 2 H), 3.36-3.57 (m, 2 H), 4.30 (q, J = 8.8 Hz, 2 H), 6.70-6.86 (m, 2 H), 7.18-7.26 (m, 1 H) | CDCl3 | 303 [M + H]+ |
| 284 | 1'-benzyl-4-fluoro-1-(2-hydroxy-2-methylpropyl)spiro[indoline-3,4'-piperidin]-2-one | | | | 383 [M + H]+ |
| 285 | 4-fluoro-1-(2-hydroxy-2-methyl-propyl)spiro[indoline-3,4'-piperidin]-2-one | | 1.23-1.32 (m, 6 H), 1.68-1.82 (m, 2 H), 2.17-2.43 (m, 3 H), 2.71-2.82 (m, 1 H), 3.01-3.12 (m, 2 H), 3.43-3.58 (m, 2 H), 3.71 (s, 2 H), 6.67-6.86 (m, 2 H), 7.17-7.26 (m, 1 H) | CDCl3 | 293 [M + H]+ |
| 286 | -benzyl-4-fluoro-1-((tetrahydrofuran-2-yl)methyl)spiro[indoline-3,4'-piperidin]-2-one | | | | 395 [M + H]+ |
| 287 | 4-fluoro-1-((tetra-hydrofuran-2-yl)methyl)spiro[indoline-3,4'-piperidin]-2-one | | 1.63-2.05 (m, 6 H), 2.13-2.44 (m, 3 H), 2.93-3.11 (m, 2 H), 3.44-3.60 (m, 2 H), 3.62-3.78 (m, 2 H), 3.78-3.91 (m, 2 H), 4.14-4.27 (m, 1 H), 6.66-6.87 (m, 2 H), 7.12-7.26 (m, 1 H) | CDCl3 | 305 [M + H]+ |
| 288 | 1'-benzyl-4-fluoro-1-(2-methoxyethyl)spiro[indoline-3,4'-piperidin]-2-one | | | | 369 [M + H]+ |

TABLE 36-continued

| Reference Example | Compound Name | Structural formula | 1H NMR δ ppm | Solvent | ESI MS m/z |
|---|---|---|---|---|---|
| 289 | 4-fluoro-1-(2-methoxyethyl)spiro[indoline-3,4'-piperidin]-2-one | | 1.70-1.86 (m, 2 H), 2.12-2.30 (m, 2 H), 2.92-3.09 (m, 2 H), 3.33 (s, 3 H), 3.34-3.53 (m, 2 H), 3.55-3.64 (m, 2 H), 3.81-3.92 (m, 2 H), 6.68-6.81 (m, 2 H), 7.17-7.26 (m, 1 H) | CDCl3 | 279 [M + H]+ |

Example 1

5-methoxy-1'-(4-oxo-3,4,5,6,7,8-hexahydroquinazolin-2-yl)-3H-spiro[isobenzofuran-1,4'-piperidin]-3-one (Test Target Compound 89)

Example 2

5-hydroxy-1'-(4-oxo-3,4,5,6,7,8-hexahydroquinazolin-2-yl)-3H-spiro[isobenzofuran-1,4'-piperidin]-3-one (Test Target Compound 90)

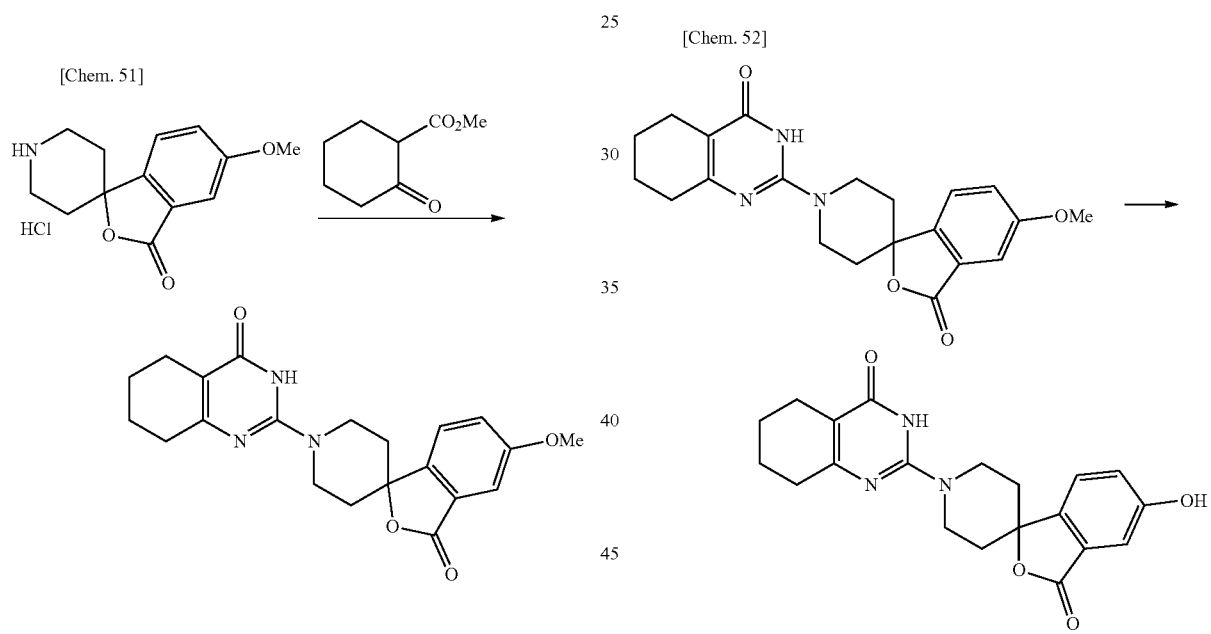

[Chem. 51]

[Chem. 52]

Triethylamine (0.11 mL) and 1-amidinopyrazole hydrochloride (35 mg) were added to a solution of 5-methoxy-3H-spiro[isobenzofuran-1,4'-piperidin]-3-one hydrochloride (54 mg) in acetonitrile (1.9 mL), and the mixture was stirred at room temperature for 2 hours. The reaction mixture was concentrated under reduced pressure, and the obtained residue was dissolved in ethanol (1.8 mL). Then, 2-oxocyclohexanecarboxylic acid ethyl ester (0.04 mL) and a 20% sodium ethoxide ethanol solution were added thereto, and the mixture was refluxed for 4 hours. The reaction mixture was cooled to room temperature, and the precipitate generated was collected by filtration to obtain the title compound (64 mg).

$^1$H-NMR (400 MHz, DMSO-$d_6$) δ: 1.58-1.71 (m, 6H), 2.13-2.32 (m, 4H), 2.33-2.44 (m, 2H), 3.17 (t, J=12.0 Hz, 2H), 3.84 (s, 3H), 4.46 (d, J=13.3 Hz, 1H), 7.29 (s, 1H), 7.32 (d, J=8.2 Hz, 1H), 7.69 (d, J=8.2 Hz, 1H), 11.12 (br.s, 1H).

MS(ESI) m/z: 382[M+H]+.

First, δ-methoxy-1'-(4-oxo-3,4,5,6,7,8-hexahydroquinazolin-2-yl)-3H-spiro[isobenzofuran-1,4'-piperidin]-3-one (90 mg) was dissolved in methylene chloride (7.1 mL), the obtained mixture was cooled to −78° C., and boron tribromide (1 M methylene chloride solution) (1.9 mL) was added dropwise thereto. The mixture was heated to room temperature, was stirred for 24 hours, and was further refluxed for 6 hours. A 6.5% sodium hydrogen carbonate aqueous solution was added to the reaction mixture under ice cooling, followed by extraction with ethyl acetate. The organic layer was washed with saturated brine, and was dried with anhydrous magnesium sulfate. The solvent was removed by evaporation under reduced pressure. Ethyl acetate and n-hexane were added to the residue, and the precipitate generated was collected by filtration to obtain the title compound (40 mg).

$^1$H-NMR (400 MHz, DMSO-$d_6$) δ: 1.55-1.71 (m, 6H), 2.13 (m, 2H), 2.26 (m, 2H), 2.38 (m, 2H), 3.16 (t, J=12.0 Hz,

2H), 4.41 (br.m, 2H), 7.07 (s, 1H), 7.13 (d, J=7.9 Hz, 1H), 7.56 d, J=8.3 Hz, 1H), 10.11 (s, 1H), 11.14 (br.s, 1H).
MS(ESI) m/z: 368 [M+H]$^+$.

Example 3

5-[2-(dimethylamino)ethoxy]-1'-(4-oxo-3,4,5,6,7,8-hexahydro quinazolin-2-yl)-3H-spiro[isobenzofuran-1,4'-piperidin]-3-one (Test Target Compound 91)

[Chem. 53]

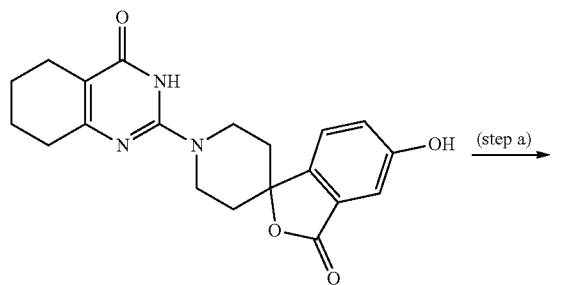

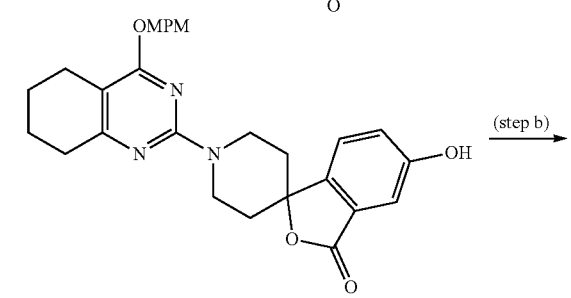

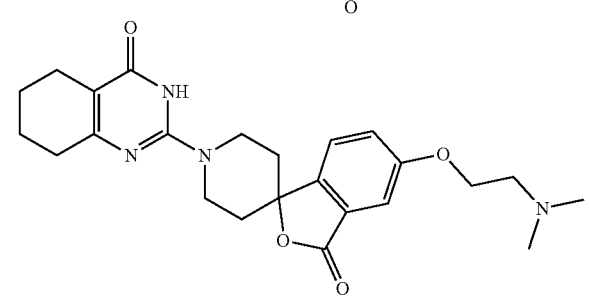

<Step a>

First, 5-hydroxy-1'-(4-oxo-3,4,5,6,7,8-hexahydro quinazolin-2-yl)-3H-spiro[isobenzofuran-1,4'-piperidin]-3-one (86 mg) was dissolved in N,N-dimethylformamide (4.3 mL), then potassium carbonate (39 mg) and 4-methoxybenzyl chloride (0.032 mL) were added thereto, and the mixture was stirred at room temperature for 16 hours. The reaction mixture was diluted with water, and the pH of the mixture was adjusted to 7 by adding a 5% potassium hydrogensulfate aqueous solution thereto, followed by extraction with ethyl acetate. After that, the organic layer was washed with saturated brine and was dried with anhydrous magnesium sulfate, and the solvent was removed by evaporation under reduced pressure. The residue was purified by silica gel column chromatography (ethyl acetate/n-hexane=40/60) to obtain 5-hydroxy-1'-{4-[(4-methoxybenzyl)oxy]-5,6,7,8-tetrahydroquinazolin-2-yl}-3H-spiro[isobenzofuran-1,4'-piperidin]-3-one (48 mg).

$^1$H-NMR (400 MHz, CDCl$_3$) δ: 1.61-1.84 (m, 6H), 1.98-2.11 (m, 2H), 2.49 (t, J=6.0 Hz, 2H), 2.63 (t, J=5.9 Hz, 2H), 3.31-3.43 (m, 2H), 3.80 (s, 3H), 4.78 (d, J=9.3 Hz, 2H), 5.32 (s, 2H), 6.85-6.93 (m, 2H), 7.16 (d, J=1.5 Hz, 2H), 7.30-7.42 (m, 2H)

<Step b>

The 5-hydroxy-1'-{4-[(4-methoxybenzyl)oxy]-5,6,7,8-tetrahydroquinazolin-2-yl}-3H-spiro[isobenzofuran-1,4'-piperidin]-3-one (12 mg) was dissolved in N,N-dimethylformamide (0.5 mL), then potassium carbonate (10 mg) and chloride 2-dimethylaminoethyl hydrochloride (4.5 mg) were added thereto, and the mixture was stirred at 70° C. for 3 hours. The reaction mixture was diluted with water, followed by extraction with 2-butanone. The organic layer was washed with saturated brine and was dried with anhydrous magnesium sulfate. The solvent was concentrated under reduced pressure. The obtained residue was purified by silica gel column chromatography (ethyl acetate/hexane=50/50). The obtained intermediate was dissolved in methylene chloride (0.5 mL), and trifluoroacetic acid (0.2 mL) was added thereto under ice cooling. The mixture was stirred at room temperature for 1 hour, and the reaction mixture was concentrated under reduced pressure. The obtained residue was purified by silica gel column chromatography (methanol/ethyl acetate=5/95) to obtain the title compound (6.2 mg).

$^1$H-NMR (400 MHz, CDCl$_3$) δ: 1.60-1.83 (m, 8H), 2.17 (dt, J=4.7, 13.4 Hz, 2H), 2.32-2.38 (m, 8H), 2.48 (t, J=6.1 Hz, 2H), 2.77 (t, J=5.5 Hz, 2H), 3.44 (t, J=12.2 Hz, 2H), 4.13 (t, J=5.6 Hz, 2H), 4.59 (d, J=13.9 Hz, 2H), 7.24-7.26 (m, 2H), 7.28-7.38 (m, 1H).
MS(ESI) m/z: 439[M+H]$^+$.

Example 4

5-methoxy-1'-(4-oxo-3,5,7,8-tetrahydro-4H-thiopyrano[4,3-d]pyrimidin-2-yl)-3H-spiro[isobenzofuran-1,4'-piperidin]-3-one (Test Target Compound 98)

[Chem. 54]

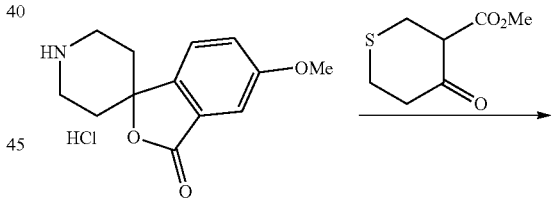

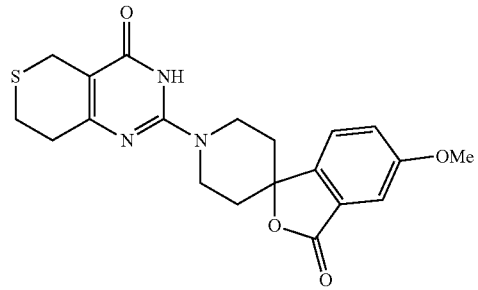

Triethylamine (0.25 mL) and 1-amidinopyrazole hydrochloride (99 mg) were added to a suspension of 5-methoxy-3H-spiro[isobenzofuran-1,4'-piperidin]-3-one hydrochloride (121 mg) in acetonitrile (4.5 mL), and the mixture was stirred at room temperature for 1 hour. The reaction mixture was concentrated under reduced pressure. The obtained residue was dissolved in ethanol (4 mL), then methyl 4-oxotetrahydro-2H-thiopyran-3-carboxylate ester (0.082 mL) and a 20% sodium ethoxide ethanol solution (0.47 mL) were added thereto, and the obtained mixture was refluxed for 5 hours. The reaction mixture was cooled to 0° C., and the precipitate generated was collected by filtration to obtain the title compound (103 mg).

$^1$H-NMR (400 MHz, CDCl$_3$) δ: 1.79 (d, J=13.8 Hz, 2H), 2.16 (td, J=13.4, 4.6 Hz, 2H), 2.77-2.87 (m, 4H), 3.42-3.52 (m, 4H), 3.89 (s, 3H), 4.55-4.64 (m, 2H), 4.24-7.30 (m, 2H, 7.32-3.39 (m, 1H), 11.77 (br.m, 1H).

MS(ESI) m/z: 400[M+H]$^+$.

Example 5

7-fluoro-5-methoxy-1'-(4-oxo-3,4,5,6,7,8-hexahydro quinazolin-2-yl)-3H-spiro[isobenzofuran-1,4'-piperidin]-3-one (Test Target Compound 106)

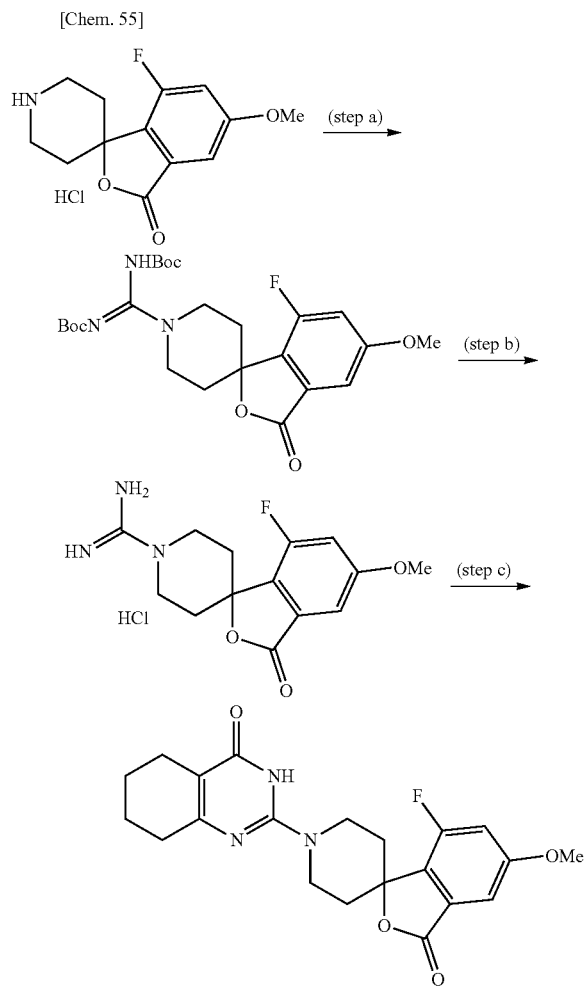

<Step a>

First, 7-fluoro-5-methoxy-3H-spiro[isobenzofuran-1,4'-piperidin]-3-one hydrochloride (32 mg) was dissolved in acetonitrile (1.1 mL), then triethylamine (0.047 mL) and N-tert-butyloxycarbonyl-N'-tert-butyloxycarbonyl-1H-pyrazole-1-carboximidamide (41 mg) were added thereto, and the mixture was stirred at room temperature for 2.5 hours. The reaction mixture was concentrated under reduced pressure. The obtained residue was purified by silica gel column chromatography (ethyl acetate/n-hexane=20/80 to 50/50) to obtain N-tert-butyloxycarbonyl-N'-tert-butyloxycarbonyl-7-fluoro-5-methoxy-3-oxo-3H-spiro[isobenzofuran-1,4'-piperidine]-1'-carboximidamide (32 mg).

$^1$H-NMR (400 MHz, CDCl$_3$) δ: 1.51 (m, 18H), 1.73 (d, J=12.3 Hz, 2H), 2.44-2.62 (m, 2H), 10.22 (br.s, 1H), 3.44 (t, J=12.1 Hz, 2H), 3.88 (s, 3H), 6.92 (dd, J=10.4, 2.1 Hz, 1H), 7.18 (d, J=2.0 Hz, 1H).

<Step b>

A 4 M hydrogen chloride/1,4-dioxane solution was added to the N-tert-butyloxycarbonyl-N'-tert-butyloxycarbonyl-7-fluoro-5-methoxy-3-oxo-3H-spiro[isobenzofuran-1,4'-piperidine]-1'-carboximidamide (32 mg), and the mixture was stirred at room temperature for 2 hours. The reaction mixture was concentrated under reduced pressure, ethyl acetate and n-hexane were added thereto, and the precipitate generated was collected by filtration to obtain 7-fluoro-5-methoxy-3-oxo-3H-spiro[isobenzofuran-1,4'-piperidine]-1'-carboximidamide hydrochloride (18 mg).

MS(ESI) m/z: 294[M+H]$^+$.

<Step c>

Then, 2-oxocyclohexane ethyl carboxylate ester (0.06 mL) and a 20% sodium ethoxide ethanol solution (0.011 mL) were added to a solution of the 7-fluoro-5-methoxy-3-oxo-3H-spiro[isobenzofuran-1,4'-piperidine]-1'-carboximidamide hydrochloride (18 mg) in ethanol (0.5 mL), and the mixture was stirred at 90° C. for 4 hours. The reaction mixture was diluted with water and then was rendered acidic by a 5% potassium hydrogen sulfate aqueous solution. After that, the precipitate generated was collected by filtration to obtain the title compound (14 mg).

$^1$H-NMR (400 MHz, DMSO-d$_6$) δ: 1.60-1.70 (m, 4H), 1.79 (d, J=13.8 Hz, 2H), 2.11-2.28 (m, 4H), 2.39 (br.m, 2H), 3.14 (t, J=12.1 Hz, 2H), 3.87 (s, 3H), 4.43 (br.m, 2H), 7.24 (d, J=2.1 Hz, 1H), 7.29 (dd, J=11.1, 2.0 Hz, 1H), 11.20 (br.s, 1H).

MS(ESI) m/z: 400[M+H]$^+$.

Example 6

5-[2-(dimethylamino)ethoxy]-7-fluoro-1'-(4-oxo-3,4,5,6,7,8-hexahydropyrido[2,3-d]pyrimidin-2-yl)-3H-spiro[isobenzofuran-1,4'-piperidin]-3-one (Test Target Compound 59)

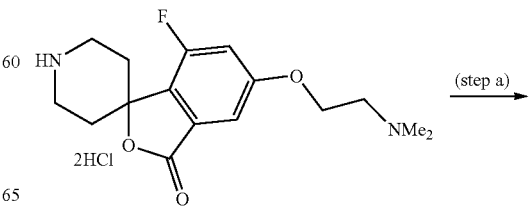

-continued

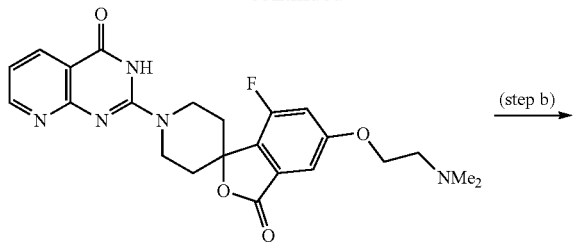

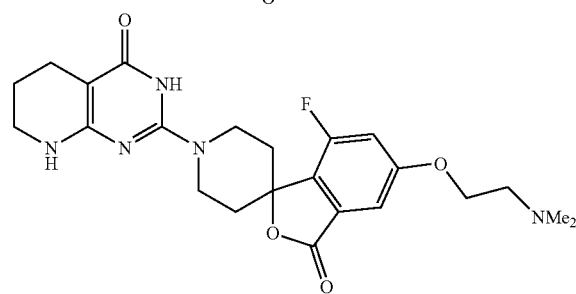

<Step a>

First, 5-[2-(dimethylamino)ethoxy]-7-fluoro-3H-spiro[isobenzofuran-1,4'-piperidin]-3-one dihydrochloride (101 mg) and 2-chloropyrido[2,3-d]pyrimidin-4(3H)-one (48.1 mg) were dissolved in ethanol (2 mL). Triethylamine (0.114 mL) was added to this solution, and the mixture was heated at 150° C. for 30 minutes by the microwave reaction apparatus. The reaction solution was cooled to room temperature, and then was stirred overnight with the result that a solid precipitated. The obtained solid was collected by filtration, was washed three times with ethanol (0.5 mL), and then was dried by heating under reduced pressure to obtain 5-[2-(dimethylamino)ethoxy]-7-fluoro-1'-(4-oxo-3,4-dihydropyrido[2,3-d]pyrimidin-2-yl)-3H-spiro[isobenzofuran-1,4'-piperidin]-3-one (79.6 mg).

$^1$H NMR (270 MHz, DMSO-$d_6$) δ: 1.81-1.95 (m, 2H), 2.18-2.36 (m, 2H), 2.80 (s, 6H), 3.14-3.32 (m, 4H), 4.49 (br.s, 2H), 4.55-4.70 (m, 2H), 7.12-7.28 (m, 1H), 7.33-7.42 (m, 2H), 8.27 (dd, J=7.6, 2.0 Hz, 1H), 8.68 (dd, J=4.3, 2.0 Hz, 1H).

MS(ESI) m/z: 454 [M+H]$^+$.

<Step b>

The 5-[2-(dimethylamino)ethoxy]-7-fluoro-1'-(4-oxo-3,4-dihydropyrido[2,3-d]pyrimidin-2-yl)-3H-spiro[isobenzofuran-1,4'-piperidin]-3-one (68.6 mg) was suspended in methanol (2 mL) and tetrahydrofuran (2 mL), and 2 M hydrochloric acid (0.227 mL) was further added thereto. Next, platinum oxide(IV) (4 mg) was added thereto, and the obtained mixture was stirred under a hydrogen atmosphere at room temperature for 14 hours. The platinum oxide was filtered out by celite, and the filtrate was washed with methanol, and was concentrated and dried to obtain a crude product (76.6 mg). The crude product was purified by amino-silica gel column chromatography (chloroform/methanol=98/2) to obtain the title compound (50.2 mg).

$^1$H-NMR (270 MHz, DMSO-$d_6$) δ: 1.61-1.88 (m, 4H), 2.07-2.32 (m, 10H), 2.59-2.71 (m, 2H), 3.03-3.21 (m, 4H), 4.18 (br.S, 2H), 4.28-4.55 (m, 2H), 6.45 (br.s, 1H), 7.21-7.38 (m, 2H), 10.41 (br.s, 1H).

MS(ESI) m/z: 458 [M+H]$^+$.

Example 7

5-[2-(dimethylamino)ethoxy]-7-fluoro-1'-(8-methyl-4-oxo-3,4,5,6,7,8-hexahydropyrido[2,3-d]pyrimidin-2-yl)-3H-spiro[iso benzofuran-1,4'-piperidin]-3-one (Test Target Compound 60)

[Chem. 57]

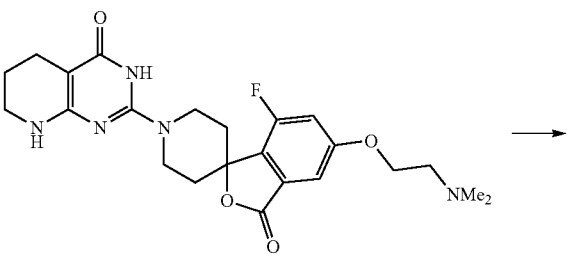

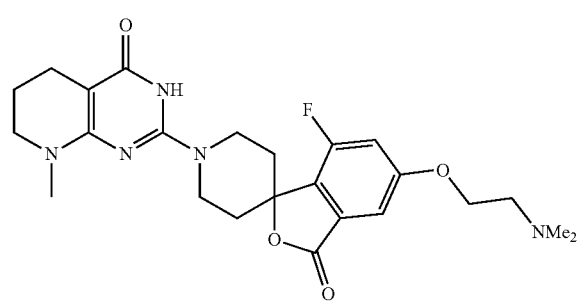

First, 5-[2-(dimethylamino)ethoxy]-7-fluoro-1'-(4-oxo-3,4,5,6,7,8-hexahydropyrido[2,3-d]pyrimidin-2-yl)-3H-spiro[isobenzofuran-1,4'-piperidin]-3-one (21.0 mg) was suspended in 1,2-dichloroethane (1 mL), then paraformaldehyde (9.2 mg) and acetic acid (0.050 mL) were added thereto, and the mixture was stirred at room temperature for 80 minutes. Sodium triacetoxyborohydride (48.6 mg) was added thereto, and the mixture was stirred at room temperature for 90 hours. After that, the reaction mixture was diluted with ethyl acetate and was washed with a saturated sodium hydrogen carbonate aqueous solution, and the aqueous layer was subjected again to extraction with ethyl acetate. The organic layer thus obtained all together was washed with saturated brine and was dried with magnesium sulfate, and the solvent was concentrated under reduced pressure. The residue was purified by silica gel column chromatography (chloroform/methanol=85/15) to obtain the title compound (14.4 mg).

$^1$H-NMR (270 MHz, CDCl$_3$) δ: 1.60-1.89 (m, 4H), 2.30 (s, 6H), 2.36-2.48 (m, 4H), 2.75 (br.t, J=5.3 Hz, 2H), 3.07 (s, 3H), 3.19-3.43 (m, 4H), 4.05-4.16 (m, 2H), 4.65 (br.d, J=12.5 Hz, 2H), 6.95 (br.d, J=9.9 Hz, 1H), 7.18 (s, 1H).

MS(ESI) m/z: 472 [M+H]$^+$.

Example 8

5-[methyl(pyridin-3-ylmethyl)amino]-1'-(4-oxo-3,4,5,6,7,8-hexahydroquinazolin-2-yl)-3H-spiro[isobenzofuran-1,4'-piperidin]-3-one (Test Target Compound 117)

[Chem. 58]

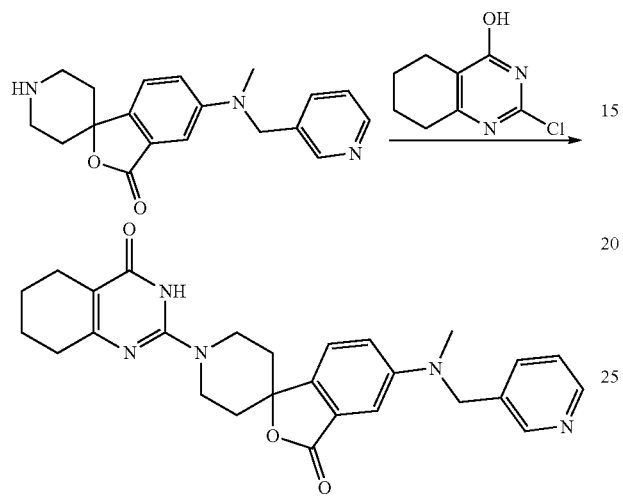

First, 5-[methyl(pyridin-3-ylmethyl)amino]-3H-spiro[isobenzofuran-1,4'-piperidin]-3-one (16 mg) was dissolved in N,N-dimethylformamide (0.5 mL), then 2-chloro-5,6,7,8-tetrahydroquinazolin-4(3H)-one (11 mg) and N,N-diisopropyl ethylamine (0.049 mL) were added thereto, and the mixture was stirred at 100° C. for 6 hours. The solvent was removed by evaporation under reduced pressure, and the residue was purified by silica gel column chromatography (NH silica gel, ethyl acetate/methanol=95/5). After that, ethanol and n-hexane were added thereto, and the precipitate generated was collected by filtration to obtain the title compound (15 mg)

$^1$H-NMR (400 MHz, CDCl$_3$) δ: 1.58-1.83 (m, 6H), 2.14 (td, J=13.5, 4.7 Hz, 2H), 2.34 (t, J=5.9 Hz, 2H), 2.48 (t, J=6.1 Hz, 2H), 3.12 (s, 3H), 3.43 (t, J=12.2 Hz, 2H), 4.55 (d, J=13.9 Hz, 2H), 4.63 (s, 2H), 7.02 (dd, J=8.3, 4.0 Hz, 1H), 7.13-7.21 (m, 2H), 7.23-7.29 (m, 1H), 7.50-7.55 (m, 1H), 8.48-8.57 (m, 2H).

MS(ESI) m/z: 472[M+H]$^+$.

Example 9

2-(spiro[indoline-3,4'-piperidine]-1'-yl)-5,6,7,8-tetrahydroquinazolin-4(3H)-one (Test Target Compound 1)

[Chem. 59]

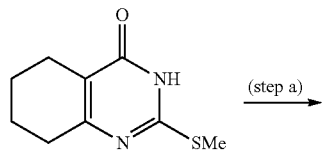

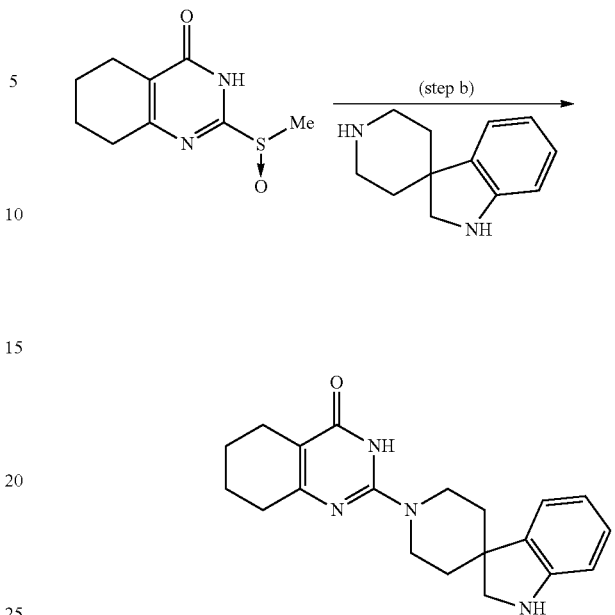

<Step a>

First, 2-(methylthio)-5,6,7,8-tetrahydroquinazolin-4(3H)-one (75 mg) was suspended in dichloromethane (3 mL), and the mixture was cooled in a sodium chloride-ice bath (at about −15° C.). Methachloroperbenzoic acid (a content of about 70%, 94 mg) was added thereto, and the mixture was stirred for 1.5 to 2 hours in the sodium chloride-ice bath. Formation of the corresponding sulfoxide structure was confirmed by LC-MS, and the reaction solution was concentrated under reduced pressure. Then, an operation of adding 1,2-dimethoxyethane to the concentrated residue, dissolving the residue, and concentrating the obtained mixture under reduced pressure was performed three times to remove the dichloromethane, thereby obtaining 2-(methylsulfinyl)-5,6,7,8-tetrahydroquinazolin-4(3H)-one. This compound was not purified but was used as it was in a reaction of the next step.

<Step b>

The above-obtained 2-(methylsulfinyl)-5,6,7,8-tetrahydroquinazolin-4(3H)-one was dissolved in 1,2-dimethoxyethane (2 mL), then spiro[indoline-3,4'-piperidine] (129 mg) and triethylamine (0.080 mL) were added thereto, and the mixture was stirred at 80° C. overnight. The reaction solution was left to cool to room temperature, and the generated solid was collected by filtration, was washed with 1,2-dimethoxyethane, and then was dried under reduced pressure. Water (4 mL) was added to the dried solid, followed by stirring at room temperature for about 3 hours. Then, the solid was collected by filtration and was washed with water. This solid was dried under reduced pressure to obtain the title compound (93 mg).

$^1$H-NMR (400 MHz, DMSO-d$_6$) δ: 1.53-1.73 (m, 8H), 2.20-2.30 (m, 2H), 2.32-2.40 (m, 2H), 2.91-3.05 (m, 2H), 3.30 (s, 2H), 4.20-4.30 (m, 2H), 5.53 (s, 1H), 6.45-6.57 (m, 2H), 6.87-7.00 (m, 2H), 11.00 (br.s, 1H).

MS(ESI) m/z: 337 [M+H]$^+$.

Example 10

2-(1-methylspiro[indoline-3,4'-piperidine]-1'-yl)-5,6,7,8-tetrahydroquinazolin-4(3H)-one (Test Target Compound 112)

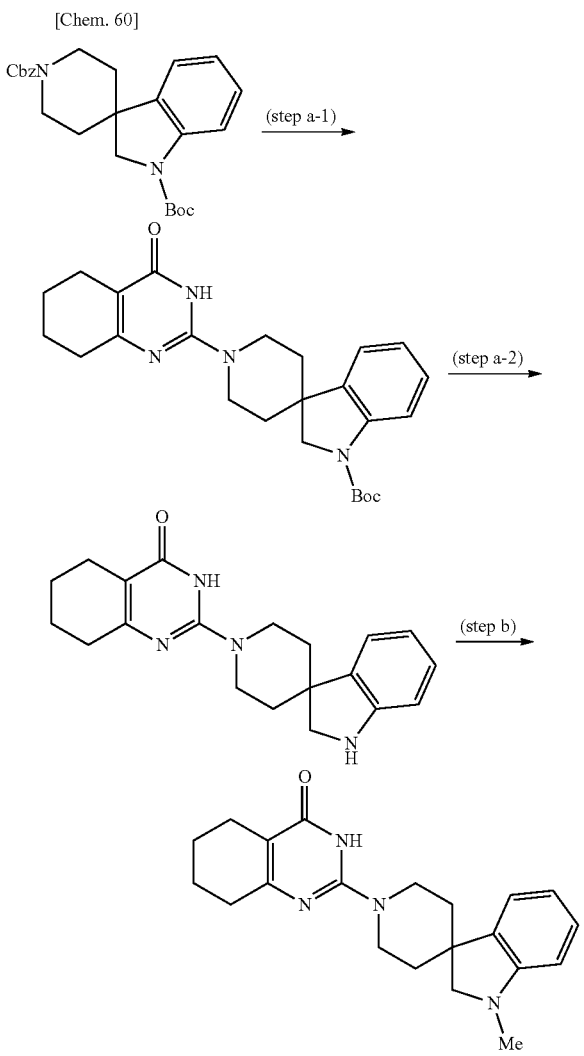

<Step a-1>

First, 1'-benzyloxycarbonyl-1-tert-butyloxycarbonylspiro[indoline-3,4'-piperidine] (587.3 mg) was dissolved in methanol (10 mL), then 10% palladium carbon (74.0 mg) and ammonium formate (263.0 mg) were added thereto, and the mixture was refluxed by heating for 1 hour. The reaction solution was filtered through celite, and the filtrate was concentrated under reduced pressure. The obtained residue was dissolved in acetonitrile (15 mL), then 1-amidinopyrazole hydrochloride (244.5 mg) and triethylamine (0.581 mL) were added thereto, and the mixture was stirred at room temperature for 1 hour. The residue obtained by concentrating the reaction solution was dissolved in ethanol (15 mL), then 2-oxocyclohexaneethyl carboxylate (0.265 mg) and a 21% sodium ethoxide ethanol solution (1.35 mL) were added thereto, and the mixture was stirred under reflux by heating for 5 hours. An ammonium chloride aqueous solution was added to the reaction solution, followed by extraction with chloroform. The organic layer was dried with anhydrous magnesium sulfate and was concentrated under reduced pressure, and the obtained residue was purified by silica gel column chromatography (methanol/chloroform=10/90) to obtain 1-tert-butyloxycarbonyl-1'-(4-oxo-3,4,5,6,7,8-hexahydro quinazolin-2-yl)spiro[indoline-3,4'-piperidine].

<Step a-2>

Hydrogen chloride (4 M 1,4-dioxane solution) was added to the above-obtained 1-tert-butyloxycarbonyl-1'-(4-oxo-3,4,5,6,7,8-hexahydro quinazolin-2-yl)spiro[indoline-3,4'-piperidine], and the mixture was stirred at room temperature for 1 hour. The reaction mixture was concentrated under reduced pressure, a saturated sodium hydrogen carbonate aqueous solution was added to the residue, followed by extraction with a mixture solvent of chloroform and tetrahydrofuran. The solvent was removed by evaporation under reduced pressure, and the obtained solid residue was washed with ethyl acetate to obtain 2-(spiro[indoline-3,4'-piperidine]-1'-yl)5,6,7,8-tetrahydro quinazolin-4(3H)-one (376.1 mg).

$^1$H-NMR (400 MHz, CDCl$_3$) δ: 1.65-1.71 (m, 4H), 1.80-1.87 (m, 2H), 1.89-1.97 (m, 2H), 2.34-2.39 (m, 2H), 2.45-2.50 (m, 2H), 3.06-3.15 (m, 2H), 3.54 (s, 2H), 4.30-4.37 (m, 2H), 6.65-6.69 (m, 1H), 6.73-6.77 (m, 1H), 7.04-7.09 (m, 2H), 11.04 (br.s, 1H).

MS(ESI) m/z: 337 [M+H]$^+$.

<Step b>

The 2-(spiro[indoline-3,4'-piperidine]-1'-yl)5,6,7,8-tetrahydro quinazolin-4(3H)-one (35.5 mg) was dissolved in dimethylsulfoxide (1 mL), then iodomethane (0.008 mL) and triethylamine (0.018 mL) were added thereto, and the mixture was stirred at room temperature for 1 hour. Water was added to the reaction solution, followed by extraction with ethyl acetate. The organic layer was dried with anhydrous magnesium sulfate and was concentrated under reduced pressure, and the obtained residue was purified by silica gel column chromatography (methanol/chloroform=10/90) to obtain the title compound (13.5 mg).

$^1$H-NMR (400 MHz, CDCl$_3$) δ: 1.63-1.97 (m, 8H), 2.32-2.36 (m, 2H), 2.45-2.50 (m, 2H), 2.80 (s, 3H), 3.07-3.16 (m, 2H), 3.30 (s, 2H), 4.39-4.45 (m, 2H), 6.50-6.53 (m, 1H), 6.68-6.73 (m, 1H), 7.01-7.04 (m, 1H), 7.10-7.15 (m, 1H), 11.95 (br.s, 1H).

MS(ESI) m/z: 351[M+H]$^+$.

Example 11

2-(1-benzylspiro[indoline-3,4'-piperidine]-1'-yl)-5,6,7,8-tetrahydroquinazolin-4(3H)-one (Test Target Compound 23)

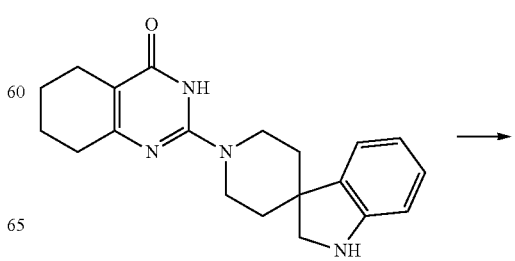

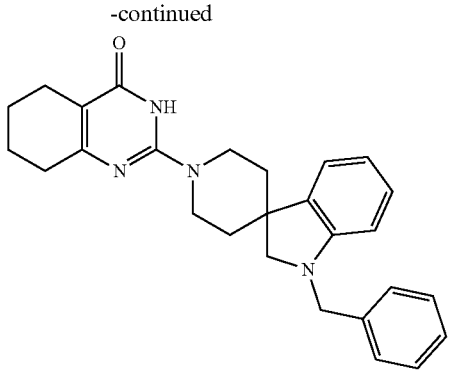

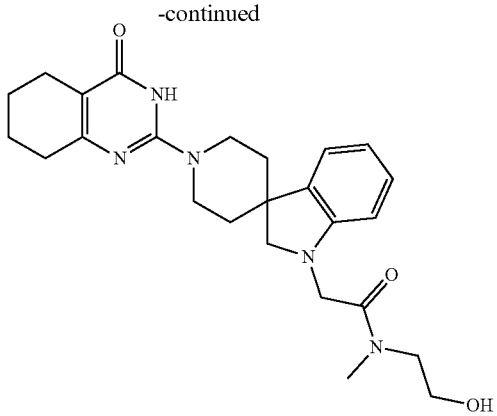

First, 2-(spiro[indoline-3,4'-piperidine]-1'-yl)-5,6,7,8-tetrahydroquinazolin-4(3H)-one (25.3 mg) was dissolved in methanol (1 mL), and then benzaldehyde (0.040 mL), acetic acid (0.020 mL), and sodium cyanotrihydroborate (20.6 mg) were added thereto. The mixture was stirred at room temperature for 1 hour 20 minutes. Saturated brine and a saturated sodium hydrogen carbonate aqueous solution were added to the reaction solution, followed by four times extraction with chloroform. The organic layer was washed with saturated brine, then was dried with anhydrous sodium sulfate, and was concentrated under reduced pressure. The obtained residue was purified by amino-silica gel column chromatography (chloroform and methanol-based), was concentrated under reduced pressure, and was dried to obtain the title compound (31.5 mg).

$^1$H-NMR (270 MHz, CDCl$_3$) δ: 1.62-2.00 (m, 8H), 2.34 (br.t, J=5.6 Hz, 2H), 2.46 (br.t, J=5.8 Hz, 2H), 2.95-3.09 (m, 2H), 3.30 (s, 2H), 4.30-4.42 (m, 2H), 4.32 (s, 2H), 6.54 (d, J=7.6 Hz, 1H), 6.71 (dd, J=7.3, 7.3 Hz, 1H), 7.03-7.14 (m, 2H), 7.27-7.40 (m, 5H), 11.85 (br.s, 1H).

MS(ESI) m/z: 427 [M+H]$^+$.

Example 12

N-(2-hydroxyethyl)-N-methyl-2-[1'-(4-oxo-3,4,5,6,7,8-hexahydroquinazolin-2-yl)spiro[indoline-3,4'-piperidine]-1-yl]acetamide (Test Target Compound 48)

[Chem. 62]

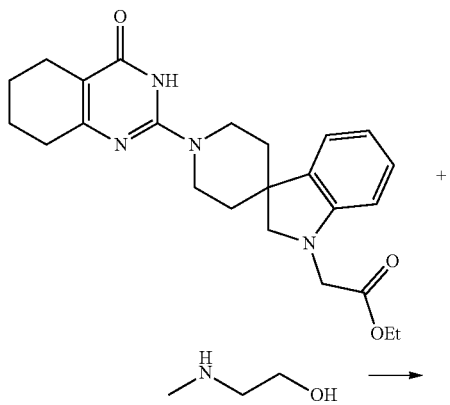

First, ethyl 2-[1'-(4-oxo-3,4,5,6,7,8-hexahydroquinazolin-2-yl)spiro[indoline-3,4'-piperidine]-1-yl]acetate (13.6 mg) was dissolved in tetrahydrofuran (0.5 mL), and the mixture was cooled to 0° C. Then, a 1 M sodium hydroxide aqueous solution (0.064 mL) was added thereto, and the mixture was stirred at room temperature for 18.5 hours. Next, 1 M hydrochloric acid (0.097 mL), 2-(methylamino) ethanol (0.0052 mL), and 4-(4,6-dimethoxy-1,3,5-triazin-2-yl)-4-methylmorpholinium chloride n hydrate (21.2 mg) were added to the reaction solution, and the mixture was stirred at room temperature for 2 hours 15 minutes. Water was added to the reaction solution, followed by four times of extraction with chloroform. The organic layer was washed with saturated brine, then was dried with anhydrous sodium sulfate, and was concentrated under reduced pressure. The obtained residue was purified by silica gel column chromatography (methanol/chloroform=0/100 to 10/90) to obtain the title compound (10.3 mg).

$^1$H-NMR (270 MHz, CDCl$_3$) δ: 1.62-1.98 (m, 8H), 2.30-2.41 (m, 2H), 2.43-2.52 (m, 2H), 2.97 及 び 3.15 (2:3) (s, 3H), 2.99-3.11 (m, 2H), 3.47 (br.s, 2H), 3.50-3.56 及 び 3.56-3.65 (2:3) (m, 2H), 3.76-3.85 (m, 2H), 3.98, 4.14 (3:2) (s, 2H), 4.23-4.39 (m, 2H), 6.43-6.51 (m, 1H), 6.63-6.76 (m, 1H), 6.96-7.13 (m, 2H).

MS(ESI) m/z: 452 [M+H]$^+$.

Example 13 benzyl 1'-(4-oxo-4,5,7,8-tetrahydro-3H-pyrano[4,3-d]pyrimidin-2-yl)spiro[indoline-5,4'-piperidine]-1-carboxylate (Test Target Compound 53)

[Chem. 63]

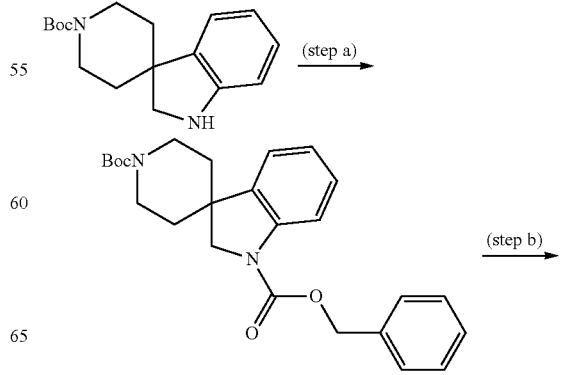

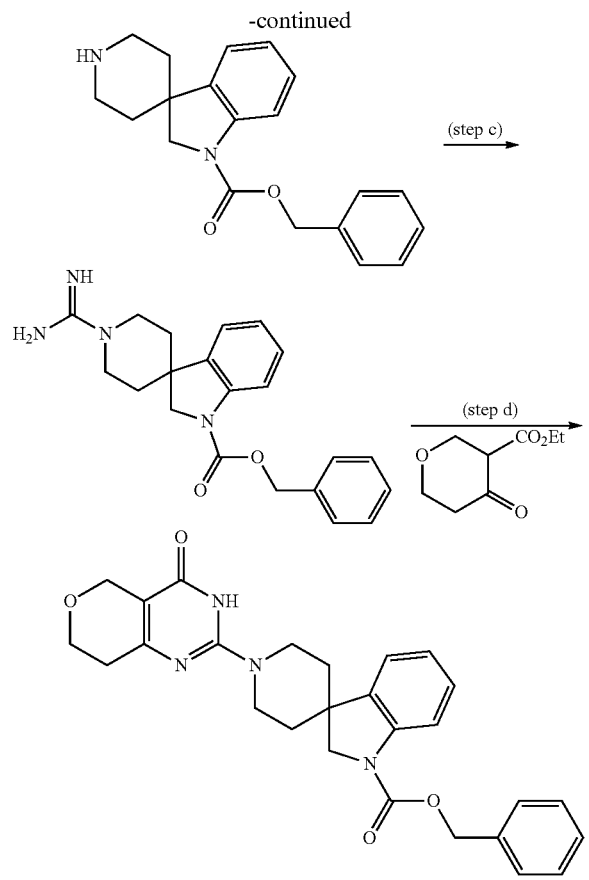

<Step a>

First, 1'-tert-butyloxycarbonylspiro[indoline-3,4 piperidine] (392.4 mg) was dissolved in dichloromethane (5 mL), the mixture was cooled to 0° C., then triethylamine (0.286 mL) and benzyl chloroformate (30 to 35% toluene solution) (0.968 mL) were added thereto, and the mixture was stirred at room temperature for 20 hours. Water was added to the reaction solution, followed by four times of extraction with chloroform. The organic layer was washed with saturated brine, then was dried with anhydrous sodium sulfate, and was concentrated under reduced pressure. The obtained residue was purified by silica gel column chromatography (ethyl acetate/n-hexane=0/100 to 10/90) to obtain benzyl 1'-tert-butyloxycarbonylspiro[indoline-3,4'-piperidine]-1-carboxylate (277.9 mg).

$^1$H-NMR (270 MHz, CDCl$_3$) δ: 1.49 (m, 9H), 1.59-1.70 (m, 2H), 1.72-1.88 (m, 2H), 2.87 (br.t, J=12.7 Hz, 2H), 3.92 (s, 2H), 4.13 (br.d, J=11.5 Hz, 2H), 5.28 (s, 2H), 6.96-7.06 (m, 1H), 7.08-7.16 (m, 1H), 7.16-7.25 (m, 1H), 7.27-7.52 (m, 6H).

MS(ESI) m/z: 423[M+H]$^+$.

<Step b>

The benzyl 1'-tert-butyloxycarbonylspiro[indoline-3,4'-piperidine]-1-carboxylate (268.3 mg) was dissolved in dichloromethane (2 mL), the mixture was cooled to 0° C., then trifluoroacetic acid (2 mL) was added thereto, and the mixture was stirred at 0° C. for 1 hour. A saturated sodium hydrogen carbonate aqueous solution and saturated brine were added to the reaction solution, followed by four times of extraction with chloroform. Then, the organic layer was dried with anhydrous sodium sulfate, and was concentrated under reduced pressure to obtain benzyl spiro[indoline-3,4'-piperidine]-1-carboxylate (235.2 mg).

$^1$H-NMR (270 MHz, CDCl$_3$) δ: 1.78 (br.d, J=14.8 Hz, 2H), 2.12 (td, J=13.5, 4.3 Hz, 2H), 2.85-3.00 (m, 2H), 3.32 (br.d, J=12.9 Hz, 2H), 3.94 (s, 2H), 5.29 (s, 2H), 6.99-7.09 (m, 1H), 7.16-7.26 (m, 2H), 7.27-7.50 (m, 6H).

MS(ESI) m/z: 323[M+H]$^+$.

<Step c>

The benzyl spiro[indoline-3,4'-piperidine]-1-carboxylate (230.2 mg) was dissolved in acetonitrile (4.8 mL), then 1-aminopyrazole (157.3 mg) and N,N-diisopropyl ethylamine (0.182 mL) were added thereto, and the mixture was stirred at room temperature for 15 hours. The reaction mixture was concentrated under reduced pressure to obtain benzyl 1'-carbamimidoylspiro[indoline-3,4'-piperidine]-1-carboxylate (423.5 mg).

MS(ESI) m/z: 365[M+H]$^+$.

<Step d>

The benzyl 1'-carbamimidoylspiro[indoline-3,4'-piperidine]-1-carboxylate (53.9 mg) was dissolved in distilled water (1.2 mL), then ethyl 4-oxotetrahydro-2H-pyran-3-carboxylate (46.1 mg) and potassium carbonate (34.7 mg) were added thereto, and the mixture was stirred at room temperature for 142 hours. Water was added to the reaction solution, followed by extraction with chloroform. The organic layer was washed with saturated brine, and then was dried with anhydrous sodium sulfate, and the solvent was removed by evaporation under reduced pressure. The obtained residue was purified by silica gel column chromatography (chloroform) to obtain the title compound (16.2 mg).

$^1$H-NMR (270 MHz, CDCl$_3$) δ: 1.74-1.97 (m, 4H), 2.56 (br.t, J=5.4 Hz, 2H), 3.06 (br.t, J=12.6 Hz, 2H), 3.88-3.94 (m, 2H), 3.96-4.07 (m, 2H), 4.44 (s, 2H), 4.46-4.59 (m, 2H), 5.28 (br.s, 2H), 6.89-7.08 (m, 1H), 7.11 (br.d, J=7.3 Hz, 1H), 7.19-7.31 (m, 1H), 7.32-7.61 (m, 5H), 7.82-8.03 (m, 1H), 11.83 (br.s, 1H).

MS(ESI) m/z: 473[M+H]$^+$.

Example 14

2-(5-bromoespiro[indoline-3,4'-piperidine]-1'-yl)-5,6,7,8-tetrahydroquinazolin-4(3H)-one (Test Target Compound 146)

[Chem. 64]

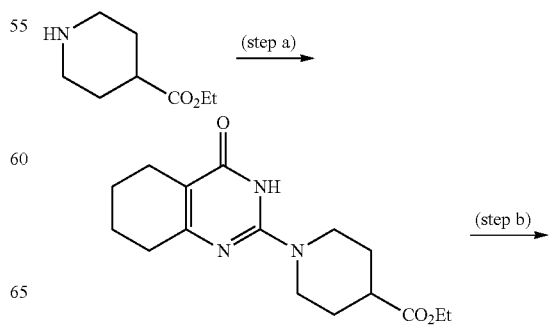

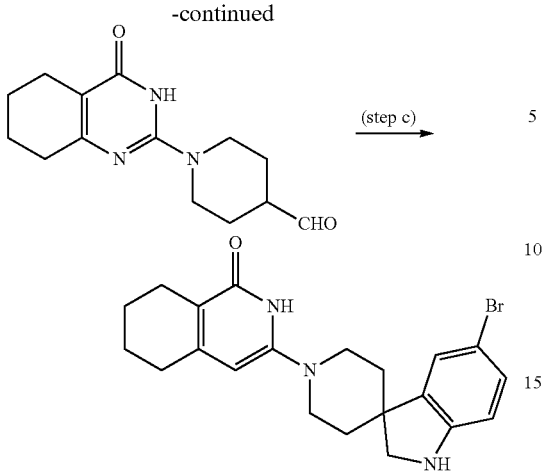

Step a

First, 4-piperidine ethyl carboxylate (1.57 g) was dissolved in acetonitrile (50 mL), then 1-amidinopyrazole hydrochloride (1.76 g) and triethylamine (4.2 mL) were added thereto, and the mixture was stirred at room temperature for 1 hour. The reaction solution was concentrated and the obtained residue was dissolved in ethanol (50 mL). Then, 2-oxocyclohexane ethyl carboxylate (1.9 mL) and a 21% sodium ethoxide ethanol solution (9.7 mL) were added thereto, and the mixture was stirred under reflux by heating for 3 hours. An ammonium chloride aqueous solution was added to the reaction solution, followed by extraction with chloroform. The organic layer was dried with anhydrous magnesium sulfate and was concentrated under reduced pressure, and the obtained residue was purified by silica gel column chromatography (methanol/chloroform=10/90) to obtain 1-(4-oxo-3,4,5,6,7,8-hexahydroquinazolin-2-yl)piperidin-4-ethyl carboxylate (2.56 g).

$^1$H-NMR (400 MHz, CDCl$_3$) δ: 1.26 (t, J=7.2 Hz, 3H), 1.66-1.81 (m, 6H), 1.95-2.02 (m, 2H), 2.36-2.41 (m, 2H), 2.44-2.58 (m, 3H), 3.00-3.19 (m, 2H), 4.15 (q, J=7.2 Hz, 2H), 4.28-4.35 (m, 2H), 11.37 (br.s, 1H).

MS(ESI) m/z: 306[M+H]$^+$.

Step b

The 1-(4-oxo-3,4,5,6,7,8-hexahydroquinazolin-2-yl)piperidin-4-ethyl carboxylate (2.68 g) was dissolved in tetrahydrofuran (50 mL), then lithium borohydride (573.0 mg) was added thereto, and the mixture was stirred at room temperature for 14 hours. An ammonium chloride aqueous solution was added to the reaction solution, followed by extraction with chloroform. The organic layer was dried with anhydrous magnesium sulfate and was concentrated under reduced pressure, the obtained residue was dissolved in chloroform (50 mL), a Dess-Martin reagent (4.464 g) was added thereto, and the mixture was stirred at room temperature for 1 hour. A sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (methanol/chloroform=10/90) to obtain 1-(4-oxo-3,4,5,6,7,8-hexahydroquinazolin-2-yl)piperidin-4-carboaldehyde (966.5 mg).

MS(ESI) m/z: 262 [M+H]$^+$.

Step c

The title compound (31.1 mg) was obtained from the 1-(4-oxo-3,4,5,6,7,8-hexahydroquinazolin-2-yl)piperidin-4-carboaldehyde (130.7 mg) and 4-bromophenylhydrazine hydrochloride (223.5 mg) in the same way as in <Step 1> of Reference Example 33.

$^1$H-NMR (400 MHz, CDCl$_3$) δ: 1.64-1.93 (m, 8H), 2.32-2.38 (m, 2H), 2.45-2.50 (m, 2H), 3.03-3.11 (m, 2H), 3.55 (s, 2H), 4.40-4.47 (m, 2H), 6.52 (d, J=8.3 Hz, 1H), 7.10-7.15 (m, 2H), 12.07 (br.s, 1H).

MS(ESI) m/z: 415[M+H]$^+$.

Example 15

1'-(4-oxo-3,4,5,6,7,8-hexahydroquinazolin-2-yl)spiro[indoline-3,4'-piperidine]-5-carboxylic Acid (Test Target Compound 151)

[Chem. 65]

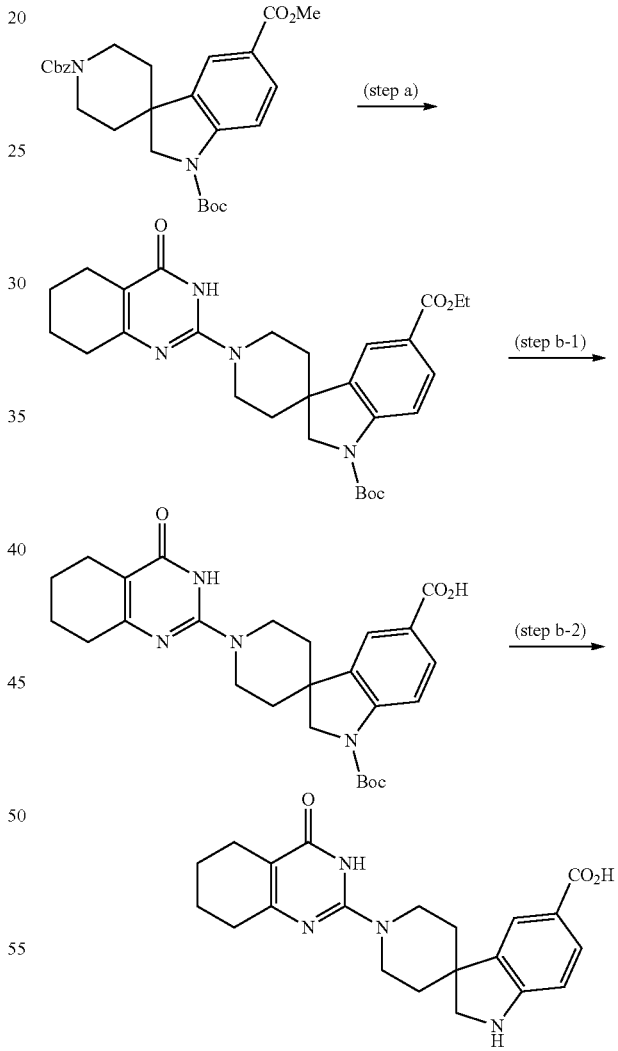

Step a

First, 1-tert-butyloxycarbonyl-1'-(4-oxo-3,4,5,6,7,8-hexahydroquinazolin-2-yl)spiro[indoline-3,4'-piperidine]-5-ethyl carboxylate (82.6 mg) was obtained from 1'-benzyloxycarbonyl-1-tert-butyloxycarbonylspiro[indoline-3,4'-piperidine]-5-methyl carboxylate (186.2 mg) in the same way as in <Step a-1> of Example 10.

¹H-NMR (400 MHz, CDCl₃) δ: 1.38 (t, J=7.1 Hz, 3H), 1.60 (s, 9H), 1.65-1.81 (m, 6H), 1.95-2.05 (m, 2H), 2.34-2.40 (m, 2H), 2.46-2.52 (m, 2H), 3.01-3.10 (m, 2H), 3.97 (br.s, 2H), 4.34 (q, J=7.1 Hz, 2H), 4.54-4.62 (m, 2H), 7.58-7.61 (m, 1H), 7.76-7.79 (m, 1H), 7.92-7.96 (m, 1H), 12.05 (br. s, 1H).

MS(ESI) m/z: 509415[M+H]⁺.

<Steps b-1 and b-2>

The 1-tert-butyloxycarbonyl-1'-(4-oxo-3,4,5,6,7,8-hexahydro quinazolin-2-yl)spiro[indoline-3,4'-piperidine]-5-ethyl carboxylate (172.3 mg) was dissolved in ethanol (3 mL), a 5 M sodium hydroxide aqueous solution (1 mL) was added thereto, and the mixture was stirred under reflux by heating for 14 hours. A 1 M hydrochloric acid aqueous solution was added to the reaction solution, followed by extraction with chloroform. The organic layer was dried with anhydrous magnesium sulfate and was concentrated under reduced pressure to obtain 1-(tert-butyloxycarbonyl)-1'-(4-oxo-3,4,5,6,7,8-hexahydroquinazolin-2-yl)spiro[indoline-3,4'-piperidine]-5-carboxylic acid as a crude product. The obtained crude product was dissolved in chloroform, trifluoroacetic acid was added thereto, and the mixture was stirred at room temperature for 1 hour. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (hexane/ethyl acetate=50/50) to obtain the title compound (19.6 mg).

¹H-NMR (400 MHz, DMSO-d₆) δ: 1.64-1.77 (m, 6H), 1.90-2.00 (m, 2H), 2.29-2.34 (m, 2H), 2.66-2.71 (m, 2H), 3.26-3.35 (m, 2H), 3.60 (s, 2H), 4.36-4.44 (m, 2H), 6.54 (d, J=8.2 Hz, 1H), 7.60-7.64 (m, 1H).

MS(ESI) m/z: 381[M+H]⁺.

Example 16

1'-(4-oxo-3,4,5,6,7,8-hexahydroquinazolin-2-yl)-N-[2-(piperidin-1-yl)ethyl]spiro[indoline-3,4'-piperidine]-5-carboxamide (Test Target Compound 152)

[Chem. 66]

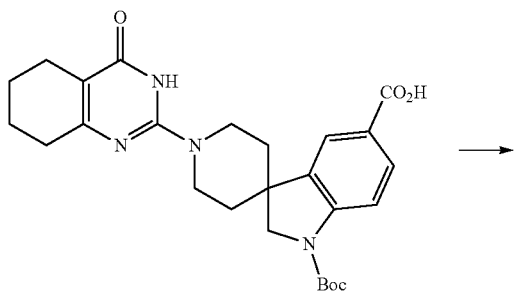

→

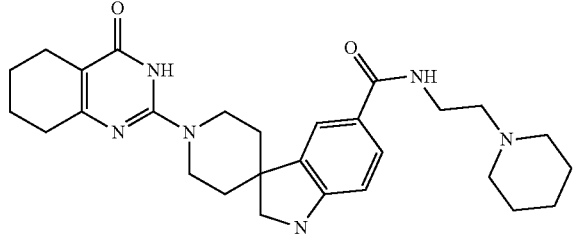

First, 1-tert-butyloxycarbonyl-1'-(4-oxo-3,4,5,6,7,8-hexahydroquinazolin-2-yl)spiro[indoline-3,4'-piperidine]-5-carboxylic acid (20.0 mg) was dissolved in chloroform, then 1-(3-dimethylaminopropyl)-3-ethylcarbodiimide (9.6 mg), dimethylaminopyridine (0.0005 mg), triethylamine (0.007 mg), and 1-(2-aminoethyl)piperidine (0.007 mg) were added thereto, and the mixture was stirred at room temperature for 1 hour. A saturated sodium hydrogen carbonate aqueous solution was added to the reaction solution, followed by extraction with chloroform. The organic layer was dried with anhydrous magnesium sulfate and was concentrated under reduced pressure. The obtained residue was dissolved in chloroform, trifluoroacetic acid was added thereto, and the mixture was stirred at room temperature for 1 hour. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (chloroform/methanol=90/10) to obtain the title compound (3.9 mg).

¹H-NMR (400 MHz, CDCl₃) δ: 1.42-1.48 (m, 2H), 1.55-1.62 (m, 4H), 1.65-1.85 (m, 8H), 1.90-2.00 (m, 2H), 2.34-2.39 (m, 2H), 2.42-2.50 (m, 4H), 2.53-2.58 (m, 2H), 3.05-3.14 (m, 2H), 3.48-3.54 (m, 2H), 3.60 (s, 2H), 4.08 (br.s, 1H), 4.34-4.42 (m, 2H), 6.60 (d, J=8.1 Hz, 1H), 6.84 (br.s, 1H), 7.48-7.52 (m, 1H), 7.56 (d, J=1.6 Hz, 1H).

MS(ESI) m/z: 491[M+H]⁺.

Example 17

2-{6-[(2-morpholinoethoxy)methyl]spiro[indoline-3,4'-piperidine]-1'-yl}-5,6,7,8-tetrahydroquinazolin-4(3H)-one (Test Target Compound 168)

[Chem. 67]

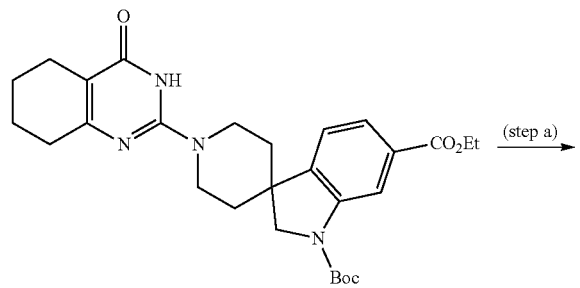 (step a) → 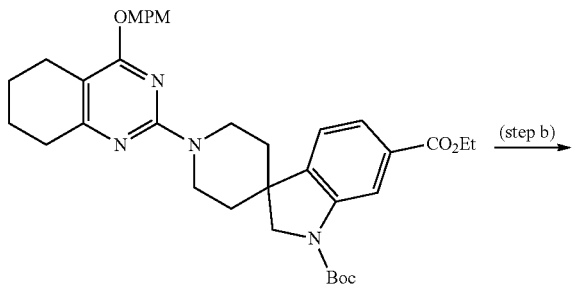 (step b) →

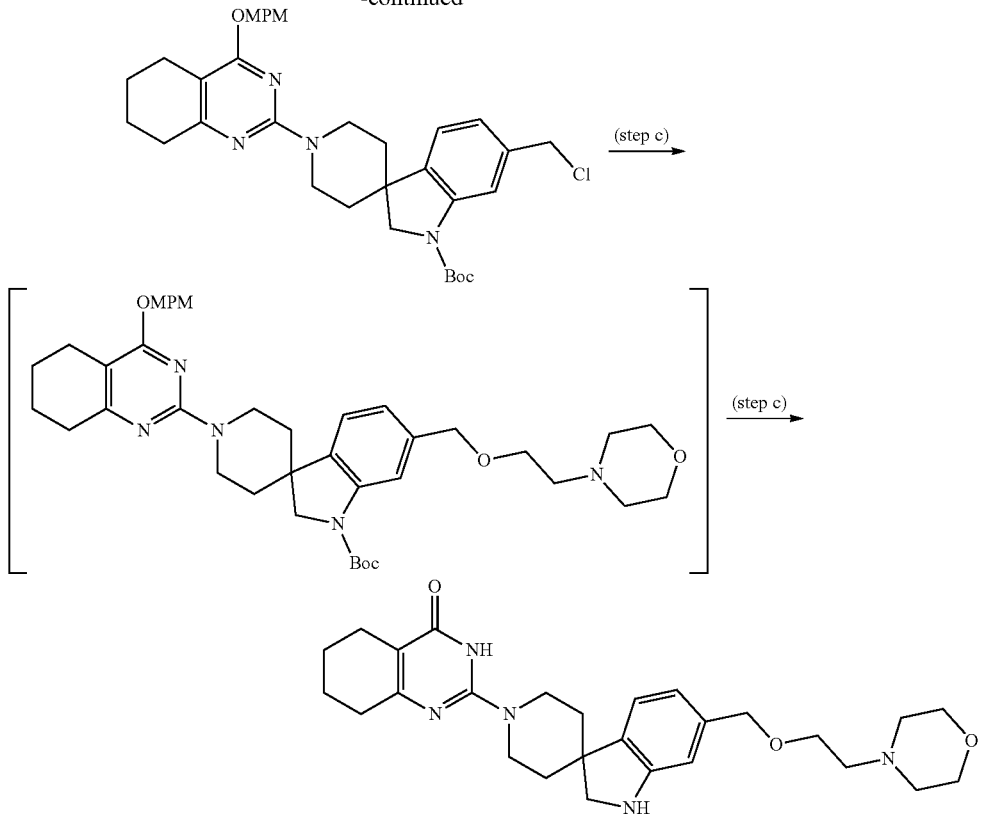

<Step a>

First, 1-(tert-butyloxycarbonyl)-1'-(4-oxo-3,4,5,6,7,8-hexahydroquinazolin-2-yl)spiro[indoline-3,4'-piperidine]-6-ethyl carboxylate (451.6 mg) was dissolved in N,N-dimethylformamide, then 4-methoxybenzyl chloride (0.145 mL) and potassium carbonate (184.1 mg) were added thereto, and the mixture was stirred at room temperature for 14 hours. A saturated ammonium chloride aqueous solution was added to the reaction solution, followed by extraction with chloroform. The organic layer was dried with anhydrous magnesium sulfate and was concentrated under reduced pressure, and the obtained residue was purified by silica gel column chromatography (methanol/chloroform=10/90) to obtain 1-(tert-butyloxycarbonyl)-1'-{4-[(4-methoxybenzyl)oxy]-5,6, 7,8-tetrahydroquinazolin-2-yl}spiro[indoline-3,4'-piperidine]-6-ethyl carboxylate (338.4 mg).

MS(ESI) m/z: 629[M+H]$^+$.

<Step b>

The 1-(tert-butyloxycarbonyl)-1'-{4-[(4-methoxybenzyl)oxy]-5,6, 7,8-tetrahydroquinazolin-2-yl}spiro[indoline-3,4'-piperidine]-6-ethyl carboxylate (104.0 mg) was dissolved in tetrahydrofuran, then lithium tetrahydroborate (10.8 mg) was added thereto, and the mixture was stirred under reflux by heating for 5 hours. A saturated ammonium chloride aqueous solution was added to the reaction solution, followed by extraction with chloroform. The organic layer was dried with anhydrous magnesium sulfate and was concentrated under reduced pressure, and the obtained residue was dissolved in chloroform. Then, methanesulfonic acid chloride (0.038 mL) and triethylamine (0.069 mL) were added thereto and the mixture was stirred at room temperature for 14 hours. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (methanol/chloroform=10/90) to obtain 1-(tert-butyloxycarbonyl)-6-(chloromethyl)-1'-{4-[(4-methoxybenzyl)oxy]-5,6,7,8-tetrahydroquinazolin-2-yl}spiro[indoline-3,4'-piperidine] (64.0 mg).

MS(ESI) m/z: 605[M+H]$^+$.

<Step c>

The 1-(tert-butyloxycarbonyl)-6-(chloromethyl)-1'-{4-[(4-methoxybenzyl)oxy]-5,6,7,8-tetrahydroquinazolin-2-yl}spiro[indoline-3,4'-piperidine] (40.0 mg) was dissolved in tetrahydrofuran, then 4-(2-hydroxyethyl)morpholine (0.024 mL) and sodium hydride (7.9 mg) were added thereto, and the mixture was stirred under reflux by heating for 5 hours. A saturated ammonium chloride aqueous solution was added to the reaction solution, followed by extraction with chloroform. The organic layer was dried with anhydrous magnesium sulfate and was concentrated under reduced pressure, and the obtained residue was dissolved in chloroform, trifluoroacetic acid was added thereto, and the mixture was stirred at room temperature for 14 hours. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (methanol/chloroform=10/90) to obtain the title compound (19.6 mg).

$^1$H-NMR (400 MHz, CDCl$_3$) δ: 1.63-1.85 (m, 6H), 1.87-1.96 (m, 2H), 2.31-2.37 (m, 2H), 2.45-2.53 (m, 6H), 2.61 (t, J=5.7 Hz, 2H), 3.05-3.14 (m, 2H), 3.54 (s, 2H), 3.59 (t, J=5.7

Hz, 2H), 3.70-3.74 (m, 4H), 4.37-4.45 (m, 4H), 6.65 (d, J=1.3 Hz, 1H), 6.69 (dd, J=7.5, 1.3 Hz, 1H), 7.00 (d, J=7.5 Hz, 1H), 11.93 (br.s, 1H

MS(ESI) m/z: 480[M+H]⁺.

Example 18

2-[6-(3-morpholinopropoxy)spiro[indoline-3,4'-piperidine]-1'-yl-]-5,6,7,8-tetrahydroquinazolin-4(3H)-one (Test Target Compound 196)

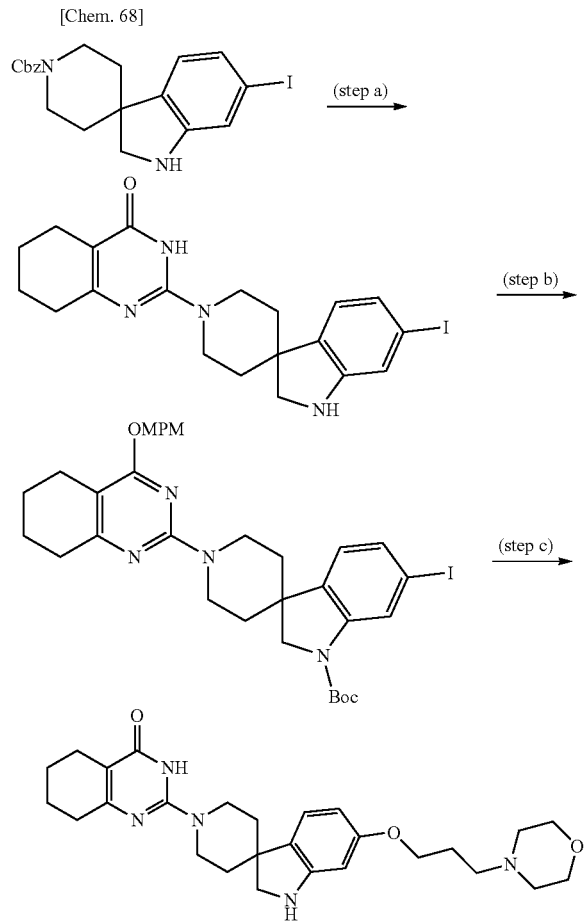

<Step a>

First, 2-(6-iodo-spiro[indoline-3,4'-piperidine]-1'-yl-)-5,6,7,8-tetrahydroquinazolin-4(3H)-one (725.3 mg) was obtained from 1'-benzyloxycarbonyl-6-iodospiro[indoline-3,4'-piperidine] (815.6 mg) in the same way as in <Step a-1> of Example 10.

¹H-NMR (400 MHz, CDCl₃) δ: 1.65-1.92 (m, 8H), 2.33-2.38 (m, 2H), 2.45-2.50 (m, 2H), 3.02-3.11 (m, 2H), 3.51 (s, 2H), 4.31-4.38 (m, 2H), 6.76 (d, J=7.7 Hz, 1H), 6.97 (d, J=1.3 Hz, 1H), 7.02-7.05 (m, 1H).

MS(ESI) m/z: 463 [M+H]+.

<Step b>

The 2-(6-iodo-spiro[indoline-3,4'-piperidine]-1'-yl-)-5,6,7,8-tetrahydroquinazolin-4(3H)-one (725.3 mg) was dissolved in chloroform, then di-tert-butyl dicarbonate (1.081 mL) and dimethylaminopyridine (19.2 mg) were added thereto, and the mixture was stirred at room temperature for 5 hours. A saturated sodium hydrogen carbonate aqueous solution was added to the reaction solution, followed by extraction with chloroform. The organic layer was dried with anhydrous magnesium sulfate and was concentrated under reduced pressure. The obtained residue was dissolved in N,N-dimethylformamide, then 4-methoxybenzyl chloride (0.32 mL) and potassium carbonate (433.6 mg) were added thereto, and the mixture was stirred at room temperature for 14 hours. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (methanol/chloroform=10/90) to obtain 1-tert-butyloxycarbonyl-6-iodo-1'-{4-[(4-methoxybenzyl)oxy]-5,6,7,8-tetrahydroquinazolin-2-yl}spiro[indoline-3,4'-piperidine] (430.6 mg).

<Step c>

The 1-tert-butyloxycarbonyl-6-iodo-1'-{4-[(4-methoxybenzyl)oxy]-5,6,7,8-tetrahydroquinazolin-2-yl}spiro[indoline-3,4'-piperidine] (20.7 mg) was dissolved in toluene, then 4-(3-hydroxypropyl)morpholine (0.013 mL), cesium carbonate (14.8 mg), palladium acetate (0.2 mg), and 5-[di(1-adamantyl)phosphino]-1',3',5'-triphenyl-1'H-[1,4']bipyrazole (1.0 mg) were added thereto, and the mixture was stirred at 80° C. for 5 hours. A saturated sodium hydrogen carbonate aqueous solution was added to the reaction solution, followed by extraction with chloroform. The organic layer was dried with anhydrous magnesium sulfate and was concentrated under reduced pressure, and the obtained residue was dissolved in chloroform, then trifluoroacetic acid was added thereto, and the mixture was stirred at room temperature for 14 hours. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (methanol/chloroform=10/90) to obtain the title compound (15.3 mg).

¹H-NMR (400 MHz, CDCl₃) δ: 1.64-1.98 (m, 10H), 2.33-2.38 (m, 2H), 2.44-2.54 (m, 8H), 3.06-3.14 (m, 2H), 3.52 (s, 2H), 3.70-3.74 (m, 4H), 3.94-3.99 (m, 2H), 4.28-4.35 (m, 2H), 6.24 (d, J=2.2 Hz, 1H), 6.28 (dd, J=8.1, 2.2 Hz, 1H), 6.92 (d, J=8.1 Hz, 1H), 11.20 (br.s, 1H).

MS(ESI) m/z: 480[M+H]⁺.

Example 19

(E)-2-[6-(4-morpholino-buta-1-ene-1-yl)spiro[indoline-3,4'-piperidine]-1'-yl-]-5,6,7,8-tetrahydroquinazolin-4(3H)-one (Test Target Compound 197)

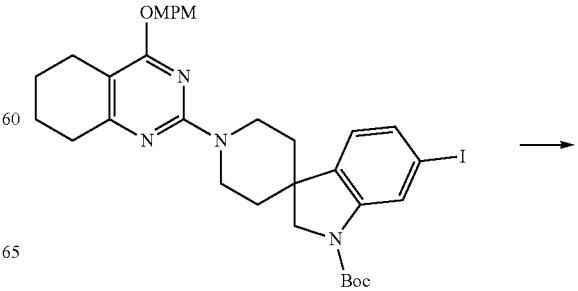

-continued

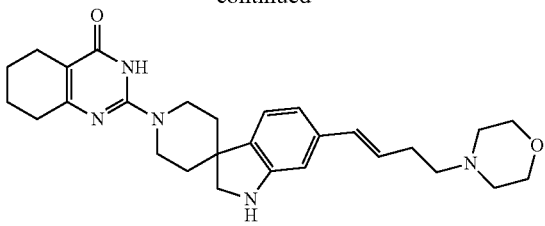

First, 1-tert-butyloxycarbonyl-6-iodo-1'-{4-[(4-methoxybenzyl)oxy]-5,6,7,8-tetrahydroquinazolin-2-yl}spiro[indoline-3,4'-piperidine] (44.6 mg) was dissolved in 1,4-dioxane, then 4-(3-butene-1-yl)morpholine (27.7 mg), potassium carbonate (18.1 mg), and [1,1'-bis(diphenylphosphino)ferrocene]palladium(II) dichloride (dichloromethane adduct) (5.3 mg) were added thereto, and the mixture was stirred under reflux by heating for 14 hours. A saturated sodium hydrogen carbonate aqueous solution was added to the reaction solution, followed by extraction with chloroform. The organic layer was dried with anhydrous magnesium sulfate and was concentrated under reduced pressure. The obtained residue was dissolved in chloroform, then trifluoroacetic acid was added thereto, and the mixture was stirred at room temperature for 14 hours. A saturated sodium hydrogen carbonate aqueous solution was added to the reaction solution, followed by extraction with chloroform. The organic layer was dried with anhydrous magnesium sulfate and was concentrated under reduced pressure, and the obtained residue was purified by silica gel column chromatography (methanol/chloroform=10/90) to obtain the title compound (24.6 mg).

$^1$H-NMR (400 MHz, CDCl$_3$) δ: 1.65-1.94 (m, 10H), 2.28-2.54 (m, 12H), 3.06-3.16 (m, 2H), 3.52 (s, 2H), 3.70-3.76 (m, 4H), 4.21-4.29 (m, 2H), 6.67-6.68 (m, 1H), 6.70-6.73 (m, 1H), 6.96-6.98 (d, 1H)

MS(ESI) m/z: 476[M+H]$^+$.

Compounds (test target compounds) of Example 20 to Example 389 presented below in Tables 37 to 103 were each obtained according to a combination of some methods among the methods used in Examples described above and their applied methods as well as the methods known by literatures and their applied methods by using materials such as commercially available reagents, compounds synthesized in accordance with the methods known by literatures and their applied methods, and the intermediates in Examples described above.

TABLE 37

| Example | Compound Name | Structure | 1H NMR δ ppm | Solvent | ESI MS m/z |
|---|---|---|---|---|---|
| 20 | 1'-(4-oxo-3,4,5,6,7,8-hexahydroquinazolin-2-yl)-3H-spiro[isobenzofuran-1,4-piperidin]-3-one | (Test Target Compound 88) | 1.56-1.74 (m, 6H), 2.16-2.28 (m, 4H), 2.34-2.44 (m, 2H), 3.18 (t, J = 12.0 Hz, 2H), 4.48 (d, J = 13.3 Hz, 2H), 7.60 (t, J = 7.13 Hz, 1H), 7.74-7.82 (m, 2H), 7.82-7.85 (m, 1H), 11.14 (br. s, 1H). | DMSO-d6 | 352 [M + H]+ |
| 21 | 1'-(4-oxo-3,4,5,6,7,8-hexahydroquinazolin-2-yl)spiro[isochromene-3,4'-piperidin]-1-one | (Test Target Compound 92) | 1.57-1.82 (m, 8H), 2.23 (m, 2H), 2.30-2.41 (m, 2H), 3.15 (s, 2H), 3.29-3.33 (m, 2H), 4.00 (d, J = 14.7 Hz, 2H), 7.36 (d, J = 7.6 Hz, 1H), 7.44 (t, J = 7.6 Hz, 1H), 7.65 (t, J = 7.4 Hz, 1H), 7.93 (dd, J = 7.7, 1.0 Hz, 1H), 11.08 (br. s, 1H). | CDCl3 | 366 [M + H]+ |

TABLE 37-continued

| Example | Compound Name | Structure | 1H NMR δ ppm | Solvent | ESI MS m/z |
|---|---|---|---|---|---|
| 22 | 4-methoxy-1'-(4-oxo-3,4,5,6,7,8-hexahydroquinazolin-2-yl)-3H-spiro[isobenzofuran-1,4'-piperidin]-3-one | (Test Target Compound 93) | 1.56-1.71 (m, 6H), 2.07-2.19 (m, 2H), 2.25 (m, 2H), 2.38 (m, 2H), 3.14 (t, J = 12.1 Hz, 2H), 3.90 (s, 3H), 4.45 (d, J = 10.9 Hz, 2H), 7.12 (d, J = 8.3 Hz, 1H), 7.25 (d, J = 7.3 Hz, 1H), 7.69 (t, J = 7.8 Hz, 1H), 11.13 (br. s, 1H). | DMSO-d6 | 382 [M + H]+ |
| 23 | 6-methoxy-1'-(4-oxo-3,4,5,6,7,8-hexahydro-quinazolin-2-yl)-3H-spiro[isobenzofuran-1,4'-piperidin]-3-one | (Test Target Compound 94) | 1.56-1.71 (m, 6H), 2.16-2.30 (m, 4H), 2.39 (t, J = 5.6 Hz, 2H), 3.17 (t, J = 12.3 Hz, 2H), 3.86 (s, 3H), 4.50 (d, J = 12.3 Hz, 2H), 7.10 (dd, J = 8.4, 2.2 Hz, 1H), 7.38 (d, J = 2.1 Hz, 1H), 7.72 (d, J = 8.4 Hz, 1H), 11.04 (br. s, 1H). | DMSO-d6 | 382 [M + H]+ |
| 24 | 1'-(4-oxo-3,4,5,6,7,8-hexahydroquinazolin-2-yl)-5H-spiro[furo[3,4-b]pyridine-7,4'-piperidin]-5-one | (Test Target Compound 5) | 1.53-1.86 (m, 6 H), 2.24-2.56 (m, 6 H), 3.49-3.61 (m, 2 H), 4.55 (m, 2 H), 7.50 (dd, J = 7.8, 4.9 Hz, 1 H), 8.21 (dd, J = 7.8, 1.6 Hz, 1 H), 8.84 (dd, J = 4.9, 1.6 Hz, 1 H), 12.05 (br. s., 1 H). | CDCl3 | 353 [M + H]+ |
| 25 | 1'-(4-oxo-3,4,5,6,7,8-hexahydroquinazolin-2-yl)-1H-spiro[furo[3,4-c]pyridine-3,4'-piperidin]-1-one | (Test Target Compound 2) | 1.75-1.93 (m, 4 H), 1.94-2.01 (m, 2 H), 2.41-2.53 (m, 4 H), 2.70-2.77 (m, 2 H), 3.57-3.69 (m, 2 H), 4.51-4.53 (m, 2 H), 7.90 (dd, J = 5.1, 1.1 Hz, 1 H), 8.88 (d, J = 5.1 Hz, 1 H), 9.00 (d, J = 1.1 Hz, 1 H). | CD3OD | 353 [M + H]+ |

TABLE 38

| Example | Compound Name | Structure | 1H NMR δ ppm | Solvent | ESI MS m/z |
|---|---|---|---|---|---|
| 26 | 1'-(4-oxo-3,4,5,6,7,8-hexahydraquinazolin-2-yl)-7H-spira[furo[3,4-b]pyridine-5,4'-piperidin]-7-one | (Test Target Compound 76) | 1.61-1.78 (m, 4 H), 1.78-1.88 (m, 2 H), 2.22 (dt, J = 13.4, 4.8 Hz, 2 H), 2.32 (t, J = 6.2 Hz, 2 H), 2.48 (t, J = 6.2 Hz, 2 H), 3.40-3.54 (m, 2 H), 4.64 (dd, J = 12.0, 2.1 Hz, 2 H), 7.58 (dd, J = 7.9, 4.7 Hz, 1 H), 7.80 (dd, J = 7.9, 1.4 Hz, 1 H), 8.93 (dd, J = 4.7, 1.4 Hz, 1 H). 12.24 (br. s., 1 H). | CDCl3 | 353 [M + H]+ |
| 27 | 1'-(4-oxo-3,4,5,6,7,8-hexahydroquinazolin-2-yl)-4H-spira[furo[3,4-b]furan-6,4'-piperidin]-4-one | (Test Target Compound 95) | 1.64-1.79 (m, 4H), 1.89-2.00 (m, 2H), 2.19 (ddd, J = 14.0, 10.0,4.2 Hz, 2H), 2.35 (t, J = 6.0 Hz, 2H), 2.49 (t, J = 6.1 Hz, 2H), 3.73 (ddd, J = 13.8, 10.3, 2.9 Hz, 2H), 4.22-4.30 (m, 2H), 6.64 (d, J = 2.0 Hz, 1H), 7.55 (d, J = 2.0 Hz, 1H), 12.02 (br. s, 1H). | CDCl3 | 342 [M + H]+ |
| 28 | 1-(4-oxo-3,4,5,6,7,8-hexahydroquinazolin-2-yl)-4'H-spiro[piperidine-4,6'-thieno[2,3-c]furan]-4'-one | (Test Target Compound 96) | 1.63-1.79 (m, 2H), 2.02-2.16 (m, 2H), 2.36 (t, J = 6.2 Hz, 1H), 2.49 (t, J = 6.0 Hz, 1H), 3.72 (ddd, J = 13.9, 10.2, 3.3 Hz, 1H), 4.25 (dt, J = 14.3, 4.1 Hz, 1H), 7.25 (d, J = 5.0 Hz, 1H), 7.43 (d, J = 5.0 Hz, 1H). | CDCl3 | 358 [M + H]+ |
| 29 | 1-(4-oxo-3,4,5,6,7,8-hexahydroquinazolin-2-yl)-6'H-spiro[piperidine-4,4,-thieno[2,3-c]furan]-6'-one | (Test Target Compound 97) | 1.65-1.80 (m, 4H), 1.91 (d, J = 12.7 Hz, 2H), 2.09-2.22 (m, 2H), 2.36 (t, J = 6.0 Hz, 2H), 2.49 (t, J = 6.2 Hz, 2H), 3.46-3.59 (m, 2H), 4.39-4.45 (m, 2H), 7.00 (d, J = 4.8 Hz, 1H), 7.85 (d, J = 4.8 Hz, 1H), 11.36 (br. s, 1H). | CDCl3 | 358 [M + H]+ |

TABLE 38-continued

| Example | Compound Name | Structure | 1H NMR δ ppm | Solvent | ESI MS m/z |
|---|---|---|---|---|---|
| 30 | 7-(fluoro-1'-(4-oxo-3,4,5,6,7,8-hexahydroquinazolin-2-yl)-3H-spiro[isobenzofuran-1,4'-piperidin]-3-one (Test Target Compound 99) | 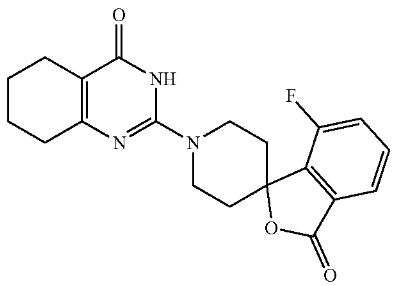 | 1.63-1.85 (m,6H), 2.35 (t, J = 6.1 Hz, 2H), 2.42-2.53 (m, 4H), 3.43 (t, J = 12.4 Hz, 2H), 4.59-4.67 (m, 2H), 7.36 (t, J = 8.4 Hz, 1H), 7.53-7.59 (m, 1H), 7.75 (d, J = 7.6 Hz, 1H), 11.74 (br. s, 1H). | CDCl3 | 370 [M + H]+ |

TABLE 39

| Example | Compound Name | Structure | 1H NMR δ ppm | Solvent | ESI MS m/z |
|---|---|---|---|---|---|
| 31 | 5,7-difluoro-1'-(4-oxo-3,4,5,6,7,8-hexahydroquinazolin-2-yl)-3H-spiro[isobenzofuran-1,4'-piperidin]-3-one | | 1.62-1.84 (m, 6H), 2.32-2.51 (m, 6H), 3.40 (t, J = 12.3 Hz, 2H), 4.64 (dd, J = 12.8, 3.6 Hz, 2H), 7.13 (td, J = 8.7, 2.1 Hz, 1H), 7.44 (dd, J = 6.6, 2.1 Hz, 1H), 11.88 (br. s, 1H). | CDCl3 | 388 [M + H]+ |
| 32 | 6-fluoro-1'-(4-oxo-3,4,5,6,7,8-hexahydroquinazolin-2-yl)-3H-spiro[isobenzofuran-1,4'-piperidin]-3-one (Test Target Compound 101) | 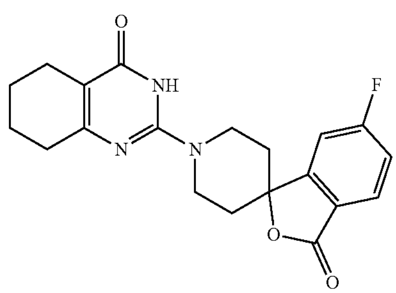 | 1.65-1.85 (m, 6H), 2.17 (td, J = 13.5, 4.8 Hz, 2H), 2.35 (t, J = 6.1 Hz, 2H), 2.49 (t, J = 6.2 Hz, 2H), 3.39-3.51 (m, 2H), 4.59 (d, J = 12.2 Hz, 2H), 7.06 (dd, J = 7.7, 2.0 Hz, 1H), 7.23-7.26 (m, 1H), 7.92 (dd, J = 8.5, 4.7 Hz, 1H), 11.66 (br. s, 1H). | CDCl3 | 370 [M + H]+ |
| 33 | 5-fluoro-1'-(4-oxo-3,4,5,6,7,8-hexahydroquinazolin-2-yl)-3H-spiro[isobenzofuran-1,4'-piperidin]-3-one (Test Target Compound 102) | 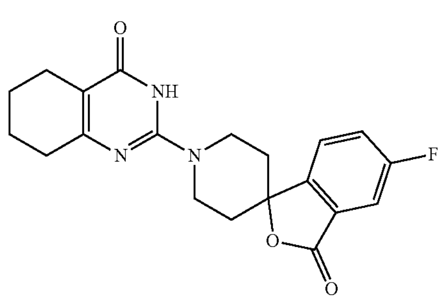 | 1.62-1.83 (m, 6H), 2.19 (td, J = 13.4, 4.8 Hz, 2H), 2.34 (t, J = 6.2 Hz, 2H), 2.49 (t, J = 6.2 Hz, 2H), 3.39-3.49 (m, 2H), 4.60 (dd, J = 11.6, 2.3 Hz, 2H), 7.33-7.43 (m, 2H), 7.57 (d, J = 6.8 Hz, 1H), 11.74 (s, 1H). | CDCl3 | 370 [M + H]+ |

TABLE 39-continued

| Example | Compound Name | Structure | 1H NMR δ ppm | Solvent | ESI MS m/z |
|---|---|---|---|---|---|
| 34 | 4-fluoro-1'-(4-oxo-3,4,5,6,7,8-hexahydroquinazolin-2-yl)-3H-spiro(isobenzofuran-1,4'-piperidin]-3-one (Test Target Compound 103) | 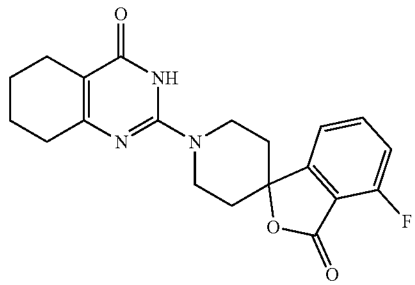 | 1.61-1.86 (m, 6H), 2.19 (td, J = 13.5, 4.7 Hz, 2H), 2.34 (t, J = 6.2 Hz, 2H), 2.49 (t, J = 6.2 Hz, 2H), 3.37-3.51 (m, 2H), 4.60 (dd, J = 11.7, 2.3 Hz, 2H), 7.15-7.24 (m, 2H), 7.68 (td, J = 7.9, 4.6 Hz, 1H), 11.65 (br. s, 1H). | CDCl3 | 370 [M + H]+ |
| 35 | 7-methoxy-1'-(4-oxo-3,4,5,6,7,8-hexahydroquinazolin-2-yl)-3H-spira[isobenzofuran-1,4'-piperidin]-3-one (Test Target Compound 104) | | 1.61-1.80 (m, 6H), 2.36 (t, J = 6.2 Hz, 2H), 2.50 (t, J = 6.1 Hz, 2H), 2.61 (td, J = 13.6, 4.8 Hz, 2H), 3.33-3.48 (m, 2H), 3.90 (s, 3H), 4.51-4.63 (m, 2H) 7.10-7.16 (m, 1H), 7.46-7.55 (m, 2H). | CDCl3 | 382 [M + H]+ |
| 36 | 4,5-difluoro-1'-(4-oxo-3,4,5,6,7,8-hexahydroquinazolin-2-yl)-3H-spiro[isobenzofuran-1,4'-piperidin]-3-one (Test Target Compound 105) | 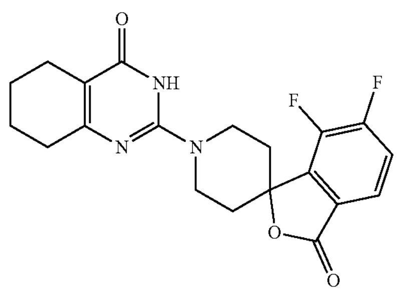 | 1.66-1.88 (m, 6H), 2.34-2.52 (m, 6H), 3.42 (t, J = 12.5 Hz, 2H), 4.62 (d, J = 9.5 Hz, 2H), 7.39 (ddd, J = 9.8, 8.3, 6.5 Hz, 1H), 7.72 (dd, J = 5.0 Hz, 1H), 11.55 (br. s. 1H). | CDCl3 | 388 [M + H]+ |

TABLE 40

| Example | Compound Name | Structure | 1H NMR δ ppm | Solvent | ESI MS m/z |
|---|---|---|---|---|---|
| 37 | 6-hydroxy-1'-(4-oxo-3,4,5,6,7,8-hexahydroquinazolin-2-yl)-3H-spiro[isobenzofuran-1,4'-piperidin]-3-one (Test Target Compound 107) | 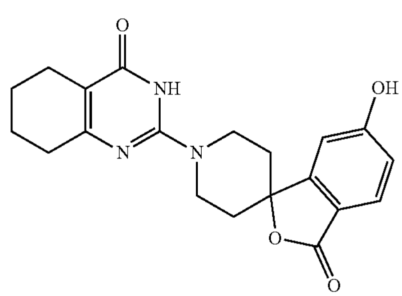 | 1.56-1.72 (m, 6H), 2.07-2.20 (m, 2H), 2.26 (m, 2H), 2.39 (m, 2H), 3.15 (t, J = 12.3 Hz, 2H), 4.45 (br. m, 2H), 6.52 (s, 1H), 6.93-7.00 (m, 2H), 7.64 (d, J = 8.3 Hz, 1H), 10.70 (br. s, 1H), 11.13 (br. s, 1H). | DMSO-d6 | 368 [M + H]+ |

TABLE 40-continued

| Example | Compound Name | Structure | 1H NMR δ ppm | Solvent | ESI MS m/z |
|---|---|---|---|---|---|
| 38 | 5-(2-morpholinoethoxy)-1'-(4-oxo-3,4,5,6,7,8-hexahydroqinazoline-2-yl)-3H-spiro[isobenzofuran-1,4'-piperidin]-3-one | (Test Target Compound 108) | 1.68 (d, J = 5.1 Hz, 2H), 1.71-1.80 m, 4H), 2.17 (td, J = 13.4, 4.5 Hz, 2H), 2.33 (t, J = 5.6 Hz, 2H), 2.48 (t, J = 6.1 Hz, 2H), 2.60 (m, 4H), 2.85 (m, 2H), 3.44 (t, J = 12.2 Hz, 2H), 3.72-3.79 (m, 4H), 4.18 (t, J = 5.6 Hz, 2H), 4.60 (d, J = 13.0 Hz, 2H), 7.26 (m, 2H), 7.34 (s, 1H), 12.03 (br. s, 1H). | CDCl3 | 481 [M + H]+ |
| 39 | 1'-(4-oxo-3,4,5,6,7,8-hexahydroquinazolin-2-yl)-5-[2-(piperidin-1-yl]ethoxy-3H-spiro[isobenzofuran-1,4'-piperidin]-3-one | (Test Target Compound 109) | 1.35-1.87 (m, 14H), 2.16 (td, J = 13.4, 4.6 Hz, 2H), 2.35 (t, J = 6.2 Hz, 2H), 2.49 (t, J = 6.2 Hz, 2H), 2.58 (br. m, 2H), 2.89 (br. m, 2H), 3.36-3.52 (m, 2H), 4.21 (br. m, 2H), 4.46-4.60 (m, 2H), 7.24-7.26 (m, 2H), 7.32-7.36 (m, 1H), 11.40 (br. m, 1H). | CDCl3 | 479 [M + H]+ |
| 40 | 5-(2-morpholoethoxy)-1'-(4-oxo-3,5,7,8-letrahydro-4H-thiopyrano[4,3-d]pyrimidin-2-yl)-3H-spiro[isobenzofuran-1,4'-piperidin]-3-one | (Test Target Compound 110) | 1.78 (d, J = 13.6 Hz, 2H), 2.15 (td,J = 13.5, 4.6 Hz, 2H), 2.66-2.93 (m, 8H), 3.09 (br. m, 2H), 3.39-3.51 (m, 4H), 4.84 (br. m, 4H), 4.29 (br. m, 2H), 4.52-4.70 (m, 2H), 7.22-7.37 (m, 2H), 7.28-7.36 (m, 1H). | CDCl3 | 499 [M + H]+ |
| 41 | 7-fluono-5-[(4-methoxybenzyl)oxy)-1'-(4-oxo-3,4,5,6,7,8-hexahydroquinazolin-2-yl)-3H-spiro[isobenzofuran-1,4'-piperidin]-3-one | (Test Target Compound 111) | 1.66-1.82 (m, 6H), 2.32-2.52 (m, 6H), 3.40 (t, J = 12.5 Hz, 2H), 3.84 (s, 3H), 4.58 (d, J = 12.1 Hz, 2H), 5.05 (s, 2H), 6.92-6.99 (m, 3H), 7.24-7.27 (m, 1H), 7.36 (d, J = 8.6 Hz, 2H), 11.44 (br. s, 1H). | CDCl3 | 506 [M + H]+ |
| 42 | 7-fluoro-1'-(4-oxo-3,4,5,6,7,8-hexahydroquinazolin-2-yl)-5-[2-(pyrrolidin-1-yl)ethoxy]-3H-spiro[isobenzofuran-1,4'-piperidin]-3-one | (Test Target Compound 72) | 1.65-1.91 (10 H, m), 2.27-2.54 (6 H, m), 2.57-2.71 (4 H, m), 2.94 (2 H, br t, J = 5.6 Hz), 3.39 (2 H, br t, J = 12.5 Hz), 4.17 (2 H, t, J = 5.6 Hz), 4.64 (2 H, br d, J = 12.9 Hz), 6.95 (1 H, dd, J = 10.6, 2.0 Hz), 7.19(1 H, d, J = 2.0 Hz) | CDCl3 | 483 [M + H]+ |

TABLE 41

| Example | Compound Name | Structure | 1H NMR δ ppm | Solvent | ESI MS m/z |
|---|---|---|---|---|---|
| 43 | 7-fluoro-5-[2-(4-methylpiperazine-1-yl)ethoxy]-1'-(4-oxo-3,4,5,6,7,8-hexahydro-quinazolin-2-yl)-3H-spiro[isobenzofuran-1,4'-piperidin]-3-one | (Test Target Compound 73) | 1.61-1.84 (6 H, m), 2.27-2.38 (6 H, m), 2.38-2.67(11 H, m), 2.84 (2 H, t, J = 5.6 Hz), 3.39 (2 H, br t, J = 12.7 Hz), 4.15 (2 H, t, J = 5.6 Hz), 4.63 (2 H, br d, J = 12.9 Hz), 6.93 (1 H, br dd, J = 10.2, 2.0 Hz), 7.19 (1 H, d, J = 2.0 Hz) | CDCl3 | 512 [M + H]+ |
| 44 | 5-[2-(1,1-dioxidomorph-olino)ethoxy]-7-fluoro-1'-(4-oxo-3,4,5,6,7,8-hexahydro-quinazolin-2-yl)-3H-spiro[isobenzofuran-1,4'-piperidin]-3-one | (Test Target Compound 74) | 1.66-1.84 (6 H, m), 2.29-2.54 (6 H, m), 2.99-3.12(6 H, m), 3.12-3.19(4 H, m), 3.39 (2 H, br t, J = 12.7 Hz), 4.15 (2 H, t, J = 5.1 Hz), 4.65 (2 H, br d, J = 12.5 Hz), 6.92 (1 H, br dd, J = 10.6, 2.0 Hz), 7.17 (1 H, d, J = 2.0 Hz) | CDCl3 | 547 [M + H]+ |
| 45 | 7-fluoro-5-(2-hydroxyethoxy)-1'-(4-oxo-3,4,5,6,7,8-hexahydro-quinazolin-2-yl)-3H-spiro[isobenzofuran-1,4'-piperidin]-3-one | (Test Target Compound 61) | 1.58-1.71 (4 H, m), 1.79 (2 H, br d, J = 13.5 Hz), 2.08-2.30 (4 H, m), 2.34-2.43 (2 H, m), 3.15 (2 H, t, J = 12.9 Hz), 3.68-3.76 (2 H, m), 4.13 (2 H, br t, J = 4.6 Hz), 4.45 (2 H, br d, J = 12.5 Hz), 4.93 (1 H, br s), 7.24 (1 H, d, J = 2.0 Hz), 7.29 (1 H, dd, J = 10.9, 2.0 Hz), 11.19 (1 H, br s) | DMSO-d6 | 430 [M + H]+ |
| 46 | 2-{[7-fluoro-3-oxo-1'-(4-oxo-3,4,5,6,7,8-hexahydro-quinazolin-2-yl)-3H-spiro[isobenzofuran-1,4'-piperidin]-5-yl]oxy} acetic acid | (Test Target Compound 75) | 1.58-1.72 (4 H, m), 1.81 (2 H, br d, J = 13.5 Hz), 2.08-2.31 (4 H, m), 2.34-2.45 (2 H, m), 3.15 (2 H, t, J = 12.2 Hz), 4.45 (2 H, br d, J = 11.9 Hz), 4.88 (2 H, s), 7.21 (1 H, d, J = 2.0 Hz), 7.33 (1 H, dd, J = 10.9, 2.0 Hz) | DMSO-d6 | 444 [M + H]+ |
| 47 | 7-fluono-5-[2-oxo-2-(pyrrolidine-1-yl)ethoxy)-1'-(4-oxo-3,4,5,6,7,8-hexahydro-quinazolin-2-yl)-3H-spiro[isobenzofuran-1,4'-piperidin]-3-one | (Test Target Compound 77) | 1.59-1.96 (10 H, m), 2.08-2.33 (4 H, m), 2.34-2.45 (2 H, m), 3.07-3.30 (4 H, m), 3.40-3.52 (2 H, m), 4.45 (2 H, br d, J = 13.5 Hz), 4.93 (2 H, s), 7.23 (1 H, br s), 7.27-7.35 (1 H, m), 11.22 (1 H, br s) | DMSO-d6 | 497 [M + H]+ |

TABLE 42

| Example | Compound Name | Structure | 1H NMR δ ppm | Solvent | ESI MS m/z |
|---|---|---|---|---|---|
| 48 | 7-fluoro-5-(2-morpholino-2-oxoethoxy)-1'-(4-oxo-3,4,5,6,7,8-hexahydro-quinazolin-2-yl)-3H-spiro[iso-benzofuran-1,4'-piperidin]-3-one | (Test Target Compound 78) | 1.66-1.85 (6 H, m), 2.30-2.51 (6 H, m), 3.39 (2 H, br t, J = 12.5 Hz), 3.49-3.60 (2 H, m), 3.62-3.77 (6 H, m), 4.63 (2 H, br d, J = 12.5 Hz), 4.79 (2 H, s), 7.02 (1 H, dd, J = 9.9, 2.0 Hz), 7.15 (1 H, d, J = 2.0 Hz), 11.98 (1 H, br s) | CDCl3 | 513 [M + H]+ |
| 49 | 2-{[7-fluoro-3-oxo-1'-(4-oxo-3,4,5,6,7,8-hexahydro-quinazolin-2-yl)-3H-spiro[iso-benzofuran-1,4'-piperidin]-5-yl]oxy}-N,N-dimethyl-acetamide | (Test Target Compound 79) | 1.66-1.87 (6 H, m), 2.28-2.53 (6 H, m), 3.01 (3 H, s), 3.07 (3 H, s), 3.38 (2 H, br t, J = 12.5 Hz), 4.65 (2 H, br d, J = 12.5 Hz), 4.80 (2 H, s), 7.03 (1 H, dd, J = 10.2, 2.0 Hz), 7.12 (1 H, d, J = 2.0 Hz), 12.15 (1 H, br s) | CDCl3 | 471 [M + H]+ |
| 50 | 2-{[7-fluoro-3-oxo-1'-(4-oxo-3,4,5,6,7,8-hexahydro-quinazolin-2-yl)-3H-spiro[iso-benzofuran-1,4'-piperidin]-5-yl]oxy}acetamide | (Test Target Compound 80) | 1.59-1.71 (4 H, m), 1.80 (2 H, br d, J = 13.5 Hz), 2.08-2.30 (4 H, m), 2.34-2.46 (2 H, m), 3.14 (2 H, t, J = 12.9 Hz), 4.45 (2 H, br d, J = 13.2 Hz), 4.61 (2 H, s), 7.23 (1 H, d, J = 2.0 Hz), 7.32 (1 H, dd, J = 11.2, 2.0 Hz), 7.46 (1 H, br s), 7.64 (1 H, br s) | DMSO-d6 | 443 [M + H]+ |
| 51 | Ethyl 2-{[7-fluoro-3-oxo-1'-(4-oxo-3,4,5,6,7,8-hexahydro-pyrido[2,3-d)pyrimidin-2-yl)-3H-spiro[isobenzo-furan-1,4'-piperidin]-5-yl)oxy}acetate | (Test Target Compound 81) | 1.33 (3 H, t, J = 7.1 Hz), 1.67-1.87 (4 H, m), 2.32-2.46 (4 H, m), 3.24-3.40 (4 H, m), 4.29 (2 H, q, J = 7.1 Hz), 4.54-4.67 (3 H, m), 4.69 (2 H, s), 6.99 (1 H, dd, J = 9.9, 2.0 Hz), 7.10 (1 H, d, J = 2.0 Hz) | CDCl3 | 473 [M + H]+ |
| 52 | 2-{[7-fluoro-3-oxo-1'-(4-oxo-3,4,5,6,7,8-hexahydro-pyrido[2,3-d]pyrimidin-2-yl)-3H-spiro[isobenzo-furan-1,4'-piperidin]-5-yl)oxy}acetic acid | (Test Target Compound 82) | 1.62-1.83 (4 H, m), 2.05-2.21 (2 H, m), 2.27 (2 H, br t, J = 5.9 Hz), 3.04-3.20 (4 H, m), 4.40 (2 H, br d, J = 12.5 Hz), 4.88 (2 H, s), 6.47 (1 H, s), 7.21 (1 H, d, J = 2.0 Hz), 7.34 (1 H, dd, J = 10.9, 2.0 Hz) | DMSO-d6 | 445 [M + H]+ |

TABLE 43

| Example | Compound Name | Structure | 1H NMR δ ppm | Solvent | ESI MS m/z |
|---|---|---|---|---|---|
| 53 | Ethyl 2-{[7-fluoro-1'-(8-methyl-4-oxo-3,4,5,6,7,8-hexahydro-pyrido[2,3-d]pyrimidin-2-yl)-3-oxo-3H-spiro[isobenzo-furan-1,4'-piperidin]-5-yl] acetate | 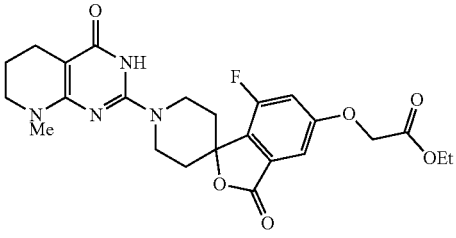<br>(Test Target Compound 83) | 1.33 (3 H, t, J = 7.1 Hz), 1.66-1.88 (4 H, m), 2.33-2.51 (4 H, m), 3.07 (3 H, s), 3.16-3.45 (4 H, m), 4.29 (2 H, q, J = 7.1 Hz), 4.59-4.68 (2 H, m), 4.69 (2 H, s), 6.98 (1 H, dd, J = 10.2, 2.0 Hz), 7.10 (1 H, d, J = 2.0 Hz) | CDCl3 | 487 [M + H]+ |
| 54 | 2-{[7-fluoro-1'-(8-methyl-4-oxo-3,4,5,6,7,8-hexahydro-pyrido[2,3-d]pyrimidin-2-yl)-3-oxo-3H-spiro[isobenzo-furan-1,4'-piperidin]-5-yl]oxy}acetic acid | 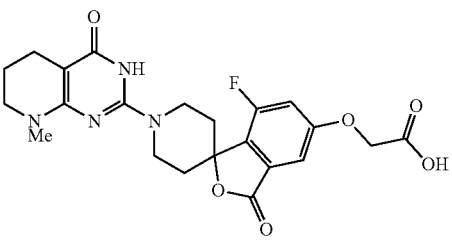<br>(Test Target Compound 84) | 1.69-1.87 (4 H, m), 2.06-2.25 (2 H, m), 2.32 (2 H, br t, J = 6.1 Hz), 3.00 (3 H, s), 3.06-3.27 (4 H, m), 4.46 (2 H, br d, J = 13.2 Hz), 4.88 (2 H, s), 7.21 (1 H, d, J = 2.0 Hz), 7.33 (1 H, dd, J = 11.2, 2.0 Hz) | DMSO-d6 | 459 [M + H]+ |
| 55 | 2-{[7-fluoro-1'-(8-methyl-4-oxo-3,4,5,6,7,8-hexahydro-pyrido[2,3-d]pyrimidin-2-yl)-3-oxo-3H-spiro[isobenzo-furan-1,4'-piperidin)-5-yl]oxy}-N,N-dimethyl-acetamid | 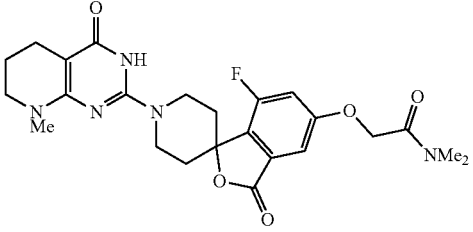<br>(Test Target Compound 85) | 1.67-1.89 (4 H, m), 2.32-2.49 (4 H, m), 3.01 (3 H, s), 3.07 (6 H, s), 3.19-3.42 (4 H, m), 4.66 (2 H, br d, J = 11.9 Hz), 4.79 (2 H, s), 7.02 (1 H, dd, J = 10.2, 2.0 Hz), 7.11 (1 H, d, J = 2.0 Hz) | CDCl3 | 486 [M + H]+ |
| 56 | 7-fluono-1'-(8-methyl-4-oxo-3,4,5,6,7,8-hexahydro-pyrido[2,3-d]pyrimidin-2-yl)-5-[2-oxo-2-(pyrrolidin-1-yl)ethoxy]-3H-spiro[isobenzo-furan-1,4'-piperidin]-3-one | 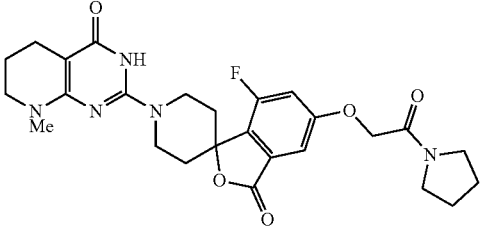<br>(Test Target Compound 86) | 1.69-1.96 (6 H, m), 1.98-2.11 (2 H, m), 2.32-2.48 (4 H, m), 3.07 (3 H, s), 3.21-3.42 (4 H, m), 3.47 (2 H, t, J = 6.8 Hz), 3.54 (2 H, t, J = 6.9 Hz), 4.59-4.69 (2 H, m), 4.70 (2 H, s), 7.02 (1 H, dd, J = 10.2, 2.0 Hz), 7.12 (1 H, d, J = 2.0 Hz) | CDCl3 | 512 [M + H]+ |
| 57 | 7-fluono-1'-(8-methyl-4-oxo-3,4,5,6,7,8-hexahydro-pyrido[2,3-d]pyrimidin-2-yl)-5-[2-(4-methylpiperazin-1-yl)-2-oxoethoxy]-3H-spiro[isobenzo-furan-1,4'-piperidin]-3-one | 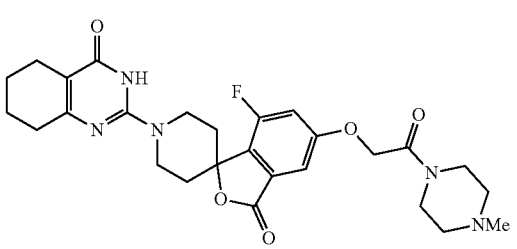<br>(Test Target Compound 87) | 1.67-1.90 (4 H, m), 2.33 (3 H, s), 2.36-2.52 (8 H, m), 3.07 (3 H, s), 3.21-3.46 (4 H, m), 3.47-3.55 (2 H, m), 3.62-3.71 (2 H, m), 4.63 (2 H, br d, J = 11.2 Hz), 4.78 (2 H, s), 7.01 (1 H, dd, J = 10.2, 2.0 Hz), 7.14(1 H, m, J = 2.0 Hz) | CDCl3 | 541 [M + H]+ |

TABLE 44

| Example | Compound Name | Structure | 1H NMR δ ppm | Solvent | ESI MS m/z |
|---|---|---|---|---|---|
| 58 | 2-(3H-spiro(isobenzofuran-1,4'-piperidin)-1'-yl)-5,6,7,8-tetrahydroquinazoline-4(3H)-one | (Test Target Compound 64) | 1.57-1.71 (m, 6 H), 1.80-1.92 (m, 2 H), 2.20-2.30 (m, 2 H), 2.32-2.40 (m, 2 H), 3.10-3.20 (m, 2 H), 4.29-4.41 (m, 2 H), 5.00 (s, 2H), 7.20-7.30 (m, 4 H), 11.02 (br. s, 1 H). | DMSO-d6 | 338 [M + H]+ |
| 59 | 2-(7-fluoro-5-methoxy-3H-spiro[isobenzofuran-1,4'-piperidin]-1'-yl)-5,6,7,8-tetrahydroquinazolin-4(3H)-one | (Test Target Compound 113) | 1.57-1.75 (m, 6H), 1.94 (td, J = 13.1, 4.5 Hz, 2H), 2.22-2.26 (m, 2H), 2.31-2.43 (m, 2H), 3.11 (t, J = 12.3 Hz, 2H), 3.76 (s, 3H), 4.33 (d, J = 12.1 Hz, 2H), 5.02 (s, 2H), 3.27 (br. s, 1H), 6.68-6.72 (m, 1H), 6.74 (d, J = 2.0 Hz, 1H), 11.04 (br. s, 1H). | DMSO-d6 | 386 [M + H]+ |
| 60 | 2-(7-methoxy-3H-spiro(isobenzofuran-1.4'-piperidin)-1'-yl)-5,6,7,8-tetrahydroquinazolin-4(3H)-one | (Test Target Compound) | 1.53-1.70 (m, 6H), 2.13-2.28 (m, 4H), 2.31-2.42 (m, 2H), 3.02-3.16 (m, 2H), 3.77 (s, 3H), 4.32 (d, J = 12.3 Hz, 2H), 5.00 (s, 2H), 6.87 (m, 2H), 7.27 (t, J = 7.5 Hz, 1H), 10.99 (br. s, 1H). | DMSO-d6 | 368 [M + H]+ |
| 61 | 2-(7-fluoro-4-methoxy-3H-spiro[isobenzofuran-1,4'-piperidin]-1'-yl)-5,6,7,8-tetrahydroquinazolin-4(3H)-one | (Test Target Compound 114) | 1.57-1.70 (m, 4H), 1.74 (d, J = 13.3 Hz, 2H), 1.96 (td, J = 13.2, 4.5 Hz, 2H), 2.18-2.29 (m, 2H), 2.33-2.43 (m, 2H), 3.11 (t, J = 12.3 Hz, 2H), 3.78 (s, 3H), 4.33 (d, J = 13.0 Hz, 2H), 5.01 (s, 2H), 6.91 (dd, J = 8.9, 3.4 Hz, 1H), 7.07 (t, J = 9.1 Hz, 1H), 11.06 (br. s, 1H). | DMSO-d6 | 368 [M + H]+ |
| 62 | 2-(5,7-difluoro-3H-spiro[isobenzofuran-1,4'-piperidin)-1'-yl)-5,6,7,8-tetrahydroquinazolin-4(3H)-one | (Test Target Compound 115) | 1.54-1.70 (m, 4H), 1.70-1.80 (m, 2H), 1.96 (td, J = 13.1, 4.4 Hz, 1.7H), 2.03-2.15 (m, 0.3H), 2.24 (t, J = 5.4 Hz, 2H), 2.32-2.34 (m, 1.7H), 2.34-2.46 (m, 0.3H), 3.11 (t, J = 12.4 Hz, 2H), 3.97 (d, J = 11.6 Hz, 0.3H), 4.34 (d, J = 11.9 Hz, 1.7H), 5.07 (s, 2H), 7.06-7.16 (m, 2H), 11.05 (br. s, 1H). It was observed as a tautomer mixture having a ratio of 7:3. | DMSO-d6 | 374 [M + H]+ |

TABLE 44-continued

| Example | Compound Name | Structure | 1H NMR δ ppm | Solvent | ESI MS m/z |
|---|---|---|---|---|---|
| 63 | 1'-(4-oxo-3,4,5,6,7,8-hexahydroquinazolin-2-yl)-2H-spiro(benzofuran-3,4'-piperidin]-2-one | (Test Target Compound 62) | 1.57-1.73 (m, 4 H), 1.83-2.00 (m, 4 H), 2.22-2.30 (m, 2 H), 2.35-2.45 (m, 2 H), 3.69-3.80 (m, 2 H), 3.99-4.10 (m, 2H), 7.15-7.30 (m, 2 H), 7.34-7.40 (m, 1 H), 7.60-7.68 (m, 1 H), 11.16 (br. s, 1 H). | DMSO-d6 | 352 [M + H]+ |

TABLE 45

| Example | Compound Name | Structure | 1H NMR δ ppm | Solvent | ESI MS m/z |
|---|---|---|---|---|---|
| 64 | 2-(2H-spiro[benzofuran-3,4'-piperidin]-1'-yl)-5,6,7,8-tetrahydroquinazolin-4(3H)-one | (Test Target Compound 63) | 1.58-1.72 (m, 6 H), 1.73-1.86 (m, 2 H), 2.21-2.29 (m, 2 H), 2.32-2.40 (m, 2 H), 2.94-3.10 (m, 2 H), 4.22-4.35 (m, 2 H), 4.46 (s, 2 H), 6.73-6.80 (m, 1 H), 6.80-6.87 (m, 1 H), 7.08-7.15 (m, 1 H), 7.21-7.26 (m, 1 H), 11.05 (br. s, 1 H). | DMSO-d6 | 338 [M + H]+ |
| 65 | 2-(2H-spiro[benzofuran-3,4'-piperidin)-1'-yl)-7,8-dihydro-3H-thiopyrano[4,3-d]pyrimidin-4(5H)-one | (Test Target Compound 65) | 1.79-2.00 (4 H, m), 2.76-2.90 (4 H, m), 3.32-3.46 (2 H, m), 3.52 (2 H,s), 4.27-4.40 (2 H, m), 5.12 (2 H, s), 7.07-7.14 (1 H, m), 7.22-7.33 (3 H, m). | CDCl3-CD3OD | 356 [M + H]+ |
| 66 | 4-fluoro-1'-(4-oxo-3,4,5,6,7,8-hexahydroquinazolin-2-yl)-2H-spiro[benzofuran-3,4'-piperidin]-2-one | (Test Target Compound 116) | 1.61-1.80 (m, 4H), 2.00 (d, J = 14.3 Hz, 2H), 2.29-2.41 (m, 4H), 2.48 (t, J = 6.2 Hz, 2H), 3.76-3.86 (m, 2H), 4.32 (d, J = 14.1 Hz, 2H), 6.87 (t, J = 9.0 Hz, 1H), 6.95 (dd, J = 8.1, 0.7 Hz, 1H), 7.27-7.34 (m, 1H). | CDCl3 | 370 [M + H]+ |

TABLE 45-continued

| Example | Compound Name | Structure | 1H NMR δ ppm | Solvent | ESI MS m/z |
|---|---|---|---|---|---|
| 67 | 5-{methyl[(1-methylpiperidin-4-ylmethyl)amino]}-1'-(4-oxo-3,4,5,6,7,8-hexahydroquinazolin-2-yl)-3H-spiro[isobenzofuran-1,4'-piperidin]-3-one | (Test Target Compound 118) | 1.28-1.42 (m, 2H), 1.63-1.82 (m, 9H), 1.88 (t, J = 10.9 Hz, 2H), 2.14 (td, J = 13.4, 4.6 Hz, 2H), 2.27 (s, 3H), 2.31-2.38 (m, 2H), 2.49 (t, J = 6.0 Hz, 2H), 2.87 (d, J = 11.6 Hz, 2H), 3.04 (s, 3H), 3.26 (d, J = 6.8 Hz, 2H), 3.44 (t, J = 12.3 Hz, 2H), 4.55 (d, J = 13.1 Hz, 2H), 6.95 (dd, J = 8.6, 2.4 Hz, 1H), 7.04 (d, J = 2.3 Hz, 1H), 7.18 (d, J = 8.6 Hz, 1H). | CDCl3 | 492 [M + H]+ |
| 68 | 7-fluoro-5-(methyl(pyridin-3-ylmethyl)amino]-1'-(4-oxo-3,4,5,6,7,&-hexahydroquinazolin-2-yl)-3H-spiro[isobenzofuran-1,4'-piperidin]-3-one | (Test Target Compound 119) | 1.62-1.80 (m, 6H), 2.31-2.41 (m, 4H), 2.48 (t, J = 6.2 Hz, 2H), 3.12 (m, 3H), 3.39 (t, J = 12.4 Hz, 2H), 4.53 (d, J = 9.7 Hz, 2H), 4.61 (s, 2H), 6.63 (dd, J = 12.2, 2.1 Hz, 1H), 6.97 (d, J = 2.1 Hz, 1H), 7.28 (dd, J = 3.0, 0.8 Hz, 1H), 7.51 (d, J = 7.6 Hz, 1H), 8.48 (d, J = 1.6 Hz, 1H), 8.55 (dd, J = 4.8, 1.6 Hz, 1H), 11.26 (br. s, 1H). | CDCl3 | 490 [M + H]+ |
| 69 | 5-{[3-(dimethyl-amino]propyl)(methyl)amino]-7-fluoro-1'-(4-oxo-3,4,5,6,7,8-hexahydroquinazolin-2-yl)-3H-spiro[isobenzofuran-1,4'-piperidin]-3-one | (Test Target Compound 120) | 1.64-1.82 (m, 8H), 2.23 (s, 6H), 2.25-2.32 (m, 2H), 2.32-2.45 (m, 4H), 2.45-2.49 (m, 2H), 2.99 (s, 3H), 3.34-3.49 (m, 4H), 4.47-4.57 (m, 2H), 6.67 (dd, J = 12.8, 2.1 Hz, 1H), 6.93 (d, J = 2.1 Hz, 1H), 11.12 (br. s, 1H). | CDCl3 | 484 [M + H]+ |

TABLE 46

| Example | Compound Name | Structure | 1H NMR δ ppm | Solvent | ESI MS m/z |
|---|---|---|---|---|---|
| 70 | 2-(dimethylamino)-N-3-oxo-1'-(4-oxo-3,4,5,6,7,8-hexahydroquinazolin-2-yl)-3H-spiro[isobenzofuran-1,4'-piperidin)-5-yl)acetamide | (Test Target Compound 121) | 1.54-1.72 (m, 6H), 2.10-2.21 (m, 2H), 2.24-2.31 (m, 8H), 2.35-2.43 (m, 2H), 3.11 (s, 2H), 3.18 (t, J = 12.0 Hz, 2H), 4.45(d, J = 12.3 Hz, 2H), 7.70 (d, J = 8.3 Hz, 1H), 7.91 (dd, J = 8.3, 2.0 Hz, 1H), 8.23 (d, J = 1.6 Hz, 1H), 10.11 (s, 1H), 10.83 (br. s, 1H). | DMSO-d6 | 484 [M + H]+ |

TABLE 46-continued

| Example | Compound Name | Structure | 1H NMR δ ppm | Solvent | ESI MS m/z |
|---|---|---|---|---|---|
| 71 | 2-(3,4-dihydro-2H-spiro[isoquinoline-1,4'-piperidin]-1-yl)-5,6,7,8-tetrahydroquinazolin-4(3H)-on | (Test Target Compound 66) | 1.58-1.86 (m, 6 H), 2.09 (td, J = 13.4, 4.6 Hz, 2 H), 2.28-2.40 (m, 2 H), 2.41-2.53 (m, 2 H), 2.78 (t, J = 5.8 Hz, 2 H), 3.04-3.14 (m, 2 H), 3.30-3.44 (m, 2 H), 4.33 (br d, J = 13.2 Hz, 2 H), 7.03-7.25 (m, 4 H) | CDCl3 | 351 [M + H]+ |
| 72 | 2-(2',3'-dihydro-1'H-spiro[pipendine-4,4'-quinolin]-1-yl)-5,6,7,8-tetrahydroquinazolin-4(3H)-one | (Test Target Compound 67) | 1.49-1.70 (m, 6 H), 1.77-1.93 (m, 4 H), 2.19-2.28 (m, 2 H), 2.31-2.40 (m, 2 H), 3.00-3.18 (m, 4 H), 4.17 (br d, J = 12.9 Hz, 2 H), 5.67 (br s, 1 H), 6.41-6.48 (m, 2 H), 6.80-6.87 (m, 1 H), 7.04-7.11 (m, 1 H) | DMSO-d6 | 351 [M + H]+ |
| 73 | 2-(3-oxo-3,4-dihydro-2H-spiro(isoquinoline-1,4'-piperidin]-yl)-5,6,7,8-tetrahydroquinazolin-4(3H)-one | (Test Target Compound 68) | 1.55-1.81 (m, 6 H), 1.90-2.08 (m, 2 H), 2.18-2.29 (m, 2 H), 2.33-2.43 (m, 2 H), 3.45-3.56 (m, 2 H), 3.59 (s, 2 H), 4.26 (br d, J = 14.8 Hz, 2 H), 7.18-7.28 (m, 3 H), 7.37-7.43 (m, 1 H), 8.22 (s, 1 H) | DMSO-d6 | 365 [M + H] |
| 74 | 2-(2'-oxo-2',3'-dihydro-1'H-spiro[piperidine-4,4'-quinolin]-1-yl)-5,6,7,8-tetrahydroquinazolin-4(3H)-one | (Test Target Compound 69) | 1.52-1.72 (m, 6 H), 1.73-1.89 (m, 2 H), 2.19-2.29 (m, 2 H), 2.32-2.41 (m, 2 H), 2.66 (s, 2 H), 3.16 (br t, J = 11.9 Hz, 2H), 4.18 (br d, J = 14.2 Hz, 2 H), 6.87-6.94 (m, 1 H), 6.94-7.02 (m, 1 H), 7.13-7.21 (m, 1 H), 7.29-7.36 (m, 1 H), 10.19 (br s, 1 H), 10.98 (br s, 1 H) | DMSO-d6 | 365 [M + H]+ |
| 75 | 2-(2',4'-dihydro-1'H-spiro[piperidine-4,3'-quinolin)-1-yl)-5,6,7,8-tetrahydroquinazolin-4(3H)-one | (Test Target Compound 70) | 1.26-1.44 (m, 4 H), 1.55-1.69 (m, 4 H), 2.19-2.27 (m, 2 H), 2.30-2.39 (m, 2 H), 2.52-2.56 (m, 2 H), 2.93-3.00 (m, 2 H), 3.51-3.61 (m, 4 H), 5.73 (br s, 1 H), 6.38-6.46 (m, 2 H), 6.81-6.88 (m, 2 H), 10.95 (br s, 1 H) | CDCl3 | 351 [M + H]+ |

TABLE 47

| Example | Compound Name | Structure | 1H NMR δ ppm | Solvent | ESI MS m/z |
|---|---|---|---|---|---|
| 76 | 2-(2'-oxo-2',4,-dihydro-1'H-spiro[pipendine-4,3'-quinolin]-1-yl)-5,6,7,6-tetrahydroquinazolin-4(3H)-one | (Test Target Compound 71) | 1.20-1.49 (m, 2 H), 1.53-1.88 (m, 6 H), 2.22 (br s, 2 H), 2.28-2.44 (m, 2 H), 2.83-2.98 (m, 2 H), 3.43-3.61 (m, 2 H), 3.76 (br s, 2 H), 6.79-7.03 (m, 2 H), 7.17 (br s, 2 H), 10.12 (br s, 1 H), 11.00 (br s, 1 H) | CDCl3 | 365 [M + H]+ |
| 77 | 2-(spiro[indoline-3,4'-piperidin]-1'-yl)-7,8-dihydro-3H-thiopyrano[4,3-d]pyrimidin-4(5H)-one | (Test Target Compound 3) | 1.78-1.98 (4 H, m), 2.83 (4 H, dd, J = 10.9, 4.9 Hz), 3.13 (2 H, s), 3.50-3.55 (4 H, m), 4.24 (2 H, br d, J = 13.5 Hz), 6.69-6.82 (2 H, m), 7.03-7.13 (2 H, m) | CDCl3-CD3OD | 355 [M + H]+ |
| 78 | 2-(spiro(indoline-3,4'-piperidin)-1'-yl)quinazolin-4(3H)-one | (Test Target Compound 4) | 1.83-2.14 (m, 4 H), 3.17-3.33 (m, 2 H), 3.59 (s, 2 H), 4.52 (br d, J = 13.8 Hz, 2 H), 6.67-6.80 (m, 2 H), 7.04-7.19 (m, 3 H), 7.38-7.47 (m, 1 H), 7.60 (dd, J = 7.7, 7.7 Hz, 1 H), 8.02 (dd, J = 7.9, 1.6 Hz, 1 H) | CDCl3 | 333 [M + H]+. |
| 79 | 8-methyl-2-spiro[indoline-3,4'-pipendin)-1'-yl)quinazolin-4(3H)-one | (Test Target Compound 22) | 1.87-2.12 (m, 4 H), 2.49 (s, 3 H), 3.24 (br t, J = 11.7 Hz, 2 H), 3.61 (s, 2 H), 4.51 (br d, J = 13.5 Hz, 2 H), 6.68-6.84 (m, 2 H), 6.99-7.15 (m, 3 H), 7.43-7.52 (m, 1 H), 7.90 (br d, J = 7.3 Hz, 1 H), 11.22 (br s, 1 H). | CDCl3 | 347 [M + H] |
| 80 | 2-(spiro[indoline-3,4'-pipendin]-1'-yl)-8-(trifluoromethyl)quinazolin-4(3H)-one | (Test Target Compound 6) | 1.61-1.86 (m, 4 H), 3.07-3.23 (m, 2 H), 3.43 (s, 2 H), 4.43 (br d, J = 13.8 Hz, 2 H), 5.54 (br s, 1 H), 6.46-6.57 (m, 2 H), 6.88-6.97 (m, 1 H), 6.97-7.05 (m, 1 H), 7.14-7.26 (m, 1 H), 7.90-7.97 (m, 1 H), 8.12-8.20 (m, 1 H), 11.60 (br s, 1 H) | DMSO-d6 | 401 [M + H]+ |

TABLE 47-continued

| Example | Compound Name | Structure | 1H NMR δ ppm | Solvent | ESI MS m/z |
|---|---|---|---|---|---|
| 81 | 2-[1-(cyclopropyl-methyl)spiro[indoline-3,4'-piperidin)-1'-yl)-5,6,7,8-tetrahydroquinazolin-4(3H)-one | (Test Target Compound 7) | 0.16-0.29 (m, 2 H), 0.49-0.62 (m, 2 H), 0.80-0.93 (m, 1 H), 1.75-2.06 (m, 8 H), 2.33-2.42 (m, 2 H), 2.44-2.52 (m, 2 H), 3.00 (d, J = 6.6 Hz, 2 H), 3.06-3.20 (m, 2 H), 3.44 (s, 2 H), 4.24-4.43 (m, 2 H), 6.47-6.54 (m, 1 H), 6.63-6.72 (m, 1 H), 6.99-7.06 (m, 1 H), 7.06-7.15 (m, 1 H) | CDCl3 | 391 [M + H]+ |

TABLE 48

| Example | Compound Name | Structure | 1H NMR δ ppm | Solvent | ESI MS m/z |
|---|---|---|---|---|---|
| 82 | 2-[1-(2,2,2-trifluoro-ethyl)spiro[indoline-3,4'-piperidin]-1'-yl)-5,6,7,8-tetrahydroquinazolin-4(3H)-one | (Test Target Compound 8) | 1.49-2.10 (m, 8 H), 2.36 (br s, J = 5.4Hz, 2 H), 2.48 (br s, J = 5.8Hz, 2 H), 2.98-3.08 (m, 2 H), 3.55 (s, 2 H), 3.70 (q, J = 8.1 Hz, 2 H), 4.41 (br d, J = 12.5 Hz, 2 H), 6.55 (d, J = 8.1Hz, 1 H), 6.78 (ddd, J = 8.1, 8.1, 1.0 Hz, 1 H), 7.06 (dd, J = 8.1, 1.0 Hz, 1 H), 7.15 (ddd, J = 8.1, 8.1, 1.0 Hz, 1 H) | CDCl3 | 419 [M + H]+ |
| 83 | 2-[1-(2-tert-butyldimethyl-silyloxy-ethyl)spiro[indoline-3,4'-piperidin]-1'-yl)-5,6,7,8-tetrahydroquinazolin-4(3H)-one | (Test Target Compound 9) | 0.06 (s, 6 H), 0.90 (s, 9 H), 1.65-1.77 (m, 4 H), 1.77-1.91 (m, 4 H), 2.34-2.42 (m, 2 H), 2.45-2.51 (m, 2 H), 3.00-3.16 (m, 2 H), 3.26 (t, J = 5.9 Hz, 2 H), 3.47 (s, 2 H), 3.83 (t, J = 5.9 Hz, 2 H), 4.21-4.34 (m, 2 H), 6.48 (d, J = 7.6 Hz, 1 H), 6.66 (dd, J = 7.6, 7.4 Hz, 1 H), 7.00 (d, J = 7.4 Hz, 1 H), 7.09 (dd, J = 7.6, 7.6 Hz, 1 H). | CDCl3 | 495 [M + H]+. |
| 84 | 2-[1-(2-hydroxy-ethyl)spiro[indoline-3,4'-piperidin]-1'-yl)-5,6,7,8-tetrahydnoquinazolin-4(3H)-one | (Test Target Compound 10) | 1.72-1.99 (m, 8 H), 2.32-2.42 (m, 2 H), 2.45-2.56 (m, 2 H), 3.13 (br t, J = 12.5 Hz, 2 H), 3.31 (t, J = 5.4 Hz, 2 H), 3.41 (s, 2 H), 3.85 (t, J = 5.4 Hz, 2 H), 4.36 (br d, J = 14.2 Hz, 2 H), 6.59 (d, J = 7.4 Hz, 1 H), 6.75 (dd, J = 7.4, 7.4 Hz, 1 H), 7.05 (d, J = 7.4 Hz, 1 H), 7.13 (dd, J = 7.4, 7.4 Hz, 1 H). | CDCl3 | 381 [M + H]+ |

TABLE 48-continued

| Example | Compound Name | Structure | 1H NMR δ ppm | Solvent | ESI MS m/z |
|---|---|---|---|---|---|
| 85 | 2-[1-(3-hydroxy-propyl)spiro[indoline-3,4'-piperidin]-1'-yl]-5,6,7,8-tetrahydroquinazolin-4(3H)-one | (Test Target Compound 11) | 1.62-2.02 (m, 10 H), 2.35 (br t, J = 5.8 Hz, 2 H), 2.43-2.55 (m, 2 H), 3.12 (br t, J = 11.4 Hz, 2 H), 3.28 (t, J = 6.8 Hz, 2 H), 3.36 (s, 2 H), 3.81 (t, J = 5.9 Hz, 2 H), 4.40 (br d, J = 13.8 Hz, 2 H), 6.58 (d, J = 7.9 Hz, 1 H), 6.68-6.77 (m, 1 H), 7.01-7.06 (m, 1 H), 7.13 (ddd, J = 7.7, 7.7, 1.2 Hz, 1 H) | CDCl3 | 395 [M + H]+ |
| 86 | 2-[1-(2-hydroxy-2-methyl-propyl)spiro[indoline-3,4'-piperidin]-1'-yl]-5,6,7,8-tetrahydroquinazolin-4(3H)-one | (Test Target Compound 12) | 1.31 (s, 6 H), 1.65-2.05 (m, 8 H), 2.33-2.41 (m, 2 H), 2.44-2.53 (m, 2H), 3.03-3.17 (m, 2 H), 3.07 (s, 2 H), 3.52 (s, 2 H), 4.36 (br d, J = 13.2 Hz, 2 H), 6.58-6.64 (m, 1 H), 6.70-6.78 (m, 1 H), 7.03-7.16 (m, 2 H), 11.27 (br s, 1 H) | CDCl3 | 409 [M + H]+ |

TABLE 49

| Example | Compound Name | Structure | 1H NMR δ ppm | Solvent | ESI MS m/z |
|---|---|---|---|---|---|
| 87 | 2-[1-(2-hydroxy-propyl)spiro[indoline-3,4'-piperidin]-1'-yl]-5,6,7,8-tetrahydroquinazolin-4(3H)-one | (Test Target Compound 13) | 1.27 (d, J = 6.3 Hz, 3 H), 1.60-2.10 (m, 8 H), 2.34 (br t, J = 5.8 Hz, 2 H), 2.48 (br t, J = 5.6 Hz, 2 H), 2.94-3.29 (m, 5 H), 3.53-3.67 (m, 1 H), 4.02-4.14 (m, 1 H), 4.36-4.50 (m, 2 H), 6.59 (d, J = 7.6 Hz, 1 H), 6.75 (dd, J = 7.3, 7.3 Hz, 1 H), 7.03-7.17 (m, 2 H), 11.94 (br s, 1 H) | CDCl3 | 395 [M + H]+ |
| 88 | 2-[1-(2-methoxy-ethyl)spiro[indoline-3,4'-piperidin]-1'-yl]-5,6,7,8-tetrahydroquinazolin-4(3H)-one | (Test Target Compound 14) | 1.45-2.01 (m, 8 H), 2.27-2.43 (m, 2 H), 2.43-2.56 (m, 2 H), 3.10 (br t, J = 11.2 Hz, 2 H), 3.27-3.37 (m, 2 H), 3.39 (s, 3 H), 3.45 (s, 2 H), 3.56-3.67 (m, 2 H), 4.37 (br d, J = 13.5 Hz, 2 H), 6.50 (d, J = 7.6 Hz, 1 H), 6.68 (dd, J = 7.3, 7.3 Hz, 1 H), 7.02 (d, J = 7.3 Hz, 1 H), 7.10 (dd, J = 7.3, 7.6 Hz, 1 H), 11.35 (br s, 1 H) | CDCl3 | 395 [M + H]+ |

TABLE 49-continued

| Example | Compound Name | Structure | 1H NMR δ ppm | Solvent | ESI MS m/z |
|---|---|---|---|---|---|
| 89 | 2-[1-(3-methoxy-propyl)spiro[indoline-3,4'-piperidin]-1'-yl]-5,6,7,8-tetrahydroquinazolin-4(3H)-one (Test Target Compound 15) | 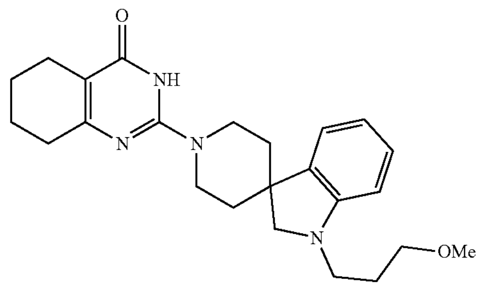 | 1.59-2.06 (m, 10 H), 2.28-2.42 (m, 2 H), 2.42-2.56 (m, 2 H), 3.10 (br t, J = 11.4 Hz, 2 H), 3.22 (t, J = 7.1 Hz, 2 H), 3.36 (s, 3 H), 3.36 (s, 2 H), 3.47 (t, J = 6.1 Hz, 2 H), 4.42 (br d, J = 13.5 Hz, 2H), 6.50 (d, J = 7.9 Hz, 1 H), 6.62-6.71 (m, 1 H), 6.98-7.05 (m, 1 H), 7.10 (t, J = 7.3 Hz, 1 H), 7.26 (s, 1 H), 11.87 (br s, 1 H) | CDCl3 | 409 [M + H]+ |
| 90 | (S)-2-[1-(2,3-dihydroxy-propyl)spiro[indoline-3,4'-piperidin]-1'-yl]-5,6,7,8-tetrahydroquinazolin-4(3H)-one (Test Target Compound 16) | 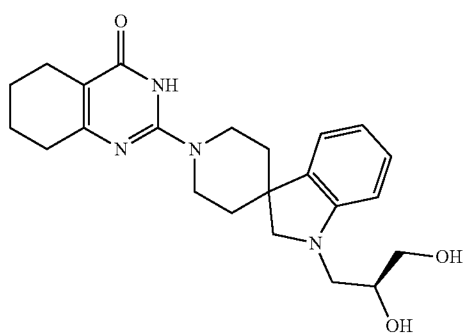 | 1.60-2.06 (m, 8 H), 2.30-2.42 (m, 2 H), 2.44-2.56 (m, 2 H), 3.00-3.20 (m, 3 H), 3.24-3.43 (m, 2 H), 3.47-3.70 (m, 3 H), 3.76-3.87 (m, 1 H), 3.98-4.07 (m, 1 H), 4.30-4.45 (m, 2 H), 6.59 (d, J = 7.9 Hz, 1 H), 6.75 (dd, J = 7.3, 7.3 Hz, 1 H), 7.04 (d, J = 7.3 Hz, 1 H), 7.08-7.17 (m, 1 H) | CDCl3 | 411 [M + H]+ |
| 91 | (R)-2-[1-(2,3-dihydroxy-propyl)spiro[indoline-3,4'-piperidin]-1'-yl]-5,6,7,8-tetrahydroquinazolin-4(3H)-one (Test Target Compound 17) | 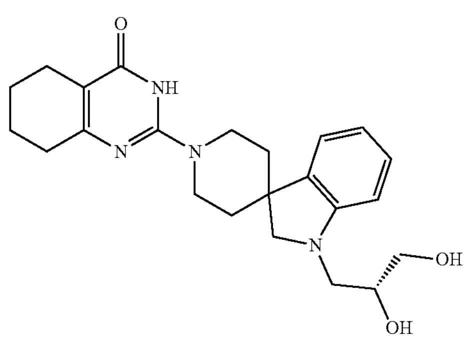 | 1.54-2.08 (m, 8 H), 2.27-2.41 (m, 2 H), 2.41-2.57 (m, 2 H), 2.96-3.20 (m, 3 H), 3.20-3.42 (m, 2 H), 3.45-3.71 (m, 3 H), 3.73-3.90 (m, 1 H), 3.94-4.10 (m, 1 H), 4.27-4.47 (m, 2 H), 6.57 (br d, J = 7.9 Hz, 1 H), 6.67-6.80 (m, 1 H), 6.96-7.22 (m, 2 H) | CDCl3 | 411 [M + H]+ |

TABLE 50

| Example | Compound Name | Structure | 1H NMR δ ppm | Solvent | ESI MS m/z |
|---|---|---|---|---|---|
| 92 | 2-[1-(2-hydroxy-3-methoxy-propyl)spiro[indoline-3,4'-piperidin]-1'-yl]-5,6,7,8-tetrahydroquinazolin-4(3H)-one | (Test Target Compound 18) | 1.60-2.03 (m, 8 H), 2.34 (br t, J = 5.6 Hz, 2 H), 2.44-2.54 (m, 2 H), 3.02-3.27 (m, 4 H), 3.35-3.56 (m, 4 H), 3.42 (s, 3 H), 4.02-4.11 (m, 1 H), 4.43 (br d, J = 12.5 Hz, 2 H), 6.55 (d, J = 7.9 Hz, 1 H), 6.72 (dd, J = 7.3, 7.3 Hz, 1 H), 7.04 (dd, J = 7.3, 1.0 Hz, 1 H), 7.08-7.15 (m, 1 H), 11.87 (br s, 1 H) | CDCl3 | 425 [M + H]+ |
| 93 | (S)-2-(1-{3-[(tert-butyldi-methylsilyl)oxy]-2-hydroxy-propyl}spiro[indoline-3,4'-piperidin]-1'-yl)-5,6,7,8-tetrahydroquinazolin-4(3H)-one | (Test Target Compound 19) | | | 511 [M + H]+ |
| 94 | (R)-2-(1-{3-[(tert-butyldimethyl-silyl)oxy]-2-hydroxy-propyl}spiro[indoline-3,4'-piperidin]-1'-yl)-5,6,7,8-tetrahydroquinazolin-4(3H)-one | (Test Target Compound 20) | | | 525 [M + H]+ |
| 95 | 2-[1-(3-(benzyl-oxy)propyl)spiro[indoline-3,4'-piperidin]-1'-yl]-5,6,7,8-tetrahydroquinazolin-4(3H)-one | (Test Target Compound 21) | 1.61-1.98 (m, 10 H), 2.34 (br t, J = 5.6 Hz, 2 H), 2.52 (br s, 2 H), 3.10 (br t, J = 11.2 Hz, 2H), 3.25 (t, J = 7.1 Hz, 2 H), 3.32 (s, 2 H), 3.58 (t, J = 6.1 Hz, 2 H), 4.41 (br d, J = 12.9 Hz, 2 H), 4.52 (s, 2 H), 6.50 (d, J = 7.7 Hz, 1 H), 6.66 (ddd, J = 7.7, 7.7, 1.0 Hz, 1 H), 7.01 (td, J = 7.7, 1.0 Hz, 1 H), 7.10 (ddd, J = 7.7, 7.7, 1.2 Hz, 1 H), 7.27-7.40 (m, 5 H) | CDCl3 | 485 [M + H]+ |

TABLE 50-continued

| Example | Compound Name | Structure | 1H NMR δ ppm | Solvent | ESI MS m/z |
|---|---|---|---|---|---|
| 96 | 2-[1-(2-methyl-benzyl)spiro[indoline-3,4''-piperidin]-1'-yl]-5,6,7,8-tetrahydroquinazolin-4(3H)-one | (Test Target Compound 24) | 1.63-2.12 (m, 8 H), 2.26-2.34 (m, 2 H), 2.35 (s, 3 H), 2.40-2.49 (m, 2 H), 3.01 (br t, J = 11.4 Hz, 2 H), 3.25 (s, 2 H), 4.25 (s, 2 H), 4.37 (br d, J = 13.8 Hz, 2 H), 6.53 (d, J = 7.9 Hz, 1 H), 6.71 (dd, J = 7.4, 7.4 Hz, 1 H), 7.00-7.36 (m, 6 H), 12.06 (br s, 1 H) | CDCl3 | 441 [M + H]+ |

TABLE 51

| Example | Compound Name | Structure | 1H NMR δ ppm | Solvent | ESI MS m/z |
|---|---|---|---|---|---|
| 97 | 2-[1-(2-fluoro-benzyl)spiro[indoline-3,4'-piperidin]-1'-yl]-5,6,7,8-tetrahydroquinazolin-4(3H)-one | (Test Target Compound 25) | 1.60-2.02 (m, 8 H), 2.33 (br t, J = 5.6 Hz, 2 H), 2.40-2.54 (m, 2 H), 3.04 (br t, J = 11.4 Hz, 2H), 3.37 (s, 2 H), 4.32-4.46 (m, 2 H), 4.37 (s, 2 H), 6.55 (d, J = 7.6 Hz, 1 H), 6.71 (dd, J = 7.3, 7.3 Hz, 1 H), 6.99-7.16 (m, 4 H), 7.20-7.41 (m, 2 H), 12.09 (br s, 1 H) | CDCl3 | 445 [M + H]+ |
| 98 | 2-[1-(2-methoxy-benzyl)spiro[indoline-3,4'-piperidin]-1'-yl]-5,6,7,8-tetrahydroquinazolin-4(3H)-one | (Test Target Compound 26) | 1.63-1.76 (m, 4 H), 1.77-2.11 (m, 4 H), 2.30-2.40 (m, 2 H), 2.41-2.52 (m, 2 H), 2.95-3.16 (m, 2 H), 3.41 (s, 2 H), 3.85 (s, 3 H), 4.27-4.48 (m, 2 H), 4.33 (s, 2 H), 6.49 (d, J = 7.6 Hz, 1 H), 6.62-6.74 (m, 1 H), 6.86-6.96 (m, 2 H), 7.00-7.14 (m, 2 H), 7.23-7.43 (m, 2 H), 11.98 (br s, 1 H) | CDCl3 | 457 [M + H]+ |

TABLE 51-continued

| Example | Compound Name | Structure | 1H NMR δ ppm | Solvent | ESI MS m/z |
|---|---|---|---|---|---|
| 99 | 2-[1-(3-methoxy-benzyl)spiro[indoline-3,4'-piperidin]-1'-yl]-5,6,7,8-tetrahydroquinazolin-4(3H)-one | (Test Target Compound 27) | 1.63-2.00 (m, 8 H), 2.34 (br t, J = 5.6 Hz, 2 H), 2.41-2.53 (m, 2 H), 3.03 (br t, J = 11.4 Hz, 2 H), 3.31 (s, 2 H), 3.79 (s, 3 H), 4.29 (s, 2 H), 4.38 (br d, J = 13.5 Hz, 2 H), 6.54 (d, J = 7.9 Hz, 1 H), 6.68-6.75 (m, 1 H), 6.83 (dd, J = 8.2, 2.0 Hz, 1 H), 6.89-6.96 (m, 2 H), 7.02-7.14 (m, 2 H), 7.20-7.33 (m, 1 H), 11.82 (br s, 1 H) | CDCl3 | 457 [M + H]+ |
| 100 | 2-[1-(pyridin-4-ylmethyl)spiro[indoline-3,4'-piperidin]-1'-yl]-5,6,7,8-tetrahydroquinazolin-4(3H)-one | (Test Target Compound 28) | 1.61-2.06 (m, 8 H), 2.35 (br t, J = 5.8 Hz, 2 H), 2.47 (br t, J = 5.8 Hz, 2 H), 2.97-3.13 (m, 2 H), 3.36 (s, 2 H), 4.32 (s, 2 H), 4.36-4.48 (m, 2 H), 6.45 (d, J = 7.9 Hz, 1 H), 6.70-6.80 (m, 1 H), 7.04-7.14 (m, 2 H), 7.25-7.31 (m, 2 H), 8.54-8.62 (m, 2 H), 12.03 (br s, 1 H) | CDCl3 | 428 [M + H]+ |
| 101 | 2-[1-(pyridin-3-ylmethyl)spiro[indoline-3,4'-piperidin]-1'-yl]-5,6,7,8-tetrahydroquinazolin-4(3H)-one | (Test Target Compound 29) | 1.62-1.70 (m, 2 H), 1.70-1.77 (m, 2 H), 1.81 (br d, J = 13.4 Hz, 2 H), 1.89-1.99 (m, 2 H), 2.33 (br t, J = 5.9 Hz, 2 H), 2.47 (br t, J = 5.6 Hz, 2 H), 3.02 (br t, J = 11.7 Hz, 2 H), 3.29 (s, 2 H), 4.33 (s, 2 H), 4.39 (br d, J = 13.7 Hz, 2 H), 6.54 (d, J = 7.6 Hz, 1 H), 6.74 (dd, J = 7.6, 7.3 Hz, 1 H), 7.06 (d, J = 7.3 Hz, 1 H), 7.11 (dd, J = 7.6, 7.6 Hz, 1 H), 7.29 (dd, J = 7.8, 4.8 Hz, 1 H), 7.68 (br d, J = 7.8 Hz, 1 H), 8.52-8.57 (m, 1 H), 8.58-8.64 (m, 1 H), 11.91 (br s, 1 H) | CDCl3 | 428 [M + H]+ |

TABLE 52

| Example | Compound Name | Structure | 1H NMR δ ppm | Solvent | ESI MS m/z |
|---|---|---|---|---|---|
| 102 | 2-[1-(pyridin-2-ylmethyl)spiro[indoline-3,4'-piperidin]-1'-yl]-5,6,7,8-tetrahydroquinazolin-4(3H)-one | (Test Target Compound 30) | 1.59-2.07 (m, 8 H), 2.29-2.40 (m, 2 H), 2.45-2.54 (m, 2 H), 3.07 (br t, J = 10.9 Hz, 2 H), 3.45 (s, 2 H), 4.39 (br d, J = 13.8 Hz, 2 H), 4.47 (s, 2 H), 6.49 (d, J = 7.9 Hz, 1 H), 6.65-6.78 (m, 1 H), 7.01-7.15 (m, 2 H), 7.15-7.25 (m, 1 H), 7.37 (d, J = 7.7 Hz, 1 H), 7.67 (ddd, J = 7.7, 7.7, 1.6 Hz, 1 H), 8.60 (br d, J = 4.6 Hz, 1 H) | CDCl3 | 428 [M + H]+ |
| 103 | 8-methyl-2-[1-(pyridin-3-ylmethyl)spiro[indoline-3,4-piperidin]-1'-yl]quinazolin-4(3H)-one | (Test Target Compound 31) | 1.85-1.97 (m, 2 H), 1.97-2.13 (m, 2 H), 2.48 (s, 3 H), 3.10-3.29 (m, 2 H), 3.35 (s, 2 H), 4.35 (s, 2 H), 4.52 (br d, J = 13.8 Hz, 2 H), 6.57 (d, J = 7.6 Hz, 1 H), 6.72-6.80 (m, 1 H), 7.01-7.17 (m, 3 H), 7.31 (dd, J = 8.1, 1.0 Hz, 1 H), 7.43-7.51 (m, 1 H), 7.67-7.75 (m, 1 H), 7.85-7.93 (m, 1 H), 8.55-8.61 (m, 1 H), 8.63-8.67 (m, 1 H), 11.61 (br s, 1 H) | CDCl3 | 438 [M + H]+ |
| 104 | 2-[1-(pyrimidin-5-ylmethyl)spiro[indoline-3,4'-piperidin]-1'-yl]-5,6,7,8-tetrahydroquinazolin-4(3H)-one | (Test Target Compound 32) | 1.65-2.06 (m, 8 H), 2.34 (br t, J = 5.8 Hz, 2 H), 2.47 (br t, J = 5.6 Hz, 2 H), 2.96-3.11 (m, 2 H), 3.32 (s, 2 H), 4.34 (s, 2 H), 4.42 (br d, J = 13.5 Hz, 2 H), 6.55 (d, J = 7.4 Hz, 1 H), 6.79 (ddd, J = 7.4, 7.4, 1.0 Hz, 1 H), 7.06-7.18 (m, 2 H), 8.76 (s, 2 H), 9.19 (s, 1 H), 12.08 (br s, 1 H) | CDCl3 | 429 [M + H]+ |
| 105 | 2-[1-(pyrimidin-2-ylmethyl)spiro[indoline-3,4-piperidin]-1'-yl]-5,6,7,8-tetrahydroquinazolin-4(3H)-one | (Test Target Compound 33) | 1.61-1.79 (m, 4 H), 1.79-2.10 (m, 4 H), 2.35 (br t, J = 5.6 Hz, 2 H), 2.48 (br t, J = 5.9 Hz, 2 H), 3.00-3.15 (m, 2 H), 3.60-3.71 (m, 2 H), 4.41 (br d, J = 13.8 Hz, 2 H), 4.58-4.65 (m, 2 H), 4.65 (m, 2 H), 6.58 (d, J = 7.9 Hz, 1 H), 6.68 (dd, J = 7.3, 7.3 Hz, 1 H), 7.00-7.11 (m, 2 H), 7.20 (t, J = 4.9 Hz, 1 H), 8.73 (d, J = 4.9 Hz, 2 H) | CDCl3 | 429 [M + H]+ |

TABLE 52-continued

| Example | Compound Name | Structure | 1H NMR δ ppm | Solvent | ESI MS m/z |
|---------|---------------|-----------|--------------|---------|------------|
| 106 | 2-{1-[(1H-pyrazol-3-yl)methyl]spiro[indoline-3,4'-piperidin]-1'-yl}-5,6,7,8-tetrahydroquinazolin-4(3H)-one (Test Target Compound 34) | 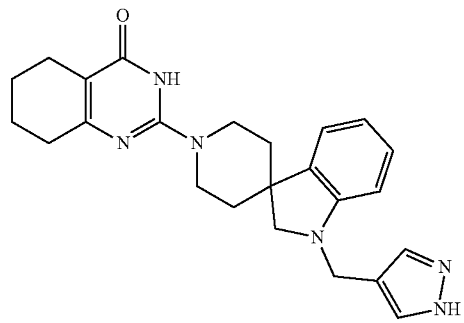 | 1.52-1.81 (m, 8 H), 2.16-2.30 (m, 2 H), 2.30-2.45 (m, 2 H), 2.92-3.06 (m, 2 H), 3.17 (s, 2 H), 4.05-4.18 (m, 2 H), 4.75 (m, 2 H), 6.50-6.61 (m, 2 H), 6.84-6.99 (m, 2 H), 7.34-7.53 (m, 2 H) | CD3OD | 417 [M + H]+ |

TABLE 53

| Example | Compound Name | Structure | 1H NMR δ ppm | Solvent | ESI MS m/z |
|---------|---------------|-----------|--------------|---------|------------|
| 107 | 2-(1-[(1-trityl-1H-pyrazol-4-yl)methyl]spiro[indoline-3,4'-piperidin]-1'-yl]-5,6,7,8-tetrahydroquinazolin-4(3H)-one (Test Target Compound 35) | 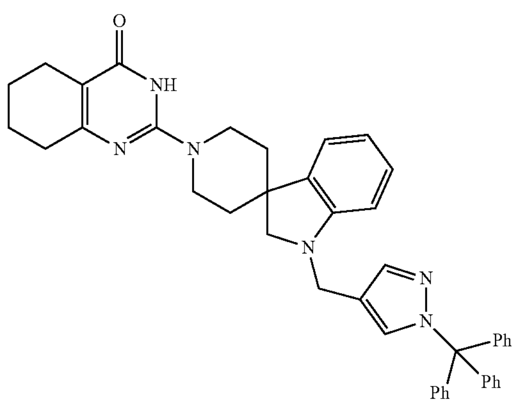 | 1.51-1.98 (m, 8 H), 2.30-2.38 (m, 2 H), 2.43-2.52 (m, 2 H), 3.01 (br t, J = 12.5 Hz, 2 H), 3.21 (s, 2 H), 4.18 (s, 2 H), 4.35-4.45 (m, 2 H), 6.55 (br d, J = 7.8 Hz, 1 H), 6.65-6.73 (m, 1 H), 6.97-7.03 (m, 1 H), 7.03-7.20 (m, 7 H), 7.20-7.35 (m, 10 H), 7.58 (s, 1 H), 11.84 (br s, 1 H) | CDCl3 | 659 [M + H]+ |
| 108 | 2-[1-(furan-2-ylmethyl)spiro[indoline-3,4'-piperidin]-1'-yl]-5,6,7,8-tetrahydroquinazolin-4(3H)-one (Test Target Compound 36) | 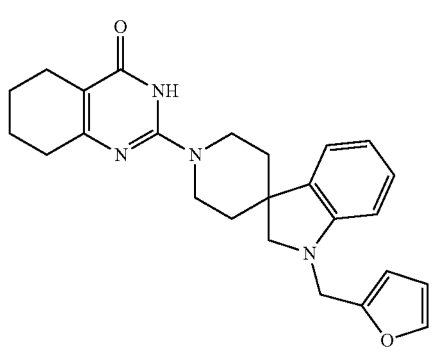 | 1.60-2.01 (m, 8 H), 2.34 (br t, J = 5.6 Hz, 2 H), 2.41-2.54 (m, 2 H), 3.06 (br t, J = 11.2 Hz, 2 H), 3.36 (s, 2 H), 4.31 (s, 2 H), 4.40 (br d, J = 13.8 Hz, 2 H), 6.22 (d, J = 3.3 Hz, 1 H), 6.32 (dd, J = 3.1, 1.8 Hz, 1 H), 6.62 (d, J = 7.9 Hz, 1 H), 6.72 (ddd, J = 7.7, 7.4, 1.0 Hz, 1 H), 7.00-7.07 (m, 1 H), 7.12 (ddd, J = 7.9, 7.7, 1.2 Hz, 1 H), 7.37 (dd, J = 1.8, 0.8 Hz, 1 H), 11.84 (br s, 1 H) | CDCl3 | 417 [M + H]+ |

TABLE 53-continued

| Example | Compound Name | Structure | 1H NMR δ ppm | Solvent | ESI MS m/z |
|---|---|---|---|---|---|
| 109 | 2-[1-(thiophen-2-yl-methyl)spiro[indoline-3,4'-piperidin]-1'-yl]-5,6,7,8-tetrahydroquinazolin-4(3H)-one | (Test Target Compound 37) | 1.56-2.00 (m, 8 H), 2.34 (br t, J = 5.6 Hz, 2 H), 2.42-2.53 (m, 2 H), 2.97-3.11 (m, 2 H), 3.33 (s, 2 H), 4.37 (br d, J = 13.5 Hz, 2 H), 4.51 (s, 2 H), 6.62 (d, J = 7.9 Hz, 1 H), 6.73 (ddd, J = 7.7, 7.3, 1.0 Hz, 1 H), 6.94-7.01 (m, 2 H), 7.04 (dd, J = 7.3, 1.0 Hz, 1 H), 7.13 (ddd, J = 7.9, 7.7, 1.0 Hz, 1 H), 7.20-7.25 (m, 1 H), 11.72 (br s, 1 H) | CDCl3 | 433 [M + H]+ |
| 110 | 2-[1-(isoquinolin-3-ylmethyl)spiro[indoline-3,4'-piperidin]-1'-yl]-5,6,7,8-tetrahydroquinazolin-4(3H)-one | (Test Target Compound 38) | 1.60-2.05 (m, 8 H), 2.34 (br t, J = 5.4 Hz, 2 H), 2.46 (br t, J = 5.4 Hz, 2 H), 2.94-3.10 (m, 2 H), 3.42 (s, 2 H), 4.32-4.47 (m, 2 H), 4.63 (s, 2 H), 6.55 (d, J = 8.1 Hz, 1 H), 6.74 (dd, J = 8.1, 8.1 Hz, 1 H), 7.09-7.14 (m, 2 H), 7.47-7.60 (m, 2 H), 7.69-7.78 (m, 1 H), 7.79-7.82 (m, 1 H), 8.09 (d, J = 8.1 Hz, H), 8.14 (d, J = 8.1 Hz, 1 H), 11.84 (br s, 1 H) | CDCl3 | 478 [M + H]+ |

TABLE 54

| Example | Compound Name | Structure | 1H NMR δ ppm | Solvent | ESI MS m/z |
|---|---|---|---|---|---|
| 111 | 2-(1-phenylethyl)spiro[indoline-3,4'-piperidin]-1'-yl)-5,6,7,8-tetrahydroquinazolin-4(3H)-one | (Test Target Compound 39) | 1.62-1.97 (m, 8 H), 2.35 (br t, J = 5.8 Hz, 2 H), 2.43-2.61 (m, 2 H), 2.91 (t, J = 8.1 Hz, 2 H), 2.97-3.13 (m, 2 H), 3.32 (s, 2 H), 3.39 (t, J = 8.1 Hz, 2 H), 4.40 (br d, J = 13.5 Hz, 2 H), 6.50 (d, J = 7.9 Hz, 1 H), 6.68 (td, J = 7.9, 0.8 Hz, 1 H), 7.01 (dd, J = 7.3, 0.8 Hz, 1 H), 7.09-7.18 (m, 1 H), 7.18-7.47 (m, 5 H), 11.82 (br s, 1 H) | CDCl3 | 441 [M + H]+ |

TABLE 54-continued

| Example | Compound Name | Structure | 1H NMR δ ppm | Solvent | ESI MS m/z |
|---|---|---|---|---|---|
| 112 | ((S)-2-(1-(pyrrolidin-2-ylmethyl)spiro[indoline-3,4'-piperidin]-1'-yl)-5,6,7,8-tetrahydroquinazolin-4(3H)-one (Test Target Compound 40) | 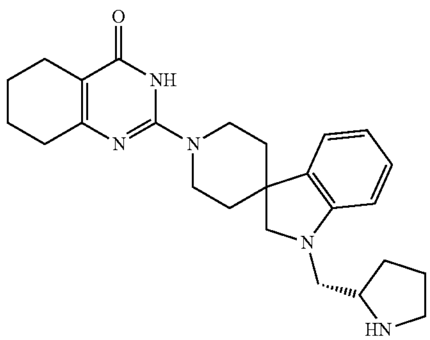 | 1.41-1.53 (m, 1 H), 1.60-1.99 (m, 11 H), 2.35 (br t, J = 6.0 Hz, 2 H), 2.47 (br t, J = 5.9 Hz, 2 H), 2.89-2.96 (m, 1 H), 2.99-3.20 (m, 5 H), 3.35-3.39 (m, 1 H), 3.40-3.47 (m, 1 H), 3.47-3.52 (m, 1 H), 4.33-4.44 (m, 2 H), 6.52 (d, J = 7.8 Hz, 1 H), 6.64-6.71 (m, 1 H), 7.01 (d, J = 7.3 Hz, 1 H), 7.09 (ddd, J = 7.8, 7.7, 1.0 Hz, 1 H) | CDCl3 | 420 [M + H]+ |
| 113 | (S)-2-[1-(1-methylpyrrolidin-2-ylmethyl)spiro[indoline-3,4'-piperidin]-1'-yl]-5,6,7,8-tetrahydroquinazolin-4(3H)-one (Test Target Compound 41) | 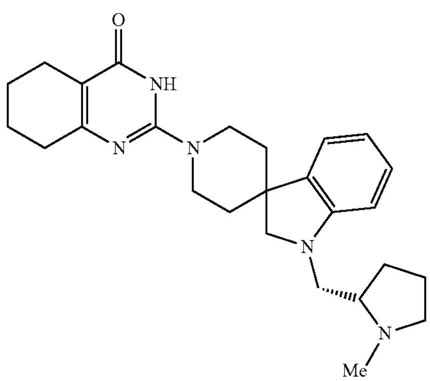 | 1.54-1.96 (m, 12 H), 2.32-2.39 (m, 2 H), 2.43-2.52 (m, 2 H), 2.46 (s, 3H), 2.92-2.98 (m, 1 H), 2.99-3.19 (m, 5 H), 3.27-3.35 (m, 1 H), 3.36-3.46 (m, 2 H), 4.33-4.42 (m, 2 H), 6.51 (d, J = 7.8 Hz, 1 H), 6.67 (dd, J = 7.2, 7.2 Hz, 1 H), 7.02 (d, J = 7.2 Hz, 1 H), 7.07-7.13 (m, 1 H), 11.66 (br s, 1 H) | CDCl3 | 434 [M + H]+ |
| 114 | (S)-tert-butyl 2-{(1'-(4-oxo-3,4,5,6,7,8-hexahydroquinazolin-2-yl)spiro[indoline-3,4'-piperidin]-1-yl]methyl}pyrrolidine-1-carboxylate (Test Target Compound 42) | 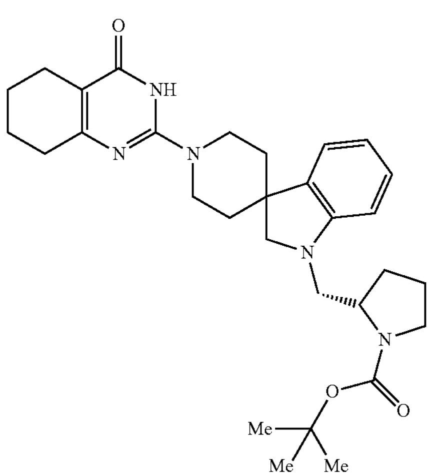 | 1.48, 1.53 (5:4) (s, 9 H), 1.64-2.02 (m, 12 H), 2.31-2.39 (m, 2 H), 2.44-2.55 (m, 2 H), 3.03-3.15 (m, 2 H), 3.16-3.54 (m, 6 H), 3.99-4.16 (m, 1 H), 4.43 (br d, J = 12.7 Hz, 2 H), 6.49-6.62 (m, 1 H), 6.61-6.73 (m, 1 H), 6.97-7.07 (m, 1 H), 7.07-7.13 (m, 1 H), 12.00 (br s, 1 H) | CDCl3 | 520 [M + H]+ |

TABLE 54-continued

| Example | Compound Name | Structure | 1H NMR δ ppm | Solvent | ESI MS m/z |
|---|---|---|---|---|---|
| 115 | 2-{1-[(3-methyloxetan-3-yl)methyl]spiro[indoline-3,4'-piperidin]-1'-yl}-5,6,7,8-tetrahydroquinazolin-4(3H)-one (Test Target Compound 43) | 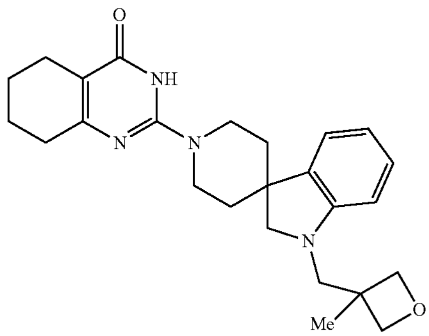 | 1.41 (s, 3 H), 1.64-1.86 (m, 6 H), 1.90-2.00 (m, 2 H), 2.35 (br t, J = 5.9 Hz, 2 H), 2.48 (br t, J = 5.7 Hz, 2 H), 3.04-3.14 (m, 2 H), 3.30 (s, 2 H), 3.33 (s, 2 H), 4.35-4.42 (m, 2 H), 4.43 (d, J = 5.9 Hz, 2 H), 4.59 (d, J = 5.9 Hz, 2 H), 6.48 (d, J = 7.8 Hz, 1 H), 6.67-6.75 (m, 1 H), 7.05 (d, J = 7.3 Hz, 1 H), 7.11 (ddd, J = 7.7, 7.3, 1.0 Hz, 1 H), 012.11 (br s, 1 H) | CDCl3 | 421 [M + H] |

TABLE 55

| Example | Compound Name | Structure | 1H NMR δ ppm | Solvent | ESI MS m/z |
|---|---|---|---|---|---|
| 116 | Ethyl 2-[1'-(4-oxo-3,4,5,6,7,8-hexahydroquinazolin-2-yl)spiro[indoline-3,4'-piperidin]-1-yl]acetate (Test Target Compound 44) | 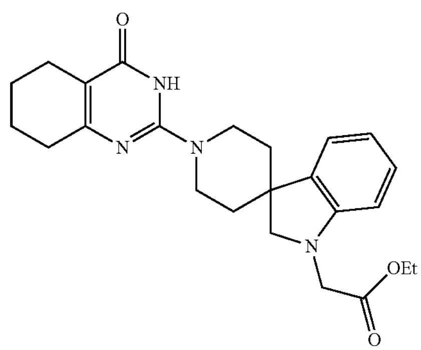 | 1.22-1.45 (m, 3 H), 1.71-2.01 (m, 8 H), 2.32-2.43 (m, 2 H), 2.43-2.60 (m, 2 H), 3.01-3.17 (m, 2 H), 3.51-3.64 (m, 2 H), 3.91-4.03 (m, 2 H), 4.20 (br t, J = 7.3 Hz, 2 H), 4.30-4.52 (m, 2 H), 6.36-6.52 (m, 1 H), 6.67-6.79 (m, 1 H), 7.01-7.18 (m, 2 H). | CDCl3 | 423 [M + H]+ |
| 117 | Methyl-2-[1'-(4-oxo-3,4,5,6,7,8-hexahydroquinazolin-2-yl)spiro[indoline-3,4'-piperidin]-1-yl]acetamide (Test Target Compound 45) | 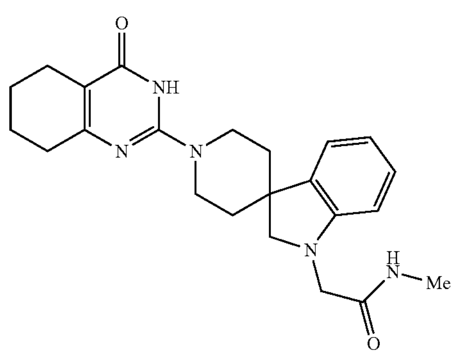 | 1.60-2.05 (m, 8 H), 2.36 (br t, J = 5.9 Hz, 2 H), 2.49 (br t, J = 5.9 Hz, 2 H), 2.88 (d, J = 4.9 Hz, 3 H), 3.05-3.18 (m, 2 H), 3.45 (s, 2 H), 3.72 (s, 2 H), 4.43 (br d, J = 13.5 Hz, 2 H), 6.49 (d, J = 7.6 Hz, 1 H), 6.63-6.73 (m, 1 H), 6.81-6.88 (m, 1 H), 7.08-7.19 (m, 2 H). | CDCl3 | 408 [M + H]+ |

TABLE 55-continued

| Example | Compound Name | Structure | 1H NMR δ ppm | Solvent | ESI MS m/z |
|---|---|---|---|---|---|
| 118 | N-(2-morpholinoethyl)-2-[1'-(4-oxo-3,4,5,6,7,8-hexahydroquinazolin-2-yl)spiro[indoline-3,4'-piperidin]-1-yl]acetamide | (Test Target Compound 46) | 1.60-2.08 (m, 8 H), 2.29-2.40 (m, 6 H), 2.40-2.55 (m, 4 H), 3.05-3.19 (m, 2 H), 3.36-3.55 (m, 8 H), 3.74 (s, 2 H), 4.38 (m, 2 H), 6.44-6.49 (m, 1 H), 6.77-6.88 (m, 1 H), 7.08-7.16 (m, 2 H), 7.17-7.22 (m, 1 H) | CDCl3 | 254 [M + H]2+ |
| 119 | N-(2-hydroxyethyl)-2-[1'-(4-oxo-3,4,5,6,7,8-hexahydroquinazolin-2-yl)spiro[indoline-3,4'-piperidin]-1-yl]acetamide | (Test Target Compound 47) | 1.53-2.09 (m, 8 H), 2.27-2.42 (m, 2 H), 2.42-2.59 (m, 2 H), 3.12 (br t, J = 11.4 Hz, 2 H), 3.36-3.57 (m, 2 H), 3.44 (s, 2 H), 3.70-3.82 (m, 2 H), 3.75 (s, 2 H), 4.39 (br d, J = 13.2 Hz, 2 H), 6.52 (br d, J = 7.6 Hz, 1 H), 6.72-6.97 (m, 1 H), 7.03-7.21 (m, 2 H). | CDCl3 | 438 [M + H]+ |
| 120 | 2-[1-(pyrimidin-2-yl)spiro[indoline-3,4'-piperidine]-1'-yl)-5,6,7,8-tetrahydroquinazolin-4(3H)-one | (Test Target Compound 49) | 1.61-1.91 (m, 6 H), 2.02 (td, J = 13.1, 4.1 Hz, 2 H), 2.34 (br t, J = 5.8 Hz, 2 H), 2.48 (br t, J = 5.9 Hz, 2 H), 3.09-3.23 (m, 2 H), 4.23 (s, 2 H), 4.57 (br d, J = 13.8 Hz, 2 H), 6.75 (t, J = 4.8 Hz, 1 H), 6.96-7.05 (m, 1 H), 7.16-7.22 (m, 1 H), 7.22-7.33 (m, 1 H), 8.44 (d, J = 8.2 Hz, 1 H), 8.54 (d, J = 4.9 Hz, 2 H), 12.02 (br s, 1 H) | CDCl3 | 415 [M + H]+ |

TABLE 56

| Example | Compound Name | Structure | 1H NMR δ ppm | Solvent | ESI MS m/z |
|---|---|---|---|---|---|
| 121 | 2-(1-acetylspiro[indoline-3,4'-piperidin]-1'-yl)-5,6,7,8-tetrahydroquinazolin-4(3H)-one (Test Target Compound 50) | 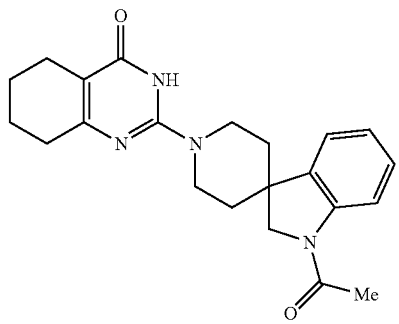 | 1.55-1.82 (m, 8 H), 2.15-2.30 (m, 4 H), 2.32-2.40 (m, 2 H), 2.90-3.10 (m, 2 H), 3.30 (s, 3 H), 4.10 (s, 2 H), 4.28-4.42 (m, 2 H), 6.88-7.05 (m, 1 H), 7.12-7.20 (m, 1 H), 7.21-7.31 (m, 1 H), 8.00-8.10 (m, 1 H), 11.05 (br. s, 1 H). | DMSO-d6 | 379 [M + H]+ |
| 122 | 2-{1-(methylsulfonyl)spiro[indoline-3,4'-piperidin]-1'-yl}-5,6,7,8-tetrahydroquinazolin-4(3H)-one (Test Target Compound 51) | 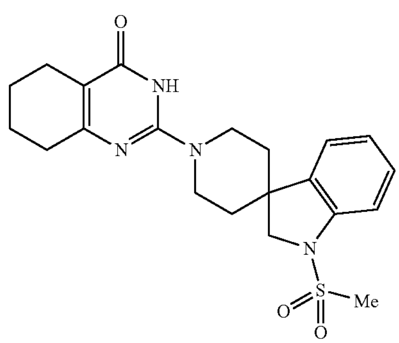 | 1.59-1.82 (m, 8 H), 2.20-2.30 (m, 2 H), 2.35-2.42 (m, 2 H), 2.95-3.04 (m, 2 H), 3.06 (s, 3 H), 3.93 (s, 2 H), 4.30-4.40 (m, 2 H), 7.01-7.09 (m, 1 H), 7.20-7.33 (m, 3 H), 11.03 (br. s, 1 H). | DMSO-d6 | 415 [M + H]+ |
| 123 | Benzyl 1'-(4-oxo-3,4,5,6,7,8-hexahydroquinazolin-2-yl)spiro[indoline-5,4'-piperidin]-1-carboxylate (Test Target Compound 52) | 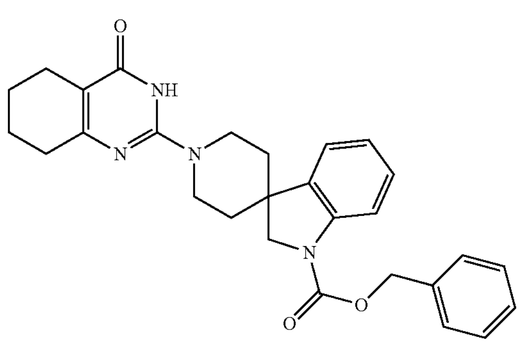 | 1.50-1.84 (4 H, m), 1.84-2.08 (4 H, m), 2.35 (2 H, br t, J = 5.8 Hz), 2.47 (2 H, br t, J = 5.9 Hz), 3.03 (2 H, br t, J = 12.4 Hz), 3.93-4.07 (2 H, m), 4.48 (2 H, br d, J = 13.5 Hz), 5.30 (2 H, br s), 6.97-7.05 (1 H, m), 7.12 (1 H, d, J = 7.5 Hz), 7.18-7.25 (1 H, m), 7.28-7.51 (6 H, m), 7.60 (1 H, d, J = 2.0 Hz). | CDCl3 | 471 [M + H]+ |

TABLE 56-continued

| Example | Compound Name | Structure | 1H NMR δ ppm | Solvent | ESI MS m/z |
|---|---|---|---|---|---|
| 124 | Benzyl 1'-(6,6-difluoro-4-oxo-3,4,5,6,7,8-hexahydroquinazolin-2-yl)spiro[indoline-5,4'-piperidin]-1-carboxylate | (Test Target Compound 54) | 1.73-2.04 (m, 4 H), 2.08-2.34 (m, 2 H), 2.60-2.79 (m, 2 H), 2.79-2.90 (m, 2 H), 2.98-3.21 (m, 2 H), 3.93-4.14 (m, 2 H), 4.46-4.67 (m, 2 H), 5.29 (s, 2 H), 6.91-7.06 (m, 1 H), 7.06-7.15 (m, 1 H), 7.16-7.25 (m, 1 H), 7.29-7.61 (m, 5 H), 7.83-8.05 (m, 1 H), 12.08 (br s, 1 H) | CDCl3 | 507 [M + H]+ |
| 125 | 2-(1-methylspiro[indoline-3,4'-piperidin]-1'-yl)-5,6,7,8-tetrahydroquinazolin-4(3H)-one | (Test Target Compound 122) | 1.63-1.97 (m, 8 H), 2.32-2.36 (m, 2 H), 2.45-2.50 (m, 2 H), 2.80 (s, 3 H), 3.07-3.16 (m, 2 H), 3.30 (s, 2 H), 4.39-4.45 (m, 2 H), 6.50-6.53 (m, 1 H), 6.68-6.73 (m, 1 H), 7.01-7.04 (m, 1 H), 7.10-7.15 (m, 1 H), 11.95 (br s, 1 H). | CDCl3 | 351 [M + H]+ |

TABLE 57

| Example | Compound Name | Structure | 1H NMR δ ppm | Solvent | ESI MS m/z |
|---|---|---|---|---|---|
| 126 | 2-(1-(4-methoxybenzyl)spiro[indoline-3,4'-piperidin]-1'-yl]-5,6,7,8-tetrahydro-quinazolin-4(3H)-one | (Test Target Compound 123) | 1.64-1.96 (m, 8 H), 2.31-2.36 (m, 2 H), 2.44-2.49 (m, 2 H), 2.97-3.06 (m, 2 H), 3.26 (s, 2 H), 3.81 (s, 3 H), 4.25 (s, 2 H), 4.32-4.39 (m, 2 H), 6.53-6.57 (m, 1 H), 6.67-6.72 (m, 1 H), 6.85-6.90 (m, 2 H), 7.02-7.05 (m, 1 H), 7.07-7.12 (m, 1 H), 7.23-7.27 (m, 2 H), 11.74 (br s, 1 H). | CDCl3 | 457 [M + H]+ |

TABLE 57-continued

| Example | Compound Name | Structure | 1H NMR δ ppm | Solvent | ESI MS m/z |
|---|---|---|---|---|---|
| 127 | 2-oxo-2-(1'-(4-oxo-3,4,5,6,7,8-hexa-hydroquinazolin-2-yl)spiro[indoline-3,4'-piperidin]-1-yl)ethyl-acetate | (Test Target Compound 124) | 1.43 (t, J = 7.1 Hz, 3 H), 1.63-1.84 (m, 6 H), 1.94-2.64 (m, 2 H), 2.30-2.37 (m, 2 H), 2.45-2.51 (m, 2 H), 2.98-3.08 (m, 2 H), 4.20 (s, 2 H), 4.41 (q, J = 7.1 Hz, 2 H), 4.50-4.57 (m, 2 H), 7.14-7.23 (m, 2 H), 7.27-7.32 (m, 1 H), 8.21-8.24 (m, 1 H), 12.16 (br s, 1 H). | CDCl3 | 437 [M + H]+ |
| 128 | 2-oxo-2-(1'-(4-oxo-3,4,5,6,7,8-hexahydroquinazolin-2-yl)spiro[indoline-3,4'-piperidin]-1-yl)-acetic acid | (Test Target Compound 125) | 1.59-1.72 (m, 6 H), 1.77-1.86 (m, 2 H), 2.23-2.28 (m, 2 H), 2.37-2.42 (m, 2 H), 2.93-3.03 (m, 2 H), 4.15 (s, 2 H), 4.32-4.39 (m, 2 H), 7.11-7.16 (m, 1 H), 7.25-7.30 (m, 1 H), 7.25-7.30 (m, 1 H), 7.36-7.39 (m, 1 H), 8.00-8.03 (m, 1 H). | DMSO-d6 | 409 [M + H]+ |
| 129 | N,N-dimethyl-1'-(4-oxo-3,4,5,6,7,8-hexahydroquinazolin-2-yl)spiro[indoline-3,4'-piperidin]-1-carboxamide | (Test Target Compound 126) | 1.65-1.82 (m, 6 H), 1.90-1.99 (m, 2 H), 2.33-2.38 (m, 2 H), 2.45-2.50 (m, 2 H), 2.95 (s, 6 H), 3.05-3.13 (m, 2 H), 3.87 (s, 2 H), 4.40-4.47 (m, 2 H), 6.90-6.95 (m, 2 H), 7.11-7.14 (m, 1 H), 7.16-7.21 (m, 1 H), 11.61 (br. s, 1 H). | CDCl3 | 408 [M + H]+ |

TABLE 57-continued

| Example | Compound Name | Structure | 1H NMR δ ppm | Solvent | ESI MS m/z |
|---|---|---|---|---|---|
| 130 | 2-oxo-2-(1'-(4-oxo-3,4,5,6,7,8-hexahydroquinazolin-2-yl)spiro[indoline-3,4'-piperidin]-1-yl)ethyl-acetate (Test Target Compound 127) | 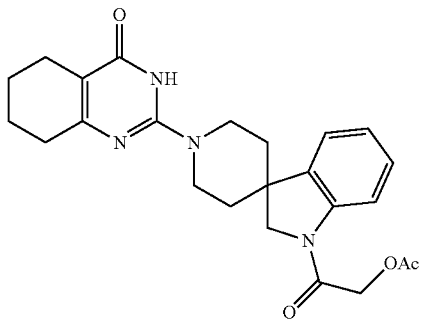 | 1.64-1.84 (m, 6 H), 1.95-2.06 (m, 2 H), 2.25 (s, 3 H), 2.31-2.37 (m, 2 H), 2.46-2.51 (m, 2 H), 2.99-3.08 (m, 2 H), 3.96 (s, 2 H), 4.53-4.61 (m, 2 H), 4.81 (s, 2 H), 7.07-7.12 (m, 1 H), 7.14-7.19 (m, 1 H), 7.23-7.28 (m, 1 H), 8.19-8.24 (m, 1 H), 11.23 (br. s, 1 H). | CDCl3 | 437 [M + H]+ |

TABLE 58

| Example | Compound Name | Structure | 1H NMR δ ppm | Solvent | ESI MS m/z |
|---|---|---|---|---|---|
| 131 | 2-(1-(2-hydroxyacetyl)spiro[indoline-3,4'-piperidin]-1'-yl)-5,6,7,8-tetrahydroquinazolin-4(3H)-one (Test Target Compound 128) | 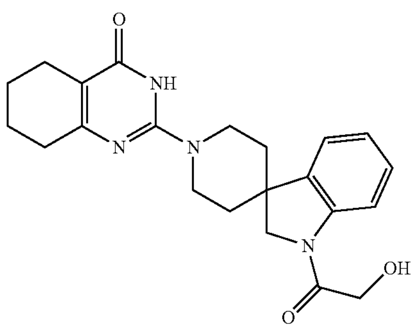 | 1.60-1.71 (m, 6 H), 1.74-1.83 (m, 2 H), 2.23-2.28 (m, 2 H), 2.36-2.41 (m, 2 H), 2.96-3.05 (m, 2 H), 4.00 (s, 2 H), 4.24-4.28 (m, 2 H), 4.32-4.40 (m, 2 H), 4.85-4.89 (m, 1 H), 7.01-7.05 (m, 1 H), 7.19-7.24 (m, 1 H), 7.27-7.31 (m, 1 H), 8.07-8.11 (m, 1 H), 11.07 (br. s, 1 H). | DMSO-d6 | 395 [M + H]+ |
| 132 | 2-(1-(2-benzyloxycarbonyl-aminoacetyl)spiro[indoline-3,4'-piperidin]-1'-yl)-5,6,7,8-tetrahydroquinazolin-4(3H)-one (Test Target Compound 129) | 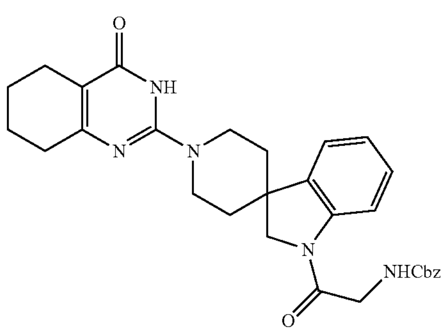 | 1.65-1.81 (m, 6 H), 1.95-2.04 (m, 2 H), 2.32-2.37 (m, 2 H), 2.46-2.51 (m, 2 H), 2.98-3.07 (m, 2 H), 3.95 (s, 2 H), 4.15-4.19 (m, 2 H), 4.49-4.56 (m, 2 H), 5.16 (s, 2 H), 5.85 (br. s, 1 H), 7.08-7.13 (m, 1 H), 7.14-7.18 (m, 1 H), 7.24-7.29 (m, 1 H), 7.30-7.41 (m, 5 H), 8.17-8.22 (m, 1 H), 11.69 (br. s, 1 H). | CDCl3 | 528 [M + H]+ |

TABLE 58-continued

| Example | Compound Name | Structure | 1H NMR δ ppm | Solvent | ESI MS m/z |
|---|---|---|---|---|---|
| 133 | 2-(1-glycyl-spiro[indoline-3,4'-piperidin]-1'-yl)-5,6,7,8-tetrahydroquinazolin-4(3H)-one | (Test Target Compound 130) | 1.59-1.71 (m, 6 H), 1.74-1.83 (m, 2 H), 2.23-2.29 (m, 2 H), 2.36-2.41 (m, 2 H), 2.98-3.07 (m, 2 H), 3.55 (s, 2 H), 4.02 (s, 2 H), 4.32-4.40 (m, 2 H), 7.00-7.05 (m, 1 H), 7.18-7.23 (m, 1 H), 7.27-7.30 (m, 1 H), 8.08-8.12 (m, 1 H). | DMSO-d6 | 394 [M + H]+ |
| 134 | N-(2-oxo-2-(1'-(4-oxo-3,4,5,6,7,8-hexahydroquinazoline-2-yl)spiro[indoline-3,4'-piperidin]-1'-yl]ethyl)acetamide | (Test Target Compound 131) | 1.60-1.71 (m, 6 H), 1.75-1.84 (m, 2 H), 1.93 (s, 3 H), 2.24-2.29 (m, 2 H), 2.36-2.41 (m, 2 H), 3.00-3.09 (m, 2 H), 4.09-4.14 (m, 4 H), 4.32-4.41 (m, 2 H), 7.01-7.06 (m, 1 H), 7.18-7.23 (m, 1 H), 7.28-7.31 (m, 1 H), 8.04-8.08 (m, 1 H), 8.12-8.16 (m, 1 H), 11.07 (br. s, 1 H). | DMSO-d6 | 436 [M + H]+ |
| 135 | 7-methyl-2-(1-methylspiro[indoline-3,4'-piperidin]-1'-yl)-3,7-dihydro-4H-pyrrolo[2,3-d]pyrimidin-4-one | (Test Target Compound 132) | 1.82-1.89 (m, 2 H), 1.95-2.03 (m, 2 H), 2.80 (s, 3 H), 3.15-3.24 (m, 2 H), 3.32 (s, 2 H), 3.62 (s, 3 H), 4.36-4.43 (m, 2 H), 6.45 (d, J = 3.5 Hz, 1 H), 6.50-6.53 (m, 1 H), 6.55 (d, J = 3.5 Hz, 1 H), 6.68-6.73 (m, 1 H), 7.02-7.05 (m, 1 H), 7.10-7.15 (m, 1 H), 10.98 (br. s, 1 H). | CDCl3 | 350 [M + H]+ |

TABLE 59

| Example | Compound Name | Structure | 1H NMR δ ppm | Solvent | ESI MS m/z |
|---|---|---|---|---|---|
| 136 | 7-ethyl-2-(1-methyl-spiro[indoline-3,4'-piperidin]-1'-yl)-3,7-dihydro-4H-pyrrolo[2,3-d]pyrimidin-4-one | (Test Target Compound 133) | 1.39 (t, J = 7.3 Hz, 3 H), 1.81-1.88 (m, 2 H), 1.94-2.03 (m, 2 H), 2.80 (s, 3 H), 3.14-3.23 (m, 2 H), 3.31 (s, 2 H), 4.04 (q, J = 7.3 Hz, 2 H), 4.33-4.41 (m, 2H), 6.46 (d, J = 3.4 Hz, 1 H), 6.50-6.53 (m, 1 H), 6.60 (d, J = 3.4 Hz, 1 H), 6.68-6.73 (m, 1 H), 7.02-7.05 (m, 1 H), 7.10-7.15 (m, 1 H), 10.95 (br. s, 1 H). | CDCl3 | 364 [M + H]+ |
| 137 | 7-(hydroxyethyl)-2-(1-methylspiro[indoline-3,4'-piperidin]-1'-yl)pyrrolo[2,3-d]pyrimidin-4-one | (Test Target Compound 134) | 1.83-1.90 (m, 2 H), 1.94-2.03 (m, 2 H), 2.80 (s, 3 H), 3.15-3.24 (m, 2 H), 3.30 (s, 2 H), 3.92-3.97 (m, 2 H), 4.16-4.20 (m, 2 H), 4.24-4.32 (m, 2 H), 4.44 (br. s, 1 H), 6.43-6.45 (m, 1 H), 6.50-6.53 (m, 1 H), 6.57 (d, J = 3.4 Hz, 1 H), 6.68-6.73 (m, 1 H), 7.01-7.05 (m, 1 H), 7.10-7.15 (m, 1 H), 11.06 (br. s, 1 H). | CDCl3 | 380 [M + H]+ |
| 138 | 2-(1-methylspiro[indoline-3,4'-piperidin]-1'-yl)pyrido[2,3-d]pyrimidin-4(3H)-one | (Test Target Compound 135) | 1.88-2.06 (m, 4 H), 2.83 (s, 3 H), 3.29-3.39 (m, 4 H), 4.63-4.71 (m, 2 H), 6.54 (d, J = 7.8 Hz, 1 H), 6.69-6.74 (m, 1 H), 7.01-7.08 (m, 2 H), 7.12-7.17 (m, 1 H), 8.26-8.31 (m, 1 H), 8.74-8.78 (m, 1 H), 11.63 (br. s, 1 H). | CDCl3 | 348 [M + H]+ |
| 139 | 2-(1-methylspiro[indoline-3,4'-piperidin]-1'-yl)-5,6,7,8-tetrahydropyrido[2,3-d]pyrimidin-4(3H)-one | (Test Target Compound 136) | 1.75-1.94 (m, 6 H), 2.40-2.44 (m, 2 H), 2.79 (s, 3 H), 3.03-3.12 (m, 2 H), 3.27-3.32 (m, 4 H), 4.33-4.40 (m, 2 H), 4.70 (br. s, 1 H), 6.49-6.52 (m, 1 H), 6.68-6.73 (m, 1 H), 7.00-7.03 (m, 1 H), 7.10-7.15 (m, 1 H), 11.41 (br. s, 1 H). | CDCl3 | 352 [M + H]+ |

TABLE 59-continued

| Example | Compound Name | Structure | 1H NMR δ ppm | Solvent | ESI MS m/z |
|---|---|---|---|---|---|
| 140 | (2-(1-methylspiro[indoline-3,4'-piperidin]-1'-yl)-4-oxo-3,4-dihydroquinazolin-8-yl)methyl acetate | (Test Target Compound 137) | 1.88-1.94 (m, 2 H), 1.96-2.05 (m, 2 H), 2.13 (s, 3H), 2.82 (s, 3 H), 3.21-3.31 (m, 2 H), 3.35 (s, 2 H), 4.49-4.56 (m, 2 H), 5.48 (s, 2 H), 6.51-6.55 (m, 1 H), 6.69-6.74 (m, 1 H), 7.02-7.06 (m, 1 H), 7.09-7.17 (m, 2 H), 7.62-7.66 (m, 1 H), 7.98-8.01 (m, 1 H), 11.54 (br. s, 1 H). | CDCl3 | 419 [M + H]+ |
| 141 | 8-(hydroxymethyl)-2-(1-methylspiro[indoline-3,4'-piperidin]-1'-yl)quinazolin-4(3H)-one | (Test Target Compound 138) | 1.90-2.08 (m, 4 H), 2.82 (s, 3 H), 3.24-3.35 (m, 4 H), 4.41-4.48 (m, 2 H), 4.90 (s, 2 H), 6.52-6.56 (m, 1 H), 6.70-6.75 (m, 1H), 7.04-7.17 (m, 3 H), 7.47-7.50 (m, 1 H), 7.93-7.97 (m, 1 H), 11.60 (br. s, 1 H). | CDCl3 | 377 [M + H]+ |

TABLE 60

| Example | Compound Name | Structure | 1H NMR δ ppm | Solvent | ESI MS m/z |
|---|---|---|---|---|---|
| 142 | 8-methyl-2-(1-methylspiro[indoline-3,4'-piperidin]-1'-yl)quinazolin-4(3H)-one | (Test Target Compound 139) | 1.88-1.94 (m, 2 H), 1.98-2.07 (m, 2 H), 2.49 (s, 3 H), 2.82 (s, 3 H), 3.21-3.30 (m, 2 H), 3.35 (s, 2 H), 4.42-4.49 (m, 1 H), 6.52-6.55 (m, 1 H), 6.70-6.75 (m, 1 H), 7.02-7.07 (m, 2 H), 7.12-7.17 (m, 1 H), 7.45-7.49 (m, 1 H), 7.89-7.93 (m, 1 H), 10.79 (br. s, 1 H). | CDCl3 | 361 [M + H]+ |
| 143 | 2-(1-(2-hydroxyethyl)spiro[indoline-3,4'-piperidin]-1'-yl)-8-methylquinazolin-4(3H)-one | (Test Target Compound 140) | 1.87-1.94 (m, 2 H), 2.00-2.10 (m, 2 H), 2.48 (s, 3 H), 3.18-3.28 (m, 2 H), 3.30-3.36 (m, 2 H), 3.46 (s, 2 H), 3.84-3.89 (m, 2 H), 4.51-4.58 (m, 2 H), 6.60 (d, J = 7.8 Hz, 1 H), 6.72-6.77 (m, 1 H), 7.01-7.09 (m, 2 H), 7.11-7.16 (m, 1 H), 7.44-7.48 (m, 1 H), 7.87-7.91 (m, 1 H), 11.66 (br. s, 1 H). | CDCl3 | 390 [M + H]+ |

TABLE 60-continued

| Example | Compound Name | Structure | 1H NMR δ ppm | Solvent | ESI MS m/z |
|---|---|---|---|---|---|
| 144 | 2-[1-(2-tert-butyloxy-carbonyl-aminoethyl)spiro[indoline-3,4'-piperidin]-1'-yl]-5,6,7,8-tetrahydroquinazolin-4(3H)-one | (Test Target Compound 141) | 1.44 (s, 9 H), 1.65-1.96 (m, 8 H), 2.34-2.39 (m, 2 H), 2.45-2.50 (m, 2 H), 3.05-3.14 (m, 2 H), 3.21-3.26 (m, 2 H), 3.35-3.42 (m, 4 H), 4.32-4.39 (m, 2 H), 4.75 (br s, 1 H), 6.50-6.54 (m, 1 H), 6.68-6.73 (m, 1 H), 7.00-7.04 (m, 1 H), 7.08-7.14 (m, 1 H), 11.22 (br s, 1 H). | CDCl3 | 480 [M + H]+ |
| 145 | 2-[1-(2-aminoethyl)spiro[indoline-3,4'-piperidin]-5,6,7,8-tetrahydroquinazolin-4(3H)-one | (Test Target Compound 142) | 1.63-1.84 (m, 6 H), 1.88-1.98 (m, 2 H), 2.32-2.37 (m, 2 H), 2.45-2.50 (m, 2 H), 2.96 (t, J = 6.1 Hz, 2 H), 3.06-3.15 (m, 2 H), 3.20 (t, J = 6.1 Hz, 2 H), 3.37 (s, 2 H), 4.37-4.44 (m, 2 H), 6.53-6.56 (m, 1 H), 6.67-6.72 (m, 1 H), 7.01-7.04 (m, 1 H), 7.08-7.13 (m, 1 H). | CDCl3 | 380 [M + H]+ |
| 146 | 2-(5-methoxyspiro[indoline-3,4'-piperidin]-1'-yl)-5,6,7,8-tetrahydroquinazolin-4(3H)-one | (Test Target Compound 143) | 1.63-1.95 (m, 8 H), 2.32-2.37 (m, 2 H), 2.45-2.50 (m, 2 H), 3.03-3.12 (m, 2 H), 3.52 (s, 2 H), 3.74 (s, 3 H), 4.42-4.49 (m, 2 H), 6.59-6.68 (m, 3 H), 11.98 (br s, 1 H). | CDCl3 | 368 [M + H]+ |
| 147 | 2-(5-methoxy-1-methylspiro[indoline-3,4'-piperidin]-1'-yl)-5,6,7,8-tetrahydroquinazolin-4(3H)-one | (Test Target Compound 144) | 1.65-1.95 (m, 8 H), 2.31-2.37 (m, 2 H), 2.45-2.50 (m, 2 H), 3.06-3.15 (m, 2 H), 3.25 (s, 2 H), 3.74 (s, 3 H), 4.40-4.47 (m, 2 H), 6.46 (d, J = 8.3 Hz, 1 H), 6.65-6.71 (m, 2 H), 12.03 (br s, 1 H). | CDCl3 | 381 [M + H]+ |

TABLE 61

| Example | Compound Name | Structure | 1H NMR δ ppm | Solvent | ESI MS m/z |
|---|---|---|---|---|---|
| 148 | 2-(7-methoxyspiro[indoline-3,4'-piperidin]-1'-yl)-5,6,7,8-tetrahydroquinazolin-4(3H)-one | (Test Target Compound 145) | 1.65-2.02 (m, 8 H) 2.35-2.53 (m, 4 H) 3.06-3.18 (m, 2 H) 3.56 (s, 2 H) 3.84 (s, 3 H) 4.15-4.27 (m, 2 H) 6.66-6.79 (m, 3 H) | CDCl3 | 367 [M + H]+ |
| 149 | 2-(7-bromospiro[indolin-3,4'-piperidin]-1'-yl)-5,6,7,8-tetrahydroquinazolin-4(3H)-one | (Test Target Compound 147) | 1.63-1.95 (m, 8 H), 2.31-2.37 (m, 2 H), 2.45-2.50 (m, 2 H), 3.04-3.12 (m, 2 H), 3.60 (s, 2 H), 4.02 (br s, 1 H), 4.39-4.46 (m, 2 H), 6.58-6.64 (m, 1 H), 6.95-6.98 (m, 1 H), 7.18-7.22 (m, 1 H), 12.01 (br s, 1 H). | CDCl3 | 415 [M + H]+ |
| 150 | 2-(6-bromospiro[indoline-3,4'-piperidin]-1'-yl)-5,6,7,8-tetrahydroquinazolin-4(3H)-one | (Test Target Compound 148) | 1.63-1.93 (m, 8 H), 2.31-2.37 (m, 2 H), 2.44-2.51 (m, 2 H), 3.03-3.12 (m, 2 H), 3.55 (s, 2 H), 4.37-4.44 (m, 2 H), 6.76 (d, J = 1.6 Hz, 1 H), 6.83 (dd, J = 7.8, 1.6 Hz, 1 H), 6.88 (d, J = 7.8 Hz, 1 H), 11.88 (br s, 1 H). | CDCl3 | 415 [M + H]+ |
| 151 | 2-(4-bromospiro[indoline-3,4'-piperidin]-1'-yl)-5,6,7,8-tetrahydroquinazolin-4(3H)-one | (Test Target Compound 149) | 1.63-1.77 (m, 6 H), 2.34-2.39 (m, 2 H), 2.45-2.51 (m, 2 H), 2.68-2.78 (m, 2 H), 2.92-3.01 (m, 2 H), 3.61 (s, 2 H), 4.47-4.54 (m, 2 H), 6.55 (dd, J = 7.6, 1.1 Hz, 1 H), 6.82 (dd, J = 8.0, 1.1 Hz, 1 H), 6.86-6.91 (m, 1 H), 11.81 (br s, 1 H). | CDCl3 | 415 [M + H]+ |

TABLE 61-continued

| Example | Compound Name | Structure | 1H NMR δ ppm | Solvent | ESI MS m/z |
|---|---|---|---|---|---|
| 152 | Ethyl 1'-(4-oxo-3,4,5,6,7,8-hexahydroquinazolin-2-yl)spiro[indoline-3,4'-piperidin]-5-ethyl-carboxylate | (Test Target Compound 150) | 1.35 (t, J = 7.1 Hz, 3 H), 1.62-1.96 (m, 8 H), 2.31-2.36 (m, 2 H), 2.47-2.52 (m, 2 H), 3.00-3.10 (m, 2 H), 3.59 (s, 2 H), 4.27-4.35 (m, 4 H), 6.56 (d, J = 8.3 Hz, 1 H), 7.67-7.69 (m, 1 H), 7.78-7.82 (m, 1 H), 10.80 (br s, 1 H). | CDCl3 | 409 [M + H]+ |
| 153 | 1'-(4-oxo-3,4,5,6,7,8-hexahydroquinazolin-2-yl)-N-[3-(piperidin-1-yl)propyl]spiro[indoline-3,4'-piperidine]-5-carboxamide | (Test Target Compound 153) | 1.41-1.48 (m, 2 H), 1.57-1.86 (m, 14 H), 1.97-2.01 (m, 2 H), 2.34-2.39 (m, 2 H), 2.44-2.57 (m, 6 H), 3.02-3.14 (m, 2 H), 3.50-3.55 (m, 2H), 3.59 (s, 2 H), 4.27-4.45 (m, 2 H), 6.60 (d, J = 8.2 Hz, 1 H), 7.55 (d, J = 1.5 Hz, 1 H), 7.59-7.62 (m, 1 H). | CDCl3 | 505 [M + H]+ |

TABLE 62

| Example | Compound Name | Structure | 1H NMR δ ppm | Solvent | ESI MS M/z |
|---|---|---|---|---|---|
| 154 | N,N-dimethyl-1'-(4-oxo-3,4,5,6,7,8-hexahydroquinazolin-2-yl)spiro[indoline-3,4'-piperidine]-5-carboxamide | (Test Target Compound 154) | 1.65-1.96 (m, 8 H), 2.33-2.38 (m, 2 H), 2.45-2.50 (m, 2 H), 3.03-3.13 (m, 8 H), 3.58 (s, 2 H), 4.36-4.43 (m, 2 H), 6.59 (d, J = 7.9 Hz, 1 H), 7.15-7.20 (m, 2 H), 11.70 (br. s, 1 H). | CDCl3 | 408 [M + H]+ |
| 155 | N-(3-morpholinopropyl)-1'-(4-oxo-3,4,5,6,7,8-hexahydroquinazolin-2-yl)spiro[indoline-3,4'-piperidine]-5-carboxamide | (Test Target Compound 155) | 1.65-1.85 (m, 8 H), 1.91-2.00 (m, 2 H), 2.33-2.38 (m, 2 H), 2.45-2.55 (m, 8 H), 3.02-3.11 (m, 2 H), 3.49-3.55 (m, 2 H), 3.61 (s, 2 H), 3.66-3.71 (m, 4 H), 4.09 (br. s, 1 H), 4.40-4.47 (m, 2 H), 6.59 (d, J = 8.2 Hz, 1 H), 7.37-7.42 (m, 1 H), 7.50 (dd, J = 8.2, 1.7 Hz, 1 H), 7.55 (d, J = 1.7 Hz, 1 H), 11.67 (br. s, 1 H). | CDCl3 | 507 [M + H]+ |

TABLE 62-continued

| Example | Compound Name | Structure | 1H NMR δ ppm | Solvent | ESI MS M/z |
|---|---|---|---|---|---|
| 156 | N-(2-morpholino-ethyl)-1'-(4-oxo-3,4,5,6,7,8-hexahydroquinazoline-3,4'-piperidine]-5-carboxamide | (Test Target Compound 156) | 1.64-1.84 (m, 6 H), 1.90-2.00 (m, 2 H), 2.32-2.38 (m, 2 H), 2.45-2.53 (m, 6 H), 2.57-2.62 (m, 2 H), 3.03-3.12 (m, 2 H), 3.58-3.56 (m, 2 H), 3.61 (s, 2 H), 3.68-3.73 (m, 4 H), 4.14 (br. s, 1 H), 4.40-4.47 (m, 2 H), 6.58-6.64 (m, 2 H), 7.48 (dd, J = 8.2, 1.7 Hz, 1 H), 7.53 (d, J = 1.7 Hz, 1 H), 12.00 (br. s, 1 H). | CDCl3 | 493 [M + H]+ |
| 157 | N-[2-(dimethylamino)ethyl]-1'-(4-oxo-3,4,5,6,7,8-hexahydroquinazolin-2-yl)spiro[indoline-3,4'-piperidine]-5-carboxamide | (Test Target Compound 157) | 1.64-1.82 (m, 6 H), 1.88-1.98 (m, 2 H), 2.30 (s, 6 H), 2.33-2.38 (m, 2 H), 2.45-2.50 (m, 2 H), 2.54-2.59 (m, 2 H), 3.01-3.10 (m, 2 H), 3.49-3.55 (m, 2 H), 3.59 (s, 2 H), 4.38-4.45 (m, 2 H), 6.56-6.59 (m, 1 H), 6.80-6.85 (m, 1 H), 7.50-7.54 (m, 2 H). | CDCl3 | 451 [M + H]+ |
| 158 | N-[3-(dimethylamino)propyl]-1'-(4-oxo-3,4,5,6,7,8-hexahydroquinazolin-2-yl)spiro[indoline-3,4'-piperidine]-5-carboxamide | (Test Target Compound 158) | 1.66-1.79 (m, 8 H), 1.92-2.02 (m, 2 H), 2.26 (s, 6 H), 2.34-2.39 (m, 2 H), 2.45-2.53 (m, 4 H), 3.01-3.10 (m, 2 H), 3.50-3.56 (m, 2 H), 3.96 (s, 2 H), 4.51-4.58 (m, 2 H), 7.54-7.95 (m, 3 H), 8.40 (br. s, 1 H). | CDCl3 | 465 [M + H]+ |
| 159 | ethyl 1'-(4-oxo-3,4,5,6,7,8-hexahydroquinazolin-2-yl)spiro[indoline-3,4'-piperidine]-6-carboxylate | (Test Target Compound 159) | 1.37 (t, J = 7.1 Hz, 3 H), 1.64-1.98 (m, 8 H), 2.33-2.38 (m, 2 H), 2.45-2.50 (m, 2 H), 3.05-3.14 (m, 2 H), 3.59 (s, 2 H), 3.89 (br s, 1 H), 4.34 (q, J = 7.1 Hz, 2 H), 4.38-4.44 (m, 2 H), 7.08 (d, J = 7.7 Hz, 1 H), 7.28-7.30 (m, 1 H), 7.44-7.47 (m, 1 H), 11.50 (br s, 1 H). | CDCl3 | 409 [M + H]+ |

TABLE 63

| Example | Compound Name | Structure | 1H NMR δ ppm | Solvent | ESI MS m/z |
|---|---|---|---|---|---|
| 160 | 1'-(4-oxo-3,4,5,6,7,8-hexahydroquinazolin-2-yl)spiro[indoline-3,4'-piperidine]-6-carboxylic acid | (Test Target Compound 160) | 1.64-1.77 (m, 4 H), 1.86-1.92 (m, 2 H), 1.98-2.07 (m, 2 H), 2.29-2.34 (m, 2 H), 2.71-2.76 (m, 2 H), 3.35-3.43 (m, 2 H), 3.79 (s, 2 H), 4.49-4.56 (m, 2 H), 7.53-7.57 (m, 1 H), 7.73-7.75 (m, 1 H), 7.85-7.89 (m, 1 H). | DMSO-d6 | 381 [M + H]+ |
| 161 | 1'-(4-oxo-3,4,5,6,7,8-hexahydroquinazolin-2-yl)-N-[2-(piperidin-1-yl)ethyl]spiro[indoline-3,4'-piperidine]-6-carboxamide | (Test Target Compound 161) | 1.44-1.51 (m, 2 H), 1.59-1.96 (m, 14 H), 2.35-2.39 (m, 2 H), 2.44-2.51 (m, 4 H), 2.56-2.61 (m, 2 H), 3.05-3.15 (m, 2 H), 3.50-3.59 (m, 4 H), 3.92 (br. s, 1 H), 4.29-4.37 (m, 2 H), 7.05-7.14 (m, 3 H). | CDCl3 | 491 [M + H]+ |
| 162 | 1'-(4-oxo-3,4,5,6,7,8-hexahydroquinazolin-2-yl)-N-[3-(piperidin-1-yl)propyl]spiro[indoline-3,4'-piperidine]-6-carboxamide | (Test Target Compound 162) | 1.43-1.52 (m, 2 H), 1.57-1.97 (m, 16 H), 2.33-2.38 (m, 2 H), 2.43-2.54 (m, 4 H), 3.04-3.14 (m, 2 H), 3.50-3.59 (m, 4 H), 4.36-4.44 (m, 2 H), 6.68-6.80 (m, 1 H), 7.02-7.06 (m, 1 H), 7.14-71.8 (m, 1 H). | CDCl3 | 505 [M + H]+ |
| 163 | N,N-dimethyl-1'-(4-oxo-3,4,5,6,7,8-hexahydroquinazolin-2-yl)spiro[indoline-3,4'-piperidine]-6-carboxamide | (Test Target Compound 163) | 1.64-1.84 (m, 6 H), 1.86-1.95 (m, 2 H), 2.32-2.37 (m, 2 H), 2.46-2.51 (m, 2 H), 2.97-3.14 (m, 8 H), 3.55 (s, 2 H), 4.38-4.45 (m, 2 H), 6.67 (d, J = 1.2, 1 H), 6.73 (dd, J = 7.5, 1.2 Hz, 1 H), 7.02 (d, J = 7.5 Hz, 1 H), 11.95 (br. s, 1 H). | CDCl3 | 408 [M + H]+ |
| 164 | N-(3-morpholinopropyl)-1'-(4-oxo-3,4,5,6,7,8-hexahydroquinazolin-2-yl)spiro[indoline-3,4'-piperidine]-6-carboxamide | (Test Target Compound 164) | 1.64-1.86 (m, 8 H), 1.88-1.97 (m, 2 H), 2.32-2.37 (m, 2 H), 2.45-2.57 (m, 8 H), 3.05-3.14 (m, 2 H), 3.50-3.56 (m, 2 H), 3.58 (s, 2 H), 3.69-3.75 (m, 4 H), 3.95 (br. s, 1 H), 4.40-4.47 (m, 2 H), 7.04-7.07 (m, 1 H), 7.09-7.13 (m, 2 H), 7.67-7.72 (m, 1 H), 11.97 (br. s, 1 H). | CDCl3 | 507 [M + H]+ |

TABLE 63-continued

| Example | Compound Name | Structure | 1H NMR δ ppm | Solvent | ESI MS m/z |
|---|---|---|---|---|---|
| 165 | N-(2-morpholino-ethyl)-1'-(4-oxo-3,4,5,6,7,8-hexahydroquinazolin-2-yl)spiro[indoline-3,4'-piperidine]-6-carboxamide | (Test Target Compound 165) | 1.64-1.77 (m, 4 H), 1.80-1.87 (m, 2 H), 1.88-1.97 (m, 2 H), 2.32-2.37 (m, 2 H), 2.45-2.55 (m, 6 H), 2.58-2.63 (m, 2 H), 3.05-3.14 (m, 2 H), 3.51-3.56 (m, 2 H), 3.59 (s, 2 H), 3.70-3.76 (m, 4 H), 4.40-4.47 (m, 2 H), 6.70-6.75 (m, 1 H), 7.05-7.10 (m, 3 H), 11.99 (br. s, 1 H). | CDCl3 | 493 [M + H]+ |

TABLE 64

| Example | Compound Name | Structure | 1H NMR δ ppm | Solvent | ESI MS m/z |
|---|---|---|---|---|---|
| 166 | N-[2-(dimethylamino)ethyl]-1'-(4-oxo-3,4,5,6,7,8-hexahydroquinazolin-2-yl)spiro[indolin-3,4'-piperidine]-6-carboxamide | (Test Target Compound 166) | 1.64-1.85 (m, 6 H), 1.87-1.96 (m, 2 H), 2.30 (s, 6 H), 2.32-2.37 (m, 2 H), 2.45-2.50 (m, 2 H), 2.54-2.58 (m, 2 H), 3.04-3.13 (m, 2 H), 3.49-3.54 (m, 2 H), 3.57 (s, 2 H), 4.39-4.46 (m, 2 H), 6.87-6.91 (m, 1 H), 7.03-7.06 (m, 1 H), 7.08-7.09 (m, 1 H), 7.10-7.14 (m, 1 H). | CDCl3 | 451 [M + H]+ |
| 167 | N-[3-(dimethylamino)propyl]-1'-(4-oxo-3,4,5,6,7,8-hexahydroquinazolin-2-yl)spiro[indoline-3,4'-piperidine]-6-carboxamide | (Test Target Compound 167) | 1.65-1.86 (m, 8 H), 1.88-1.97 (m, 2 H), 2.32-2.39 (m, 8 H), 2.45-2.50 (m, 2 H), 2.52-2.57 (m, 2 H), 3.05-3.14 (m, 2 H), 3.50-3.55 (m, 2 H), 3.57 (s, 2 H), 4.37-4.44 (m, 2 H), 7.04-7.06 (m, 1 H), 7.08-7.11 (m, 1 H), 7.12-7.14 (m, 1 H), 7.97-8.01 (m, 1 H). | CDCl3 | 465 [M + H]+ |
| 168 | methyl 1'-(4-oxo-3,4,5,6,7,8-hexahydroquinazolin-2-yl)spiro[indoline-3,4'-piperidine]-6-carboxylate | (Test Target Compound 169) | 1.60-2.00 (m, 8 H), 2.30-2.40 (m, 2 H), 2.45-2.55 (m, 2 H), 3.05-3.15 (m, 2 H), 3.59 (s, 2 H), 3.88 (s, 3 H), 4.35-4.50 (m, 2 H), 7.80 (d, J = 7.6 Hz, 1 H), 7.28 (s, 1 H), 7.40-7.50 (m, 1 H). | CDCl3 | 395 [M + H]+ |

TABLE 64-continued

| Example | Compound Name | Structure | 1H NMR δ ppm | Solvent | ESI MS m/z |
|---|---|---|---|---|---|
| 169 | 2-morpholinoethyl 1'-(4-oxo-3,4,5,6,7,8-hexahydroquinazolin-2-yl)spiro[indoline-3,4'-piperidine]-6-carboxylate | (Test Target Compound 170) | 1.60-2.00 (m, 8 H), 2.30-2.40 (m, 2 H), 2.45-2.55 (m, 2 H), 2.55-2.65 (m, 4 H), 2.75-2.85 (m, 2 H), 3.05-3.15 (m, 2 H), 3.59 (s, 2 H), 3.75-3.85 (m, 4 H), 3.85-4.00 (m, 1 H), 4.40-4.50 (m, 4 H), 7.08 (d, J = 7.6 Hz, 1 H), 7.27 (s, 1 H), 7.40-7.50 (m, 1 H), 11.80 (br. s, 1 H). | CDCl3 | 494 [M + H]+ |
| 170 | N-(2-morpholino-ethyl)-1'-(4-oxo-3,4,5,6,7,8-hexahydroquinazolin-2-yl)-1-(pyridin-3-yl-methyl)spiro[indoline-3,4'-piperidine]-6-carboxamide | (Test Target Compound 171) | 1.00-1.35 (m, 6 H), 1.74-2.15 (m, 8 H), 2.40-2.50 (m, 2 H), 2.60-2.70 (m, 2 H), 3.15-3.25 (m, 2 H), 3.60-3.90 (m, 6 H), 4.00-4.10 (m, 2 H), 4.35-4.50 (m, 2 H), 4.73 (s, 2 H), 7.30-7.30 (m, 2 H), 7.30-7.40 (m, 1 H), 8.10-8.20 (m, 1 H), 8.70-8.75 (m, 1 H), 8.80-8.85 (m, 1 H), 8.90-8.95 (m, 1 H). | CD3OD | 584 [M + H]+ |
| 171 | N-(2-morpholino-ethyl)-1'-(4-oxo-3,5,7,8-tetrahydro-4H-thio-pyrano[4,3-d]pyrimidin-2-yl)spiro[indoline-3,4'-piperidine]-6-carboxamide | (Test Target Compound 172) | 1.80-1.95 (m, 4 H), 2.84-2.54 (m, 2 H), 2.58-2.63 (m, 2 H), 2.76-2.81 (m, 2 H), 2.82-2.86 (m, 2 H), 3.08-3.16 (m, 2 H), 3.49 (s, 2 H), 3.51-3.57 (m, 2 H), 3.59 (s, 2 H), 3.71-3.75 (m, 4 H), 4.36-4.43 (m, 2 H), 6.70 (br. s, 1 H), 7.04-7.10 (m, 3 H). | CDCl3 | 511 [M + H]+ |

TABLE 65

| Example | Compound Name | Structure | 1H NMR δ ppm | Solvent | ESI MS m/z |
|---|---|---|---|---|---|
| 172 | N-methyl-N-(2-morpho-linoethyl)-1'-(4-oxo-3,4,5,6,7,8-hexahydro-quinazolin-2-yl)spiro[indoline-3,4'-piperidine]-6-carboxamide | (Test Target Compound 173) | 1.64-1.95 (m, 8 H), 2.25-2.69 (m, 10 H), 2.98-3.14 (m, 5 H), 3.36-3.91 (m, 8 H), 4.32-4.40 (m, 2 H), 6.66 (d, J = 1.1 Hz, 1 H), 6.72-6.75 (m, 1 H), 7.01 (d, J = 7,6 Hz, 1 H), 11.36 (br. s, 1 H). | CDCl3 | 507 [M + H]+ |

TABLE 65-continued

| Example | Compound Name | Structure | 1H NMR δ ppm | Solvent | ESI MS m/z |
|---|---|---|---|---|---|
| 173 | 1-methyl-N-(2-morpholinoethyl)-1'-(4-oxo-3,4,5,6,7,8-hexahydroquinazolin-2-yl)spiro[indoline-3,4'-piperidine]-6-carboxamide | (Test Target Compound 174) | 1.64-1.84 (m, 6 H), 1.87-1.96 (m, 2 H), 2.31-2.37 (m, 2 H), 2.45-2.54 (m, 6 H), 2.58-2.63 (m, 2 H), 2.85 (s, 3 H), 3.06-3.15 (m, 2 H), 3.37 (s, 2 H), 3.52-3.57 (m, 2 H), 3.70-3.75 (m, 2 H), 4.39-4.46 (m, 2 H), 6.72-6.76 (m, 1 H), 6.94 (s, 1 H), 7.00-7.04 (m, 2 H). | CDCl3 | 507 [M + H]+ |
| 174 | N-(2-(dimethylamino)ethyl)-1-methyl-1'-(4-oxo-3,4,5,6,7,8-hexahydroquinazolin-2-yl)spiro[indoline-3,4'-piperidine]-6-carboxamide | (Test Target Compound 175) | 1.70-1.95 (m, 8 H), 2.30-2.40 (m, 2 H), 2.44 (s, 6 H), 2.50-2.55 (m, 2 H), 2.70-2.75 (m, 2 H), 2.84 (s, 3 H), 3.15-3.25 (m, 2 H), 3.39 (s, 2 H), 3.50-3.60 (m, 2 H), 4.25-4.35 (m, 2 H), 6.95-7.00 (m, 1 H), 7.05-7.20 (m, 1 H). | CD3OD | 465 [M + H]+ |
| 175 | 1-methyl-1'-(4-oxo-3,4,5,6,7,8-hexahydroquinazolin-2-yl)-N-(2-(piperidin-1-yl)ethyl)spiro[indoline-3,4'-piperidine]-6-carboxamide | (Test Target Compound 176) | 1.55-1.95 (m, 14 H), 2.30-2.40 (m, 2 H), 2.45-2.55 (m, 2 H), 2.84 (s, 3 H), 2.90-3.05 (m, 6 H), 3.15-3.40 (m, 2 H), 3.60-3.70 (m, 2 H), 4.25-4.30 (m, 2 H), 6.95-7.00 (m, 1 H), 7.05-7.15 (m, 1 H), 7.15-7.20 (m, 1 H). | CD3OD | 505 [M + H]+ |
| 176 | 2-(4-(hydroxymethyl)spiro[indoline-3,4'-piperidin]-1'-yl)-5,6,7,8-tetrahydroquinazolin-4(3H)-one | 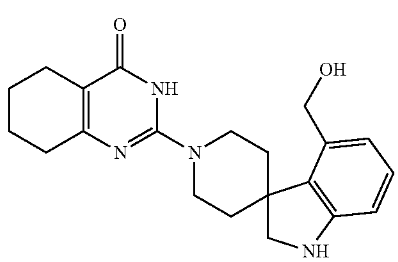 [SMILES: O=c1[nH]c(N2CCC3(CC2)CNc2cccc(CO)c23)nc2c1CCCC2] | 1.55-1.75 (m, 6 H), 2.05-2.15 (m, 2 H), 2.20-2.30 (m, 2 H), 2.35-2.45 (m, 2 H), 2.85-2.95 (m, 2 H), 3.40 (s, 2H), 4.25-4.40 (m, 2 H), 4.44 (d, J = 5.6 Hz, 2 H), 4.96 (t, J = 5.6 Hz, 1 H), 5.54 (s, 1 H), 6.40-6.45 (m, 1 H), 6.60-6.65 (m, 1 H), 6.85-6.95 (m, 1 H), 10.99 (br. s, 1 H). | DMSO-d6 | 367 [M + H]+ |

TABLE 65-continued

| Example | Compound Name | Structure | 1H NMR δ ppm | Solvent | ESI MS m/z |
|---|---|---|---|---|---|
| 177 | 2-(6-(hydroxymethyl)spiro[indoline-3,4'-piperidin]-1'-yl)-5,6,7,8-tetrahydroquinazolin-4(3H)-one | (Test Target Compound 177) | 1.60-2.00 (m, 8 H), 2.35-2.40 (m, 2 H), 2.45-2.50 (m, 2 H), 3.05-3.15 (m, 2 H), 3.54 (s, 2 H), 4.25-4.35 (m, 2 H), 4.60 (s, 2 H), 6.65-6.75 (m, 2 H), 7.02 (d, J = 7.6 Hz, 1 H). | CDCl3 | 367 [M + H]+ |

TABLE 66

| Example | Compound Name | Structure | 1H NMR δ ppm | Solvent | ESI MS m/z |
|---|---|---|---|---|---|
| 178 | 1'-(4-oxo-3,4,5,6,7,8-hexahydroquinazolin-2-yl)spiro[indoline-3,4'-piperidine]-6-aldehyde | (Test Target Compound 178) | 1.50-2.00 (m, 8 H), 2.25-2.55 (m, 4 H), 3.05-3.15 (m, 2 H), 3.55-3.65 (m, 2 H), 4.38 (d, J = 13.6 Hz, 2 H), 7.10-7.25 (m, 3 H), 9.88 (s, 1 H), 11.20 (br. s, 1 H). | CDCl3 | 365 [M + H]+ |
| 179 | 2-(6-(3-morpholinopropanoyl)spiro[indoline-3,4'-piperidin]-1'-yl)-5,6,7,8-tetrahydroquinazolin-4(3H)-one | (Test Target Compound 179) | 1.50-2.00 (m, 8 H), 2.30-2.40 (m, 2 H), 2.45-2.55 (m, 2 H), 2.55-2.70 (m, 4 H), 2.90-3.30 (m, 6 H), 3.60 (s, 2 H), 3.75-3.85 (m, 4 H), 4.35-4.45 (m, 2 H), 7.10 (d, J = 7.6 Hz, 1 H), 7.20-7.25 (m, 1 H), 7.35-7.40 (m, 1 H), 10.70-11.50 (m, 1 H). | CDCl3 | 478 [M + H]+ |
| 180 | 1'-(4-oxo-3,4,5,6,7,8-hexahydroquinazolin-2-yl)spiro[indoline-3,4'-piperidine]-6-carboxamide | (Test Target Compound 180) | 1.55-1.80 (m, 8 H), 2.20-2.45 (m, 4 H), 2.95-3.10 (m, 2 H), 3.43 (s, 2 H), 4.20-4.30 (m, 2 H), 5.71 (s, 1 H), 6.95-7.10 (m, 4 H), 7.69 (s, 1 H), 11.03 (s, 1 H). | DMSO-d6 | 380 [M + H]+ |

TABLE 66-continued

| Example | Compound Name | Structure | 1H NMR δ ppm | Solvent | ESI MS m/z |
|---|---|---|---|---|---|
| 181 | 7-bromo-N-(2-morpholino-ethyl)-1'-(4-oxo-3,4,5,6,7,8-hexahydro-quinazolin-2-yl) spiro[indoline-3,4'-piperidine]-6-carboxamide | (Test Target Compound 181) | 1.65-2.00 (m, 8 H), 2.30-2.65 (m, 10 H), 3.00-3.15 (m, 2 H), 3.50-3.75 (m, 8 H), 4.20 (s, 1 H), 4.43 (d, J = 13.6 Hz, 2 H), 6.50-6.60 (m, 1 H), 6.88 (d, J = 7.6 Hz, 1 H), 6.99 (d, J = 7.6 Hz, 1 H), 12.00 (br. s, 1 H). | CDCl3 | 571 [M + H]+ |
| 182 | 2-(2-oxospiro[indoline-3,4'-piperidin]-1'-yl)-5,6,7,8-tetra-hydro-quinazolin-4(3H)-one | (Test Target Compound 55) | 1.55-1.80 (m, 8 H), 2.20-2.30 (m, 2 H), 2.30-2.40 (m, 2 H), 3.80-3.88 (m, 2 H), 3.93-4.05 (m, 2 H), 6.85-6.88 (m, 1 H), 6.92-7.00 (m, 1 H), 7.17-7.22 (m, 1 H), 7.43-7.50 (m, 1 H), 10.44 (br. s, 1 H). | DMSO-d6 | 351 [M + H]+ |
| 183 | 2-(1-methyl-2-oxospiro[indoline-3,4'-piperidin]-1'-yl)-5,6,7,8-tetrahydro-quinazolin-4(3H)-one | (Test Target Compound 56) | 1.59-1.80 (m, 8 H), 2.20-2.30 (m, 2 H), 2.35-2.42 (m, 2 H), 3.13 (s, 3 H), 3.89-3.99 (m, 4 H), 7.02-7.08 (m, 2 H), 7.27-7.33 (m, 1 H), 7.50-7.55 (m, 1 H), 11.07 (br. s, 1 H). | DMSO-d6 | 365 [M + H]+ |

TABLE 67

| Example | Compound Name | Structure | 1H NMR δ ppm | Solvent | ESI MS m/z |
|---|---|---|---|---|---|
| 184 | 2-(4-fluoro-2-oxospiro[indoline-3,4'-piperidin]-1'-yl)-5,6,7,8-tetra-hydropyrido[2,3-d]pyrimidine-4(3H)-one | (Test Target Compound 57) | 1.79-2.02 (m, 4 H), 2.20-2.35 (m, 2 H), 2.46-2.55 (m, 2 H), 3.27-3.39 (m, 2 H), 3.86-4.07 (m, 4 H), 4.71 (br s, 1 H), 6.64-6.79 (m, 2 H), 7.10-7.24 (m, 1 H) | CDCl3 | 370 [M + H]+ |

| Example | Compound Name | Structure | 1H NMR δ ppm | Solvent | ESI MS m/z |
|---|---|---|---|---|---|
| 185 | 2-(4-fluoro-2-oxospiro[indoline-3,4'-piperidin]-1'-yl)-8-methyl-5,6,7,8-tetrahydropyrido[2,3-d]pyrimidine-4(3H)-one | (Test Target Compound 58) | 1.82-2.05 (m, 4 H), 2.17-2.36 (m, 2 H), 2.46-2.58 (m, 2 H), 3.10 (s, 3H), 3.25-3.35 (m, 2 H), 3.91-4.08 (m, 4 H), 6.65-6.78 (m, 2 H), 7.12-7.23 (m, 2 H). | CDCl3 | 384 [M + H]+ |
| 186 | N-(2-morpholinoethyl)-2-oxo-1'-(4-oxo-3,4,5,6,7,8-hexahydroquinazolin-2-yl)spiro[indoline-3,4'-piperidine]-6-carboxamide | (Test Target Compound 182) | 1.60-1.80 (m, 4 H), 1.80-2.00 (m, 4 H), 2.30-2.40 (m, 2 H), 2.40-2.50 (m, 2 H), 2.50-2.60 (m, 4 H), 2.60-2.70 (m, 2 H), 3.55-3.65 (m, 2 H), 3.70-3.75 (m, 4 H), 3.95-4.15 (m, 4 H), 6.90 (br. s, 1 H), 7.25-7.45 (m, 3 H), 9.55 (br. s, 1 H). | CDCl3 | 507 [M + H]+ |
| 187 | N-(2-morpholinoethyl)-2-oxo-1'-(4-oxo-3,4,5,6,7,8-hexahydroquinazolin-2-yl)-1-(pyridin-3-yl)methylspiro[indoline-3,4'-piperidine]-6-carboxamide | (Test Target Compound 183) | 1.60-2.10 (m, 8 H), 2.30-2.40 (m, 2 H), 2.40-2.65 (m, 8 H), 3.50-3.60 (m, 2 H), 3.65-3.75 (m, 4 H), 4.05-4.30 (m, 4 H), 4.98 (s, 2 H), 6.70-6.85 (m, 1 H), 7.25-7.40 (m, 4 H), 7.60-7.70 (m, 1 H), 8.50-8.60 (m, 2 H), 11.80 (br. s, 1 H). | CDCl3 | 598 [M + H]+ |
| 188 | N-(2-morpholinoethyl)-2-oxo-1'-(4-oxo-3,4,5,6,7,8-hexahydroquinazolin-2-yl)spiro[indoline-3,4'-piperidine]-4-carboxamide | 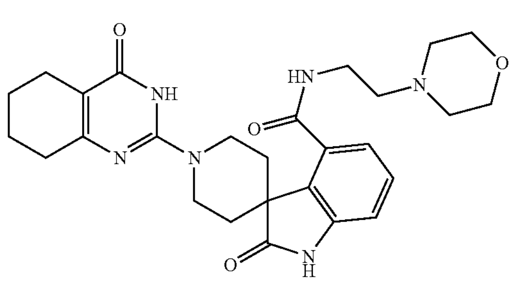 [SMILES: O=C(NCCN1CCOCC1)c1cccc2c1C1(CCN(c3nc4c(c(=O)[nH]3)CCCC4)CC1)C(=O)N2] | 1.60-1.90 (m, 8 H), 2.30-2.65 (m, 8 H), 2.70-2.80 (m, 2 H), 3.45-3.55 (m, 2 H), 3.60-3.75 (m, 4 H), 3.75-3.90 (m, 2 H), 4.05-4.20 (m, 2 H), 6.56 (br. s, 1 H), 6.95-7.05 (m, 2 H), 7.20-7.30 (m, 1 H), 9.97 (br. s, 1 H), 10.70 (br. s, 1 H). | CDCl3 | 507 [M + H]+ |

TABLE 67-continued

| Example | Compound Name | Structure | 1H NMR δ ppm | Solvent | ESI MS m/z |
|---|---|---|---|---|---|
| 189 | N-(2-morpholino-ethyl)-2-oxo-1'-(4-oxo-3,4,5,6,7,8-hexahydro quinazolin-2-yl)-1-(pyridin-3-ylmethyl) spiro [indoline-3,4'-piperidine]-4-carboxamide | 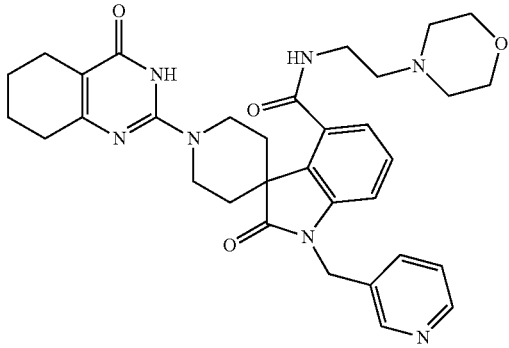 [SMILES: O=C(NCCN1CCOCC1)c1cccc2c1C1(CCN(c3nc4c(c(=O)[nH]3)CCCC4)CC1)C(=O)N2Cc1cccnc1] | 1.55-2.00 (m, 8 H), 2.30-2.60 (m, 8 H), 2.75-2.90 (m, 2 H), 3.40-3.50 (m, 2 H), 3.65-3.75 (m, 4 H), 3.85-3.95 (m, 2 H), 4.25-4.40 (m, 2 H), 4.94 (s, 2 H), 6.35-6.45 (m, 1 H), 6.75-6.85 (m, 1 H), 7.00-7.05 (m, 1 H), 7.20-7.30 (m, 2 H), 7.55-7.65 (m, 1 H), 8.50-8.60 (m, 2 H), 10.80 (br. s, 1 H). | CDCl3 | 598 [M + H]+ |

TABLE 68

| Example | Compound Name | Structure | 1H NMR δ ppm | Solvent | ESI MS m/z |
|---|---|---|---|---|---|
| 190 | 4-chloro-N-(2-morpholinoethyl)-2-oxo-1'-(4-oxo-3,4,5,6,7,8-hexahydroquinazolin-2-yl)spiro [indoline-3,4'-piperidine]-6-carboxamide | 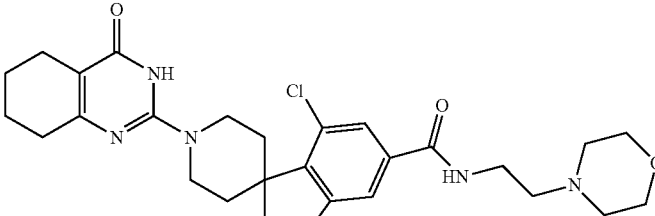(Test Target Compound 184) | 1.60-1.85 (m, 6 H), 2.25-2.80 (m, 12 H), 3.50-3.65 (m, 2 H), 3.70-3.80 (m, 4 H), 3.85-4.05 (m, 2 H), 4.10-4.30 (m, 2 H), 6.90-7.20 (m, 1 H), 7.25-7.45 (m, 2 H), 9.70-10.20 (m, 1 H). | CDCl3 | 541 [M + H]+ |
| 191 | 4-chloro-2-oxo-1'-(4-oxo-3,4,5,6,7,8-hexahydro-quinazolin-2-yl) spiro [indoline-3,4'-piperidine]-6-carboxamide | 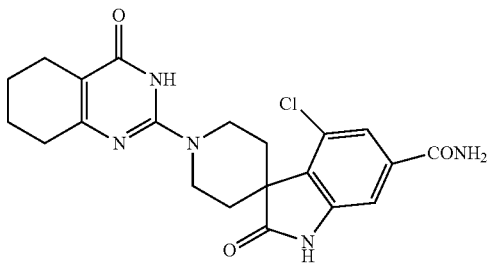(Test Target Compound 185) | 1.60-1.75 (m, 6 H), 2.20-2.55 (m, 6 H), 3.55-3.70 (m, 2 H), 4.25-4.35 (m, 2 H), 6.64 (s, 0.3 H), 6.88 (s, 0.7 H), 7.28 (d, J = 1.6 Hz, 1 H), 7.45-7.55 (m, 2 H), 8.06 (br. s, 1 H), 10.85 (br. s, 1 H), 11.10 (br. s, 1 H). | DMSO-d6 | 428 [M + H]+ |
| 192 | ethyl 4-chloro-1'-(4-oxo-3,4,5,6,7,8-hexahydro quinazolin-2-yl)spiro [indoline-3,4'-piperidine]-6-carboxylate | 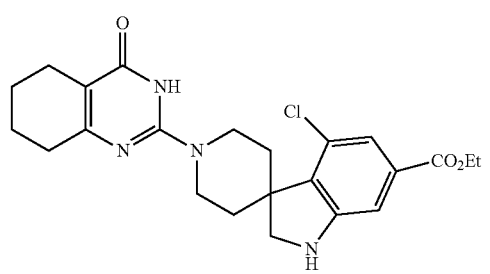(Test Target Compound 186) | 1.37 (t, J = 7.2 Hz, 3 H), 1.60-1.85 (m, 6 H), 2.30-2.40 (m, 2 H), 2.45-2.50 (m, 2 H), 2.60-2.70 (m, 2 H), 2.90-3.00 (m, 2 H), 3.66 (s, 2 H), 3.95-4.05 (m, 1 H), 4.33 (q, J = 7.2 Hz, 2 H), 4.45-4.55 (m, 2 H), 7.13 (d, J = 1.2 Hz, 1 H), 7.32 (d, J = 1.2 Hz, 1 H), 11.90 (br. s, 1 H). | CDCl3 | 443 [M + H]+ |

TABLE 68-continued

| Example | Compound Name | Structure | 1H NMR δ ppm | Solvent | ESI MS m/z |
|---|---|---|---|---|---|
| 193 | ethyl 4-chloro-1'-(4-oxo-3,4,5,6,7,8-hexahydroquinazolin-2-yl)-1-(pyridin-3-yl)methylspiro[indoline-3,4'-piperidine]-6-carboxylate | (Test Target Compound 187) | 1.37 (t, J = 7.2 Hz, 3 H), 1.65-1.80 (m, 6 H), 2.30-2.40 (m, 2 H), 2.45-2.50 (m, 2 H), 2.60-2.75 (m, 2 H), 2.80-2.90 (m, 2 H), 3.41 (s, 2 H), 4.30-4.45 (m, 6 H), 7.07 (d, J = 1.6 Hz, 1 H), 7.25-7.35 (m, 2 H), 7.60-7.65 (m, 1 H), 8.55-8.60 (m, 2 H), 10.90-11.40 (m, 1 H). | CDCl3 | 534 [M + H]+ |
| 194 | ethyl 4-chloro-1-(2-hydroxyethyl)-1'-(4-oxo-3,4,5,6,7,8-hexahydroquinazolin-2-yl)spiro[indoline-3,4'-piperidine]-6-carboxylate | (Test Target Compound 188) | 1.37 (t, J = 7.2 Hz, 3 H), 1.65-1.80 (m, 6 H), 2.35-2.40 (m, 2 H), 2.45-2.55 (m, 2 H), 2.65-2.75 (m, 2 H), 2.90-3.05 (m, 2 H), 3.35-3.45 (m, 2 H), 3.60 (s, 2 H), 3.85-3.90 (m, 2 H), 4.34 (q, J = 7.2 Hz, 2 H), 4.45-4.55 (m, 2 H), 7.02 (d, J = 1.2 Hz, 1 H), 11.30-11.80 (m, 1 H). | CDCl3 | 487 [M + H]+ |
| 195 | 4-chloro-N-(2-morpholinoethyl)-1'-(4-oxo-3,4,5,6,7,8-hexahydroquinazolin-2-yl)spiro[indoline-3,4'-piperidine]-6-carboxamide | (Test Target Compound 189) | 1.60-1.90 (m, 8 H), 2.30-2.40 (m, 2 H), 2.40-2.70 (m, 8 H), 2.90-3.60 (m, 2 H), 3.45-3.55 (m, 2 H), 3.65-3.80 (m, 6 H), 4.05-4.10 (m, 1 H), 4.45-4.55 (m, 2 H), 6.60-6.70 (m, 1 H), 6.91 (d, J = 1.2 Hz, 1 H), 6.95 (d, J = 1.2 Hz, 1 H), 11.35-11.60 (m, 1 H). | CDCl3 | 527 [M + H]+ |

TABLE 69

| Example | Compound Name | Structure | 1H NMR δ ppm | Solvent | ESI MS m/z |
|---|---|---|---|---|---|
| 196 | 4-chloro-N-(2-morpholinoethyl)-1'-(4-oxo-3,4,5,6,7,8-hexahydroquinazolin-2-yl)-1-(pyridin-3-ylmethyl)spiro[indoline-3,4'-piperidine]-6-carboxamide | (Test Target Compound 190) | 1.40-1.85 (m, 8 H), 2.35-2.70 (m, 10 H), 2.80-2.95 (m, 2 H), 3.43 (s, 2 H), 3.50-3.60 (m, 2 H), 3.70-3.80 (m, 4 H), 4.35-4.45 (m, 4 H), 6.70-7.00 (m, 2 H), 7.25-7.35 (m, 1 H), 7.60-6.65 (m, 1 H), 8.55-8.65 (m, 2 H). | CDCl3 | 618 [M + H]+ |
| 197 | 4-chloro-1-(2-hydroxyethyl)-N-(2-morpholinoethyl)-1'-(4-oxo-3,4,5,6,7,8-hexahydroquinazolin-2-yl)methyl-spiro[indoline-3,4'-piperidine]-6-carboxamide | (Test Target Compound 191) | 1.45-1.85 (m, 8 H), 2.35-2.70 (m, 10 H), 2.90-3.00 (m, 2 H), 3.35-3.45 (m, 2 H), 3.50-3.55 (m, 2 H), 3.60 (s, 2 H), 3.70-3.80 (m, 4 H), 3.85-3.90 (m, 2 H), 4.35-4.45 (m, 2 H), 6.70-6.75 (m, 1 H), 6.85 (d, J = 1.2 Hz, 1 H), 6.88 (d, J = 1.2 Hz, 1 H). | CDCl3 | 571 [M + H]+ |
| 198 | 4-chloro-1'-(4-oxo-3,4,5,6,7,8-hexahydroquinazolin-2-yl)spiro[indoline-3,4'-piperidine]-6-carbonitrile | (Test Target Compound 192) | 1.65-1.80 (m, 6 H), 2.35-2.40 (m, 2 H), 2.45-2.55 (m, 2 H), 2.60-2.70 (m, 2 H), 2.90-3.00 (m, 2 H), 3.67 (s, 2 H), 4.10-4.20 (m, 1 H), 4.40-4.50 (m, 2 H), 6.68 (d, J = 1.2 Hz, 1 H), 6.90 (d, J = 1.2 Hz, 1 H). | CDCl3 | 396 [M + H]+ |
| 199 | 4-chloro-1'-(4-oxo-3,4,5,6,7,8-hexahydroquinazolin-2-yl)spiro[indoline-3,4'-piperidine]-6-carboxamide | (Test Target Compound 193) | 1.55-1.75 (m, 6 H), 2.20-2.45 (m, 6 H), 2.85-2.95 (m, 2 H), 3.55 (s, 2 H), 4.30-4.40 (m, 2 H), 6.18 (s, 1 H), 6.89 (d, J = 1.2 Hz, 1 H), 6.98 (d, J = 1.2 Hz, 1 H), 7.26 (br. s, 1 H), 7.84 (br. s, 1 H), 11.05 (br. s, 1 H). | DMSO-d6 | 414 [M + H]+ |

TABLE 69-continued

| Example | Compound Name | Structure | 1H NMR δ ppm | Solvent | ESI MS m/z |
|---|---|---|---|---|---|
| 200 | methyl 1'-(4-oxo-3,4,5,6,7,8-hexahydroquinazolin-2-yl)spiro[indoline-3,4'-piperidine]-4-carboxylate | 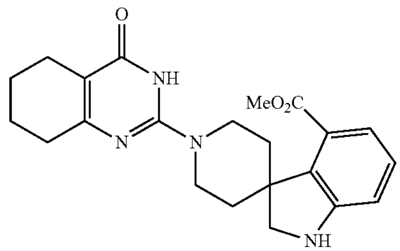 [SMILES: COC(=O)c1cccc2c1C1(CCN(c3nc4c(c(=O)[nH]3)CCCC4)CC1)CN2] | 1.64-1.78 (m, 6 H), 2.34-2.39 (m, 2 H), 2.45-2.50 (m, 2 H), 2.56-2.65 (m, 2 H), 2.95-3.04 (m, 2 H), 3.59 (s, 2 H), 3.76 (s, 3 H), 3.91 (br s, 1 H), 4.38-4.45 (m, 2 H), 6.77-6.80 (m, 1 H), 7.07-7.12 (m, 2 H), 11.19 (br s, 1 H). | CDCl3 | 395 [M + H]+ |
| 201 | 1'-(4-oxo-3,4,5,6,7,8-hexahydroquinazolin-2-yl)spiro[indoline-3,4'-piperidine]-4-carboxylic acid | 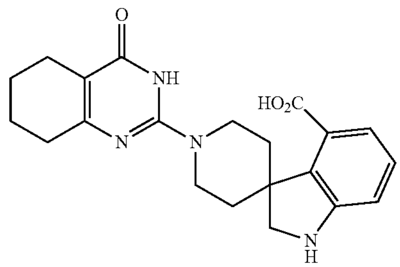 [SMILES: O=C(O)c1cccc2c1C1(CCN(c3nc4c(c(=O)[nH]3)CCCC4)CC1)CN2] | 1.48-1.74 (m, 8 H), 2.24-2.30 (m, 2 H), 2.44-2.56 (m, 2 H), 3.00-3.13 (m, 2 H), 3.50 (s, 2 H), 4.33-4.43 (m, 2 H), 6.70-6.75 (m, 1 H), 6.88-6.93 (m, 1 H), 7.01-7.07 (m, 1 H). | CDCl3 | 381 [M + H]+ |

TABLE 70

| Example | Compound Name | Structure | 1H NMR δ ppm | Solvent | ESI MS m/z |
|---|---|---|---|---|---|
| 202 | 1'-(4-oxo-3,4,5,6,7,8-hexahydroquinazolin-2-yl)spiro[indoline-3,4'-piperidine]-4-carbonitrile | (Test Target Compound 194) | 1.64-1.86 (m, 6 H), 2.33-2.39 (m, 2 H), 2.42-2.52 (m, 4 H), 2.91-3.00 (m, 2 H), 3.65 (s, 2 H), 4.02 (br. s, 1 H), 4.53-4.60 (m, 2 H), 6.79 (d, J = 7.8 Hz, 1 H), 6.95 (d, J = 7.6 Hz, 1 H), 7.07-7.12 (m, 1 H), 11.89 (br. s, 1 H). | CDCl3 | 362 [M + H]+ |
| 203 | 1-(2-hydroxyethyl)-1'-(4-oxo-3,4,5,6,7,8-hexahydroquinazolin-2-yl)spiro[indoline-3,4'-piperidine]-4-carbonitrile | (Test Target Compound 195) | 1.65-1.83 (m, 6 H), 2.35-2.39 (m, 2 H), 2.45-2.54 (m, 4 H), 2.93-3.01 (m, 2 H), 3.35 (t, J = 5.4 Hz, 2 H), 3.58 (s, 2 H), 3.87 (t, J = 5.4 Hz, 2 H), 4.47-4.53 (m, 2 H), 6.68-6.71 (m, 1 H), 6.88-6.91 (m, 1 H), 7.12-7.17 (m, 1 H), 11.32 (br. s, 1 H). | CDCl3 | 406 [M + H]+ |

TABLE 70-continued

| Example | Compound Name | Structure | 1H NMR δ ppm | Solvent | ESI MS m/z |
|---|---|---|---|---|---|
| 204 | N-(2-hydroxyethyl)-1'-(4-oxo-3,4,5,6,7,8-hexahydroquinazolin-2-yl)spiro[indoline-3,4'-piperidine]-6-carboxamide | 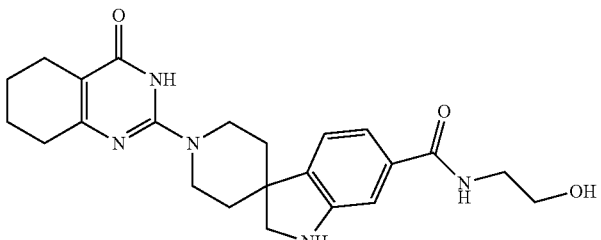<br>(Test Target Compound 198) | 1.56-1.76 (m, 8 H), 2.23-2.28 (m, 2 H), 2.35-2.40 (m, 2 H), 2.97-3.06 (m, 2 H), 3.25-3.31 (m, 2 H), 3.43-3.50 (m, 4 H), 4.23-4.31 (m, 2 H), 4.68 (t, J = 5.6 Hz, 1 H), 5.74 (s, 1 H), 6.93-6.95 (m, 1 H), 7.02-7.08 (m, 2 H), 8.12 (t, J = 5.6 Hz, 1 H), 11.03 (br. s, 1 H). | CDCl3 | 424 [M + H]+ |
| 205 | 2-{6-[(3-morpholinopropyl)amino]spiro[indoline-3,4'-piperidin]-1'-yl}-5,6,7,8-tetrahydroquinazolin-4(3H)-one | 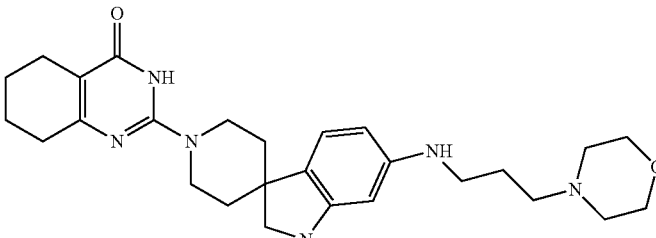<br>(Test Target Compound 199) | 1.64-1.92 (m, 10 H), 2.32-2.37 (m, 2 H), 2.44-2.49 (m, 8 H), 3.06-3.17 (m, 4 H), 3.49 (s, 2 H), 3.71-3.75 (m, 4 H), 4.29-4.35 (m, 2 H), 5.97 (d, J = 2.0 Hz, 1 H), 6.01 (dd, J = 7.9, 2.0 Hz, 1 H), 6.85 (d, J = 7.9 Hz, 1 H), 11.53 (br. s, 1 H). | CDCl3 | 479 [M + H]+ |
| 206 | 2-{6-[3-(dimethylamino)propoxy]spiro[indoline-3,4'-piperidin]-1'-yl}-5,6,7,8-tetrahydroquinazolin-4(3H)-one | 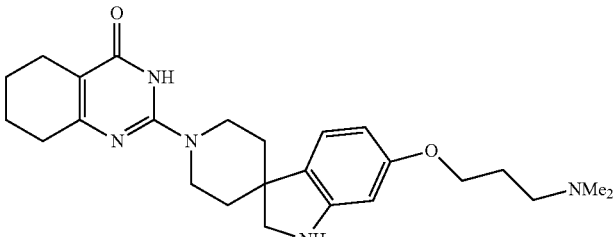<br>(Test Target Compound 200) | 1.65-1.92 (m, 8 H), 1.94-2.01 (m, 2 H), 2.33 (s, 6 H), 2.35-2.39 (m, 2 H), 2.45-2.50 (m, 2 H), 2.51-2.57 (m, 2 H), 3.06-3.14 (m, 2 H), 3.52 (s, 2 H), 3.96 (t, J = 6.8 Hz, 2 H), 4.24-4.31 (m, 2 H), 6.24 (d, J = 2.2 Hz, 1 H), 6.25-6.29 (m, 1 H), 6.91 (d, J = 8.1 Hz, 1 H). | CDCl3 | 438 [M + H]+ |
| 207 | 2-{6-[3-(piperidin-1-yl)propoxy]spiro[indoline-3,4'-piperidin]-1'-yl}-5,6,7,8-tetrahydroquinazolin-4(3H)-one | 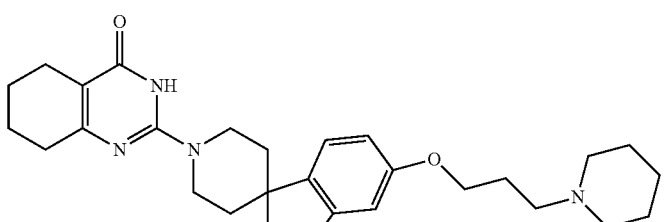<br>(Test Target Compound 201) | 1.44-1.52 (m, 2 H), 1.64-1.92 (m, 12 H), 1.98-2.06 (m, 2 H), 2.34-2.39 (m, 2 H), 2.45-2.63 (m, 8 H), 3.06-3.14 (m, 2 H), 3.52 (s, 2 H), 3.95 (t, J = 6.2 Hz, 2 H), 4.25-4.32 (m, 2 H), 6.23 (d, J = 2.1 Hz, 1 H), 6.25-6.28 (m, 1 H), 6.91 (d, J = 8.1 Hz, 1 H), 1089 (br. s, 1 H). | CDCl3 | 478 [M + H]+ |

TABLE 71

| Example | Compound Name | Structure | 1H NMR δ ppm | Solvent | ESI MS m/z |
|---|---|---|---|---|---|
| 208 | 3-morpholino-N-(1'-(4-oxo-3,4,5,6,7,8-hexahydroquinazolin-2-yl)spiro[indoline-3,4'-piperidin]-6-yl)propanamide | (Test Target Compound 202) | 1.64-1.94 (m, 8 H), 2.32-2.38 (m, 2 H), 2.45-2.55 (m, 4 H), 2.58-2.64 (m, 4 H), 2.70-2.75 (m, 2 H), 3.05-3.14 (m, 2 H), 3.54 (s, 2 H), 3.78-3.84 (m, 4 H), 4.32-4.39 (m, 2 H), 6.61 (dd, J = 7.9, 1.8 Hz, 1 H), 6.95 (d, J = 7.9 Hz, 1 H), 7.17 (d, J = 1.8 Hz, 1 H), 10.58 (s, 1 H), 11.48 (br. s, 1 H). | CDCl3 | 493 [M + H]+ |
| 209 | 6-iodo-1'-(4-oxo-3,4,5,6,7,8-hexahydroquinazolin-2-yl)spiro[indoline-3,4'-piperidin]-2-one | (Test Target Compound 203) | 1.57-1.77 (m, 8 H) 2.20-2.28 (m, 2 H) 2.34-2.41 (m, 2 H) 3.78-4.00 (m, 4 H) 7.17 (s, 1 H) 7.27-7.35 (m, 2 H) 10.52 (br. s., 1 H). | DMSO-d6 | 477 [M + H]+ |
| 210 | 4-iodo-1'-(4-oxo-3,4,5,6,7,8-hexahydroquinazolin-2-yl)spiro[indoline-3,4'-piperidin]-2-one | (Test Target Compound 204) | 1.50 (d, J = 14.18 Hz, 2 H) 1.56-1.73 (m, 4 H) 2.16-2.27 (m, 2 H) 2.35-2.43 (m, 2 H) 2.59-2.69 (m, 2 H) 3.60-3.74 (m, 2 H) 4.22-4.41 (m, 2 H) 6.83-6.89 (m, 1 H) 6.90-6.96 (m, 1 H) 7.38 (dd, J = 7.89, 1.04 Hz, 1 H) 10.53 (s, 1 H) 11.08 (br. s., 1 H). | DMSO-d6 | 477 [M + H]+ |
| 211 | 2-(4-iodospiro[indole-3,4'-piperidin]-1'-yl)-5,6,7,8-tetrahydroquinazolin-4(3H)-one | (Test Target Compound 205) | 1.37-1.44 (m, 2 H) 1.66-1.82 (m, 4 H) 2.41 (t, J = 6.30 Hz, 2 H) 2.51 (t, J = 6.11 Hz, 2 H) 2.96-3.08 (m, 2 H) 3.29-3.41 (m, 2 H) 4.51-4.62 (m, 2 H) 7.09 (t, J = 7.83 Hz, 1 H) 7.61-7.75 (m, 2 H) 8.63 (s, 1 H). | CDCl3 | 461 [M + H]+ |
| 212 | 6-bromo-1'-(4-oxo-3,4,5,6,7,8-hexahydroquinazolin-2-yl)spiro[indoline-3,4'-piperidin]-2-one | (Test Target Compound 206) | 1.70-1.82 (m, 4 H) 1.85-1.91 (m, 4 H) 2.33-2.39 (m, 2 H) 2.46-2.60 (m, 2 H) 3.94-4.08 (m, 4 H) 7.08 (d, J = 1.59 Hz, 1 H) 7.15-7.20 (m, 1 H) 7.30 (d, J = 7.82 Hz, 1 H). | CD3OD | 429 [M + H]+ |

TABLE 71-continued

| Example | Compound Name | Structure | 1H NMR δ ppm | Solvent | ESI MS m/z |
|---|---|---|---|---|---|
| 213 | 4-bromo-1'-(4-oxo-3,4,5,6,7,8-hexahydroquinazolin-2-yl)spiro[indoline-3,4'-piperidin]-2-one | (Test Target Compound 207) | 1.51-1.73 (m, 6 H) 2.18-2.30 (m, 2 H) 2.35-2.42 (m, 2 H) 2.54-2.64 (m, 2 H) 3.59-3.70 (m, 2 H) 4.23-4.34 (m, 2 H) 6.83-6.88 (m, 1 H) 7.06-7.16 (m, 2 H). | DMSO-d6 | 429 [M + H]+ |

TABLE 72

| Example | Compound Name | Structure | 1H NMR δ ppm | Solvent | ESI MS m/z |
|---|---|---|---|---|---|
| 214 | 2-(7-chlorospiro[indoline-3,4'-piperidin]-1'-yl)-5,6,7,8-tetrahydroquinazolin-4(3H)-one | (Test Target Compound 208) | 1.61-1.80 (m, 4 H) 1.80-2.03 (m, 4 H) 2.30-2.55 (m, 4 H) 3.01-3.20 (m, 2 H) 3.60 (d, J = 1.96 Hz, 2 H) 4.03 (s, 1 H) 4.19-4.37 (m, 2 H) 6.63-6.71 (m, 1 H) 6.89-6.96 (m, 1 H) 7.04-7.10 (m, 1 H) 10.37 (br. s, 1 H). | CDCl3 | 371 [M + H]+ |
| 215 | 2-(5-chlorospiro[indoline-3,4'-piperidin]-1'-yl)-5,6,7,8-tetrahydroquinazolin-4(3H)-one | (Test Target Compound 209) | 1.65-1.94 (m, 8H) 2.32-2.54 (m, 4 H) 3.00-3.16 (m, 2 H) 3.55 (s, 2 H) 3.77 (br. s., 1 H) 4.21-4.32 (m, 2 H) 6.56 (d, J = 8.1 Hz, 1 H) 6.96-7.04 (m, 2 H). | CDCl3 | 371 [M + H]+ |
| 216 | 2-(6-chlorospiro[indoline-3,4'-piperidin]-1'-yl)-5,6,7,8-tetrahydroquinazolin-4(3H)-one | (Test Target Compound 210) | 1.57-1.73 (m, 8 H), 2.22-2.28 (m, 2 H), 2.34-2.40 (m, 2 H), 2.94-3.03 (m, 2 H), 3.44 (s, 2 H), 4.22-4.30 (m, 2 H), 5.88 (s, 1 H), 6.46 (d, J = 1.8 Hz, 1 H), 6.48-6.52 (m, 1 H), 6.99 (d, J = 7.8 Hz, 1 H), 11.04 (br. s, 1 H). | DMSO-d6 | 371 [M + H]+ |

TABLE 72-continued

| Example | Compound Name | Structure | 1H NMR δ ppm | Solvent | ESI MS m/z |
|---|---|---|---|---|---|
| 217 | 2-(6-chloro-1-(2-hydroxyethyl)spiro[indoline-3,4'-piperidin]-1'-yl)-5,6,7,8-tetrahydroquinazolin-4(3H)-one | (Test Target Compound 211) | 1.65-1.81 (m, 6 H), 1.84-1.93 (m, 2 H), 2.31-2.37 (m, 2 H), 2.44-2.51 (m, 2 H), 3.02-3.11 (m, 2 H), 3.29 (t, J = 5.4 Hz, 2 H), 3.47 (s, 2 H), 3.84 (t, J = 5.4 Hz, 2 H), 4.37-4.45 (m, 2 H), 6.50 (d, J = 1.8 Hz, 1 H), 6.65 (dd, J = 7.8, 1.8 Hz, 1 H), 6.89 (d, J = 7.8 Hz, 1 H). | CDCl3 | 415 [M + H]+ |
| 218 | 2-(6-chloro-1-(pyridin-3-ylmethyl)spiro[indoline-3,4'-piperidin]-1'-yl)-5,6,7,8-tetrahydroquinazolin-4(3H)-one | (Test Target Compound 212) | 1.60-2.00 (m, 8 H), 2.30-2.40 (m, 2 H), 2.45-2.55 (m, 2 H), 2.95-3.05 (m, 2 H), 3.33 (s, 2 H), 4.30-4.40 (m, 4 H), 6.45-6.50 (m, 1 H), 6.65-6.70 (m, 1 H), 6.90-6.95 (m, 1 H), 7.25-7.35 (m, 1 H), 7.60-7.70 (m, 1 H), 8.55-8.60 (m, 2 H), 11.65 (br. s, 1 H). | CDCl3 | 462 [M + H]+ |
| 219 | 2-(4-chloro-1-(2-hydroxyethyl)spiro[indoline-3,4'-piperidin]-1'-yl)-5,6,7,8-tetrahydroquinazolin-4(3H)-one | (Test Target Compound 213) | 1.65-1.78 (m, 6 H), 2.34-2.40 (m, 2 H), 2.45-2.50 (m, 2 H), 2.62-2.72 (m, 2 H), 2.92-3.01 (m, 2 H), 3.33 (t, J = 5.5 Hz, 2 H), 3.52 (s, 2 H), 3.84 (t, J = 5.5 Hz, 2 H), 4.45-4.51 (m, 2 H), 6.42 (dd, J = 7.9, 0.7 Hz, 1 H), 6.60 (dd, J = 8.0, 0.7 Hz, 1 H), 6.98-7.03 (m, 1 H). | CDCl3 | 415 [M + H]+ |

TABLE 73

| Example | Compound Name | Structure | 1H NMR δ ppm | Solvent | ESIMS m/z |
|---|---|---|---|---|---|
| 220 | 2-(4-chlorospiro[indoline-3,4'-piperidin]-1'-yl)-5,6,7,8-tetrahydroquinazolin-4(3H)-one | (Test Target Compound 214) | 1.64-1.78 (m, 6 H), 2.35-2.40 (m, 2 H), 2.45-2.50 (m, 2 H), 2.60-2.69 (m, 2 H), 2.92-3.01 (m, 2 H), 3.61 (s, 2 H), 3.89 (br. s, 1 H), 4.42-4.49 (m, 2 H), 6.51 (dd, J = 7.8, 0.9 Hz, 1 H), 6.64 (dd, J = 8.1, 0.9 Hz, 1 H), 6.94-6.98 (m, 1 H), 11.28 (br s, 1 H). | CDCl3 | 371 [M + H]+ |

TABLE 73-continued

| Example | Compound Name | Structure | 1H NMR δ ppm | Solvent | ESIMS m/z |
|---|---|---|---|---|---|
| 221 | 2-[4-chloro-1-(pyridin-3-yl)methylspiro[indoline-3,4'-piperidin]1'-yl)-5,6,7,8-tetrahydroquinazolin-4(3H)-one | (Test Target Compound 215) | 1.60-1.80 (m, 6 H), 2.30-2.40 (m, 2 H), 2.45-2.55 (m, 2 H), 2.60-2.75 (m, 2 H), 2.80-2.95 (m, 2 H), 3.39 (s, 2 H), 4.35 (s, 2 H), 4.40-4.50 (m, 2 H), 6.40 (d, J = 7.2 Hz, 1 H), 6.60-6.65 (m, 1 H), 6.95-7.05 (m, 1 H), 7.25-7.35 (m, 1 H), 7.60-7.70 (m, 1 H), 8.55-8.60 (m, 2 H), 11.50 (br. s, 1 H). | CDCl3 | 462 [M + H]+ |
| 222 | 6-chloro-1'-(4-oxo-3,4,5,6,7,8-hexahydroquinazolin-2-yl)spiro[indoline-3,4'-piperidin]-2-one | (Test Target Compound 216) | 1.60-1.75 (m, 8 H), 2.23-2.28 (m, 2 H), 2.35-2.41 (m, 2 H), 3.84-3.96 (m, 4 H), 6.87 (d, J = 2.0 Hz, 1 H), 6.98 (dd, J = 8.1, 2.0 Hz, 1 H), 7.51 (d, J = 8.1 Hz, 1 H), 10.58 (s, 1 H), 11.09 (br. s, 1 H). | DMSO-d6 | 385 [M + H]+ |
| 223 | 6-chloro-1-(2-hydroxyethyl)-1'-(4-oxo-3,4,5,6,7,8-hexahydro-quinazolin-2-yl)spiro[indoline-3,4'-piperidin]-2-one | (Test Target Compound 217) | 1.65-1.78 (m, 4 H), 1.87-1.92 (m, 4 H), 2.34-2.39 (m, 2 H), 2.45-2.50 (m, 2 H), 3.85-3.94 (m, 4 H), 3.98-4.11 (m, 4 H), 6.97 (d, J = 1.7 Hz, 1 H), 7.04 (dd, J = 7.9, 1.7 Hz, 1 H), 7.18 (d, J = 7.9 Hz, 1 H), 10.73 (br. s, 1 H). | CDCl3 | 429 [M + H]+ |
| 224 | 4-chloro-1'-(4-oxo-3,4,5,6,7,8-hexahydroquinazolin-2-yl)spiro[indoline-3,4'-piperidin]-2-one | (Test Target Compound 218) | 1.59-1.71 (m, 6 H), 2.23-2.28 (m, 2 H), 2.36-2.41 (m, 2 H), 2.43-2.53 (m, 2 H), 3.60-3.69 (m, 2 H), 4.24-4.31 (m, 2 H), 6.83 (dd, J = 7.7, 0.9 Hz, 1 H), 6.96 (dd, J = 8.2, 0.9 Hz, 1 H), 7.19-7.24 (m, 1 H), 10.66 (s, 1 H), 11.09 (br. s, 1 H). | DMSO-d6 | 385 [M + H]+ |

TABLE 73-continued

| Example | Compound Name | Structure | 1H NMR δ ppm | Solvent | ESIMS m/z |
|---|---|---|---|---|---|
| 225 | 4-chloro-1-(2-hydroxy-ethyl)-1'-(4-oxo-3,4,5,6,7,8-hexahydro-quinazolin-2-yl)spiro[indoline-3,4'-piperidin]-2-one (Test Target Compound 219) | 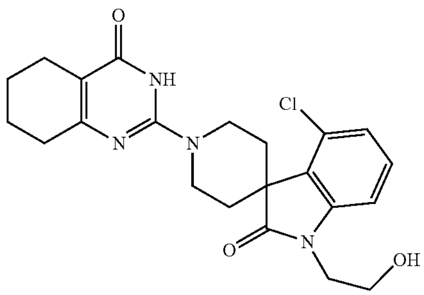 | 1.63-1.77 (m, 6 H), 2.32-2.39 (m, 2 H), 2.46-2.51 (m, 2 H), 2.73-2.82 (m, 2 H), 3.82-3.91 (m, 6 H), 4.38-4.45 (m, 2 H), 6.32-6.35 (m, 1 H), 6.85 (dd, J = 7.9, 0.8 Hz, 1 H), 6.97 (dd, J = 8.2, 0.8 Hz, 1 H), 7.16-7.22 (m, 1 H), 7.57-7.59 (m, 1 H). | CDCl3 | 429 [M + H]+ |

TABLE 74

| Example | Compound Name | Structure | 1H NMR δ ppm | Solvent | ESI MS m/z |
|---|---|---|---|---|---|
| 226 | 4-chloro-1'-(4-oxo-3,4,5,6,7,8-hexahydroquinazolin-2-yl)-1-(pyridin-3-ylmethyl)spiro[indoline-3,4'-piperidin]-2-one (Test Target Compound 220) | 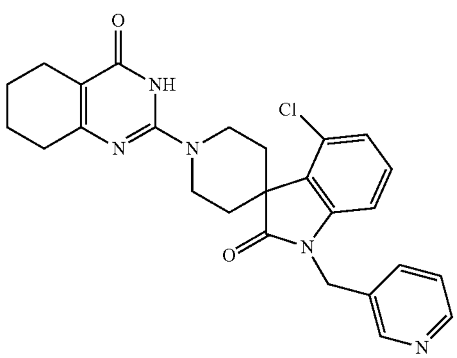 | 1.60-1.80 (m, 6 H), 2.35-2.40 (m, 2 H), 2.45-2.55 (m, 2 H). 2.80-2.90 (m, 2 H), 3.85-4.00 (m, 2 H), 4.40-4.50 (m, 2 H), 4.92 (s, 2 H), 6.63 (d, J = 7.2 Hz, 1 H), 6.95-7.00 (m, 1 H), 7.10-7.20 (m, 1 H), 7.25-7.35 (m, 1 H), 7.55-7.60 (m, 1 H), 8.55-8.65 (m, 2 H), 11.40 (br. s, 1 H). | CDCl3 | 476 [M + H]+ |
| 227 | 2-(4,6-dichlorospiro[indoline-3,4'-piperidin]-1'-yl)-5,6,7,8-tetrahydroquinazolin-4(3H)-one (Test Target Compound 221) | 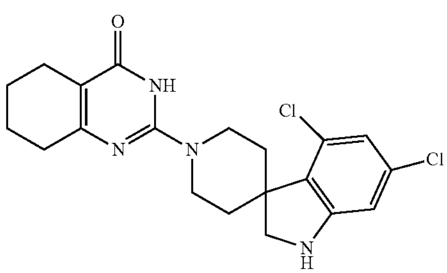 | 1.55-1.70 (m, 6 H), 2.20-2.45 (m, 6 H), 2.80-2.95 (m, 2 H), 3.55 (s, 2 H), 4.25-4.40 (m, 2 H), 6.33 (br. s, 1 H), 6.42 (d, J = 2.0 Hz, 1 H), 6.49 (d, J = 2.0 Hz, 1 H), 11.04 (br. s, 1 H). | DMSO-d6 | 405 [M + H]+ |
| 228 | 2-[4,6-dichloro-1-(2-hydroxyethyl)spiro[indoline-3,4'-piperidin]-1'-yl]-5,6,7,8-tetrahydroquinazolin-4(3H)-one (Test Target Compound 222) | 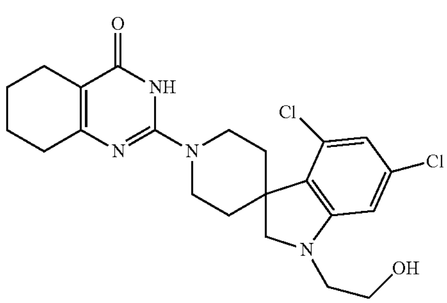 | 1.67-1.77 (m, 6 H), 2.38-2.43 (m, 2 H), 2.46-2.50 (m, 2 H), 2.57-2.66 (m, 2 H), 2.92-3.00 (m, 2 H), 3.57 (s, 2 H), 3.83-3.87 (m, 2 H), 4.25-4.32 (m, 2 H), 6.36 (d, J = 1.7 Hz, 1 H), 6.59 (d, J = 1.7 Hz, 1 H). | CDCl3 | 449 [M + H]+ |

TABLE 74-continued

| Example | Compound Name | Structure | 1H NMR δ ppm | Solvent | ESI MS m/z |
|---|---|---|---|---|---|
| 229 | 4,6-dichloro-1'-(4-oxo-3,4,5,6,7,8-hexahydro-quinazolin-2-yl)spiro[indoline-3,4'-piperidin]-2-one | (Test Target Compound 223) | 1.55-1.75 (m, 6 H), 2.20-2.45 (m, 6 H), 3.55-3.65 (m, 2 H), 4.20-4.35 (m, 2 H), 6.84 (d, J = 2.0 Hz, 1 H), 7.10 (d, J = 2.0 Hz, 1 H), 10.70-11.00 (m, 2 H). | DMSO-d6 | 419 [M + H]+ |
| 230 | 4,6-dichloro-1-methyl-1'-(4-oxo-3,4,5,6,7,8-hexahydro-quinazolin-2-yl)spiro[indoline-3,4'-piperidin]-2-one | (Test Target Compound 224) | 1.59-1.79 (m, 6 H), 2.32-2.37 (m, 2 H), 2.46-2.51 (m, 2 H), 2.67-2.77 (m, 2 H), 3.19 (s, 3 H), 3.81-3.89 (m, 2 H), 4.44-4.51 (m, 2 H), 6.75 (d, J = 1.7 Hz, 1 H), 6.99 (d, J = 1.7 Hz, 1 H), 12.23 (br. s, 1 H). | CDCl3 | 433 [M + H]+ |
| 231 | 4,6-dichloro-1-(2-hydroxyethyl)-1'-(4-oxo-3,4,5,6,7,8-hexahydro-quinazolin-2-yl)spiro[indoline-3,4'-piperidin]-2-one | (Test Target Compound 225) | 1.60-1.78 (m, 6 H), 2.31-2.37 (m, 2 H), 2.45-2.50 (m, 2 H), 2.67-2.77 (m, 2 H), 3.77-3.91 (m, 6 H), 4.38-4.45 (m, 2 H), 6.89 (d, J = 1.7 Hz, 1 H), 6.98 (d, J = 1.7 Hz, 1 H), 11.59 (br. s, 1 H). | CDCl3 | 463 [M + H]+ |

45

TABLE 75

| Example | Compound Name | Structure | 1H NMR δ ppm | Solvent | ESI MS m/z |
|---|---|---|---|---|---|
| 232 | 2-(4,7-dichlorospiro[indoline-3,4'-piperidin]-1'-yl)-5,6,7,8-tetrahydro-quinazolin-4(3H)-one | (Test Target Compound 226) | 1.66-1.83 (m, 6 H) 2.35-2.53 (m, 4 H) 2.55-2.70 (m, 2 H) 2.92-3.03 (m, 2 H) 3.66 (d, J = 2.0 Hz, 2 H) 4.13 (br. s, 1 H) 4.26 (br. d, J = 12.7 Hz, 2 H) 6.57 (d, J = 8.6 Hz, 1 H) 6.99 (d, J = 8.6 Hz, 1 H). | CDCl3 | 405 [M + H]+ |

TABLE 75-continued

| Example | Compound Name | Structure | 1H NMR δ ppm | Solvent | ESI MS m/z |
|---|---|---|---|---|---|
| 233 | 4,7-dichloro-1'-(4-oxo-3,4,5,6,7,8-hexahydroquinazolin-2-yl)spiro[indoline-3,4'-piperidin]-2-one | (Test Target Compound 227) | 1.54-1.72 (m, 6 H) 2.20-2.30 (m, 2 H) 2.35-2.40 (m, 2 H) 2.41-2.47 (m, 2 H) 3.55-3.73 (m, 2 H) 4.15-4.37 (m, 2 H) 6.99 (d, J = 8.80 Hz, 1 H) 7.31 (d, J = 8.80 Hz, 1 H) 11.08 (br. s., 2 H) | DMSO-d6 | 419 [M + H]+ |
| 234 | 4-chloro-6-hydroxy-1-methyl-1'-(4-oxo-3,4,5,6,7,8-hexahydroquinazolin-2-yl)spiro[indoline-3,4'-piperidin]-2-one | (Test Target Compound 228) | 1.52-1.70 (m, 6 H), 2.22-2.27 (m, 2 H), 2.35-2.47 (m, 4 H), 3.07 (s, 3 H), 3.57-3.66 (m, 2 H), 4.21-4.29 (m, 2 H), 6.38-6.42 (m, 2 H), 10.03 (s, 1 H), 11.07 (br. s, 1 H). | DMSO-d6 | 415 [M + H]+. |
| 235 | 2-(5-fluorospiro[indoline-3,4'-piperidin]-1'-yl)-5,6,7,8-tetrahydroquinazolin-4(3H)-one | (Test Target Compound 229) | 1.65-1.92 (m, 8 H), 2.37 (t, J = 6.1 Hz, 2 H), 2.48 (t, J = 6.1 Hz, 2 H), 3.04-3.12 (m, 2 H), 3.55 (s, 2 H), 3.67 (br. s, 1 H), 4.32-4.39 (m, 2 H), 6.55-6.59 (m, 1 H), 6.73-6.78 (m, 2 H), 11.23 (br. s, 1 H). | CDCl3 | 355 [M + H]+. |
| 236 | 2-(7-fluorospiro[indoline-3,4'-piperidin]-1'-yl)-5,6,7,8-tetrahydroquinazolin-4(3H)-one | (Test Target Compound 230) | 1.68-1.79 (m, 4 H) 1.82-1.97 (m, 4 H) 2.36-2.52 (m, 4 H) 3.06-3.17 (m, 2 H) 3.57-3.62 (m, 2 H) 3.85 (br. s., 1 H) 4.15-4.26 (m, 2 H) 6.61-6.76 (m, 1 H) 6.80-6.91 (m, 2 H). | CDCl3 | 355 [M + H]+. |
| 237 | 2-(6-fluorospiro[indoline-3,4'-piperidin]-1'-yl)-5,6,7,8-tetrahydroquinazolin-4(3H)-one | (Test Target Compound 231) | 1.67-1.93 (m, 8 H) 2.32-2.45 (m, 2 H) 2.45-2.62 (m, 2 H) 3.00-3.20 (m, 2 H) 3.56 (s, 2 H) 4.14-4.35 (m, 2 H) 6.30-6.36 (m, 1 H) 6.36-6.43 (m, 1 H) 6.87-6.97 (m, 1 H) | CDCl3 | 355 [M + H]+. |

TABLE 76

| Example | Compound Name | Structure | 1H NMR δ ppm | Solvent | ESI MS m/z |
|---|---|---|---|---|---|
| 238 | 2-(4-fluorospiro[indoline-3,4'-piperidin]-1'-yl)-5,6,7,8-tetrahydroquinazolin-4(3H)-one | 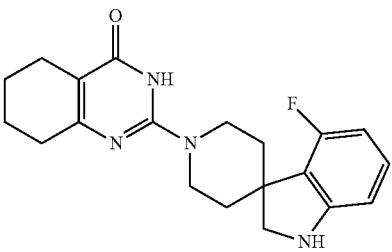<br>(Test Target Compound 232) | 1.64-1.80 (m, 4 H) 1.86 (d, J = 13.94 Hz, 2 H) 2.22-2.34 (m, 2 H) 2.36-2.42 (m, 2 H) 2.42-2.53 (m, 2 H) 2.95-3.08 (m, 2 H) 3.58 (s, 2 H) 3.89 (br. s., 1 H) 4.31 (br. d, J = 13.30 Hz, 2 H) 6.33-6.43 (m, 2 H) 6.93-7.06 (m, 1 H)CDCl3 | CDCl3 | 355 [M + H]+ |
| 239 | 2-(5,7-difluorospiro[indoline-3,4'-piperidin]-1'-yl)-5,6,7,8-tetrahydroquinazolin-4(3H)-one | 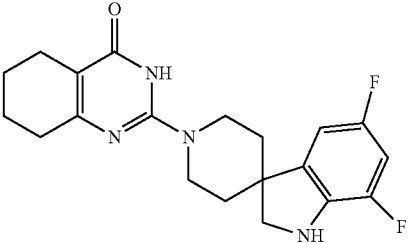<br>(Test Target Compound 233) | 1.55-1.75 (m, 6 H), 2.20-2.45 (m, 6 H), 3.55-3.65 (m, 2 H), 4.20-4.35 (m, 2 H), 6.84 (d, J = 2.0 Hz, 1 H), 7.10 (d, J = 2.0 Hz, 1 H), 10.70-11.00 (m, 2 H). | DMSO-d6 | 373 [M + H]+. |
| 240 | 2-(4,7-difluorospiro[indoline-3,4'-piperidin]-1'-yl)-5,6,7,8-tetrahydroquinazolin-4(3H)-one | 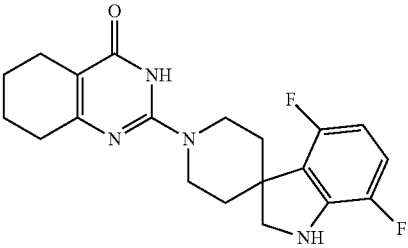<br>(Test Target Compound 234) | 1.64-1.78 (m, 4 H), 1.83-1.90 (m, 2 H), 2.22-2.38 (m, 4 H), 2.44-2.50 (m, 2 H), 2.93-3.04 (m, 2 H), 3.65 (s, 2 H), 3.94 (br. s, 1 H), 4.45-4.53 (m, 2 H), 6.26-6.32 (m, 1 H), 6.74-6.81 (m, 1 H), 11.90 (br. s, 1 H) | CDCl3 | 373 [M + H]+. |
| 241 | 2-(4,6-difluorospiro[indoline-3,4'-piperidin]-1'-yl)-5,6,7,8-tetrahydroquinazolin-4(3H)-one | 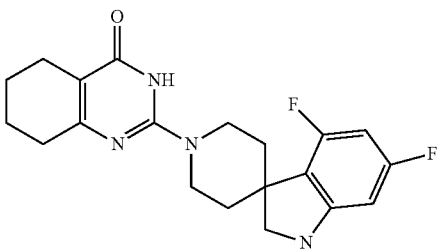<br>(Test Target Compound 235) | 1.66-1.78 (m, 6 H), 1.80-1.86 (m, 2 H), 2.19-2.28 (m, 2 H), 2.36-2.41 (m, 2 H), 2.45-2.50 (m, 2 H), 2.93-3.02 (m, 2 H), 3.60 (s, 2 H), 3.98 (br. s, 1 H), 4.32-4.39 (m, 2 H), 6.07-6.14 (m, 2 H), 10.71 (br. s, 1 H). | CDCl3 | 373 [M + H]+. |
| 242 | 2-(4,6-difluoro-1-(2-hydroxyethyl)spiro[indoline-3,4'-piperidin]-1'-yl)-5,6,7,8-tetrahydroquinazolin-4(3H)-one | 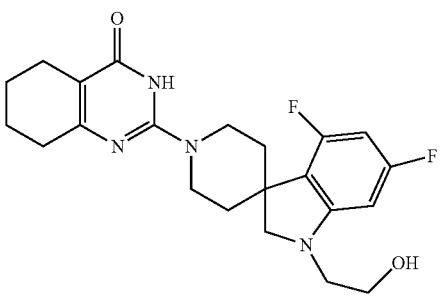<br>(Test Target Compound 236) | 1.64-1.83 (m, 6 H), 2.20-2.30 (m, 2 H), 2.33-2.38 (m, 2 H), 2.45-2.50 (m, 2 H), 2.91-3.00 (m, 2 H), 3.30 (t, J = 5.4 Hz, 2 H), 3.54 (s, 2 H), 3.84 (t, J = 5.4 Hz, 2 H), 4.42-4.49 (m, 2 H), 6.00-6.09 (m, 2 H), 11.69 (br. s, 1 H) | CDCl3 | 417 [M + H]+. |

TABLE 76-continued

| Example | Compound Name | Structure | 1H NMR δ ppm | Solvent | ESI MS m/z |
|---|---|---|---|---|---|
| 243 | N-{2-[4,6-difluoro-1'-(4-oxo-3,4,5,6,7,8-hexahydro-quinazolin-2-yl)spiro[indoline-3,4'-piperidin]-1-yl]ethyl}acetamide (Test Target Compound 237) | 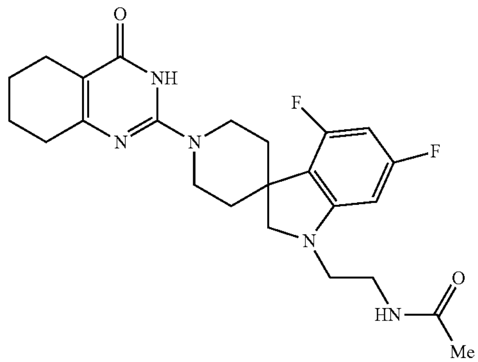 | 1.64-1.81 (m, 6 H), 1.97 (s, 3 H), 2.20-2.29 (m, 2 H), 2.33-2.38 (m, 2 H), 2.45-2.50 (m, 2 H), 2.92-3.01 (m, 2 H), 3.24-3.29 (m, 2 H), 3.46-3.52 (m, 4 H), 4.42-4.49 (m, 2 H), 5.63-5.68 (m, 1 H), 5.97-6.01 (m, 1 H), 6.02-6.09 (m, 1 H), 11.58 (br. s, 1 H). | CDCl3 | 458 [M + H]+. |

TABLE 77

| Example | Compound Name | Structure | 1H NMR δ ppm | Solvent | ESI MS m/z |
|---|---|---|---|---|---|
| 244 | N-{2-[4,6-difluoro-1'-(4-oxo-3,4,5,6,7,8-hexahydro-quinazolin-2-yl)spiro[indoline-3,4'-piperidin]-1-yl]ethyl}-2-hydroxy-acetamide (Test Target Compound 238) | 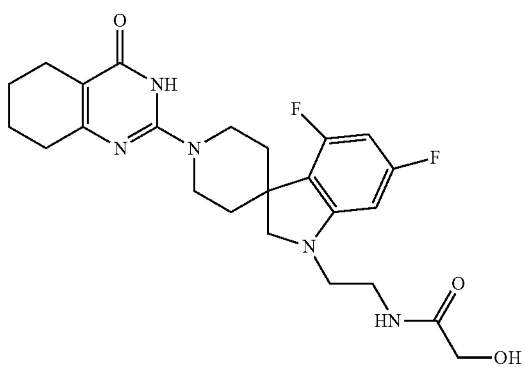 | 1.64-1.82 (m, 6 H), 2.17-2.26 (m, 2 H), 2.32-2.37 (m, 2 H), 2.45-2.50 (m, 2 H), 2.93-3.02 (m, 2 H), 3.29 (t, J = 6.1 Hz, 2 H), 3.50 (s, 2 H), 3.52-3.58 (m, 2 H), 4.09 (s, 2 H), 4.32-4.39 (m, 2 H), 5.96-6.00 (m, 1 H), 6.01-6.08 (m, 1 H), 6.87-6.91 (m, 1 H), 11.11 (br. s, 1 H). | CDCl3 | 474 [M + H]+. |
| 245 | N-{2-[4,6-difluoro-1'-(4-oxo-3,4,5,6,7,8-hexahydro-quinazolin-2-yl)spiro[indoline-3,4'-piperidin]-1-yl]ethyl}-2-methoxy-acetamide (Test Target Compound 239) | 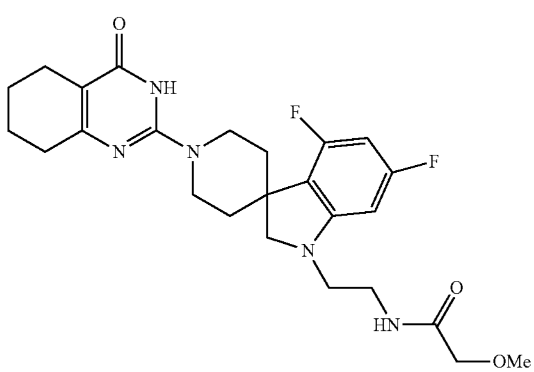 | 1.58-1.81 (m, 6 H), 2.19-2.28 (m, 2 H), 2.33-2.38 (m, 2 H), 2.45-2.50 (m, 2 H), 2.90-3.00 (m, 2 H), 3.38 (s, 3 H), 3.50-3.57 (m, 4 H), 3.86 (s, 2 H), 4.42-4.49 (m, 2 H), 5.99 (dd, J = 9.8, 2.0 Hz, 1 H), 6.02-6.08 (m, 1 H), 6.68-6.72 (m, 1 H), 11.68 (br. s, 1 H). | CDCl3 | 488 [M + H]+. |

TABLE 77-continued

| Example | Compound Name | Structure | 1H NMR δ ppm | Solvent | ESI MS m/z |
|---|---|---|---|---|---|
| 246 | 2-{4,6-difluoro-1-[(2,2-dimethyl-1,3-dioxan-5-yl)methyl]spiro[indoline-3,4'-piperidin]-1'-yl}-5,6,7,8-tetrahydroquinazolin-4(3H)-one | (Test Target Compound 240) | 1.45 (s, 3 H), 1.47 (s, 3 H), 1.60-1.85 (m, 6 H), 1.90-2.00 (m, 1 H), 2.20-2.30 (m, 2 H), 2.30-2.40 (m, 2 H), 2.40-2.50 (m, 2 H), 2.85-3.00 (m, 2 H), 3.20-3.30 (m, 2 H), 3.47 (s, 2 H), 3.65-3.70 (m, 2 H), 4.00-4.10 (m, 2 H), 4.40-4.50 (m, 2 H), 6.00-6.10 (m, 2 H), 11.55-11.85 (m, 1 H). | CDCl3 | 501 [M + H]+. |
| 247 | 2-{4,6-difluoro-1-[3-hydroxy-2-(hydroxymethyl)propyl]spiro[indoline-3,4'-piperidin]-1'-yl}-5,6,7,8-tetrahydroquinazolin-4(3H)-one | (Test Target Compound 241) | 1.65-1.85 (m, 6 H), 2.05-2.15 (m, 1 H), 2.20-2.30 (m, 2 H), 2.35-2.45 (m, 2 H), 2.45-2.50 (m, 2 H), 2.90-3.05 (m, 2 H), 3.20-3.30 (m, 2 H), 3.49 (s, 2 H), 3.75-3.85 (m, 2 H), 3.85-3.95 (m, 2 H), 4.30-4.40 (m, 2 H), 6.00-6.10 (m, 2 H). | CDCl3 | 461 [M + H]+. |
| 248 | 2-[4,6-difluoro-1-(1,3-dihydroxypropan-2-yl)spiro[indoline-3,4'-piperidin]-1'-yl]-5,6,7,8-tetrahydroquinazolin-4(3H)-one | (Test Target Compound 242) | 1.65-1.85 (m, 6 H), 2.20-2.30 (m, 2 H), 2.35-2.45 (m, 2 H), 2.45-2.50 (m, 2 H), 2.90-3.05 (m, 2 H), 3.62 (s, 2 H), 3.70-3.75 (m, 1 H), 3.90-3.95 (m, 4 H), 4.25-4.35 (m, 2 H), 6.00-6.10 (m, 2 H). | CDCl3 | 447 [M + H]+. |

TABLE 78

| Example | Compound Name | Structure | 1H NMR δ ppm | Solvent | ESI MS m/z |
|---|---|---|---|---|---|
| 249 | 2-[4,6-difluoro-1-(3-nitrobenzyl)spiro[indoline-3,4'-piperidin]-1'-yl]-5,6,7,8-tetrahydroquinazolin-4(3H)-one | (Test Target Compound 243) | 1.65-1.90 (m, 6 H), 2.25-2.40 (m, 4 H), 2.40-2.50 (m, 2 H), 2.85-2.95 (m, 2 H), 3.44 (s, 2 H), 4.35-4.45 (m, 4 H), 5.95-6.00 (m, 1 H), 6.10-6.20 (m, 1 H), 7.50-7.70 (m, 2 H), 8.15-8.20 (m, 2 H), 11.00-11.30 (m, 1 H). | CDCl3 | 508 [M + H]+. |
| 250 | 2-[1-(3-aminobenzyl)-4,6-difluorospiro[indoline-3,4'-piperidin]-1'-yl]-5,6,7,8-tetrahydroquinazolin-4(3H)-one | (Test Target Compound 244) | 1.60-1.85 (m, 6 H), 2.20-2.40 (m, 4 H), 2.45-2.50 (m, 2 H), 2.85-2.95 (m, 2 H), 3.41 (s, 2 H), 3.55-3.80 (m, 2 H), 4.21 (s, 2 H), 4.35-4.45 (m, 2 H), 5.95-6.10 (m, 2 H), 6.55-6.70 (m, 3 H), 7.10-7.15 (m, 1 H), 11.20-11.50 (m, 1 H). | CDCl3 | 478 [M + H]+. |
| 251 | 2-[4,6-difluoro-1-(pyridin-3-yl)methyl-spiro[indoline-3,4'-piperidin]-1'-yl]-5,6,7,8-tetrahydroquinazolin-4(3H)-one | (Test Target Compound 245) | 1.60-1.85 (m, 6 H), 2.20-2.50 (m, 6 H), 2.80-2.95 (m, 2 H), 3.40 (s, 2 H), 4.33 (s, 2 H), 4.40-4.50 (m, 2 H), 6.00-6.15 (m, 2 H), 7.25-7.35 (m, 1 H), 7.60-7.65 (m, 1 H), 8.55-8.60 (m, 2 H), 11.70 (br. s, 1 H). | CDCl3 | 464 [M + H]+. |

TABLE 78-continued

| Example | Compound Name | Structure | 1H NMR δ ppm | Solvent | ESI MS m/z |
|---|---|---|---|---|---|
| 252 | 2-[4,6-difluoro-1-(pyrimidin-5-yl)methyl-spiro[indoline-3,4'-piperidin]-1'-yl]-5,6,7,8-tetrahydroquinazolin-4(3H)-one | (Test Target Compound 246) | 1.55-1.85 (m, 6 H), 2.20-2.40 (m, 4 H), 2.40-2.50 (m, 2 H), 2.70-2.95 (m, 2 H), 3.42 (s, 2 H), 4.34 (s, 2 H), 4.40-4.50 (m, 2 H), 6.00-6.05 (m, 1 H), 6.10-6.20 (m, 1 H), 8.71 (s, 2 H), 9.20 (s, 1 H), 11.70 (br. s, 1 H). | CDCl3 | 465 [M + H]+. |
| 253 | 2-[4,6-difluoro-1-(pyridin-2-yl)methyl-spiro[indoline-3,4'-piperidin]-1'-yl]-5,6,7,8-tetrahydroquinazolin-4(3H)-one | (Test Target Compound 247) | 1.65-1.90 (m, 6 H), 2.20-2.40 (m, 4 H), 2.45-2.50 (m, 2 H), 2.85-2.95 (m, 2 H), 3.56 (s, 2 H), 4.40-4.50 (m, 4 H), 5.95-6.00 (m, 1 H), 6.05-6.15 (m, 1 H), 7.20-7.30 (m, 2 H), 7.65-7.75 (m, 1 H), 8.55-8.65 (m, 1 H), 11.80 (br. s, 1 H). | CDCl3 | 464 [M + H]+. |

TABLE 79

| Example | Compound Name | Structure | 1H NMR δ ppm | Solvent | ESI MS m/z |
|---|---|---|---|---|---|
| 254 | 2-[4,6-difluoro-1-(pyridin-4-yl)methyl-spiro[indoline-3,4'-piperidin]-1'-yl]-5,6,7,8-tetrahydroquinazolin-4(3H)-one | (Test Target Compound 248) | 1.65-1.90 (m, 6 H), 2.25-2.45 (m, 4 H), 2.45-2.50 (m, 2 H), 2.85-2.95 (m, 2 H), 3.46 (s, 2 H), 4.32 (s, 2 H), 4.40-4.50 (m, 2 H), 5.90-6.00 (m, 1 H), 6.10-6.15 (m, 1 H), 7.20-7.25 (m, 2 H), 8.55-8.65 (m, 2 H), 11.80 (br. s, 1 H). | CDCl3 | 464 [M + H]+. |

TABLE 79-continued

| Example | Compound Name | Structure | 1H NMR δ ppm | Solvent | ESI MS m/z |
|---|---|---|---|---|---|
| 255 | 2-[4,6-difluoro-1-(imidazo[5,1-b]thiazol-3-yl-methyl)spiro[indoline-3,4'-piperidin]-1'-yl]-5,6,7,8-tetrahydro-quinazolin-4(3H)-one | 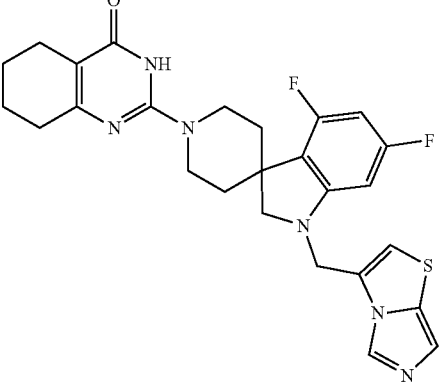<br>(Test Target Compound 249) | 1.65-1.85 (m, 6 H), 2.20-2.30 (m, 2 H), 2.30-2.40 (m, 2 H), 2.40-2.50 (m, 2 H), 2.85-2.95 (m, 2 H), 3.40 (s, 2 H), 4.30-4.40 (m, 2 H), 4.41 (s, 2 H), 6.10-6.25 (m, 2 H), 6.72 (s, 1 H), 7.15 (s, 1 H), 7.93 (s, 1 H). | CDCl3 | 509 [M + H]+. |
| 256 | 2-(4,6-di-fluoro-1-methylspiro[indoline-3,4'-piperidin]-1'-yl)-8-methyl-quinazolin-4(3H)-one | 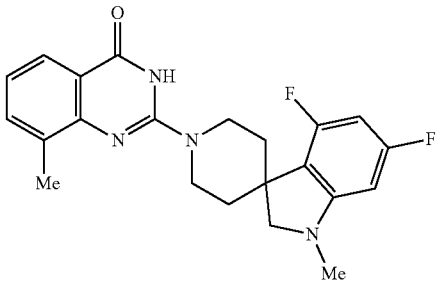<br>(Test Target Compound 250) | 1.86-1.92 (m, 2 H), 2.29-2.38 (m, 2 H), 2.48 (s, 3 H), 2.81 (s, 3 H), 3.07-3.16 (m, 2 H), 3.45 (s, 2 H), 4.44-4.50 (m, 2 H), 5.97 (dd, J = 9.8, 2.1, 1 H), 6.03-6.10 (m, 1 H), 7.03-7.08 (m, 1 H), 7.46-7.49 (m, 1 H), 7.90-7.94 (m, 1 H), 10.45 (br. s, 1 H). | CDCl3 | 397 [M + H]+. |
| 257 | 2-(4,6-di-fluoro-1-methylspiro[indoline-3,4'-piperidin]-1-yl)-8-(hydroxy-methyl)-quinazolin-4(3H)-one | 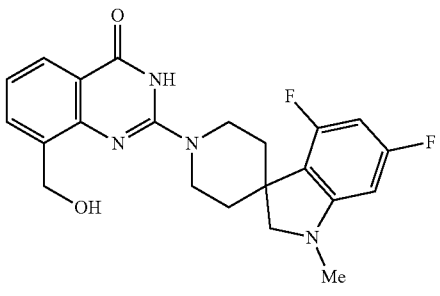<br>(Test Target Compound 251) | 1.89-1.96 (m, 2 H), 2.30-2.39 (m, 2 H), 2.81 (s, 3 H), 3.13-3.22 (m, 2 H), 3.45 (s, 2 H), 4.40-4.47 (m, 2 H), 4.91 (s, 2 H), 5.98 (dd, J = 9.7, 2.1 Hz, 1 H), 6.04-6.10 (m, 1 H), 7.09-7.14 (m, 1 H), 7.48-7.51 (m, 1 H), 7.96-8.00 (m, 1 H), 11.01 (br. s, 1 H). | CDCl3 | 413 [M + H]+. |
| 258 | 2-[4,6-di-fluoro-1-(2-hydroxy-ethyl)spiro[indoline-3,4'-piperidin]-1'-yl]-8-methyl-quinazolin-4(3H)-one | 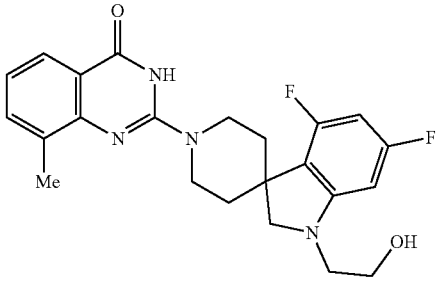<br>(Test Target Compound 252) | 1.56-1.92 (m, 2 H), 2.32-2.41 (m, 2 H), 2.48 (s, 3 H), 3.05-3.14 (m, 2 H), 3.30-3.34 (m, 2 H), 3.59 (s, 2 H), 3.84-3.88 (m, 2 H), 4.52-4.59 (m, 2 H), 6.02-6.10 (m, 2 H), 7.03-7.07 (m, 1 H), 7.45-7.49 (m, 1 H), 7.89-7.92 (m, 1 H), 11.21 (br. s, 1 H). | CDCl3 | 427 [M + H]+. |

TABLE 79-continued

| Example | Compound Name | Structure | 1H NMR δ ppm | Solvent | ESI MS m/z |
|---|---|---|---|---|---|
| 259 | 2-[4,6-difluoro-1-(2-hydroxyethyl)spiro[indoline-3,4'-piperidin]-1'-yl]-8-(hydroxymethyl)-quinazolin-4(3H)-one (Test Target Compound 253) | 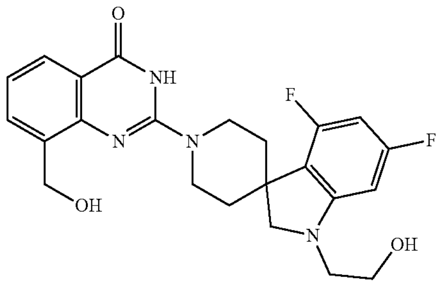 | 1.73-1.80 (m, 2 H), 1.98-2.07 (m, 2 H), 2.95-3.05 (m, 2 H), 3.22-3.26 (m, 2 H), 3.58-3.65 (m, 4 H), 4.36-4.43 (m, 2 H), 4.73 (t, J = 5.5 Hz, 1 H), 4.79 (s, 2 H), 5.10 (br. s, 1 H), 6.11-6.22 (m, 2 H), 7.11-7.16 (m, 1 H), 7.66-7.70 (m, 1 H), 7.79-7.83 (m, 1 H), 11.41 (br. s, 1 H). | DMSO-d6 | 443 [M + H]+. |

TABLE 80

| Example | Compound Name | Structure | 1H NMR δ ppm | Solvent | ESI MS m/z |
|---|---|---|---|---|---|
| 260 | 2-(4,6-difluoro-1-(pyridin-3-ylmethyl)-spiro[indoline-3,4'-piperidin]-1'-yl)-8-methylquinazolin-4(3H)-one (Test Target Compound 254) | 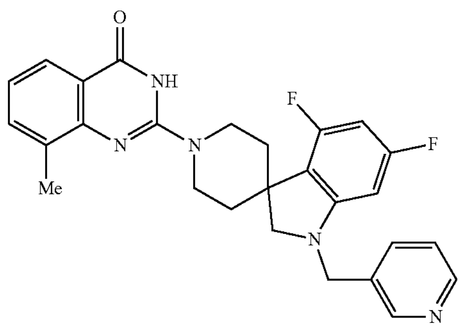 | 1.85-1.91 (m, 2 H), 2.32-2.41 (m, 2 H), 2.47 (s, 3 H), 3.45 (s, 3 H), 4.35 (s, 2 H), 4.46-4.53 (m, 2 H), 6.04 (dd, J = 9.7, 2.1 Hz, 1 H), 6.09-6.15 (m, 1 H), 7.03-7.08 (m, 1 H), 7.30-7.34 (m, 1 H), 7.45-7.49 (m, 1 H), 7.62-7.66 (m, 1 H), 7.88-7.92 (m, 1 H), 8.57-8.61 (m, 2 H), 10.89 (br. s, 1 H). | CDCl3 | 474 [M + H]+. |
| 261 | 2-(4,6-difluoro-1-(pyridin-3-ylmethyl)-spiro[indoline-3,4'-piperidin]-1'-yl]-8-(hydroxymethyl)-quinazolin-4(3H)-one (Test Target Compound 255) | 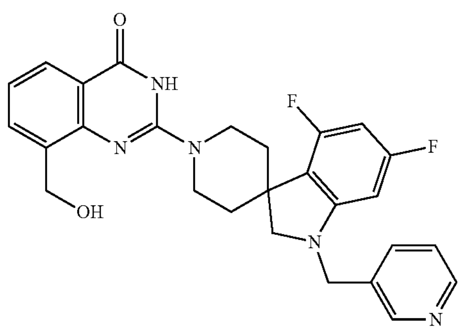 | 1.87-1.94 (m, 2 H), 2.32-2.41 (m, 2 H), 3.03-3.12 (m, 2 H), 3.44 (s, 2 H), 4.35 (s, 2 H), 4.38-4.45 (m, 2 H), 4.89 (s, 2 H), 6.06 (dd, J = 9.7, 2.1 Hz, 1 H), 6.09-6.16 (m, 1 H), 7.10-7.14 (m, 1 H), 7.30-7.35 (m, 1 H), 7.47-7.51 (m, 1 H), 7.62-7.66 (m, 1 H), 7.95-7.98 (m, 1 H), 8.57-8.60 (m, 2 H), 11.09 (br. s, 1 H). | CDCl3 | 490 [M + H]+. |
| 262 | 6-fluoro-1'-(4-oxo-3,4,5,6,7,8-hexahydro-quinazolin-2-yl)spiro-[indoline-3,4'-piperidin]-2-one (Test Target Compound 256) | 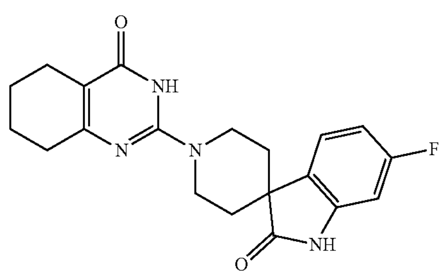 | 1.52-1.78 (m, 8 H) 2.20-2.31 (m, 2 H) 2.35-2.42 (m, 2 H) 3.80-4.00 (m, 4 H) 6.64-6.69 (m, 1 H) 6.70-6.77 (m, 1 H) 7.51 (dd, J = 8.31, 5.50 Hz, 1 H) 10.57 (s, 1 H) 11.05 (br. s., 1 H) | CDCl3 | 369 [M + H]+. |

TABLE 80-continued

| Example | Compound Name | Structure | 1H NMR δ ppm | Solvent | ESI MS m/z |
|---|---|---|---|---|---|
| 263 | 4-fluoro-1'-(4-oxo-3,4,5,6,7,8-hexahydro-quinazolin-2-yl)spiro[indoline-3,4'-piperidin]-2-one (Test Target Compound 257) | 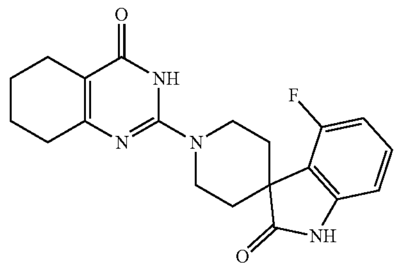 | 1.54-1.72 (m, 4 H) 1.73-1.85 (m, 2H) 1.94-2.05 (m, 2 H) 2.19-2.29 (m, 2 H) 2.35-2.42 (m, 2 H) 3.67-3.81 (m, 2 H) 4.00-4.16 (m, 2 H) 6.71 (d, J = 7.58 Hz, 1 H) 6.73-6.80 (m, 1 H) 7.19-7.27 (m, 1 H) 10.65 (s, 1 H) | DMSO-d6 | 369 [M + H]+. |
| 264 | 4,7-difluoro-1'-(4-oxo-3,4,5,6,7,8-hexa-hydroquinazolin-2-yl)spiro[indoline-3,4'-piperidin]-2-one (Test Target Compound 258) | 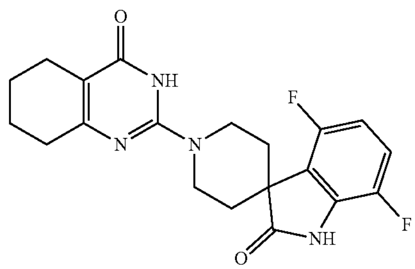 | 1.65-1.79 (m, 4 H), 1.92-1.99 (m, 2 H), 2.24-2.33 (m, 2 H), 2.36-2.42 (m, 2 H), 2.45-2.51 (m, 2 H), 3.90-3.99 (m, 2 H), 4.13-4.21 (m, 2 H), 6.63-6.69 (m, 1 H), 6.94-7.01 (m, 1 H), 8.58 (br. s, 1 H), 10.80 (br. s, 1 H) | CDCl3 | 387 [M + H]+. |
| 265 | 4,7-difluoro-1-(2-hydroxyethyl)-1'-(4-oxo-3,4,5,6,7,8-hexa-hydroquinazolin-2-yl)spiro[indoline-3,4'-piperidin]-2-one (Test Target Compound 259) | 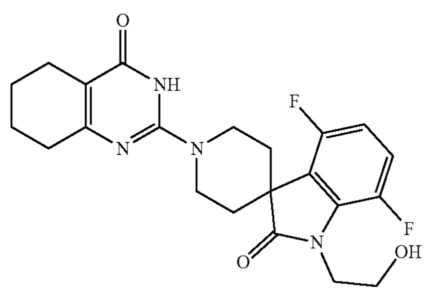 | 1.63-1.77 (m, 4 H), 1.82-1.90 (m, 2 H), 2.27-2.37 (m, 4 H), 2.45-2.51 (m, 2 H), 3.84-3.94 (m, 4 H), 4.03-4.08 (m, 2 H), 4.28-4.36 (m, 2 H), 6.63-6.70 (m, 1 H), 6.94-7.02 (m, 1 H), 11.32 (br. s, 1 H). | CDCl3 | 431 [M + H]+. |

TABLE 81

| Example | Compound Name | Structure | 1H NMR δ ppm | Solvent | ESI MS m/z |
|---|---|---|---|---|---|
| 266 | 4,6-difluoro-1'-(4-oxo-3,4,5,6,7,8-hexa-hydroquinazolin-2-yl)spiro[indoline-3,4'-piperidin]-2-one (Test Target Compound 260) | 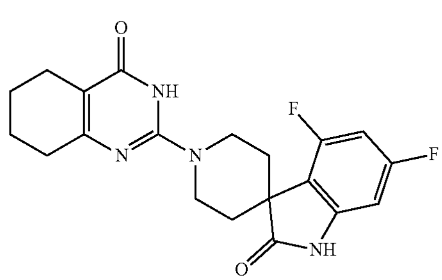 | 1.59-1.70 (m, 4 H), 1.76-1.82 (m, 2 H), 1.92-2.01 (m, 2 H), 2.22-2.28 (m, 2 H), 2.35-2.41 (m, 2 H), 3.15-3.19 (m, 2 H), 3.68-3.77 (m, 2 H), 4.03-4.11 (m, 2 H), 6.55-6.59 (m, 1 H), 6.74-6.81 (m, 1 H), 10.81 (s, 1 H), 11.09 (br. s, 1 H). | DMSO-d6 | 387 [M + H]+. |

TABLE 81-continued

| Example | Compound Name | Structure | 1H NMR δ ppm | Solvent | ESI MS m/z |
|---|---|---|---|---|---|
| 267 | 4,6-difluoro-1-(2-hydroxyethyl)-1'-(4-oxo-3,4,5,6,7,8-hexahydroquinazolin-2-yl)spiro[indoline-3,4'-piperidin]-2-one | (Test Target Compound 261) | 1.65-1.78 (m, 4 H), 1.82-1.89 (m, 2 H), 2.22-2.31 (m, 2 H), 2.34-2.39 (m, 2 H), 2.45-2.50 (m, 2 H), 3.83-3.94 (m, 6 H), 4.19-4.26 (m, 2 H), 6.45-6.50 (m, 1 H), 6.56 (dd, J = 8.6, 2.0 Hz, 1 H), 10.70 (br. s, 1 H). | CDCl3 | 431 [M + H]+. |
| 268 | 4,6-difluoro-1-(2-hydroxyethyl)-1'-(8-methyl-4-oxo-3,4-dihydroquinazolin-2-yl)spiro[indoline-3,4'-piperidin]-2-one | (Test Target Compound 262) | 1.82-1.90 (m, 2 H), 2.09-2.18 (m, 2 H), 2.40 (s, 3 H), 3.58-3.64 (m, 2 H), 3.73-3.86 (m, 4 H), 4.21-4.28 (m, 2 H), 4.85 (t, J = 5.8 Hz, 1 H), 6.80-6.87 (m, 1 H), 7.00 (dd, J = 9.3, 2.2 Hz, 1 H), 7.03-7.08 (m, 1 H), 7.48-7.51 (m, 1 H), 7.77-7.81 (m, 1 H), 11.45 (br. s, 1 H). | DMSO-d6 | 441 [M + H]+. |
| 269 | 4,6-difluoro-1-(2-hydroxyethyl)-1'-(8-(hydroxymethyl)-4-oxo-3,4-dihydroquinazolin-2-yl)-spiro[indoline-3,4'-piperidin]-2-one | (Test Target Compound 263) | 1.83-1.89 (m, 2 H), 2.08-2.17 (m, 2 H), 3.58-3.64 (m, 2 H), 3.73-3.84 (m, 4 H), 4.18-4.26 (m, 2 H), 4.78-4.81 (m, 2 H), 4.85 (t, J = 5.8 Hz, 1 H), 5.07 (t, J = 5.7 Hz, 1 H), 6.80-6.87 (m, 1 H), 7.00 (d, J = 9.3, 2.1 Hz, 1 H), 7.14-7.19 (m, 1 H), 7.69-7.72 (m, 1 H), 7.81-7.85 (m, 1 H), 11.46 (br. s, 1 H). | DMSO-d6 | 457 [M + H]+. |
| 270 | 4,6-difluoro-1-methyl-1'-(8-methyl-4-oxo-3,4-dihydroquinazolin-2-yl)spiro[indoline-3,4'-piperidin]-2-one | (Test Target Compound 264) | 1.88-1.95 (m, 2 H), 2.31-2.40 (m, 2 H), 2.48 (s, 3 H), 3.21 (s, 3 H), 4.02-4.11 (m, 2 H), 4.34-4.41 (m, 2 H), 6.43-6.51 (m, 1 H), 7.00-7.05 (m, 1 H), 7.45-7.48 (m, 1 H), 7.88-7.92 (m, 1 H), 10.77 (br. s, 1 H). | CDCl3 | 411 [M + H]+. |

TABLE 81-continued

| Example | Compound Name | Structure | 1H NMR δ ppm | Solvent | ESI MS m/z |
|---|---|---|---|---|---|
| 271 | 4,6-difluoro-1'-[8-(hydroxymethyl)-4-oxo-3,4-dihydro-quinazolin-2-yl]-1-methylspiro[indoline-3,4'-piperidin]-2-one (Test Target Compound 265) | 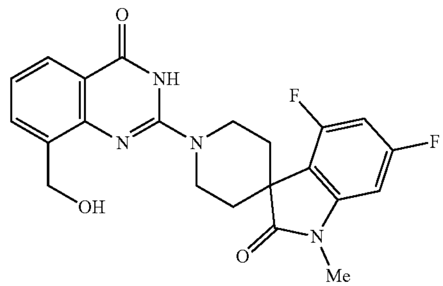 | 1.92-1.98 (m, 2 H), 2.30-2.40 (m, 2 H), 3.21 (s, 3 H), 4.04-4.13 (m, 2 H), 4.23-4.30 (m, 2 H), 4.90 (s, 2 H), 6.44-6.53 (m, 2 H), 7.08-7.13 (m, 1 H), 7.47-7.50 (m, 1 H), 7.96-8.00 (m, 1 H), 11.52 (br. s, 1 H). | CDCl3 | 427 [M + H]+. |

TABLE 82

| Example | Compound Name | Structure | 1HNMR δ ppm | Solvent | ESI MS m/z |
|---|---|---|---|---|---|
| 272 | 4,6-difluoro-1'-(8-methyl-4-oxo-3,4-dihydroquinazolin-2-yl)-1-(pyridin-3-ylmethyl)spiro[indoline-3,4'-piperidin]-2-one (Test Target Compound 266) | 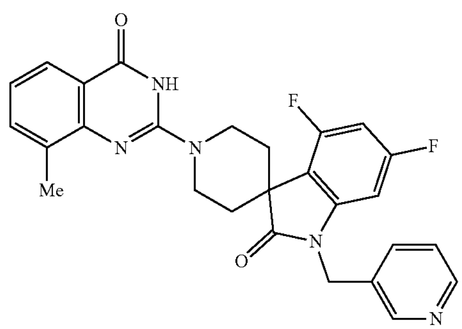 | 1.92-1.99 (m, 2 H), 2.38-2.47 (m, 2 H), 2.49 (s, 3 H), 4.03-4.12 (m, 2 H), 4.39-4.46 (m, 2 H), 4.91 (s, 2 H), 6.33 (dd, J = 8.2, 2.0 Hz, 1 H), 6.45-6.51 (m, 1 H), 7.02-7.07 (m, 1 H), 7.29-7.33 (m, 1 H), 7.46-7.49 (m, 1 H), 7.58-7.62 (m, 1 H), 7.90-7.93 (m, 1 H), 8.58-8.62 (m, 2 H), 10.77 (br. s, 1 H). | CDCl3 | 488 [M + H]+. |
| 273 | 4,6-difluoro-1'-[8-(hydroxymethyl)-4-oxo-3,4-dihydro-quinazolin-2-yl]-1-(pyridin-3-ylmethyl)-spiro[indoline-3,4'-piperidin]-2-one (Test Target Compound 267) | 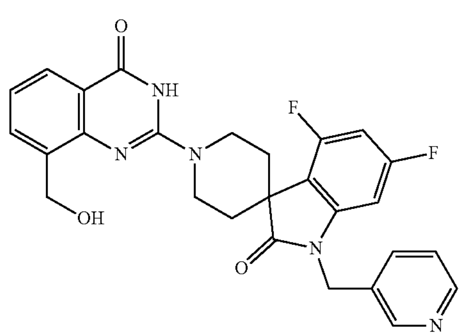 | 1.96-2.03 (m, 2 H), 2.38-2.47 (m, 2 H), 4.06-4.15 (m, 2 H), 4.33-4.40 (m, 2 H), 4.89-4.93 (m, 4 H), 6.35 (dd, J = 8.2, 2.0 Hz, 1 H), 6.46-6.52 (m, 1 H), 7.09-7.14 (m, 1 H), 7.30-7.34 (m, 1 H), 7.48-7.52 (m, 1 H), 7.59-7.63 (m, 1 H), 7.97-8.00 (m, 1 H), 8.58-8.62 (m, 2 H), 11.09 (br. s, 1 H). | CDCl3 | 504 [M + H]+. |

TABLE 82-continued

| Example | Compound Name | Structure | 1HNMR δ ppm | Solvent | ESI MS m/z |
|---|---|---|---|---|---|
| 274 | 4,6-difluoro-1-(2-oxo-2-phenylethyl)-1'-(4-oxo-3,4,5,6,7,8-hexahydroquinazolin-2-yl)spiro[indoline-3,4'-piperidin]-2-one | (Test Target Compound 268) | 1.64-1.80 (m, 4H), 1.96 (d, J = 14.2 Hz, 2H), 2.30-2.43 (m, 4H), 2.50 (t, J = 6.0 Hz, 2H), 3.91 (t, J = 11.5 Hz, 2H), 4.26 (d, J = 13.7 Hz, 2H), 6.24 (dd, J = 8.3, 1.9 Hz, 1H), 5.10 (s, 2H), 6.50 (t, J = 9.7 Hz, 1H), 7.55 (t, J = 7.6 Hz, 2H), 7.65-7.70 (m, 1H), 8.02 (d, J = 7.6 Hz, 2H), 10.67 (br. s., 1H). | CDCl3 | 505 [M + H]+. |
| 275 | 2-(4,7-dimethylspiro-[indoline-3,4'-piperidin]-1'-yl)-5,6,7,8-tetrahydro-quinazolin-4(3H)-one | (Test Target Compound 269) | 1.51-1.74 (m, 6 H) 1.99 (s, 3 H) 2.00-2.11 (m, 2 H) 2.17 (s, 3 H) 2.24 (br. s., 2 H) 2.33-2.41 (m, 2 H) 2.91 (t, J = 12.47 Hz, 2 H) 3.42 (s, 2 H) 4.19-4.39 (m, 2 H) 5.21 (s, 1 H) 6.22 (d, J = 7.5 Hz, 1 H) 6.65 (d, J = 7.5 Hz, 1 H) 10.97 (br. s., 1 H) | DMSO-d6 | 365 [M + H]+. |
| 276 | 2-(1',2'-dihydrospiro-[piperidine-4,3'-pyrrolo[2,3-c]-pyridin]-1-yl)-5,6,7,8-tetra-hydroquinazolin-4(3H)-one | (Test Target Compound 270) | 1.66-1.79 (m, 4 H) 1.80-2.00 (m, 4 H) 2.35-2.57 (m, 4 H) 3.04-3.20 (m, 2 H) 3.57 (s, 2 H) 3.83 (br. s., 1 H) 4.16-4.32 (m, 2 H) 6.95-7.03 (m, 1 H) 7.98-8.10 (m, 2 H) | CDCl3 | 338 [M + H]+. |
| 277 | 2-(1',2'-dihydrospiro-[piperidine-4,3'-pyrrolo[3,2-b]-pyridin]-1-yl)-5,6,7,8-tetra-hydroquinazolin-4(3H)-one | (Test Target Compound 271) | 1.65-1.81 (m, 6 H) 2.02-2.19 (m, 2 H) 2.38-2.50 (m, 4 H) 3.29-3.39 (m, 2 H) 3.53 (s, 2 H) 3.76 (br. s., 1 H) 4.16 (d, J = 14.55 Hz, 2 H) 6.82-6.88 (m, 1 H) 6.89-6.96 (m, 1 H) 7.85-7.92 (m, 1 H) | CDCl3 | 338 [M + H]+. |

TABLE 83

| Example | Compound Name | Structure | 1H NMR δ ppm | Solvent | ESI MS m/z |
|---|---|---|---|---|---|
| 278 | 2-(6'-chlorospiro-1',2'-dihydrospiro-[piperidine-4,3'-pyrrolo[3,2-b]-pyridine-1-yl)-5,6,7,8-tetrahydro-quinazoline-4(3H)-one | 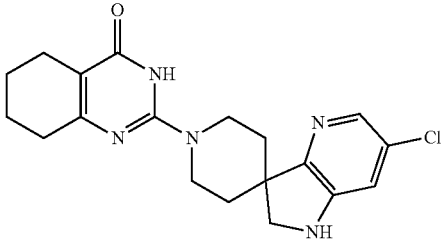<br>(Test Target Compound 272) | 1.63-1.83 (m, 6 H) 2.00-2.12 (m, 2 H) 2.36-2.52 (m, 4 H) 3.31-3.44 (m, 2 H) 3.57 (s, 2 H) 3.86 (s, 1 H) 4.07-4.20 (m, 2 H) 6.81 (d, J = 2.0 Hz, 1 H) 7.81 (d, J = 2.0 Hz, 1 H) | CDCl3 | 372 [M + H]+. |
| 279 | 2-(4'-chloro-1',2-dihydro[piperidine-4,3'-pyrrolo[2,3-c]-pyridine]-1-yl)-5,6,7,8-tetrahydro-quinazoline-4(3H)-one | 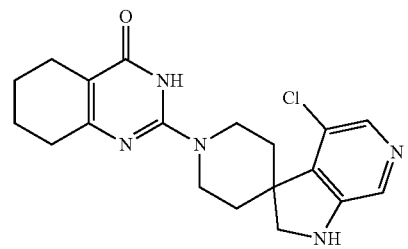<br>(Test Target Compound 273) | 1.67-1.81 (m, 4 H) 1.84-1.91 (m, 4 H) 2.37-2.53 (m, 4 H) 3.06-3.22 (m, 2 H) 3.60 (d, J = 1.3 Hz, 2 H) 4.13-4.24 (m, 2 H) 4.53 (s, 1 H) 7.17 (d, J = 2.1 Hz, 1 H) 7.84 (d, J = 2.1 Hz, 1 H) | CDCl3 | 372 [M + H]+. |
| 280 | 1-(4-oxo-3,4,5,6,7,8-hexa-hydroquinazoline-2-yl)spiro(piper-idine-4,3'-pyrrolo-[2,3-b]pyridine-2'(1'H)-one | 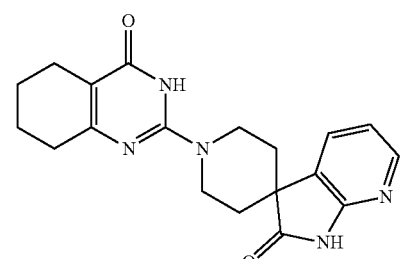<br>(Test Target Compound 274) | 1.67-1.79 (m, 4 H) 1.84-1.95 (m, 2 H) 1.97-2.05 (m, 2 H) 2.37-2.44 (m, 2 H) 2.45-2.53 (m, 2 H) 3.87-4.07 (m, 4 H) 6.95-7.02 (m, 1 H) 7.49-7.56 (m, 1 H) 8.10-8.21 (m, 1 H) | CDCl3 | 352 [M + H]+. |
| 281 | 7-methyl-N-(2-morpholinoethyl)-2-oxo-1'-(4-oxo-3,4,5,6,7,8-hexa-hydroquinazoline-2-yl)spiro[indoline-3,4'-piperidine]-6-carboxamide | 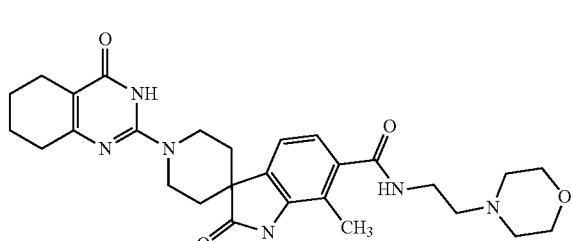<br>(Test Target Compound 275) | 1.20-1.80 (m, 8 H) 1.90-2.00 (m, 4 H), 2.37 (s, 3 H), 2.40-2.70 (m, 6 H), 3.50-3.60 (m, 2 H), 3.70-3.80 (m, 4 H), 3.95-4.15 (m, 4 H), 6.35 (br. s, 1 H), 7.10 (s, 2 H), 9.15 (br. s, 1 H). | CDCl3 | 521 [M + H]+. |
| 282 | 2-(spiro[iso-indoline-1,4'-piperidin]-1'-yl-5,6,7,8-tetrahydro-quinazoline-4(3H)-one | 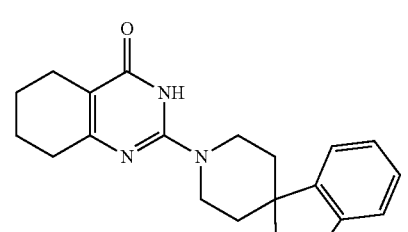<br>(Test Target Compound 276) | 1.62-1.77 (m, 6 H), 1.95-2.04 (m, 2 H), 2.30-2.35 (m, 2 H), 2.44-2.50 (m, 2 H), 3.27-3.36 (m, 2 H), 4.25 (s, 2 H), 4.46-4.53 (m, 2 H), 7.12-7.17 (m, 1 H), 7.22-7.27 (m, 3 H). | CDCl3 | 337 [M + H]+. |

TABLE 83-continued

| Example | Compound Name | Structure | 1H NMR δ ppm | Solvent | ESI MS m/z |
|---|---|---|---|---|---|
| 283 | 2-[2-(2-hydroxy-ethyl)spiro-[isoindoline-1,4'-piperidin]-1'-yl]-5,6,7,8-tetrahydro-quinazoline-4(3H)-one | 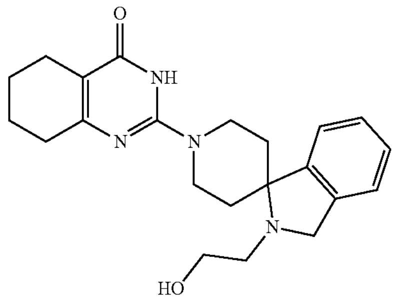 [SMILES: O=c1[nH]c(N2CCC3(CC2)c2ccccc2CN3CCO)nc2c1CCCC2] | 1.65-1.87 (m, 6 H), 1.97-2.06 (m, 2 H), 2.32-2.37 (m, 2 H), 2.45-2.50 (m, 2 H), 2.85-2.90 (m, 2 H), 3.50-3.59 (m, 2 H), 3.66-3.71 (m, 2 H), 3.72-3.77 (m, 1 H), 4.04 (s, 2 H), 4.34-4.41 (m, 2 H), 7.23-7.31 (m, 3 H), 7.55-7.59 (m, 1 H), 11.68 (br, s, 1 H). | CDCl3 | 381 [M + H]+. |

TABLE 84

| Example | Compound Name | Structure | 1H NMR δ ppm | Solvent | ESI MS m/z |
|---|---|---|---|---|---|
| 284 | methyl 1'-(4-oxo-3,4,5,6,7,8-hexa-hydroquinazoline-2-yl)spiro[indoline-3,4'-piperidine]-7-carboxylate | (Test Target Compound 277) | 1.64-1.78 (m, 4 H), 1.81-1.95 (m, 4 H), 2.33-2.38 (m, 2 H), 2.45-2.50 (m, 2 H), 3.02-3.11 (m, 2 H), 3.69 (s, 2 H), 3.87 (s, 3 H), 4.37-4.44 (m, 2 H), 6.12 (br. s, 1 H), 6.59-6.63 (m, 1 H), 7.10-7.13 (m, 1 H), 7.61 (dd, J = 8.1, 1.2 Hz, 1 H), 11.43 (br. s, 1 H). | CDCl3 | 395 [M + H]+. |
| 285 | 2-(6-(4-(morpho-linomethyloxazole-2-yl)spiro[indoline-3,4'-piperidin]-1'-yl]5,6,7,8-tetra-hydroquinazoline-4(3H)-one | (Test Target Compound 278) | 1.65-2.00 (m, 8 H), 2.30-2.40 (m, 2 H), 2.45-2.60 (m, 6 H), 3.05-3.15 (m, 2 H), 3.52 (s, 2 H), 3.59 (s, 2 H), 3.70-3.80 (m, 4 H), 4.40-4.50 (m, 2 H), 7.10 (d, J = 7.6 Hz, 1 H), 7.32 (s, 1 H), 7.40-7.50 (m, 1 H), 7.55-7.60 (m, 1 H), 11.80 (br. s, 1 H). | CDCl3 | 503 [M + H]+. |
| 286 | 2-{6-(4-(morpho-line-4-carbonyl)-oxazole-2-yl]spiro-[indoline-3,4'-piperidin]-1'-yl}-5,6,7,8-tetrahydro-quinazolline-4(3H)-one | (Test Target Compound 279) | 1.60-1.80 (m, 4 H), 1.80-2.00 (m, 4 H), 2.30-2.40 (m, 2 H), 2.40-2.60 (m, 2 H), 3.05-3.25 (m, 2 H), 3.61 (s, 2 H), 3.70-3.85 (m, 6 H), 4.15-4.30 (m, 2 H), 4.35-4.50 (m, 2 H), 7.12 (d, J = 7.6 Hz, 1 H), 7.25-7.30 (m, 1 H), 7.40-7.45 (m, 1 H), 8.19 (s, 1 H). | CDCl3 | 517 [M + H]+. |

TABLE 84-continued

| Example | Compound Name | Structure | 1H NMR δ ppm | Solvent | ESI MS m/z |
|---|---|---|---|---|---|
| 287 | 1-methyl-1'-(7-methyl-4-oxo-4,7-dihydro-3H-pyrrolo[2,3-d]-pyrimidin-2-yl)-spiro[indoline-3,4'-piperidine]-2-one | (Test Target Compound 280) | 1.93-1.98 (m, 4 H), 3.23 (s, 3 H), 3.62 (s, 3H), 4.13-4.17 (m, 4 H), 6.44 (d, J = 3.4 Hz, 1 H), 6.55 (d, J = 3.4 Hz, 1 H), 6.86-6.89 (m, 1 H), 7.05-7.09 (m, 1 H), 7.28-7.33 (m, 2 H), 10.85 (br. s, 1 H). | CDCl3 | 364 [M + H]+. |
| 288 | 1-methyl-1'-(7-ethyl-4-oxo-4,7-dihydro-3H-pyrrolo[2,3-d]-pyrimidin-2-yl)-spiro[indoline-3,4'-piperidine]-2-one | (Test Target Compound 281) | 1.39 (t, J = 7.3 Hz, 3 H), 1.93-1.98 (m, 4 H), 3.23 (s, 3 H), 4.04 (q, J = 7.3 Hz, 2 H), 4.11-4.17 (m, 4 H), 6.44 (d, J = 3.4 Hz, 1 H), 6.60 (d, J = 3.4 Hz, 1 H), 6.85-6.89 (m, 1 H), 7.04-7.09 (m, 1 H), 7.28-7.32 (m, 2 H), 10.89 (br. s, 1 H). | CDCl3 | 378 [M + H]+. |
| 289 | 1'-[7-(2-hydroxy-ethyl)-4-oxo-4,7-dihydro-3H-pyrrolo-[2,3-d]pyrimidin-2-yl]-1-methylspiro-[indoline-3,4 piperidine]-2-one | (Test Target Compound 282) | 1.94-1.98 (m, 4 H), 3.23 (s, 3 H), 3.92-3.97 (m, 2 H), 4.02-4.25 (m, 7 H), 6.45 (d, J = 3.5 Hz, 1 H), 6.58 (d, J = 3.5 Hz, 1 H), 6.86-6.89 (m, 1 H), 7.05-7.10 (m, 1 H), 7.26-7.33 (m, 2 H), 10.39 (br. s, 1 H). | CDCl3 | 394 [M + H]+. |

TABLE 85

| Example | Compound Name | Structure | 1H NMR δ ppm | Solvent | ESI MS m/z |
|---|---|---|---|---|---|
| 290 | 1-methyl-1'-(4-oxo-3,4-dihydropyrido-[2,3-d]pyrimidin-2-yl)spiro[indoline-3,4'-piperidin]-2-one | (Test Target Compound 283) | 1.96-2.07 (m, 4 H), 3.24 (s, 3 H), 4.24-4.31 (m, 2 H), 4.38-4.45 (m, 2 H), 6.87-6.90 (m, 1 H), 7.06-7.10 (m, 2 H), 7.24-7.27 (m, 1 H), 7.29-7.34 (m, 1 H), 8.33 (dd, J = 7.8, 2.0 Hz, 1 H), 8.76 (dd, J = 4.7, 2.0 Hz, 1 H). | CDCl3 | 362 [M + H]+. |

TABLE 85-continued

| Example | Compound Name | Structure | 1H NMR δ ppm | Solvent | ESI MS m/z |
|---|---|---|---|---|---|
| 291 | 1-methyl-1'-(4-oxo-3,4,5,6,7,8-hexa-hydropyrido[2,3-d]-pyrimidin-2-yl)spiro-[indoline-3,4'-piperidine]-2-one | (Test Target Compound 284) | 1.75-1.82 (m, 2 H), 1.85-1.91 (m, 4 H), 2.35-2.42 (m, 2 H), 3.21 (s, 3 H), 3.26-3.32 (m, 2 H), 4.02-4.17 (m, 4 H), 4.67-4.73 (m, 1 H), 6.83-6.88 (m, 1 H), 7.04-7.09 (m, 1 H), 7.26-7.32 (m, 2 H), 11.77 (br. s, 1 H). | CDCl3 | 366 [M + H]+. |
| 292 | 1-methyl-1'-(8-methyl-4-oxo-3,4,5,6,7,8-hexa-hydropyrido-[2,3-d]-pyrimidin-2-yl)-spiro[indoline-3,4'-piperidine]-2-one | (Test Target Compound 285) | 1.79-1.92 (m, 6 H), 2.42-2.47 (m, 2 H), 3.07 (s, 3 H), 3.21-3.27 (m, 5 H), 4.03-4.14 (m, 4H), 6.85-6.88 (m, 1 H), 7.05-7.09 (m, 1 H), 7.27-7.32 (m, 2 H), 11.03 (br. s, 1 H). | CDCl3 | 380 [M + H]+. |
| 293 | 1'-[7-(tert-butyl-carbonyl)-4-oxo-3,4,5,6,7,8-hexa-hydropyrido[3,4-d]-pyrimidin-2-yl]-1-methylspiro[indoline-3,4'-piperidine]-2-one | 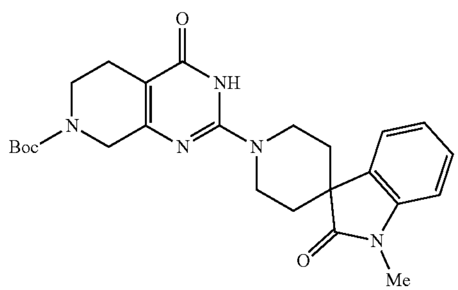 [SMILES: CN1C(=O)C2(CCN(c3nc4c(c(=O)[nH]3)CCN(C(=O)OC(C)(C)C)C4)CC2)c2ccccc21] | 1.47 (s, 9H), 1.87-1.94 (m, 4 H), 2.38-2.44 (m, 2 H), 3.23 (s, 3 H), 3.51-3.57 (m, 2 H), 4.10-4.24 (m, 6 H), 6.86-6.90 (m, 1 H), 7.06-7.10 (m, 1 H), 7.26-7.34 (m, 2 H), 11.85 (br. s, 1 H). | CDCl3 | 466 [M + H]+. |
| 294 | 1-methyl-1'-(4-oxo-3,4,5,6,7,8-hexa-hydropyrido[3,4-d]-pyrimidin-2-yl)spiro-[indoline-3,4'-piperidine]-2-one | 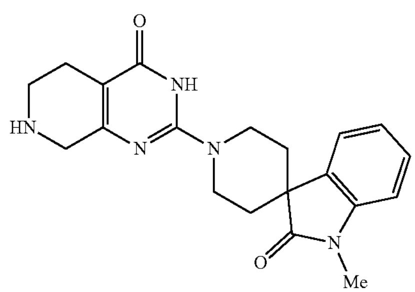 [SMILES: CN1C(=O)C2(CCN(c3nc4c(c(=O)[nH]3)CCNC4)CC2)c2ccccc21] | 1.88-1.93 (m, 4 H), 2.37 (t, J = 5.9 Hz, 2 H), 3.01 (t, J = 5.9 Hz, 2 H), 3.23 (s, 3 H), 3.65 (s, 2 H), 4.06-4.17 (m, 4 H), 6.86-6.89 (m, 1 H), 7.05-7.10 (m, 1 H), 7.27-7.33 (m, 2 H). | CDCl3 | 366 [M + H]+. |
| 295 | 1-methyl-1'-(7-methyl-4-oxo-3,4,5,6,7,8-hexa-hydrorpyrido-[3,4-d]pyrimidin-2-yl)spiro(indoline-3,4'-piperidine]-2-one | 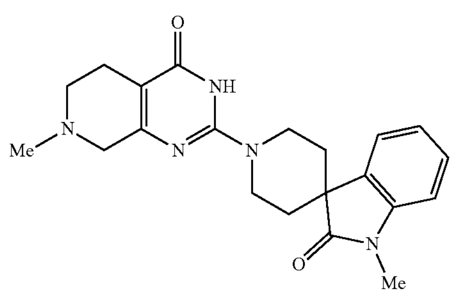 [SMILES: CN1CCc2c(nc(N3CCC4(CC3)C(=O)N(C)c3ccccc34)[nH]c2=O)C1] | 1.87-1.93 (m, 4 H), 2.41 (s, 3 H), 2.44-2.50 (m, 2 H), 2.56-2.61 (m, 2 H), 3.22 (s, 3 H), 3.27 (s, 2 H), 4.05-4.17 (m, 4 H), 6.87 (d, J = 7.6 Hz, 1 H), 7.05-7.10 (m, 1 H), 7.26-7.33 (m, 2 H), 11.44 (br. s, 1 H). | CDCl3 | 380 [M + H]+. |

TABLE 861

| Example | Compound Name | Structure | 1H NMR δ ppm | Solvent | ESI MS m/z |
|---|---|---|---|---|---|
| 296 | 1-methyl-1'-(9-methyl-6-oxo-6,9-dihydro-1H-purine-2-yl)spiro[indoline-3,4'-piperidine]-2-one | (Test Target Compound 286) | 1.91-2.04 (m, 4 H), 3.22 (s, 3 H), 3.64 (s, 3 H), 4.19-4.25 (m, 4 H), 6.85-6.88 (m, 1 H), 7.04-7.08 (m, 1 H), 7.27-7.32 (m, 2 H), 7.46 (s, 1 H), 11.06 (br. s, 1 H). | CDCl3 | 365 [M + H]+. |
| 297 | 1-methyl-1'-(7-methyl-6-oxo-6,7-dihydro-1H-purine-2-yl)spiro[indoline-3,4'-piperidine]-2-one | 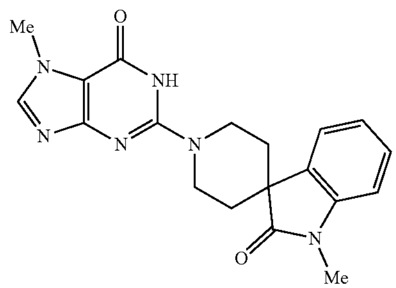 [SMILES: CN1C(=O)C2(CCN(c3nc4ncn(C)c4c(=O)[nH]3)CC2)c2ccccc21] | 1.90-2.01 (m, 4 H), 3.23 (s, 3 H), 3.92 (s, 3 H), 4.13-4.24 (m, 4 H), 6.86-6.89 (m, 1 H), 7.04-7.09 (m, 1 H), 7.25-7.33 (m, 2 H), 7.64 (s, 1 H), 10.84 (br. s, 1 H). | CDCl3 | 365 [M + H]+. |
| 298 | 1-methyl-1'-(8-methyl-4-oxo-3,4-dihydroquinazoline-2-yl)spiro[indoline-3,4'-piperidine]-2-one | (Test Target Compound 287) | 1.97-2.03 (m, 4 H), 2.48 (s, 3 H), 3.25 (s, 3 H), 4.16-4.27 (m, 4 H), 6.87-6.90 (m, 1 H), 7.01-7.10 (m, 2 H), 7.29-7.34 (m, 2 H), 7.45-7.48 (m, 1 H), 7.88-7.91 (m, 1 H), 10.73 (br. s, 1 H). | CDCl3 | 375 [M + H]+. |
| 299 | [2-(1-methyl-2-oxo spiro[indoline-3,4'-piperidine]-1'-yl)-4-oxo-3,4-dihydro-quinazolin-8-yl-methylacetate | (Test Target Compound 288) | 1.96-2.01 (m, 4 H), 2.12 (s, 3 H), 3.25 (s, 3 H), 4.16-4.27 (m, 4 H), 5.47 (s, 2 H), 6.87-6.90 (m, 1 H), 7.05-7.14 (m, 2 H), 7.27-7.34 (m, 2 H), 7.63-7.66 (m, 1 H), 7.99-8.03 (m, 1 H), 10.79 (br. s, 1 H). | CDCl3 | 433 [M + H]+. |

TABLE 861-continued

| Example | Compound Name | Structure | 1H NMR δ ppm | Solvent | ESI MS m/z |
|---|---|---|---|---|---|
| 300 | 1'-[8-(hydroxymethyl)-4-oxo-3,4-dihydroquinazoline-2-yl]-1-methyl-spiro[indoline-3,4-piperidine]-2-one | (Test Target Compound 289) | 1.99-2.05 (m, 4 H), 3.25 (s, 3 H), 4.20-4.25 (m, 4 H), 4.90 (s, 2 H), 6.88-6.91 (m, 1 H), 7.06-7.11 (m, 2 H), 7.25-7.35 (m, 2 H), 7.47-7.50 (m, 1 H), 7.94-7.97 (m, 1 H), 11.05 (br. s, 1 H). | CDCl3 | 391 [M + H]+. |
| 301 | 1'-[8-(2-hydroxyethyl)-4-oxo-3,4,5,6,7,8-hexahydropyrido[2,3-d]pyrimidin-2-yl]-1-methylspiro[indoline-3,4'-piperidine]-2-one | (Test Target Compound 290) | 1.81-1.92 (m, 6 H), 2.41-2.46 (m, 2 H), 3.22 (s, 3 H), 3.33-3.38 (m, 2 H), 3.66-3.70 (m, 2 H), 3.76-3.79 (m, 2 H), 4.05-4.09 (m, 4 H), 6.84-6.87 (m, 1 H), 7.04-7.09 (m, 1 H), 7.25-7.32 (m, 2 H), 10.98 (br. s, 1 H). | CDCl3 | 410 [M + H]+. |

TABLE 87

| Example | Compound Name | Structure | 1H NMR δ ppm | Solvent | ESI MS m/z |
|---|---|---|---|---|---|
| 302 | 2-(1-methyl-2-oxo-spiro[indoline-3,4'-piperidine]-1'-yl)-3,5,6,7-tetrahydro-4H-pyrano[2,3-d]pyrimidine-4-one | (Test Target Compound 291) | 1.84-1.93 (m, 6 H), 2.33-2.38 (m, 2 H), 3.22 (s, 3 H), 4.08-4.16 (m, 2 H), 4.19-4.26 (m, 4 H), 6.85-6.88 (m, 1 H), 7.05-7.10 (m, 1 H), 7.26-7.33 (m, 2 H), 712.02 (br. s, 1 H). | CDCl3 | 367 [M + H]+. |
| 303 | 8-methyl-2-(1-methyl-2-oxospiro[indoline-3,4'-piperidine]-1'-yl)-7,8-dihydropyrido[2,3-d]pyrimidin-4,5(3H,6H)-dione | (Test Target Compound 292) | 1.80-1.93 (m, 4 H), 2.70 (t, J = 7.2 Hz, 2 H), 3.15 (s, 3 H), 3.22 (s, 3 H), 3.54 (t, J = 7.2 Hz, 2H), 4.18-4.26 (m, 2 H), 4.41-4.48 (m, 2 H), 6.85-6.88 (m, 1 H), 7.04-7.09 (m, 1 H), 7.26-7.32 (m, 2 H), 13.37 (br. s, 1 H). | CDCl3 | 394 [M + H]+. |

TABLE 87-continued

| Example | Compound Name | Structure | 1H NMR δ ppm | Solvent | ESI MS m/z |
|---|---|---|---|---|---|
| 304 | 2-oxo-1'-(4-oxo-3,4,5,6,7,8-hexahydro-quinazoline-2-yl)-spiro[indoline-3,4'-piperidine]-4-carbonitrile | (Test Target Compound 293) | 1.60-1.79 (m, 6 H), 2.21-2.30 (m, 4 H), 2.37-2.42 (m, 2 H), 3.58-3.67 (m, 2 H), 4.24-4.35 (m, 2 H), 7.17 (dd, J = 6.4, 2.6 Hz, 1 H), 7.37-7.43 (m, 2 H), 10.82 (br. s, 1 H), 11.12 (br. s, 1 H). | DMSO-d6 | 376 [M + H]+. |
| 305 | 1-methyl-2-oxo-1'-(4-oxo-3,4,5,6,7,8-hexahydroquinazoline-2-yl)-spiro[indoline-3,4'-piperidine]-4-carbonitrile | (Test Target Compound 294) | 1.64-1.78 (m, 6 H), 2.34-2.39 (m, 2 H), 2.46-2.50 (m, 2 H), 2.54-2.63 (m, 2 H), 3.23 (s, 3 H), 3.83-3.91 (m, 2 H), 4.38-4.44 (m, 2 H), 7.04 (dd, J = 7.8, 1.1 Hz, 1 H), 7.30 (dd, J = 8.0, 1.1 Hz, 1 H), 7.36-7.41 (m, 1 H), 10.92 (br. s, 1 H). | CDCl3 | 390 [M + H]+. |
| 306 | 1-(2-hydroxyethyl)-2-oxo-1'-(4-oxo-3,4,5,6,7,8-hexahydroquinazoline-2-yl)-spiro[indoline-3,4'-piperidine]-4-carbonitrile | (Test Target Compound 295) | 1.65-1.80 (m, 6 H), 2.34-2.39 (m, 2 H), 2.46-2.51 (m, 2 H), 2.55-2.64 (m, 2 H), 3.80-3.94 (m, 6 H), 4.35-4.42 (m, 2 H), 7.19 (dd, J = 7.9, 1.1 Hz, 1 H), 7.29 (dd, J = 8.0, 1.1 Hz, 1 H), 7.34-7.39 (m, 1 H), 10.74 (br. s, 1 H). | CDCl3 | 420 [M + H]+. |
| 307 | 2-[6-(trifluoromethyl)-spiro[indoline-3,4'-piperidin]-1'-yl]-5,6,7,8-tetrahydro-quinazolin-4(3H)-one | (Test Target Compound 296) | 1.64-1.97 (m, 8 H), 2.33-2.38 (m, 2 H), 2.46-2.51 (m, 2 H), 3.04-3.13 (m, 2 H), 3.60 (s, 2 H), 3.93 (br. s, 1 H), 4.38-4.45 (m, 2 H), 6.83 (d, J = 1.0 Hz, 1 H), 6.96-7.00 (m, 1 H), 7.10 (d, J = 7.0 Hz, 1 H), 11.63 (br. s, 1 H). | CDCl3 | 405 [M + H]+. |

TABLE 88

| Example | Compound Name | Structure | 1H NMR δ ppm | Solvent | ESI MS m/z |
|---|---|---|---|---|---|
| 308 | 2-[4-(trifluoromethyl)spiro-[indoline-3,4'-piperidin]-1'-yl]-5,6,7,8-tetrahydroquinazoline-4(3H)-one | (Test Target Compound 297) | 1.65-1.84 (m, 6 H), 2.29-2.40 (m, 4 H), 2.45-2.50 (m, 2 H), 2.95-3.04 (m, 2 H), 3.60 (s, 2 H), 3.98 (br. s, 1 H), 4.34-4.41 (m, 2 H), 6.81-6.84 (m, 1 H), 7.00-7.03 (m, 1 H), 7.12-7.17 (m, 1 H), 10.88 (br. s, 1 H). | CDCl3 | 405 [M + H]+. |
| 309 | 2-[1-(2-hydroxyethyl)-4-trifluoromethyl)spiro-[indoline-3,4'-piperidin]-1'-yl]-5,6,7,8-tetrahydroquinazoline-4(3H)-one | (Test Target Compound 298) | 1.64-1.81 (m, 6 H), 2.31-2.40 (m, 4 H), 2.47-2.52 (m, 2 H), 2.98-3.07 (m, 2 H), 3.34 (t, J = 5.5 Hz, 2 H), 3.51 (s, 2 H), 3.88 (t, J = 5.5 Hz, 2 H), 4.39-4.45 (m, 2 H), 6.75 (d, J = 7.9 Hz, 1 H), 6.99 (d, J = 7.5 Hz, 1 H), 7.17-7.22 (m, 1 H), 11.27 (br. s, 1 H). | CDCl3 | 449 [M + H]+. |
| 310 | 5-hydroxy-1-methyl-1'-(4-oxo-3,4,5,6,7,8-hexahydroquinazoline-2-yl)spiro-[indoline-3,4'-piperidine]-2-one | (Test Target Compound 299) | 1.61-1.76 (m, 8 H), 2.24-2.29 (m, 2 H), 2.37-2.43 (m, 2 H), 3.09 (s, 3 H), 3.86-3.97 (m, 4 H), 6.69 (dd, J = 8.3, 2.3 Hz, 1 H), 6.83 (d, J = 8.3 Hz, 1 H), 6.90 (d, J = 2.3 Hz, 1 H), 9.08 (s, 1 H), 11.11 (br. s, 1 H). | DMSO-d6 | 381 [M + H]+. |
| 311 | 1-methyl-5-(3-morpholinopropoxy)-1'-(4-oxo-3,4,5,6,7,8-hexahydroquinazoline-2-yl)spiro-[indoline-3,4'-piperidine]-2-one | (Test Target Compound 300) | 1.65-1.78 (m, 4 H), 1.82-2.01 (m, 6 H), 2.33-2.38 (m, 2 H), 2.46-2.56 (m, 8 H), 3.19 (s, 3 H), 3.71-3.75 (m, 4 H), 3.96-4.01 (m, 2 H), 4.06-4.12 (m, 4 H), 6.75 (d, J = 8.4 Hz, 1 H), 6.82 (dd, J = 8.4, 2.3 Hz, 1 H), 6.89 (d, J = 2.3 Hz, 1 H), 11.04 (br. s, 1 H). | CDCl3 | 508 [M + H]+. |
| 312 | 4-hydroxy-1'-(4-oxo-3,4,5,6,7,8-hexahydroquinazoline-2-yl)spiro-[indoline-3,4'-piperidine]-2-one | (Test Target Compound 301) | 1.52-1.71 (m, 6 H), 2.23-2.41 (m, 6 H), 3.63-3.71 (m, 2 H), 4.17-4.25 (m, 2 H), 6.29-6.32 (m, 1 H), 6.94-6.99 (m, 1 H), 9.59 (s, 1 H), 10.24 (s, 1 H), 11.01 (br. s, 1 H). | DMSO-d6 | 367 [M + H]+. |

TABLE 88-continued

| Example | Compound Name | Structure | 1H NMR δ ppm | Solvent | ESI MS m/z |
|---|---|---|---|---|---|
| 313 | 4-methoxy-1-methyl-1'-(4-oxo-3,4,5,6,7,8-hexahydroquinazoline-2-yl)spiro[indoline-3,4'-piperidine]-2-one | (Test Target Compound 302) | 1.63-1.79 (m, 6 H), 2.31-2.38 (m, 2 H), 2.46-2.58 (m, 4 H), 3.18 (s, 3 H), 3.80 (s, 3 H), 3.83-3.92 (m, 2 H), 4.29-4.36 (m, 2 H), 6.50 (d, J = 7.8 Hz, 1 H), 6.61 (d, J = 8.2 Hz, 1 H), 7.22-7.27 (m, 1 H), 11.26 (br. s, 1 H). | CDCl3 | 395 [M + H]+. |

TABLE 89

| Example | Compound Name | Structure | 1H NMR δ ppm | Solvent | ESI MS m/z |
|---|---|---|---|---|---|
| 314 | 6-(3-morpholinopropoxy)-1'-(4-oxo-3,4,5,6,7,8-hexahydroquinazoline-2-yl)-spiro[indoline-3,4'-piperidine]-2-one | (Test Target Compound 303) | 1.64-2.00 (m, 10 H), 2.35-2.40 (m, 2 H), 2.43-2.55 (m, 8 H), 3.70-3.74 (m, 4 H), 3.98-4.11 (m, 6 H), 6.52-6.56 (m, 2 H), 7.14 (d, J = 8.8 Hz, 1 H), 9.34 (br. s, 1 H), 11.33 (br. s, 1 H). | CDCl3 | 494 [M + H]+. |
| 315 | 1-methyl-6-(3-morpholinopropoxy)-1'-(4-oxo-3,4,5,6,7,8-hexahydroquinazoline-2-yl)spiro[indoline-3,4'-piperidine]-2-one | (Test Target Compound 304) | 1.62-1.77 (m, 4 H), 1.79-2.03 (m, 6 H), 2.30-2.35 (m, 2 H), 2.43-2.57 (m, 8 H), 3.19 (s, 3 H), 3.70-3.75 (m, 4 H), 4.02-4.17 (m, 6 H), 6.45 (d, J = 2.3 Hz, 1 H), 6.55 (dd, J = 8.2, 2.3 Hz, 1 H), 7.19 (d, J = 8.2 Hz, 1 H), 11.86 (br. s, 1 H). | CDCl3 | 508 [M + H]+. |
| 316 | 2-[4,6-difluoro-1-(pyrimidin-2-ylmethyl)spiro[indoline-3,4'-piperidine]-1'-yl]-5,6,7,8-tetrahydroquinazoline-4(3H)-one | (Test Target Compound 305) | 1.60-1.75 (m, 4 H), 1.75-1.90 (m, 2 H), 2.20-2.40 (m, 4 H), 2.40-2.50 (m, 2 H), 2.90-3.00 (m, 2 H), 3.75 (s, 2 H), 4.45-4.50 (m, 2 H), 4.57 (s, 2 H), 6.00-6.10 (m, 2 H), 7.22 (t, J = 4.8 Hz, 1 H), 8.72 (d, J = 4.8 Hz, 2 H), 11.70 (br. s, 1 H). | CDCl3 | 465 [M + H]+. |

TABLE 89-continued

| Example | Compound Name | Structure | 1H NMR δ ppm | Solvent | ESI MS m/z |
|---|---|---|---|---|---|
| 317 | 2-[6-(piperidin-4-yl)spiro]-indoline-3,4'-piperidin]-1'-yl]-5,6,7,8-tetrahydro-quinazolin-4(3H)-one | 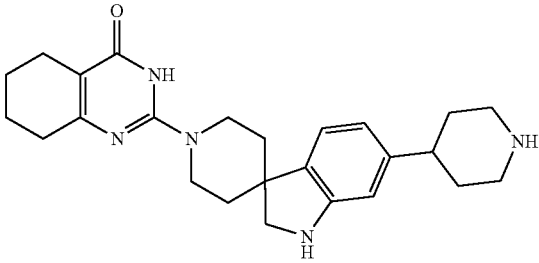<br>(Test Target Compound 306) | 1.70-2.10 (m, 12 H), 2.30-2.40 (m, 2 H), 2.45-2.55 (m, 2 H), 2.75-2.90 (m, 1 H), 3.05-3.25 (m, 4 H), 3.45-3.55 (m, 2 H), 3.60-3.65 (m, 2 H), 4.20-4.35 (m, 2 H), 6.55-6.65 (m, 2 H), 6.95-7.05 (m, 1 H). | CD3OD | 420 [M + H]+. |
| 318 | 4,6-difluoro-1-(2-hydroyethyl)-1'-(8-formyl-4-oxo-3,4,5,6,7,8-hexahydropyrido[2,3-d]pyrimidin-2-yl)spiro[indoline-3,4'-piperidin]-2-one | 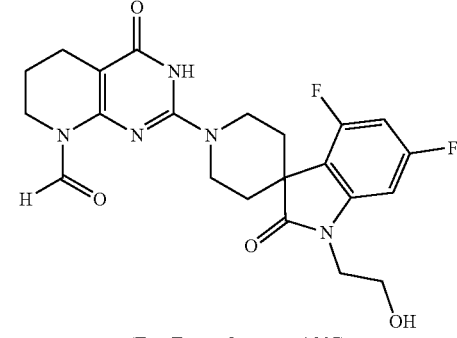<br>(Test Target Compound 307) | 1.80-1.90 (m, 6 H), 2.25-2.35 (m, 2 H), 2.40-2.50 (m, 2 H), 3.70-3.80 (m, 2 H), 3.80-4.00 (m, 6 H), 4.25-4.35 (m, 2 H), 6.45-6.60 (m, 2 H), 9.67 (s, 1 H), 11.50 (br. s, 1 H). | CDCl3 | 460 [M + H]+. |
| 319 | 4,6-difluoro-1-(2-formyloxy-ethyl)-1'-(4-oxo-3,4,5,6,7,8-hexahydropyrido[2,3-d]pyrimidin-2-yl)-spiro[indoline-3,4'-piperidin]-2-one | 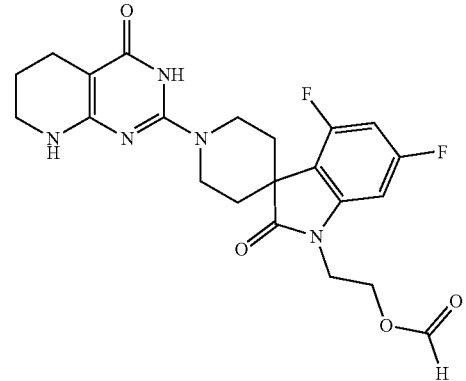<br>(Test Target Compound 308) | 1.80-1.90 (m, 4 H), 2.20-2.30 (m, 2 H), 2.40-2.50 (m, 2 H), 3.30-3.40 (m, 2 H), 3.80-3.90 (m, 2 H), 3.90-4.00 (m, 2 H), 4.15-4.25 (m, 2 H), 4.40-4.45 (m, 2 H), 4.67 (br. s, 1 H), 6.45-6.55 (m, 2 H), 8.00 (s, 1 H). | CDCl3 | 460 [M + H]+. |

TABLE 90

| Example | Compound Name | Structure | 1H NMR δ ppm | Solvent | ESI MS m/z |
|---|---|---|---|---|---|
| 320 | 2-(4-chloro-7-iodospiro[indoline-3,4'-piperidine]-1'-yl)-5,6,7,8-tetrahydroquinazolin-4(3H)-one | 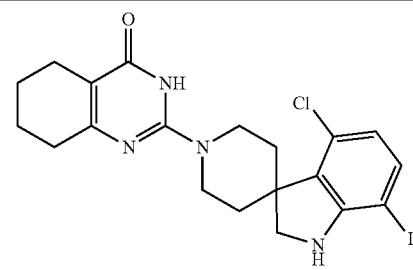<br>(Test Target Compound 309) | 1.60-1.90 (m, 4 H), 2.20-2.40 (m, 4 H), 2.55-2.65 (m, 2 H), 2.75-2.95 (m, 4 H), 3.50-3.60 (m, 2 H), 4.25-4.45 (m, 2 H), 5.81 (br. s, 1 H), 6.32 (d, J = 8.4 Hz, 1 H), 7.31 (d, J = 8.4 Hz, 1 H). | DMSO-d6 | 497 [M + H]+. |

TABLE 90-continued

| Example | Compound Name | Structure | 1H NMR δ ppm | Solvent | ESI MS m/z |
|---|---|---|---|---|---|
| 321 | 1'-(8-methoxy-4-oxo-3,4-dihydro-quinazoline-2-yl)-1-methylspiro[indoline-3,4'-piperidin]-2-one | (Test Target Compound 310) | 1.95-2.05 (m, 4 H), 3.24 (s, 3 H), 3.96 (s, 3 H), 4.20-4.35 (m, 4 H), 6.85-6.90 (m, 1 H), 7.05-7.15 (m, 3 H), 7.30-7.35 (m, 2 H), 7.60-8.25 (m, 1 H), 11.00-11.40 (m, 1 H). | CDCl3 | 391 [M + H]+. |
| 322 | 4-chloro-1-methyl-2-oxo-1'-(4-oxo-3,4,5,6,7,8-hexahydroquinazoline-2-yl)spiro[indoline-3,4'-piperidine]-6-carboxamide | (Test Target Compound 311) | 1.60-1.75 (m, 6 H), 2.20-2.30 (m, 2 H), 2.35-2.45 (m, 2 H), 2.45-2.55 (m, 2 H), 3.17 (s, 3 H), 3.55-3.70 (m, 2 H), 4.25-4.40 (m, 2 H), 7.48 (d, J = 1.2 Hz, 1 H), 7.55-7.60 (m, 2 H), 8.09 (br. s, 1 H), 11.10 (br. s, 1 H). | DMSO-d6 | 442 [M + H]+. |
| 323 | 4-chloro-1-methyl-6-[4-(morpholine-4-carbonyl)oxazole-2-yl]-1'-(4-oxo-3,4,5,6,7,8-hexahydroquinazoline-2-yl)spiro[indoline-3,4'-piperidin]-2-one | (Test Target Compound 312) | 1.60-1.80 (m, 6 H), 2.30-2.40 (m, 2 H), 2.40-2.50 (m, 2 H), 2.70-2.85 (m, 2 H), 3.28 (s, 3 H), 3.70-3.95 (m, 8 H), 4.10-4.30 (m, 2 H), 4.35-4.50 (m, 2 H), 7.36 (d, J = 1.2 Hz, 1 H), 7.69 (d, J = 1.2 Hz, 1 H), 8.25 (s, 1 H), 11.15 (br. s, 1H). | CDCl3 | 579 [M + H]+. |
| 324 | 4,6-difluoro-1'-(8-fluoro-4-oxo-3,4-dihydro-quinazoline-2-yl)-1-(2-hydroxy-ethyl)spiro[indoline-3,4'-piperidin]-2-one | (Test Target Compound 313) | 1.90-2.00 (m, 2 H), 2.35-2.45 (m, 2 H), 3.85-4.00 (m, 4 H), 4.05-4.15 (m, 2 H), 4.40-4.50 (m, 2 H), 6.45-6.55 (m, 1 H), 6.55-6.60 (m, 1 H), 7.00-7.10 (m, 1 H), 7.30-7.40 (m, 1 H), 7.75-7.85 (m, 1 H), 10.85 (br. s, 1 H). | CDCl3 | 445 [M + H]+. |

TABLE 90-continued

| Example | Compound Name | Structure | 1H NMR δ ppm | Solvent | ESI MS m/z |
|---|---|---|---|---|---|
| 325 | 4,6-difluoro-1-(2-hydroxyethyl)-1'-(8-acetyl-4-oxo-3,4,5,6,7,8-hexahydropyrido[2,3-d]pyrimidin-2-yl)-spiro[indoline-3,4'-piperidin]-2-one | (Test Target Compound 314) | 1.80-1.95 (m, 4 H), 2.20-2.35 (m, 2 H), 2.40-2.50 (m, 2 H), 2.51 (s, 3 H), 3.75-4.05 (m, 8 H), 4.25-4.35 (m, 2 H), 6.45-6.60 (m, 2 H), 11.75-12.10 (m, 1 H). | CDCl3 | 474 [M + H]+. |

TABLE 91

| Example | Compound Name | Structure | 1H NMR δ ppm | Solvent | ESI MS m/z |
|---|---|---|---|---|---|
| 326 | 4-chloro-6-[4-(morpholine-4-carbonyl)-oxazol-2-yl]-1-methyl-1'-(8-methyl-4-oxo-3,4,5,6,7,8-hexahydro-pyrido[2,3-d]-pyrimidin-2-yl)spino-[indoline-3,4'-piperidin]-2-one | (Test Target Compound 315) | 1.60-1.70 (m, 2 H), 1.80-1.90 (m, 2 H), 2.45-2.50 (m, 2 H), 2.70-2.85 (m, 2 H), 3.08 (s, 3 H), 3.20-3.30 (m, 5 H), 3.75-3.95 (m, 8 H), 4.15-4.30 (m, 2 H), 4.35-4.50 (m, 2 H), 7.35 (d, J = 1.2 Hz, 1 H), 7.68 (d, J = 1.2 Hz, 1 H), 8.25 (s, 1 H). | CDCl3 | 594 [M + H]+. |
| 327 | 4-chloro-1-methyl-1'-(8-methyl-4-oxo-3,4,5,6,7,8-hexahydro-pyrido[2,3-d]-pyrimidin-2-yl)-2-oxo-spiro[indoline-3,4'-piperidine]-7-carbonitrile | (Test Target Compound 316) | 1.55-1.65 (m, 2 H), 1.80-1.90 (m, 2H), 2.40-2.50 (m, 2 H), 2.70-2.85 (m, 2 H), 3.07 (s, 3 H), 3.20-3.30 (m, 2 H), 3.58 (s, 3 H), 3.75-3.90 (m, 2 H), 4.35-4.45 (m, 2 H), 7.02 (d, J = 8.4 Hz, 1 H), 7.41 (d, J = 8.4 Hz, 1 H). | CDCl3 | 439 [M + H]+. |
| 328 | 4-chloro-6-(4-ethoxy-carbonyl-oxazole-2-yl)-1-methyl-1'-(8-methyl-4-oxo-3,4,5,6,7,8-hexahydro-pyrido[2,3-d]-pyrimidin-2-yl)spiro-[indoline-3,4'-piperidin]-2-one | (Test Target Compound 317) | 1.42 (t, J = 7.2 Hz, 3 H), 1.60-1.70 (m, 2 H), 1.80-1.90 (m, 2 H), 2.40-2.50 (m, 2 H), 2.70-2.85 (m, 2 H), 3.08 (s, 3 H), 3.25-3.35 (m, 5 H), 3.80-3.95 (m, 2 H), 4.40-4.50 (m, 2 H), 7.53 (d, J = 1.2 Hz, 1 H), 7.73 (d, J = 1.2 Hz, 1 H), 8.29 (s, 1 H). | CDCl3 | 553 [M + H]+. |

TABLE 91-continued

| Example | Compound Name | Structure | 1H NMR δ ppm | Solvent | ESI MS m/z |
|---|---|---|---|---|---|
| 329 | 4-chloro-1-methyl-1'-(8-methyl-4-oxo-3,4,5,6,7,8-hexahydro-pyrido[2,3-d]-pyrimidin-2-yl)-6-[4-(pyrroidin-1yl-methyl)oxazol-2-yl]-spiro-[indoline-3,4'-piperidin]-2-one | (Test Target Compound 318) | 1.55-1.70 (m, 2 H), 1.75-1.95 (m, 6 H), 2.40-2.50 (m, 2 H), 2.65-2.85 (m, 6 H), 3.08 (s, 3 H), 3.15-3.30 (m, 5 H), 3.70-3.80 (m, 2 H), 3.80-3.90 (m, 2 H), 4.35-4.50 (m, 2 H), 7.43 (d, J = 1.2 Hz, 1 H), 7.65-7.75 (m, 2 H). | CDCl3 | 564 [M + H]+. |
| 330 | 4-chloro-1-methyl-1'-(8-methyl-4-oxo-3,4,5,6,7,8-hexahydro-pyrido[2,3-d]-pyrimidin-2-yl)-2-oxospiro-[indoline-3,4'-piperidine]-7-carboxamide | (Test Target Compound 319) | 1.55-1.60 (m, 2 H), 1.75-1.85 (m, 2 H), 2.25-2.35 (m, 2 H), 2.55-2.65 (m, 2 H), 3.00 (s, 3 H), 3.18 (s, 3 H), 3.20-3.30 (m, 2 H), 3.60-3.70 (m, 2 H), 4.25-4.35 (m, 2 H), 7.08 (d, J = 8.4 Hz, 1 H), 7.27 (d, J = 8.4 Hz, 1 H), 7.72 (br. s, 1 H), 8.08 (br. s, 1 H), 10.38 (br. s, 1 H). | DMSO-d6 | 457 [M + H]+. |

TABLE 92

| Example | Compound Name | Structure | 1H NMR δ ppm | Solvent | ESI MS m/z |
|---|---|---|---|---|---|
| 331 | 2-{4-chloro-1-methyl-1'-(8-methyl-4-oxo-3,4,5,6,7,8-hexahydro-pyrido[2,3-d]pyrimidin-2-yl)-2-oxospiro[indoline-3,4'-piperidin]-6-yl}oxazole-4-carboxylic acid | (Test Target Compound 320) | 1.65-1.75 (m, 2 H), 1.80-1.95 (m, 2 H), 2.50-2.60 (m, 2 H), 2.65-2.75 (m, 2 H), 3.13 (s, 3 H), 3.24 (s, 3 H), 3.30-3.40 (m, 2 H), 3.90-4.00 (m, 2 H), 4.35-4.50 (m, 2 H), 7.51 (d, J = 1.2 Hz, 1 H), 7.66 (d, J = 1.2 Hz, 1 H), 8.22 (s, 1 H). | CDCl3 | 525 [M + H]+. |
| 332 | 5-methoxy-1'-(4-oxo-3,4,5,6,7,8-hexahydro-quinazolin-2-yl)spiro[indoline-3,4'-piperidin]-2-one | (Test Target Compound 321) | 1.58-1.77 (m, 4 H), 1.84-2.00 (m, 4 H), 2.36-2.41 (m, 2 H), 2.45-2.50 (m, 2 H), 3.78 (s, 3 H), 4.00-4.12 (m, 4 H), 6.73-6.77 (m, 1 H), 6.84-6.87 (m, 2 H), 8.97 (s, 1 H), 11.26 (br. s, 1 H). | CDCl3 | 381 [M + H]+. |

TABLE 92-continued

| Example | Compound Name | Structure | 1H NMR δ ppm | Solvent | ESI MS m/z |
|---|---|---|---|---|---|
| 333 | 4,6-difluoro-1'-(4-oxo-3,4,5,6,7,8-hexahydroquinazolin-2-yl)-1-(pyridin-3-ylmethyl)spiro[indoline-3,4'-piperidin]-2-one | (Test Target Compound 322) | 1.65-1.78 (m, 4 H), 1.85-1.92 (m, 2 H), 2.26-2.39 (m, 4 H), 2.46-2.51 (m, 2 H), 3.90-3.99 (m, 2 H), 4.27-4.34 (m, 2 H), 4.88 (s, 2 H), 6.31 (dd, J = 8.2, 2.1 Hz, 1 H), 6.44-6.51 (m, 1 H), 7.28-7.32 (m, 1 H), 7.57-7.61 (m, 1 H), 8.57-8.60 (m, 2 H), 11.30 (br. s, 1 H). | CDCl3 | |
| 334 | 4-chloro-1-methyl-6-(3-morpholinopropoxy)-1'-(4-oxo-3,4,5,6,7,8-hexahydroquinazolin-2-yl)spiro[indoline-3,4'-piperidin]-2-one | (Test Target Compound 323) | 1.59-1.77 (m, 6 H), 1.93-2.01 (m, 2 H), 2.32-2.37 (m, 2 H), 2.44-2.54 (m, 8 H), 2.66-2.75 (m, 2 H), 3.16 (s, 3 H), 3.71-3.75 (m, 4 H), 3.81-3.90 (m, 2 H), 4.00-4.04 (m, 2 H), 4.38-4.45 (m, 2 H), 6.32 (d, J = 2.1 Hz, 1 H), 6.50 (d, J = 2.1 Hz, 1 H), 11.52 (br. s, 1 H). | CDCl3 | 542 [M + H]+. |
| 335 | 4-chloro-1-methyl-1'-(8-methyl-4-oxo-3,4-dihydroquinazolin-2-yl)-6-(3-morpholinopropoxy)spiro[indoline-3,4'-piperidin]-2-one | (Test Target Compound 324) | 1.66-1.73 (m, 2 H), 1.93-2.01 (m, 2 H), 2.45-2.54 (m, 9 H), 2.77-2.87 (m, 2 H), 3.19 (s, 3 H), 3.71-3.75 (m, 4 H), 3.96-4.05 (m, 4 H), 4.47-4.55 (m, 2 H), 6.34 (d, J = 2.1 Hz, 1 H), 6.49 (d, J = 2.1 Hz, 1 H), 6.99-7.04 (m, 1 H), 7.43-7.47 (m, 1 H), 7.88-7.92 (m, 1 H), 11.13 (br. s, 1 H). | CDCl3 | 552 [M + H]+. |

TABLE 93

| Example | Compound Name | Structure | 1H NMR δ ppm | Solvent | ESI MS m/z |
|---|---|---|---|---|---|
| 336 | 4-chloro-1'-[8-(hydroxymethyl)-4-oxo-3,4-dihydroquinazolin-2-yl]-1-methyl-6-(3-morpholinopropoxy)spiro[indoline-3,4'-piperidin]-2-one | (Test Target Compound 325) | 1.69-1.78 (m, 2 H), 1.93-2.01 (m, 2 H), 2.45-2.54 (m, 6 H), 2.75-2.85 (m, 2 H), 3.19 (s, 3 H), 3.70-3.75 (m, 4 H), 4.00-4.10 (m, 4 H), 4.39-4.46 (m, 2 H), 4.74 (br. s, 1 H), 4.90 (s, 2 H), 6.35 (d, J = 2.2 Hz, 1 H), 6.50 (d, J = 2.2 Hz, 1 H), 7.05-7.10 (m, 1 H), 7.46-7.49 (m, 1 H), 7.95-7.98 (m, 1 H), 11.18 (br. s, 1 H). | CDCl3 | 568 [M + H]+. |

TABLE 93-continued

| Example | Compound Name | Structure | 1H NMR δ ppm | Solvent | ESI MS m/z |
|---|---|---|---|---|---|
| 337 | 2-(4,6-difluoro-1-methylspiro[indoline-3,4'-piperidin]-1'-yl)-8-methyl-5,6,7,8-tetrahydropyrido[2,3-d]pyrimidin-4(3H)-one | (Test Target Compound 326) | 1.74-1.87 (m, 4 H), 2.18-2.27 (m, 2 H), 2.44-2.48 (m, 2 H), 2.78 (s, 3 H), 2.91-3.00 (m, 2 H), 3.07 (s, 3 H), 3.23-3.27 (m, 2 H), 3.39 (s, 2 H), 4.37-4.44 (m, 2 H), 5.94 (dd, J = 9.7, 2.0 Hz, 1 H), 6.02-6.08 (m, 1 H), 10.82 (br. s, 1 H). | CDCl3 | 402 [M + H]+. |
| 338 | 2-[4,6-difluoro-1-(2-hydroxyethyl)spiro[indoline-3,4'-piperidin]-1'-yl]-8-methyl-5,6,7,8-tetrahydropyrido[2,3-d]pyrimidin-4(3H)-one | (Test Target Compound 327) | 1.65-1.78 (m, 4 H), 1.87-1.97 (m, 2 H), 2.27-2.32 (m, 2 H), 2.82-2.91 (m, 2 H), 2.98 (s, 3 H), 3.19-3.24 (m, 4 H), 3.56-3.61 (m, 4 H), 4.27-4.34 (m, 2 H), 4.71 (t, J = 5.4 Hz, 1 H), 6.10-6.19 (m, 2 H), 10.31 (br. s, 1 H). | DMSO-d6 | 432 [M + H]+. |
| 339 | 4,6-difluoro-1-methyl-1'-(8-methyl-4-oxo-3,4,5,6,7,8-hexahydropyrido[2,3-d]pyrimidin-2-yl)spiro[indoline-3,4'-piperidin]-2-one | (Test Target Compound 328) | 1.78-1.87 (m, 4 H), 2.19-2.28 (m, 2 H), 2.43-2.48 (m, 2 H), 3.07 (s, 3 H), 3.18 (s, 3 H), 3.23-3.27 (m, 2 H), 3.86-3.94 (m, 2 H), 4.21-4.27 (m, 2 H), 6.42 (dd, J = 8.3, 2.1 Hz, 1 H), 6.45-6.51 (m, 1 H), 10.82 (br. s, 1 H). | CDCl3 | 416 [M + H]+. |
| 340 | 4,6-difluoro-1-(2-hydroxyethyl)-1'-(8-methyl-4-oxo-3,4,5,6,7,8-hexahydropyrido[2,3-d]pyrimidin-2-yl)spiro[indoline-3,4'-piperidin]-2-one | (Test Target Compound 329) | 1.79-1.88 (m, 4 H), 2.20-2.29 (m, 2 H), 2.42-2.47 (m, 2 H), 3.07 (s, 3 H), 3.23-3.28 (m, 2 H), 3.82-3.91 (m, 6 H), 4.16-4.23 (m, 2 H), 6.42-6.48 (m, 1 H), 6.55 (dd, J = 8.5, 2.0 Hz, 1 H). | CDCl3 | 446 [M + H]+. |

TABLE 94

| Example | Compound Name | Structure | 1H NMR δ ppm | Solvent | ESI MS m/z |
|---|---|---|---|---|---|
| 341 | 2-[4,6-difluoro-1-(2-fluorobenzyl)spiro[indoline-3,4'-piperidin]-1'-yl]-5,6,7,8-tetrahydroquinazolin-4(3H)-one | (Test Target Compound 330) | 1.63-1.82 (m, 6 H), 2.20-2.29 (m, 2 H), 2.33-2.38 (m, 2 H), 2.44-2.49 (m, 2 H), 2.86-2.95 (m, 2 H), 3.46 (s, 2 H), 4.35-4.43 (m, 4 H), 6.01-6.09 (m, 2 H), 7.06-7.15 (m, 2 H), 7.25-7.32 (m, 2 H), 11.49 (br. s, 1 H). | CDCl3 | 481 [M + H]+. |
| 342 | 2-[4,6-difluoro-1-(3-fluorobenzyl)spiro[indoline-3,4'-piperidin]-1'-yl]-5,6,7,8-tetrahydroquinazolin-4(3H)-one | (Test Target Compound 331) | 1.64-1.84 (m, 6 H), 2.22-2.31 (m, 2 H), 2.32-2.38 (m, 2 H), 2.44-2.49 (m, 2 H), 2.85-2.94 (m, 2 H), 3.42 (s, 2 H), 4.30 (s, 2 H), 4.41-4.48 (m, 2 H), 5.97 (dd, J = 9.7, 2.1 Hz, 1 H), 6.05-6.11 (m, 1 H), 6.96-7.02 (m, 2 H), 7.04-7.08 (m, 1 H), 7.29-7.35 (m, 1 H), 11.82 (br. s, 1 H). | CDCl3 | 481 [M + H]+. |
| 343 | 2-[4,6-difluoro-1-(4-fluorobenzyl)spiro[indoline-3,4'-piperidin]-1'-yl]-5,6,7,8-tetrahydroquinazolin-4(3H)-one | (Test Target Compound 332) | 1.64-1.82 (m, 6 H), 2.20-2.29 (m, 2 H), 2.32-2.37 (m, 2 H), 2.44-2.49 (m, 2 H), 2.84-2.93 (m, 2 H), 3.38 (s, 2 H), 4.27 (s, 2 H), 4.36-4.43 (m, 2 H), 6.00 (dd, J = 9.7, 2.0 Hz, 1 H), 6.04-6.10 (m, 1 H), 7.01-7.07 (m, 2 H), 7.22-7.27 (m, 2 H), 11.47 (br. s, 1 H). | CDCl3 | 481 [M + H]+. |
| 344 | 2-{1-[(6-chloropyridin-3-yl)methyl]-4,6-difluorospiro[indoline-3,4'-piperidin]-1'-yl]-5,6,7,8-tetrahydroquinazolin-4(3H)-one | (Test Target Compound 333) | 1.66-1.82 (m, 6 H), 2.21-2.30 (m, 2 H), 2.34-2.39 (m, 2 H), 2.44-2.49 (m, 2 H), 2.84-2.94 (m, 2 H), 3.38 (s, 2 H), 4.30 (s, 2 H), 4.33-4.40 (m, 2 H), 6.01 (dd, J = 9.5, 1.9 Hz, 1 H), 6.09-6.16 (m, 1 H), 7.34 (d, J = 8.2 Hz, 1 H), 7.57-7.61 (m, 1 H), 8.34 (d, J = 1.8 Hz, 1 H), 11.06 (br. s, 1 H). | CDCl3 | 498 [M + H]+. |

TABLE 94-continued

| Example | Compound Name | Structure | 1H NMR δ ppm | Solvent | ESI MS m/z |
|---|---|---|---|---|---|
| 345 | 2-(4,6-difluoro-1-methyl-spiro[indoline-3,4'-piperidin]-1'-yl)-7-methyl-3,7-dihydro-4H-pyrrolo[2,3-d]pyrimidin-4-one (Test Target Compound 334) | 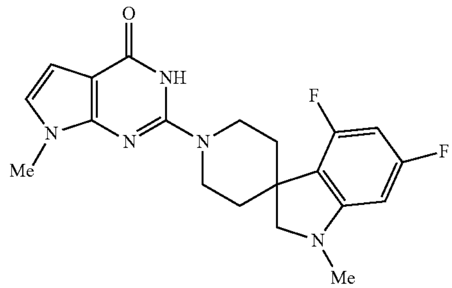 | 1.81-1.87 (m, 2 H), 2.24-2.33 (m, 2 H), 2.79 (s, 3 H), 3.03-3.11 (m, 2 H), 3.42 (s, 2 H), 3.62 (s, 3 H), 4.25-4.31 (m, 2 H), 5.96 (dd, J = 9.7, 2.0 Hz, 1 H), 6.03-6.09 (m, 1 H), 6.49 (d, J = 3.4 Hz, 1 H), 6.57 (d, J = 3.4 Hz, 1 H), 9.40 (br. s, 1 H). | CDCl3 | [M + H]+ |

TABLE 95

| Example | Compound Name | Structure | 1H NMR δ ppm | Solvent | ESI MS m/z |
|---|---|---|---|---|---|
| 346 | 2-[4,6-difluoro-1-(2-hydroxyethyl)spiro[indoline-3,4'-piperidin]-1'-yl]-7-methyl-3,7-dihydro-4H-pyrrolo[2,3-d]pyrimidin-4-one (Test Target Compound 335) | 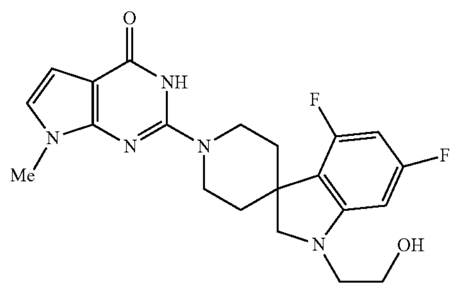 | 1.71-1.77 (m, 2 H), 1.97-2.06 (m, 2 H), 2.91-3.00 (m, 2 H), 3.21-3.25 (m, 2 H), 3.56 (s, 3 H), 3.58-3.63 (m, 4 H), 4.27-4.34 (m, 2 H), 4.73 (t, J = 5.5 Hz, 1 H), 6.11-6.21 (m, 2 H), 6.25 (d, J = 3.3 Hz, 1 H), 6.77 (d, J = 3.3 Hz, 1 H), 10.77 (br. s, 1 H). | DMSO-d6 | [M + H]+ |
| 347 | 2-[4,6-difluoro-1-(pyridin-3-ylmethyl)spiro[indoline-3,4'-piperidine]-1'-yl]-7-methyl-3,7-dihydro-4H-pyrrolo[2,3-d]pyrimidin-4-one (Test Target Compound 336) | 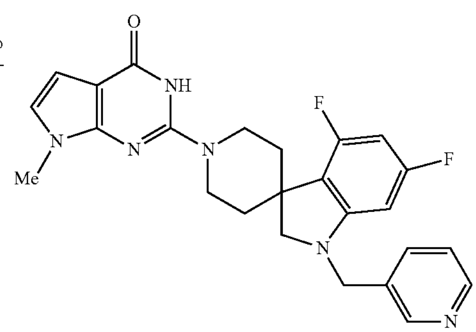 | 1.79-1.86 (m, 2 H), 2.26-2.36 (m, 2 H), 2.93-3.02 (m, 2 H), 3.41 (s, 2 H), 3.61 (s, 3 H), 4.26-4.34 (m, 4 H), 6.03 (dd, J = 9.6, 2.0 Hz, 1 H), 6.08-6.14 (m, 1 H), 6.47 (d, J = 3.4 Hz, 1 H), 6.57 (d, J = 3.4 Hz, 1 H), 7.29-7.33 (m, 1 H), 7.61-7.64 (m, 1 H), 8.56-8.59 (m, 2 H), 9.78 (br. s, 1 H). | CDCl3 | 498 [M + H]+. |
| 348 | 4,6-difluoro-1-methyl-1'-(7-methyl-4-oxo-4,7-dihydro-3H-pyrrolo[2,3-d]pyrimidin-2-yl)spiro[indoline-3,4'-piperidin]-2-one (Test Target Compound 337) | 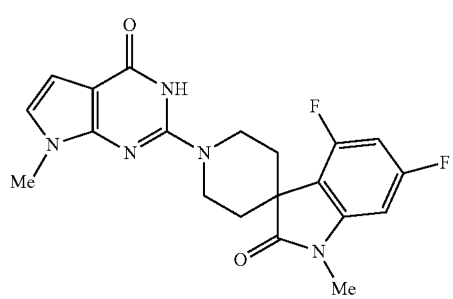 | 1.84-1.90 (m, 2 H), 2.26-2.34 (m, 2 H), 3.20 (s, 3 H), 3.62 (s, 3 H), 3.95-4.03 (m, 2 H), 4.14-4.21 (m, 2 H), 6.42-6.51 (m, 3 H), 6.57 (d, J = 3.4 Hz, 1 H), 9.56 (br. s, 1 H). | CDCl3 | 400 [M + H]+. |

TABLE 95-continued

| Example | Compound Name | Structure | 1H NMR δ ppm | Solvent | ESI MS m/z |
|---|---|---|---|---|---|
| 349 | 4,6-difluoro-1-(2-hydroxyethyl)-1'-(7-methyl-4-oxo-4,7-dihydro-3H-pyrrolo[2,3-d]pyrimidin-2-yl)spiro[indoline-3,4'-piperidin]-2-one | (Test Target Compound 338) | 1.86-1.92 (m, 2 H), 2.27-2.36 (m, 2 H), 3.61 (s, 3 H), 3.83-4.00 (m, 6 H), 4.18-4.25 (m, 2 H), 4.41-4.47 (m, 2 H), 6.52-6.57 (m, 2 H), 10.05 (br. s, 1 H). | CDCl3 | 430 [M + H]+. |
| 350 | 4,6-difluoro-1'-(7-methyl-4-oxo-4,7-dihydro-3H-pyrrolo[2,3-d]pyrimidin-2-yl)-1-(pyridin-3-ylmethyl)spiro[indoline-3,4'-piperidin]-2-one | (Test Target Compound 339) | 1.88-1.94 (m, 2 H), 2.32-2.41 (m, 2 H), 3.63 (s, 3 H), 3.96-4.04 (m, 2 H), 4.21-4.28 (m, 2 H), 4.89 (s, 2 H), 6.32 (dd, J = 8.1, 2.0 Hz, 1 H), 6.45-6.51 (m, 2 H), 6.58 (d, J = 3.4 Hz, 1 H), 7.29-7.33 (m, 1 H), 7.58-7.61 (m, 1 H), 8.57-8.60 (m, 2 H), 9.86 (br. s, 1 H). | CDCl3 | 477 [M + H]+. |

TABLE 96

| Example | Compound Name | Structure | 1H NMR δ ppm | Solvent | ESI MS m/z |
|---|---|---|---|---|---|
| 351 | 2-[4,6-difluoro-1-(pyridin-3-ylmethyl)spiro[indoline-3,4'-piperidine]-1'-yl]-8-methyl-5,6,7,8-tetrahydropyrido[2,3-d]pyrimidin-4(3H)-one | (Test Target Compound 340) | 1.73-1.87 (m, 4 H), 2.20-2.29 (m, 2 H), 2.42-2.47 (m, 2 H), 2.81-2.90 (m, 2 H), 3.05 (s, 3 H), 3.22-3.27 (m, 2 H), 3.39 (s, 2 H), 4.32 (s, 2 H), 4.37-4.44 (m, 2 H), 6.01 (dd, J = 9.7, 2.1 Hz, 1 H), 6.06-6.13 (m, 1 H), 7.28-7.32 (m, 1 H), 7.59-7.63 (m, 1 H), 8.55-8.58 (m, 2 H), 11.00 (br. s, 1 H). | CDCl3 | 479 [M + H]+. |
| 352 | 4,6-difluoro-1-(2-hydroxyethyl)-1'-(4-oxo-3,4,5,6,7,8-hexahydropyrido[2,3-d]pyrimidin-2-yl)spiro[indoline-3,4'-piperidin]-2-one | (Test Target Compound 341) | 1.78-1.86 (m, 5 H), 2.19-2.28 (m, 2 H), 2.39-2.43 (m, 2 H), 3.28-3.33 (m, 2 H), 3.81-3.90 (m, 6 H), 4.16-4.23 (m, 2 H), 4.73 (br. s, 1 H), 6.43-6.49 (m, 1 H), 6.53-6.57 (m, 1 H), 10.54 (br. s, 1 H). | CDCl3 | 432 [M + H]+. |

TABLE 96-continued

| Example | Compound Name | Structure | 1H NMR δ ppm | Solvent | ESI MS m/z |
|---|---|---|---|---|---|
| 353 | 4-fluoro-6-hydroxy-1-methyl-1'-(4-oxo-3,4,5,6,7,8-hexahydro-quinazolin-2-yl)spiro[indoline-3,4'-piperidin]-2-one | (Test Target Compound 342) | 1.60-1.77 (m, 6 H), 1.90-1.99 (m, 2 H), 2.23-2.28 (m, 2 H), 2.36-2.41 (m, 2 H), 3.08 (s, 3 H), 3.70-3.79 (m, 2 H), 4.02-4.11 (m, 2 H), 6.20 (dd, J = 11.9, 2.0 Hz, 1 H), 6.32 (d, J = 2.0 Hz, 1 H), 10.05 (s, 1 H), 11.09 (br. s, 1 H). | CDCl3 | [M + H]+ |
| 354 | 4-fluoro-6-hydroxy-1-methyl-1'-(8-methyl-4-oxo-3,4,5,6,7,8-hexahydropyrido[2,3-d]pyrimidin-2-yl)spiro[indoline-3,4'-piperidin]-2-one | (Test Target Compound 343) | 1.68-1.80 (m, 4 H), 1.90-1.98 (m, 2 H), 2.29-2.34 (m, 2 H), 2.99 (s, 3 H), 3.08 (s, 3 H), 3.20-3.24 (m, 2 H), 3.70-3.78 (m, 2 H), 4.02-4.09 (m, 2 H), 6.20 (dd, J = 11.9, 2.0 Hz, 1 H), 6.31 (d, J = 2.0 Hz, 1 H), 10.05 (br. s, 1 H), 10.34 (br. s, 1 H). | DMSO-d6 | 414 [M + H]+. |
| 355 | 4-fluoro-6-(2-hydroxy-ethoxy)-1-methyl-1'-(4-oxo-3,4,5,6,7,8-hexahydropyrido[2,3-d]pyrimidin-2-yl)spiro[indoline-3,4'-piperidinr]-2-one | (Test Target Compound 344) | 1.65-1.75 (m, 4 H), 1.90-1.99 (m, 2 H), 2.25-2.30 (m, 2 H), 3.10-3.19 (m, 5 H), 3.67-3.76 (m, 4 H), 4.00-4.08 (m, 4 H), 4.88 (t, J = 5.3 Hz, 1 H), 6.39 (br. s, 1 H), 6.46 (dd, J = 12.2, 2.0 Hz, 1 H), 6.56 (d, J = 2.0 Hz, 1 H), 10.27 (br. s. 1 H). | DMSO-d6 | [M + H]+ |

TABLE 97

| Example | Compound Name | Structure | 1H NMR δ ppm | Solvent | ESI MS m/z |
|---|---|---|---|---|---|
| 356 | 4-fluoro-6-(2-hydroxy-ethoxy)-1-methyl-1'-(8-methyl-4-oxo-3,4,5,6,7,8-hexahydro-pyrido[2,3-d]pyrimidin-2-yl)spiro[indoline-3,4'-piperidin]-2-one | (Test Target Compound 345) | 1.71-1.80 (m, 4 H), 1.92-2.01 (m, 2 H), 2.29-2.34 (m, 2 H), 3.07 (s, 3 H), 3.12 (s, 3 H), 3.20-3.25 (m, 2 H), 3.69-3.79 (m, 4 H), 4.01-4.11 (m, 4 H), 4.88 (t, J = 5.4 Hz, 1 H), 6.46 (dd, J = 12.2, 2.0 Hz, 1 H), 6.56 (d, J = 2.0 Hz, 1 H), 10.35 (br. s, 1 H). | DMSO-d6 | 458 [M + H]+. |

TABLE 97-continued

| Example | Compound Name | Structure | 1H NMR δ ppm | Solvent | ESI MS m/z |
|---|---|---|---|---|---|
| 357 | 6-[2-(dimethylamino)ethoxy]-4-fluoro-1-methyl-1'-(8-methyl-4-oxo-3,4,5,6,7,8-hexahydropyrido[2,3-d]pyrimidin-2-yl)spiro[indoline-3,4'-piperidin]-2-one | (Test Target Compound 346) | 1.78-1.86 (m, 4 H), 2.14-2.24 (m, 2 H), 2.36 (s, 6 H), 2.45 (t, J = 6.3 Hz, 2 H), 2.75 (t, J = 5.6 Hz, 2 H), 3.06 (s, 3 H), 3.16 (s, 3 H), 3.22-3.26 (m, 2 H), 3.89-3.97 (m, 2 H), 4.06 (t, J = 5.6 Hz, 2 H), 4.18-4.25 (m, 2 H), 6.24-6.30 (m, 2 H), 10.94 (br. s, 1 H). | CDCl3 | 458 [M + H]+. |
| 358 | 4-fluoro-1-methyl-1'-(8-methyl-4-oxo-3,4,5,6,7,8-hexahydropyrido[2,3-d]pyrimidin-2-yl)-6-[2-(pyrrolidin-1-yl)ethoxy]spiro[indoline-3,4'-piperidin]-2-one | (Test Target Compound 347) | 1.79-1.88 (m, 8 H), 2.14-2.23 (m, 2 H), 2.43-2.48 (m, 2 H), 2.64-2.74 (m, 4 H), 2.92-2.98 (m, 2 H), 3.07 (s, 3 H), 3.16 (s, 3 H), 3.22-3.27 (m, 2 H), 3.88-3.97 (m, 2 H), 4.10-4.22 (m, 4 H), 6.25-6.30 (m, 2 H), 10.55 (br. s, 1 H). | CDCl3 | 511 [M + H]+. |
| 359 | 4-fluoro-1-methyl-1'-(8-methyl-4-oxo-3,4,5,6,7,8-hexahydropyrido[2,3-d]pyrimidin-2-yl)-6-[(2-piperidin-1-yl)ethoxy]spiro[indoline-3,4'-piperidin]-2-one | (Test Target Compound 248) | 1.43-1.50 (m, 2 H), 1.60-1.67 (m, 4 H), 1.79-1.88 (m, 4 H), 2.14-2.23 (m, 2 H), 2.44-2.59 (m, 6 H), 2.77-2.83 (m, 2 H), 3.07 (s, 3 H), 3.16 (s, 3 H), 3.23-3.28 (m, 2 H), 3.88-3.97 (m, 2 H), 4.08-4.18 (m, 4 H), 6.24-6.29 (m, 2 H). | CDCl3 | 425 [M + H]+. |
| 360 | 4-fluoro-1-methyl-1'-(8-methyl-4-oxo-3,4,5,6,7,8-hexahydropyrido[2,3-d]pyrimidin-2-yl)-6-(2-morpholinoethoxy)spiro[indoline-3,4'-piperidin]-2-one | (Test Target Compound 349) | 1.79-1.88 (m, 4 H), 2.15-2.23 (m, 2 H), 2.44-2.49 (m, 2 H), 2.56-2.60 (m, 4 H), 2.78-2.83 (m, 2 H), 3.07 (s, 3 H), 3.16 (s, 3 H), 3.23-3.27 (m, 2 H), 3.72-3.76 (m, 4 H), 3.88-3.96 (m, 2 H), 4.07-4.12 (m, 2 H), 4.13-4.20 (m, 2 H), 6.24-6.28 (m, 2 H), 10.33 (br. s, 1 H). | CDCl3 | 527 [M + H]+. |

TABLE 98

| Example | Compound Name | Structure | 1H NMR δ ppm | Solvent | ESI MS m/z |
|---|---|---|---|---|---|
| 361 | 6-[2-(1,1-dioxidothiomorpholino)ethoxy]-4-fluoro-1-methyl-1'-(8-methyl-4-oxo-3,4,5,6,7,8-hexahydropyrido[2,3-d]pyrimidin-2-yl)spiro[indoline-3,4'-piperidin]-2-one | 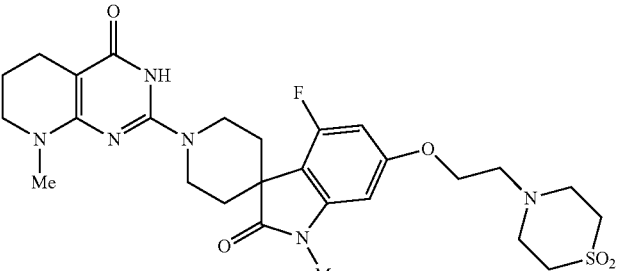<br>(Test Target Compound 350) | 1.78-1.87 (m, 4 H), 2.15-2.24 (m, 2 H), 2.44-2.49 (m, 2 H), 2.98-3.02 (m, 2 H), 3.05-3.11 (m, 7 H), 3.14-3.19 (m, 7 H), 3.23-3.27 (m, 2 H), 3.88-3.96 (m, 2 H), 4.05-4.09 (m, 2 H), 4.14-4.21 (m, 2 H), 6.21-6.26 (m, 2 H), 10.31 (br. s, 1 H). | CDCl3 | 575 [M + H]+. |
| 362 | 4-fluoro-1-methyl-1'-(8-methyl-4-oxo-3,4,5,6,7,8-hexahydropyrido[2,3-d]pyrimidin-2-yl)-6-[2-(4-methylpiperazin-1-yl)ethoxy]spiro[indoline-3,4'-piperidin]-2-one | 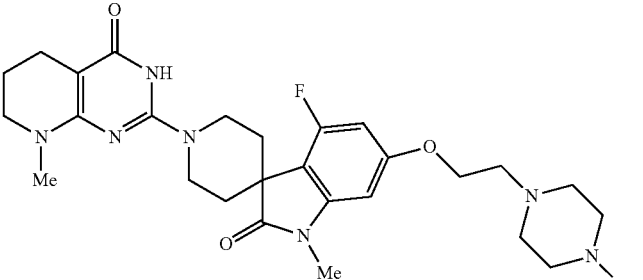<br>(Test Target Compound 351) | 1.78-1.87 (m, 4 H), 2.14-2.23 (m, 2 H), 2.31 (s, 3 H), 2.42-2.69 (m, 10 H), 2.80-2.84 (m, 2 H), 3.07 (s, 3 H), 3.16 (s, 3 H), 3.23-3.27 (m, 2 H), 3.88-3.96 (m, 2 H), 4.06-4.11 (m, 2 H), 4.13-4.20 (m, 2 H), 6.23-6.28 (m, 2 H), 10.32 (br. s, 1 H). | CDCl3 | 540 [M + H]+. |
| 363 | 6-[3-(dimethylamino)propoxy]-4-fluoro-1-methyl-1'-(8-methyl-4-oxo-3,4,5,6,7,8-hexahydropyrido[2,3-d]pyrimidin-2-yl)spiro[indoline-3,4'-piperidin]-2-one | 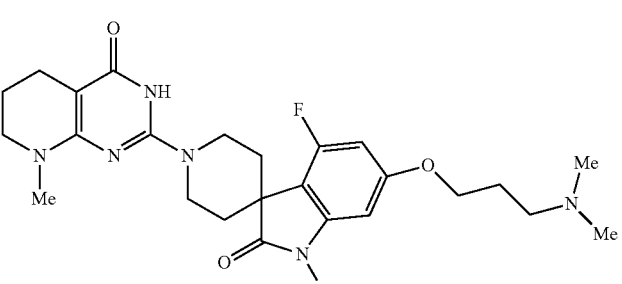<br>(Test Target Compound 352) | 1.79-1.87 (m, 4 H), 1.93-1.99 (m, 2 H), 2.15-2.23 (m, 2 H), 2.27 (s, 6 H), 2.43-2.49 (m, 4 H), 3.07 (s, 3 H), 3.16 (s, 3 H), 3.23-3.27 (m, 2 H), 3.88-3.96 (m, 2 H), 3.98-4.03 (m, 2 H), 4.14-4.21 (m, 2 H), 6.24-6.28 (m, 2 H), 10.36 (br. s, 1 H). | CDCl3 | 499 [M + H]+. |
| 364 | 4-fluoro-1-methyl-1'-(8-methyl-4-oxo-3,4,5,6,7,8-hexahydropyrido[2,3-d]pyrimidin-2-yl)-6-[(3-piperidin-1-yl)propoxy]spiro[indoline-3,4'-piperidin]-2-one | 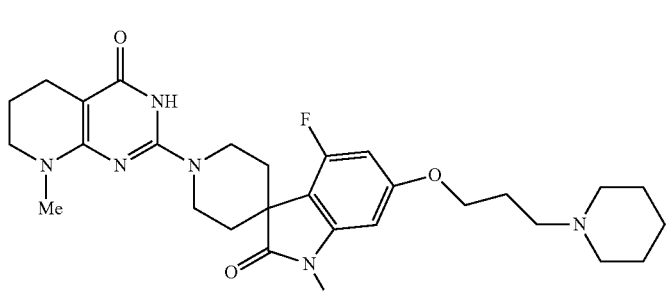<br>(Test Target Compound 353) | 1.42-1.48 (m, 2 H), 1.57-1.63 (m, 4 H), 1.79-1.86 (m, 4 H), 1.94-2.02 (m, 2 H), 2.15-2.23 (m, 2 H), 2.38-2.49 (m, 8 H), 3.07 (s, 3 H), 3.16 (s, 3 H), 3.22-3.27 (m, 2 H), 3.89-3.97 (m, 2 H), 3.98-4.02 (m, 2 H), 4.15-4.22 (m, 2 H), 6.23-6.28 (m, 2 H), 10.58 (br. s, 1 H). | CDCl3 | 539 [M + H]+. |

TABLE 98-continued

| Example | Compound Name | Structure | 1H NMR δ ppm | Solvent | ESI MS m/z |
|---|---|---|---|---|---|
| 365 | 4-fluoro-1-methyl-1'-(8-methyl-4-oxo-3,4,5,6,7,8-hexahydro-pyrido[2,3-d]pyrimidin-2-yl)-6-(3-morpholinopropoxy)spiro[indoline-3,4'-piperidin]-2-one | (Test Target Compound 354) | 1.79-1.87 (m, 4 H), 1.94-2.02 (m, 2 H), 2.15-2.23 (m, 2 H), 2.43-2.55 (m, 8 H), 3.07 (s, 3 H), 3.17 (s, 3 H), 3.22-3.27 (m, 2 H), 3.71-3.76 (m, 4 H), 3.88-3.97 (m, 2 H), 3.99-4.04 (m, 2 H), 4.16-4.24 (m, 2 H), 6.23-6.29 (m, 2 H), 10.75 (br. s, 1 H). | CDCl3 | 541 [M + H]+. |

TABLE 99

| Example | Compound Name | Structure | 1H NMR δ ppm | Solvent | ESI MS m/z |
|---|---|---|---|---|---|
| 366 | 4-fluoro-6-(2-methoxy)-1-methyl-1'-(8-methyl-4-oxo-3,4,5,6,7,8-hexahydropyrido[2,3-d]pyrimidin-2-yl)spiro[indoline-3,4'-piperidin]-2-one | (Test Target Compound 355) | 1.79-1.87 (m, 4 H), 2.14-2.23 (m, 2 H), 2.44-2.49 (m, 2 H), 3.08 (s, 3 H), 3.15 (s, 3 H), 3.25-3.29 (m, 2 H), 3.45 (s, 3 H), 3.73-3.77 (m, 2 H), 3.90-3.98 (m, 2 H), 4.09-4.12 (m, 2 H), 4.17-4.23 (m, 2 H), 6.24-6.31 (m, 2 H), 10.76 (br. s, 1 H). | CDCl3 | 472 [M + H]+. |
| 367 | 4-fluoro-1-methyl-1'-(8-methyl-4-oxo-3,4,5,6,7,8-hexahydropyrido[2,3-d]pyrimidin-2-yl)-6-[3-(pyrrolidin-1-yl)propoxy]spiro[indoline-3,4'-piperidin]-2-one | (Test Target Compound 356) | 1.77-1.87 (m, 4 H), 1.91-2.01 (m, 4 H), 2.14-2.24 (m, 4 H), 2.43-2.49 (m, 2 H), 2.81-3.01 (m, 4 H), 3.07 (s, 3 H), 3.16 (s, 3 H), 3.22-3.27 (m, 2 H), 3.87-3.96 (m, 2 H), 4.04-4.10 (m, 2 H), 4.14-4.21 (m, 2 H), 6.24-6.29 (m, 2 H), 10.47 (br. s, 1 H). | CDCl3 | 525 [M + H]+. |
| 368 | 6-[2-(dimethylamino)ethoxy]-4-fluoro-1-methyl-1'-(4-oxo-3,4,5,6,7,8-hexahydro-quinazolin-2-yl)-spiro[indoline-3,4'-piperidinr]-2-one | (Test Target Compound 357) | 1.63-1.77 (m, 4 H), 1.81-1.88 (m, 2 H), 2.15-2.24 (m, 2 H), 2.32-2.42 (m, 8 H), 2.45-2.49 (m, 2 H), 2.77-2.82 (m, 2 H), 3.16 (s, 3 H), 3.91-4.00 (m, 2 H), 4.07-4.11 (m, 2 H), 4.20-4.27 (m, 2 H), 6.25-6.31 (m, 2 H), 11.32 (br. s, 1 H). | CDCl3 | 470 [M + H]+. |

TABLE 99-continued

| Example | Compound Name | Structure | 1H NMR δ ppm | Solvent | ESI MS m/z |
|---|---|---|---|---|---|
| 369 | 4,6-difluoro-1-(2-hydroxyethyl)-1'-(7-methyl-4-oxo-4,5,6,7-tetrahydro-3H-pyrrolo[2,3-d]pyrimidin-2-yl)spiro[indoline-3,4'-piperidin]-2-one | (Test Target Compound 358) | 1.85-1.91 (m, 2 H), 2.17-2.26 (m, 2 H), 2.66-2.72 (m, 2 H), 2.87 (s, 3 H), 3.41-3.47 (m, 2 H), 3.79-3.92 (m, 6 H), 4.28-4.35 (m, 2 H), 6.34-6.41 (m, 1 H), 6.56 (dd, J = 8.7, 2.0 Hz, 1 H), 10.11 (br. s, 1 H). | CDCl3 | 432 [M + H]+. |
| 370 | 4,6-difluoro-1-(2-hydroxyethyl)-1'-[8-(methyl-d3)-4-oxo-3,4,5,6,7,8-hexahydropyrido[2,3-d]pyrimidin-2-yl]spiro[indoline-3,4'-piperidin]-2-one | (Test Target Compound 359) | 1.72-1.82 (m, 4 H), 1.96-2.07 (m, 2 H), 2.29-2.35 (m, 2 H), 3.20-3.25 (m, 2 H), 3.57-3.62 (m, 2 H), 3.65-3.76 (m, 4 H), 4.10-4.18 (m, 2 H), 4.84 (t, J = 5.7 Hz, 1 H), 6.80-6.87 (m, 1 H), 6.98 (dd, J = 9.3, 2.1 Hz, 1 H), 10.37 (br. s, 1 H). | DMSO-d6 | 449 [M + H]+. |

TABLE 100

| Example | Compound Name | Structure | 1H NMR δ ppm | Solvent | ESI MS m/z |
|---|---|---|---|---|---|
| 371 | Methyl 2-{2-[4,6-difluoro-1-(2-hydroxyethyl)-2-oxo-spiro[indoline-3,4'-piperidin]-1'-yl]-4-oxo-3,5,6,7-tetrahydropyrido[2,3-d]pyrimidin-8(4H)-yl}acetate | (Test Target Compound 360) | 1.78-1.91 (m, 4 H), 2.16-2.25 (m, 2 H), 2.43-2.48 (m, 2 H), 3.36-3.40 (m, 2 H), 3.68 (s, 3 H), 3.80-3.90 (m, 6 H), 4.13-4.19 (m, 4 H), 6.43-6.49 (m, 1 H), 6.55 (dd, J = 8.6, 2.1 Hz, 1 H), 10.79 (br. s, 1 H). | CDCl3 | 504 [M + H]+. |
| 372 | 4-fluoro-6-methoxy-1-methyl-1'-(8-methyl-4-oxo-3,4,5,6,7,8-hexahydropyrido[2,3-d]pyrimidin-2-yl)spiro[indoline-3,4'-piperidin]-2-one | (Test Target Compound 361) | 1.79-1.87 (m, 4 H), 2.15-2.24 (m, 2 H), 2.44-2.49 (m, 2 H), 3.07 (s, 3 H), 3.17 (s, 3 H), 3.23-3.27 (m, 2 H), 3.81 (s, 3 H), 3.89-3.97 (m, 2 H), 4.14-4.21 (m, 2 H), 6.23-6.28 (m, 2 H), 10.45 (br. s, 1 H). | CDCl3 | 428 [M + H]+. |

TABLE 100-continued

| Example | Compound Name | Structure | 1H NMR δ ppm | Solvent | ESI MS m/z |
|---|---|---|---|---|---|
| 373 | 4-fluoro-1-(2-hydroxy-ethyl)-6-methoxy-1'-(8-methyl-4-oxo-3,4,5,6,7,8-hexahydropyrido[2,3-d]pyrimidin-2-yl)spiro[indoline-3,4'-piperidin]-2-one | (Test Target Compound 362) | 1.81-1.88 (m, 4 H), 2.17-2.25 (m, 2 H), 2.47-2.51 (m, 2 H), 3.08 (s, 3 H), 3.24-3.29 (m, 2 H), 3.80 (s, 3 H), 3.83-3.93 (m, 6 H), 4.06-4.13 (m, 2 H), 6.26 (dd, J = 11.6, 2.1, 1 H), 6.34 (d, J = 2.1, 1 H). | CDCl3 | 458 [M + H]+. |
| 374 | 2-(4,6-difluoro-1'-(8-methyl-4-oxo-3,4,5,6,7,8-hexahydropyrido[2,3-d]pyrimidin-2-yl)-2-oxospiro[indoline-3,4'-piperidin]-1-yl)acetonitrile | (Test Target Compound 363) | 1.80-1.87 (m, 4 H), 2.26-2.34 (m, 2 H), 2.43-2.47 (m, 2 H), 3.07 (s, 3 H), 3.23-3.27 (m, 2 H), 3.76-3.85 (m, 2 H), 4.30-4.37 (m, 2 H), 4.63 (s, 2 H), 6.56-6.62 (m, 2 H), 11.11 (br. s, 1 H). | CDCl3 | 441 [M + H]+. |
| 375 | 4-chloro-6-[2-(dimethylamino)ethoxy]-1-methyl-1'-(8-methyl-4-oxo-3,4,5,6,7,8-hexahydropyrido[2,3-d]pyrimidin-2-yl)spiro[indoline-3,4'-piperidin]-2-one | (Test Target Compound 364) | 1.57-1.63 (m, 2 H), 1.80-1.87 (m, 2 H), 2.34 (s, 6 H), 2.45-2.50 (m, 2 H), 2.64-2.70 (m, 2 H), 2.72 (t, J = 5.6 Hz, 2 H), 3.07 (s, 3 H), 3.15 (s, 3 H), 3.23-3.27 (m, 2 H), 3.79-3.88 (m, 2 H), 4.05 (t, J = 5.6 Hz, 2 H), 4.26-4.33 (m, 2 H), 6.38 (d, J = 2.1 Hz, 1 H), 6.49 (d, J = 2.1 Hz, 1 H), 10.17 (br. s, 1 H). | CDCl3 | 501 [M + H]+. |

TABLE 101

| Example | Compound Name | Structure | 1H NMR δ ppm | Solvent | ESI MS m/z |
|---|---|---|---|---|---|
| 376 | 4-chloro-1-methyl-1'-(8-methyl-4-oxo-3,4,5,6,7,8-hexahydropyrido[2,3-d]pyrimidin-2-yl)-6-(2-(piperidin-1-yl)ethoxy)spiro[indoline-3,4'-piperidin]-2-one | (Test Target Compound 365) | 1.43-1.49 (m, 2 H), 1.56-1.66 (m, 6 H), 1.80-1.87 (m, 2 H), 2.44-2.56 (m, 6 H), 2.64-2.73 (m, 2 H), 2.76-2.81 (m, 2 H), 3.07 (s, 3 H), 3.15 (s, 3 H), 3.23-3.27 (m, 2 H), 3.79-3.88 (m, 2 H), 4.11 (t, J = 5.7 Hz, 2 H), 4.28-4.35 (m, 2 H), 6.35 (d, J = 2.1 Hz, 1 H), 6.49 (d, J = 2.1 Hz, 1 H), 10.31 (br. s, 1 H). | CDCl3 | 541 [M + H]+. |

TABLE 101-continued

| Example | Compound Name | Structure | 1H NMR δ ppm | Solvent | ESI MS m/z |
|---|---|---|---|---|---|
| 377 | 4-chloro-1-methyl-1'-(8-methyl-4-oxo-3,4,5,6,7,8-hexahydropyrido[2,3-d]pyrimidin-2-yl)-6-(2-morpholinoethoxy)spiro[indoline-3,4'-piperidin]-2-one | (Test Target Compound 366) | 1.56-1.63 (m, 2 H), 1.80-1.87 (m, 2 H), 2.44-2.49 (m, 2 H), 2.55-2.59 (m, 4 H), 2.64-2.73 (m, 2 H), 2.80 (t, J = 5.6 Hz, 2 H), 3.07 (s, 3 H), 3.15 (s, 3 H), 3.22-3.27 (m, 2 H), 3.72-3.76 (m, 4 H), 3.78-3.87 (m, 2 H), 4.09 (t, J = 5.6 Hz, 2 H), 4.30-4.37 (m, 2 H), 6.35 (d, J = 2.1 Hz, 1 H), 6.49 (d, J = 2.1 Hz, 1 H), 10.49 (br. s, 1 H). | CDCl3 | 543 [M + H]+. |
| 378 | 4-chloro-6-[2-(1,1-dioxidothiomorpholino)ethoxy]-1-methyl-1'-(8-methyl-4-oxo-3,4,5,6,7,8-hexahydropyrido[2,3-d]pyrimidin-2-yl)spiro[indoline-3,4'-piperidin]-2-one | (Test Target Compound 367) | 1.57-1.63 (m, 2 H), 1.80-1.87 (m, 2 H), 2.45-2.49 (m, 2 H), 2.63-2.73 (m, 2 H), 3.00 (t, J = 5.1 Hz, 2 H), 3.06-3.11 (m, 7 H), 3.14-3.19 (m, 7 H), 3.24-3.28 (m, 2 H), 3.79-3.88 (m, 2 H), 4.08 (t, J = 5.1 Hz, 2 H), 4.28-4.35 (m, 2 H), 6.31 (d, J = 2.1 Hz, 1 H), 6.47 (d, J = 2.1 Hz, 1 H), 10.23 (br. s, 1 H). | CDCl3 | 591 [M + H]+. |
| 379 | 2-[4-fluoro-6-methoxy-1'-(8-methyl-4-oxo-3,4,5,6,7,8-hexahydropyrido[2,3-d]pyrimidin-2-yl)-2-oxospiro[indoline-3,4'-piperidin]-1-yl]acetonitrile | (Test Target Compound 368) | 1.80-1.87 (m, 4 H), 2.21-2.30 (m, 2 H), 2.43-2.48 (m, 2 H), 3.07 (s, 3 H), 3.23-3.27 (m, 2 H), 3.78-3.87 (m, 5 H), 4.23-4.30 (m, 2 H), 4.61 (s, 2 H), 6.35 (dd, J = 11.6, 2.0 Hz, 1 H), 6.39 (d, J = 2.1 Hz, 1 H), 10.84 (br. s, 1 H). | CDCl3 | 453 [M + H]+. |
| 380 | 4-fluoro-1-methyl-1'-(8-methyl-4-oxo-3,4,5,6,7,8-hexahydropyrido[2,3-d]pyrimidin-2-yl)-6-[(1-methylpiperidin-4-yl)oxy]spiro[indoline-3,4'-piperidin]-2-one | (Test Target Compound 369) | 1.79-1.90 (m, 6 H), 1.98-2.06 (m, 2 H), 2.14-2.23 (m, 2 H), 2.28-2.36 (m, 5 H), 2.44-2.49 (m, 2 H), 2.65-2.73 (m, 2 H), 3.07 (s, 3 H), 3.16 (s, 3 H), 3.23-3.27 (m, 2 H), 3.88-3.97 (m, 2 H), 4.13-4.20 (m, 2 H), 4.26-4.32 (m, 1 H), 6.23-6.28 (m, 2 H), 10.26 (br. s, 1 H). | CDCl3 | 511 [M + H]+. |

TABLE 102

| Example | Compound Name | Structure | 1H NMR δ ppm | Solvent | ESI MS m/z |
|---|---|---|---|---|---|
| 381 | 4-fluoro-6-(2-hydroxy-thoxy)-1-(2-hydroxyethyl)-1'-(8-methyl-4-oxo-3,4,5,6,7,8-hexahydropyrido[2,3-d]pyrimidin-2-yl)spiro[indoline-3,4'-piperidin]-2-one | (Test Target Compound 370) | 1.69-1.80 (m, 4 H), 1.91-2.00 (m, 2 H), 2.29-2.34 (m, 2 H), 2.99 (s, 3 H), 3.20-3.24 (m, 2 H), 3.54-3.59 (m, 2 H), 3.64-3.76 (m, 4 H), 4.05-4.12 (m, 2 H), 4.85 (t, J = 5.6 Hz, 1 H), 6.18 (dd, J = 11.9, 2.0 Hz, 1 H), 6.39 (d J = 2.0 Hz, 1 H), 10.00 (br. s, 1 H), 10.37 (br. s, 1 H). | DMSO-d6 | [M + H]+. |
| 382 | 1'-(8-ethyl-4-oxo-3,4,5,6,7-hexahydropyrido-[2,3-d]pyrimidin-2-yl)-4,6-difluoro-1-(2-hydroxyethyl)spiro[indoline-3,4'-piperidin]-2-one | (Test Target Compound 371) | 1.11 (t, J = 7.1 Hz, 3 H), 1.78-1.87 (m, 4 H), 2.20-2.28 (m, 2 H), 2.40-2.44 (m, 2 H), 3.25-3.29 (m, 2 H), 3.55 (q, J = 7.1 Hz, 2 H), 3.82-3.90 (m, 6 H), 4.16-4.23 (m, 2 H), 6.41-6.47 (m, 1 H), 6.56 (dd, J = 8.5, 2.0 Hz, 1 H). | CDCl3 | 460 [M + H]+. |
| 383 | 4-fluoro-1-(2-hydroxyethyl)-6-(2-methoxyethoxy)-1'-(8-methyl-4-oxo-3,4,5,6,7,8-hexahydropyrido[2,3-d]pyrimidin-2-yl))spiro[indoline-3,4'-piperidin]-2-one | (Test Target Compound 372) | 1.80-1.87 (m, 4 H), 2.16-2.25 (m, 2 H), 2.43-2.48 (m, 2 H), 3.07 (s, 3 H), 3.23-3.27 (m, 2 H), 3.44 (s, 3 H), 3.72-3.75 (m, 2 H), 3.81-3.93 (m, 6 H), 4.07-4.11 (m, 2 H), 4.13-4.19 (m, 2 H), 6.27 (dd, J = 11.6, 2.1 Hz, 1 H), 6.40 (d, J = 2.1 Hz, 1 H). | CDCl3 | 502 [M + H]+. |
| 384 | 4-fluoro-6-hydroxy-1-(2-hydroxyethyl)-1'-(8-methyl-4-oxo-3,4,5,6,7,8-hexahydropyrido[2,3-d]pyrimidin-2-yl)spiro[indoline-3,4'-piperidin]-2-one | (Test Target Compound 373) | 1.69-1.80 (m, 4 H), 1.91-2.00 (m, 2 H), 2.29-2.34 (m, 2 H), 2.99 (s, 3 H), 3.20-3.24 (m, 2 H), 3.54-3.59 (m, 2 H), 3.64-3.76 (m, 4 H), 4.05-4.12 (m, 2 H), 4.85 (t, J = 5.6 Hz, 1 H), 6.18 (dd, J = 11.9, 2.0 Hz, 1 H), 6.39 (d, J = 2.0 Hz, 1 H), 10.00 (br. s, 1 H), 10.37 (br. s, 1 H). | DMSO-d6 | 444 [M + H]+. |

TABLE 102-continued

| Example | Compound Name | Structure | 1H NMR δ ppm | Solvent | ESI MS m/z |
|---|---|---|---|---|---|
| 385 | 6-[2-(dimethylamino)ethoxy]-4-fluoro-1-(2-hydroxyethyl)-1'-(8-methyl-4-oxo-3,4,5,6,7,8-hexahydropyrido[2,3-d]pyrimidin-2-yl)spiro[indoline-3,4'-piperidin]-2-one | 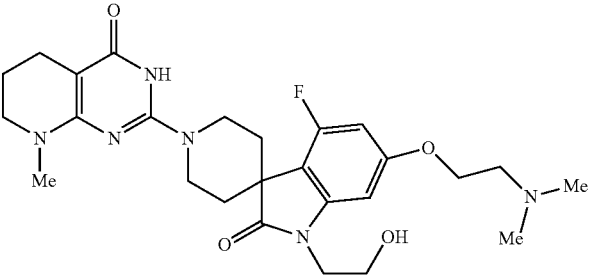 (Test Target Compound 374) | 1.80-1.86 (m, 4 H), 2.16-2.24 (m, 2 H), 2.33 (s, 6 H), 2.43-2.47 (m, 2 H), 2.70-2.73 (m, 2 H), 3.06 (s, 3 H), 3.23-3.27 (m, 2 H), 3.81-3.93 (m, 6 H), 4.01-4.05 (m, 2 H), 4.13-4.20 (m, 2 H), 6.26 (dd, J = 11.6, 2.1 Hz, 1 H), 6.40 (d J = 2.1 Hz, 1 H). | CDCl3 | 515 [M + H]+. |

TABLE 103

| Example | Compound Name | Structure | 1H NMR δ ppm | Solvent | ESI MS m/z |
|---|---|---|---|---|---|
| 386 | 4-fluoro-1-(2-hydroxy-ethyl)-1'-(8-methyl-4-oxo-3,4,5,6,7,8-hexahydropyrido[2,3-d]pyrimidin-2-yl)-6-(2-morpholino-ethoxy)spiro[indoline-3,4'-piperidin]-2-one | 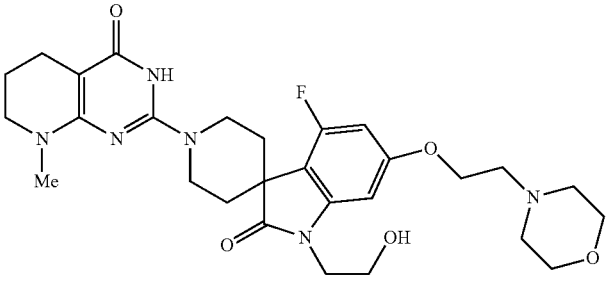 (Test Target Compound 375) | 1.79-1.87 (m, 4 H), 2.16-2.25 (m, 2 H), 2.44-2.48 (m, 2 H), 2.55-2.59 (m, 4 H), 2.77-2.81 (m, 2 H), 3.07 (s, 3 H), 3.23-3.27 (m, 2 H), 3.71-3.75 (m, 4 H), 3.82-3.92 (m, 6 H), 4.05-4.09 (m, 2 H), 4.12-4.18 (m, 2 H), 6.26 (dd, J = 11.6, 2.0 Hz, 1 H), 6.37 (d J = 2.0 Hz, 1 H). | CDCl3 | 557 [M + H]+. |
| 387 | 4-fluoro-1-methyl-1'-(8-methyl-4-oxo-3,4,5,6,7,8-hexahydropyrido[2,3-d]pyrimidin-2-yl)-6-(4-methylpiperazin-1-yl)spiro[indoline-3,4'-piperidin]-2-one | 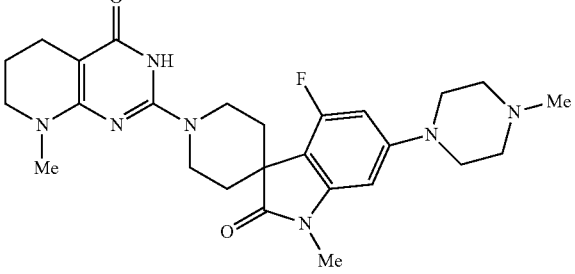 (Test Target Compound 376) | 1.80-1.87 (m, 4 H), 2.11-2.20 (m, 2 H), 2.36 (s, 3 H), 2.44-2.49 (m, 2 H), 2.55-2.60 (m, 4 H), 3.07 (s, 3 H), 3.17 (s, 3 H), 3.21-3.27 (m, 6 H), 3.89-3.98 (m, 4 H), 4.10-4.17 (m, 2 H), 6.19-6.25 (m, 2 H), 10.32 (br. s, 1 H). | CDCl3 | 496 [M + H]+. |
| 388 | 4-fluoro-1-methyl-1'-(8-methyl-4-oxo-3,4,5,6,7,8-hexahydropyrido[2,3-d]pyrimidin-2-yl)-6-(oxetan-3-ylmethoxy)spiro[indoline-3,4'-piperidin]-2-one | 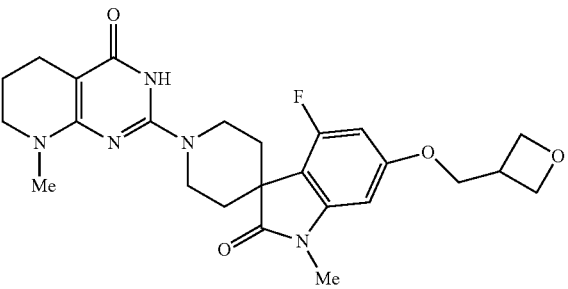 (Test Target Compound 377) | 1.79-1.86 (m, 4 H), 2.15-2.24 (m, 2 H), 2.43-2.48 (m, 2 H), 3.07 (s, 3 H), 3.17 (s, 3 H), 3.22-3.27 (m, 2 H), 3.40-3.47 (m, 1 H), 3.88-3.97 (m, 2 H), 4.17-4.24 (m, 4 H), 4.54-4.58 (m, 2 H), 4.87-4.92 (m, 2 H), 6.25-6.30 (m, 2 H), 10.76 (br. s, 1 H). | CDCl3 | 484 [M + H]+. |

TABLE 103-continued

| Example | Compound Name | Structure | 1H NMR δ ppm | Solvent | ESI MS m/z |
|---|---|---|---|---|---|
| 389 | 4-fluoro-1-methyl-1'-(8-methyl-4-oxo-3,4,5,6,7,8-hexahydropyrido[2,3-d]pyrimidin-2-yl)-6-[(tetrahydro-2H-pyran-4-yl)oxy]spiro[indoline-3,4'-piperidin]-2-one | (Test Target Compound 378) | 1.75-1.86 (m, 6 H), 1.99-2.07 (m, 2 H), 2.15-2.24 (m, 2 H), 2.43-2.48 (m, 2 H), 3.07 (s, 3 H), 3.17 (s, 3 H), 3.22-3.27 (m, 2 H), 3.56-3.63 (m, 2 H), 3.88-4.01 (m, 4 H), 4.16-4.23 (m, 2 H), 4.43-4.49 (m, 1 H), 6.24-6.28 (m, 2 H), 10.63 (br. s, 1 H). | CDCl3 | 498 [M + H]+. |

Example 395

4-fluoro-1'-(4-hydroxy-8-methyl-6,7-dihydro-5H-pyrido[2,3-d]pyrimidin-2-yl)-6-(2-pyrrolidin-1-ylethoxy)spiro[2-benzofuran-3,4'-piperidine]-1-one

[Chem. 70]

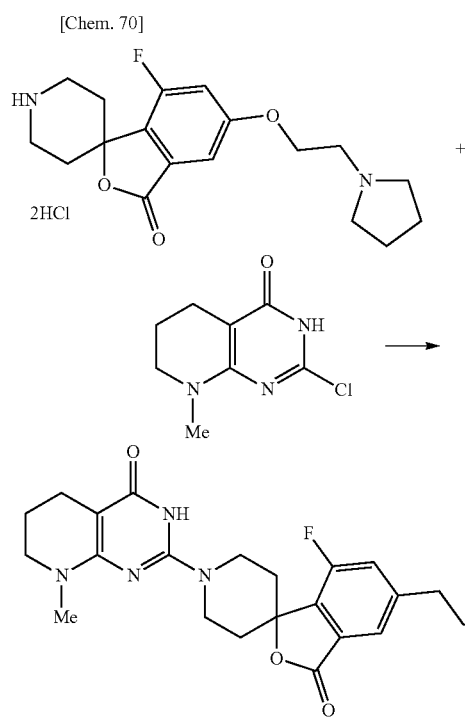

First, 4-fluoro-6-(2-pyrrolidin-1-ylethoxy)spiro[2-benzofuran-3,4'-piperidine]-1-one dihydrochloride (44.9 mg) and 2-chloro-8-methyl-5,6,7,8-tetrahydropyrido[2,3-d]pyrimidin-4 (3H)-one (22.0 mg) were placed in a microwave reaction vessel, and ethanol (1 mL) and triethylamine (46 μL) were added thereto. The vessel was set in the microwave reaction apparatus, and a reaction was allowed to proceed at 150° C. for 30 minutes. After termination of the reaction, the solvent was concentrated and the residue was purified by silica gel column chromatography (chloroform/methanol=95/5 to 85/15) to obtain the title compound (28.1 mg) as a light-yellow solid.

$^{1}$H-NMR (270 MHz, CDCl$_3$) δ: 1.69-1.93 (m, 8H), 2.18-2.50 (m, 4H), 2.69 (br.s, 4H), 2.97 (t J=5.6 Hz, 2H), 3.07 (s, 2H), 3.15-3.43 (m, 4H), 4.19 (t, J=5.6 Hz, 2H), 4.64 (br.d, J=10.2 Hz, 2H), 6.94 (dd, J=10.2, 2.0 Hz, 1H), 7.19 (d, J=2.0 Hz, 1H).

MS(ESI) m/z: 498 [M+H]$^+$.

Example 418

4-fluoro-1-(2-methoxyethyl)-1'-(8-methyl-4-oxo-3,4,5,6,7,8-hexahydropyrido[2,3-d]pyrimidin-2-yl)-6-[(1H-tetrazole-5-yl) methoxy]spiro[indoline-3,4'-piperidine]-2(1H)-one

[Chem. 71]

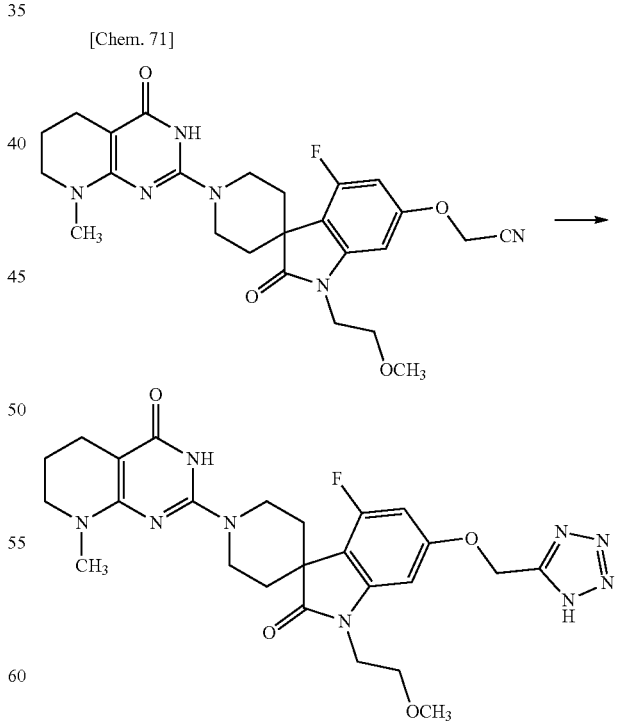

Sodium azide (12 mg) and ammonium chloride (10 mg) were added to a solution of 2-{[4-fluoro-1-(2-methoxyethyl)-1'-(8-methyl-4-oxo-3,4,5,6, 7,8-hexahydropyrido[2, 3-d]pyrimidin-2-yl)-2-oxospiro[indoline-3,4'-piperidine]-6- yl]oxy}acetonitrile (30 mg) in N,N-dimethylformamide (1 mL), and the mixture was stirred under microwave irradiation at 150° C. for 30 minutes. Brine and 1 M hydrochloric acid were added to the reaction solution, followed by six times of extraction with chloroform. The organic layer was dried with anhydrous magnesium sulfate, and the solvent was removed by evaporation under reduced pressure. The obtained residue was purified by reverse phase column chromatography (acetonitrile/water=5/95 to 80/20) to obtain the title compound (12 mg).

$^1$H-NMR (400 MHz, DMSO-$d_6$) δ: 1.65-1.80 (m, 4H), 1.95-2.05 (m, 2H), 2.30-2.35 (m, 2H), 2.99 (s, 3H), 3.20-3.30 (m, 5H), 3.50-3.55 (m, 2H), 3.65-3.75 (m, 2H), 3.80-3.90 (m, 2H), 4.05-4.15 (m, 2H), 5.51 (s, 2H), 6.62 (dd, J=11.6, 2.0 Hz, 1H), 6.75 (d, J=2.0 Hz, 1H).

MS(ESI) m/z: 540[M+H]$^+$.

Example 430

[4,6-difluoro-1'-(8-methyl-4-oxo-3,4,5,6,7,8-hexahydropyrido[2,3-d]pyrimidin-2-yl)-2-oxospiro[indoline-3,4'-piperidine]-1(2H)-yl]ethanimidamide

[Chem. 72]

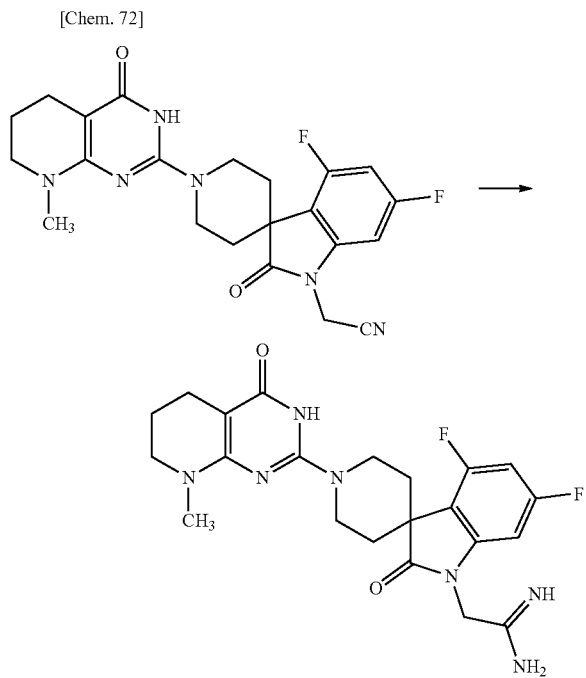

First, 2-[4,6-difluoro-1'-(8-methyl-4-oxo-3,4,5,6,7,8-hexahydropyrido[2,3-d]pyrimidin-2-yl)-2-oxospiro[indoline-3,4'-piperidine]-1-yl]acetonitrile (38 mg) was suspended in methanol (2 mL), then a 1 M sodium methoxide methanol solution (0.12 mL) was added thereto, and the mixture was stirred at room temperature for 1 hour. Ammonium chloride (14 mg) was added thereto, and the mixture was stirred at 50° C. for 4 hours. After that, water was added to the reaction solution, followed by five times of extraction with chloroform. The organic layer was dried with anhydrous magnesium sulfate, and the solvent was removed by evaporation under reduced pressure. The obtained residue was purified by reverse phase column chromatography (acetonitrile/water=5/95 to 80/20) to obtain the title compound (19 mg).

$^1$H-NMR (400 MHz, CD$_3$OD) δ: 1.80-1.90 (m, 2H), 1.95-2.05 (m, 2H), 2.20-2.30 (m, 2H), 2.40-2.50 (m, 2H), 3.10 (s, 3H), 3.30-3.40 (m, 2H), 3.75-3.85 (m, 2H), 4.15-4.25 (m, 2H), 4.78 (s, 2H), 6.70-6.75 (m, 1H), 6.80 (dd, J=8.4, 2.0 Hz, 1H).

MS(ESI) m/z: 458[M+H]$^+$.

Example 442

({[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidine]-6-yl]oxy}methyl) phosphonic Acid

[Chem. 72]

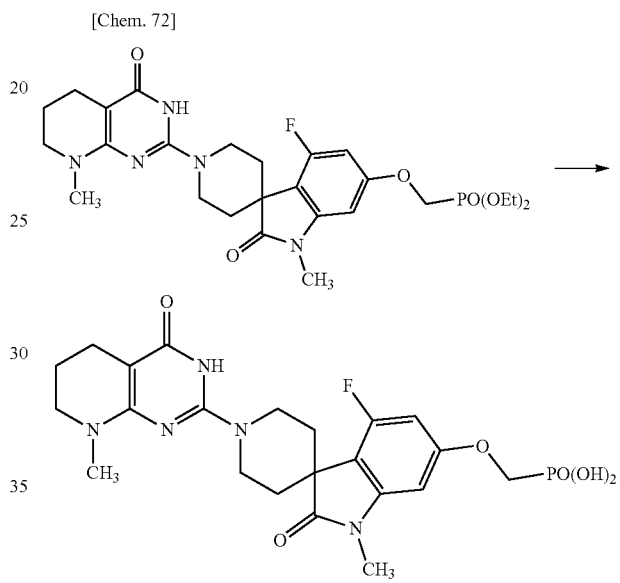

Trimethylsilyl bromide (0.024 mL) was added to a solution of ({[1'-(tert-butyloxycarbonyl)-4-fluoro-1-methyl-2-oxospiro[indoline-3,4'-piperidine]-6-yl]oxy}methyl) diethyl phosphonate (21 mg) in dichloromethane (1 mL), and the mixture was stirred at room temperature for 19 hours. The reaction solution was concentrated and dried, methanol (1 mL) was added thereto, and the mixture was stirred at room temperature for 30 minutes. After that, the mixture was purified by reverse phase column chromatography (acetonitrile/water=5/95 to 80/20) to obtain the title compound (9.5 mg).

$^1$H-NMR (400 MHz, CD$_3$OD) δ: 1.75-2.05 (m, 4H), 2.10-2.55 (m, 4H), 3.12 (s, 3H), 3.18 (s, 3H), 3.30-3.40 (m, 2H), 3.85-4.25 (m, 6H), 6.45-6.65 (m, 2H).

MS(ESI) m/z: 508[M+H]$^+$.

Compounds of Example 390 to Example 394, Example 396 to Example 417, Example 419 to Example 429, Example 431 to Example 441, and Example 443 to Example 474 presented below in Tables 104 to 119 were each obtained according to a combination of some methods among the methods used in Examples described above and their applied methods as well as the methods known by literatures and their applied methods by using materials such as commercially available reagents, compounds synthesized in accordance with the methods known by literatures and their applied methods, and the intermediates in Examples described above.

TABLE 104

| Example | Compound Name | Structure | 1H NMR δ ppm | Solvent | ESI MS m/z |
|---|---|---|---|---|---|
| 390 | 6-(cis-3,5-dimethyl-piperazin-1-yl)-4-fluoro-1-methyl-1'-(8-methyl-4-oxo-3,4,5,6,7,8-hexahydropyrido[2,3-d]pyrimidin-2-yl)spiro[indoline-3,4'-piperidin]-2(1H)-one | 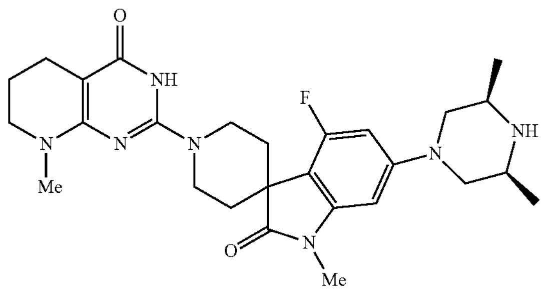 [SMILES: C[C@@H]1CN(c2cc(F)c3c(c2)N(C)C(=O)C32CCN(c3nc4c(c(=O)[nH]3)CCCN4C)CC2)C[C@H](C)N1] | 1.17 (d, J = 6.0 Hz, 6 H), 1.80-1.90 (m, 4 H), 2.10-2.20 (m, 2 H), 2.30-2.50 (m, 4 H), 2.95-3.05 (m, 2 H), 3.07 (s, 3 H), 3.19 (s, 3 H), 3.20-3.30 (m, 2 H), 3.45-3.55 (m, 2 H), 3.90-4.00 (m, 2 H), 4.10-4.20 (m, 2 H), 6.15-6.25 (m, 2 H). | CDCl3 | 510 [M + H]+ |
| 391 | 6-(3,8-diazabicyclo[3.2.1]octan-3-yl)-4-fluoro-1-methyl-1'-(8-methyl-4-oxo-3,4,5,6,7,8-hexahydropyrido[2,3-d]pyrimidin-2-yl)spiro[indoline-3,4'-piperidin]-2(1H)-one | 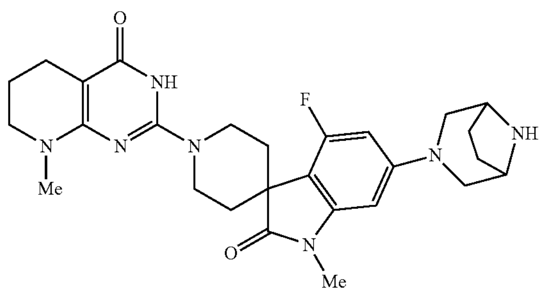 [SMILES: CN1CCCc2c1nc(N1CCC3(CC1)C(=O)N(C)c1cc(N4CC5CCC(C4)N5)cc(F)c13)[nH]c2=O] | 1.75-1.95 (m, 8 H), 2.10-2.20 (m, 2 H), 2.45-2.50 (m, 2 H), 3.00-3.10 (m, 5 H), 3.17 (s, 3 H), 3.25-3.30 (m, 2 H), 3.40-3.50 (m, 2 H), 3.70-3.75 (m, 2 H), 3.85-4.00 (m, 2 H), 4.00-4.15 (m, 2 H), 6.05-6.15 (m, 2 H). | CDCl3 | 508 [M + H]+ |
| 392 | 2-{[4-fluoro)-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy} acetic acid | 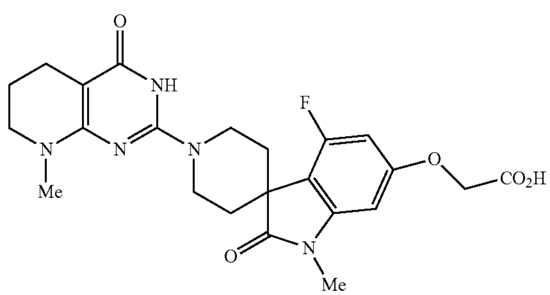 [SMILES: CN1CCCc2c1nc(N1CCC3(CC1)C(=O)N(C)c1cc(OCC(=O)O)cc(F)c13)[nH]c2=O] | 1.38-1.49 (m, 2 H), 1.72-1.81 (m, 2 H), 1.83-1.90 (m, 2 H), 2.49-2.54 (m, 2 H), 3.09 (s, 3 H), 3.14 (s, 3 H), 3.30-3.35 (m, 2 H), 3.77-3.94 (m, 4 H), 4.65 (s, 2 H), 6.22-6.28 (m, 2 H). | CDCl3 | 472 [M + H]+ |
| 393 | 6-[(1H-tetrazol-5-yl)methoxy]-4-fluoro-1-methyl-1'-(8-methyl-4-oxo-3,4,5,6,7,8-hexahydropyrido[2,3-d]pyrimidin-2-yl)spiro[indoline-3,4'-piperidin]-2(1H)-one | 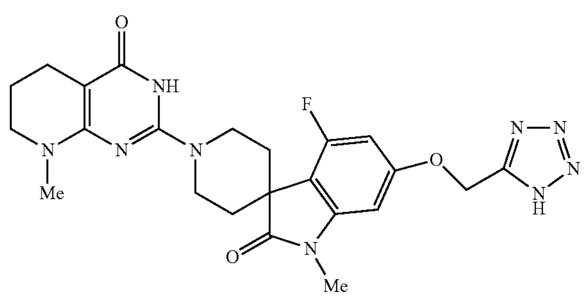 [SMILES: CN1CCCc2c1nc(N1CCC3(CC1)C(=O)N(C)c1cc(OCc4nnn[nH]4)cc(F)c13)[nH]c2=O] | 1.64-1.71 (m, 2 H), 1.87-1.95 (m, 2 H), 2.01-2.10 (m, 2 H), 2.57-2.62 (m, 2 H), 3.13-3.15 (m, 6 H), 3.34-3.39 (m, 2 H), 3.95-4.04 (m, 2 H), 4.16-4.23 (m, 2 H), 5.33 (s, 2 H), 6.28 (dd, J = 11.2, 2.1, 1 H), 6.33 (d, J = 2.1 Hz, 1 H). | CDCl3 | 496 [M + H]+ |
| 394 | 4-fluoro-6-{2-[2-(hydroxymethyl)pyrrolidin-1-yl]ethoxy}-1-methyl-1'-(8-methyl-4-oxo-3,4,5,6,7,8-hexahydropyrido[2,3-d]pyrimidin-2-yl)spiro[indoline-3,4'-piperidin]-2(1H)-one | 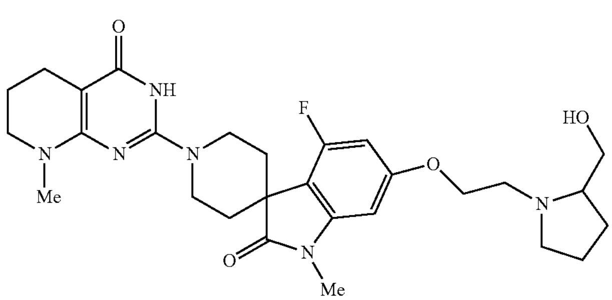 [SMILES: CN1CCCc2c1nc(N1CCC3(CC1)C(=O)N(C)c1cc(OCCN4CCCC4CO)cc(F)c13)[nH]c2=O] | 1.73-1.94 (m, 8 H), 2.14-2.23 (m, 2 H), 2.41-2.50 (m, 3 H), 2.73-2.83 (m, 2 H), 3.07 (s, 3 H), 3.14-3.21 (m, 4 H), 3.23-3.28 (m, 3 H), 3.39-3.44 (m, 1 H), 3.63-3.68 (m, 1 H), 3.88-3.97 (m, 2 H), 4.00-4.09 (m, 2 H), 4.11-4.18 (m, 2 H), 6.23-6.28 (m, 2 H). | CDCl3 | 541 [M + H]+ |

TABLE 105

| Example | Compound Name | Structure | 1H NMR δ ppm | Solvent | ESI MS m/z |
|---|---|---|---|---|---|
| 396 | 4-chloro-7-[2-(dimethylamino)ethoxy]-1-methyl-1'-(8-methyl-4-oxo-3,4,5,6,7,8-hexahydropyrido[2,3-d]pyrimidin-2-yl)spiro[indoline-3,4'-piperidin]-2(1H)-one | 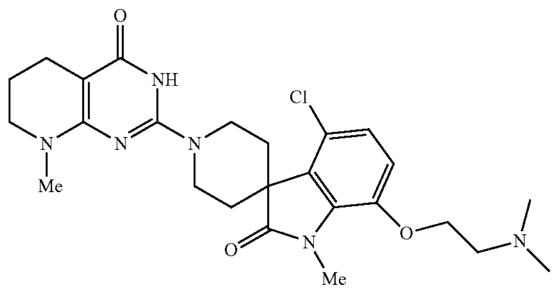 [SMILES: CN(C)CCOc1ccc(Cl)c2c1N(C)C(=O)C21CCN(c2nc3c(c(=O)[nH]2)CCCN3C)CC1] | 1.55-1.65 (m, 2 H), 1.80-1.90 (m, 2 H), 2.34 (s, 6 H), 2.45-2.50 (m, 2 H), 2.70-2.80 (m, 4 H), 3.07 (s, 3 H), 3.20-3.30 (m, 2 H), 3.48 (s, 3 H), 3.80-3.90 (m, 2 H), 4.05-4.15 (m, 2 H), 4.25-4.35 (m, 2 H), 6.79 (d, J = 8.8 Hz, 1 H), 6.88 (d, J = 8.8 Hz, 1 H). | CDCl3 | 501 [M + H]+ |
| 397 | 4-fluoro-6-(4-(2-methoxyethyl)piperazin-1-yl)-1-methyl-1'-(8-methyl-4-oxo-3,4,5,6,7,8-hexahydropyrido[2,3-d]pyrimidin-2-yl)spiro[indoline-3,4'-piperidin]-2(1H)-one | 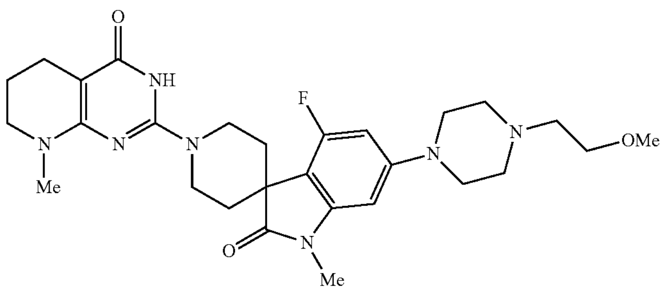 [SMILES: COCCN1CCN(c2cc(F)c3c(c2)N(C)C(=O)C32CCN(c3nc4c(c(=O)[nH]3)CCCN4C)CC2)CC1] | 1.79-1.88 (m, 4 H), 2.11-2.20 (m, 2 H), 2.45-2.50 (m, 2 H), 2.62-2.69 (m, 6 H), 3.07 (s, 3 H), 3.17 (s, 3 H), 3.23-3.28 (m, 6 H), 3.38 (s, 3 H), 3.56 (t, J = 5.4 Hz, 2 H), 3.88-3.97 (m, 2 H), 4.06-4.13 (m, 2 H), 6.18-6.24 (m, 2 H). | CDCl3 | 540 [M + H]+ |
| 398 | 4-fluoro-1-methyl-1'-(8-methyl-4-oxo-3,4,5,6,7,8-hexahydropyrido[2,3-d]pyrimidin-2-yl)-6-(4-(oxetan-3-yl)piperazin-1-yl)spiro[indoline-3,4'-piperidin]-2(1H)-one | 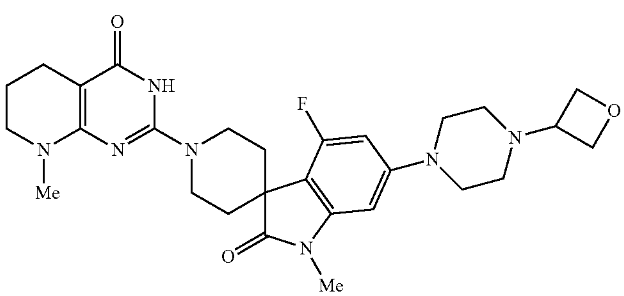 [SMILES: CN1CCCc2c1nc(N1CCC3(CC1)C(=O)N(C)c1cc(N4CCN(C5COC5)CC4)cc(F)c13)[nH]c2=O] | 1.80-1.88 (m, 4 H), 2.11-2.20 (m, 2 H), 2.44-2.52 (m, 6 H), 3.07 (s, 3H), 3.18 (s, 3 H), 3.22-3.28 (m, 6 H), 3.52-3.60 (m, 1 H), 3.88-3.98 (m, 2 H), 4.08-4.16 (m, 2 H), 4.63-4.68 (m, 2 H), 4.69-4.74 (m, 2 H), 6.18-6.25 (m, 2 H). | CDCl3 | 538 [M + H]+ |
| 399 | 4-fluoro-6-(2-hydroxyethoxy)-1'-(8-methyl-4-oxo-3,4,5,6,7,8-hexahydropyrido[2,3-d]pyrimidin-2-yl)-1-(2,2,2-trifluoroethyl)spiro[indoline-3,4'-piperidin]-2(1H)-one | 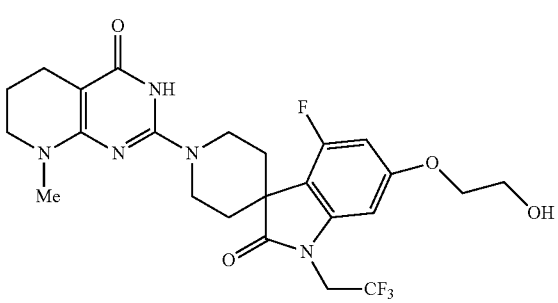 [SMILES: CN1CCCc2c1nc(N1CCC3(CC1)C(=O)N(CC(F)(F)F)c1cc(OCCO)cc(F)c13)[nH]c2=O] | 1.77-1.87 (m, 4 H), 2.20-2.30 (m, 2 H), 2.44-2.49 (m, 2 H), 3.07 (s, 3 H), 3.23-3.28 (m, 2 H), 3.79-3.88 (m, 2 H), 3.96-4.00 (m, 2 H), 4.05-4.09 (m, 2 H), 4.20-4.31 (m, 4 H), 6.31-6.39 (m, 2 H). | CDCl3 | 526 [M + H]+ |

TABLE 105-continued

| Example | Compound Name | Structure | 1H NMR δ ppm | Solvent | ESI MS m/z |
|---|---|---|---|---|---|
| 400 | 6-[2-(dimethylamino)ethoxy]-4-fluoro-1'-(8-methyl-4-oxo-3,4,5,6,7,8-hexahydropyrido[2,3-d]pyrimidin-2-yl)-1-(2,2,2-trifluoroethyl)spiro[indoline-3,4'-piperidin]-2(1H)-one | 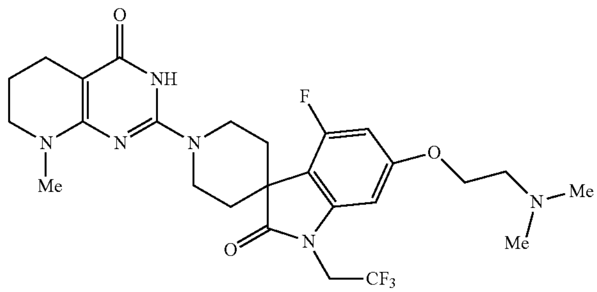 [SMILES: CN(C)CCOc1cc(F)c2c(c1)N(CC(F)(F)F)C(=O)C21CCN(c2nc3c(c(=O)[nH]2)CCCN3C)CC1] | 1.79-1.87 (m, 4 H), 2.21-2.31 (m, 2 H), 2.34 (s, 6 H), 2.44-2.49 (m, 2 H), 2.73 (t, J = 5.6 Hz, 2 H), 3.07 (s, 3 H), 3.23-3.27 (m, 2 H), 3.80-3.89 (m, 2 H), 4.04 (t, J = 5.6 Hz, 2 H), 4.21-4.30 (m, 4 H), 6.30-6.39 (m, 2 H). | CDCl3 | 553 [M + H]+ |

TABLE 106

| Example | Compound Name | Structure | 1H NMR δ ppm | Solvent | ESI MS m/z |
|---|---|---|---|---|---|
| 401 | 7-[2-(dimethylamino)ethoxy]-4-fluoro-1'-(4-hydroxy-8-methyl-6,7-dihydro-5H-pyrido[2,3-d]pyrimidin-2-yl)-1-methylspiro[indole-3,4'-piperidin]-2-one | 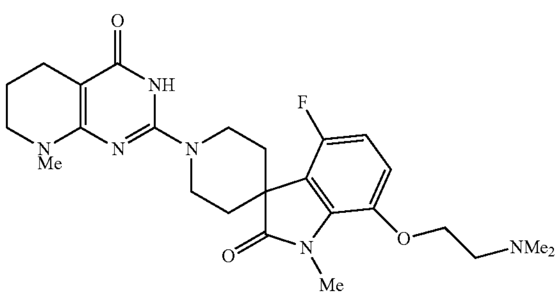 [SMILES: CN(C)CCOc1ccc(F)c2c1N(C)C(=O)C21CCN(c2nc3c(c(=O)[nH]2)CCCN3C)CC1] | 1.77-1.97 (m, 4 H), 2.22-2.31 (m, 2 H), 2.34 (s, 6 H), 2.39-2.49 (m, 2 H), 2.74 (t, J = 5.8 Hz, 2 H), 3.07 (s, 3 H), 3.17-3.32 (m, 2 H), 3.48 (s, 3 H), 3.89 (br t, J = 12.0 Hz, 2 H), 4.08 (t, J = 5.8 Hz, 2 H), 4.26 (br d, J = 13.5 Hz, 2 H), 6.64 (t, J = 8.9 Hz, 1 H), 6.80 (dd, J = 9.2, 4.0 Hz, 1 H). | CDCl3 | 485 [M + H]+ |
| 402 | [4-fluoro-1'-(8-methyl-4-oxo-3,4,5,6,7,8-hexahydropyrido[2,3-d]pyrimidin-2-yl)-6-(4-methylpiperazin-1-yl)-2-oxo-spiro[indoline-3,4'-piperidin]-1(2H)-yl]acetonitrile | 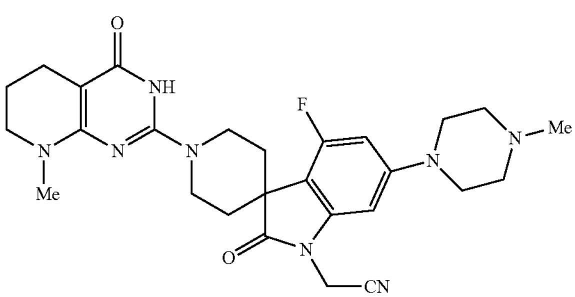 [SMILES: CN1CCN(c2cc(F)c3c(c2)N(CC#N)C(=O)C32CCN(c3nc4c(c(=O)[nH]3)CCCN4C)CC2)CC1] | 1.80-1.87 (m, 4 H), 2.17-2.26 (m, 2 H), 2.37 (s, 3 H), 2.43-2.48 (m, 2 H), 2.56-2.61 (m, 4 H), 3.07 (s, 3 H), 3.23-3.29 (m, 2 H), 3.80-3.89 (m, 2 H), 4.18-4.26 (m, 2 H), 4.62 (s, 2 H), 6.27-6.32 (m, 2 H). | CDCl3 | 521 [M + H]+ |
| 403 | 6-(4-acetylpiperazin-1-yl)-4-fluoro-1-methyl-1'-(8-methyl-4-oxo-3,4,5,6,7,8-hexahydropyrido[2,3-d]pyrimidin-2-yl)-spiro[indoline-3,4'-piperidin]-2(1H)-one | 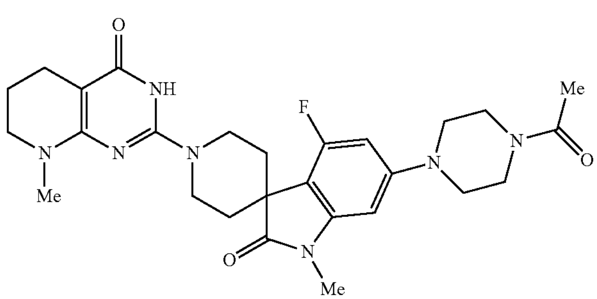 [SMILES: CC(=O)N1CCN(c2cc(F)c3c(c2)N(C)C(=O)C32CCN(c3nc4c(c(=O)[nH]3)CCCN4C)CC2)CC1] | 1.80-1.91 (m, 5 H), 2.11-2.23 (m, 5 H), 2.43-2.53 (m, 2 H), 3.08 (s, 3 H), 3.15-3.33 (m, 10 H), 3.16-3.30 (m, 9 H), 3.59-3.68 (m, 2 H), 3.75-3.82 (m, 2 H), 3.94 (t, J = 10.6 Hz, 2 H), 4.08-4.18 (m, 2 H), 6.18-6.26 (m, 2 H). | CDCl3 | 524 [M + H]+ |

TABLE 106-continued

| Example | Compound Name | Structure | 1H NMR δ ppm | Solvent | ESI MS m/z |
|---|---|---|---|---|---|
| 404 | 4-fluoro-1'-(8-methyl-4-oxo-3,4,5,6,7,8-hexahydropyrido[2,3-d]pyrimidin-2-yl)-6-[2-(pyrrolidin-1-yl)ethoxy]-1-(2,2,2-trifluoroethyl)spiro[indoline-3,4'-piperidin]-2(1H)-one | 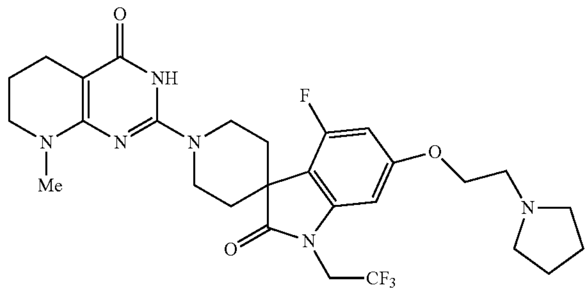 [SMILES: CN1CCCc2c1nc(N1CCC3(CC1)C(=O)N(CC(F)(F)F)c1cc(OCCN4CCCC4)cc(F)c13)[nH]c2=O] | 1.79-1.87 (m, 8 H), 2.21-2.30 (m, 2 H), 2.44-2.49 (m, 2 H), 2.60-2.65 (m, 4 H), 2.90 (t, J = 5.8 Hz, 2 H), 3.07 (s, 3 H), 3.23-3.28 (m, 2 H), 3.80-3.89 (m, 2 H), 4.08 (t, J = 5.8 Hz, 2 H), 4.18-4.30 (m, 4 H), 6.30-6.38 (m, 2 H). | CDCl3 | 579 [M + H]+ |
| 405 | 6-[2-(dimethylamino)ethoxy]-4-fluoro-1-(2-methoxyethyl)-1'-(8-methyl-4-oxo-3,4,5,6,7,8-hexahydropyrido[2,3-d]pyrimidin-2-yl)-)spiro[indoline-3,4'-piperidin]-2(1H)-one | 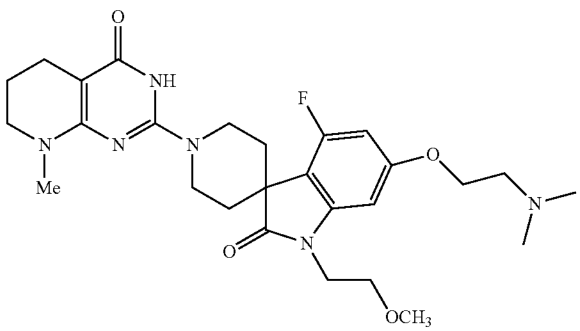 [SMILES: COCCN1C(=O)C2(CCN(c3nc4c(c(=O)[nH]3)CCCN4C)CC2)c2c(F)cc(OCCN(C)C)cc21] | 1.75-1.90 (m, 4 H), 2.15-2.25 (m, 2 H), 2.35 (s, 6 H), 2.45-2.50 (m, 2 H), 2.70-2.80 (m, 2 H), 3.07 (s, 3 H), 3.25-3.30 (m, 2 H), 3.33 (s, 3 H), 3.55-3.60 (m, 2 H), 3.80-4.00 (m, 4 H), 4.00-4.10 (m, 2 H), 4.10-4.25 (m, 2 H), 6.26 (dd, J = 11.6, 2.0 Hz, 1 H), 6.42 (d, J = 2.0 Hz, 1 H). | CDCl3 | 529 [M + H]+ |

TABLE 107

| Example | Compound Name | Structure | 1H NMR δ ppm | Solvent | ESI MS m/z |
|---|---|---|---|---|---|
| 406 | 4-fluoro-1'-(8-methyl-4-oxo-3,4,5,6,7,8-hexahydropyrido[2,3-d]pyrimidin-2-yl)-6-[2-(4-methylpiperazin-1-yl)ethoxy]-1-(2,2,2-trifluoroethyl)spiro[indoline-3,4'-piperidin]-2(1H)-one | 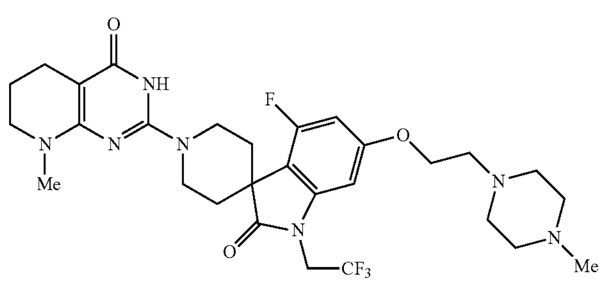 [SMILES: CN1CCN(CCOc2cc(F)c3c(c2)N(CC(F)(F)F)C(=O)C32CCN(c3nc4c(c(=O)[nH]3)CCCN4C)CC2)CC1] | 1.78-1.87 (m, 4 H), 2.21-2.32 (m, 5 H), 2.41-2.68 (m, 10 H), 2.81 (t, J = 5.8 Hz, 2 H), 3.06 (s, 3 H), 3.22-3.27 (m, 2 H), 3.80-3.89 (m, 2 H), 4.08 (t, J = 5.8 Hz, 2 H), 4.22-4.33 (m, 4 H), 6.29-6.36 (m, 2 H). | CDCl3 | 608 [M + H]+ |
| 407 | 4-fluoro-1-(2-methoxyethyl)-1'-(8-methyl-4-oxo-3,4,5,6,7,8-hexahydropyrido[2,3-d]pyrimidin-2-yl)-6-(4-methylpiperazin-1-yl)spiro[indoline-3,4'-piperidin]-2(1H)-one | 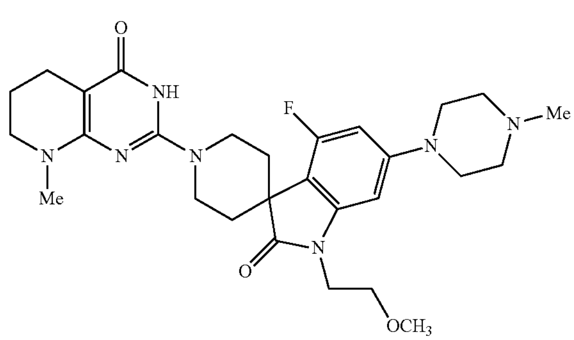 [SMILES: COCCN1C(=O)C2(CCN(c3nc4c(c(=O)[nH]3)CCCN4C)CC2)c2c(F)cc(N3CCN(C)CC3)cc21] | 1.80-1.90 (m, 4 H), 2.15-2.25 (m, 2 H), 2.39 (s, 3 H), 2.40-2.50 (m, 2 H), 2.55-2.65 (m, 4 H), 3.06 (s, 3 H), 3.20-3.25 (m, 6 H), 3.34 (s, 3 H), 3.55-3.65 (m, 2 H), 3.80-3.95 (m, 4 H), 4.10-4.20 (m, 2 H), 6.21 (dd, J = 12.8, 2.0 Hz, 1 H), 6.36 (d, J = 2.0 Hz, 1 H). | CDCl3 | 540 [M + H]+ |

TABLE 107-continued

| Example | Compound Name | Structure | 1H NMR δ ppm | Solvent | ESI MS m/z |
|---|---|---|---|---|---|
| 408 | {[4-fluoro-2'-(8-methyl-4-oxo-3,4,5,6,7,8-hexahydropyrido[2,3-d]pyrimidin-2-yl)-2-oxo-1-(2,2,2-trifluoroethyl)spiro[indoline-3,4'-piperidin]-6-yl]oxy}acetic acid | 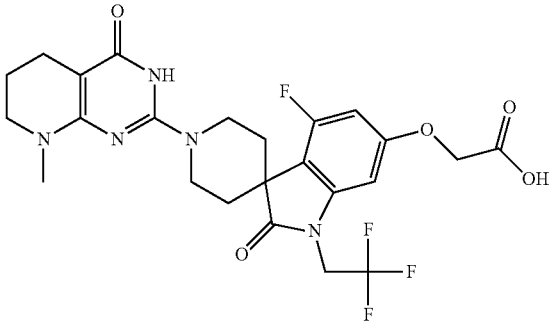 [SMILES: CN1CCCc2c1nc(N1CCC3(CC1)C(=O)N(CC(F)(F)F)c1cc(OCC(=O)O)cc(F)c13)[nH]c2=O] | 1.71-1.81 (m, 4 H), 1.98-2.08 (m, 2 H), 2.29-2.35 (m, 2 H), 3.00 (s, 3 H), 3.20-3.25 (m, 2 H), 3.61-3.71 (m, 2 H), 4.11-4.19 (m, 2 H), 4.74 (s, 2 H), 6.53 (dd, J = 12.0, 2.0 Hz, 1 H), 6.83-6.86 (m, 1 H). | CDCl3 | 540 [M + H]+ |
| 409 | {[4-fluoro-1-(2-methoxyethyl)-1'-(8-methyl-4-oxo-3,4,5,6,7,8-hexahydropyrido[2,3-d]pyridmidin-2-yl))-2-oxospiro[indoline-3,4'-piperidin]-6-yl]oxy}acetic acid | 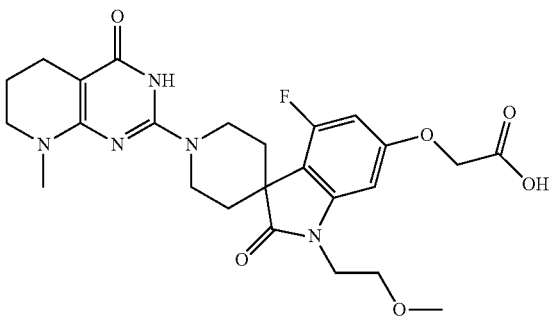 [SMILES: COCCN1C(=O)C2(CCN(c3nc4c(c(=O)[nH]3)CCCN4C)CC2)c2c(F)cc(OCC(=O)O)cc21] | 1.35-1.50 (m, 2 H), 1.75-1.90 (m, 4 H), 2.45-2.55 (m, 2 H), 3.08 (s, 3 H), 3.25-3.35 (m, 5 H), 3.50-3.55 (m, 2 H), 3.75-3.95 (m, 6 H), 4.64 (s, 2 H), 6.20-6.30 (m, 1 H), 6.35-6.40 (m, 1 H), 12.38 (br. s, 1 H). | CDCl3 | 516 [M + H]+ |
| 410 | 4-fluoro-6-(2-hydroxyethoxy)-1-(2-methoxyethyl)-1'-(8-methyl-4-oxo-3,4,5,6,7,8-hexahydropyrido[2,3-d]pyrimidin-2-yl)spiro[indoline-3,4'-piperidin]-2(1H)-one | 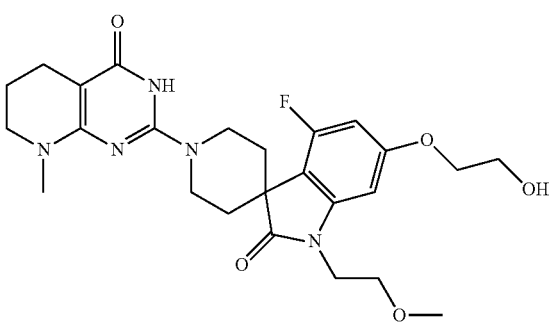 [SMILES: COCCN1C(=O)C2(CCN(c3nc4c(c(=O)[nH]3)CCCN4C)CC2)c2c(F)cc(OCCO)cc21] | 1.75-1.90 (m, 4 H), 2.15-2.25 (m, 2 H), 2.45-2.50 (m, 2 H), 3.08 (s, 3 H), 3.25-3.30 (m, 2 H), 3.33 (s, 3 H), 3.55-3.60 (m, 2 H), 3.80-4.00 (m, 6 H), 4.05-4.20 (m, 4 H), 6.27 (dd, J = 11.6, 2.0 Hz, 1 H), 6.42 (d, J = 2.0 Hz, 1 H). | CDCl3 | 502 [M + H]+ |

TABLE 108

| Example | Compound Name | Structure | 1H NMR δ ppm | Solvent | ESI MS m/z |
|---|---|---|---|---|---|
| 412 | 2-[4-fluoro-1'-(4-hydroxy-8-methyl-6,7-dihydro-5H-pyrido[2,3-d]pyrimidin-2-yl)-1-methyl-2-oxospiro[indole-3,4'-piperidin]-7-yl]oxyacetic acid | 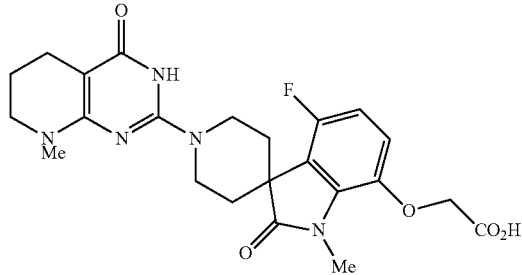 [SMILES: CN1CCCc2c1nc(N1CCC3(CC1)C(=O)N(C)c1c(OCC(=O)O)ccc(F)c13)[nH]c2=O] | 1.67-1.82 (m, 4 H), 1.96-2.12 (m, 2 H), 2.31 (br t, J = 6.1 Hz, 2 H), 2.99 (s, 3 H), 3.19-3.25 (m, 2 H), 3.42 (s, 3 H), 3.58-3.74 (m, 2 H), 4.17 (br d, J = 13.5 Hz, 2 H), 4.74 (s, 2 H), 6.79 (t, J = 9.2 Hz, 1 H), 7.00 (dd, J = 9.4, 4.1 Hz, 1 H). | DMSO-d6 | 472 [M + H]+ |

TABLE 108-continued

| Example | Compound Name | Structure | 1H NMR δ ppm | Solvent | ESI MS m/z |
|---|---|---|---|---|---|
| 413 | 4-fluoro-1'-(4-hydroxy-8-methyl-6,7-dihydro-5H-pyrido[2,3-d]pyrimidin-2-yl)-1-methyl-7-[(1-methylpiperidin-4-yl)methoxy]spiro]indole-3,4'-piperidin]-2-one | 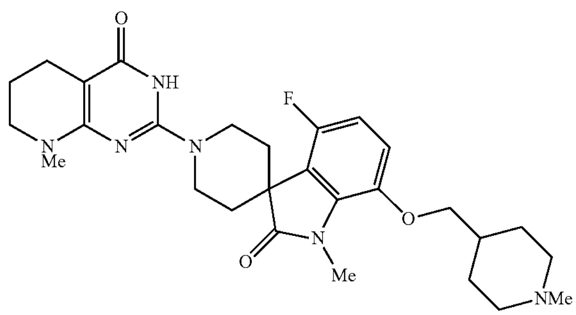 [SMILES: CN1CCC(COc2ccc(F)c3c2N(C)C(=O)C32CCN(c3nc4c(c(=O)[nH]3)CCCN4C)CC2)CC1] | 1.78-1.88 (m, 6 H), 2.06 (br t, J = 11.0 Hz, 4 H), 2.27 (br d, J = 11.9 Hz, 2 H), 2.34 (s, 3 H), 2.45 (br t, J = 6.1 Hz, 2 H), 2.97 (br d, J = 11.5 Hz, 2 H), 3.06 (s, 3 H), 3.24 (br t, J = 5.3 Hz, 2 H), 3.47 (s, 3 H), 3.65 (s, 1 H), 3.79-3.95 (m, 4 H), 4.27 (br d, J = 13.8 Hz, 2 H), 6.63 (t, J = 8.9 Hz, 1 H), 6.76 (dd, J = 9.2, 4.0 Hz, 1 H). | CDCl3 | 525 [M + H]+ |
| 414 | 4-fluoro-7-(2-hydroxyethoxy)-1'-(4-hydroxy-5,6,7,8-tetrahydro-pyrido[2,3-d]pyrimidin-2-yl)-1-methyl-spiro[indole-3,4'-piperidin]-2-one | 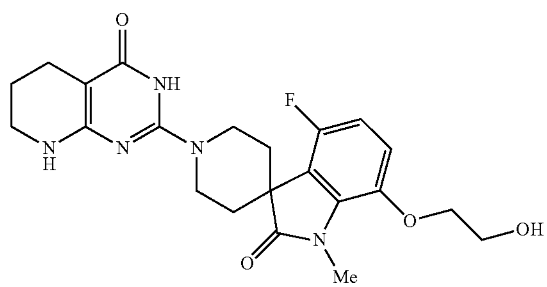 [SMILES: CN1C(=O)C2(CCN(c3nc4c(c(=O)[nH]3)CCCN4)CC2)c2c(F)ccc(OCCO)c21] | 1.69 (br s, 4 H), 1.91-2.09 (m, 2 H), 2.27 (br t, J = 6.1 Hz, 2 H), 3.10-3.20 (m, 2 H), 3.39 (s, 3 H), 3.59-3.78 (m, 4 H), 4.00-4.18 (m, 4 H), 4.89 (t, J = 5.3 Hz, 1 H), 6.40 (br s, 1 H), 6.79 (t, J = 9.4 Hz, 1 H), 7.03 (dd, J = 9.2, 4.3 Hz, 1 H), 10.26 (br s, 1 H). | DMSO-d6 | 444 [M + H]+ |
| 415 | 4-chloro-1'-(4-hydroxy-8-methyl-6,7-dihydro-5H-pyrido[2,3-b]pyrimidin-2-yl)-1-methyl-7-(2H-tetrazol-5-yl-methoxy)spiro[indole-3,4'-piperidin]-2-one | 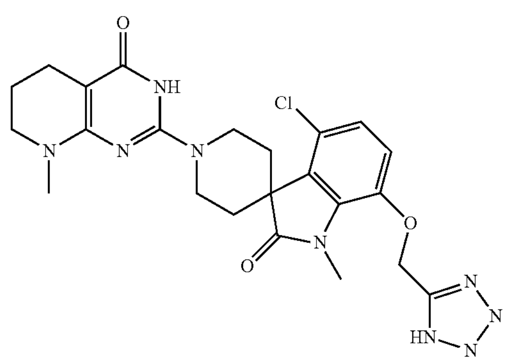 [SMILES: CN1CCCc2c1nc(N1CCC3(CC1)C(=O)N(C)c1c(OCC4=NNNN4)ccc(Cl)c13)[nH]c2=O] | 1.45-1.71 (m, 3 H), 1.75-1.98 (m, 3 H), 2.41-2.49 (m, 2 H), 2.71-2z.80 (m, 2 H), 3.10 (s, 3 H), 3.38 (s, 3 H), 3.78-3.92 (m, 3 H), 4.17-4.30 (m, 3 H), 5.36 (s, 3 H), 6.95 (d, J = 9.2 Hz, 1 H), 7.15 (d, J = 9.2 Hz, 2 H). | CD3OD | 512 [M + H]+ |
| 416 | 4-fluoro-1-(2-methoxyethyl)-1'-(8-methyl-4-oxo-3,4,5,6,7,8-hexahydro-pyrido[2,3-d]pyrimidin-2-yl)-)-6-(piperazin-1-yl)spiro[indoline-3,4'-piperidin]-2(1H)-one | 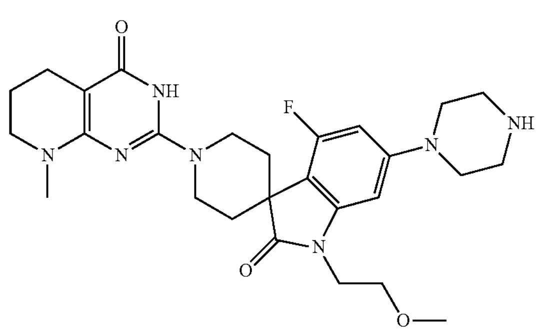 [SMILES: COCCN1C(=O)C2(CCN(c3nc4c(c(=O)[nH]3)CCCN4C)CC2)c2c(F)cc(N3CCNCC3)cc21] | 1.80-1.90 (m, 4 H), 2.15-2.25 (m, 2 H), 2.45-2.50 (m, 2 H), 3.00-3.10 (m, 7 H), 3.15-3.30 (m, 6 H), 3.34 (s, 3 H), 3.55-3.65 (m, 2 H), 3.80-3.95 (m, 4 H), 4.05-4.15 (m, 2 H), 6.21 (dd, J = 12.8, 2.0 Hz, 1 H), 6.36 (d, J = 2.0 Hz, 1 H). | CDCl3 | 526 [M + H]+ |

TABLE 109

| Example | Compound Name | Structure | 1H NMR δ ppm | Solvent | ESI MS m/z |
|---|---|---|---|---|---|
| 417 | 6-(cis-3,5-dimethyl-piperazin-1-yl)-4-fluoro-1'-(8-methyl-4-oxo-3,4,5,6,7,8-hexahydropyrido[2,3-d]pyrimidin-2-yl)-1-(2,2,2-trifluoroethyl)spiro[indoline-3,4'-piperidin]-2-one | 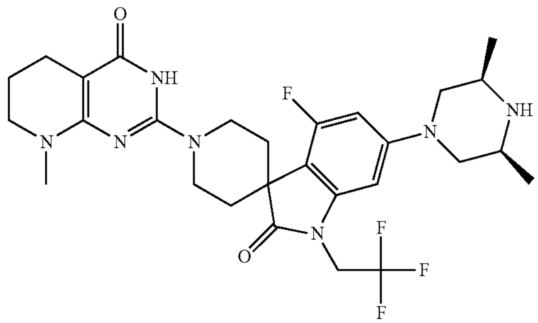 [SMILES: C[C@@H]1CN(c2cc(F)c3c(c2)N(CC(F)(F)F)C(=O)C32CCN(c3nc4c(c(=O)[nH]3)CCCN4C)CC2)C[C@H](C)N1] | 1.16 (d, J = 6.2 Hz, 6 H), 1.79-1.88 (m, 4 H), 2.18-2.27 (m, 2 H), 2.32-2.40 (m, 2 H), 2.44-2.49 (m, 2 H), 2.97-3.08 (m, 5 H), 3.23-3.28 (m, 2 H), 3.43-3.49 (m, 2 H), 3.81-3.90 (m, 2 H), 4.17-4.25 (m, 2 H), 4.29 (q, J = 8.6 Hz, 2 H), 6.24-6.29 (m, 2 H). | CDCl3 | 578 [M + H]+ |
| 419 | 6-[(1H-tetrazol-5-yl)methoxy]-4-fluoro-1'-(8-methyl-4-oxo-3,4,5,6,7,8-hexahydro-pyrido[2,3-d]pyrimidin-2-yl)-1-(2,2,2-trifluoro-ethyl)spiro[indoline-3,4'-piperidin]-2(1H)-one | 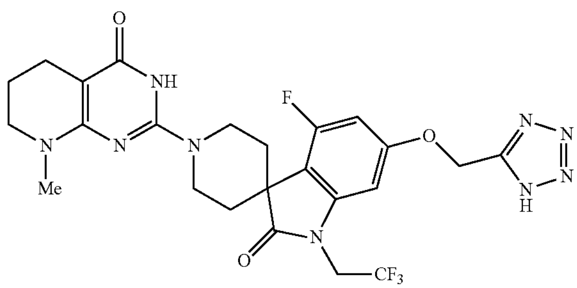 [SMILES: CN1CCCc2c1nc(N1CCC3(CC1)C(=O)N(CC(F)(F)F)c1cc(OCc4nnn[nH]4)cc(F)c13)[nH]c2=O] | 1.75-1.82 (m, 2 H), 2.00-2.10 (m, 2 H), 2.34-2.39 (m, 2 H), 3.04 (s, 3 H), 3.25-3.30 (m, 2 H), 3.65-3.74 (m, 2 H), 4.13-4.21 (m, 2 H), 4.64 (q, J = 9.4 Hz, 2 H), 5.51-5.55 (m, 2 H), 6.73 (dd, J = 11.9, 2.0 Hz, 2 H), 6.92-6.94 (m, 1 H). | DMSO-d6 | 564 [M + H]+ |
| 420 | 4-fluoro-1'-(4-hydroxy-8-methyl-6,7-dihydro-5H-pyrido[2,3-d]pyrimidin-2-yl)-1-methyl-7-(1-methylpiperidin-4-yl)oxyspiro[indole-3,4'-piperidin]-2-one | 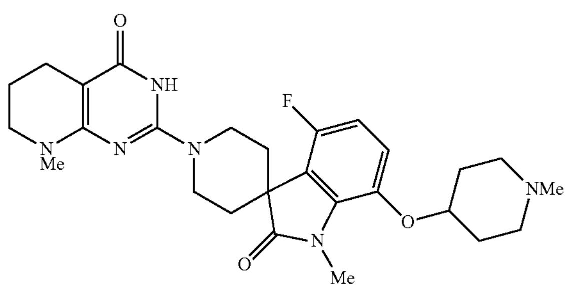 [SMILES: CN1CCC(Oc2ccc(F)c3c2N(C)C(=O)C32CCN(c3nc4c(c(=O)[nH]3)CCCN4C)CC2)CC1] | 1.79-1.95 (m, 6 H), 2.01-2.10 (m, 2 H), 2.22-2.38 (m, 7 H), 2.40-2.49 (m, 2 H), 2.64-2.77 (m, 2 H), 3.07 (s, 3 H), 3.17-3.34 (m, 2 H), 3.45-3.51 (m, 3 H), 3.88 (br t, J = 12.2 Hz, 2 H), 4.12-4.38 (m, 3 H), 6.62 (t, J = 8.9 Hz, 1 H), 6.78 (dd, J = 9.2, 4.3 Hz, 1 H). | CDCl3 | 511 [M + H]+ |
| 421 | 4-fluoro-1'-(4-hydroxy-8-methyl-6,7-dihydro-5H-pyrido[2,3-d]pyrimidin-2-yl)-1-methyl-7-(piperidin-4-ylmethoxy)spiro[indole-3,4'-piperidin]-2-one | 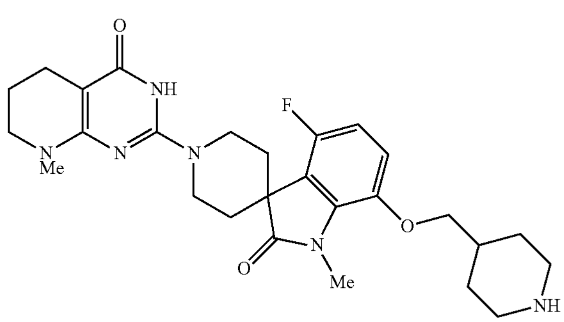 [SMILES: CN1CCCc2c1nc(N1CCC3(CC1)C(=O)N(C)c1c(OCC4CCNCC4)ccc(F)c13)[nH]c2=O] | 1.30-1.46 (m, 2 H), 1.75-2.05 (m, 7 H), 2.22-2.36 (m, 2 H), 2.39-2.50 (m, 2 H), 2.61-2.76 (m, 2 H), 3.07 (s, 3 H), 3.14-3.28 (m, 4 H), 3.48 (s, 3 H), 3.77-3.96 (m, 4 H), 4.31 (br d, J = 13.2 Hz, 2 H), 6.63 (t, J = 9.2 Hz, 1 H), 6.76 (dd, J = 9.6, 4.0 Hz, 1 H). | CDCl3 | 511 [M + H]+ |

TABLE 109-continued

| Example | Compound Name | Structure | 1H NMR δ ppm | Solvent | ESI MS m/z |
|---|---|---|---|---|---|
| 422 | 1-[4-fluoro-1-methyl-1'-(8-methyl-4-oxo-3,4,5,6,7,8-hexahydro-pyrido[2,3-d]pyrimidin-2-yl)-2-oxospiro[indoline-3,4'-piperidin]-6-yl]piperidine-4-carboxylic acid | 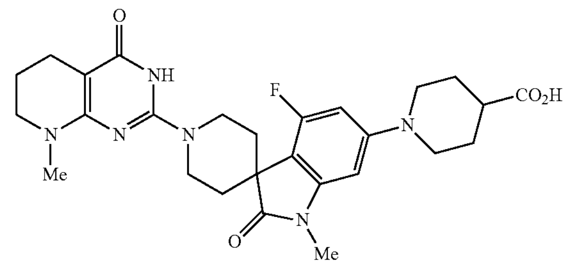 [SMILES: CN1CCCc2c1nc(N1CCC3(CC1)C(=O)N(C)c1cc(N4CCC(C(=O)O)CC4)cc(F)c13)[nH]c2=O] | 1.67-1.93 (m, 8 H), 2.02-2.12 (m, 2 H), 2.48-2.54 (m, 2 H), 2.55-2.64 (m, 1 H), 3.00-3.08 (m, 2 H), 3.09 (s, 3 H), 3.16 (s, 3 H), 3.28-3.33 (m, 2 H), 3.62-3.70 (m, 2 H), 3.92-4.01 (m, 2 H), 4.09-4.18 (m, 2 H), 6.11-6.18 (m, 2 H). | CDCl3 | 525 [M + H]+ |

TABLE 110

| Example | Compound Name | Structure | 1H NMR δ ppm | Solvent | ESI MS m/z |
|---|---|---|---|---|---|
| 423 | 1-[4-fluoro-1-methyl-1'-(8-methyl-4-oxo-3,4,5,6,7,8-hexahydro-pyrido[2,3-d]pyrimidin-2-yl)-2-oxospiro[indoline-3,4'-piperidin]-6-yl]azetidine-3-carboxylic acid | 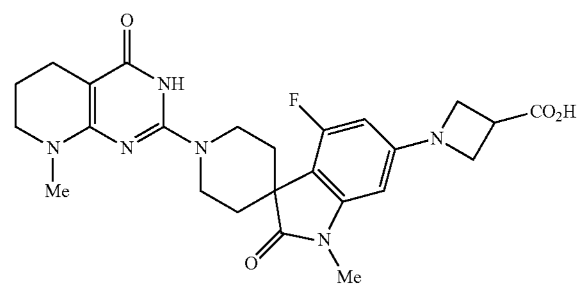 [SMILES: CN1CCCc2c1nc(N1CCC3(CC1)C(=O)N(C)c1cc(N4CC(C(=O)O)C4)cc(F)c13)[nH]c2=O] | 1.76-1.90 (m, 4 H), 2.01-2.10 (m, 2 H), 2.48-2.53 (m, 2 H), 3.10 (s, 3 H), 3.17 (s, 3 H), 3.29-3.34 (m, 2 H), 3.59-3.68 (m, 1 H), 3.87-4.02 (m, 4 H), 4.07-4.16 (m, 4 H), 5.70-7.75 (m, 2 H). | CDCl3 | 497 [M + H]+ |
| 424 | 2-[4,6-difluoro-1'-(8-methyl-4-oxo-3,4,5,6,7,8-hexahydropyrido[2,3-d]pyrimidin-2-yl)-2-oxospiro[indoline-3,4'-piperidin]-1(2H)-yl]acetamide | 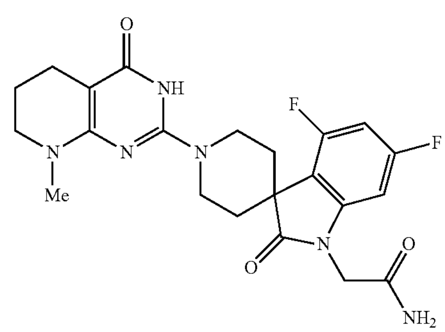 [SMILES: CN1CCCc2c1nc(N1CCC3(CC1)C(=O)N(CC(N)=O)c1cc(F)cc(F)c13)[nH]c2=O] | 1.73-1.82 (m, 4 H), 1.99-2.08 (m, 2 H), 2.29-2.35 (m, 2 H), 3.00 (s, 3 H), 3.20-3.25 (m, 2 H), 3.62-3.71 (m, 2 H), 4.12-4.20 (m, 2 H), 4.30 (s, 2 H), 6.82-6.89 (m, 2 H), 7.26 (br. s., 1 H), 7.64 (br. s., 1 H), 10.56 (br. s, 1 H). | DMSO-d6 | 459 [M + H]+ |
| 425 | 4-chloro-1'-(4-hydroxy-8-methyl-6,7-dihydro-5H-pyrido[2,3-d]pyrimidin-2-yl)-1-methyl-7-[(8-methyl-8-azabicyclo[3.2.1]octan-3-yl)oxy]spiro[indole-3,4'-piperidin]-2-one | 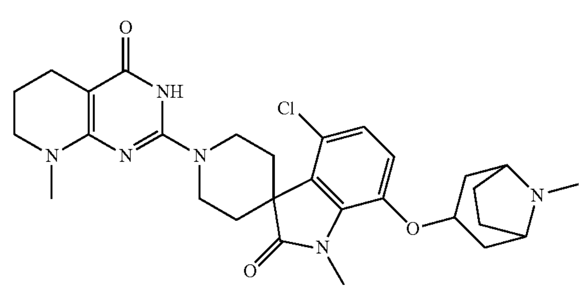 [SMILES: CN1CCCc2c1nc(N1CCC3(CC1)C(=O)N(C)c1c(OC4CC5CCC(C4)N5C)ccc(Cl)c13)[nH]c2=O] | 1.53-1.56 (m, 2 H), 1.63-1.74 (m, 2 H), 1.77-1.92 (m, 2 H), 1.95-2.10 (m, 4 H), 2.08-2.20 (m, 2 H), 2.41 (s, 3 H), 2.43-2.52 (m, 2 H), 2.64-2.83 (m, 2 H), 3.07 (s, 3 H), 3.18-3.31 (m, 2 H), 3.32-3.39 (m, 2 H), 3.43 (s, 3 H), 3.78-3.94 (m, 2 H), 4.25-4.38 (m, 2 H), 4.39-4.58 (m, 1 H), 6.73-6.91 (m, 2 H). | CDCl3 | 277 [M + 2H] 2+ |

TABLE 110-continued

| Example | Compound Name | Structure | 1H NMR δ ppm | Solvent | ESI MS m/z |
|---|---|---|---|---|---|
| 426 | 4-fluoro-7-(2-hydroxy-2-methylpropoxy)-1'-(4-hydroxy-5,6,7,8-tetrahydropyrido[2,3-d]pyrimidin-2-yl)-1-methyl-spiro[indole-3,4'-piperidin]-2-one | 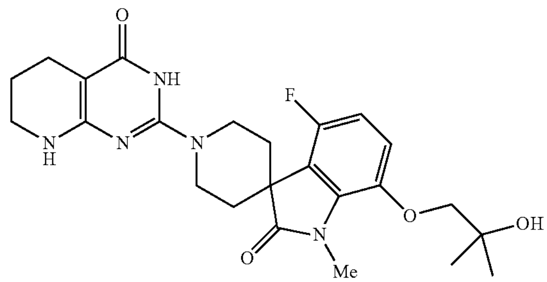 [SMILES: CN1C(=O)C2(CCN(c3nc4c(c(=O)[nH]3)CCCN4)CC2)c2c(F)ccc(OCC(C)(C)O)c21] | 1,22(s, 6 H), 1.61-1.76 (m, 4 H), 1.94-2.09 (m, 2 H), 2.21-2.31 (m, 2 H), 3.10-3.19 (m, 2 H), 3.37-3.44 (m, 3 H), 3.59-3.78 (m, 4 H), 4.06-4.18 (m, 2 H), 4.70 (br s, 1 H), 6.41 (br s, 1 H), 6.79 (t, J = 9.2 Hz, 1 H), 6.99 (dd, J = 9.2, 4.3 Hz, 1 H), 10.28 (br s, 1 H). | DMSO-d6 | 472 [M + H]+ |
| 427 | 2-{[4-fluoro-1-methyl-1'-(8-methyl-4-oxo-3,4,5,6,7,8-hexahydro-pyrido[2,3-d]pyrimidin-2-yl)-2-oxospiro[indoline-3,4'-piperidin]-6-yl]oxy}-N-(methyl-sulfonyl)acetamide | 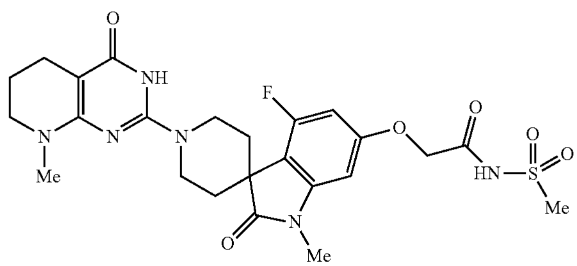 [SMILES: CN1CCCc2c1nc(N1CCC3(CC1)C(=O)N(C)c1cc(OCC(=O)NS(C)(=O)=O)cc(F)c13)[nH]c2=O] | 1.67-1.81 (m, 4 H), 1.87-2.03 (m, 2 H), 2.25-2.36 (m, 2 H), 2.73 (s, 3 H), 2.98 (s, 3 H), 3.09 (m, 3 H), 3.18-3.33 (m, 2 H), 4.05 (d, J = 13.4 Hz, 2 H), 4.00-4.10 (m, 2 H), 4.29 (s, 2 H), 6.29 (d, J = 12.1 Hz, 1 H), 6.47 (d, J = 2.0 Hz, 1 H). | DMSO-d6 | 459 [M + H]+ |

TABLE 111

| Example | Compound Name | Structure | 1H NMR δ ppm | Solvent | ESI MS m/z |
|---|---|---|---|---|---|
| 428 | 6-[2-(N,N-dimethyl-sulfamoyl)amino-ethoxy]-4-fluoro-1-methyl-1'-(8-methyl-4-oxo-3,4,5,6,7,8-hexahydro-pyrido[2,3-d]pyrimidin-2-yl)spiro[indoline-3,4'-piperidin]-2(1H)-one | 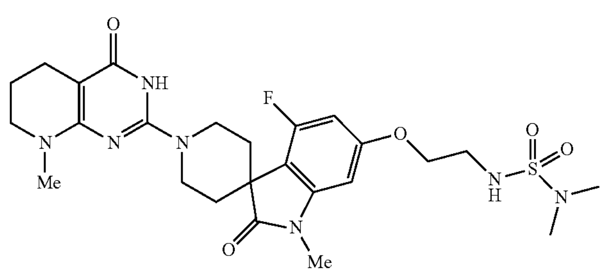 [SMILES: CN1CCCc2c1nc(N1CCC3(CC1)C(=O)N(C)c1cc(OCCNS(=O)(=O)N(C)C)cc(F)c13)[nH]c2=O] | 1.75-1.90 (m, 4 H), 2.10-2.20 (m, 2 H), 2.40-2.50 (m, 2 H), 2.77 (s, 6 H), 3.09 (s, 3 H), 3.18 (s, 3 H), 3.30-3.45 (m, 4 H), 3.85-3.95 (m, 2 H), 4.05-4.15 (m, 4 H), 6.40 (dd, J = 12.0, 2.0 Hz, 1 H), 6.51 (d, J = 2.0 Hz, 1 H). | CD3OD | 564 [M + H]+ |
| 429 | {[4-fluoro-1-(2-hydroxy-ethyl)-1'-(8-methyl-4-oxo-3,4,5,6,7,8-hexahydro-pyrido[2,3-d]pyrimidin-2-yl)-2-oxospiro[indoline-3,4'-piperidin]-6-yl]oxy}acetonitrile | 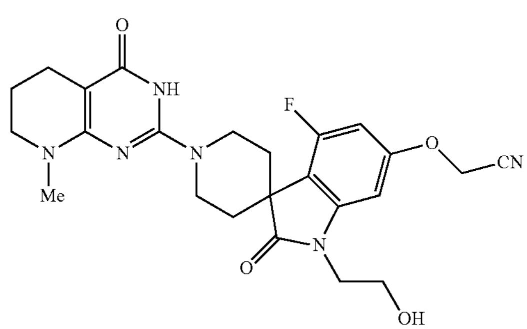 [SMILES: CN1CCCc2c1nc(N1CCC3(CC1)C(=O)N(CCO)c1cc(OCC#N)cc(F)c13)[nH]c2=O] | 1.80-1.90 (m, 4 H), 2.15-2.30 (m, 2 H), 2.40-2.50 (m, 2 H), 3.08 (s, 3 H), 3.25-3.30 (m, 2 H), 3.80-3.95 (m, 6 H), 4.15-4.25 (m, 2 H), 4.77 (s, 2 H), 6.34 (dd, J = 10.8, 2.0 Hz, 1 H), 6.49 (d, J = 2.0 Hz, 1 H). | CDCl3 | 483 [M + H]+ |

TABLE 111-continued

| Example | Compound Name | Structure | 1H NMR δ ppm | Solvent | ESI MS m/z |
|---|---|---|---|---|---|
| 431 | 4-fluoro-1-methyl-1'-(8-methyl-4-oxo-3,4,5,6,7,8-hexahydropyrido[2,3-d]pyrimidin-2-yl)-2-oxospiro[indoline-3,4'-piperidine]-6-carboxylic acid | 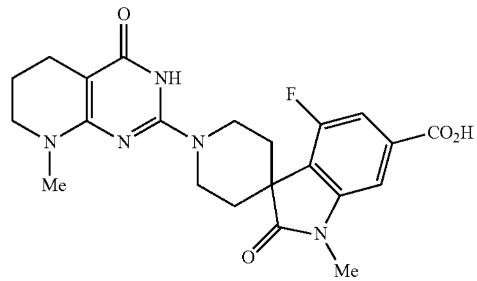 [SMILES: CN1CCCc2c1nc(N1CCC3(CC1)C(=O)N(C)c1cc(C(=O)O)cc(F)c13)[nH]c2=O] | 1.74-1.85 (m, 4 H), 2.01-2.10 (m, 2 H), 2.31-2.36 (m, 2 H), 3.01 (s, 3 H), 3.20 (s, 3 H), 3.22-3.27 (m, 2 H), 3.69-3.78 (m, 2 H), 4.11-4.19 (m, 2 H), 7.36-7.41 (m, 2 H). | DMSO-d6 | 442 [M + H]+ |
| 432 | N-(2-{[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy}ethyl)methanesulfonamide | 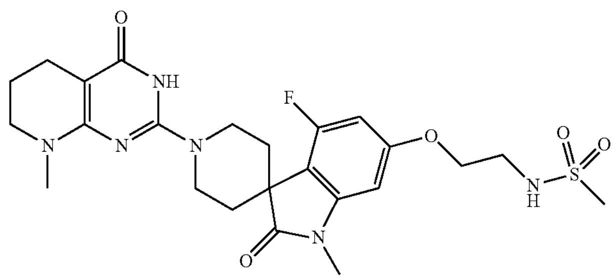 [SMILES: CN1CCCc2c1nc(N1CCC3(CC1)C(=O)N(C)c1cc(OCCNS(C)(=O)=O)cc(F)c13)[nH]c2=O] | 1.75-1.90 (m, 4 H), 2.10-2.25 (m, 2 H), 2.40-2.50 (m, 2 H), 3.03 (s, 3 H), 3.07 (s, 3 H), 3.16 (s, 3 H), 3.20-3.30 (m, 2 H), 3.50-3.60 (m, 2 H), 3.75-3.95 (m, 2 H), 4.05-4.20 (m, 4 H), 5.80-6.10 (m ,1 H), 6.20-6.30 (m, 2 H). | CDCl3 | 535 [M + H]+ |
| 433 | 4-chloro-1'-(4-hydroxy-8-methyl-6,7-dihydro-5H-pyrido[2,3-d]pyrimidin-2-yl)-1-methyl-7-(oxolan-3-yloxy)spiro[indole-3,4'-piperidin]-2-one | 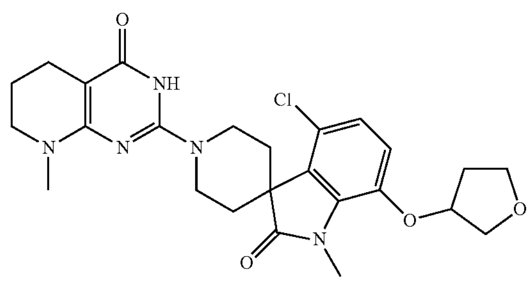 [SMILES: CN1CCCc2c1nc(N1CCC3(CC1)C(=O)N(C)c1c(OC4CCOC4)ccc(Cl)c13)[nH]c2=O] | 1.55-1.61 (m, 2 H), 1.81-1.90 (m, 2 H), 2.15-2.29 (m, 2 H), 2.49 (t, J = 6.1 Hz, 2 H), 2.68-2.80 (m, 2 H), 3.08 (s, 3 H), 3.23-3.30 (m, 2 H), 3.46 (s, 3 H), 3.82-4.04 (m, 6 H), 4.17-4.29 (m, 2 H), 4.94-4.99 (m, 1 H), 6.71 (d, J = 8.9 Hz, 1 H), 6.89 (d, J= 8.9 Hz, 1 H). | CDCl3 | 500 [M + H]+ |

TABLE 112

| Example | Compound Name | Structure | 1H NMR δ ppm | Solvent | ESI MS m/z |
|---|---|---|---|---|---|
| 434 | 6-(4-tert-butylpiperazin-1-yl)-4-fluoro-1'-(4-hydroxy-8-methyl-6,7-dihydro-5H-pyrido[2,3-d]pyrimidin-2-yl)spiro[2,3-benzofuran-3,4'-piperidine]-1-one | 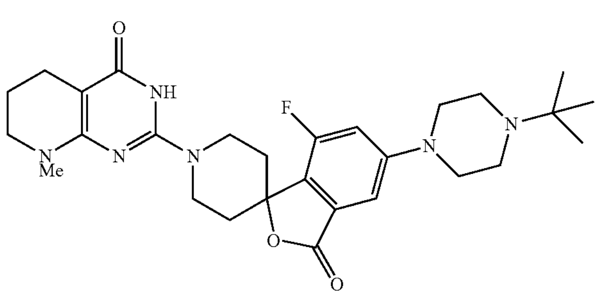 [SMILES: CN1CCCc2c1nc(N1CCC3(CC1)OC(=O)c1cc(N4CCN(C(C)(C)C)CC4)cc(F)c13)[nH]c2=O] | 1.11 (s, 9 H), 1.71-1.89 (m, 4 H), 2.30-2.49 (m, 4 H), 2.73 (br s, 4 H), 3.07 (s, 3 H), 3.20-3.42 (m, 8 H), 4.63 (br d, J = 14.5 Hz, 2 H), 6.82 (br d, J = 12.2 Hz, 1 H), 7.12 (s, 1 H). | CDCl3 | 525 [M + H]+ |

TABLE 112-continued

| Example | Compound Name | Structure | 1H NMR δ ppm | Solvent | ESI MS m/z |
|---|---|---|---|---|---|
| 435 | 2-[4-fluoro-2-oxo-1'-(4-oxo-3,4,5,6,7-hexahydropyrido[2,3-d]pyrimidin-2-yl)-1-(2,2,2-trifluoroethyl)spiro[indole-3,4'-piperidine]-6-yl]oxyacetonitrile | 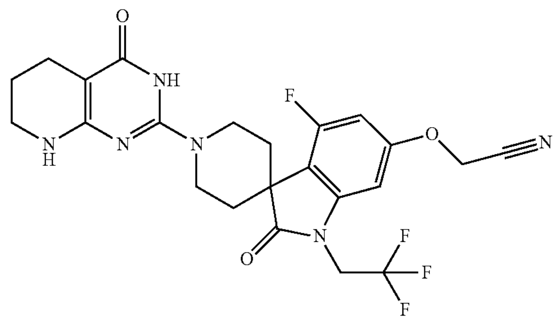 [SMILES: N#CCOc1cc(F)c2c(c1)N(CC(F)(F)F)C(=O)C21CCN(c2nc3c(c(=O)[nH]2)CCCN3)CC1] | 1.78-1.86 (m, 4 H), 2.23-2.32 (m, 2 H), 2.41-2.46 (m, 2 H), 3.28-3.33 (m, 2 H), 3.77-3.86 (m, 2 H), 4.24-4.33 (m, 4 H), 4.64 (br. s, 1 H), 4.78 (s, 2 H), 6.40-6.44 (m, 2 H), 10.85 (br. s, 1 H). | CDCl3 | 507 [M + H]+ |
| 437 | 7-[2-(tert-butylamino)ethoxy]-4-fluoro-1'-(4-hydroxy-8-methyl-6,7-dihydro-5H-pyrido[2,3-d]pyrimidin-2-yl)-1-methylspiro[indole-3,4'-piperidine]-2-one | 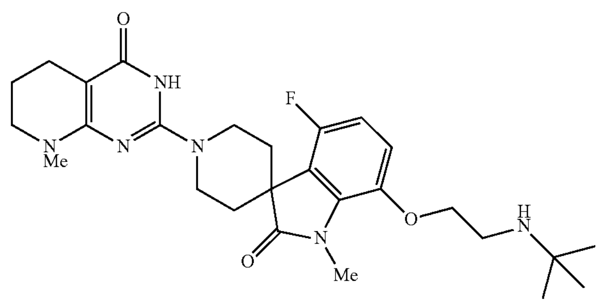 [SMILES: CN1CCCc2c1nc(N1CCC3(CC1)C(=O)N(C)c1c(OCCNC(C)(C)C)ccc(F)c13)[nH]c2=O] | 1.32 (s, 9 H), 1.64-1.82 (m, 4 H), 1.97-2.13 (m, 2 H), 2.24-2.38 (m, 2 H), 2.99 (s, 3 H), 3.13-3.32 (m, 2 H), 3.36-3.42 (m, 5 H), 3.68 (br t, J = 12.5 Hz, 2 H), 4.11-4.28 (m, 4 H), 6.86 (t, J = 9.2 Hz, 1 H), 7.09 (dd, J = 9.2, 4.6 Hz, 1 H), 8.65 (br s, 1 H). | DMSO-d6 | 513 [M + H]+ |
| 438 | 4-chloro-1'-(4-oxo-3,4,5,6,7,8-hexahydropyrido[2,3-d]pyrimidin-2-yl)-1-methyl-7-(oxolan-3-yloxy)spiro[indole-3,4'-piperidine]-2-one | 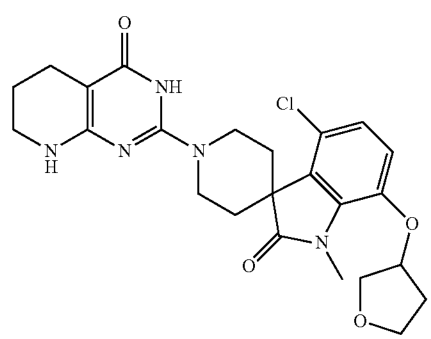 [SMILES: CN1C(=O)C2(CCN(c3nc4c(c(=O)[nH]3)CCCN4)CC2)c2c(Cl)ccc(OC3CCOC3)c21] | 1.53-1.64 (m, 2 H), 1.79-1.91 (m, 2 H), 2.15-2.30 (m, 2 H), 2.35-2.54 (m, 2 H), 2.66-2.85 (m, 2 H), 3.28-3.38 (m, 2 H), 3.45 (s, 3 H), 3.80-4.02 (m, 6 H), 4.19-4.33 (m, 2 H), 4.66-4.76 (m, 1 H), 4.93-5.02 (m, 1 H), 6.71 (d, J = 8.8 Hz, 1 H), 6.89 (d, J = 8.8 Hz, 1 H). | CDCl3 | 486 [M + H]+ |
| 439 | 4-fluoro-1'-(4-hydroxy-8-methyl-6,7-dihydro-5H-pyrido[2,3-d]pyrimidin-2-yl)-6-[4-(2-hydroxy-2-methylpropyl)piperazin-1-yl]spiro[2,3-benzofuran-3,4'-piperidine]-1-one | 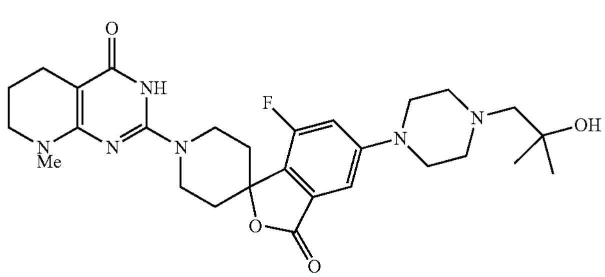 [SMILES: CN1CCCc2c1nc(N1CCC3(CC1)OC(=O)c1cc(N4CCN(CC(C)(C)O)CC4)cc(F)c13)[nH]c2=O] | 1.11 (s, 6 H), 1.68-1.82 (m, 4 H), 2.04-2.20 (m, 2 H), 2.24 (s, 2 H), 2.26-2.36 (m, 2 H), 2.57-2.69 (m, 4 H), 3.00 (s, 3 H), 3.05-3.28 (m, 8 H), 4.17 (br s, 1 H), 4.45 (br d, J = 11.9 Hz, 2 H), 7.09 (d, J = 1.6 Hz, 1 H), 7.16-7.25 (m, 1 H), 10.50 (br s, 1 H). | DMSO-d6 | 541 [M + H]+ |

TABLE 113

| Example | Compound Name | Structure | 1H NMR δ ppm | Solvent | ESI MS m/z |
|---|---|---|---|---|---|
| 440 | 4-fluoro-6-[4-(2-hydroxyethyl)piperazin-1-yl]-1'-(4-hydroxy-8-methyl-6,7-dihydro-5H-pyrido[2,3-d]pyrimidin-2-yl)spiro[2-benzofuran-3,4'-piperidine]-1-one | 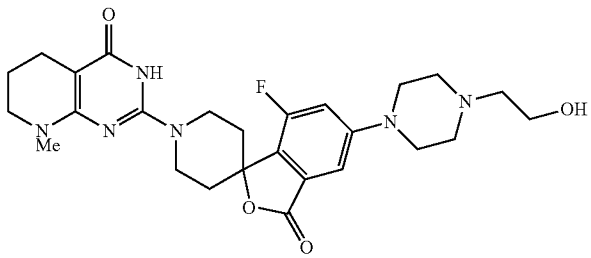 [SMILES: CN1CCCc2c1nc(N1CCC3(CC1)OC(=O)c1cc(N4CCN(CCO)CC4)cc(F)c13)[nH]c2=O] | 1.68-1.82 (m, 4 H), 2.03-2.21 (m, 2 H), 2.32 (br t, J = 6.1 Hz, 2 H), 2.43 (t, J = 6.1 Hz, 2 H), 2.53-2.58 (m, 4 H), 3.00 (s, 3 H), 3.06-3.30 (m, 8 H), 3.46-3.57 (m, 2 H), 4.38-4.53 (m, 3 H), 7.10 (d, J = 2.0 Hz, 1 H), 7.15-7.30 (m, 1 H), 10.49 (br s, 1 H). | DMSO-d6 | 513 [M + H]+ |
| 441 | 1-[2-(4-acetylpiperazin-1-yl)ethyl]-4-chloro-1'-(4-hydroxy-8-methyl-6,7-dihydro-5H-pyrido[2,3-d]pyrimidin-2-yl)-7-methoxyspiro[indole-3,4'-piperidine]-2-one | 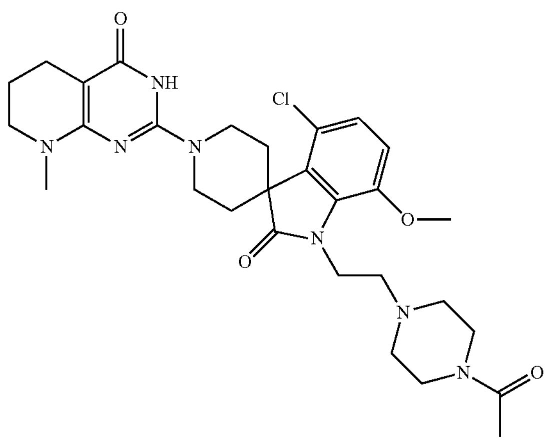 [SMILES: COc1ccc(Cl)c2c1N(CCN1CCN(C(C)=O)CC1)C(=O)C21CCN(c2nc3c(c(=O)[nH]2)CCCN3C)CC1] | 1.52-1.65 (m, 2 H), 1.76-1.90 (m, 2 H), 2.08 (s, 3 H), 2.38-2.47 (m, 4 H), 2.47-2.62 (m, 4 H), 2.68-2.85 (m, 2 H), 3.08 (s, 3 H), 3.18-3.31 (m, 2 H), 3.32-3.43 (m, 2 H), 3.45-3.62 (m, 2 H), 3.78-3.93 (m, 5 H), 4.08 (t, J = 6.3 Hz, 2 H), 4.32-4.45 (m, 2 H), 6.80 (d, J = 8.9 Hz, 1 H), 6.93 (d, J = 8.9 Hz, 1 H). | CDCl3 | 584 [M + H]+ |
| 443 | 4-chloro-1'-(4-hydroxy-3,5,6,7,8-tetrahydropyrido[2,3-d]pyrimidin-2-yl)-7-methoxy-1-(2,2,2-trifluoroethyl)spiro[indole-3,4'-piperidine]-2-one | 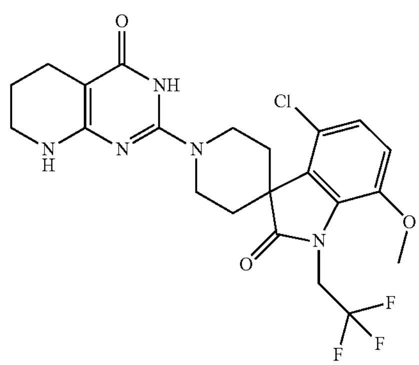 [SMILES: COc1ccc(Cl)c2c1N(CC(F)(F)F)C(=O)C21CCN(c2nc3c(c(=O)[nH]2)CCCN3)CC1] | 1.54-1.70 (m, 2 H), 1.70-1.91 (m, 2 H), 2.43 (t, J = 6.3 Hz, 2 H), 2.70-2.89 (m, 2 H), 3.26-3.38 (m, 2 H), 3.74-3.85 (m, 2 H), 3.88 (s, 3 H), 4.32-4.45 (m, 2 H), 4.64-4.76 (m, 3 H), 6.83 (d, J = 8.9 Hz, 1 H), 6.98 (d, J = 8.9 Hz, 1 H). | CDCl3 | 498 [M + H]+ |
| 444 | 4-fluoro-1'-(4-hydroxy-8-methyl-6,7-dihydro-5H-pyrido[2,3-d]pyrimidin-2-yl)-6-[4-(4-methylpiperazin-1-yl)phenyl]spiro[2-benzofuran-3,4'-piperidine]-1-one | 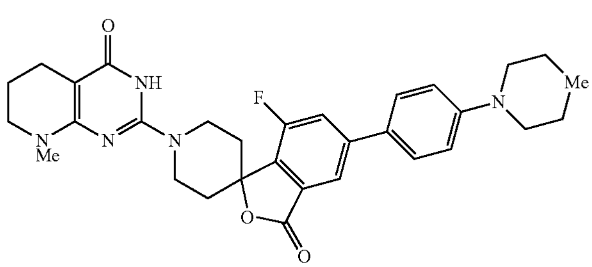 | 1.71-1.92 (m, 4 H), 2.38 (s, 3 H), 2.39-2.55 (m, 4 H), 2.55-2.63 (m, 4 H), 3.08 (s, 3 H), 3.17-3.46 (m, 8 H), 4.69 (br d, J = 11.2 Hz, 2 H), 7.01 (d, J = 8.9 Hz, 2 H), 7.48-7.56 (m, 3 H), 7.88 (d, J = 1.0 Hz, 1 H). | CDCl3 | 559 [M + H]+ |

TABLE 113-continued

| Example | Compound Name | Structure | 1H NMR δ ppm | Solvent | ESI MS m/z |
|---|---|---|---|---|---|
| 445 | 4-chloro-1'-(4-hydroxy-8-methyl-6,7-dihdyro-5H-pyrido[2,3-d]pyrimidin-2-yl)-7-methoxy-1-[3-oxo-3-[3-(trifluoromethyl)-6,8-dihydro-5H-imidazo[1,2-a]pyrazin-7-yl]propyl]spiro[indole-3,4'-piperidine]-2-one | 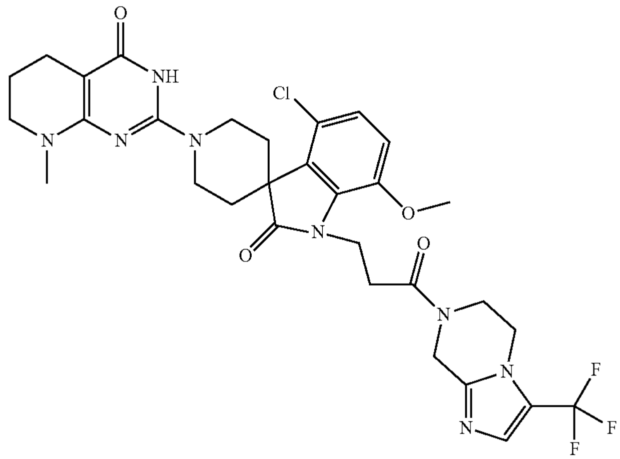 [SMILES: COc1ccc(Cl)c2c1N(CCC(=O)N1CCn3c(C(F)(F)F)cnc3C1)C(=O)C21CCN(c2nc3c(c(=O)[nH]2)CCCN3C)CC1] | 1.51-1.65 (m, 6 H), 1.80-1.90 (m, 2 H), 2.44-2.54 (m, 2 H), 2.65-2.84 (m, 4 H), 3.09 (s, 3 H), 3.20-3.31 (m, 2 H), 3.80-3.87 (m, 5 H), 4.05 (br s, 2 H), 4.15-4.24 (m, 2 H), 4.25-4.34 (m, 2 H), 4.78-4.87 (m, 2 H), 6.76-6.84 (m, 1 H), 6.90-6.97 (m, 1 H). | CDCl3 | 675 [M + H]+ |

TABLE 114

| Example | Compound Name | Structure | 1H NMR δ ppm | Solvent | ESI MS m/z |
|---|---|---|---|---|---|
| 446 | 4-chloro-1'-(4-hydroxy-8-methyl-6,7-dihydro-5H-pyrido[2,3-d]pyrimidin-2-yl)-1-(2-hydroxy-2-methylpropyl)-7-methoxy-spiro[indole-3,4'-piperidine]-2-one | 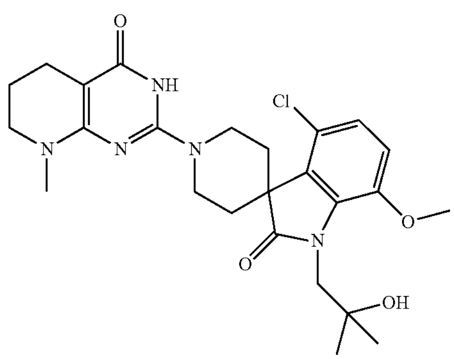 [SMILES: COc1ccc(Cl)c2c1N(CC(C)(C)O)C(=O)C21CCN(c2nc3c(c(=O)[nH]2)CCCN3C)CC1] | 1.23 (s, 6 H), 1.55-1.66 (m, 2 H), 1.74-1.90 (m, 2 H), 2.49 (t, J = 6.3 Hz, 2 H), 2.73-2.87 (m, 2 H), 3.08 (s, 3 H), 3.22-3.36 (m, 2 H), 3.81-3.92 (m, 5 H), 4.13 (s, 2 H), 4.23-4.35 (m, 2 H), 6.82 (d, J = 8.9 Hz, 1 H), 6.95 (d, J = 8.9 Hz, 1 H). | CDCl3 | 502 [M + H]+ |
| 447 | 4-fluoro-1'-(4-hydroxy-8-methyl-6,7-dihydro-5H-pyrido[2,3-d]pyrimidin-2-yl)-1-(2-hydroxy-2-methylpropyl)spiro[indole-3,4'-piperidine]-2-one | 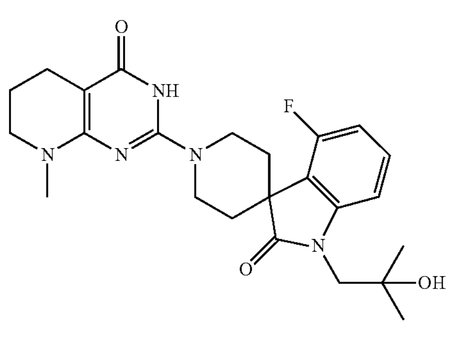 [SMILES: CN1CCCc2c1nc(N1CCC3(CC1)C(=O)N(CC(C)(C)O)c1cccc(F)c13)[nH]c2=O] | 1.29 (s, 6 H), 1.76-1.91 (m, 4 H), 2.25-2.42 (m, 2 H), 2.47 (br t, J = 6.1 Hz, 2 H), 3.08 (s, 3 H), 3.22-3.32 (m, 2 H), 3.73 (s, 2 H), 3.83-3.99 (m, 2 H), 4.20-4.33 (m, 1 H), 6.70-6.80 (m, 1 H), 6.80-6.87 (m, 1 H), 7.19-7.25 (m, 1 H). | CDCl3 | 456 [M + H]+ |

TABLE 114-continued

| Example | Compound Name | Structure | 1H NMR δ ppm | Solvent | ESI MS m/z |
|---|---|---|---|---|---|
| 448 | 4-chloro-1'-(2-hydroxy-2-methyl)propyl)-1'-(4-hydroxy-5,6,7,8-tetrahydropyrido[2,3-d]pyrimidin-2-yl)-7-methoxyspiro[indole-3,4'-piperidine]-2-one | 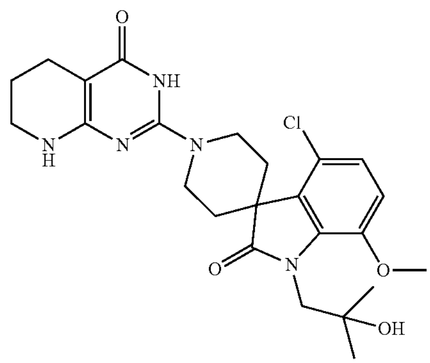 [SMILES: COc1ccc(Cl)c2c1N(CC(C)(C)O)C(=O)C21CCN(c2nc3c(c(=O)[nH]2)CCCN3)CC1] | 1.23 (s, 6 H), 1.52-1.66 (m, 2 H), 1.77-1.88 (m, 2 H), 2.37-2.50 (m, 2 H), 2.70-2.89 (m, 2 H), 3.25-3.41 (m, 2 H), 3.71-3.86 (m, 2 H), 3.89 (s, 3 H), 4.13 (br s, 2 H), 4.26-4.41 (m, 2 H), 4.63-4.71 (m, 1 H), 6.78-6.85 (m, 1 H), 6.89-6.98 (m, 1 H). | CDCl3 | 488 [M + H]+ |
| 449 | 6-[4-(dimethylamino)phenyl]-4-fluoro-1'-(4-hydroxy-8-methyl-6,7-dihydro-5H-pyrido[2,3-d]pyrimidin-2-yl)spiro[2-benzofuran-3,4'-piperidine]-1-one | 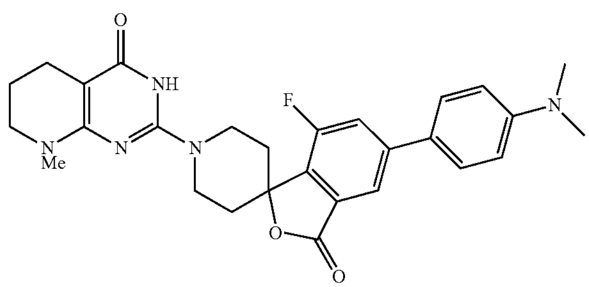 [SMILES: CN(C)c1ccc(-c2cc(F)c3c(c2)C(=O)OC32CCN(c3nc4c(c(=O)[nH]3)CCCN4C)CC2)cc1] | 1.69-2.01 (m, 4 H), 2.09-2.37 (m, 4 H), 2.97 (s, 6 H), 3.01 (s, 3 H), 3.14-3.26 (m, 2 H), 3.41-3.55 (m, 2 H), 4.35-4.58 (m, 2 H), 6.81 (d, J = 8.9 Hz, 2 H), 7.68 (d, J = 8.9 Hz, 2 H), 7.83-7.94 (m, 2 H), 8.33 (s, 1 H). | DMSO-d6 | 504 [M + H]+ |
| 450 | 4-fluoro-1'-(4-hydroxy-8-methyl-6,7-dihydro-5H-pyrido[2,3-d]pyrimidin-2-yl)-6-(1-methylpyrazol-4-yl)spiro[2-benzofuran-3,4'-piperidine]-1-one | 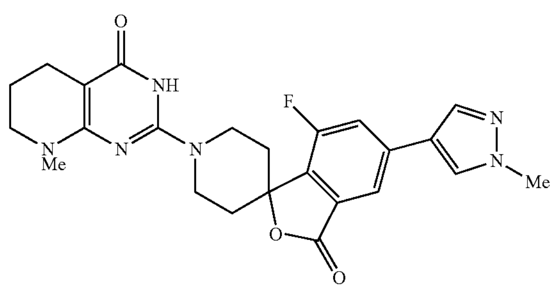 [SMILES: CN1CCCc2c1nc(N1CCC3(CC1)OC(=O)c1cc(-c4cnn(C)c4)cc(F)c13)[nH]c2=O] | 1.71-1.90 (m, 4 H), 2.34-2.55 (m, 4 H), 3.08 (s, 3 H), 3.19-3.30 (m, 2 H), 3.38 (br t, J = 12.5 Hz, 2 H), 3.98 (s, 3 H), 4.68 (br d, J = 13.2 Hz, 2 H), 7.42 (dd, J = 10.1, 1.2 Hz, 1 H), 7.69 (s, 1 H), 7.74-7.82 (m, 2 H). | CDCl3 | 465 [M + H]+ |

TABLE 115

| Example | Compound Name | Structure | 1H NMR δ ppm | Solvent | ESI MS m/z |
|---|---|---|---|---|---|
| 451 | 4-fluoro-1'-(4-hydroxy-5,6,7,8-tetrahydropyrido[2,3-d]pyrimidin-2-yl)-1-(2,2,2-trifluoroethyl)spiro[indole-3,4'-piperidine]-2-one | 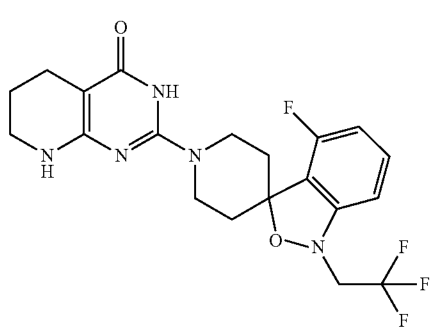 [SMILES: O=c1[nH]c(N2CCC3(CC2)ON(CC(F)(F)F)c2cccc(F)c23)nc2c1CCCN2] | 1.71-1.90 (m, 4 H), 2.36-2.47 (m, 4 H), 3.28-3.34 (m, 2 H), 3.78-3.96 (m, 2 H), 4.24-4.37 (m, 4 H), 4.63-4.74 (m, 1 H), 6.73-6.88 (m, 2 H), 7.30-7.34 (m, 1 H). | CDCl3 | 452 [M + H]+ |

TABLE 115-continued

| Example | Compound Name | Structure | 1H NMR δ ppm | Solvent | ESI MS m/z |
|---|---|---|---|---|---|
| 452 | 4-fluoro-1-(2-hydroxy-2-methylpropyl)-1'-(4-hydroxy-5,6,7,8-tetrahydropyrido[2,3-d]pyrimidin-2-yl)spiro[indole-3,4'-piperidine]-2-one | 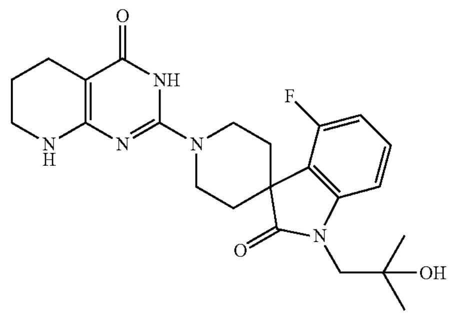 [SMILES: CC(C)(O)CN1C(=O)C2(CCN(c3nc4c(c(=O)[nH]3)CCCN4)CC2)c2c(F)cccc21] | 1.29 (d, J = 5.3 Hz, 3 H), 1.27-1.32 (m, 6 H), 1.55-1.65 (m, 2 H), 1.76-1.95 (m, 4 H), 2.24-2.39 (m, 2 H), 2.41-2.51 (m, 2 H), 3.29-3.41 (m, 2 H), 3.73 (s, 2 H), 3.81-3.96 (m, 1 H), 4.12-4.25 (m, 2 H), 4.59-4.73 (m, 1 H), 6.71-6.88 (m, 2 H), 6.80-6.80 (m, 1 H), 7.19-7.24 (m, 1 H). | CDCl3 | 442 [M + H]+ |
| 453 | 1-{[4-fluoro-1-methyl-1'-(8-methyl-4-oxo-3,4,5,6,7,8-hexahydropyrido[2,3-d]pyrimidin-2-yl)-2-oxospiro[indole-3,4'-piperidine]-6-yl]oxy}-N-methylmethanesulfonamide | 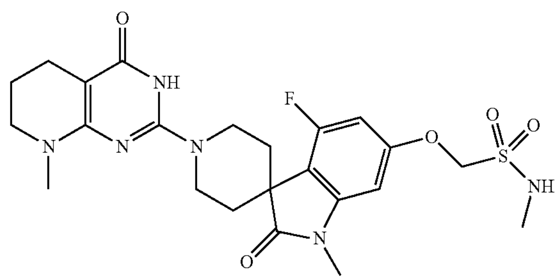 [SMILES: CNS(=O)(=O)COc1cc(F)c2c(c1)N(C)C(=O)C21CCN(c2nc3c(c(=O)[nH]2)CCCN3C)CC1] | 1.72-1.93 (m, 4 H), 2.05-2.19 (m, 2 H), 2.45-2.57 (m, 2 H), 2.90 (s, 3 H), 3.09 (s, 3 H), 3.15 (s, 3 H), 3.25-3.34 (m, 2 H), 3.83-3.96 (m, 2 H), 4.03-4.14 (m, 2 H), 5.00 (s, 2 H), 6.36-6.46 (m, 2 H), 9.05 (br. s, 1 H). | CDCl3 | 521 [M + H]+ |
| 454 | 1-{[4-fluoro-1-methyl-1'-(8-methyl-4-oxo-3,4,5,6,7,8-hexahydropyrido[2,3-d]pyrimidin-2-yl)-2-oxospiro[indole-3,4'-piperidine]-6-yl]oxy}methanesulfonamide | 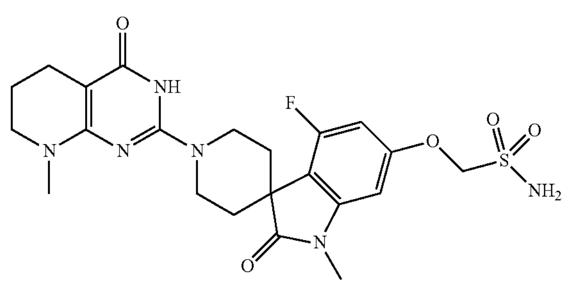 [SMILES: CN1CCCc2c1nc(N1CCC3(CC1)C(=O)N(C)c1cc(OCS(N)(=O)=O)cc(F)c13)[nH]c2=O] | 1.67-1.93 (m, 4 H), 2.03-2.17 (m, 2 H), 2.41-2.54 (m, 2 H), 3.09 (s, 3 H), 3.13 (s, 3 H), 3.24-3.34 (m, 2 H), 3.80-3.94 (m, 2 H), 4.00-4.13 (m, 2 H), 5.07 (s, 2 H), 6.36-6.48 (m, 2 H). | CDCl3 | 507 [M + H]+ |
| 455 | 6-(1,1-dioxothiomorpholino)-4-fluoro-1-methyl-1'-(8-methyl-4-oxo-3,4,5,6,7,8-hexahydropyrido[2,3-d]pyrimidin-2-yl)spiro[indole-3,4'-piperidine]-2-one | 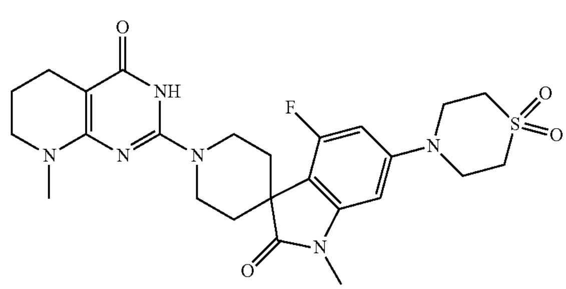 | 1.79-1.87 (m, 4 H), 2.13-2.22 (m, 2 H), 2.43-2.49 (m, 2 H), 3.07 (s, 3 H), 3.10-3.15 (m, 4 H), 3.18 (s, 3 H), 3.22-3.27 (m, 2 H), 3.85-3.98 (m, 6 H), 4.15-4.22 (m, 2 H), 6.16 (d, J = 2.1 Hz, 1 H), 6.22 (dd, J = 12.2, 2.1 Hz, 1 H), 10.65 (br. s, 1 H). | CDCl3 | 584 [M + H]+ |

TABLE 116

| Example | Compound Name | Structure | 1H NMR δ ppm | Solvent | ESI MS m/z |
|---|---|---|---|---|---|
| 456 | N-[[4-fluoro-1-methyl-1'-(8-methyl-4-oxo-3,4,5,6,7,8-hexahydropyrido[2,3-d]pyrimidin-2-yl)-2-oxospiro[indole-3,4'-piperidine]-6-yl]oxymethylsulfonyl]acetamide | 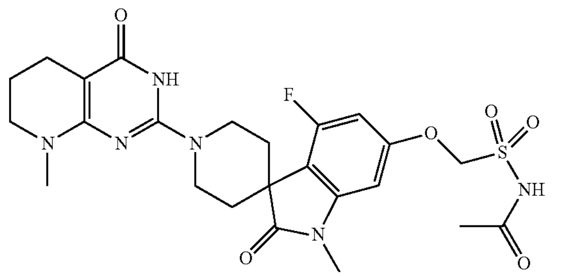 [SMILES: CC(=O)NS(=O)(=O)COc1cc(F)c2c(c1)N(C)C(=O)C21CCN(c2nc3c(c(=O)[nH]2)CCCN3C)CC1] | 1.46-1.59 (m, 2 H), 1.82-1.97 (m, 4 H), 2.28 (s, 3 H), 2.44-2.57 (m, 2 H), 3.09 (s, 3 H), 3.13 (s, 3 H), 3.27-3.36 (m, 2 H), 3.72-3.84 (m, 2 H), 3.85-3.97 (m, 2 H), 5.37 (s, 2 H), 6.37 (d, J = 2.1 Hz, 1 H), 6.43 (dd, J = 10.9, 2.1 Hz, 1 H), 9.05 (br. s, 1 H). | CDCl3 | 549 [M + H]+ |
| 457 | 4-fluoro-1-methyl-1'-(8-methyl-4-oxo-3,4,5,6,7,8-hexahydropyrido[2,3-d]pyrimidin-2-yl)-6-piperazin-1-yl-spiro[indole-3,4'-piperidine]-2(1H)-one | 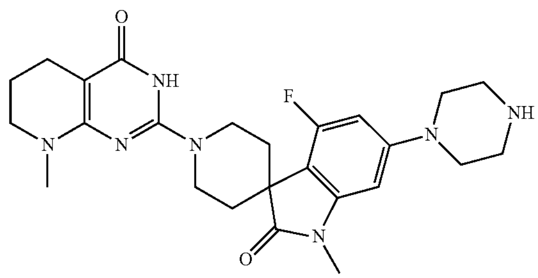 [SMILES: CN1CCCc2c1nc(N1CCC3(CC1)C(=O)N(C)c1cc(N4CCNCC4)cc(F)c13)[nH]c2=O] | 1.82-2.02 (m, 4H), 2.08-2.23 (m, 2 H), 2.51-2.62 (m, 2 H), 3.18-3.26 (m, 6 H), 3.33-3.41 (m, 2 H), 3.47-3.58 (m, 6 H), 3.96-4.08 (m, 4 H), 4.11-4.24 (m, 2 H), 6.40-6.61 (m, 2 H). | CD3OD | 482 [M + H]+ |
| 458 | 4-[4-fluoro-1-methyl-1'-(8-methyl-4-oxo-3,4,5,6,7,8-hexahydropyrido[2,3-d]pyrimidin-2-yl)-2-oxospiro[indole-3,4'-piperidine]-6-yl]-N,N-dimethylpiperazine-1-sulfonamide | 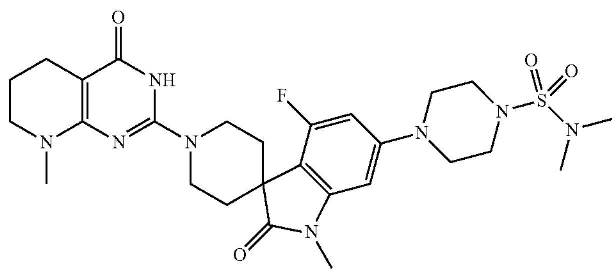 [SMILES: CN1CCCc2c1nc(N1CCC3(CC1)C(=O)N(C)c1cc(N4CCN(S(=O)(=O)N(C)C)CC4)cc(F)c13)[nH]c2=O] | 1.76-1.89 (m, 4 H), 2.09-2.21 (m, 2 H), 2.41-2.52 (m, 2 H), 2.87 (s, 6H), 3.07 (s, 3 H), 3.18 (s, 3 H), 3.21-3.31 (m, 6 H), 3.46-3.42 (m, 4 H), 3.87-3.99 (m, 2 H), 4.15-4.27 (m, 2 H), 6.16-6.26 (m, 2 H), 10.27 (br. s, 1 H). | CDCl3 | 589 [M + H]+ |
| 459 | 1-benzyl-4-[4-fluoro-1-methyl-1'-(8-methyl-4-oxo-3,4,5,6,7,8-hexahydropyrido[2,3-d]pyrimidin-2-yl)-2-oxospiro[indole-3,4'-piperidine]-6-yl]piperazine-2,6-dione | 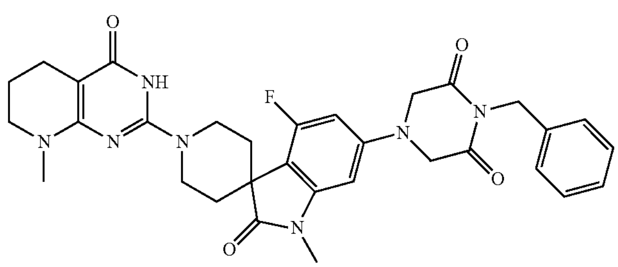 [SMILES: CN1CCCc2c1nc(N1CCC3(CC1)C(=O)N(C)c1cc(N4CC(=O)N(Cc5ccccc5)C(=O)C4)cc(F)c13)[nH]c2=O] | 1.75-1.90 (m, 4 H), 2.10-2.20 (m, 2 H), 2.45-2.50 (m, 2 H), 3.07 (s, 3 H), 3.15 (s, 3 H), 3.20-3.30 (m, 2 H), 3.85-3.95 (m, 2 H), 4.10-4.20 (m, 6 H), 4.99 (s, 2 H), 6.15-6.25 (m, 2 H), 7.25-7.40 (m, 5 H). | CDCl3 | 600 [M + H]+ |
| 460 | 4-fluoro-6-[4-(2-hydroxyacetyl)piperazin-1-yl]-1-methyl-1'-(8-methyl-4-oxo-3,4,5,6,7,8-hexahydropyrido[2,3-d]pyrimidin-2-yl)spiro[indole-3,4'-piperidine]-2-one | 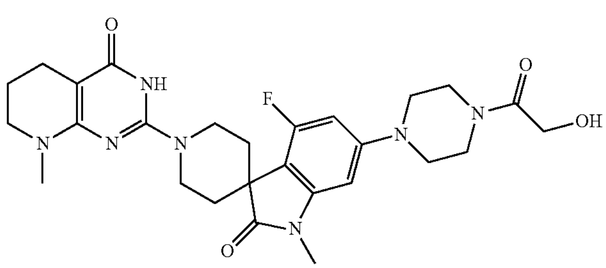 [SMILES: CN1CCCc2c1nc(N1CCC3(CC1)C(=O)N(C)c1cc(N4CCN(C(=O)CO)CC4)cc(F)c13)[nH]c2=O] | 1.76-1.89 (m, 4 H), 2.11-2.22 (m, 2 H), 2.41-2.49 (m, 2 H), 3.07 (s, 3 H), 3.11 (s, 1 H), 3.18 (s, 3 H), 3.20-3.32 (m, 6 H), 3.41-3.49 (m, 2 H), 3.79-3.87 (m, 2 H), 3.88-4.00 (m, 2 H), 4.15-4.27 (m, 2 H), 6.17-6.25 (m, 2 H), 11.23 (br. s., 1 H). | CDCl3 | 540 [M + H]+ |

TABLE 117

| Example | Compound Name | Structure | 1H NMR δ ppm | Solvent | ESI MS m/z |
|---|---|---|---|---|---|
| 461 | 4-fluoro-1-methyl-1'-(8-methyl-4-oxo-3,4,5,6,7,8-hexahydropyrido[2,3-d]pyrimidin-2-yl)-6-(4-methylsulfonylpiperazin-1-yl)spiro[indole-3,4'-piperidine]-2(1H)-one | 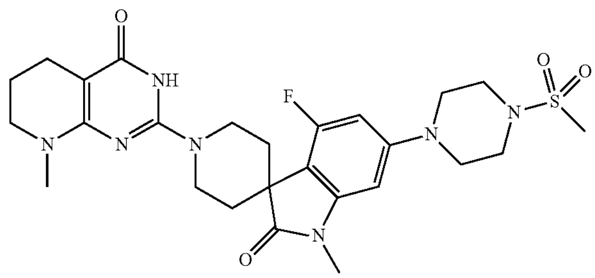 [SMILES: CN1CCCc2c1nc(N1CCC3(CC1)C(=O)N(C)c1cc(N4CCN(S(C)(=O)=O)CC4)cc(F)c13)[nH]c2=O] | 1.77-1.87 (m, 4 H), 2.10-2.20 (m, 2 H), 2.39-2.50 (m, 2 H), 2.84 (s, 3 H), 3.07 (s, 3 H), 3.18 (s, 3 H), 3.20-3.28 (m, 2 H), 3.28-3.35 (m, 4 H), 3.36-3.43 (m, 4 H), 3.86-3.98 (m, 2 H), 4.09-4.22 (m, 2 H), 6.18-6.28 (m, 2 H), 10.55 (br. s., 1 H). | CDCl3 | 560 [M + H]+ |
| 462 | methyl 4-[4-fluoro-1-methyl-1'-(8-methyl-4-oxo-3,4,5,6,7,8-hexahydropyrido[2,3-d]pyrimidin-2-yl)-2-oxospiro[indole-3,4'-piperidine]-6-yl]piperazine-1-carboxylate | 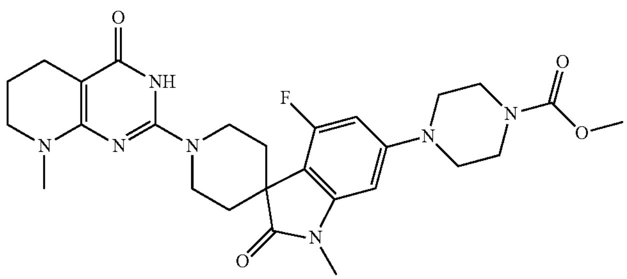 [SMILES: COC(=O)N1CCN(c2cc(F)c3c(c2)N(C)C(=O)C32CCN(c3nc4c(c(=O)[nH]3)CCCN4C)CC2)CC1] | 1.76-1.89 (m, 4 H), 2.10-2.21 (m, 2 H), 2.41-2.49 (m, 2 H), 3.06 (s, 3 H), 3.14-3.21 (m, 7 H), 3.22-3.29 (m, 2 H), 3.74 (s, 3 H), 3.57-3.68 (m, 4 H), 3.88-3.99 (m, 2 H), 4.10-4.21 (m, 2 H), 6.16-6.25 (m, 2 H), 10.59 (br. s, 1 H). | CDCl3 | 540 [M + H]+ |
| 463 | 6-[cis-2,6-dimethylmorpholin-4-yl]-4-fluoro-1'-(8-methyl-4-oxo-3,4,5,6,7,8-hexahydropyrido[2,3-d]pyrimidin-2-yl)-1-methyl-spiro[indole-3,4'-piperidine]-2(1H)-one | 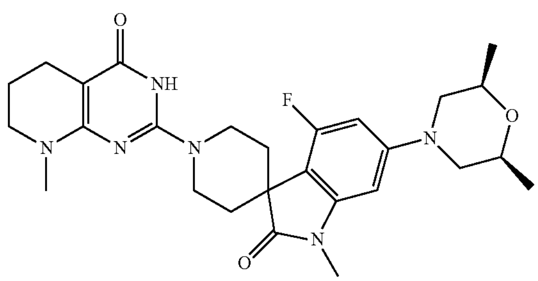 [SMILES: C[C@@H]1CN(c2cc(F)c3c(c2)N(C)C(=O)C32CCN(c3nc4c(c(=O)[nH]3)CCCN4C)CC2)C[C@H](C)O1] | 1.27 (d, J = 6.2 Hz, 6 H), 1.79-1.87 (m, 4 H), 2.11-2.20 (m, 2 H), 2.42-2.49 (m, 4 H), 3.07 (s, 3 H), 3.19 (s, 3 H), 3.23-3.27 (m, 2 H), 3.40-3.45 (m, 2 H), 3.73-3.82 (m, 2 H), 3.89-3.97 (m, 2 H), 4.07-4.15 (m, 2 H), 6.16-6.23 (m, 2 H). | CDCl3 | 511 [M + H]+ |
| 464 | 4-fluoro-1-methyl-1'-(8-methyl-4-oxo-3,4,5,6,7,8-hexahydropyrido[2,3-d]pyrimidin-2-yl)-6-(4-methylsulfonylpiperidin-1-yl)spiro[indole-3,4'-piperidine]-2(1H)-one | 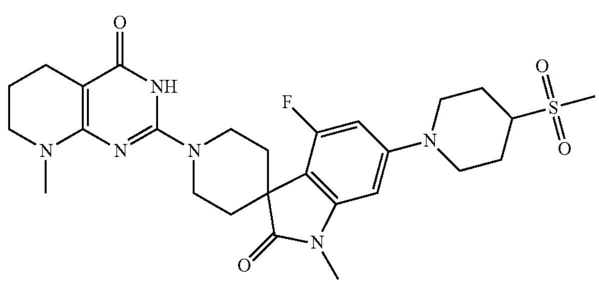 [SMILES: CN1CCCc2c1nc(N1CCC3(CC1)C(=O)N(C)c1cc(N4CCC(S(C)(=O)=O)CC4)cc(F)c13)[nH]c2=O] | 1.78-1.87 (m, 4 H), 1.91-2.04 (m, 2 H), 2.11-2.20 (m, 2 H), 2.21-2.28 (m, 2 H), 2.43-2.48 (m, 2 H), 2.81-2.91 (m, 5 H), 2.98-3.08 (m, 4 H), 3.18 (s, 3 H), 3.22-3.27 (m, 2 H), 3.82-3.98 (m, 4 H), 4.11-4.19 (m, 2 H), 6.18-6.25 (m, 2 H). | CDCl3 | 559 [M + H]+ |
| 465 | 4-fluoro-6-(4-methoxypiperidin-1-yl)-1-methyl-1'-(8-methyl-4-oxo-3,4,5,6,7,8-hexahydropyrido[2,3-d]pyrimidin-2-yl)spiro[indole-3,4'-piperidine]-2(1H)-one | 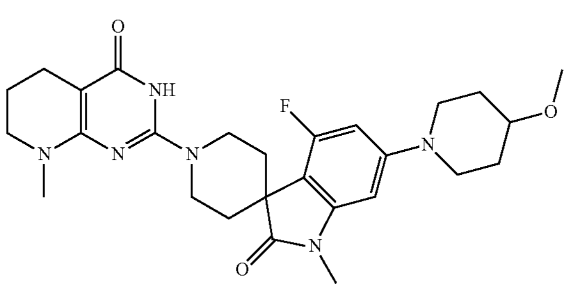 [SMILES: COC1CCN(c2cc(F)c3c(c2)N(C)C(=O)C32CCN(c3nc4c(c(=O)[nH]3)CCCN4C)CC2)CC1] | 1.66-1.76 (m, 2 H), 1.79-1.87 (m, 4 H), 1.96-2.04 (m, 2 H), 2.10-2.20 (m, 2 H), 2.43-2.48 (m, 2 H), 2.96-3.04 (m, 2 H), 3.06 (s, 3 H), 3.17 (s, 3 H), 3.22-3.27 (m, 4 H), 3.36-3.44 (m, 2 H), 3.47-3.55 (m, 2 H), 3.89-3.98 (m, 2 H), 4.09-4.17 (m, 2 H), 6.19-6.24 (m, 2 H). | CDCl3 | 511 [M + H]+ |

TABLE 118

| Example | Compound Name | Structure | 1H NMR δ ppm | Solvent | ESI MS m/z |
|---|---|---|---|---|---|
| 466 | 4-[4-fluoro-1-methyl-1'-(8-methyl-4-oxo-3,4,5,6,7,8-hexahydropyrido[2,3-d]pyrimidin-2-yl)-2-oxospiro[indole-3,4'-piperidine]-6-yl]piperazine-1-carboxamide | 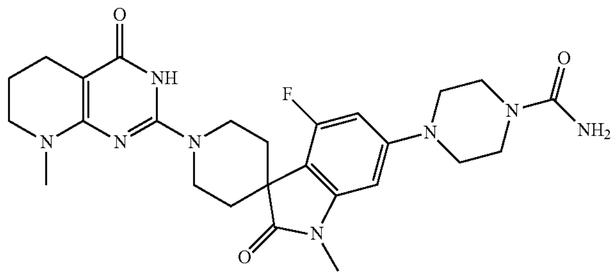 [SMILES: CN1CCCc2c1nc(N1CCC3(CC1)C(=O)N(C)c1cc(N4CCN(C(N)=O)CC4)cc(F)c13)[nH]c2=O] | 1.75-1.90 (m, 4H), 2.10-2.21 (m, 2 H), 2.42-2.50 (m, 2 H), 3.07 (s, 3 H), 3.18 (s, 3 H), 3.20-3.31 (m, 6 H), 3.52-3.61 (m, 4 H), 3.86-3.99 (m, 2 H), 4.14-4.23 (m, 2 H), 4.98 (br. S, 2 H), 6.16-6.23 (m, 2 H), 10.88 (br. s, 1 H). | CDCl3 | 525 [M + H]+ |
| 467 | 1-[4-fluoro-1-methyl-1'-(8-methyl-4-oxo-3,4,5,6,7,8-hexahydropyrido[2,3-]pyrimidin-2-yl)-2-oxospiro[indole-3,4'-piperidine]-6-yl]piperidine-4-carbonitrile | 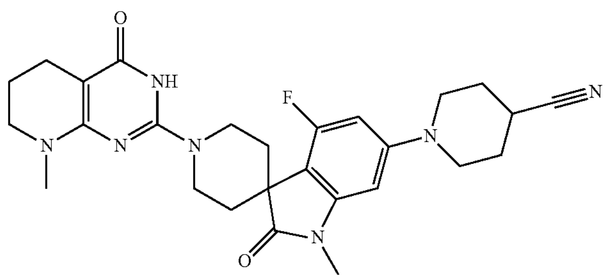 [SMILES: CN1CCCc2c1nc(N1CCC3(CC1)C(=O)N(C)c1cc(N4CCC(C#N)CC4)cc(F)c13)[nH]c2=O] | 1.79-1.87 (m, 4 H), 1.95-2.21 (m, 6 H), 2.44-2.49 (m, 2 H), 2.44-2.49 (m, 2 H), 2.80-2.88 (m, 1 H), 3.07 (s, 3 H), 3.13-3.21 (m, 5 H), 3.22-3.27 (m, 2 H), 3.40-3.48 (m, 2 H), 3.88-3.97 (m, 2 H), 4.09-4.17 (m, 2 H), 6.18-6.25 (m, 2 H). | CDCl3 | 506 [M + H]+ |
| 468 | 4-fluoro-6-(4-hydroxycyclohexyl)-1-methyl-1'-(8-methyl-4-oxo-3,4,5,6,7,8-hexahydropyrido[2,3-d]pyrimidin-2-yl)spiro[indole-3,4'-piperidine]-2(1H)-one | 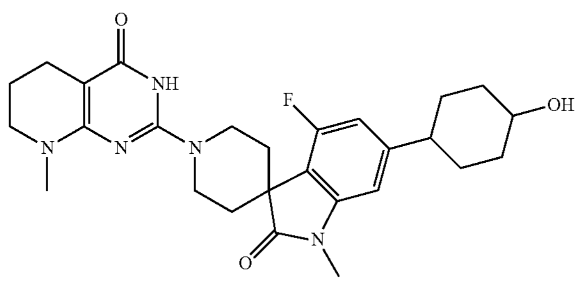 [SMILES: CN1CCCc2c1nc(N1CCC3(CC1)C(=O)N(C)c1cc(C4CCC(O)CC4)cc(F)c13)[nH]c2=O] | 1.37-1.59 (m, 4 H), 1.78-1.87 (m, 4 H), 1.90-1.98 (m, 2 H), 2.04 (s, 1 H), 2.07-2.15 (m, 2 H), 2.15-2.28 (m, 2 H), 2.39-2.55 (m, 3 H), 3.07 (s, 3 H), 3.19 (s, 3 H), 3.21-3.26 (m, 2 H), 3.64-3.74 (m, 1 H), 3.88-3.98 (m, 2 H), 4.16-4.25 (m, 2 H), 6.48 (d, J = 1.0 Hz, 1 H), 6.58 (dd, J = 11.0, 1.0 Hz, 1 H). | CDCl3 | 495 [M + H]+ |
| 469 | 4-fluoro-1'-(4-hydroxy-5,6,7,8-tetrahydroypyrido[2,3-d]pyrimidin-2-yl)-1-(oxolan-2-ylmethyl)spiro[indole-3,4'-piperidine]-2-one | 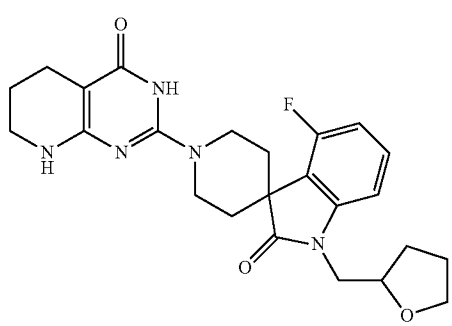 [SMILES: O=C1N(CC2CCCO2)c2cccc(F)c2C12CCN(c1nc3c(c(=O)[nH]1)CCCN3)CC2] | 1.60-1.71 (m, 2 H), 1.81-2.08 (m, 6 H), 2.20-2.52 (m, 4 H), 3.26-3.35 (m, 2 H), 3.65-3.79 (m, 2 H), 3.79-3.96 (m, 4 H), 4.13-4.29 (m, 3 H), 4.66 (br s, 1 H), 6.66-6.79 (m, 1 H), 6.80-6.89 (m, 1 H), 716-7.23 (m, 1 H). | CDCl3 | 454 [M + H]+ |

TABLE 118-continued

| Example | Compound Name | Structure | 1H NMR δ ppm | Solvent | ESI MS m/z |
|---|---|---|---|---|---|
| 470 | 4-fluoro-1'-(4-hydroxy-5,6,7,8-tetrahydropyrido[2,3-d]pyrimidin-2-yl)-1-(2-methoxyethyl)spiro[indole-3,4'-piperidin]-2-one | 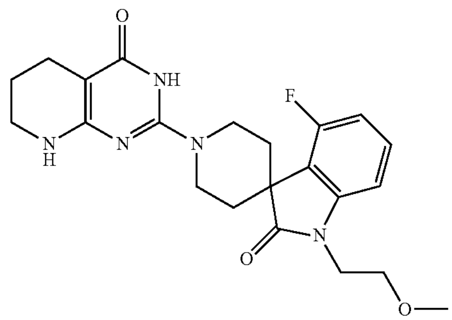 [SMILES: COCCN1C(=O)C2(CCN(c3nc4c(c(=O)[nH]3)CCCN4)CC2)c2c(F)cccc21] | 1.77-1.88 (m, 4 H), 2.21-2.42 (m, 2 H), 2.45 (t, J = 6.3 Hz, 2 H), 3.28-3.41 (m, 5 H), 3.58-3.66 (m, 2 H), 3.83-3.97 (m, 4 H), 4.14-4.32 (m, 2 H), 4.67 (br s, 1 H), 6.69-6.83 (m, 2 H), 7.17-7.24 (m, 1 H). | CDCl3 | 428 [M + H]+ |

TABLE 119

| Example | Compound Name | Structure | 1H NMR δ ppm | Solvent | ESI MS m/z |
|---|---|---|---|---|---|
| 471 | 7-fluoro-1'-(4-hydroxy-6,7-dihydro-5H-pyrido[2,3-d]pyrimidin-2-yl)-6-morpholino-4-ylspiro[2-benzofuran-3,4'-piperidin]-1-one和名変更必要 | 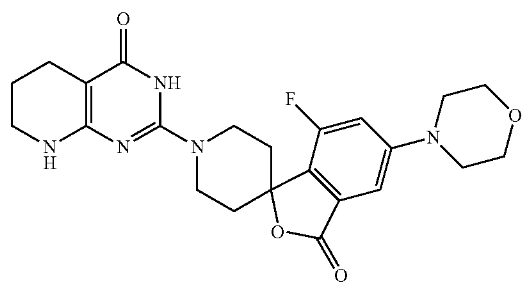 [SMILES: O=C1OC2(CCN(c3nc4c(c(=O)[nH]3)CCCN4)CC2)c2c(F)cc(N3CCOCC3)cc21] | 1.73-1.90 (m, 4 H), 2.30-2.48 (m, 4 H), 3.19-3.27 (m, 4 H), 3.28-3.41 (m, 4 H), 3.82-3.93 (m, 4 H), 4.53-4.70 (m, 3 H), 6.84 (dd, J = 11.9, 1.6 Hz, 1 H), 7.13 (d, J = 1.6 Hz, 1 H). | CDCl3 | 456 [M + H]+ |
| 472 | 6-(2,6-dimethylmorpholin-4-yl)-4-fluoro-1'-(4-hydroxy-5,6,7,8-tetrahydropyrido[2,3-d]pyrimidin-2-yl)spiro[2-benzofuran-3,4'-piperidin]-1-one | 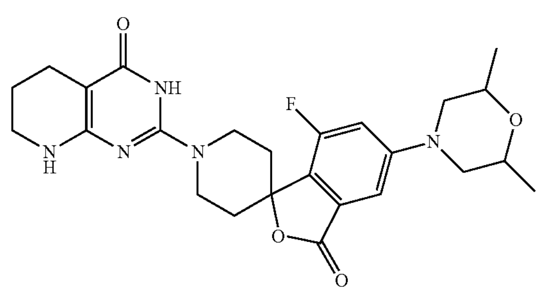 [SMILES: CC1CN(c2cc(F)c3c(c2)C(=O)OC32CCN(c3nc4c(c(=O)[nH]3)CCCN4)CC2)CC(C)O1] | 1.26 (s, 3 H), 1.29 (s, 3 H), 1.72-1.88 (m, 4 H), 2.30-2.56 (m, 6 H), 3.25-3.53 (m, 6 H), 3.65-3.84 (m, 2 H), 4.53-4.69 (m, 3 H), 6.83 (dd, J = 12.2, 2.0 Hz, 1 H), 7.12 (d, J = 2.0 Hz, 1 H). | CDCl3 | 484 [M + H]+ |
| 473 | 2-(4-fluoro-1-(2-hydroxy-2-methylpropyl)-7-methoxyspiro[indoline-3,4'-piperidin]-1'-yl)-5,6,7,8-tetrahydropyido[2,3-d]pyrimidin-4(3H)-one | 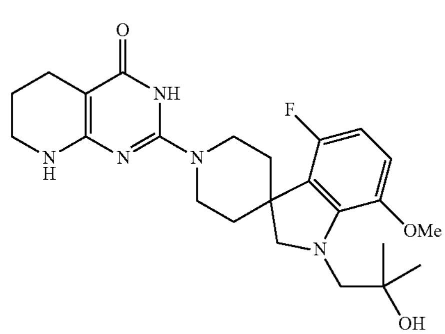 [SMILES: COc1ccc(F)c2c1N(CC(C)(C)O)CC21CCN(c2nc3c(c(=O)[nH]2)CCCN3)CC1] | 1.09-1.17 (m, 6 H), 1.59-1.70 (m, 4 H), 1.86-2.00 (m, 2 H), 2.26 (br t, J = 6.2 Hz, 2 H), 3.13 (br s, 2 H), 3.61 (s, 2 H), 3.68 (s, 3 H), 4.28 (br d, J = 13.2 Hz, 2 H), 4.32-4.38 (m, 1 H), 6.25 (br t, J = 9.2 Hz, 1 H), 6.38 (br s, 1 H), 6.68 (dd, J = 8.9, 4.5 Hz, 1 H), 10.26 (br s, 1 H) | DMSO-d6 | 458 [M + H]+ |

TABLE 119-continued

| Example | Compound Name | Structure | 1H NMR δ ppm | Solvent | ESI MS m/z |
|---|---|---|---|---|---|
| 474 | 2-(4-fluoro-7-methoxyspiro[indoline-3,4'-piperidin]-1'-yl)-5,6,7,8-tetrahydropyrido[2,3-d]pyrimidin-4(3H)-one 日本語、間違い- 1-7 | 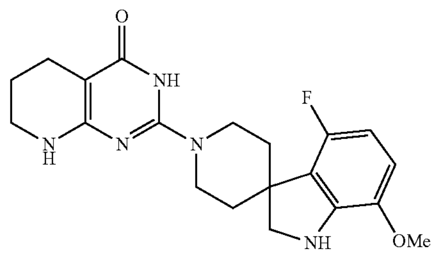 [SMILES: COc1ccc(F)c2c1NCC21CCN(c2nc3c(c(=O)[nH]2)CCCN3)CC1] | 1.59-1.72 (m, 4 H), 1.86-1.98 (m, 2 H), 2.26 (br t, J = 6.1 Hz, 2 H), 2.87 (br t, J = 12.8 Hz, 2 H), 3.09-3.18 (m, 2 H), 3.45-3.50 (m, 2 H), 3.66-3.75 (m, 3 H), 4.25 (br d, J = 13.7 Hz, 2 H), 5.51 (br s, 1 H), 6.25 (dd, J = 9.7, 8.9 Hz, 1 H), 6.38 (br s, 1 H), 6.64 (dd, J = 8.9, 4.0 Hz, 1 H), 10.20 (br s, 1 H) | DMSO-d6 | 386 [M + H]+ |

(Test Example 1) Tankyrase Inhibitory Activity Test

For each of the compounds obtained in Examples (the test target compounds), the tankyrase inhibitory activity (an inhibitory activity against tankyrase 1 (TNKS 1) and an inhibitory activity against tankyrase 2 (TNKS 2)) was evaluated by measuring the enzymatic activity of tankyrase 1 and the enzymatic activity of tankyrase 2 by the ELISA technique using self-polyADP ribosylation as an index. First, Flag-tag fusion tankyrase 1 (1,024-1,327aa, SAM+PARP) and tankyrase 2 (613-1, 116aa, ANK5+SAM+PARP) were each synthesized by a cell-free protein synthesis system and diluted with a Tris buffer (50 mM Tris-HCl (pH 8.0), 150 mM NaCl, 10% glycerol). Then, 50 μL of the diluted tankyrase 1 or tankyrase 2 was added to a plate on which the anti-FLAGM 2 monoclonal antibody was immobilized (Anti-FLAG high sensitivity M2 coated plate) (SIGMA Corporation), and was allowed to stand at 4° C. overnight. Thereafter, the plate was washed four times with a PBS buffer containing 0.1% Triton X-100 (PBST buffer).

Subsequently, the test target compound diluted with an assay buffer (50 mM Tris-HCl (pH 8.0), 4 mM $MgCl_2$, 0.2 mM DTT) (using DMSO as a control) was added to each well of the plate and was allowed to stand at room temperature for 10 minutes. Thereafter, a biotin-labeled NAD solution (225 μM NAD, 25 μM 6-Biotin-17-NAD (Trevigen Inc.)) was added as a donor substrate and mixed with the resultant test target compound, and the reaction was allowed to proceed at 30° C. for 45 minutes. Instead of the biotin-labeled NAD solution, distilled water was added to blank wells. After the reaction, the plate was washed four times with the PBST buffer. Thereafter, HRP (horseradish peroxidase)-labeled streptavidin (Trevigen Inc.) diluted 1,000-fold with the PBS buffer was added to each well, and the reaction was allowed to proceed at room temperature for 20 minutes. After the plate was washed four times with the PBST buffer, a chemiluminescent substrate solution TACS-Sapphire (Trevigen Inc.) was added to each well and the reaction was allowed to proceed at room temperature for 20 minutes. Then, the chemiluminescence intensity was measured using a chemiluminescence measuring apparatus.

The residual enzyme activity in the presence of the test target compound was determined in accordance with the following formula. Based on the residual enzyme activity at multiple concentrations of the test target compound, an enzyme inhibition activity was calculated as a 50% inhibitory concentration ($IC_{50}$ value) using data analysis software named Origin (LightStone Corp.).

Residual activity (%)={(Chemiluminescence intensity with test target compound added)−(Chemiluminescence intensity of blank)}/{(Chemiluminescence intensity of control)−(Chemiluminescence intensity of blank)}

The inhibitory activity against tankyrase 1 (TNKS 1) and the inhibitory activity against tankyrase 2 (TNKS 2) of each test target compound measured by this method were evaluated as "A" for an $IC_{50}$ value of less than 0.02 μM, "B" for an $IC_{50}$ value of 0.02 μM or more and less than 0.2 μM, "C" for an $IC_{50}$ value of 0.2 μM or more and less than 1 μM, and "D" for an $IC_{50}$ value of 1 μM or more. The results are shown in Tables 120 to 123.

(Test Example 2) Cell Proliferation Inhibitory Activity Test

The cell proliferation inhibitory activity of the compound obtained in each of Examples against human colorectal cancer cell line, COLO-320DM was evaluated by Celltiter-Glo Luminescent Cell Viability Assay (Promega Corporation, G7573). The COLO-320 DM cells were cultured in a RPMI-1640 medium (Wako Pure Chemical Industries, Ltd., 189-02025) containing 10% fetal bovine serum and 2 mM of glutamine. The cultured cells were washed with PBS and then detached with trypsin/EDTA to prepare a cell solution containing $3 \times 10^4$ cells/mL.

Next, the cell solution was seeded in a 96 well microplate (Thermo/Nunc, 136101) in an amount of 70 μL/well and was cultured overnight under conditions at 37° C. with 5% $CO_2$. On the next day, 10 μL/well of a solution in which the test target compound (DMSO solution) was diluted with the cell culture medium (a final DMSO concentration of 1%) was added and the reaction was allowed to proceed under conditions at 37° C. with 5% $CO_2$ for 96 hours (a 1% DMSO solution was used as a control). Subsequently, 80 μL/well of Celltiter-Glo Luminescent Cell Viability Assay reagent (Promega Corporation, G7573) was added, followed by agitation for 2 minutes with a shaker under shielding with aluminum foil. Thereafter, the resultant solution was allowed to stand for reaction at room temperature for 10 minutes.

After that, the luminescent signal was measured with a luminometer (Biotech, Synergy). The cell proliferation inhibitory activity was evaluated by obtaining a percentage of a cell proliferation volume of each compound-added group with respect to a cell proliferation volume (100%) of a control group in which no test target component solution was added, and calculating a value of compound concentration (GI50) required to reduce the remaining cell volume to 50% of the remaining cell volume of the control. The cell proliferation inhibitory activity (COLO-320DM) of each of the test target compounds against the COLO-320DM, which was measured in accordance with the aforementioned method, was evaluated as "A" for a GI50 value of less than 0.1 µM, "B" for a GI50 value of 0.1 µM or more and less than 0.6 µM, and "C" for a GI50 value of 0.6 µM or more and less than 1 µM. The results are shown in Tables 120 to 123 together with the results of the tankyrase inhibition activity test.

TABLE 120

| Example | TNKS1 | TNKS2 | COLO-320 DM |
|---|---|---|---|
| Example 7 | A | A | C |
| Example 55 | A | A | C |
| Example 99 | B | A | C |
| Example 100 | A | B | C |
| Example 101 | B | B | C |
| Example 147 | B | A | C |
| Example 185 | A | A | B |
| Example 193 | B | B | B |
| Example 196 | A | A | C |
| Example 218 | B | A | C |
| Example 221 | A | A | B |
| Example 226 | A | A | B |
| Example 234 | A | A | B |
| Example 251 | A | A | B |
| Example 252 | A | A | B |
| Example 253 | A | A | B |
| Example 254 | A | A | B |
| Example 258 | A | A | C |
| Example 259 | A | A | C |
| Example 273 | A | A | C |
| Example 292 | A | A | B |
| Example 316 | A | A | B |
| Example 323 | A | A | C |
| Example 326 | B | B | C |
| Example 327 | A | A | B |
| Example 328 | B | A | B |
| Example 329 | B | B | C |
| Example 330 | A | A | C |
| Example 331 | A | A | C |
| Example 333 | A | A | B |
| Example 334 | A | A | C |
| Example 337 | A | A | B |
| Example 338 | B | A | B |
| Example 339 | A | A | B |
| Example 340 | A | A | B |
| Example 341 | B | B | C |
| Example 342 | B | A | C |
| Example 344 | A | A | B |
| Example 347 | B | B | C |
| Example 351 | B | A | B |
| Example 354 | A | A | B |
| Example 356 | A | A | B |
| Example 357 | A | A | C |
| Example 360 | A | A | B |
| Example 361 | A | A | C |
| Example 362 | A | A | B |

TABLE 121

| Example | TNKS1 | TNKS2 | COLO-320 DM |
|---|---|---|---|
| Example 365 | A | A | C |
| Example 366 | A | A | B |
| Example 367 | A | A | B |
| Example 370 | A | A | B |
| Example 372 | A | A | B |
| Example 373 | A | A | A |
| Example 374 | A | A | A |
| Example 375 | A | A | B |
| Example 376 | A | A | B |
| Example 377 | A | A | B |
| Example 378 | A | A | C |
| Example 379 | A | A | A |
| Example 380 | A | A | C |
| Example 381 | A | A | B |
| Example 382 | A | A | B |
| Example 383 | A | A | B |
| Example 384 | A | A | B |
| Example 386 | A | A | C |
| Example 387 | A | A | A |
| Example 388 | A | A | A |
| Example 389 | A | A | A |

TABLE 122

| Example | TNKS1 | TNKS2 | COLO-320 DM |
|---|---|---|---|
| Example 390 | A | A | B |
| Example 391 | A | A | C |
| Example 392 | A | A | B |
| Example 393 | A | A | B |
| Example 394 | A | A | C |
| Example 395 | A | A | C |
| Example 396 | A | A | B |
| Example 397 | B | B | B |
| Example 398 | A | A | B |
| Example 399 | A | A | B |
| Example 400 | B | B | B |
| Example 401 | A | A | B |
| Example 402 | B | A | B |
| Example 403 | A | A | B |
| Example 404 | B | B | C |
| Example 405 | A | A | C |
| Example 406 | B | B | A |
| Example 407 | B | A | B |
| Example 408 | A | A | A |
| Example 409 | A | A | C |
| Example 410 | A | A | B |
| Example 412 | A | A | C |
| Example 413 | B | A | C |
| Example 414 | A | A | C |
| Example 415 | A | A | C |
| Example 416 | A | A | B |
| Example 417 | A | A | C |
| Example 418 | A | A | B |
| Example 419 | A | A | A |
| Example 420 | A | A | B |
| Example 421 | A | A | B |
| Example 422 | A | A | A |
| Example 423 | A | A | A |
| Example 424 | A | A | B |
| Example 425 | A | A | B |
| Example 426 | A | A | B |
| Example 427 | A | A | C |
| Example 428 | A | A | B |
| Example 429 | A | A | B |
| Example 430 | A | A | C |
| Example 431 | A | A | C |
| Example 432 | B | B | B |
| Example 433 | A | A | A |
| Example 434 | A | A | C |
| Example 435 | A | A | B |
| Example 437 | B | B | B |

TABLE 123

| Example | TNKS1 | TNKS2 | COLO-320 DM |
|---|---|---|---|
| Example 438 | A | A | C |
| Example 439 | A | A | B |
| Example 440 | A | A | B |
| Example 441 | B | A | B |
| Example 442 | B | B | C |
| Example 443 | A | A | C |
| Example 444 | B | B | B |

TABLE 123-continued

| Example | TNKS1 | TNKS2 | COLO-320 DM |
|---|---|---|---|
| Example 445 | A | A | B |
| Example 446 | A | A | A |
| Example 447 | A | A | A |
| Example 448 | A | A | B |
| Example 449 | B | B | B |
| Example 450 | A | A | A |
| Example 451 | A | A | B |
| Example 452 | B | A | B |
| Example 453 | A | A | B |
| Example 454 | A | A | B |
| Example 455 | A | A | B |
| Example 456 | A | A | B |
| Example 457 | B | B | C |
| Example 458 | B | A | B |
| Example 459 | B | B | B |
| Example 460 | A | A | B |
| Example 461 | A | A | A |
| Example 462 | B | A | A |
| Example 463 | A | A | A |
| Example 464 | A | A | B |
| Example 465 | B | A | A |
| Example 466 | B | A | C |
| Example 467 | B | A | A |
| Example 468 | A | B | A |
| Example 469 | B | A | B |
| Example 470 | A | A | B |
| Example 471 | A | A | C |
| Example 472 | A | A | C |
| Example 473 | B | A | C |
| Example 474 | A | A | B |

INDUSTRIAL APPLICABILITY

As has been described above, the present invention makes it possible to provide a compound or a pharmaceutically acceptable salt thereof which has excellent tankyrase inhibitory activity and which is useful for the treatment and prophylaxis of proliferative diseases such as cancer, for example, and is also useful for the treatment of other diseases such as Herpes virus, multiple sclerosis, glucose metabolism diseases, skin and cartilage injuries, and pulmonary fibrosis, and further to provide a tankyrase inhibitor and a pharmaceutical composition comprising the same. Furthermore, the present invention makes it possible to provide a method for producing the compound and the pharmaceutically acceptable salt thereof and to provide an intermediate compound useful for the production.

The invention claimed is:
1. A compound or a pharmaceutically acceptable salt thereof, the compound being represented by the following general formula (1):

[Chem. 1]

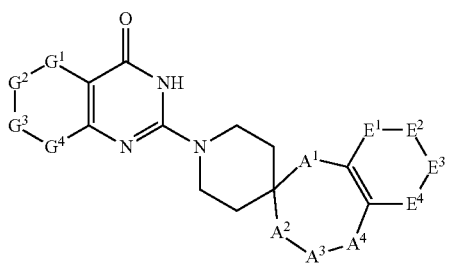

(1)

in the formula (1),
$A^1$, $A^2$, $A^3$, and $A^4$ are defined such that both of $A^1$ and $A^2$ represent a single bond, one of $A^1$ and $A^2$ represents a single bond and the other represents $CH_2$, or $A^1$ represents a single bond and $A^4$ represents $CH_2$,
one of $A^3$ and $A^4$ is $CH_2$ or CO and the other is O or $NR^1$ when both of $A^1$ and $A^2$ represent a single bond or when $A^1$ represents $CH_2$ and $A^2$ represents a single bond, one of $A^3$ and $A^4$ is $NR^1$ and the other is $CH_2$ or CO when $A^1$ represents a single bond and $A^2$ represents $CH_2$, or one of $A^2$ and $A^3$ is $NR^1$ and the other is $CH_2$ or CO when $A^1$ represents a single bond and $A^4$ is $CH_2$,
where $R^1$ represents a hydrogen atom, an optionally substituted $C_{1-6}$ alkyl group, an optionally substituted heteroaryl group, an optionally substituted $C_{3-8}$ cycloalkyl $C_{1-3}$ alkyl group, an optionally substituted aryl $C_{1-3}$ alkyl group, an optionally substituted heteroaryl $C_{1-3}$ alkyl group, an optionally substituted 3- to 7-membered heterocycloalkyl $C_{1-3}$ alkyl group, a group represented by the following formula: $-(CH_2)_m-C(=O)-L$, or a group represented by the following formula: $-S(=O)_2-R^{13}$,
m is 0, 1, 2, or 3, and L is $R^{11}$ when m is 0 or L is $R^{12}$ when m is 1, 2, or 3,
$R^{11}$ is a hydrogen atom, an optionally substituted $C_{1-6}$ alkyl group, $OR^{51}$, a group represented by the following formula: $-C(=O)-OR^{52}$, or a group represented by the following formula: $-N(R^{53a})-R^{53b}$,
$R^{51}$ is an optionally substituted aryl $C_{1-3}$ alkyl group,
$R^2$ is a hydrogen atom or an optionally substituted $C_{1-6}$ alkyl group,
$R^{53a}$ and $R^{53b}$ are each independently a hydrogen atom or an optionally substituted $C_{1-6}$ alkyl group, or $R^{53a}$ and $R^{53b}$ together form a 3- to 7-membered heterocycloalkyl group which may contain at least one atom or group selected from the group consisting of an oxygen atom, a sulfur atom, and $NR^{101}$,
$R^{101}$ is a hydrogen atom or an optionally substituted $C_{1-6}$ alkyl group, and
$R^{12}$ is an optionally substituted aryl group, $OR^{54}$ or a group represented by the following formula: $-N(R^{55a})-R^{55b}$,
$R^{54}$ is a hydrogen atom, an optionally substituted $C_{1-6}$ alkyl group, an optionally substituted aryl $C_{1-3}$ alkyl group, or an optionally substituted heteroaryl $C_{1-3}$ alkyl group, and
$R^{55a}$ and $R^{55b}$ are each independently a hydrogen atom, an optionally substituted $C_{1-6}$ alkyl group, an optionally substituted aryl $C_{1-3}$ alkyl group, an optionally substituted heteroaryl $C_{1-3}$ alkyl group, or a group represented by the following formula: $-(C=O)-R^{102}$, or $R^{55a}$ and $R^{55b}$ together form a 3- to 7-membered heterocycloalkyl group which may contain at least one atom or group selected from the group consisting of an oxygen atom, a sulfur atom, and $NR^{103}$, or together form an optionally substituted 6,8-dihydro-5H-imidazo[1,2-a]pyrazin-7-yl group,
$R^{102}$ is a hydrogen atom, an optionally substituted $C_{1-6}$ alkyl group, or an optionally substituted aryl $C_{1-3}$ alkyl group, and $R^{103}$ is a hydrogen atom or an optionally substituted $C_{1-6}$ alkyl group, and $R^{13}$ is an optionally substituted $C_{1-6}$ alkyl group;

a structure composed of $E^1$, $E^2$, $E^3$, and $E^4$ is a group represented by the following formula: -$E^1$-$E^2$-$E^3$-$E^4$- (in this formula, bonds between $E^1$, $E^2$, $E^3$, and $E^4$ each represent a single bond or a double bond) where $E^1$ is N or $CR^2$, $E^2$ is N or $CR^3$, $E^3$ is $CR^4$, and $E^4$ is N or $CR^5$, is a group in which $E^1$ represents a single bond and which is represented by the following formula: -$E^2$-$E^3$=$E^4$- where $E^2$ is O or S and $E^3$ and $E^4$ are CH, or is a group in which $E^1$ represents a single bond and which is represented by the following formula: -$E^2$=$E^3$-$E^4$- where $E^2$ and $E^3$ are CH and $E^4$ is S, $R^2$, $R^3$, $R^4$, and $R^5$ are each independently a hydrogen atom, a fluorine atom, a chlorine atom, a bromine atom, an iodine atom, a cyano group, an optionally substituted $C_{1-6}$ alkyl group, an optionally substituted aryl group, an optionally substituted heteroaryl group, an optionally substituted 3- to 7-membered heterocycloalkyl group, or a group represented by the following formula: -Q-$(CH_2)_n$—$R^{14}$, n is 0, 1, 2, or 3, and Q is a group represented by the following formula: —CH=CH—, O, CO, a group represented by the following formula: —C(=O)—O—, a group represented by the following formula: —C(=O)—N($R^{56}$)—, $NR^{56}$, a group represented by the following formula: —N($R^{56}$)—C(=O)—, or a group represented by the following formula: —N($R^{56}$)—C(=O)—O—, $R^{56}$ is a hydrogen atom, an optionally substituted $C_{1-3}$ alkyl group or a group represented by the following formula: —C(=O)—$R^{104}$, $R^{104}$ is a hydrogen atom, an optionally substituted $C_{1-6}$ alkyl group, an optionally substituted aryl group, an optionally substituted $C_{1-6}$ alkyloxy group, or an optionally substituted aryloxy group, and $R^{14}$ is a hydrogen atom, an optionally substituted $C_{1-6}$ alkyl group, an optionally substituted aryl group, an optionally substituted heteroaryl group, an optionally substituted $C_{3-8}$ cycloalkyl group, or an optionally substituted 3- to 7-membered heterocycloalkyl group; and a structure composed of $G^1$, $G^2$, $G^3$, and $G^4$ is a group represented by the following formula: -$G^1$-$G^2$-$G^3$-$G^4$- (in this formula, bonds between $G^1$, $G^2$, $G^3$, and $G^4$ each represent a single bond), and represented by the following formula: —$CH_2$—$CH_2$—$CH_2$—$CH_2$—, or the following formula: —$CH_2$—$CH_2$—$CH_2$—N($R^7$), $R^7$ is a hydrogen atom, an optionally substituted $C_{1-6}$ alkyl group, an optionally substituted $C_{3-8}$ cycloalkyl group, an optionally substituted $C_{3-8}$ cycloalkyl $C_{1-3}$ alkyl group, an optionally substituted 3- to 7-membered heterocycloalkyl group, an optionally substituted 3- to 7-membered heterocycloalkyl $C_{1-3}$ alkyl group, a group represented by the following formula: —C(=O)—$R^{15}$, or a group represented by the following formula: —$(CH_2)_p$—C(=O)—$OR^{16}$, p is 0, 1, 2, or 3, $R^{15}$ is a hydrogen atom, an optionally substituted $C_{1-6}$ alkyl group, or $OR^{57}$, $R^{57}$ is an optionally substituted $C_{1-6}$ alkyl group or an optionally substituted aryl $C_{1-3}$ alkyl group, and $R^{16}$ is a hydrogen atom or an optionally substituted $C_{1-6}$ alkyl group.

2. The compound or the pharmaceutically acceptable salt thereof according to claim 1, wherein in the general formula (1), both of $A^1$ and $A^2$ represent a single bond, while one of $A^3$ and $A^4$ is $CH_2$ or CO and the other is O.

3. The compound or the pharmaceutically acceptable salt thereof according to claim 1, wherein in the general formula (1), both of $A^1$ and $A^2$ represent a single bond, while one of $A^3$ and $A^4$ is $CH_2$ or CO and the other is $NR^1$.

4. The compound or the pharmaceutically acceptable salt thereof according to claim 2, wherein in the general formula (1), the structure composed of $E^1$, $E^2$, $E^3$, and $E^4$ is a group represented by the formula: -$E^1$-$E^2$-$E^3$-$E^4$- (in this formula, bonds between $E^1$, $E^2$, $E^3$, and $E^4$ each represent a single bond or a double bond) where $E^1$ is N or $CR^2$, $E^2$ is N or $CR^3$, $E^3$ is N or $CR^4$, and $E^4$ is N or $CR^5$.

5. The compound or the pharmaceutically acceptable salt thereof according to claim 1, wherein the compound represented by the general formula (1) is represented by the following general formula (1-1):

[Chem. 2]

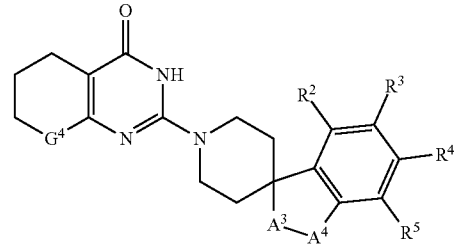

(1-1)

in formula (1-1), $A^3$ is O, $CH_2$, or CO, and $A^4$ is CO or $NR^1$ (excluding a case where both of $A^3$ and $A^4$ are CO, a case where $A^3$ is $CH_2$ and $A^4$ is CO, and a case where $A^3$ is O and $A^4$ is $NR^1$), and $G^4$ is $CH_2$ or $NR^7$ and $R^7$ is a hydrogen atom or an optionally substituted $C_{1-6}$ alkyl group.

6. The compound or the pharmaceutically acceptable salt thereof according to claim 1, wherein the compound represented by the general formula (1) is selected from the group consisting of 5-[2-(dimethylamino)ethoxy]-7-fluoro-1'-(8-methyl-4-oxo-3,4,5,6,7,8-hexahydropyrido[2,3-d]pyrimidin-2-yl)-3H-spiro[isobenzofuran-1,4'-piperidine]-3-one, 2-[{7-fluoro-1'-(8-methyl-4-oxo-3,4,5,6,7,8-hexahydropyrido[2,3-d]pyrimidin-2-yl)-3-oxo-3H-spiro[isobenzofuran-1,4'-piperidine]-5-yl}oxy]-N,N-dimethylacetamide, 2-[1-[(3-methoxybenzyl)spiro[indoline-3,4'-piperidin]-1'-yl]-5,6,7,8-tetrahydroquinazolin-4(3H)-one, 2-[1-(pyridin-4-ylmethyl)spiro[indoline-3,4'-piperidin]-1'-yl]-5,6,7,8-tetrahydroquinazolin-4(3H)-one, 2-[1-(pyridin-3-ylmethyl)spiro[indoline-3,4'-piperidin]-1'-yl]-5,6,7,8-tetrahydroquinazolin-4(3H)-one, 2-(5-methoxy-1-methylspiro[indoline-3,4'-piperidin]-1'-yl)-5,6,7,8-tetrahydroquinazolin-4(3H)-one, 2-(4-fluoro-2-oxospiro[indoline-3,4'-piperidin]-1'-yl)-8-methyl-5,6,7,8-tetrahydropyrido[2,3-d]pyrimidine-4(3H)-one, Ethyl 4-chloro-1'-(4-oxo-3,4,5,6,7,8-hexahydroquinazolin-2-yl)-1-(pyridin-3-yl)methylspiro[indoline-3,4'-piperidine]-6-carboxylate, 4-chloro-N-(2-morpholinoethyl)-1'-(4-oxo-3,4,5,6,7,8-hexahydroquinazolin-2-yl)-1-(pyridin-3-yl)methyl-spiro[indoline-3,4'-piperidine]-6-carboxamide, 2-(6-chloro-1-(pyridin-3-yl)methylspiro[indoline-3,4'-piperidin]-1'-yl)-5,6,7,8-tetrahydroquinazolin-4(3H)-one, 2-[4-chloro-1-(pyridin-3-yl)methylspiro[indoline-3,4'-piperidin]-1'-yl]-5,6,7,8-tetrahydroquinazolin-4(3H)-one, 4-chloro-1'-(4-oxo-3,4,5,6,7,8-hexahydroquinazolin-2-yl)-1-(pyridin-3-yl)methylspiro[indoline-3,4'-piperidin]-2-one, 4-chloro-6-hydroxy-1-methyl-1'-(4-oxo-3,4,5,6,7,8-hexahydroquinazolin-2-yl)spiro[indoline-3,4'-piperidin]-2-one, 2-[4,6-difluoro-1-(pyridin-3-yl)methylspiro[indoline-3,4'-piperidin]-1'-yl]-5,6,7,8-tetrahydroquinazolin-4(3H)-one, 2-[4,6-difluoro-1-(pyrimidin-5-yl)methylspiro[indoline-3,4'-piperidin]-1'-yl]-5,6,7,8-tetrahydroquinazolin-4(3H)-one, 2-[4,6-difluoro-1-(pyridin-2-yl)methylspiro[indoline-3,4'-piperidin]-1'-yl]-5,6,7,8-tetrahydroquinazolin-4(3H)-one, 2-[4,6-difluoro-1-(pyridin-4-yl)methylspiro[indoline-3,4'-piperidin]-1'-yl]-5,6,7,8-tetrahydroquinazolin-4(3H)-one, 1-methyl-1'-(8-methyl-4-oxo-3,4,5,6,7,8-hexahydropyrido[2,3-d]pyrimidin-2-yl)spiro[indoline-3,4'-piperidine]-2-one, 2-[4,6-difluoro-1-(pyrimidin-2-ylmethyl)spiro[indoline-3,4'-piperidine]-1'-yl]-5,6,7,8-tetrahydroquinazolin-4(3H)-one, 4-chloro-1-methyl-6-[4-(morpholine-4-carbonyl)oxazol-2-yl]-1'-(4-oxo-3,4,5,6,7,8-hexahydroquinazolin-2-yl)spiro[indoline-3,4'-piperidine]-2-one, 4-chloro-6-[4-(morpholine-4-carbonyl)oxazol-2-yl]-1-methyl-1'-(8-methyl-4-oxo-3,4,5,6,7,8-hexahydropyrido[2,3-d]pyrimidin-2-yl)spiro[indoline-3,4'-piperidine]-2-one, 4-chloro-1-methyl-1'-(8-methyl-4-oxo-3,4,5,6,7,8-hexahydropyrido[2,3-d]pyrimidin-2-yl)-2-oxospiro[indoline-3,4'-piperidine]-7-carbonitrile, 4-chloro-6-(4-ethoxycarbonyloxazole-2-yl)-1-methyl-1'-(8-methyl-4-oxo-3,4,5,6,7,8-hexahydropyrido[2,3-d]pyrimidin-2-yl) spiro[indoline-3,4'-piperidine]-2-one, 4-chloro-1-methyl-1'-(8-methyl-4-oxo-3,4,5,6,7,8-hexahydropyrido[2,3-d]pyrimidin-2-yl)-6-[4-(pyrrolidin-1-ylmethyl)oxazol-2-yl]spiro[indoline-3,4'-piperidine]-2-one, 4-chloro-1-methyl-1'-(8-methyl-4-oxo-3,4,5,6,7,8-hexahydropyrido[2,3-d]pyrimidin-2-yl)-2-oxospiro [indoline-3,4'-piperidine]-7-carboxamide, 2-[4-chloro-1-methyl-1'-(8-methyl-4-oxo-3,4,5,6,7,8-hexahydropyrido[2,3-d]pyrimidin-2-yl)-2-oxospiro[indoline-3,4'-piperidine]-6-yl]oxazole-4-carboxylic acid, 4,6-difluoro-1'-(4-oxo-3,4,5,6,7,8-hexahydroquinazolin-2-yl)-1-(pyridin-3-ylmethyl)spiro[indoline-3,4'-piperidine]-2-one, 4-chloro-1-methyl-6-(3-morpholinopropoxy)-1'-(4-oxo-3,4,5,6,7,8-hexahydroquinazolin-2-yl)spiro[indoline-3,4'-piperidin]-2-one, 2-(4,6-difluoro-1-methylspiro[indoline-3,4'-piperidine]-1'-yl)-8-methyl-5,6,7,8-tetrahydropyrido[2,3-d]pyrimidin-4(3H)-one, 2-[4,6-difluoro-1-(2-hydroxyethyl)spiro[indoline-3,4'-piperidine]-1'-yl]-8-methyl-5,6,7,8-tetrahydropyrido[2,3-d]pyrimidin-4(3H)-one, 4,6-difluoro-1-methyl-1'-(8-methyl-4-oxo-3,4,5,6,7,8-hexahydropyrido[2,3-d]pyrimidin-2-yl)spiro[indoline-3,4'-piperidine]-2-one, 4,6-difluoro-1-(2-hydroxyethyl)-1'-(8-methyl-4-oxo-3,4,5,6,7,8-hexahydropyrido[2,3-d]pyrimidin-2-yl)spiro[indoline-3,4'-piperidine]-2-one, 2-[4,6-difluoro-1-(2-fluorobenzyl)spiro[indoline-3,4'-piperidin]-1'-yl]-5,6,7,8-tetrahydroquinazolin-4(3H)-one, 2-[4,6-difluoro-1-(3-fluorobenzyl)spiro[indoline-3,4'-piperidin]-1'-yl]-5,6,7,8-tetrahydroquinazolin-4(3H)-one, 2-{1-[(6-chloropyridin-3-yl)methyl]-4,6-difluorospiro[indoline-3,4'-piperidine]-1'-yl]-5,6,7,8-tetrahydroquinazolin-4(3H)-one, 2-[4,6-difluoro-1-(pyridin-3-ylmethyl)spiro[indoline-3,4'-piperidine]-1'-yl]-8-methyl-5,6,7,8-tetrahydropyrido[2,3-d]pyrimidin-4(3H)-one, 4-fluoro-6-hydroxy-1-methyl-1'-(8-methyl-4-oxo-3,4,5,6,7,8-hexahydropyrido[2,3-d]pyrimidin-2-yl)spiro[indoline-3,4'-piperidin]-2-one, 4-fluoro-6-(2-hydroxyethoxy)-1-methyl-1'-(8-methyl-4-oxo-3,4,5,6,7,8-hexahydropyrido[2,3-d]pyrimidin-2-yl)spiro[indoline-3,4'-piperidin]-2-one, 6-[2-(dimethylamino)ethoxy]-4-fluoro-1-methyl-1'-(8-methyl-4-oxo-3,4,5,6,7,8-hexahydropyrido[2,3-d]pyrimidin-2-yl)spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-(2-morpholinoethoxy)spiro[indoline-3,4'-piperidin]-2-one, 6-[2-(1,1-dioxidothiomorpholino)ethoxy]-4-fluoro-1-methyl-1'-(8-methyl-4-oxo-3,4,5,6,7,8-hexahydropyrido[2,3-d]pyrimidin-2-yl)spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-[2-(4-methylpiperazin-1-yl)ethoxy]spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-(3-morpholin-4-ylpropoxy)spiro[indoline-3,4'-piperidin]-2-one, 4-fluoro-6-(2-methoxyethoxy)-1-methyl-1'-(8-methyl-4-oxo-3,4,5,6,7,8-hexahydropyrido[2,3-d]pyrimidin-2-yl) spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-[3-(pyrrolidin-1-yl)propoxy]spiro[indoline-3,4'-piperidin]-2-one, 4,6-difluoro-1-(2-hydroxyethyl)-1'-[8-(trideuteriomethyl)-4-oxo-3,4,5,6,7,8-hexapyrido[2,3-d]pyrimidin-2-yl]spiro[indoline-3,4'-piperidin]-2-one, 4-fluoro-6-methoxy-1-methyl-1'-(8-methyl-4-oxo-3,4,5,6,7,8-hexahydropyrido[2,3-d]pyrimidin-2-yl)spiro[indoline-3,4'-piperidin]-2-one, 4-fluoro-1-(2-hydroxyethyl)-6-methoxy-1'-(8-methyl-4-oxo-3,4,5,6,7,8-hexahydropyrido[2,3-d]pyrimidin-2-yl)spiro[indoline-3,4'-piperidin]-2-one, 2-[4,6-difluoro-1'-(8-methyl-4-oxo-3,4,5,6,7,8-hexahydropyrido[2,3-d]pyrimidin-2-yl)-2-oxospiro[indoline-3,4'-piperidin]-1-yl]acetonitrile, 4-chloro-6-[2-(dimethylamino)ethoxy]-1-methyl-1'-(8-methyl-4-oxo-3,4,5,6,7,8-hexahydropyrido[2,3-d]pyrimidin-2-yl) spiro[indoline-3,4'-piperidin]-2-one, 4-chloro-1-methyl-1'-(8-methyl-4-oxo-3,4,5,6,7,8-hexahydropyrido[2,3-d]pyrimidin-2-yl)-6-(2-piperidin-1-ylethoxy)spiro[indoline-3,4'-piperidin]-2-one 4-chloro-1-methyl-1'-(8-methyl-4-oxo-3,4,5,6,7,8-hexahydropyrido[2,3-d]pyrimidin-2-yl)-6-(2-morpholin-4-ylethoxy)spiro[indoline-3,4'-piperidin]-2-one, 4-chloro-6-[2-(1,1-dioxidothiomorpholino)ethoxy]-1-methyl-1'-(8-methyl-4-oxo-3,4,5,6,7,8-hexapyrido[2,3-d]pyrimidin-2-yl) spiro[indoline-3,4'-piperidin]-2-one, 2-[4-fluoro-6-methoxy-1'-(8-methyl-4-oxo-3,4,5,6,7,8-hexahydropyrido[2,3-d]pyrimidin-2-yl)-2-oxospiro[indoline-3,4'-piperidine]-1-yl]acetonitrile, 4-fluoro-1-methyl-1'-(8-methyl-4-oxo-3,4,5,6,7,8-hexahydropyrido[2,3-d]pyrimidin-2-yl)-6-(1-methylpiperidin-4-yl)oxyspiro[indoline-3,4'-piperidin]-2-one, 4-fluoro-6-(2-hydroxyethoxy)-1-(2-hydroxyethyl)-1'-(8-methyl-4-oxo-3,4,5,6,7,8-hexahydropyrido[2,3-d]pyrimidin-2-yl)spiro[indoline-3,4'-piperidin]-2-one, 1'-(8-ethyl-4-oxo-3,4,5,6,7,8-hexahydropyrido[2,3-d]pyrimidin-2-yl)-4,6-difluoro-1-(2-hydroxyethyl)spiro[indoline-3,4'-piperidin]-2-one, 4-fluoro-1-(2-hydroxyethyl)-6-(2-methoxyethoxy)-1'-(8-methyl-4-oxo-3,4,5,6,7,8-hexahydropyrido[2,3-d]pyrimidin-2-yl) spiro[indoline-3,4'-piperidin]-2-one, 4-fluoro-6-hydroxy-1-(2-hydroxyethyl)-1'-(8-methyl-4-oxo-3,4,5,6,7,8-hexahydropyrido[2,3-d]pyrimidin-2-yl)spiro[indoline-3,4'-piperidin]-2-one, 4-fluoro-1-(2-hydroxyethyl)-1'-(8-methyl-4-oxo-3,4,5,6,7,8-hexahydropyrido[2,3-d]pyrimidin-2-yl)-6-(2-morpholin-4-ylethoxy)spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-(4-methylpiperazin-1-yl)spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-(oxetan-3-ylmethoxy)spiro[indoline-3,4'-piperidin]-2-one, 4-fluoro-1-methyl,-1'-(8-methyl-4-oxo-3,4,5,6,7,8-hexahydropyrido[2,3-d]pyrimidin-2-yl)-6-[(tetrahydro-2H-pyran-4-yl)oxy]spiro[indoline-3,4'-piperidin]-2-one, 6-(cis-3,5-dimethylpiperazin-1-yl)-4-fluoro-1-methyl-1'-(8-methyl-4-oxo-3,4,5,6,7,8-hexahydropyrido[2,3-d]pyrimidin-2-yl)spiro[indoline-3,4'-piperidin]-2(1H)-one, 6-(3,8-diazabicyclo[3.2.1]octan-3-yl)-4-fluoro-1-methyl-1'-(8-methyl-4-oxo-3,4,5,6,7,8-hexahydropyrido[2,3-d]pyrimidin-2-yl)spiro[indoline-3,4'-piperidin]-2-one, 2-{[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy} acetic acid, 6-[(1H-tetrazol-5-yl)methoxy]-4-fluoro-1-methyl-1'-(8-methyl-4-oxo-3,4,5,6,7,8-hexahydropyrido[2,3-d]pyrimidin-2-yl)spiro[indoline-3,4'-piperidin]-2(1H)-one, 4-fluoro-6-{2-[2-(hydroxymethyl)pyrrolidin-1-yl]ethoxy}-1-methyl-1'-(8-methyl-4-oxo-3,4,5,6,7,8-hexahydropyrido[2,3-d]pyrimidin-2-yl) spiro[indoline-3,4'-piperidin]-2-(1H)-one, 4-fluoro-1'-(4-hydroxy-8-methyl-6,7-dihydro-5H-pyrido[2,3-d]pyrimidin-2-yl)-6-(2-pyrrolidin-1-ylethoxy)spiro[2-benzofuran-3,4'-piperidin]-1-one, 4-chloro-7-[2-(dimethylamino)ethoxy]-1-methyl-1'-(8-methyl-4-oxo-3,4,5,6,7,8-hexahydropyrido[2,3-d]pyrimidin-2-yl) spiro[indoline-3,4'-piperidin]-2-one, 4-fluoro-6-[4-(2-methoxyethyl)piperazin-1-yl]-1-methyl-1'-(8-methyl-4-oxo-3,4,5,6,7,8-hexahydropyrido[2,3-d]pyrimidin-2-yl)spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-[4-(oxetan-3-yl)piperazin-1-yl]spiro[indoline-3,4'-piperidin]-2-one, 4-fluoro-6-(2-hydroxyethoxy)-1'-(8-methyl-4-oxo-3,4,5,6,7,8-hexahydropyrido[2,3-d]pyrimidin-2-yl)-1-(2,2,2-trifluoroethyl)spiro[indoline-3,4'-piperidin]-2-one, 6-[2-(dimethylamino)ethoxy]-4-fluoro-1'-(8-methyl-4-oxo-3,4,5,6,7,8-hexahydropyrido[2,3-d]pyrimidin-2-yl)-1-(2,2,2-trifluoroethyl)spiro[indoline-3,4'-piperidin]-2-one, 7-[2-(dimethylamino)ethoxy]-4-fluoro-1'-(4-hydroxy-8-methyl-6,7-dihydro-5H-pyrido[2,3-d]pyrimidin-2-yl)-1-methylspiro[indoline-3,4'-piperidin]-2-one,

[4-fluoro-1'-(8-methyl-4-oxo-3,4,5,6,7,8-hexahydropyrido[2,3-d]pyrimidin-2-yl)-6-(4-methylpiperazin-1-yl)-2-oxospiro[indoline-3,4'-piperidin]-1(2H)-yl]acetonitrile, 6-(4-acetylpiperazin-1-yl)-4-fluoro-1-methyl-1'-(8-methyl-4-oxo-3,4,5,6,7,8-hexahydropyrido[2,3-d]pyrimidin-2-yl) spiro[indoline-3,4'-piperidin]-2(1H)-one, 4-fluoro-1'-(8-methyl-4-oxo-3,4,5,6,7,8-hexahydropyrido[2,3-d]pyrimidin-2-yl)-6-(2-pyrrolidin-1-ylethoxy)-1-(2,2,2-trifluoroethyl)spiro[indoline-3,4'-piperidin]-2(1H)-one, 6-[2-(dimethylamino)ethoxy]-4-fluoro-1-(2-methoxyethyl)-1'-(8-methyl-4-oxo-3,4,5,6,7,8-hexahydropyrido[2,3-d]pyrimidin-2-yl) spiro[indoline-3,4'-piperidin]-2(1H)-one, 4-fluoro-1'-(8-methyl-4-oxo-3,4,5,6,7,8-hexahydropyrido[2,3-d]pyrimidin-2-yl)-6-[2-(4-methylpiperazin-1-yl)ethoxy]-1-(2,2,2-trifluoroethyl)spiro[indoline-3,4'-piperidin]-2(1H)-one, 4-fluoro-1-(2-methoxyethyl)-1'-(8-methyl-4-oxo-3,4,5,6,7,8-hexahydropyrido[2,3-d]pyrimidin-2-yl)-6-(4-methylpiperazin-1-yl)spiro[indoline-3,4'-piperidin]-2(1H)-one, {[4-fluoro-1'-(8-methyl-4-oxo-3,4,5,6,7,8-hexahydropyrido[2,3-d]pyrimidin-2-yl)-2-oxo-1-(2,2,2-trifluoroethyl)spiro[indoline-3,4'-piperidin]-6-yl]oxy} acetic acid, {[4-fluoro-1-(2-methoxyethyl)-1'-(8-methyl-4-oxo-3,4,5,6,7,8-hexahydropyrido[2,3-d]pyrimidin-2-yl)-2-oxospiro[indoline-3,4'-piperidin]-6-yl]oxy} acetic acid, 4-fluoro-6-(2-hydroxyethoxy)-1-(2-methoxyethyl)-1'-(8-methyl-4-oxo-3,4,5,6,7,8-hexahydropyrido[2,3-d]pyrimidin-2-yl) spiro[indoline-3,4'-piperidin]-2(1H)-one, 2-[4-fluoro-1'-(4-hydroxy-8-methyl-6,7-dihydro-5H-pyrido[2,3-d]pyrimidin-2-yl)-1-methyl-2-oxospiro[indole-3,4'-piperidin]-7-yl]oxyacetic acid, 4-fluoro-1'-(4-hydroxy-8-methyl-6,7-dihydro-5H-pyrido[2,3-d]pyrimidin-2-yl)-1-methyl-7-[(1-methylpiperidin-4-yl)methoxy]spiro[indole-3,4'-piperidin]-2-one, 4-fluoro-7-(2-hydroxyethoxy)-1'-(4-hydroxy-5,6,7,8-tetrahydropyrido[2,3-d]pyrimidin-2-yl)-1-methyl-spiro[indole-3,4'-piperidin]-2-one, 4-chloro-1'-(4-hydroxy-8-methyl-6,7-dihydro-5H-pyrido[2,3-d]pyrimidin-2-yl)-1-methyl-7-(2H-tetrazol-5-ylmethoxy)spiro[indole-3,4'-piperidin]-2-one, 4-fluoro-1-(2-methoxyethyl)-1'-(8-methyl-4-oxo-3,4,5,6,7,8-hexahydropyrido[2,3-d]pyrimidin-2-yl)-6-(piperazin-1-yl)spiro[indoline-3,4'-piperidin]-2(1H)-one, 6-[cis-3,5-dimethylpiperazin-1-yl]-4-fluoro-1'-(8-methyl-4-oxo-3,4,5,6,7,8-hexahydropyrido[2,3-d]pyrimidin-2-yl)-1-(2,2,2-trifluoroethyl)spiro[indoline-3,4'-piperidin]-2-one, 4-fluoro-1-(2-methoxyethyl)-1'-(8-methyl-4-oxo-3,4,5,6,7,8-hexahydropyrido[2,3-d]pyrimidin-2-yl)-6-[(1H-tetrazol-5-yl)methoxy]spiro[indoline-3,4'-piperidin]-2-one, 6-[(1H-tetrazol-5-yl)methoxy]-4-fluoro-1'-(8-methyl-4-oxo-3,4,5,6,7,8-hexahydropyrido[2,3-d]pyrimidin-2-yl)-1-(2,2,2-trifluoroethyl)spiro[indoline-3,4'-piperidin]-2(1H)-one, 4-fluoro-1'-(4-hydroxy-8-methyl-6,7-dihydro-5H-pyrido[2,3-d]pyrimidin-2-yl)-1-methyl-7-(1-methylpiperidin-4-yl)oxyspiro[indole-3,4'-piperidin]-2-one, 4-fluoro-1'-(4-hydroxy-8-methyl-6,7-dihydro-5H-pyrido[2,3-d]pyrimidin-2-yl)-1-methyl-7-(piperidin-4-ylmethoxy)spiro[indole-3,4'-piperidin]-2-one, 1-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]piperidine-4-carboxylic acid, 1-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]azetidine-3-carboxylic acid, 2-[4,6-difluoro-1'-(8-methyl-4-oxo-3,4,5,6,7,8-hexahydropyrido[2,3-d]pyrimidin-2-yl)-2-oxospiro[indoline-3,4'-piperidin]-1(2H)-yl]acetamide, 4-chloro-1'-(4-hydroxy-8-methyl-6,7-dihydro-5H-pyrido[2,3-d]pyrimidin-2-yl)-1-methyl-7-[(8-methyl-8-azabicyclo[3.2.1]octan-3-yl)oxy]spiro[indole-3,4'-piperidin]-2-one, 4-fluoro-7-(2-hydroxy-2-methylpropoxy)-1'-(4-hydroxy-5,6,7,8-tetrahydropyrido[2,3-d]pyrimidin-2-yl)-1-methylspiro[indole-3,4'-piperidin]-2-one, 2-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy-N-(methylsulfonyl)acetamide, 6-[2-(N,N-dimethylsulfamoyl)aminoethoxy]-4-fluoro-1-methyl-1'-(8-methyl-4-oxo-3,4,5,6,7,8-hexahydropyrido[2,3-d]pyrimidin-2-yl) spiro[indoline-3,4'-piperidin]-2(1H)-one, {[4-fluoro-1-(2-hydroxyethyl)-1'-(8-methyl-4-oxo-3,4,5,6,7,8-hexahydropyrido[2,3-d]pyrimidin-2-yl)-2-oxospiro[indoline-3,4'-piperidin]-6-yl]oxy}acetonitrile,

[4,6-difluoro-1'-(8-methyl-4-oxo-3,4,5,6,7,8-hexahydropyrido[2,3-d]pyrimidin-2-yl)-2-oxospiro[indoline-3,4'-piperidin]-1(2H)-yl]ethanimidamide, 4-fluoro-1-methyl-1'-(8-methyl-4-oxo-3,4,5,6,7,8-hexahydropyrido[2,3-d]pyrimidin-2-yl)-2-oxospiro[indoline-3,4'-piperidine]-6-carboxylic acid, N-(2-{[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy}ethyl)methanesulfonamide, 4-chloro-1'-(4-hydroxy-8-methyl-6,7-dihydro-5H-pyrido[2,3-d]pyrimidin-2-yl)-1-methyl-7-(oxolan-3-yloxy)spiro[indole-3,4'-piperidin]-2-one, 6-(4-tert-butylpiperazin-1-yl)-4-fluoro-1'-(4-hydroxy-8-methyl-6,7-dihydro-5H-pyrido[2,3-d]pyrimidin-2-yl)spiro[2-benzofuran-3,4'-piperidin]-1-one, 2-{[4-fluoro-2-oxo-1'-(4-oxo-3,4,5,6,7,8-hexahydropyrido[2,3-d]pyrimidin-2-yl)-1-(2,2,2-trifluoroethyl)spiro[indoline-3,4'-piperidin]-6-yl]oxy} acetonitrile, 7-[2-(tert-butylamino)ethoxy]-4-fluoro-1'-(4-hydroxy-8-methyl-6,7-dihydro-5H-pyrido [2,3-d]pyrimidin-2-yl)-1-methylspiro[indole-3,4'-piperidin]-2-one, 4-chloro-1'-(4-hydroxy-5,6,7,8-tetrahydropyrido[2,3-d]pyrimidin-2-yl)-1-methyl-7-(oxolan-3-yloxy)spiro[indole-3,4'-piperidin]-2-one, 4-fluoro-1'-(4-hydroxy-8-methyl-6,7-dihydro-5H-pyrido[2,3-d]pyrimidin-2-yl)-6-[4-(2-hydroxy-2-methylpropyl)piperazin-1-yl]spiro[2-benzofuran-3,4'-piperidin]-1-one, 4-fluoro-6-[4-(2-hydroxyethyl)piperazin-1-yl]-1'-(4-hydroxy-8-methyl-6,7-dihydro-5H-pyrido[2,3-d]pyrimidin-2-yl)spiro[2-benzofuran-3,4'-piperidin]-1-one, 1-[2-(4-acetylpiperazin-1-yl)ethyl]-4-chloro-1'-(4-hydroxy-8-methyl-6,7-dihydro-5H-pyrido[2,3-d]pyrimidin-2-yl)-7-methoxyspiro[indole-3,4'-piperidin]-2-one, ({[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy}methyl) phosphonic acid, 4-chloro-1'-(4-hydroxy-5,6,7,8-tetrahydropyrido[2,3-d]pyrimidin-2-yl)-7-methoxy-1-(2,2,2-trifluoroethyl)spiro[indole-3,4'-piperidin]-2-one, 4-fluoro-1'-(4-hydroxy-8-methyl-6,7-dihydro-5H-pyrido[2,3-d]pyrimidin-2-yl)-6-[4-(4-methylpiperazin-1-yl)phenyl]spiro[2-benzofuran-3,4'-piperidin]-1-one, 4-chloro-1'-(4-hydroxy-8-methyl-6,7-dihydro-5H-pyrido[2,3-d]pyrimidin-2-yl)-7-methoxy-1-[3-oxo-3-[3-(trifluoromethyl)-6,8-dihydro-5H-imidazo[1,2-a]pyrazin-7-yl]propyl]spiro[indole-3,4'-piperidin]-2-one, 4-chloro-1'-(4-hydroxy-8-methyl-6,7-dihydro-5H-pyrido[2,3-d]pyrimidin-2-yl)-1-(2-hydroxy-2-methylpropyl)-7-methoxyspiro[indole-3,4'-piperidin]-2-one, 4-fluoro-1'-(4-hydroxy-8-methyl-6,7-dihydro-5H-pyrido[2,3-d]pyrimidin-2-yl)-1-(2-hydroxy-2-methylpropyl)spiro[indole-3,4'-piperidin]-2-one, 4-chloro-1-(2-hydroxy-2-methylpropyl)-1'-(4-hydroxy-5,6,7,8-tetrahydropyrido[2,3-d]pyrimidin-2-yl)-7-methoxyspiro[indole-3,4'-piperidin]-2-one, 6-[4-(dimethylamino)phenyl]-4-fluoro-1'-(4-hydroxy-8-methyl-6,7-dihydro-5H-pyrido[2,3-d]pyrimidin-2-yl)spiro[2-benzofuran-3,4'-piperidin]-1-one, 4-fluoro-1'-(4-hydroxy-8-methyl-6,7-dihydro-5H-pyrido[2,3-d]pyrimidin-2-yl)-6-(1-methylpyrazol-4-yl)spiro[2-benzofuran-3,4'-piperidin]-1-one, 4-fluoro-1'-(4-hydroxy-5,6,7,8-tetrahydropyrido[2,3-d]pyrimidin-2-yl)-1-(2,2,2-trifluoroethyl)spiro[indole-3,4'-piperidin]-2-one, 4-fluoro-1-(2-hydroxy-2-methylpropyl)-1'-(4-hydroxy-5,6,7,8-tetrahydropyrido[2,3-d]pyrimidin-2-yl)spiro[indole-3,4'-piperidin]-2-one, 1-{[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy}-N-methylmethanesulfonamide, 1-{[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy}methanesulfonamide, 6-(1,1-dioxothiomorpholino)-4-fluoro-1-methyl-1'-(8-methyl-4-oxo-3,4,5,6,7,8-hexahydropyrido[2,3-d]pyrimidin-2-yl)spiro[indoline-3,4'-piperidin]-2-one, N-({[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy}methylsulfonyl)acetamide, 4-fluoro-1-methyl-1'-(8-methyl-4-oxo-3,4,5,6,7,8-hexahydropyrido[2,3-d]pyrimidin-2-yl)-6-(piperazin-1-yl)spiro[indoline-3,4'-piperidin]-2(1H)-one, 4-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]-N,N-dimethylpiperazine-1-sulfonamide, 1-benzyl-4-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]piperazine-2,6-dione, 4-fluoro-6-[4-(2-hydroxyacetyl)piperazin-1-yl]-1-methyl-1'-(8-methyl-4-oxo-3,4,5,6,7,8-hexahydropyrido[2,3-d]pyrimidin-2-yl)spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-(4-methylsulfonylpiperazin-1-yl)spiro[indoline-3,4'-piperidin]-2(1H)-one, methyl=4-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]piperazine-1-carboxylate, 6-[cis-2,6-dimethylmorpholin-4-yl]-4-fluoro-1-methyl-1'-(8-methyl-4-oxo-3,4,5,6,7,8-hexahydropyrido[2,3-d]pyrimidin-2-yl) spiro[indoline-3,4'-piperidin]-2(1H)-one, 4-fluoro-1-methy-1'-(8-methyl-4-oxo-3,4,5,6,7,8-hexahydropyrido[2,3-d]pyrimidin-2-yl)l-6-(4-methylsulfonylpiperidin-1-yl)spiro[indoline-3,4'-piperidin]-2(1H)-one, 4-fluoro-6-(4-methoxypiperidin-1-yl)-1-methyl-1'-(8-methyl-4-oxo-3,4,5,6,7,8-hexahydropyrido[2,3-d]pyrimidin-2-yl)spiro[indoline-3,4'-piperidin]-2(1H)-one, 4-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]piperazine-1-carboxamide, 1-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]piperidine-4-carbonitrile, 4-fluoro-6-(4-hydroxycyclohexyl)-1-methyl-1'-(8-methyl-4-oxo-3,4,5,6,7,8-hexahydropyrido[2,3-d]pyrimidin-2-yl)spiro[indoline-3,4'-piperidin]-2(1H)-one, 4-fluoro-1'-(4-hydroxy-5,6,7,8-tetrahydropyrido[2,3-d]pyrimidin-2-yl)-1-(oxolan-2-ylmethyl)spiro[indole-3,4'-piperidin]-2-one, 4-fluoro-1'-(4-hydroxy-5,6,7,8-tetrahydropyrido[2,3-d]pyrimidin-2-yl)-1-(2-methoxyethyl)spiro[indole-3,4'-piperidin]-2-one, 4-fluoro-1'-(4-hydroxy-6,7-dihydro-5H-pyrido[2,3-d]pyrimidin-2-yl)-6-morpholine-4-ylspiro[2-benzofuran-3,4'-piperidin]-1-one, 6-(2,6-dimethylmorpholin-4-yl)-4-fluoro-1'-(4-hydroxy-5,6,7,8-tetrahydropyrido[2,3-d]pyrimidin-2-yl) spiro[2-benzofuran-3,4'-piperidin]-1-one, 2-(4-fluoro-1-(2-hydroxy-2-methylpropyl)-7-methoxyspiro[indoline-3,4'-piperidin]-1'-yl)-5,6,7,8-tetrahydropyrido[2,3-d]pyrimidin-4(3H)-one and 2-(4-fluoro-7-methoxyspiro[indoline-3,4'-piperidin]-1'-yl)-5,6,7,8-tetrahydropyrido[2,3-d]pyrimidin-4(3H)-one.

7. The compound or the pharmaceutically acceptable salt thereof according to claim 1, wherein
in the general formula (1), the structure composed of $G^1$, $G^2$, $G^3$, and $G^4$ is a group represented by the following formula: —CH$_2$—CH$_2$—CH$_2$—CH$_2$—.

8. The compound or the pharmaceutically acceptable salt thereof according to claim 7, wherein
the compound represented by the general formula (1) is selected from the group consisting of
2-[1-[(3-methoxybenzyl)spiro[indoline-3,4'-piperidin]-1'-yl]-5,6,7,8-tetrahydroquinazolin-4(3H)-one,
2-[1-(pyridin-4-ylmethyl)spiro[indoline-3,4'-piperidin]-1'-yl]-5,6,7,8-tetrahydroquinazolin-4(3H)-one,
2-[1-(pyridin-3-ylmethyl)spiro[indoline-3,4'-piperidin]-1'-yl]-5,6,7,8-tetrahydroquinazolin-4(3H)-one,
2-(5-methoxy-1-methylspiro[indoline-3,4'-piperidin]-1'-yl)-5,6,7,8-tetrahydroquinazolin-4(3H)-one,
Ethyl 4-chloro-1'-(4-oxo-3,4,5,6,7,8-hexahydroquinazolin-2-yl)-1-(pyridin-3-yl)methylspiro[indoline-3,4'-piperidine]-6-carboxylate,
4-chloro-N-(2-morpholinoethyl)-1'-(4-oxo-3,4,5,6,7,8-hexahydroquinazolin-2-yl)-1-(pyridin-3-yl)methylspiro[indoline-3,4'-piperidine]-6-carboxamide,
2-(6-chloro-1-(pyridin-3-yl)methylspiro[indoline-3,4'-piperidin]-1'-yl)-5,6,7,8-tetrahydroquinazolin-4(3H)-one,
2-(4-chloro-1-(pyridin-3-yl)methylspiro[indoline-3,4'-piperidin]-1'-yl)-5,6,7,8-tetrahydroquinazolin-4(3H)-one,
4-chloro-1'-(4-oxo-3,4,5,6,7,8-hexahydroquinazolin-2-yl)-1-(pyridin-3-yl)methylspiro[indoline-3,4'-piperidin]-2-one,
4-chloro-6-hydroxy-1-methyl-1'-(4-oxo-3,4,5,6,7,8-hexahydroquinazolin-2-yl)spiro[indoline-3,4'-piperidin]-2-one,
2-[4,6-difluoro-1-(pyridin-3-yl)methylspiro[indoline-3,4'-piperidin]-1'-yl]-5,6,7,8-tetrahydroquinazolin-4(3H)-one,
2-[4,6-difluoro-1-(pyrimidin-5-yl)methylspiro[indoline-3,4'-piperidin]-1'-yl]-5,6,7,8-tetrahydroquinazolin-4(3H)-one,
2-[4,6-difluoro-1-(pyridin-2-yl)methylspiro[indoline-3,4'-piperidin]-1'-yl]-5,6,7,8-tetrahydroquinazolin-4(3H)-one,
2-[4,6-difluoro-1-(pyridin-4-yl)methylspiro[indoline-3,4'-piperidin]-1'-yl]-5,6,7,8-tetrahydroquinazolin-4(3H)-one,
2-[4,6-difluoro-1-(pyrimidin-2-ylmethyl)spiro[indoline-3,4'-piperidine]-1'-yl]-5,6,7,8-tetrahydroquinazolin-4(3H)-one,
4-chloro-1-methyl-6-[4-(morpholine-4-carbonyl)oxazol-2-yl]-1'-(4-oxo-3,4,5,6,7,8-hexahydroquinazolin-2-yl)spiro[indoline-3,4'-piperidine]-2-one,
4,6-difluoro-1'-(4-oxo-3,4,5,6,7,8-hexahydroquinazolin-2-yl)-1-(pyridin-3-ylmethyl)spiro[indoline-3,4'-piperidine]-2-one,
4-chloro-1-methyl-6-(3-morpholinopropoxy)-1'-(4-oxo-3,4,5,6,7,8-hexahydroquinazolin-2-yl)spiro[indoline-3,4'-piperidin]-2-one,
2-[4,6-difluoro-1-(2-fluorobenzyl)spiro[indoline-3,4'-piperidin]-1'-yl]-5,6,7,8-tetrahydroquinazolin-4(3H)-one,
2-[4,6-difluoro-1-(3-fluorobenzyl)spiro[indoline-3,4'-piperidine]-1'-yl]-5,6,7,8-tetrahydroquinazolin-4(3H)-one, and 2-{1-[(6-chloropyridin-3-yl)methyl]-4,6-difluorospiro[indoline-3,4'-piperidine]-1'-yl}-5,6,7,8-tetrahydroquinazolin-4(3H)-one.

9. The compound or the pharmaceutically acceptable salt thereof according to claim 1, wherein
in the general formula (1), the structure composed of $G^1$, $G^2$, $G^3$, and $G^4$ is a group represented by the following formula: —$CH_2$—$CH_2$—$CH_2$—$N(R^7)$—.

10. The compound or the pharmaceutically acceptable salt thereof according to claim 9, wherein
the compound represented by the general formula (1) is selected from the group consisting of
5-[2-(dimethylamino)ethoxy]-7-fluoro-1'-(8-methyl-4-oxo-3,4,5,6,7,8-hexahydropyrido[2,3-d]pyrimidin-2-yl)-3H-spiro[isobenzofuran-1,4'-piperidine]-3-one,
2-[{7-fluoro-1'-(8-methyl-4-oxo-3,4,5,6,7,8-hexahydropyrido[2,3-d]pyrimidin-2-yl)-3-oxo-3H-spiro[isobenzofuran-1,4'-piperidine]-5-yl}oxy]-N,N-dimethylacetamide,
2-(4-fluoro-2-oxospiro[indoline-3,4'-piperidin]-1'-yl)-8-methyl-5,6,7,8-tetrahydropyrido[2,3-d]pyrimidine-4(3H)-one,
1-methyl-1'-(8-methyl-4-oxo-3,4,5,6,7,8-hexahydropyrido[2,3-d]pyrimidin-2-yl)spiro[indoline-3,4'-piperidine]-2-one,
4-chloro-6-[4-(morpholine-4-carbonyl)oxazol-2-yl]-1-methyl-1'-(8-methyl-4-oxo-3,4,5,6,7,8-hexahydropyrido[2,3-d]pyrimidin-2-yl)spiro[indoline-3,4'-piperidine]-2-one,
4-chloro-1-methyl-1'-(8-methyl-4-oxo-3,4,5,6,7,8-hexahydropyrido[2,3-d]pyrimidin-2-yl)-2-oxospiro[indoline-3,4'-piperidine]-7-carbonitrile,
4-chloro-6-(4-ethoxycarbonyloxazole-2-yl)-1-methyl-1'-(8-methyl-4-oxo-3,4,5,6,7,8-hexahydropyrido[2,3-d]pyrimidin-2-yl) spiro[indoline-3,4'-piperidine]-2-one,
4-chloro-1-methyl-1'-(8-methyl-4-oxo-3,4,5,6,7,8-hexahydropyrido[2,3-d]pyrimidin-2-yl)-6-[4-(pyrrolidin-1-ylmethyl)oxazol-2-yl]spiro[indoline-3,4'-piperidine]-2-one,
4-chloro-1-methyl-1'-(8-methyl-4-oxo-3,4,5,6,7,8-hexahydropyrido[2,3-d]pyrimidin-2-yl)-2-oxospiro [indoline-3,4'-piperidine]-7-carboxamide,
2-[4-chloro-1-methyl-1'-(8-methyl-4-oxo-3,4,5,6,7,8-hexahydropyrido[2,3-d]pyrimidin-2-yl)-2-oxospiro[indoline-3,4'-piperidine]-6-yl]oxazole-4-carboxylic acid,
2-(4,6-difluoro-1-methylspiro[indoline-3,4'-piperidine]-1'-yl)-8-methyl-5,6,7,8-tetrahydropyrido[2,3-d]pyrimidin-4(3H)-one,
2-[4,6-difluoro-1-(2-hydroxyethyl)spiro[indoline-3,4'-piperidine]-1'-yl]-8-methyl-5,6,7,8-tetrahydropyrido[2,3-d]pyrimidin-4(3H)-one,
4,6-difluoro-1-methyl-1'-(8-methyl-4-oxo-3,4,5,6,7,8-hexahydropyrido[2,3-d]pyrimidin-2-yl)spiro[indoline-3,4'-piperidine]-2-one,
4,6-difluoro-1-(2-hydroxyethyl)-1'-(8-methyl-4-oxo-3,4,5,6,7,8-hexahydropyrido[2,3-d]pyrimidin-2-yl)spiro[indoline-3,4'-piperidine]-2-one,
2-[4,6-difluoro-1-(pyridin-3-ylmethyl)spiro[indoline-3,4'-piperidine]-1'-yl]-8-methyl-5,6,7,8-tetrahydropyrido[2,3-d]pyrimidin-4(3H)-one,
4-fluoro-6-hydroxy-1-methyl-1'-(8-methyl-4-oxo-3,4,5,6,7,8-hexahydropyrido[2,3-d]pyrimidin-2-yl)spiro[indoline-3,4'-piperidin]-2-one,
4-fluoro-6-(2-hydroxyethoxy)-1-methyl-1'-(8-methyl-4-oxo-3,4,5,6,7,8-hexahydropyrido[2,3-d]pyrimidin-2-yl)spiro[indoline-3,4'-piperidin]-2-one,
6-[2-(dimethylamino)ethoxy]-4-fluoro-1-methyl-1'-(8-methyl-4-oxo-3,4,5,6,7,8-hexahydropyrido[2,3-d]pyrimidin-2-yl)spiro[indoline-3,4'-piperidin]-2-one,
4-fluoro-1-methyl-1'-(8-methyl-4-oxo-3,4,5,6,7,8-hexahydropyrido[2,3-d]pyrimidin-2-yl)-6-(2-morpholinoethoxy)spiro[indoline-3,4'-piperidin]-2-one,
6-[2-(1,1-dioxidothiomorpholino)ethoxy]-4-fluoro-1-methyl-1'-(8-methyl-4-oxo-3,4,5,6,7,8-hexahydropyrido[2,3-d]pyrimidin-2-yl)spiro[indoline-3,4'-piperidin]-2-one,
4-fluoro-1-methyl-1'-(8-methyl-4-oxo-3,4,5,6,7,8-hexahydropyrido[2,3-d]pyrimidin-2-yl)-6-[2-(4-methylpiperazin-1-yl)ethoxy]spiro[indoline-3,4'-piperidin]-2-one,
4-fluoro-1-methyl-1'-(8-methyl-4-oxo-3,4,5,6,7,8-hexahydropyrido[2,3-d]pyrimidin-2-yl)-6-(3-morpholin-4-ylpropoxy)spiro[indoline-3,4'-piperidin]-2-one,
4-fluoro-6-(2-methoxyethoxy)-1-methyl-1'-(8-methyl-4-oxo-3,4,5,6,7,8-hexahydropyrido[2,3-d]pyrimidin-2-yl) spiro[indoline-3,4'-piperidin]-2-one,
4-fluoro-1-methyl-1'-(8-methyl-4-oxo-3,4,5,6,7,8-hexahydropyrido[2,3-d]pyrimidin-2-yl)-6-[3-(pyrrolidin-1-yl)propoxy]spiro[indoline-3,4'-piperidin]-2-one,
4,6-difluoro-1-(2-hydroxyethyl)-1'-[8-(trideuteriomethyl)-4-oxo-3,4,5,6,7,8-hexapyrido[2,3-d]pyrimidin-2-yl]spiro[indoline-3,4'-piperidin]-2-one,
4-fluoro-6-methoxy-1-methyl-1'-(8-methyl-4-oxo-3,4,5,6,7,8-hexahydropyrido[2,3-d]pyrimidin-2-yl)spiro[indoline-3,4'-piperidin]-2-one,
4-fluoro-1-(2-hydroxyethyl)-6-methoxy-1'-(8-methyl-4-oxo-3,4,5,6,7,8-hexahydropyrido[2,3-d]pyrimidin-2-yl)spiro[indoline-3,4'-piperidin]-2-one,
2-[4,6-difluoro-1'-(8-methyl-4-oxo-3,4,5,6,7,8-hexahydropyrido[2,3-d]pyrimidin-2-yl)-2-oxospiro[indoline-3,4'-piperidin]-1-yl]acetonitrile,
4-chloro-6-[2-(dimethylamino)ethoxy]-1-methyl-1'-(8-methyl-4-oxo-3,4,5,6,7,8-hexahydropyrido[2,3-d]pyrimidin-2-yl) spiro[indoline-3,4'-piperidin]-2-one,
4-chloro-1-methyl-1'-(8-methyl-4-oxo-3,4,5,6,7,8-hexahydropyrido[2,3-d]pyrimidin-2-yl)-6-(2-piperidin-1-ylethoxy)spiro[indoline-3,4'-piperidin]-2-one
4-chloro-1-methyl-1'-(8-methyl-4-oxo-3,4,5,6,7,8-hexahydropyrido[2,3-d]pyrimidin-2-yl)-6-(2-morpholin-4-ylethoxy)spiro[indoline-3,4'-piperidin]-2-one,
4-chloro-6-[2-(1,1-dioxidothiomorpholino)ethoxy]-1-methyl-1'-(8-methyl-4-oxo-3,4,5,6,7,8-hexapyrido[2,3-d]pyrimidin-2-yl) spiro[indoline-3,4'-piperidin]-2-one,
2-[4-fluoro-6-methoxy-1'-(8-methyl-4-oxo-3,4,5,6,7,8-hexahydropyrido[2,3-d]pyrimidin-2-yl)-2-oxospiro[indoline-3,4'-piperidine]-1-yl]acetonitrile,
4-fluoro-1-methyl-1'-(8-methyl-4-oxo-3,4,5,6,7,8-hexahydropyrido[2,3-d]pyrimidin-2-yl)-6-(1-methylpiperidin-4-yl)oxyspiro[indoline-3,4'-piperidin]-2-one,
4-fluoro-6-(2-hydroxyethoxy)-1-(2-hydroxyethyl)-1'-(8-methyl-4-oxo-3,4,5,6,7,8-hexahydropyrido[2,3-d]pyrimidin-2-yl)spiro[indoline-3,4'-piperidin]-2-one,
1'-(8-ethyl-4-oxo-3,4,5,6,7,8-hexahydropyrido[2,3-d]pyrimidin-2-yl)-4,6-difluoro-1-(2-hydroxyethyl)spiro[indoline-3,4'-piperidin]-2-one,
4-fluoro-1-(2-hydroxyethyl)-6-(2-methoxyethoxy)-1'-(8-methyl-4-oxo-3,4,5,6,7,8-hexahydropyrido[2,3-d]pyrimidin-2-yl) spiro[indoline-3,4'-piperidin]-2-one,
4-fluoro-6-hydroxy-1-(2-hydroxyethyl)-1'-(8-methyl-4-oxo-3,4,5,6,7,8-hexahydropyrido[2,3-d]pyrimidin-2-yl)spiro[indoline-3,4'-piperidin]-2-one, 4-fluoro-1-(2-hydroxyethyl)-1'-(8-methyl-4-oxo-3,4,5,6,7,8-hexahydropyrido[2,3-d]pyrimidin-2-yl)-6-(2-morpholin-4-ylethoxy)spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-(4-methylpiperazin-1-yl)spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-(oxetan-3-ylmethoxy)spiro[indoline-3,4'-piperidin]-2-one, 4-fluoro-1-methyl,-1'-(8-methyl-4-oxo-3,4,5,6,7,8-hexahydropyrido[2,3-d]pyrimidin-2-yl)-6-[(tetrahydro-2H-pyran-4-yl)oxy]spiro[indoline-3,4'-piperidin]-2-one, 6-(cis-3,5-dimethylpiperazin-1-yl)-4-fluoro-1-methyl-1'-(8-methyl-4-oxo-3,4,5,6,7,8-hexahydropyrido[2,3-d]pyrimidin-2-yl)spiro[indoline-3,4'-piperidin]-2(1H)-one, 6-(3,8-diazabicyclo[3.2.1]octan-3-yl)-4-fluoro-1-methyl-1'-(8-methyl-4-oxo-3,4,5,6,7,8-hexahydropyrido[2,3-d]pyrimidin-2-yl)spiro[indoline-3,4'-piperidin]-2-one, 2-{[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy} acetic acid, 6-[(1H-tetrazol-5-yl)methoxy]-4-fluoro-1-methyl-1'-(8-methyl-4-oxo-3,4,5,6,7,8-hexahydropyrido[2,3-d]pyrimidin-2-yl)spiro[indoline-3,4'-piperidin]-2(1H)-one, 4-fluoro-6-{2-[2-(hydroxymethyl)pyrrolidin-1-yl]ethoxy}-1-methyl-1'-(8-methyl-4-oxo-3,4,5,6,7,8-hexahydropyrido[2,3-d]pyrimidin-2-yl) spiro[indoline-3,4'-piperidin]-2-(1H)-one, 4-fluoro-1'-(4-hydroxy-8-methyl-6,7-dihydro-5H-pyrido[2,3-d]pyrimidin-2-yl)-6-(2-pyrrolidin-1-ylethoxy)spiro[2-benzofuran-3,4'-piperidin]-1-one, 4-chloro-7-[2-(dimethylamino)ethoxy]-1-methyl-1'-(8-methyl-4-oxo-3,4,5,6,7,8-hexahydropyrido[2,3-d]pyrimidin-2-yl) spiro[indoline-3,4'-piperidin]-2-one, 4-fluoro-6-[4-(2-methoxyethyl)piperazin-1-yl]-1-methyl-1'-(8-methyl-4-oxo-3,4,5,6,7,8-hexahydropyrido[2,3-d]pyrimidin-2-yl)spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-[4-(oxetan-3-yl)piperazin-1-yl]spiro[indoline-3,4'-piperidin]-2-one, 4-fluoro-6-(2-hydroxyethoxy)-1'-(8-methyl-4-oxo-3,4,5,6,7,8-hexahydropyrido[2,3-d]pyrimidin-2-yl)-1-(2,2,2-trifluoroethyl)spiro[indoline-3,4'-piperidin]-2-one, 6-[2-(dimethylamino)ethoxy]-4-fluoro-1'-(8-methyl-4-oxo-3,4,5,6,7,8-hexahydropyrido[2,3-d]pyrimidin-2-yl)-1-(2,2,2-trifluoroethyl)spiro[indoline-3,4'-piperidin]-2-one, 7-[2-(dimethylamino)ethoxy]-4-fluoro-1'-(4-hydroxy-8-methyl-6,7-dihydro-5H-pyrido[2,3-d]pyrimidin-2-yl)-1-methylspiro[indoline-3,4'-piperidin]-2-one,

[4-fluoro-1'-(8-methyl-4-oxo-3,4,5,6,7,8-hexahydropyrido[2,3-d]pyrimidin-2-yl)-6-(4-methylpiperazin-1-yl)-2-oxospiro[indoline-3,4'-piperidin]-1(2H)-yl]acetonitrile, 6-(4-acetylpiperazin-1-yl)-4-fluoro-1-methyl-1'-(8-methyl-4-oxo-3,4,5,6,7,8-hexahydropyrido[2,3-d]pyrimidin-2-yl) spiro[indoline-3,4'-piperidin]-2(1H)-one, 4-fluoro-1'-(8-methyl-4-oxo-3,4,5,6,7,8-hexahydropyrido[2,3-d]pyrimidin-2-yl)-6-(2-pyrrolidin-1-ylethoxy)-1-(2,2,2-trifluoroethyl)spiro[indoline-3,4'-piperidin]-2(1H)-one, 6-[2-(dimethylamino)ethoxy]-4-fluoro-1-(2-methoxyethyl)-1'-(8-methyl-4-oxo-3,4,5,6,7,8-hexahydropyrido[2,3-d]pyrimidin-2-yl) spiro[indoline-3,4'-piperidin]-2(1H)-one, 4-fluoro-1'-(8-methyl-4-oxo-3,4,5,6,7,8-hexahydropyrido[2,3-d]pyrimidin-2-yl)-6-[2-(4-methylpiperazin-1-yl)ethoxy]-1-(2,2,2-trifluoroethyl)spiro[indoline-3,4'-piperidin]-2(1H)-one, 4-fluoro-1-(2-methoxyethyl)-1'-(8-methyl-4-oxo-3,4,5,6,7,8-hexahydropyrido[2,3-d]pyrimidin-2-yl)-6-(4-methylpiperazin-1-yl)spiro[indoline-3,4'-piperidin]-2(1H)-one, {[4-fluoro-1'-(8-methyl-4-oxo-3,4,5,6,7,8-hexahydropyrido[2,3-d]pyrimidin-2-yl)-2-oxo-1-(2,2,2-trifluoroethyl)spiro[indoline-3,4'-piperidin]-6-yl]oxy} acetic acid, {[4-fluoro-1-(2-methoxyethyl)-1'-(8-methyl-4-oxo-3,4,5,6,7,8-hexahydropyrido[2,3-d]pyrimidin-2-yl)-2-oxospiro[indoline-3,4'-piperidin]-6-yl]oxy} acetic acid, 4-fluoro-6-(2-hydroxyethoxy)-1-(2-methoxyethyl)-1'-(8-methyl-4-oxo-3,4,5,6,7,8-hexahydropyrido[2,3-d]pyrimidin-2-yl) spiro[indoline-3,4'-piperidin]-2(1H)-one, 2-[4-fluoro-1'-(4-hydroxy-8-methyl-6,7-dihydro-5H-pyrido[2,3-d]pyrimidin-2-yl)-1-methyl-2-oxospiro[indole-3,4'-piperidin]-7-yl]oxyacetic acid, 4-fluoro-1'-(4-hydroxy-8-methyl-6,7-dihydro-5H-pyrido[2,3-d]pyrimidin-2-yl)-1-methyl-7-[(1-methylpiperidin-4-yl)methoxy]spiro[indole-3,4'-piperidin]-2-one, 4-fluoro-7-(2-hydroxyethoxy)-1'-(4-hydroxy-5,6,7,8-tetrahydropyrido[2,3-d]pyrimidin-2-yl)-1-methyl-spiro[indole-3,4'-piperidin]-2-one, 4-chloro-1'-(4-hydroxy-8-methyl-6,7-dihydro-5H-pyrido[2,3-d]pyrimidin-2-yl)-1-methyl-7-(2H-tetrazol-5-ylmethoxy)spiro[indole-3,4'-piperidin]-2-one, 4-fluoro-1-(2-methoxyethyl)-1'-(8-methyl-4-oxo-3,4,5,6,7,8-hexahydropyrido[2,3-d]pyrimidin-2-yl)-6-(piperazin-1-yl)spiro[indoline-3,4'-piperidin]-2(1H)-one, 6-[cis-3,5-dimethylpiperazin-1-yl]-4-fluoro-1'-(8-methyl-4-oxo-3,4,5,6,7,8-hexahydropyrido[2,3-d]pyrimidin-2-yl)-1-(2,2,2-trifluoroethyl)spiro[indoline-3,4'-piperidin]-2-one, 4-fluoro-1-(2-methoxyethyl)-1'-(8-methyl-4-oxo-3,4,5,6,7,8-hexahydropyrido[2,3-d]pyrimidin-2-yl)-6-[(1H-tetrazol-5-yl)methoxy]spiro[indoline-3,4'-piperidin]-2-one, 6-[(1H-tetrazol-5-yl)methoxy]-4-fluoro-1'-(8-methyl-4-oxo-3,4,5,6,7,8-hexahydropyrido[2,3-d]pyrimidin-2-yl)-1-(2,2,2-trifluoroethyl)spiro[indoline-3,4'-piperidin]-2(1H)-one, 4-fluoro-1'-(4-hydroxy-8-methyl-6,7-dihydro-5H-pyrido[2,3-d]pyrimidin-2-yl)-1-methyl-7-(1-methylpiperidin-4-yl)oxyspiro[indole-3,4'-piperidin]-2-one, 4-fluoro-1'-(4-hydroxy-8-methyl-6,7-dihydro-5H-pyrido[2,3-d]pyrimidin-2-yl)-1-methyl-7-(piperidin-4-ylmethoxy)spiro[indole-3,4'-piperidin]-2-one, 1-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]piperidine-4-carboxylic acid, 1-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]azetidine-3-carboxylic acid, 2-[4,6-difluoro-1'-(8-methyl-4-oxo-3,4,5,6,7,8-hexahydropyrido[2,3-d]pyrimidin-2-yl)-2-oxospiro[indoline-3,4'-piperidin]-1(2H)-yl]acetamide, 4-chloro-1'-(4-hydroxy-8-methyl-6,7-dihydro-5H-pyrido[2,3-d]pyrimidin-2-yl)-1-methyl-7-[(8-methyl-8-azabicyclo[3.2.1]octan-3-yl)oxy]spiro[indole-3,4'-piperidin]-2-one, 4-fluoro-7-(2-hydroxy-2-methylpropoxy)-1'-(4-hydroxy-5,6,7,8-tetrahydropyrido[2,3-d]pyrimidin-2-yl)-1-methylspiro[indole-3,4'-piperidin]-2-one, 2-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy-N-(methylsulfonyl)acetamide, 6-[2-(N,N-dimethylsulfamoyl)aminoethoxy]-4-fluoro-1-methyl-1'-(8-methyl-4-oxo-3,4,5,6,7,8-hexahydropyrido[2,3-d]pyrimidin-2-yl) spiro[indoline-3,4'-piperidin]-2(1H)-one, {[4-fluoro-1-(2-hydroxyethyl)-1'-(8-methyl-4-oxo-3,4,5,6,7,8-hexahydropyrido[2,3-d]pyrimidin-2-yl)-2-oxospiro[indoline-3,4'-piperidin]-6-yl]oxy} acetonitrile,

[4,6-difluoro-1'-(8-methyl-4-oxo-3,4,5,6,7,8-hexahydropyrido[2,3-d]pyrimidin-2-yl)-2-oxospiro[indoline-3,4'-piperidin]-1(2H)-yl]ethanimidamide, 4-fluoro-1-methyl-1'-(8-methyl-4-oxo-3,4,5,6,7,8-hexahydropyrido[2,3-d]pyrimidin-2-yl)-2-oxospiro[indoline-3,4'-piperidine]-6-carboxylic acid, N-(2-{[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy}ethyl)methanesulfonamide, 4-chloro-1'-(4-hydroxy-8-methyl-6,7-dihydro-5H-pyrido[2,3-d]pyrimidin-2-yl)-1-methyl-7-(oxolan-3-yloxy)spiro[indole-3,4'-piperidin]-2-one, 6-(4-tert-butylpiperazin-1-yl)-4-fluoro-1'-(4-hydroxy-8-methyl-6,7-dihydro-5H-pyrido[2,3-d]pyrimidin-2-yl)spiro[2-benzofuran-3,4'-piperidin]-1-one, 2-{[4-fluoro-2-oxo-1'-(4-oxo-3,4,5,6,7,8-hexahydropyrido[2,3-d]pyrimidin-2-yl)-1-(2,2,2-trifluoroethyl)spiro[indoline-3,4'-piperidin]-6-yl]oxy} acetonitrile, 7-[2-(tert-butylamino)ethoxy]-4-fluoro-1'-(4-hydroxy-8-methyl-6,7-dihydro-5H-pyrido [2,3-d]pyrimidin-2-yl)-1-methylspiro[indole-3,4'-piperidin]-2-one, 4-chloro-1'-(4-hydroxy-5,6,7,8-tetrahydropyrido[2,3-d]pyrimidin-2-yl)-1-methyl-7-(oxolan-3-yloxy)spiro[indole-3,4'-piperidin]-2-one, 4-fluoro-1'-(4-hydroxy-8-methyl-6,7-dihydro-5H-pyrido[2,3-d]pyrimidin-2-yl)-6-[4-(2-hydroxy-2-methylpropyl)piperazin-1-yl]spiro[2-benzofuran-3,4'-piperidin]-1-one, 4-fluoro-6-[4-(2-hydroxyethyl)piperazin-1-yl]-1'-(4-hydroxy-8-methyl-6,7-dihydro-5H-pyrido[2,3-d]pyrimidin-2-yl)spiro[2-benzofuran-3,4'-piperidin]-1-one, 1-[2-(4-acetylpiperazin-1-yl)ethyl]-4-chloro-1'-(4-hydroxy-8-methyl-6,7-dihydro-5H-pyrido[2,3-d]pyrimidin-2-yl)-7-methoxyspiro[indole-3,4'-piperidin]-2-one, ({[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy}methyl) phosphonic acid, 4-chloro-1'-(4-hydroxy-5,6,7,8-tetrahydropyrido[2,3-d]pyrimidin-2-yl)-7-methoxy-1-(2,2,2-trifluoroethyl)spiro[indole-3,4'-piperidin]-2-one, 4-fluoro-1'-(4-hydroxy-8-methyl-6,7-dihydro-5H-pyrido[2,3-d]pyrimidin-2-yl)-6-[4-(4-methylpiperazin-1-yl)phenyl]spiro[2-benzofuran-3,4'-piperidin]-1-one, 4-chloro-1'-(4-hydroxy-8-methyl-6,7-dihydro-5H-pyrido[2,3-d]pyrimidin-2-yl)-7-methoxy-1-[3-oxo-3-[3-(trifluoromethyl)-6,8-dihydro-5H-imidazo[1,2-a]pyrazin-7-yl]propyl]spiro[indole-3,4'-piperidin]-2-one, 4-fluoro-1'-(4-hydroxy-8-methyl-6,7-dihydro-5H-pyrido[2,3-d]pyrimidin-2-yl)-1-(2-hydroxy-2-methylpropyl)-7-methoxyspiro[indole-3,4'-piperidin]-2-one, 4-fluoro-1'-(4-hydroxy-8-methyl-6,7-dihydro-5H-pyrido[2,3-d]pyrimidin-2-yl)-1-(2-hydroxy-2-methylpropyl)spiro[indole-3,4'-piperidin]-2-one, 4-chloro-1-(2-hydroxy-2-methylpropyl)-1'-(4-hydroxy-5,6,7,8-tetrahydropyrido[2,3-d]pyrimidin-2-yl)-7-methoxyspiro[indole-3,4'-piperidin]-2-one, 6-[4-(dimethylamino)phenyl]-4-fluoro-1'-(4-hydroxy-8-methyl-6,7-dihydro-5H-pyrido[2,3-d]pyrimidin-2-yl)spiro[2-benzofuran-3,4'-piperidin]-1-one, 4-fluoro-1'-(4-hydroxy-8-methyl-6,7-dihydro-5H-pyrido[2,3-d]pyrimidin-2-yl)-6-(1-methylpyrazol-4-yl)spiro[2-benzofuran-3,4'-piperidin]-1-one, 4-fluoro-1'-(4-hydroxy-5,6,7,8-tetrahydropyrido[2,3-d]pyrimidin-2-yl)-1-(2,2,2-trifluoroethyl)spiro[indole-3,4'-piperidin]-2-one, 4-fluoro-1-(2-hydroxy-2-methylpropyl)-1'-(4-hydroxy-5,6,7,8-tetrahydropyrido[2,3-d]pyrimidin-2-yl)spiro[indole-3,4'-piperidin]-2-one, 1-{[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy}-N-methylmethanesulfonamide, 1-{[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy}methanesulfonamide, 6-(1,1-dioxothiomorpholino)-4-fluoro-1-methyl-1'-(8-methyl-4-oxo-3,4,5,6,7,8-hexahydropyrido[2,3-d]pyrimidin-2-yl)spiro[indoline-3,4'-piperidin]-2-one, N-({[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]oxy}methylsulfonyl)acetamide, 4-fluoro-1-methyl-1'-(8-methyl-4-oxo-3,4,5,6,7,8-hexahydropyrido[2,3-d]pyrimidin-2-yl)-6-(piperazin-1-yl)spiro[indoline-3,4'-piperidin]-2(1H)-one, 4-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]-N,N-dimethylpiperazine-1-sulfonamide, 1-benzyl-4-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]piperazine-2,6-dione, 4-fluoro-6-[4-(2-hydroxyacetyl)piperazin-1-yl]-1-methyl-1'-(8-methyl-4-oxo-3,4,5,6,7,8-hexahydropyrido[2,3-d]pyrimidin-2-yl)spiro[indoline-3,4'-piperidin]-2-one, 4-fluoro-1-methyl-1'-(8-methyl-4-oxo-3,4,5,6,7,8-hexahydropyrido[2,3-d]pyrimidin-2-yl)-6-(4-methylsulfonylpiperazin-1-yl)spiro[indoline-3,4'-piperidin]-2(1H)-one, methyl=4-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]piperazine-1-carboxylate, 6-[cis-2,6-dimethylmorpholin-4-yl]-4-fluoro-1-methyl-1'-(8-methyl-4-oxo-3,4,5,6,7,8-hexahydropyrido[2,3-d]pyrimidin-2-yl) spiro[indoline-3,4'-piperidin]-2(1H)-one, 4-fluoro-1-methy-1'-(8-methyl-4-oxo-3,4,5,6,7,8-hexahydropyrido[2,3-d]pyrimidin-2-yl)l-6-(4-methylsulfonylpiperidin-1-yl)spiro[indoline-3,4'-piperidin]-2(1H)-one, 4-fluoro-6-(4-methoxypiperidin-1-yl)-1-methyl-1'-(8-methyl-4-oxo-3,4,5,6,7,8-hexahydropyrido[2,3-d]pyrimidin-2-yl)spiro[indoline-3,4'-piperidin]-2(1H)-one, 4-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]piperazine-1-carboxamide, 1-[4-fluoro-1-methyl-1'-(8-methyl-4-oxo-3,4,5,6,7,8-hexahydropyrido[2,3-d]pyrimidin-2-yl)-2-oxospiro[indoline-3,4'-piperidin]-6-yl]piperidine-4-carbonitrile, 4-fluoro-6-(4-hydroxycyclohexyl)-1-methyl-1'-(8-methyl-4-oxo-3,4,5,6,7,8-hexahydropyrido[2,3-d]pyrimidin-2-yl)spiro[indoline-3,4'-piperidin]-2(1H)-one, 4-fluoro-1'-(4-hydroxy-5,6,7,8-tetrahydropyrido[2,3-d]pyrimidin-2-yl)-1-(oxolan-2-ylmethyl)spiro[indole-3,4'-piperidin]-2-one, 4-fluoro-1'-(4-hydroxy-5,6,7,8-tetrahydropyrido[2,3-d]pyrimidin-2-yl)-1-(2-methoxyethyl)spiro[indole-3,4'-piperidin]-2-one, 4-fluoro-1'-(4-hydroxy-6,7-dihydro-5H-pyrido[2,3-d]pyrimidin-2-yl)-6-morpholine-4-ylspiro[2-benzofuran-3,4'-piperidin]-1-one, 6-(2,6-dimethylmorpholin-4-yl)-4-fluoro-1'-(4-hydroxy-5,6,7,8-tetrahydropyrido[2,3-d]pyrimidin-2-yl) spiro[2-benzofuran-3,4'-piperidin]-1-one, 2-(4-fluoro-1-(2-hydroxy-2-methylpropyl)-7-methoxyspiro[indoline-3,4'-piperidin]-1'-yl)-5,6,7,8-tetrahydropyrido[2,3-d]pyrimidin-4(3H)-one, and 2-(4-fluoro-7-methoxyspiro[indoline-3,4'-piperidin]-1'-yl)-5,6,7,8-tetrahydropyrido[2,3-d]pyrimidin-4(3H)-one.

11. A tankyrase inhibitor composition comprising the compound or the pharmaceutically acceptable salt thereof according to claim 1 as an active ingredient, and a pharmaceutically acceptable additive.

12. A pharmaceutical composition comprising the compound or the pharmaceutically acceptable salt thereof according to claim 1 as an active ingredient, and a pharmaceutically acceptable additive.

13. A method for treating an infection with Herpes simplex virus or Epstein-Barr virus, comprising administering the compound or the pharmaceutically acceptable salt thereof according to claim 1 to a subject in need thereof.

14. A method for treating pulmonary fibrosis, comprising administering the compound or the pharmaceutically acceptable salt thereof according to claim 1 to a subject in need thereof.

15. A method for treating multiple sclerosis, comprising administering the compound or the pharmaceutically acceptable salt thereof according to claim 1 to a subject in need thereof.

16. A method for treating amyotrophic lateral sclerosis, comprising administering the compound or the pharmaceutically acceptable salt thereof according to claim 1 to a subject in need thereof.

* * * * *